(12) United States Patent
Murai et al.

(10) Patent No.: US 7,358,249 B2
(45) Date of Patent: Apr. 15, 2008

(54) HETEROCYCLIC COMPOUNDS HAVING INHIBITORY ACTIVITY AGAINST HIV INTEGRASE

(75) Inventors: Hitoshi Murai, Osaka (JP); Takeshi Endo, Osaka (JP); Noriyuki Kurose, Osaka (JP); Teruhiko Taishi, Osaka (JP); Hiroshi Yoshida, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 395 days.

(21) Appl. No.: 10/524,281

(22) PCT Filed: Aug. 11, 2003

(86) PCT No.: PCT/JP03/10212

§ 371 (c)(1),
(2), (4) Date: Feb. 10, 2005

(87) PCT Pub. No.: WO2004/024693

PCT Pub. Date: Mar. 25, 2004

(65) Prior Publication Data

US 2006/0128669 A1 Jun. 15, 2006

(30) Foreign Application Priority Data

| Aug. 13, 2002 | (JP) | ............................. 2002-235582 |
| Aug. 26, 2002 | (JP) | ............................. 2002-245772 |
| Apr. 25, 2003 | (JP) | ............................. 2003-121726 |
| Jul. 4, 2003 | (JP) | ............................. 2003-270863 |

(51) Int. Cl.
- *A61K 31/535* (2006.01)
- *A61K 31/497* (2006.01)
- *A61K 31/44* (2006.01)
- *C07D 413/00* (2006.01)
- *C07D 471/02* (2006.01)

(52) U.S. Cl. ........................... 514/234.5; 514/253.04; 514/300; 546/122; 544/127; 544/362

(58) Field of Classification Search ................ 546/122; 514/300, 234.5, 253.04; 544/127, 362
See application file for complete search history.

(56) References Cited

U.S. PATENT DOCUMENTS 4,156,724 A 5/1979 Yamada et al. ............. 424/246

4,160,087 A 7/1979 Yamada et al. ............. 544/28
2004/0127708 A1 7/2004 Fuji et al. .................. 544/281

FOREIGN PATENT DOCUMENTS

| CA | 2263046 | * 8/2000 |
| DE | 2539664 | 3/1976 |
| WO | 99/32450 | 7/1999 |
| WO | 02/04444 | 1/2002 |
| WO | 02/30426 | 4/2002 |
| WO | 02/30930 | 4/2002 |
| WO | 02/30931 | 4/2002 |
| WO | 02/36734 | 5/2002 |
| WO | 02/055079 | 7/2002 |
| WO | 02/070486 | 9/2002 |
| WO | 03/062204 | 7/2003 |
| WO | 03/077850 | 9/2003 |
| WO | 03/077857 | 9/2003 |

* cited by examiner

*Primary Examiner*—Margaret D. Seaman
*Assistant Examiner*—Niloofar Rahmani
(74) *Attorney, Agent, or Firm*—Wenderoth, Lind & Ponack, L.L.P.

(57) ABSTRACT

A heterocyclic compound of the formula (I):

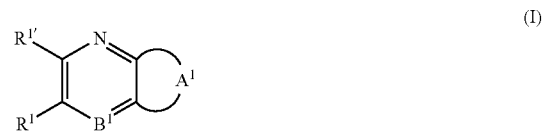

wherein $B^1$ is —$C(R^2)$= or —N=; $R^{1'}$ is H, etc.; one of $R^1$ and $R^2$ is -$Z^1$-$Z^2$-$Z^3$-$R^5$ wherein $Z^1$ and $Z^3$ are independently single bond, optionally substituted alkylene, etc.; $Z^2$ is single bond, optionally substituted alkylene, etc.; $R^5$ is optionally substituted aryl, optionally substituted heteroaryl, etc., and the other of $R^1$ and $R^2$ is H; -$A^1$- is —C(—Y)=C(—$R^4$)—C(—$R^3$)=C(—$R^4$)—, etc. wherein Y is OH, etc.; $R^4$ is —$COR^7$ wherein $R^7$ is OH, etc.; one of $R^3$ and $R^4$ is carboxy, etc., and the other of $R^1$ and $R^2$ is H, etc,
a prodrug thereof, a pharmaceutically acceptable salt thereof, and a solvate thereof, having an antiviral activity, more particularly, an inhibitory activity against HIV integrase, and a pharmaceutical composition containing the same, especially an anti-HIV drug.

14 Claims, No Drawings

HETEROCYCLIC COMPOUNDS HAVING INHIBITORY ACTIVITY AGAINST HIV INTEGRASE

This application is a U.S. national stage of International Application No. PCT/JP03/10212 filed Aug. 11, 2003.

TECHNICAL FIELD

The present invention relates to a novel compound having an antiviral activity, more particularly, a heterocyclic compound having an inhibitory activity against HIV integrase, and a pharmaceutical composition comprising the same, especially an anti-HIV drug. Further, the present invention relates to a process for preparing the present compound and an intermediate therefor.

BACKGROUND OF ART

Among viruses, human immunodeficiency virus (HIV), a kind of retrovirus, is known to cause acquired immunodeficiency syndrome (AIDS). The therapeutic agent for AIDS is mainly selected from a group of reverse transcriptase inhibitors (e.g., AZT, 3TC) and protease inhibitors (e.g., Indinavir), but they are proved to cause side effects such as nephropathy and the emergence of resistant viruses. Thus, the development of anti-HIV agents having other mechanisms of action has been desired.

A combination therapy is reported to be efficient in the treatment for AIDS because of the frequent emergence of the resistant mutant (Ref: non-patent document 1). Reverse transcriptase inhibitors and protease inhibitors are clinically used as anti-HIV agents, but agents having the same mechanism of action often exhibit cross-resistance or only an additive effect. Therefore, anti-HIV agents having the other mechanism of action have been desired.

Some integrase inhibitors have recently been reported, for Example, 1,3-dioxo butenoic acids or 1,3-propandionse disclosed (patent document 1 to 6).

Also, the integrase inhibitors having a similar structure to the present compound have been known (patent document 7 to 12). In addition, virus inhibitors having a similar structure to the present compound have been known (patent document 13 to 15). Benzimidazole derivatives that are anti-platelet agents having a similar structure to the present compound are disclosed (non-patent document 2).

Further, as a compound having HIV integrase inhibitory activity, a compound of the following formula is disclosed:

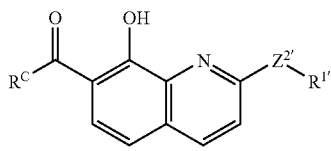

wherein $R^c$ is hydroxy or alkoxy, $Z^{2'}$ is alkylene or alkenylene, $R^{1'}$ is an optionally substituted aryl or an optionally substituted heteroaryl. (patent document 16, non-patent document 3)

Furthermore, 5-benzyl-7-acetyl-8-hydroxyquinoline and 5-phenyl-7-acetyl-8-hydroxyquinoline are disclosed (patent document 17).

In addition, patent document 18 discloses a method for synthesizing the quinoline nucleus of the present invention.

However, said process needs many steps, and the development of a more efficient process has been desired. As a known method for synthesis of quinoline nucleus, Skraup reaction has been known (non-patent document 4).

(non-patent document 1) Balzarini, J. et al, Proc. Natl. Acad. Sci. USA 1996, 93, p13152-13157
(non-patent document 2) Chem. Pharm. Bull. 42(3) 560-569 (1994)
(non-patent document 3) J. Med. Chem. 2000, 43, 1533-1540
(non-patent document 4) Organic Reactions, vol. 7 p. 59 (1953)
(patent document 1) WO99/50245
(patent document 2) WO99/62520
(patent document 3) WO99/62897
(patent document 4) WO99/62513
(patent document 5) WO00/39086
(patent document 6) WO01/00578
(patent document 7) WO2002/30426
(patent document 8) WO2002/30930
(patent document 9) WO2002/30931
(patent document 10) WO2002/36734
(patent document 11) WO2002/55079
(patent document 12) WO02/070486
(patent document 13) WO02/04444
(patent document 14) JP-A-2001-526265 (Tokuhyou)
(patent document 15) JP-A-2002-505660 (Tokuhyou)
(patent document 16) WO98/45269
(patent document 17) U.S. Pat. No. 3,113,135
(patent document 18) WO 02/070486

DISCLOSURE OF INVENTION (Problem to be Resolved)

Under the above circumstance, the development of a novel integrase inhibitor and a method for preparing the same have been desired.

(Means to Resolve the Problem)

The present inventors investigated and found compounds of the following formula (hereinafter called "compound of this invention"), i.e., a new nitrogen-containing heteroaromatic compound of the formula (I), its prodrug, its pharmaceutical acceptable salts or solvate possessing an integrase inhibiting activity:

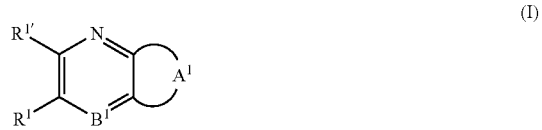

Further, the inventors also found that compounds of the present invention and medicines containing the compounds are useful as antivirals, antiretrovirals, anti-HIV, anti-HIV-1 (Human T Cell leukemia virus type 1) agent, anti-FIV (Feline immunodeficiency virus) agent, anti-SIV (Simian immunodeficiency virus) agent, especially as anti-HIV agents and integrase inhibitors.

The present invention provides compounds of this invention, prodrug thereof, pharmaceutically acceptable salts or solvates thereof, a pharmaceutical composition, antiviral agent, anti-HIV agent, integrase inhibitor or anti-HIV mixed composition containing the compounds as active ingredients. These are useful not only as anti-HIV agent, but also as anti-AIDS agent, i.e., for treating AIDS and related clinical symptoms, e.g., AIDS-related complications (ARC), progressive generalization lymphadenia (PGL), Kaposi's sarcoma, *Pneumocystis carinii* pneumonia, cataplectic purpura thrombocytopenica, AIDS related neurological syndromes, e.g., AIDS dementia complications, AIDS encephalopathy, disseminated sclerosis ortropical paraplegia, as well as anti HIV antibody-positive and HIV-positive syndrome including that in silent patients.

Thus the present invention relates to:
(1) A compound of the general formula (I):

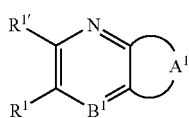

(I)

a prodrug, a pharmaceutically acceptable salt or a solvate thereof,
wherein:
$B^1$ is —C($R^2$)= or —N=;
one of $R^1$ and $R^2$ is a group of the formula: -$Z^1$-$Z^2$-$Z^3$-$R^5$ wherein
  $Z^1$ and $Z^3$ each are independently a single bond, optionally substituted alkylene or optionally substituted alkenylene;
  $Z^2$ is a single bond, optionally substituted alkylene, optionally substituted alkenylene, —CH(OH)—, —S—, —SO—, —SO$_2$—, —SO$_2$N($R^6$)—, —N($R^6$)SO$_2$—, —O—, —N($R^6$)—, —N($R^6$)CO—, —CON($R^6$)—, —C(=O)—O—, —O—C(=O)— or —CO—;
  $R^6$ is hydrogen, optionally substituted alkyl, optionally substituted alkenyl, optionally substituted aryl or optionally substituted heteroaryl;
  $R^5$ is optionally substituted aryl, optionally substituted heteroaryl, optionally substituted cycloalkyl, optionally substituted cycloalkenyl or optionally substituted heterocycle, and
the other of $R^1$ and $R^2$ is hydrogen or a substituent selected from Substituent Group A;
$R^{1'}$ is hydrogen or a substituent selected from Substituent Group A;
-$A^1$- is —C(—Y)=C(—$R^4$)—C(—$R^3$)=C(—$R^4$)—, —C(—Y)=C(—$R^4$)—C(—$R^3$)=N—, —C(—Y)=C(—$R^4$)—C(=X)—N(—$R^4$)—, —C(—Y)=C(—$R^4$)—N=C(—$R^4$)—, —C(—Y)=C(—$R^4$)—C(—$R^3$)—C(—$R^4$), —C(—Y)=C(—$R^4$)—O—C(—$R^4$)—, —C(—Y)=C(—$R^4$)—C(—$R^3$)—O—, —C(—Y)=C(—$R^4$)—O— or —C(—Y)=C(—$R^4$)—C(=X)—O— wherein
X is oxygen or sulfur;
Y is —OH, —SH or —NH$_2$;
$R^4$ is
  —C(=Z)$R^7$ wherein Z is oxygen or sulfur; $R^7$ is a substituent selected from Substituent Group A,
  —NHOH,
  —N=N$R^{10}$ wherein $R^{10}$ is hydrogen, alkyl, acyl, aralkyl, aryl or heteroaryl,
  —NHSO$_2$$R^{12}$ wherein $R^{12}$ is alkyl, aryl, aralkyl, hydroxy or amino,
  —PO(OH)$_2$,
  —PO(OH)($R^{13}$) wherein $R^{13}$ is alkyl, aryl or aralkyl, or
  a group of the formula:

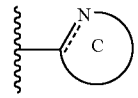

wherein Ring C is a nitrogen-containing heteroaromatic ring group optionally substituted by one to four of substituents selected from a group consisting of Substituent Group A and a substituent represented by the formula: -$Z^1$-$Z^2$-$Z^3$-$R^5$ wherein $Z^1$, $Z^2$, $Z^3$ and $R^5$ are as defined above;
$R^3$ and $R^4$ each is independently a substituent selected from Substituent Group A or hydrogen;
Substituent Group A is a group consisting of halogen, optionally substituted alkoxycarbonyl, carboxy, optionally substituted alkyl, optionally substituted alkoxy, alkoxyalkyl, nitro, hydroxy, hydroxyalkyl, optionally substituted alkenyl, optionally substituted alkynyl, alkylsulfonyl, alkyloxysulfonyl, optionally substituted amino, optionally substituted aminosulfonyl, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitroso, azido, amidino, guanidine, cyano, isocyano, mercapto, optionally substituted carbamoyl, optionally substituted carbamoylalkyl, optionally substituted sulfamoyl, sulfoamino, sulfo, formyl, alkylcarbonyl, alkylcarbonyloxy, hydrazino, morpholino, phosphono, phosphinico, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted heterocycleoxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl, optionally substituted heteroaralkylsulfonyl, optionally substituted alkylcarbonyl alkyl, optionally substituted arylcarbonyl alkyl, alkylsulfonyloxy, sulfamoyloxy and optionally substituted arylcarbonyl;

provided that (1) when -$A^1$- is —C(—Y)=C(—$R^4$)—C(—$R^3$)=C(—$R^4$)—, $R^4$ is not the following substituted carbamoyl; (2) when -$A^1$- is —C(—Y)=C(—$R^4$)—C(—$R^3$)=C(—$R^4$)—, $R^{1'}$ is hydrogen; and (3) when -$A^1$- is —C(—Y)=C(—$R^4$)—N=C(—$R^4$)—, $R^4$ is not the following substituted carbamoyl; and that, in the substituted carbamoyl of (1) and (3), its N atom is substituted with both a group of the formula: -L-$A^3$ wherein L is a single bond or alkylene, alkenylene, cycloalkylene, alkylcycloalkylene, cycloalkylalkylene or alkyl(cycloalkyl)alkylene, each optionally substituted and/or optionally interrupted by a heteroatom, —O(C=O)— or —C(=O)O—; $A^3$ is optionally substituted aryl or optionally substituted heterocycle and a group of the formula: —$R^m$ wherein $R^m$ is a hydrogen, optionally substituted alkyl or optionally substituted phenyl at the same time, or "—$R^{m}$" and "-L-$A^3$" may be combined together with the adjacent N atom to form an optionally substituted heterocycle.

In the above compound (I), when $B^1$ is $CR^2$ and $A^1$ is $-C(-Y)=C(-R^4)-C(-R^3)=C(-R^4)-$, $R^2$ is preferably a group except OH and more preferably hydrogen.

(2) The compound of the general formula (II):

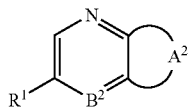

(II)

a prodrug, a pharmaceutically acceptable salt or a solvate thereof;
wherein:
$B^2$ is $-C(R^{2'})=$ or $-N=$;
one of $R^1$ and $R^{2'}$ is a group of the formula: $-Z^1-Z^2-Z^3-R^5$ wherein $Z^1$, $Z^2$, $Z^3$ and $R^5$ are as defined in the above (1) and the other $R^1$ and $R^{2'}$ is hydrogen;
$-A^2-$ is $-C(-Y)=C(-R^B)-C(-R^{24})=C(-R^{25})-$, $-C(-Y)=C(-R^B)-C(-R^{24})=N-$, $-C(-Y)=C(-R^B)-C(=X)-N(-R^{25})-$, $-C(-Y)=C(-R^B)-N=C(-R^{25})-$, $-C(-Y)=C(-R^B)-C(-R^{24})-C(-R^{25})-$, $-C(-Y)=C(-R^B)-O-C(-R^{25})-$, $-C(-Y)=C(-R^B)-C(-R^{24})-O-$, $-C(-Y)=C(-R^B)-O-$ or $-C(-Y)=C(-R^B)-C(=X)-O-$
wherein X and Y are as defined in the above (1);
$R^B$ is
$-C(=O)R^{26}$ wherein $R^{26}$ is hydroxy, alkoxy, alkyl, optionally substituted aryl or optionally substituted heterocycleoxy,
$-CON(R^8)(R^9)$ wherein $R^8$ and $R^9$ each is independently hydrogen, alkyl, aralkyl or acyl,
$-NHOH$,
$-N=NR^{10}$ wherein $R^{10}$ is hydrogen, alkyl, acyl, aralkyl, aryl or heteroaryl,
$-NHSO_2R^{12}$ wherein $R^{12}$ is alkyl, aryl, aralkyl, hydroxy or amino,
$-PO(OH)_2$,
$-PO(OH)(R^{13})$ wherein $R^{13}$ is alkyl, aryl or aralkyl, or a group of the formula:

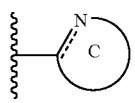

wherein ring C is as defined 1 above;
one of $R^{24}$ and $R^{25}$ is carboxy,
$-N(R^{14})(R^{15})$ wherein $R^{14}$ and $R^{15}$ each is independently hydrogen,
alkyl,
cycloalkyl,
$-(CH_2)_{1-3}OR^{16}$ wherein $R^{16}$ is hydrogen, alkyl, acyl or aryl,
$-C(=O)R^{17}$ wherein $R^{17}$ is hydrogen, hydroxy, optionally substituted alkoxy, optionally substituted alkyl, haloalkyl, optionally substituted aryl, optionally substituted heteroaryl, optionally substituted aralkyl, optionally substituted heteroaralkyl or optionally substituted amino,
$-C(=S)R^{17}$ wherein $R^{17}$ is as defined above,
$-SO_2R^{21}$ wherein $R^{21}$ is alkyl or optionally substituted amino, $R^{14}$ and $R^{15}$ may be combined to form optionally substituted thioamidino, or
$R^{14}$ and $R^{15}$ may be combined with adjacent nitrogen atom form optionally substituted nitrogen containing heterocycle optionally having nitrogen, sulfur and/or oxygen atom in the cycl,
$-(CH_2)_{0-3}OR^{18}$ wherein $R^{18}$ is hydrogen, alkyl, acyl or aryl,
$-(CH_2)_{1-3}CONHR^{19}$ wherein $R^{19}$ is hydrogen, alkyl, acyl or aryl,
$-SO_3R^{20}$ wherein $R^{20}$ is alkyl or hydroxy,
$-SO_2R^{21}$ wherein $R^{21}$ is alkyl or optionally substituted amino,
$-PO(OH)_2$,
$-PO(OH)(R^{22})$ wherein $R^{22}$ is alkyl,
haloalkyl,
$-(CH_2)_{1-3}COR^{23}$ wherein $R^{23}$ is alkyl or optionally substituted aryl,
$-(CH_2)_{0-3}CN$,
$-R^{41}-COOR^{42}$ wherein $R^{41}$ is alkenyl and $R^{42}$ is hydrogen or alkyl,
$-(CH_2)_{1-3}R^{40}$ wherein $R^{40}$ is optionally substituted aryl or optionally substituted heteroaryl,
optionally substituted aryl or
optionally substituted heteroaryl; and the other of $R^{24}$ and $R^{25}$ is hydrogen or heterocycle;
provided that (1) when $-A^1-$ is $-C(-Y)=C(-R^4)-C(-R^3)=C(-R^4)-$, $R^4$ is not the following substituted carbamoyl; (2) when $-A^1-$ is $-C(-Y)=C(-R^4)-C(-R^3)=C(-R^4)-$, $R^{1''}$ is hydrogen; and (3) when $-A^1-$ is $-C(-Y)=C(-R^4)-N=C(-R^4)-$, $R^4$ is not the following substituted carbamoyl, and that, in the substituted carbamoyl of (1) and (3), its N atom is substituted with both a group of the formula: $-L-A^3$ wherein L is a single bond or alkylene, alkenylene, cycloalkylene, alkylcycloalkylene, cycloalkylalkylene, alkyl(cycloalkyl)alkylene, each optionally substituted and/or interrupted by heteroatom(s), $-O(C=O)-$ or $-C(=O)O-$; $A^3$ is optionally substituted aryl or optionally substituted heterocycle and a group of the formula: $-R^{m}$ wherein $R^{m}$ is a hydrogen, optionally substituted alkyl or optionally substituted phenyl at the same time; or "$-R^{m''}$" and "$-L-A^3$" may be combined together with the adjacent N atom to form an optionally substituted heteroring.

In the above compound of (2), preferably $R^1$ is a group of the formula: $-Z^1-Z^2-Z^3-R^5$ and $R^{2'}$ is hydrogen.

(3) The compound of the above (1), represented by the general formula (III):

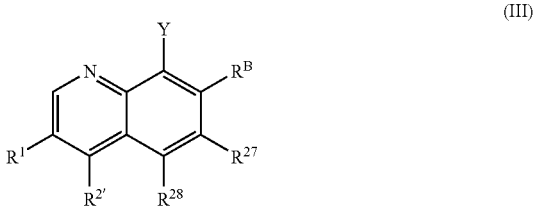

(III)

the prodrug, the pharmaceutically acceptable salt or the solvate thereof;
wherein:
Y, $R^8$, $R^1$ and $R^{2'}$ are as defined in the above (2);
one of $R^{27}$ and $R^{28}$ is
carboxy,
$-N(R^{14})(R^{15})$ wherein $R^{14}$ and $R^{15}$ each is independently hydrogen,
alkyl,
cycloalkyl,
—(CH$_2$)$_{1-3}$OR$^{16}$ wherein R$^{16}$ is hydrogen, alkyl, acyl or aryl,
—C(=O)R$^{17}$ wherein R$^{17}$ is hydrogen, hydroxy, optionally substituted alkoxy, optionally substituted alkyl, haloalkyl, optionally substituted aryl, optionally substituted heteroaryl, optionally substituted aralkyl, optionally substituted heteroalkyl or optionally substituted amino,
—C(=S)R$^{17}$ wherein R$^{17}$ is as defined above,
—SO$_2$R$^{21}$ wherein R$^{21}$ is alkyl or optionally substituted amino,
R$^{14}$ and R$^{15}$ may be combined to form optionally substituted thioamidino group, or
R$^{14}$ and R$^{15}$ may be combined together with the adjacent nitrogen to form an optionally substituted nitrogen-containing heterocycle optionally containing nitrogen, sulfur or oxygen atom in its ring,
—(CH$_2$)$_{0-3}$OR$^{18}$ wherein R$^{18}$ is hydrogen, alkyl, acyl or aryl,
—(CH$_2$)$_{1-3}$CONHR$^{19}$ wherein R$^{19}$ is hydrogen, alkyl, acyl or aryl,
—SO$_3$R$^{20}$ wherein R$^{20}$ is alkyl or hydroxy,
—SO$_2$R$^{21}$ wherein R$^{21}$ is alkyl or optionally substituted amino,
—PO(OH)$_2$,
—PO(OH)(R$^{22}$) wherein R$^{22}$ is alkyl,
haloalkyl,
—(CH$_2$)$_{1-3}$COR$^{23}$ wherein R$^{23}$ is alkyl or optionally substituted aryl,
—(CH$_2$)$_{0-3}$CN,
—R$^{41}$—COOR$^{42}$ wherein R$^{41}$ is alkenyl and R$^{42}$ is hydrogen or alkyl,
—(CH$_2$)$_{1-3}$R$^{40}$ wherein R$^{40}$ is optionally substituted aryl or optionally substituted heteroaryl,
optionally substituted aryl or
optionally substituted heteroaryl; and the other of R$^{27}$ and R$^{28}$ is hydrogen or heterocycle.

(4) The compound of the above (1), represented by the general formula (IV-1):

(IV-1)

the prodrug, the pharmaceutically acceptable salt or the solvate thereof;
wherein Y, R$^A$, R$^1$, R$^2$ and R$^3$ are as defined in the above (1).

(5) The compound of the above (1), represented by general formula (IV-2):

(IV-2)

the prodrug, the pharmaceutically acceptable salt or the solvate thereof;
wherein X, Y, R$^A$, R$^1$, R$^2$ and R$^4$ are as defined in the above (1).

(6) The compound of the above (1), represented by general formula (V):

(V)

the prodrug, the pharmaceutically acceptable salt or the solvate thereof;
wherein:
Y, R$^A$, R$^1$ and R$^2$ are as defined in the above (1);
R$^{29}$ is,
hydrogen,
carboxy,
—N(R$^{14}$)(R$^{15}$) wherein R$^{14}$ and R$^{15}$ each is independently
hydrogen,
alkyl,
cycloalkyl,
—(CH$_2$)$_{1-3}$OR$^{16}$ wherein R$^{16}$ is hydrogen, alkyl, acyl or aryl,
—C(=O)R$^{17}$ wherein R$^{17}$ is hydrogen, hydroxy, alkoxy, alkyl, haloalkyl, alkoxy alkyl, cycloalkyl, alkoxy carbonylmethyl, optionally substituted aryl or optionally substituted heteroaryl,
—C(=S)R$^{17}$ wherein R$^{17}$ is as defined above,
—SO$_2$R$^{21}$ wherein R$^{21}$ is alkyl, optionally substituted aryl, optionally substituted aralkyl or optionally substituted amino,
R$^{14}$ and R$^{15}$ may be combined together to form an optionally substituted thioamidino group, or
R$^{14}$ and R$^{15}$ may be combined together with the adjacent nitrogen atom to form optionally substituted nitrogen containing heterocycle optionally possessing nitrogen, sulfur and/or oxygen in its ring,
—(CH$_2$)$_{0-3}$OR$^{18}$ wherein R$^{18}$ is hydrogen, alkyl, acyl or aryl,
—(CH$_2$)$_{1-3}$CONHR$^{19}$ wherein R$^{19}$ is hydrogen, alkyl, acyl or aryl,
—SO$_3$R$^{20}$ wherein R$^{20}$ is alkyl or hydroxy,
—SO$_2$R$^{21}$ wherein R$^{21}$ is alkyl or optionally substituted amino,
—PO(OH)$_2$,
—PO(OH)(R$^{22}$) wherein R$^{22}$ is alkyl,
haloalkyl, —(CH)$_{1-3}$COR$^{23}$ wherein R$^{23}$ is alkyl or optionally substituted aryl,
—(CH$_2$)$_{0-3}$CN,
—R$^{41}$—COOR$^{42}$ wherein R$^{41}$ is alkenyl and R$^{42}$ is hydrogen or alkyl,
—(CH$_2$)$_{1-3}$R$^{40}$ wherein R$^{40}$ is optionally substituted aryl or optionally substituted heteroaryl,
optionally substituted aryl,
optionally substituted heteroaryl,
optionally substituted alkynyl,
optionally substituted alkylthio or
optionally substituted alkoxy.

(7) The compound of the above (1), represented by general formula (VI):

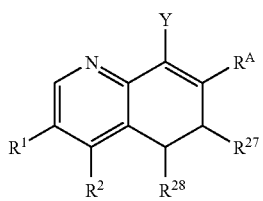

(VI)

the prodrug, the pharmaceutically acceptable salt or the solvate thereof;
wherein Y, R$^4$, R$^1$ and R$^2$ are as defined in the above (1); R$^{27}$ and R$^{28}$ are as defined in the above (3).

(8) The compound of the above (1), represented by general formula (VII):

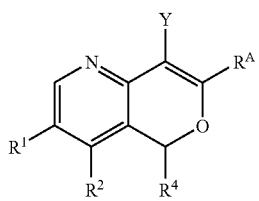

(VII)

the prodrug, the pharmaceutically acceptable salt or the solvate thereof;
wherein Y, R$^4$, R$^1$, R$^2$ and R$^4$ are as defined in the above (1).

(9) The compound of the above (1), represented by general formula (VIII):

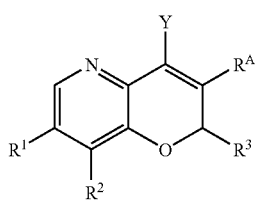

(VIII)

the prodrug, the pharmaceutically acceptable salt or the solvate thereof;
wherein Y, R$^4$, R$^1$, R$^2$ and R$^3$ are as defined in the above (1).

(10) The compound of the above (1), represented by general formula (IX):

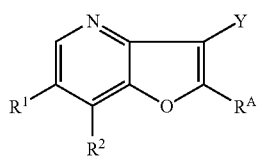

(IX)

the prodrug, the pharmaceutically acceptable salt or the solvate thereof;
wherein Y, R$^4$, R$^1$ and R$^2$ are as defined in the above (1).

(11) The compound of the above (1), represented by general formula (X):

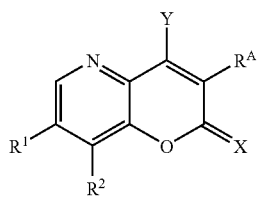

(X)

the prodrug, the pharmaceutically acceptable salt or the solvate thereof;
wherein X, Y, R$^4$, R$^1$ and R$^2$ are as defined in the above (1).

(12) The compound of the above (1), the prodrug, the pharmaceutically acceptable salt or the solvate thereof; wherein:
R$^3$ or R$^4$ is
carboxy or
—N(R$^{14}$)(R$^{15}$) wherein R$^{14}$ and R$^{15}$ each is independently
hydrogen,
alkyl,
acyl or
—SO$_2$R$^{21}$ wherein R$^{21}$ is alkyl or optionally substituted amino, or
R$^{14}$ and R$^{15}$ may be combined together with the adjacent nitrogen atom to form a nitrogen-containing heterocycle optionally containing sulfur in its ring.

(13) The compound of the above (1), the prodrug, the pharmaceutically acceptable salt or the solvate thereof; wherein:
R$^3$ or R$^4$ is
—N(R$^{14}$)(R$^{15}$) wherein R$^{14}$ and R$^{15}$ each is independently
hydrogen,
alkyl,
acyl or
—SO$_2$R$^{21}$ wherein R$^{21}$ is alkyl or optionally substituted amino, or
R$^{14}$ and R$^{15}$ may be combined together with the adjacent nitrogen atom to form a nitrogen-containing heterocycle optionally containing sulfur in its ring.

(14) The compound of the above (1), represented by formula:

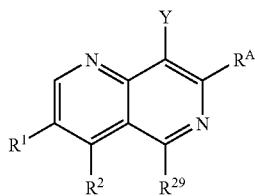

(V)

the prodrug, the pharmaceutically acceptable salt or the solvate thereof;
wherein:
$R^1$ is a group of the formula: -$Z^1$-$Z^2$-$Z^3$-$R^5$ wherein $Z^1$, $Z^2$, $Z^3$ and $R^5$ are as defined in the above (1);
$R^2$ is hydrogen;
$R^{29}$ is hydrogen, halogen, optionally substituted amino, optionally substituted alkoxy, alkylsulfonyloxy, sulfamoyloxy, alkylthio, alkylsulfonyl, optionally substituted sulfamoyl, optionally substituted alkenyl; optionally substituted alkynyl, optionally substituted aryl, carboxy, alkoxycarbonyl, optionally substituted carbamoyl, acyl or optionally substituted alkyl;
$R^4$ is a group of the formula: —C(=O)—$R^7$ wherein $R^7$ is hydroxy, optionally substituted alkoxy, optionally substituted amino, optionally substituted alkyl, optionally substituted aralkyl or optionally substituted heterocycleoxy;
Y is hydroxy.

(15) The compound of the above (14), the prodrug, the pharmaceutically acceptable salt or the solvate thereof; wherein:
$R^1$ is benzyl optionally substituted by halogen;
$R^2$ is hydrogen;
$R^{29}$ is hydrogen, halogen, optionally substituted amino, optionally substituted alkyl, optionally substituted alkenyl, optionally substituted alkynyl, optionally substituted aryl, carboxy, alkoxycarbonyl or optionally substituted carbamoyl;
$R^4$ is a group of the formula: —C(=O)—$R^7$ wherein $R^7$ is hydroxy,
optionally substituted alkoxy,
$NR^8R^9$ wherein $R^8$ and $R^9$ each is independently hydrogen, optionally substituted alkyl, optionally substituted alkoxy or optionally substituted amino,
optionally substituted alkyl or
optionally substituted heterocycleoxy; and
Y is hydroxy.

(16) The compound of the above (14), the prodrug, the pharmaceutically acceptable salt or the solvate thereof; wherein
$R^1$ is benzyl optionally substituted by halogen;
$R^2$ is hydrogen;
$R^{29}$ is hydrogen, halogen, optionally substituted amino, optionally substituted alkenyl; optionally substituted alkynyl, carboxy, alkoxycarbonyl or optionally substituted carbamoyl;
$R^4$ is a group of the formula: —C(=O)—$R^7$ wherein
$R^7$ is hydroxy,
optionally substituted alkoxy,
$NR^8R^9$ wherein $R^8$ is hydrogen and
$R^9$ is hydrogen,
alkyl optionally substituted by alkoxy or
amino optionally substituted alkyl or
optionally substituted heterocycleoxy; and
Y is hydroxy.

(17) The compound of the above (14), the prodrug, the pharmaceutically acceptable salt or the solvate thereof; wherein:
$R^1$ is a benzyl optionally substituted by halogen;
$R^2$ is hydrogen;
$R^4$ is a group of the formula: —C(=O)—$R^7$ wherein $R^7$ is hydroxy, methoxy, —$NH_2$, —$NHCH_2CH_2OCH_3$, —$NHOCH_3$, —$NHN(CH_3)_2$, $NHCH_2CH_2OCH_3$, —$(CH_2)_3OCH_3$, —$O(CH_2)_3OCH_3$, —$OCH(CH_3)CH_2OCH_3$, optionally substituted piperidyloxy or optionally substituted tetrahydropyranyloxy;
Y is hydroxy;
$R^{29}$ is any one of the following groups:

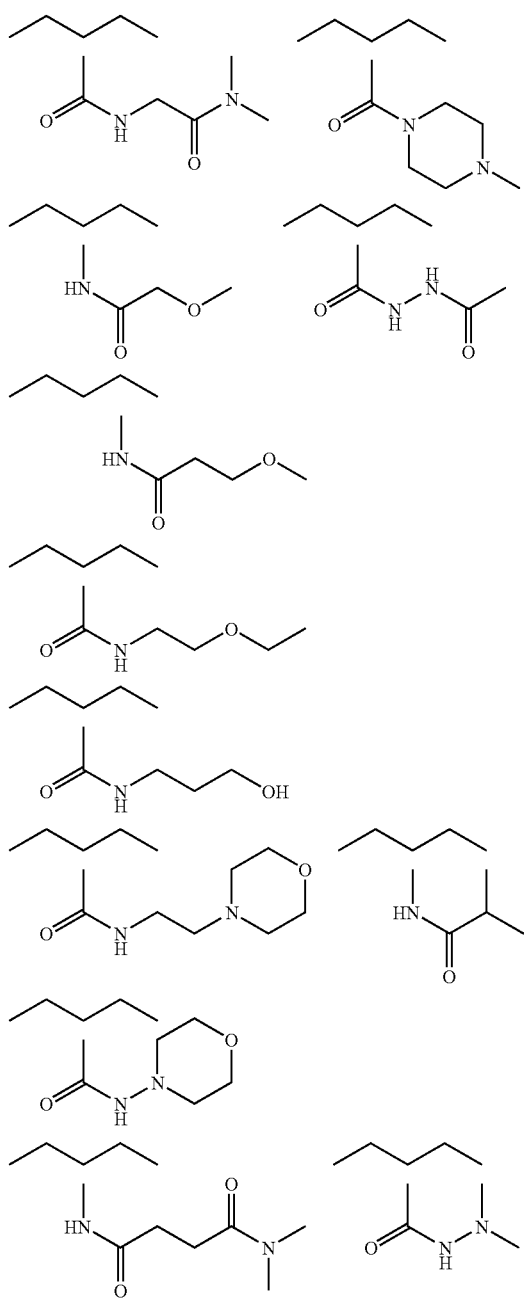

-continued

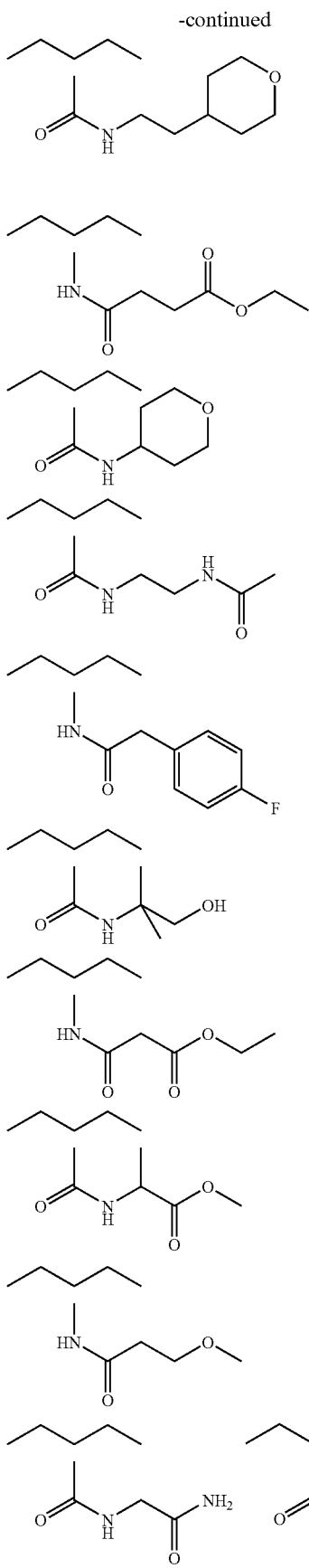

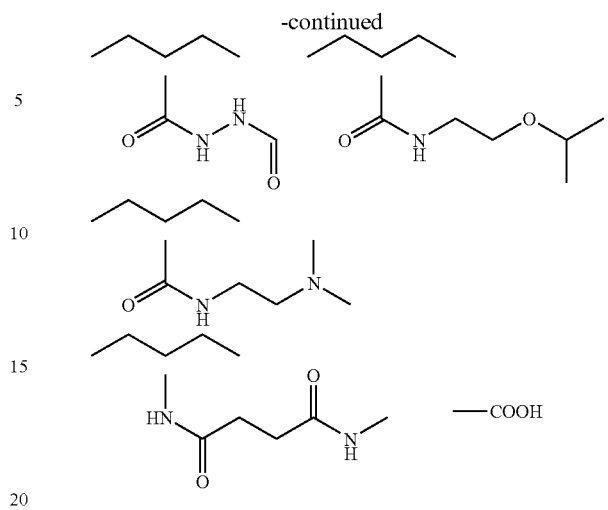

—COOH an optionally substituted amino selected from the group consisting of —NHSO₂Me, —NHCOMe, —NHSO₂NMe₂, —NHSO₂iPr, —NHSO₂-Ph-4-F, —NHSO₂Et, —NHSO₂Bn, —NHSO₂CH₂CF₃, —NHSO₂CH₂CO₂Me, —NHSO₂CHCH₂iPr, —NHSO₂CHCH₂Ph, —NHSO₂CH₂CH₂Ph, —NHCOCH₂CH₂OMe, —NHCOPh, —NHCOEt, —NHCO-c-PR, —NHCO-c-hex, —NHCOCH₂CO₂Et, —NHCO-2-thienyl, —NHCO-5-isoxazolyl, —NHCONMe₂, —NHCO₂Et, —NHCOCO₂Et, —NHCOCH₂CH₂CO₂Me, N-succinimide, —NHCOCONMe₂, —NHCO CH₂CONMe₂, —NHCOCONH₂, —NHCO₂Me, —NHCO-2-pyrimidine, —NHCO-2-furan, —NHCO-3-triazol-1-Me, —NHCO₂iPr, —NHCO₂CH₂CH₂OMe), p-toluenesulfonylamino, (2-thiazole-4-yl)acetylamino, 2-(dimethylcarbamoyl)acetylamino, thiazole-4-carbonylamino, methylaminooxazalylamino and (thiazole-5-carbonyl)amino, an optionally substituted alkynyl selected from the group consisting of —C≡CCH₂OMe, —C≡CPh, —C≡C—N—Pr, —C≡CCO₂Me, —C≡CCH₂NHAc, —C≡CCH₂NHSO₂Me, —C≡C-c-pentyl(1-OH) and —C≡CCH₂OH), an optionally substituted carbamoyl selected from the group consisting of —CONH-iPr, —CONHCH₂CH₂OMe, —CONH—N-morpholyl, —CONHNHAc, —CO-(4-Me-piperazine), —CONH-(2-thiazol), —CONHCH₂CONMe₂, —CONH(CH₂)₃OCOCF₃, —CONEt₂, —CO-morpholyl, —CONHSO₂Me, —CONMeSO₂Me and —CONHSO₂Ph, —CF₃, —COMe, —SMe, —SO₂Me, —OMe, —OCH₂CO₂Me, —OCH₂CH₂OMe, —CH₂CH=CH₂, —CN, 4-piperidinyl, —NH₂, hydrogen, Cl, Br, COOMe, 2-oxo-pyrrolidinyl, 2-oxopiperidyl or 4-(hydroxymethyl)phenyl).

(18) The compound of the above (14), the prodrug, the pharmaceutically acceptable salt or the solvate thereof; wherein:

$R^1$ is a benzyl optionally substituted by halogen;

$R^2$ is hydrogen;

$R^4$ is a group of the formula: —C(=O)—$R^7$ wherein $R^7$ is methoxy, —NHCH₂CH₂OCH₃, —NH₂, —NHN(CH)₂, —O(CH₂)₃OCH₃, —OCH(CH)CH₂OCH₃, optionally substituted piperidyloxy (substituent: acetyl or methanesulfonyloxy) or optionally substituted tetrahydropyranyloxy;

Y is hydroxy;

$R^{29}$ is an optionally substituted amino selected from the group consisting of —NHCOMe, —NHSO$_2$NMe$_2$, —NHCOCH$_2$OMe, —NHCOPh, —NHCOCH$_2$CO$_2$Et, —NHCO-2-thienyl, —NHCO$_2$Et, —NHCOCH$_2$CH$_2$CO$_2$Me, —NHCOCONMe$_2$ and —NHCOCONH$_2$, an optionally substituted alkynyl selected from the group consisting of —C≡CCH$_2$OMe, —C≡CCH$_2$NHAc, —C≡CCH$_2$NHSO$_2$Me, —C≡C-c-pen-(1-OH) and —C≡CCH$_2$OH, —CH$_2$CH=CH$_2$, 4-piperidyl or hydrogen.

(19) The compound of the above (1), represented by formula:

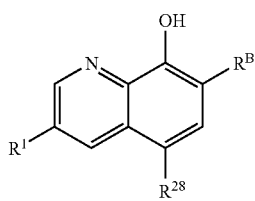

(III-1)

the pharmaceutically acceptable salt or the solvate thereof;

wherein $R^B$ is —C(=O)R$^{26}$ wherein R$^{26}$ is hydroxy, alkoxy, alkyl, alkoxyalkyl, cycloalkyl, optionally substituted aryl, optionally substituted heteroaryl or optionally substituted heterocycleoxy or —CON(R$^8$)(R$^9$) wherein R$^8$ and R$^9$ each is independently hydrogen, alkyl or alkoxy;

$R^1$ is a group of the formula: -Z$^2$-R$^5$ wherein Z$^2$ is optionally substituted alkylene and $R^5$ is optionally substituted aryl;

$R^{28}$ is carboxy,

—N(R$^{14}$)(R$^{15}$) wherein R$^{14}$ and R$^{15}$ each is independently hydrogen, alkyl, cycloalkyl, —(CH$_2$)$_{1-3}$OR$^{16}$ wherein R$^{16}$ is hydrogen, alkyl, acyl or aryl, —C(=O)R$^{17}$ wherein R$^{17}$ is hydrogen, hydroxy, optionally substituted alkoxy, optionally substituted alkyl, haloalkyl optionally substituted aryl, optionally substituted heteroaryl, optionally substituted aralkyl, optionally substituted heteroaralkyl or optionally substituted amino, —C(=S)R$^{17}$ wherein R$^{17}$ is as defined above, —SO$_2$R$^{21}$ wherein R$^{21}$ is alkyl or optionally substituted amino, R$^{14}$ and R$^{15}$ may be combined to form an optionally substituted thioamidino group, or R$^{14}$ and R$^{15}$ combined together with the adjacent nitrogen form optionally substituted nitrogen containing heterocycle optionally having nitrogen, sulfur and/or oxygen in its ring, —(CH$_2$)$_{0-3}$OR$^{18}$ wherein R$^{18}$ is hydrogen, alkyl, acyl or aryl, —(CH$_2$)$_{1-3}$CONHR$^{19}$ wherein R$^{19}$ is hydrogen, alkyl, acyl or aryl, —SO$_3$R$^{20}$ wherein R$^{20}$ is alkyl or hydroxy, —SO$_2$R$^{21}$ wherein R$^{21}$ is alkyl or optionally substituted amino,

—PO(OH)$_2$,

—PO(OH)(R$^{22}$) wherein R$^{22}$ is alkyl, haloalkyl,

—(CH$_2$)$_{1-3}$COR$^{23}$ wherein R$^{23}$ is alkyl or optionally substituted aryl,

—(CH$_2$)$_{0-3}$CN,

—R$^{41}$—COOR$^{42}$ wherein R$^{41}$ is alkenyl and R$^{42}$ is hydrogen or alkyl, —(CH$_2$)$_{1-3}$R$^{40}$ wherein R$^{40}$ is optionally substituted aryl or optionally substituted heteroaryl, optionally substituted alkenyl, optionally substituted alkynyl, optionally substituted aryl or optionally substituted heteroaryl.

(20) The compound of the above (19), the pharmaceutically acceptable salt or the solvate thereof; wherein $R^B$ is a group of the formula: —C(=O)R$^{26}$ wherein R$^{26}$ is hydroxy, alkoxy, alkyl, alkoxyalkyl, cycloalkyl or optionally substituted heterocycleoxy);

$R^1$ is a group of the formula: -Z$^2$-R$^5$ wherein Z$^2$ is methylene and R$^5$ is phenyl optionally substituted by halogen;

$R^{28}$ is carboxy,

—N(R$^{14}$)(R$^{15}$) wherein R$^{14}$ and R$^{15}$ each is independently hydrogen, alkyl, cycloalkyl, —(CH$_2$)$_{1-3}$OR$^{16}$ wherein R$^{16}$ is hydrogen, alkyl, acyl or aryl, —C(=O)R$^{17}$ wherein R$^{17}$ is hydrogen, hydroxy, optionally substituted alkoxy, optionally substituted alkyl, haloalkyl, optionally substituted aryl, optionally substituted heteroaryl, optionally substituted aralkyl, optionally substituted heteroaralkyl or optionally substituted amino, —C(=S)R$^{17}$ wherein R$^{17}$ is as defined above, —SO$_2$R$^{21}$ wherein R$^{21}$ is alkyl or optionally substituted amino, R$^{14}$ and R$^{15}$ may be combined together to form optionally substituted thioamidino group, or R$^{14}$ and R$^{15}$ may be combined together with the adjacent nitrogen atom to form an optionally substituted nitrogen-containing heterocycle optionally possessing sulfur and/or oxygen in its ring, —(CH$_2$)$_{0-3}$R$^{18}$ wherein R$^{18}$ is hydrogen, alkyl, acyl or aryl, —(CH$_2$)$_{1-3}$CONHR$^{19}$ wherein R$^{19}$ is hydrogen, alkyl, acyl or aryl, —SO$_3$R$^{20}$ wherein R$^{20}$ is alkyl or hydroxy, —SO$_2$R$^{21}$ wherein R$^{21}$ is alkyl or optionally substituted amino,

—PO(OH)$_2$,

—PO(OH)(R$^{22}$) wherein R$^{22}$ is alkyl, haloalkyl,

—(CH$_2$)$_{1-3}$COR$^{23}$ wherein R$^{23}$ is alkyl or optionally substituted aryl,

—(CH$_2$)$_{0-3}$CN,

—R$^{41}$—COOR$^{42}$ wherein R$^{41}$ is alkenyl and R$^{42}$ is hydrogen or alkyl, —(CH$_2$)$_{1-3}$R$^{40}$ wherein R$^{40}$ is optionally substituted aryl or optionally substituted heteroaryl, optionally substituted alkenyl, optionally substituted alkynyl, optionally substituted aryl or optionally substituted heteroaryl.

(21) The compound of the above (1), represented by formula:

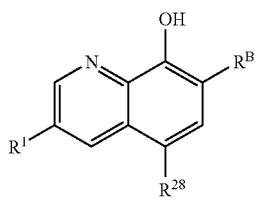

(III-1)

the pharmaceutically acceptable salt or the solvate thereof;
wherein:
$R^B$ is a group of the formula: —C(=O)$R^{26}$ wherein $R^{26}$ is hydroxy, optionally substituted alkoxy, optionally substituted alkyl, optionally substituted alkoxyalkyl, optionally substituted cycloalkyl or optionally substituted heterocycleoxy;
$R^1$ is a group of the formula: —CH$_2$—$R^5$ wherein $R^5$ is phenyl optionally substituted by halogen; and
$R^{28}$ is carboxy, optionally substituted alkyl, optionally substituted alkenyl, optionally substituted amino, optionally substituted carbamoyl, optionally substituted acyl, optionally substituted aralkyloxycarbonyl, optionally substituted heteroring, optionally substituted (heteroring)alkyl or optionally substituted aryl.

(22) The compound of the above (19), the pharmaceutically acceptable salt or the solvate thereof; wherein
$R^B$ is a group of the formula: —C(=O)$R^{26}$ wherein $R^{26}$ is hydroxy, alkoxy or optionally substituted heterocycleoxy;
$R^1$ is a group of the formula: —CH$_2$—$R^5$ wherein $R^5$ is phenyl optionally substituted by halogen; and
$R^{28}$ is a group shown below:

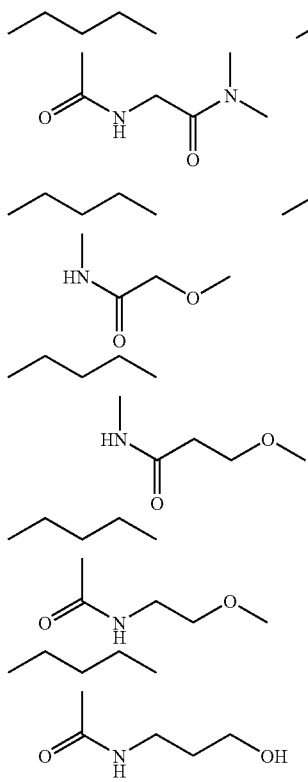

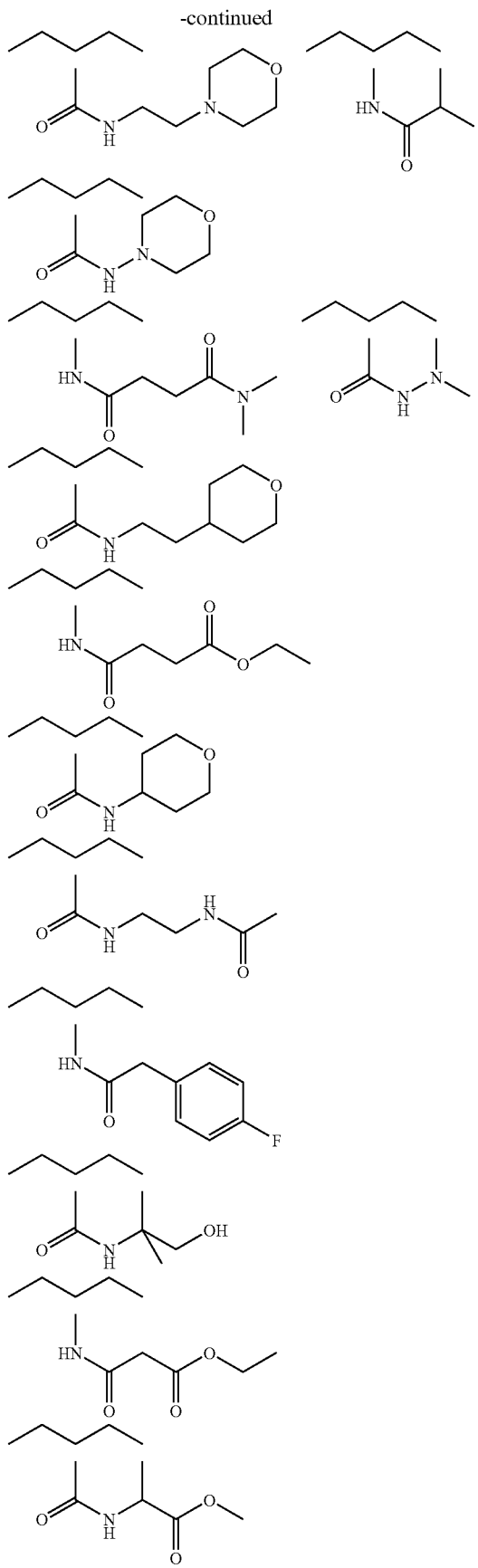

-continued

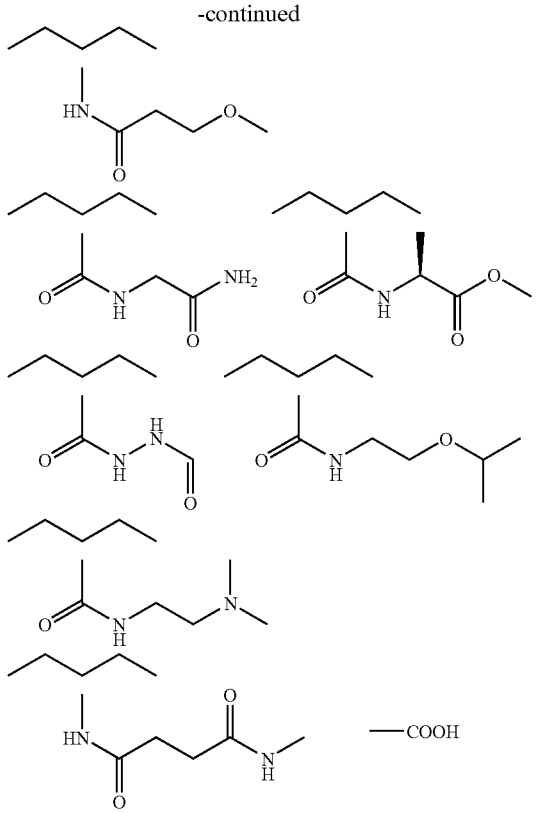

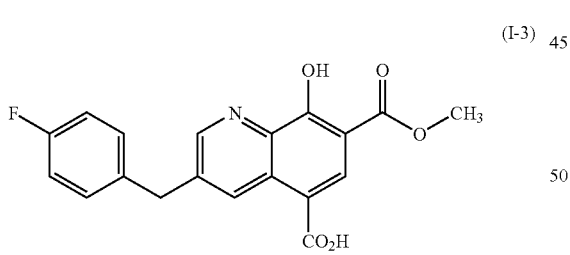

; or $R^{28}$ is a group corresponding to $R^{28}$ in the working Examples described in Table 1 of Experimental Example 1 shown below.

(23) The compound of the above (22), wherein $R^B$ is —C(=O)$R^{26}$ wherein $R^{26}$ is alkoxy.

(24) The compound of above 22, wherein $R^B$ is —C(=O) $R^{26}$ wherein $R^{26}$ is alkoxy and $R^{28}$ is carboxy.

(25) The compound of the formula:

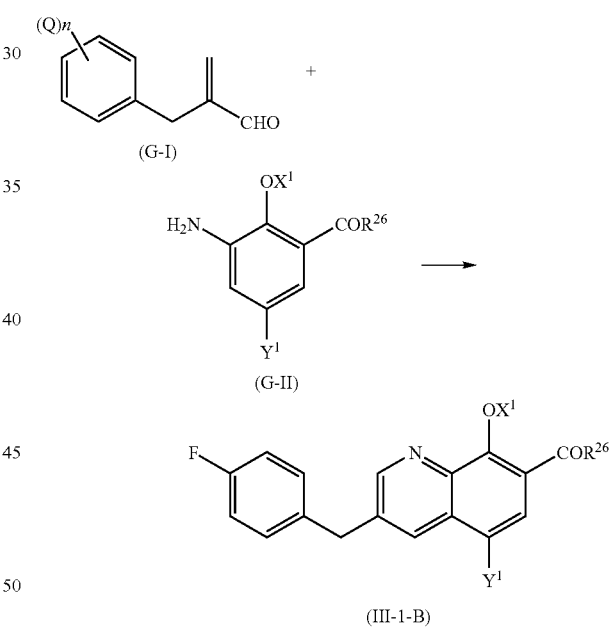

(I-3)

the pharmaceutically acceptable salt or the solvate thereof.

(26) The compound of the formula (I-3) of the above 25, the alkali metal salt, the alkali earth metal salt or the amine salt thereof.

(27) The compound of the formula (I-3) of above 25, the meglumine salt or the solvate thereof.

(28) A pharmaceutical composition comprising the compound of any one of the above (1) to (27), the prodrug, the pharmaceutically acceptable salt or the solvate thereof.

(29) The pharmaceutical composition of the above (28), that is for inhibiting an enzyme.

(30) The pharmaceutical composition of the above (28) that is for inhibiting a nucleic acid-related enzyme.

(31) The pharmaceutical composition of the above (28) that is for inhibiting an HIV integrase.

(32) The pharmaceutical composition of the above (28) that is for anti-HIV.

(33) The pharmaceutical composition of the above (28) that is for preventing or treating AIDS or AIDS-related complications.

(34) A mixed composition for anti-HIV comprising the pharmaceutical composition of the above (31) together with a reverse transcriptase inhibitor and/or a protease inhibitor.

(35) The pharmaceutical composition of the above (31) that is for elevating an anti-HIV activity of a reverse transcriptase inhibitor and/or a protease inhibitor.

(36) A method for preventing or treating AIDS or AIDS related complications, which comprises administering the pharmaceutical composition of the above (28).

(37) Use of the compound of any one of the above (1) to (27) for preparing a pharmaceutical composition for preventing or treating AIDS or AIDS-related complications.

(38) A process for preparing Compound (III-1-B), which comprises reacting Compound (G-I) and Compound (G-II) in the presence of an acid catalyst as represented by the following scheme:

wherein Q is halogen; n is an integer 0 to 3; $X^1$ is hydrogen or protective group of phenolic hydroxy; $R^{26}$ is hydroxy, alkoxy, alkyl, alkoxyalkyl, cycloalkyl, optionally substituted aryl, optionally substituted heteroaryl, optionally substituted heterocycleoxy or —N($R^8$)($R^9$) wherein $R^8$ and $R^9$ each is independently hydrogen, alkyl or alkoxy;

$Y^1$ is hydrogen,
halogen,
carboxy,
alkoxycarbonyl,
optionally substituted carbamoyl,
—N($R^{14}$)($R^{15}$) wherein $R^{14}$ and $R^{15}$ each is independently hydrogen, alkyl,
cycloalkyl,
—(CH$_2$)$_{1-3}$OR$^{16}$ wherein R$^{16}$ is hydrogen, alkyl, acyl or aryl,
—C(=O)R$^{17}$ wherein R$^{17}$ is hydrogen, hydroxy, optionally substituted alkoxy, optionally substituted alkyl, haloalkyl or optionally substituted aryl, optionally substituted heteroaryl, optionally substituted aralkyl, optionally substituted heteroaralkyl or optionally substituted amino,
—C(=S)R$^{17}$ wherein R$^{17}$ is as defined above,
—SO$_2$R$^{21}$ wherein R$^{21}$ is alkyl or optionally substituted amino,
R$^{14}$ and R$^{15}$ may be combined to form an optionally substituted thioamidino group, or
R$^{14}$ and R$^{15}$ may be combined together with the adjacent nitrogen to form optionally substituted nitrogen containing heterocycle optionally possessing nitrogen, sulfur and/or oxygen in its ring,
—(CH$_2$)$_{0-3}$OR$^{18}$ wherein R$^{18}$ is hydrogen, alkyl, acyl or aryl,
—(CH$_2$)$_{1-3}$CONHR$^{19}$ wherein R$^{19}$ is hydrogen, alkyl, acyl or aryl,
—SO$_3$R$^{20}$ wherein R$^{20}$ is alkyl or hydroxy,
—SO$_2$R$^{21}$ wherein R$^{21}$ is alkyl or optionally substituted amino,
—PO(OH)$_2$,
—PO(OH)(R$^{22}$) wherein R$^{22}$ is alkyl,
haloalkyl,
—(CH$_2$)$_{1-3}$COR$^{23}$ wherein R$^{23}$ is alkyl or optionally substituted aryl,
—(CH$_2$)$_{0-3}$CN,
—R$^{41}$—COOR$^{42}$ wherein R$^{41}$ is alkenyl and R$^{42}$ is hydrogen or alkyl,
—(CH$_2$)$_{1-3}$R$^{40}$ wherein R$^{40}$ is optionally substituted aryl or optionally substituted heteroaryl,
optionally substituted aryl or
optionally substituted heteroaryl.

(39) The process of the above (34), wherein (Q)n is F; R$^{26}$ is alkoxy; Y$^1$ is hydrogen, halogen, carboxy or alkoxycarbonyl; and X$^1$ is an ether type protecting group or an ester type protecting group.

(40) The process of the above (38), wherein (Q)n is p-F; R$^{26}$ is methoxy; Y$^1$ is hydrogen, halogen, carboxy or methoxycarbonyl; X$^1$ is hydrogen, alkyl or aralkyl.

(41) The process of the above (38), in which the reaction is carried out in the presence of an acid catalyst and an oxidizing reagent.

Further provided is a compound of the general formula (IV-3) as described in the above (1):

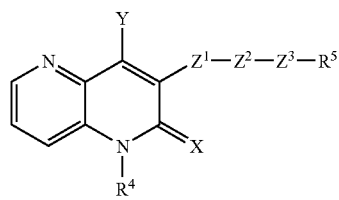

(IV-3)

wherein X, Y, Z$^1$, Z$^2$, Z$^3$, R$^4$ and R$^5$ are as defined in (1) above, a prodrug, a pharmaceutically acceptable salt or a solvate thereof and is also preferable as HIV integrase inhibitor.

The compounds of the present invention are explained in more detail below.

BEST MODE FOR CARRYING OUR THE INVENTION

The terms used in the present specification are explained below. Each term includes the same meanings as used alone or together with other terms.

Y is preferably —OH.

X is an oxygen atom.

The groups as expressed by the formula: -Z$^1$-Z$^2$-Z$^3$-R$^5$ wherein Z$^1$, Z$^2$, Z$^3$ and R$^5$ are the same meanings as above (1) include, for Example, groups of the formula: —R$^5$, the formula: —CH$_2$—R$^5$, the formula: —CH=CH—R$^5$, the formula: —CH(OH)—R$^5$, the formula: —S—R$^5$, the formula: —SO—R$^5$, the formula: —SO$_2$—R$^5$, the formula: —SO$_2$NH—R$^5$, the formula: —NHSO$_2$—R$^5$, the formula: —O—R$^5$, the formula: —NH—R$^5$, the formula: —NHCO—R$^5$, the formula: —CONH—R$^5$, the formula: —C(=O)—O—R$^5$, the formula: —O—C(=O)—R$^5$, the formula: —CO—R$^5$, the formula: —C$_2$H$_4$—R$^5$, the formula: —CH=CH—CH$_2$—R$^5$, the formula: —CH(OH)—CH$_2$—R$^5$, the formula: —S—CH$_2$—R$^5$, the formula: —SO—CH$_2$—R$^5$, the formula: —SO$_2$—CH$_2$—R$^5$, the formula: —SO$_2$NH—CH$_2$—R$^5$, the formula: —NHSO$_2$—CH$_2$—R$^5$, the formula: —O—CH$_2$—R$^5$, the formula: —NH—CH$_2$—R$^5$, the formula: —NHCO—CH$_2$—R$^5$, the formula: —CONH—CH$_2$—R$^5$, the formula: —C(=O)—O—CH$_2$—R$^5$, the formula: —O—C(=O)—CH$_2$—R$^5$, the formula: —CO—CH$_2$—R$^5$, the formula: —CH=CH—CH=CH—R$^5$, the formula: —CH=CH—CH(OH)—R$^5$, the formula: —CH=CH—S—R$^5$, the formula: —CH=CH—SO—R$^5$, the formula: —CH=CH—SO$_2$—R$^5$, the formula: —CH=CH—SO$_2$NH—R$^5$, the formula: —CH=CH—NHSO$_2$—R$^5$, the formula: —CH=CH—O—R$^5$, the formula: —CH=CH—NH—R$^5$, the formula: —CH=CH—NHCO—R$^5$, the formula: —CH=CH—CONH—R$^5$, the formula: —CH=CH—C(=O)—O—R$^5$, the formula: —CH=CH—O—C(=O)—R$^5$, the formula: —CH=CH—CO—R$^5$, the formula: —CH$_2$—CH=CH—R$^5$, the formula: —CH$_2$—CH(OH)—R$^5$, the formula: —CH$_2$—S—R$^5$, the formula: —CH$_2$—SO—R$^5$, the formula: —CH$_2$—SO$_2$—R$^5$, the formula: —CH$_2$—SO$_2$NH—R$^5$, the formula: —CH$_2$—NHSO$_2$—R$^5$, the formula: —CH$_2$—O—R$^5$, the formula: —CH$_2$—NH—R$^5$, the formula: —CH$_2$—NHCO—R$^5$, the formula: —CH$_2$—CONH—R$^5$, the formula: —CH$_2$—C(=O)—O—R$^5$, the formula: —CH$_2$—O—C(=O)—R$^5$, the formula: —CH$_2$—CO—R$^5$, the formula: —CH(OH)—CH=CH—R$^5$, the formula: —S—CH=CH—R$^5$, the formula: —SO—CH=CH—R$^5$, the formula: —SO$_2$—CH=CH—R$^5$, the formula: —SO$_2$NH—CH=CH—R$^5$, the formula: —NHSO$_2$—CH=CH—R$^5$, the formula: —O—CH=CH—R$^5$, the formula: —NH—CH=CH—R$^5$, the formula: —NHCO—CH=CH—R$^5$, the formula: —CONH—CH=CH—R$^5$, the formula: —C(=O)—O—CH=CH—R$^5$, the formula: —O—C(=O)—CH=CH—R$^5$, the formula: —CO—CH=CH—R$^5$, the formula: —C$_3$H$_6$—R$^5$, the formula: —CH$_2$—CH=CH—CH$_2$—R$^5$, the formula: —CH$_2$—CH(OH)—CH$_2$—R$^5$, the formula: —CH$_2$—S—CH$_2$—R$^5$, the formula: —CH$_2$—SO—CH$_2$—R$^5$, the formula: —CH$_2$—SO$_2$—CH$_2$—R$^5$, the formula: —CH$_2$—SO$_2$NH—CH$_2$—R$^5$, the formula: —CH$_2$—NHSO$_2$—CH$_2$—R$^5$, the formula: —CH$_2$—O—CH$_2$—R$^5$, the formula: —CH$_2$—NH—CH$_2$—R$^5$, the formula: —CH$_2$—NHCO—CH$_2$—R$^5$, the formula: —CH$_2$CONH—CH$_2$—R$^5$, the formula: —CH₂—C(=O)—O—CH₂—R⁵, the formula: —CH₂—O—C(=O)—CH₂—R⁵, the formula: —CH₂—CO—CH₂—R⁵, the formula: —C₂H₄—CH=CH—R⁵, —CH₂—CH=CH—CH=CH—R⁵, the formula: —CH₂—CH(OH)—CH=CH—R⁵, the formula: —CH₂—S—CH=CH—R⁵, the formula: CH₂—SO—CH=CH—R⁵, the formula: —CH₂—SO₂—CH=CH—R⁵, the formula: —CH₂—SO₂NH—CH=CH—R⁵, the formula: —CH₂—NHSO₂—CH=CH—R⁵, the formula: —CH₂—O—CH=CH—R⁵, the formula: —CH₂—NH—CH=CH—R⁵, the formula: —CH₂—NHCO—CH=CH—R⁵, the formula: —CH₂—CONH—CH=CH—R⁵, the formula: —CH₂—C(=O)—O—CH=CH—R⁵, the formula: —CH₂—O—C(=O)—CH=CH—R⁵, the formula: —CH₂—CO—CH₂CH—R⁵, the formula: —CH=CH—C₂H₄—R⁵, the formula: —CH=CH—CH=CH—CH₂—R⁵, the formula: —CH=CH—CH(O—CHCH₂—R⁵, the formula: —CH=CH—S—CH₂—R⁵, the formula: —CH=CH—SO—CH₂—R⁵, the formula: —CH=CH—SO₂—CH₂—R⁵, the formula: —CH=CH—SO₂NH—CH₂—R⁵, the formula: —CH=CH—NHSO₂—CH₂—R⁵, the formula: —CH=CH—O—CH₂—R⁵, the formula: —CH=CH—NH—CH₂—R⁵, the formula: —CH=CH—NHCO—CH₂—R⁵, the formula: —CH=CH—CO—CHCH₂—R⁵, the formula: —CH=CH—C(=O)—O—CH₂—R⁵, the formula: —CH=CH—O—C(=O)—CH₂—R⁵ or the formula: —CH=CH—CO—CH₂—R⁵, wherein R⁵ is optionally substituted aryl, optionally substituted heteroaryl, optionally substituted cycloalkyl, optionally substituted cycloalkenyl or optionally substituted heterocycle.

Especially, a preferable group of the formula: -Z¹-Z²-Z³-R⁵ wherein Z¹, Z², Z³ and R⁵ are the same meanings as above (1) is 1) the case in which Z¹ and Z³ are a single bond,
2) the case in which Z¹ and Z³ are a single bond, Z² is a single bond, —CO—, —O—, —S—, —SO₂— or a lower alkylene (especially —CH₂—, —(CH₂)₂—),
3) the case in which Z¹ and Z³ are a single bond, Z² is a single bond, —CO—, —O—, —S—, —SO₂— or lower alkylene (especially —CH₂—, —(CH₂)₂—), R⁵ is an optionally substituted aryl or an optionally substituted heteroaryl,
4) the case in which Z¹ and Z³ are a single bond, Z² is —SO₂—, —CH₂— or —C₂H₄—, R⁵ is an optionally substituted aryl (especially phenyl),
5) the case in which Z¹ is a single bond or an alkylene, Z³ is a single bond, Z² is an optionally substituted alkylene, an alkenylene or —O—, R⁵ is an optionally substituted aryl, an optionally substituted heteroaryl or an optionally substituted cycloalkyl,
6) the case in which Z¹ is a single bond or an alkylene,
7) the case in which Z¹ is a single bond,
8) the case in which Z² is a single bond, an alkylene, —SO₂— or —O—,
9) the case in which Z² is a single bond, an alkylene or —O—,
10) the case in which Z² is an alkylene or —O—,
11) the case in which Z³ is a single bond or an alkylene,
12) the case in which R⁵ is an optionally substituted cycloalkyl, an optionally substituted aryl or an optionally substituted heteroaryl,
13) the case in which R⁵ is an optionally substituted cycloalkyl, an optionally substituted cycloalkenyl, an optionally substituted heterocycle or an optionally substituted aryl,
14) the case in which R⁵ is an optionally substituted cycloalkyl, an optionally substituted aryl, an optionally substituted heteroaryl or an optionally substituted heterocycle,
15) the case in which R⁵ is an optionally substituted aryl,
16) the case in which Z¹ and Z³ are a single bond, Z² is an alkylene, R⁵ is an optionally substituted aryl,
17) the case in which Z¹ is a single bond or an alkylene, Z³ is a single bond, Z² is an optionally substituted alkylene, alkenylene, —S— or —O—, R⁵ is an optionally substituted aryl, an optionally substituted heteroaryl or an optionally substituted cycloalkyl.

The preferable Example of the group of the formula: -Z¹-Z²-Z³-R⁵ includes phenyl, 2-fluorophenyl, 3-fluorophenyl, 4-fluorophenyl, 2-chlorophenyl, 3-chlorophenyl, 4-chlorophenyl, 2,4-difluorophenyl, 2,6-difluorophenyl, 2,5-difluorophenyl, 3,4-difluorophenyl, 4-methylphenyl, 3-trifluoromethylphenyl, 4-trifluoromethylphenyl, 4-hydroxyphenyl, 4-methoxyphenyl, 4-bromophenyl, 4-biphenylyl, benzyl, 4-fluorobenzyl, 4-fluorobenzyl, 4-fluorobenzyl, 2-chlorobenzyl, 3-chlorobenzyl, 4-chlorobenzyl, 2,4-difluorobenzyl, 2,6-difluorobenzyl, 2,5-difluorobenzyl, 3,4-difluorobenzyl, 3,6-difluorobenzyl, 4-methylbenzyl, 3-trifluoromethylbenzyl, 4-trifluoromethylbenzyl, 4-hydroxybenzyl, 4-methoxybenzyl, 4-bromobenzyl, 4-phenylbenzyl, 2-phenylethyl, 2-(2-fluorophenyl)ethyl, 2-(3-fluorophenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-difluorophenyl)ethyl, 2-(2,6-difluorophenyl)ethyl, 2-(2,5-difluorophenyl)ethyl, 2-(3,4-difluorophenyl)ethyl, 2-(4-methylphenyl)ethyl, 2-(3-trifluoromethylphenyl)ethyl, 2-(4-trifluoromethylphenyl)ethyl, 2-(4-hydroxyphenyl)ethyl, 2-(4-methoxyphenyl)ethyl, 2-(4-bromophenyl)ethyl, 2-(4-biphenylyl)ethyl, benzenesulfonyl, 2-fluorobenzenesulfonyl, 3-fluorobenzenesulfonyl, 4-fluorobenzenesulfonyl, 2-chlorobenzenesulfonyl, 3-chlorobenzenesulfonyl, 4-chlorobenzenesulfonyl, 2,4-difluorobenzenesulfonyl, 2,6-difluorobenzenesulfonyl, 2,5-difluorobenzenesulfonyl, 3,4-difluorobenzenesulfonyl, 4-methylbenzenesulfonyl, 3-trifluoromethylbenzenesulfonyl, 4-trifluoromethylbenzenesulfonyl, 4-hydroxybenzenesulfonyl, 4-methoxybenzenesulfonyl, 4-bromobenzenesulfonyl, 4-phenylbenzenesulfonyl, phenylthio, 2-fluorophenylthio, 3-fluorophenylthio, 4-fluorophenylthio, 2-chlorophenylthio, 3-chlorophenylthio, 4-chlorophenylthio, 2,4-difluorophenylthio, 2,6-difluorophenylthio, 2,5-difluorophenylthio, 3,4-difluorophenylthio, 4-methylphenylthio, 3-trifluoromethylphenylthio, 4-trifluoromethylphenylthio, 4-hydroxyphenylthio, 4-methoxyphenylthio, 4-bromophenylthio, 4-biphenylylthio, phenoxyl, 2-fluorophenoxyl, 3-fluorophenoxyl, 4-fluorophenoxyl, 2-chlorophenoxyl, 3-chlorophenoxyl, 4-chlorophenoxyl, 2,4-difluorophenoxyl, 2,6-difluorophenoxyl, 2,5-difluorophenoxyl, 3,4-difluorophenoxyl, 4-methylphenoxyl, 3-trifluoromethylphenoxyl, 4-trifluoromethylphenoxyl, 4-hydroxyphenoxyl, 4-methoxyphenoxyl, 4-bromophenoxyl, 4-phenylphenoxyl, benzoyl, 2-fluorobenzoyl, 3-fluorobenzoyl, 4-fluorobenzoyl, 2-chlorobenzoyl, 3-chlorobenzoyl, 4-chlorobenzoyl, 2,4-difluorobenzoyl, 2,6-difluorobenzoyl, 2,5-difluorobenzoyl, 3,4-difluorobenzoyl, 4-methylbenzoyl, 3-trifluoromethylbenzoyl, 4-trifluoromethylbenzoyl, 4-hydroxybenzoyl, 4-methoxybenzoyl, 4-bromobenzoyl, 4-phenylbenzoyl, 2-thienyl, 3-thienyl, furfuryl, 3-furylmethyl, (2-chlorothiophene3-yl)methyl, 2-picolyl, 3-picolyl, 4-picolyl, (2-fluoropyridin-3-yl)methyl, (2-fluoropyridin-5-yl)methyl or (5-fluoropyridin-2-yl)methyl.

Preferably, $R^1$ is a group of the formula: $-Z^1-Z^2-Z^3-R^5$, and more preferably, a benzyl optionally substituted by a halogen, especially 4-fluorobenzyl.

The group of the formula:

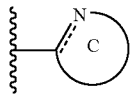

wherein Ring C is the same meaning as above (1), which includes a heteroaryl as expressed by the following (T1) and (T2) wherein an atom next to the atom at the bonding position on the Ring C is a nitrogen atom, which binds to an adjacent atom with a double bond and binds to another adjacent atom with a single bond. Especially, preferred is a heteroaryl as expressed by the following (T3) and (T4) wherein an atom next to the atom at the bonding position on the Ring C is nitrogen atom, which binds to an adjacent atom with a double bond and binds to another adjacent atom with a single bond, and further another atom next to the atom at the bonding position is a heteroatom.

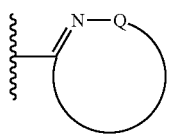 (T1)

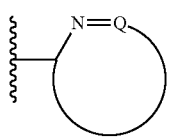 (T2)

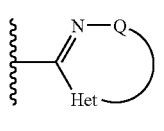 (T3)

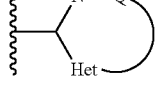 (T4)

wherein the group of T1 to T4 is a heteroaryl wherein an atom next to the atom at the bonding position is a nitrogen atom and wherein N is a nitrogen atom, Q is an atom next to the nitrogen atom; Het is a heteroatom.

Moreover, the broken line shows the presence or the absence of a bond. The part as shown by a curved line means an atom(s) and a bond(s), which constitute the Ring C and can be selected to make the Ring C aromatic. Ring C may include a heteroatom(s) other than the nitrogen atom shown in the above formula and the constituent atom of the Ring C includes carbon atom, oxygen atom, nitrogen atom and sulfur atom. The bond constructing the Ring C includes a single bond and a double bond. The Ring C is not only a monocycle but also a condensed ring (2 to 5 condensed rings), and especially a monocycle or a bicycle is preferable, and a monocycle is more preferable.

The heteroaryl of Ring C being a monocycle means 5- to 8-membered heteroaryl wherein an atom next to the atom at the bonding position is a nitrogen atom and one to four of oxygen atom, sulfur atom, and/or nitrogen atom may be included. Especially 5- or 6-membered heteroaryl is preferable. Examples thereof are pyrrol-2-yl, imidazol-2-yl, imidazol-4-yl, pyrazol-3-yl, triazol-3-yl, tetrazol-5-yl, oxazol-2-yl, oxazol-4-yl, isoxazol-3-yl, thiazol-2-yl, thiazol-4-yl, 1,3,4-thiadiazol-2-yl, 1,2,4-thiadiazol-5-yl, 1,2,4-thiadiazol-3-yl, 1,3,4-oxadiazol-2-yl, 1,2,4-oxadiazol-5-yl, 1,2,4-oxadiazol-3-yl, isothiazol-3-yl, pyridin-2-yl, pyridazin-3-yl, pyrazin-2-yl, pyrimidin-2-yl, pyrimidin-4-yl or frazan-3-yl.

Especially preferred is a heteroaryl wherein an atom next to the atom at the bonding position is a nitrogen atom, which binds to the adjacent atom with a double bond and binds to another adjacent atom with a single bond. Examples thereof are imidazol-2-yl, imidazol-4-yl, pyrazol-3-yl, triazol-3-yl, tetrazol-5-yl, oxazol-2-yl, oxazol-4-yl, isoxazol-3-yl, thiazol-2-yl, thiazol-4-yl, 1,3,4-thiadiazol-2-yl, 1,2,4-thiadiazol-5-yl, 1,2,4-thiadiazol-3-yl, 1,3,4-oxadiazol-2-yl, 1,2,4-oxadiazol-5-yl, 1,2,4-oxadiazol-3-yl, isothiazol-3-yl, pyridin-2-yl, pyridazin-3-yl, pyrazin-2-yl, pyrimidin-2-yl, pyrimidin-4-yl or frazan 3-yl.

Furthermore, preferred is a heteroaryl wherein an atom next to the atom at the bonding position is a nitrogen atom, which binds to the adjacent atom with a double bond and binds to another adjacent atom with a single bond, and further another atom next to the atom at the bonding position is a heteroatom. Examples thereof are imidazol-2-yl, triazol-3-yl, tetrazol-5-yl, oxazol-2-yl, thiazol-2-yl, 1,3,4-thiadiazol-2-yl, 1,2,4-thiadiazol-5-yl, 1,2,4-thiadiazol-3-yl, 1,3,4-oxadiazol-2-yl, 1,2,4-oxadiazol-5-yl, 1,2,4-oxadiazol-3-yl or pyrimidin-2-yl.

The heteroaryl of the Ring C being a condensed ring is a heteroaryl wherein 1 to 4 of 5- to 8-membered aromatic carbocycles (e.g., 5- to 8-membered aromatic carbocycle) and/or other 5- to 8-membered aromatic heterocycles (e.g., 5- to 8-membered aromatic heterocyle which may include 1 to 4 of oxygen atoms, sulfur atoms and/or nitrogen atoms in the ring) are condensed with the above monocycle. As a condensed aromatic ring, 5- or 6-membered ring is preferable. Examples thereof are benzimidazol-2-yl, benzooxazol-2-yl, quinoxalin-2-yl, cinnolin3-yl, quinazolin-2-yl, quinazolin-4-yl, quinolin-2-yl, phthalazinl-yl, isoquinolin-1-yl, isoquinolin-3-yl, purine-2-yl, purine-6-yl, purine-8-yl, pteridin-2-yl, pteridin-4-yl, pteridin-6-yl, pteridin-7-yl, carbazol-1-yl, phenantridin-6-yl, indol-2-yl or isoindol-1-yl.

Especially, preferred is a heteroaryl wherein an atom next to the atom at the bonding position is a nitrogen atom, which binds to the adjacent atom with a double bond and binds to another adjacent atom with a single bond. Examples thereof are benzimidazol-2-yl, benzooxazol-2-yl, quinoxalin-2-yl, cinnoline3-yl, quinazolin-2-yl, quinazolin-4-yl, quinolin-2-yl, phthalazinl-yl, isoquinolin-1-yl, isoquinolin-3-yl, purine-2-yl, purine-6-yl, purine-8-yl, pteridin-2-yl, pteridin-4-yl, pteridin-6-yl, pteridin-7-yl or phenantridin-6-yl is preferred.

Furthermore, preferred is a heteroaryl wherein an atom next to the atom at the bonding position is a nitrogen atom, which binds to the adjacent atom with a double bond and binds to another adjacent atom with a single bond and another atom next to the atom at the bonding position is a heteroatom. Examples thereof are benzimidazol-2-yl, benzooxazol-2-yl, quinazolin-2-yl, purine-2-yl, purine-8-yl or pteridin-2-yl is preferred.

Especially, the groups as shown in the following formulae are preferable.

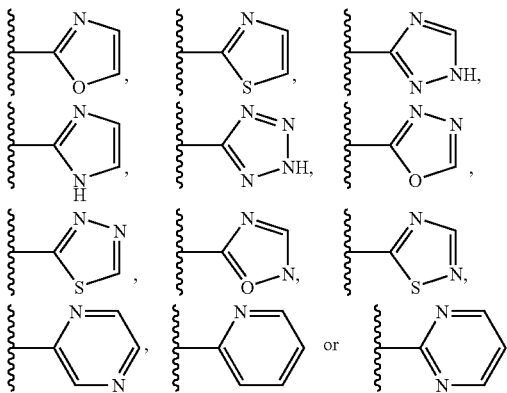

In general formula (II), when only one of $R^{24}$ and $R^{25}$ exists, the $R^{24}$ or $R^{25}$ preferably is carboxy,
—N($R^{14}$)($R^{15}$) wherein $R^{14}$ and $R^{15}$ each is independently hydrogen,
alkyl,
cycloalkyl,
—(CH$_2$)$_{1-3}$O$R^{16}$ wherein $R^{16}$ is hydrogen, alkyl, acyl or aryl,
—C(=O)$R^{17}$ wherein $R^{17}$ is hydrogen, hydroxy, optionally substituted alkoxy, optionally substituted alkyl, haloalkyl, optionally substituted aryl, optionally substituted heteroaryl, optionally substituted aralkyl, optionally substituted heteroaralkyl or optionally substituted amino,
—C(=S)$R^{17}$ wherein $R^{17}$ is as defined above,
—SO$_2R^{21}$ wherein $R^{21}$ is alkyl or optionally substituted amino,
$R^{14}$ and $R^{15}$ may be combined to form an optionally substituted thioamidino group, or
$R^{14}$ and $R^{15}$ may be combined with the adjacent nitrogen to form optionally substituted nitrogen containing heterocycle optionally having nitrogen, sulfur and/or oxygen in its ring,
—(CH$_2$)$_{0-3}$O$R^{18}$ wherein $R^{18}$ is hydrogen, alkyl, acyl or aryl,
—(CH$_2$)$_{1-3}$CONH$R^{19}$ wherein $R^{19}$ is hydrogen, alkyl, acyl or aryl,
—SO$_3R^{20}$ wherein $R^{20}$ is alkyl or hydroxy,
—SO$_2R^{21}$ wherein $R^{21}$ is alkyl or optionally substituted amino,
—PO(OH)$_2$,
—PO(OH)($R^{22}$) wherein $R^{22}$ is alkyl,
haloalkyl,
—(CH$_2$)$_{1-3}$CO$R^{23}$ wherein $R^{23}$ is alkyl or optionally substituted aryl,
—(CH$_2$)$_{0-3}$CN,
—$R^{41}$—COO$R^{42}$ wherein $R^{41}$ is alkenyl and $R^{42}$ is hydrogen or alkyl,
—(CH$_2$)$_{1-3}R^{40}$ wherein $R^{40}$ is optionally substituted aryl or optionally substituted heteroaryl,
optionally substituted aryl or
optionally substituted heteroary.

Especially, carboxy or —N($R^{14}$)($R^{15}$) wherein $R^{14}$ and $R^{15}$ each is independently hydrogen, alkyl, acyl or —SO$_2R^{21}$ wherein $R^{21}$ is alkyl or optionally substituted amino).

More preferably, —N($R^{14}$)($R^{15}$) wherein $R^{14}$ and $R^{15}$ each is independently hydrogen, alkyl, acyl or —SO$_2R^{21}$ wherein $R^{21}$ is alkyl or optionally substituted amino or $R^{14}$ and $R^{15}$ are combined with the adjacent nitrogen to form optionally substituted nitrogen containing heterocycle optionally possessing nitrogen, sulfur and/or oxygen in its ring can be cited.

The "alkylene" means a $C_1$-$C_6$ straight or branched alkylene group and includes, for Example, methylene, ethylene, trimethylene, propylene, tetramethylene, ethylethylene, pentamethylene or hexamethylene. Preferred is a $C_1$-$C_4$ straight alkylene group such as methylene, ethylene, trimethylene or tetramethylene, and more preferable one is methylene.

The "alkenylene" means a $C_2$-$C_6$ straight or branched alkenylene group, wherein the above "alkylene" is added with one or more double bonds and includes, for Example, vinylene, propenylene or butenylene. Preferred is a $C_2$-$C_3$ straight alkenylene group such as vinylene or propenylene.

The "alkyl" means a $C_1$-$C_{10}$ straight or branched alkyl group and includes, for Example, methyl, ethyl, n-propyl, isopropyl, n-butyl, isobutyl, sec-buthyl, tert-butyl, n-pentyl, isopentyl, neopentyl, tert-pentyl, n-hexyl, isohexyl, n-heptyl, n-octyl, n-nonyl or n-decyl. Preferred is a $C_1$-$C_6$ alkyl group such as methyl, ethyl, n-propyl, isopropyl, n-butyl, isobutyl, sec-buthyl, tert-butyl n-pentyl, isopentyl, neopentyl, tert-pentyl, n-hexyl or isohexyl.

The term "alkenyl" means a $C_2$-$C_8$ straight or branched alkenyl group wherein the above "alkyl" is added with one or more double bonds and includes, for Example, vinyl, 1-propenyl, 2-propenyl, 1-butenyl, 2-butenyl, 3-butenyl, 1,3-butadienyl or 3-methyl-2-butenyl.

The "aryl" means a monocyclic aromatic hydrocarbon group (e.g., phenyl) or a polycyclic aromatic hydrocarbon group (e.g., 1-naphthyl, 2-naphthyl, 1-antolyl, 2-antolyl, 9-antolyl, 1-phenantolyl, 2-phenantolyl, 3-phenantolyl, 4-phenantolyl or 9-phenantolyl). Preferred is phenyl or naphthyl (e.g., 1-naphthyl or 2-naphthyl).

The "heteroaryl" means a monocyclic aromatic heterocyclic group and a condensed aromatic heterocyclic group.

The monocycle aromatic heterocyclic group means a group which is derived from a 5- to 8-membered aromatic ring which may contain 1 to 4 of oxygen atom, sulfur atom, and/or nitrogen atom within the ring, and may have a bonding position at any substitutable position.

The condensed aromatic heterocyclic group means a group, wherein a 5- to 8-membered aromatic ring which may contain 1 to 4 of oxygen atom, sulfur atom, and/or nitrogen atom is condensed with 1 to 4 of 5- to 8-membered aromatic carboncycle or other 5- to 8-membered aromatic hetetrocycle and may have a bonding position at the any substitutable position.

The "heteroaryl" means the following groups, for Example, furyl (e.g., 2-furyl or 3-furyl), thienyl (e.g., 2-thienyl or 3-thienyl), pyrrolyl (e.g., 1-pyrrolyl, 2-pyrrolyl or 3-pyrrolyl), imidazolyl (e.g., 1-imidazolyl, 2-imidazolyl or 4-imidazolyl), pyrazolyl (e.g., 1-pyrazolyl, 3-pyrazolyl or 4-pyrazolyl), triazolyl (e.g., 1,2,4-triazol-1-yl, 1,2,4-triazolyl-3-yl or 1,2,4-triazol-4-yl), tetrazolyl (e.g., 1-tetrazolyl, 2-tetrazolyl or 5-tetrazolyl), oxazolyl (e.g., 2-oxazolyl, 4-oxazolyl or 5-oxazolyl), isoxazolyl (e.g., 3-isoxazolyl, 4-isoxazolyl or 5-isoxazolyl), thiazolyl (e.g., 2-thiazolyl, 4-thiazolyl or 5-thiazolyl), thiadiazolyl, isothiazolyl (e.g., 3-isothiazolyl, 4-isothiazolyl or 5-isothiazolyl), pyridyl (e.g., 2-pyridyl, 3-pyridyl or 4-pyridyl), pyridazinyl (e.g., 3-pyridazinyl or 4-pyridazinyl), pyrimidinyl (e.g., 2-pyrimidinyl, 4-pyrimidinyl or 5-pyrimidinyl), furazanyl (e.g., 3-furazanyl), pyrazinyl(e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl or 7-benzo[b]furyl), benzothienyl (e.g., 2-benzo[b]

thienyl, 3-benzo[b]thienyl, 4-benzo[b]thienyl, 5-benzo[b] thienyl, 6-benzo[b]thienyl or 7-benzo[b]thienyl), benzimidazolyl (e.g., 1-benzoimidazolyl, 2-benzoimidazolyl, 4-benzoimidazolyl or 5-benzoimidazolyl), dibenzofuryl, benzoxazolyl, quinoxalyl (e.g., 2-quinoxalinyl, 5-quinoxalinyl or 6-quinoxalinyl), cinnolinyl (e.g., 3-cinnolinyl, 4-cinnolinyl, 5-cinnolinyl, 6-cinnolinyl, 7-cinnolinyl or 8-cinnolinyl), quinazolyl (e.g., 2-quinazolinyl, 4-quinazolinyl, 5-quinazolinyl, 6-quinazolinyl, 7-quinazolinyl or 8-quinazolinyl), quinolyl (e.g., 2-quinolyl, 3-quinolyl, 4-quinolyl, 5-quinolyl, 6-quinolyl, 7-quinolyl or 8-quinolyl), phthalazinyl (e.g., 1-phthalazinyl, 5-phthalazinyl or 6-phthalazinyl), isoquinolyl (e.g., 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g., 2-pteridinyl, 4-pteridinyl, 6-pteridinyl or 7-pteridinyl), carbazolyl, phenantridinyl, acridinyl (e.g., 1-acridinyl, 2-acridinyl, 3-acridinyl, 4-acridinyl or 9-acridinyl), indolyl (e.g., 1-indolyl, 2-indolyl, 3-indolyl, 4-indolyl, 5-indolyl, 6-indolyl or 7-indolyl), isoindolyl, phenazinyl (e.g., 1-phenazinyl or 2-phenazinyl) or phenothiazinyl (e.g., 1-phenothiazinyl, 2-phenothiazinyl, 3-phenothiazinyl or 4-phenothiazinyl).

The term "cycloalkyl" means a $C_3$-$C_{10}$ cyclic saturated hydrocarbon group and includes, for Example, cyclopropyl, cyclobutyl, cyclopentyl, cyclohexyl, cycloheptyl or cyclooctyl. Preferred is a $C_3$-$C_6$ cycloalkyl group such as cyclopentyl or cyclohexyl.

The term "cycloalkenyl" means a $C_3$-$C_{10}$ cyclic non-aromatic hydrocarbonyl group and includes, for Example, cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl or 3-cyclopenten-1-yl), cyclohexenyl (e.g., 1-cyclohexen-1-yl, 2-cyclohexen-1-yl or 3-cyclohexen-1-yl), cycloheptenyl (e.g., 1-cycloheptenyl) or cyclooctenyl (e.g., 1-cyclooctenyl). Especially preferable is 1-cyclohexen-1-yl, 2-cyclohexen-1-yl or 3-cyclohexen-1-yl.

The term "heterocycle" means a non-aromatic heterocyclic group which contains at least one of nitrogen atom, oxygen atom and sulfur atom, and which has a bonding position at any substitutable position and includes, for Example, 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino or tetrahydropyranyl. Then, "a non-aromatic heterocyclic group" can be saturated or unsaturated.

"The optionally substituted nitrogen-containing heterocycle optionally having nitrogen, sulfur and/or oxygen atom in the cycle formed by combining $R^{14}$ and $R^{15}$ with adjacent nitrogen atom" is preferagly a 5- or 6-membered heterocycle being optionally substituted by an oxo group and includes, for Example, [1,2]-thiadinane 1,1-dioxide, isothiazolidine 1,1-dioxide, piperidin-2-one, pyrrolidin-2-one, etc.

The alkyl moiety of "alkoxy" is the same meaning as the above "alkyl". The "alkoxy" includes, for Example, methoxy, ethoxy, n-propoxy, isopropoxy, n-butoxy, isobutoxy, tert-butoxy, and especially preferably methoxy or ethoxy.

The "alkoxycarbonyl" means a carbonyl substituted with the above "alkoxy" and includes, for Example, methoxycarbonyl, ethoxycarbonyl, n-propoxycarbonyl, isopropoxycarbonyl, n-butoxycarbonyl, isobutoxycarbonyl or tert-butoxycarbonyl.

The "alkoxyalkyl" means the above "alkyl" substituted with the above "alkoxy" and includes, for Example, methoxymethyl, ethoxymethyl, n-propoxymethyl, isopropoxymethyl, n-butoxymethyl, isobutoxymethyl, tert-butoxymethyl, methoxyethyl, ethoxyethyl, n-propoxyethyl, isopropoxyethyl, n-butoxyethyl, isobutoxyethyl or tert-butoxyethyl.

The "alkynyl" means a $C_2$-$C_8$ alkynyl group, wherein the above "alkyl" having one or more triple bonds, for Example, ethynyl, 1-propynyl, 2-propynyl, 1-butynyl, 2-butynyl or 3-butynyl.

The "alkylsulfonyl" means a sulfonyl substituted with the above "alkyl" and includes, for Example, methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl, n-heptylsulfonyl, n-octylsulfonyl, n-nonylsulfonyl or n-decylsulfonyl.

The "optionally substituted amino" means a substituted or unsubstituted amino.

The "optionally substituted carbamoyl" means a substituted or unsubstituted carbamoyl.

The substituents of the "optionally substituted amino" and the "optionally substituted carbamoyl" include, for Example, an optionally substituted alkyl (e.g., methyl, ethyl, isopropyl), benzyl, carbamoylalkyl (e.g., carbamoylmethyl), a mono- or di-alkylcarbamoylalkyl (e.g., dimethylcarbamoylethyl), hydroxyalkyl, heterocyclealkyl (e.g., morpholinoethyl, tetrahydropyranylethyl), an alkoxycarbonylalkyl (e.g., ethoxycarbonylmethyl, ethoxycarbonylethyl), a mono- or dialkylaminoalkyl (e.g., dimethylaminoethyl), etc., an alkoxyalkyl (e.g., methoxyethyl, ethoxymethyl, ethoxyethyl, 1-propoxyethyl, etc.), an acyl (cf., formyl, an optionally substituted alkylcarbonyl (cf., acetyl, propironyl, butyryl, isobutyryl, valelyl, isovalelyl, pivaloyl, hexanoyl, octanoyl, methoxyethylcarbonyl, 2,2,2-trifluoroethylcarbonyl, ethoxycarbonyl, methylcarbonyl, an alkoxyalkylcarbonyl (e.g., methoxyethylcarbonyl), alkylcarbamoylalkylcarbonyl (e.g., methylcarbamoylethylcarbonyl), an alkoxycarbonylacetyl, etc.), an optionally substituted arylcarbonyl (e.g., benzoyl, toluoyl, etc.)), an optionally substituted aralkyl (e.g., benzyl, 4-F-benzyl, etc.), hydroxy, an optionally substituted alkylsulfonyl (e.g., methanesulfonyl, ethanesulfonyl, isopropylsulfonyl, 2,2,2-trifluoroethanesulfonyl, benzylsulfonyl, methoxyethylsulfonyl, etc.), an arylsulfonyl optionally substituted by an alkyl or a halogen (e.g., benzenesulfonyl, toluenesulfonyl, 4-fluorobenzenesulfonyl), a cycloalkyl (e.g., cyclopropyl etc.), an aryl optionally substituted by an alkyl (e.g., phenyl, trityl, etc.), an alkylaminosulfonyl (e.g., alkylaminosulfonyl (e.g., methylaminosulfonyl, dimethylaminosulfonyl, etc.), an alkylaminocarbonyl(e.g., dimethylaminocarbonyl, etc.), an alkoxycarbonyl (e.g., ethoxycarbonyl, etc.), a cycloalkylcarbonyl (e.g., cyclopropylcarbonyl, cyclohexylcarbonyl, etc.), an optionally substituted sulfamoyl (e.g., sulfamoyl, methylsulfamoyl, dimethylsulfamoyl, etc.), an alkylcarbonylamino (e.g., methylcarbonylamino), a heterocycle (e.g., morpholino, tetrahydropyranyl), an optionally substituted amino (e.g., mono- or dialkylamino(e.g., dimethylamino), formylamino), etc. The "optionally substituted amino" and the "optionally substituted carbamoyl" may optionally be substituted by one or two groups of the above substituents.

The amino group of the "optionally substituted amino" and the "optionally substituted carbamoyl" may be substituted by an alkylene (e.g., trimethylene, tetramethylene, pentamethylene, etc.), etc., and may form a ring optionally containing O, S together with the nitrogen atom of the amino group.

The amino group of the "optionally substituted amino" and the "optionally substituted carbamoyl" may form a nitrogen-containing heterocycle optionaly containing a sulfur atom and/or an oxygen atom together with the nitrogen atom to which two substituents of the amino group are next (e.g., prererably 5- to 7-membered ring, and preferably saturated ones), said ring being optionally substituted by an oxo or hydroxy. For Example, preferable ones are a 5- or 6-membered ring such as piperidino, morpholino, pyrrolidino, thiadinan-2-yl, 2-oxopiperidino, 2-oxopyrrolidino, 1,1-dioxide-1,2-thiadinan-2-yl, 4-hydroxymorpholino, etc.

Preferable "optionally substituted amino" and "optionally substituted carbamoyl" are groups of the following formulae (hereinafter, referred to as Substituent Group A-1). These groups are suitable for $R^{28}$ and $R^{29}$.

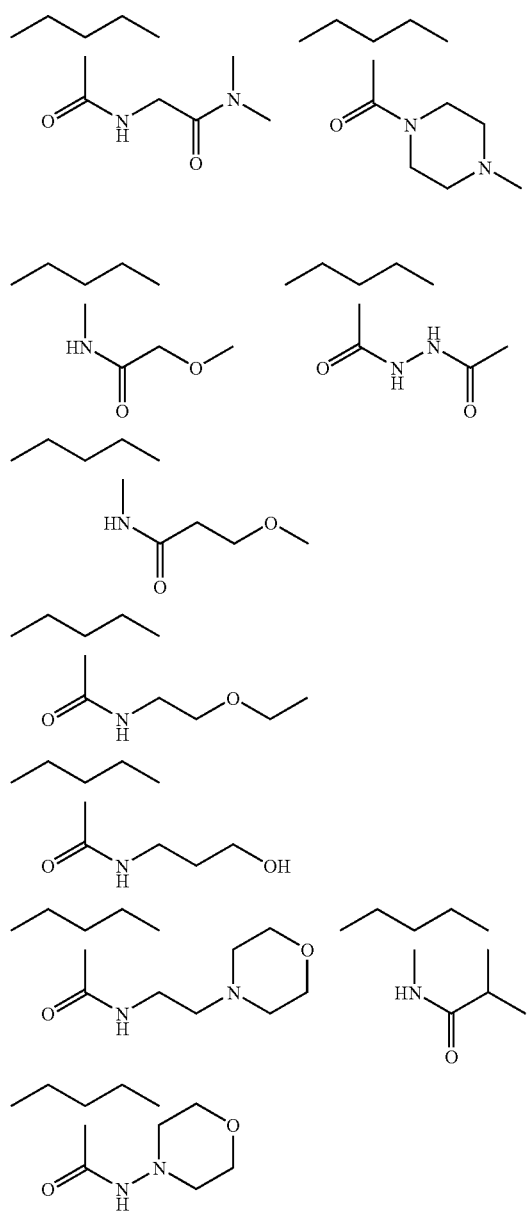

-continued

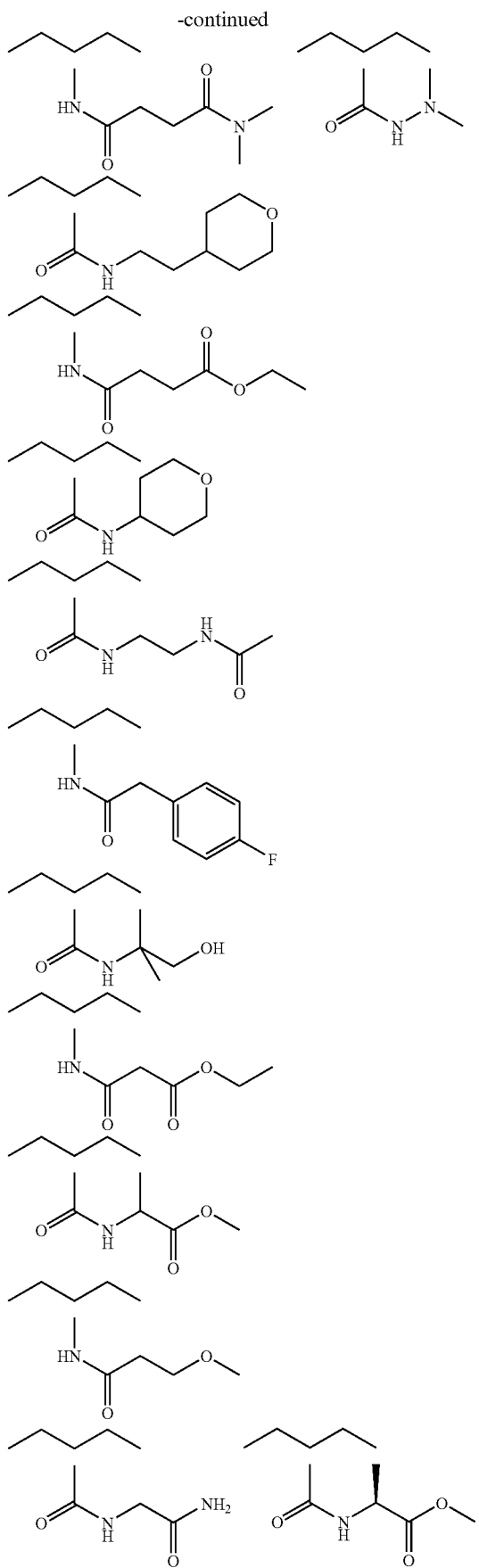

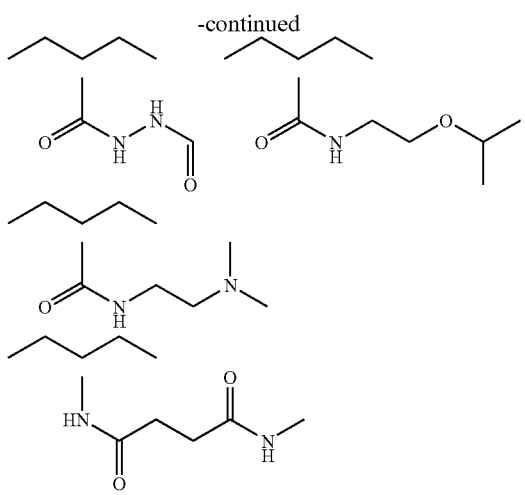

Or, optionally substituted aminos (e.g., —NHSO$_2$Me, —NHCOMe, —NHSO$_2$NMe$_2$, —NHSO$_2$iPr, —NHSO$_2$-Ph-4F, —NHSO$_2$Et, —NHSO$_2$Bn, —NHSO$_2$CH$_2$CF$_3$, —NHSO$_2$CH$_2$CO$_2$Me, —NHSO$_2$CHCH$_2$iPr, —NHSO$_2$CHCH$_2$Ph, —NHSO$_2$CH$_2$CH$_2$Ph, —NHCOCH$_2$CH$_2$OMe, —NHCOPh, —NHCOEt, —NHCO-c-Pr, —NHCO-c-hex, —NHCOCH$_2$CO$_2$Et, —NHCO-2-thienyl, —NHCO-5-isoquinazolyl, —NHCONMe$_2$, —NHCO$_2$Et, —NHCOCO$_2$Et, —NH CO CH$_2$CH$_2$CO$_2$Me, N-succinimde, —NHCOCONMe$_2$, —NHCOCONH$_2$, —NHCO$_2$Me, —NHCO-2-pyrimidine, —NHCO-2-furan, —NHCO-3-triazole-1-Me, —NHCO$_2$iPr, —NHCO$_2$CH$_2$CH$_2$OMe), an optionally substituted carbamoyl (e.g., —CONHiPr, —CONHCH$_2$CH$_2$OMe, —CONH—N-morpholinyl, —CONHNHAc, —CO-(4-Me-piperazine), —CONH-(2-thiazole), —CONHCH$_2$CONMe$_2$, —CONH(CH$_2$)$_3$OCOCF$_3$, —CONEt$_2$, —CO-morpholinyl, —CONHSO$_2$Me, —CONMeSO$_2$Me, —CONHSO$_2$Ph).

$R^{28}$ and $R^{29}$ are more preferably an optionally substituted amino (e.g., —NHCOMe, —NHSO$_2$NMe$_2$, —NHCOCH$_2$CH$_2$OMe, —NHCOPh, —NHCOCH$_2$CO$_2$Et, —NHCO-2-thienyl, —NHCO$_2$Et, —NHCOCH$_2$CH$_2$CO$_2$Me, —NHCOCONMe$_2$, —NHCOCONH$_2$); an optionally substituted alkynyl (e.g., —C≡CCH$_2$OMe, —C≡CCH$_2$NHAc, —C≡CCH$_2$NHSO$_2$Me, —C≡C-c-pen-(1-OH), —C≡CCH$_2$OH); —CH$_2$CH═CH$_2$, —N-morpholinyl or hydrogen, etc.

When $R^{28}$ and $R^{29}$ are an optionally substituted alkyl, then the substituent thereof includes the above mentioned Substituent Group A, and preferably hydroxy, an alkoxy (e.g., methoxy, ethoxy), CONH$_2$, CN, an alkoxycarbonyl (e.g., methoxycarbonyl, ethoxycarbonyl), COOH, an optionally substituted phenyl (e.g., 4-F-phenyl), etc.

The "alkylthio" means sulfur atom substituted with the above "alkyl" and includes, for Example, methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, n-heptylthio, n-octylthio, n-nonylthio or n-decylthio. A $C_1$-$C_6$ alkylthio is preferable.

The "alkylthioalkyl" means the above "alkyl" substituted with the above "alkylthio", for Example, methylthiomethyl, ethylthiomethyl, n-propylthiomethyl, isopropylthiomethyl, n-butylthiomethyl, isobutylthiomethyl, sec-butylthiomethyl, tert-butylthiomethyl, n-pentylthiomethyl, isopentylthiomethyl, neopentylthiomethyl, tert-pentylthiomethyl, n-hexylthiomethyl, isohexylthiomethyl, n-heptylthiomethyl, n-octylthiomethyl, n-nonylthiomethyl, n-decylthiomethyl, methylthioethyl, ethylthioethyl, n-propylthioethyl, isopropylthioethyl, n-butylthioethyl, isobutylthioethyl, sec-butylthioethyl, tert-butylthioethyl, n-pentylthioethyl, isopentylthioethyl, neopentylthioethyl, tert-pentylthioethyl, n-hexylthioethyl, isohexylthioethyl, n-heptylthioethyl, n-octylthioethyl, n-nonylthioethyl or n-decylthioethyl. A $C_{1-2}$ alkyl substituted with a $C_{1-6}$ alkylthio is preferable.

The "haloalkyl" means the above "alkyl" substituted with one or more halogens. A $C_1$-$C_3$ halogenated alkyl is especially preferable and includes, for Example, trifluoromethyl, chloromethyl, dichloromethyl, 1,1-dichloroethyl or 2,2,2-trichloroethyl.

The "haloalkoxy" means oxygen atom substituted with the above "haloalkyl" and includes, for Example, trifluoromethoxy, chloromethoxy, dichloromethoxy, 1,1-dichloroethoxy or 2,2,2-trichloroethoxy.

The "haloalkoxyalkyl" means the above "alkyl" substituted with the above "haloalkoxy" and includes, for Example, trifluoromethoxymethyl, chloromethoxymethyl, dichloromethoxymethyl, 1,1-dichloroethoxymethyl, 2,2,2-trichloroethoxymethyl, trifluoromethoxyethyl, chloromethoxyethyl, dichloromethoxyethyl, 1,1-dichloroethoxyethyl or 2,2,2-trichloroethoxyethyl.

The "acyl" means a carbonyl substituted with the above "alkyl" and a carbonyl substituted with the above "aryl" and includes, for Example, acetyl, propionyl, butyryl, isobutyryl, valeryl, isovaleryl, pivaloyl, hexanoyl, octanoyl, lauroyl, benzoyl.

The "alkylcarbonyl" means a carbonyl substituted with the above "alkyl" and includes, for Example, acetyl, propionyl, butyryl, isobutyryl, valeryl, isovaleryl, pivaloyl, hexanoyl, octanoyl or lauroyl.

The "alkylcarbonyloxy" means an oxygen atom substituted with the above "alkylcarbonyl" and includes, for Example, acetyloxy, propionyloxy, butyryloxy, isobutyryloxy, valeryloxy, isovaleryloxy, pivaloyloxy, hexanoyloxy, octanoyloxy or lauroyloxy.

The "aralkyl" means the above "alkyl" substituted with 1 to 3 above "aryl"s and includes, for Example, benzyl, diphenylmethyl, triphenylmethyl, phenethyl, 1-naphthylmethyl or 2-naphthylmethyl.

The "heteroaralkyl" means the above "alkyl" substituted with 1 to 3 above "heteroaryl"s. A heteroaralkyl wherein the alkyl moiety is a $C_1$-$C_4$ is preferable. A heteroaralkyl wherein the alkyl moiety is a $C_1$ or $C_2$ is especially preferable and includes, for Example, furylmethyl, thienylmethyl, pyrrolylmethyl, imidazolylmethyl, pyrazolylmethyl, triazolylmethyl, tetrazolylmethyl, oxazolylmethyl, isoxazolylmethyl, thiazolylmethyl, thiadiazolylmethyl, isothiazolylmethyl, pyridylmethyl, pyridazinylmethyl, pyrimidinylmethyl, furazanylmethyl, pyrazinylmethyl, oxadiazolylmethyl, benzofurylmethyl, benzothienylmethyl, benzimidazolylmethyl, dibenzofurylmethyl, benzooxazolylmethyl, quinoxalylmethyl, cinnolinylmethyl, quinazolylmethyl, quinolylmethyl, phthalazinylmethyl, isoquinolylmethyl, puriylmethyl, pteridinylmethyl, carbazolylmethyl, phenantridinylmethyl, acridinylmethyl, indolylmethyl, isoindolylmethyl, phenazinylmethyl, phenothiazinylmethyl, furylethyl, thienylethyl, pyrrolylethyl, imidazolylethyl, pyrazolylethyl, triazolylethyl, tetrazolylethyl, oxazolylethyl, isoxazolylethyl, thiazolylethyl, thiadiazolylethyl, isothiazolylethyl, pyridylethyl, pyridazinylethyl, pyrimidinylethyl, furazanylethyl, pyrazinylethyl, oxadiazolylethyl, benzofurylethyl, benzothienylethyl, benzimidazolylethyl, dibenzofurylethyl, benzooxazolylethyl, uinoxalylethyl, cinnolinylethyl, quinazolylethyl, quinolylethyl, phthalazinylethyl, isoquinolylethyl, purilylethyl, pteridinylethyl, carbazolylethyl, phenantridinylethyl, acridinylethyl, indolylethyl, isoindolylethyl, phenazinylethyl or phenothiazinylethyl.

Then, "aryl", "aralkyl", "heteroaryl" "heteroaralkyl" and "alkyl" of "aryloxy", "heteroaryloxy", "arylthio", "heteroarylthio", "aralkyloxy", "heteroaralkyloxy", "aralkylthio", "heteroaralkylthio", "aryloxyalkyl", "heteroaryloxyalkyl", "arylthioalkyl", "heteroarylthioalkyl", "arylsulfonyl", "heteroarylsulfonyl", "aralkylsulfonyl" and "heteroaralkylsulfonyl" are the same meanings as the above.

In the case that "optionally substituted alkylene", "optionally substituted alkenylene", "optionally substituted alkyl", "optionally substituted alkenyl", "optionally substituted aryl", "optionally substituted heteroaryl", "optionally substituted cycloalkyl", "optionally substituted cycloalkenyl", "optionally substituted heterocycle", "optionally substituted aralkyl", "optionally substituted heteroaralkyl", "optionally substituted aryloxy", "optionally substituted heteroaryloxy", "optionally substituted arylthio", "optionally substituted heteroarylthio", "optionally substituted aralkyloxy", "optionally substituted heteroaralkyloxy", "optionally substituted aralkylthio", "optionally substituted heteroaralkylthio", "optionally substituted aryloxyalkyl", "optionally substituted heteroaryl oxyalkyl", "optionally substituted arylthioalkyl", "optionally substituted heteroarylthioalkyl", "optionally substituted arylsulfonyl", "optionally substituted heteroarylsulfonyl", "optionally substituted aralkyl sulfonyl" and "optionally substituted heteroaralkylsulfonyl" have the substituents, then each of them is optionally substituted at any position with the same or different 1 to 4 substituents. Besides, these substituents can be selected from the Substituent Group A or Substituent Group A-1, and may be any one as long as these substituents do not interfere with the inhibitory activity against integrase.

The substituents are, for Example, hydroxy, carboxy, halogen (e.g., F, Cl, Br or I), halo alkyl (e.g., $CF_3$, $CH_2CF_3$ and $CH_2CCl3$), alkyl (e.g., methyl, ethyl, isopropyl and tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy and butoxy), alkenyloxy (e.g., vinyloxy and allyloxy), alkoxycarbonyl (e.g., methoxycarbonyl, ethoxycarbonyl and tert-butoxycarbonyl), nitro, nitroso, optionally substituted amino (e.g., alkylamino, methylamino, ethylamino and dimethylamino), acylamino (e.g., acetylamino and benzoylamino), aralkylamino (e.g., benzylamino, tritylamino and hydroxyamino), azide, aryl (e.g., phenyl), aralkyl (e.g., benzyl), cyano, isocyano, isocyanate, thiocyanate, isothiocyanate, mercapto, alkylthio (e.g., methylthio), alkylsulfonyl (e.g., methanesulfonyl and ethanesulfonyl), optionally substituted carbamoyl (e.g., alkylcarbamoyl methylcarbamoyl, ethylcarbamoyl and dimethylcarbamoyl, sulfamoyl, acyl (e.g., formyl and acetyl), formyloxy, haloformyl, oxal, thioformyl, thiocarboxy, dithiocarboxy, thiocarbamoyl, sulfino, sulfo, sulfoamino, hydrazino, azide, ureide, amidino, guanidino, phthalimide or oxo.

Among the substituents of "optionally substituted aryl", "optionally substituted heteroaryl", "optionally substituted cycloalkyl", "optionally substituted cycloalkenyl" and "optionally substituted heterocycle" exemplified for $R^6$, especially preferred is hydroxy, carboxy, halogen (e.g., F, Cl, Br or I), haloalkyl (e.g., $CF_3$, $CH_2CF_3$ or $CH_2CCl3$), alkyl (e.g., methyl, ethyl, isopropyl or tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy or butoxy), alkoxycarbonyl (e.g., methoxycarbonyl, ethoxycarbonyl or tert-butoxycarbonyl), nitro, optionally substituted amino (e.g., alkylamino (e.g., methylamino, ethylamino or dimethylamino), acylamino (e.g., acetyl amino or benzoylamino), aralkylamino (e.g., benzylamino, tritylamino) or hydroxyamino), azide, aryl (e.g., phenyl), aralkyl (e.g., benzyl), cyano, mercapto, alkylthio (e.g., methylthio), alkylsulfonyl (e.g., methanesulfonyl or ethanesulfonyl), optionally substituted carbamoyl, sulfamoyl, acyl (e.g., formyl or acetyl), formyloxy, thiocarbamoyl, sulfoamino, hydrazino, azide, ureide, amidino or guanidino. Especially, alkyl, haloalkyl, halogen (especially F, Cl or Br) or alkoxy (especially methoxy) mono-substitution or di-substitution being preferable.

Among the substituents of "optionally substituted alkylene" and "optionally substituted alkenylene" exemplified for $Z^1$, $Z^2$ and $Z^3$, especially preferred is hydroxy, carboxy, halogen (e.g., F, Cl, Br or I), haloalkyl (e.g., $CF_3$, $CH_2CF_3$ or $CH_2CCl_3$), alkyl (e.g., methyl, ethyl, isopropyl or tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy or butoxy), alkoxycarbonyl (e.g., methoxycarbonyl, ethoxycarbonyl or tert-butoxycarbonyl), optionally substituted amino (e.g., alkylamino (e.g., methylamino, ethylamino or dimethylamino), acylamino (e.g., acetylamino or benzoylamino), aralkylamino (e.g., benzylamino or tritylamino) or hydroxyamino), aryl (e.g., phenyl), aralkyl (e.g., benzyl), cyano, mercapto, alkylthio (e.g., methylthio), alkylsulfonyl (e.g., methanesulfonyl or ethanesulfonyl), optionally substituted carbamoyl, sulfamoyl, acyl (e.g., formyl or acetyl), formyloxy, thiocarbamoyl, sulfoamino, hydrazino, azide, ureide, amidino or guanidino.

In the case that a group selected from Substituent Group A is "optionally substituted aryl", "optionally substituted heteroaryl", "optionally substituted cycloalkyl", "optionally substituted cycloalkenyl", "optionally substituted heterocycle", "optionally substituted aralkyl", "optionally substituted heteroaralkyl", "optionally substituted aryloxy", "optionally substituted heteroaryloxy", "optionally substituted arylthio", "optionally substituted heteroarylthio", "optionally substituted aralkyloxy", "optionally substituted heteroaralkyloxy", "optionally substituted aralkylthio", "optionally substituted heteroaralkylthio", "optionally substituted aryloxyalkyl", "optionally substituted heteroaryloxyalkyl", "optionally substituted arylthioalkyl", "optionally substituted heteroarylthioalkyl", "optionally substituted arylsulfonyl", "optionally substituted heteroarylsulfonyl", "optionally substituted aralkylsulfonyl" or "optionally substituted heteroaralkylsulfonyl", then, among the above substituents, especially preferred is hydroxy, carboxy, halogen (e.g., F, Cl, Br or I), haloalkyl (e.g., $CF_3$, $CH_2CF_3$ or $CH_2CCl_3$), alkyl (e.g., methyl, ethyl, isopropyl or tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy or butoxy), alkoxycarbonyl (e.g., methoxycarbonyl, ethoxycarbonyl or tert-butoxycarbonyl), nitro, optionally substituted amino (e.g., alkylamino (e.g., methylamino, ethylamino or dimethylamino), acylamino (e.g., acetylamino or benzoylamino), aralkylamino (e.g., benzylamino or tritylamino) or hydroxyamino), azide, aryl (e.g., phenyl), aralkyl (e.g., benzyl), cyano, mercapto, alkylthio (e.g., methylthio), alkylsulfonyl (e.g., methanesulfonyl or ethanesulfonyl), optionally substituted carbamoyl, sulfamoyl, acyl (e.g., formyl or acetyl), formyloxy, thiocarbamoyl, sulfoamino, hydrazino, azide, ureide, amidino or guanidino. Especially, alkyl, haloalkyl, halogen (especially F, Cl or Br) or alkoxy (especially methoxy) is preferable, and monosubstitution or disubstitution is preferable.

The compounds of the present invention (I) include compound (II), (III), (III-1), (IV-I), (IV-2), (V), (VI), (VII), (VIII), (IX), (X), (V), etc. as explained above, and Compound (III), (III-1) and (V) are preferable.

In compound (III) or (III-1), it is preferred that Y is OH; $R^B$ is —$COR^{26}$ or —$CONR^8R^9$; $R^{27}$ is hydrogen; $R^{2\prime}$ is hydrogen; and $R^1$ is -$Z^2$-$R^5$.

More preferably, $R^B$ is —$COR^{26}$; and $R^1$ is benzyl optionally substituted by halogen, especially p-F-benzyl.

More preferably, $R^{26}$ is hydroxy, optionally substituted alkoxy, optionally substituted alkyl, optionally substituted alkoxyalkyl, optionally substituted cycloalkyl or optionally substituted heterocycleoxy; and more preferably is hydroxy, alkoxy (e.g., methoxy) or optionally substituted heterocycleoxy (e.g., optionally substituted 4-piperidyloxy (Examples of substituent: acyl (e.g., alkylcarbonyl, preferably acetyl, sulfonyl preferably alkylsulfonyl (e.g., methanesulfonyl); formyl; alkyl (e.g., methyl, ethyl, isopropyl))).

Preferably, $R^{28}$ is carboxy, said optionally substituted alkyl, optionally substituted amino or optionally substituted carbamoyl as listed in Substituent Group A-1, etc.

Preferable embodiments of Compound (III-1) are shown below.

$R^B$: —C(=O)$R^{26}$ wherein $R^{26}$ is hydroxy, optionally substituted alkoxy, optionally substituted alkyl, optionally substituted alkoxyalkyl, optionally substituted cycloalkyl or optionally substituted heterocycleoxy. Especially preferred is that $R^{26}$ is alkoxy (e.g., methoxy) or optionally substituted heterocycleoxy (e.g., 1-substituted-piperidine-4-yl)oxy.

$R^1$: a group of the formula: -$Z^2$-$R^5$ wherein, $Z^2$ is methylene; $R^5$ is phenyl optionally substituted with halogene;

$R^{28}$: carboxy, halogene, cyano or substituents exemplified below:

(1) optionally substituted carbamoyl
I-5, 6: CONHCH$_2$CH$_2$OR(R=H,Me)
I-7: CONH$_2$
I-23: CONH(CH$_2$)$_3$CH$_3$
I-47: CONHCH$_2$CF$_3$
I-84, 85: CONHNHR(R=Me,$_{CH2}$CH$_2$OH)
COR
R=

I-24: 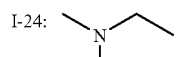

I-25: 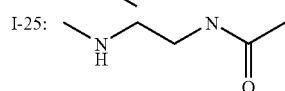

I-26: 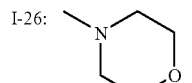

I-27: 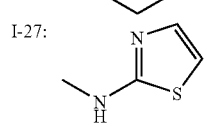

-continued

I-28: 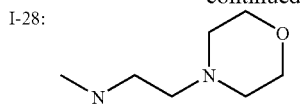

I-29: 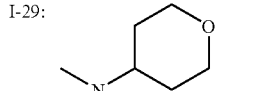

I-30: 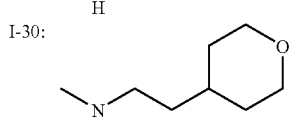

I-31: 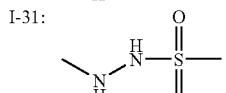

I-32: 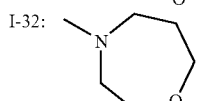

I-33: 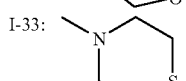

I-34: 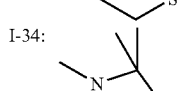

I-35: 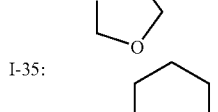

I-36: 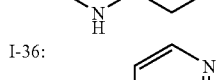

I-37: 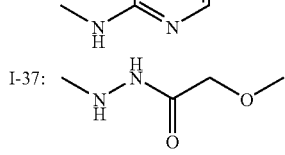

I-38: 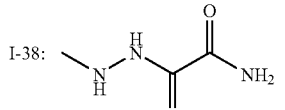

I-39: 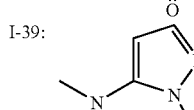

I-40: 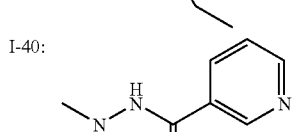

I-41: 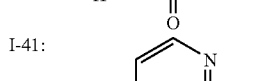 HI

I-42: 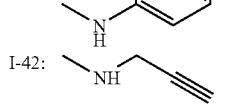

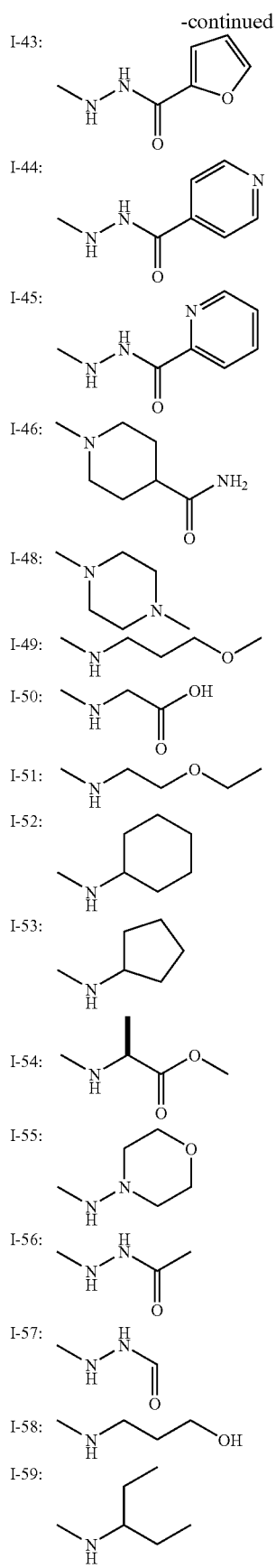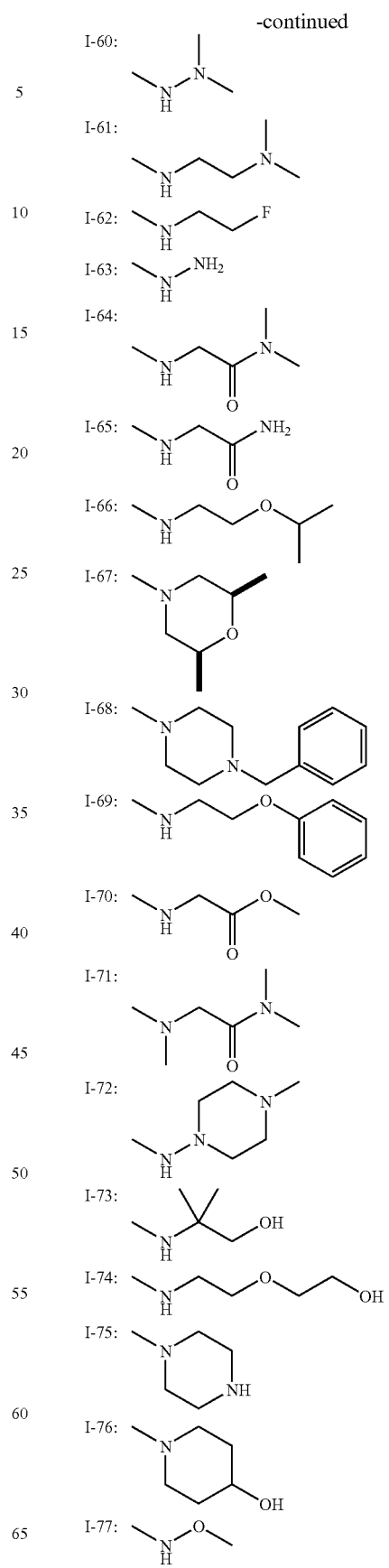

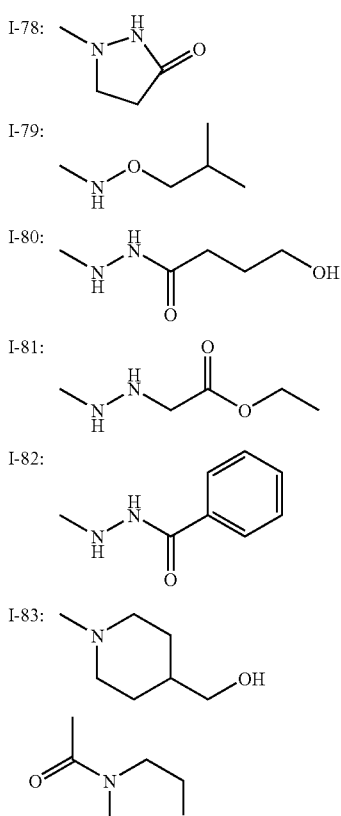

I-78:
I-79:
I-80:
I-81:
I-82:
I-83:

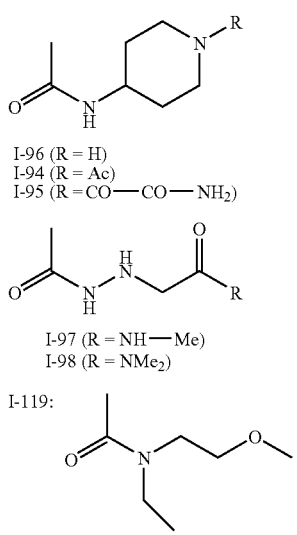

I-86 (R = Ac)
I-87 (R = CHO)
I-88 (R = CH$_2$—CO—OMe)
I-89 (R = SO$_2$—Me)
I-90 (R = CO—CO—NH$_2$)
I-91 (R = Et)
I-92 (R = CH$_2$—CH$_2$—OMe)
I-93 (R = iPr)

I-96 (R = H)
I-94 (R = Ac)
I-95 (R = CO—CO—NH$_2$)

I-97 (R = NH—Me)
I-98 (R = NMe$_2$)

I-119:

I-124:

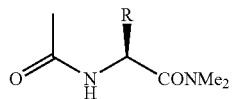

I-168 (R = Me)
I-169 (R = i-Pr)
I-170 (R = i-Bu)
I-171 (R = s-Bu)
I-172 (R = Bn)

I-173 (R = CH$_2$— 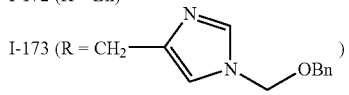 )

CONHR
R=CH$_2$CH$_2$OMe (I-198), NMe$_2$(I-197), (CH$_2$)$_3$OH (I-198), NHAc (I-199)

(2) optionally substituted acyl
I-20:CHO   I-114: acetyl

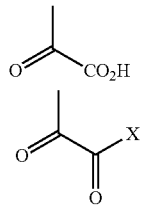

I-152

I-153 (X = NH$_2$)
I-154 (X = NMe$_2$)
I-155 (X = OMe)

(3) optionally substituted amino
I-8 to 15: NHR(R=H, alkoxycarbonyl, alkylcarbonyl, halogenoalkylcarbonyl, alkylsulfonyl, CHO, alkyl, cycloalkyl)
I-16: dialkylamino
I-17: alkylaminocarbonylamino
I-18: alkylaminothiocarbonylamino

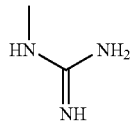

I-115

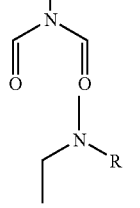

I-116

I-120 (R = COMe)
I-121 (R = CHO)
I-122 (R = SO$_2$Me)

-continued

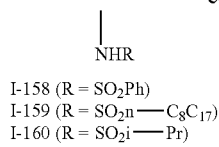

I-158 (R = SO₂Ph)
I-159 (R = SO₂n—C₈C₁₇)
I-160 (R = SO₂i—Pr)

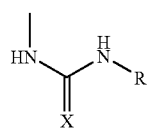

I-161 (X = S, R = CH₂Ph)
I-162 (X = S, R = CH₂CH₂Ph)
I-163 (X = O, R = Ph)
I-164 (X = O, R = i-Pr)

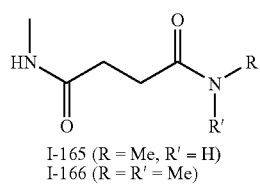

I-165 (R = Me, R' = H)
I-166 (R = R' = Me)

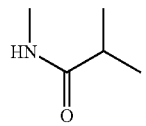

I-174

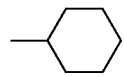

I-175

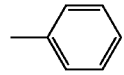

I-176

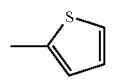

I-177

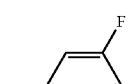

I-178

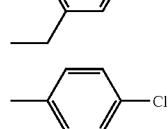

I-179

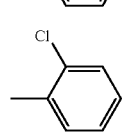

I-180

-continued

—CH₂OMe    I-181

—CH₂CH₂OMe    I-182

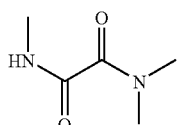    I-189

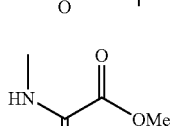    I-190

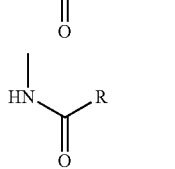

R =

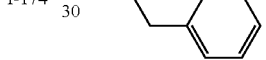    I-192

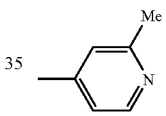    I-193

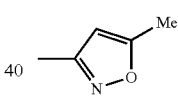    I-194

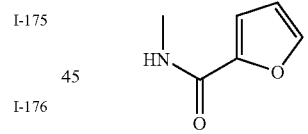    I-191

NHCOCH₂CH₂OMe (I-200)

(4) optionally substituted aralkyloxycarbonyl

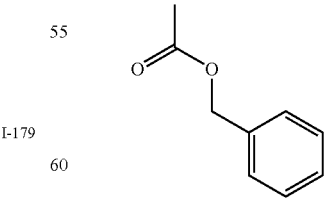    I-123

(5) optionally substituted heterocyclealkyl. The heterocyclealkyl is preferably a saturated or unsaturated, aromatic 5- to 10-membered ring which contains at least an N atom.

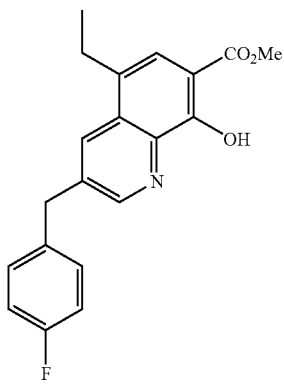

I-126

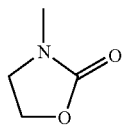

I-183

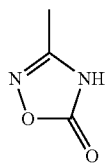

I-167

I-127

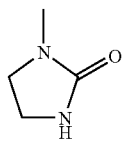

I-184

I-128

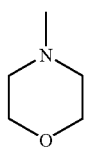

I-185

(6) optionally substituted alkyl
(Examples of substituent: hydroxy, cyano, (substituted) amino, carboxy, (substituted)carbamoyl, alkoxycarbonyl, imino)
I-129: —CH$_2$CN  I-130: CH$_2$CONH$_2$
I-131, 132: CH$_2$CO$_2$R(R=Me,H)

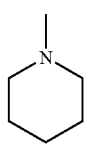

I-186

I-133

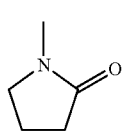

I-187

I-146 R = H
I-147 R = Me (8) optionally substituted alkenyl
(Examples of substituent: carboxy, alkoxycarbonyl)

(7) optionally substituted heterocycle. The heterocyclealkyl is preferably a saturated or unsaturated, 5- to 7-membered ring which contains at least an N atom.

I-144

I-134

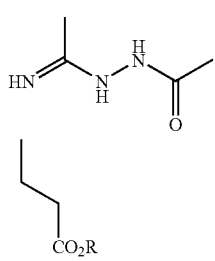

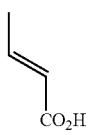

I-145

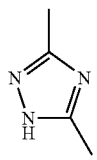

(9) optionally substituted aryl
(Examples of substituent: carboxy, alkoxycarbonyl, formyl)

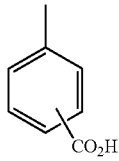

I-148 (para)
I-149 (meta)

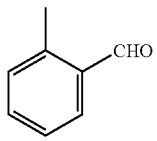

I-150

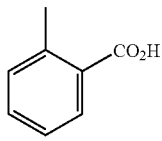

I-151

In another preferable embodiment of compound (III-1), $R^{28}$ is COOH or its derivative (e.g.,: ester, salt); $R^1$ is $-Z^2-R^5$ wherein $Z^2$ is methylene; and $R^5$ is phenyl optionally substituted with halogene; $R^B$ is $—C(=O)R^{26}$ wherein $R^{26}$ is hydroxy, optionally substituted alkoxy, optionally substituted alkyl, optionally substituted alkoxyalkyl, optionally substituted cycloalkyl, optionally substituted cycloalkyloxy, optionally substituted aryl, optionally substituted aryloxy, optionally substituted heterocycle, optionally substituted heterocycleoxy or optionally substituted amino.

In Compound (V), it is preferred that
Y is OH;
$R^A$ is $—C(=O)—R^7$ wherein $R^7$ is
 hydroxy,
 optionally substituted alkoxy,
 $NR^8R^9$ wherein $R^8$ and $R^9$ each is independently
  hydrogen,
  optionally substituted alkyl,
  optionally substituted alkoxy or
  optionally substituted amino, or
 optionally substituted heterocycleoxy;
$R^2$ is hydrogen; and $R^1$ is $-Z^2-R^5$.

More preferably, $R^A$ is a group of the formula: $—C(=O)—R^7$ wherein $R^7$ is
 hydroxy,
 optionally substituted alkoxy (e.g., methoxy),
 $NR^8R^9$ wherein $R^8$ is hydrogen and $R^9$ is hydrogen, alkyl
  optionally substituted by alkoxy (e.g., methoxyethyl) or
  amino optionally substituted by alkyl (e.g., N,N-dimethylamino)) or
 optionally substituted heterocycleoxy (e.g., optionally substituted 4-piperidyloxy (example of its substituent: acyl (e.g., alkylcarbonyl, preferably acetyl); sulfonyl, preferably alkylsulfonyl (e.g., methanesulfonyl); formyl; alkyl (e.g., methyl, ethyl, isopropyl))); and
$R^1$ is benzyl optionally substituted by halogen.
Further, $R^7$ and $R^{26}$ may be the same substituents.

$R^{29}$ is preferably hydrogen, carboxy, an optionally substituted alkyl, an optionally substituted alkenyl, an optionally substituted alkynyl or, an optionally substituted amino, an optionally substituted carbamoyl or optionally substituted aryl as described above and, especially the groups included in Substituent Group A-1 are more preferable.

More preferable Examples of compound (V) is shown below. The number inside of ( ) each corresponds to Example number.

$R^{29}$:

(1) optionally substituted amino:
 1) —NHCOR
  R=heteroaralkyl (e.g., :A-129, 188), heterocyclic group (e.g., A-127, 128, 65, 66, 67, 43), optionally substituted carbamoylalkyl (substituent:lower alkyl, e.g., A-72, 73), alkoxyalkyl (e.g., A-34, 160, 61, 187), optionally substituted carbamoyl (substituent:lower alkyl, e.g., A-118, 115, 116), alkoxycarbonylalkyl (e.g., A-41, 62), optionally substituted alkoxy (e.g., A-42, 64, 68, 69, 121), optionally substituted aryl (e.g., A-35)
 2) —NHSO₂R
  R=alkyl (e.g., A-9), alkylamino (e.g., A-26)

(2) optionally substituted aryl (e.g., A-182)

(3) hydrogen (e.g., A-79, 83, 124)

(4) optionally substituted alkenyl (e.g., A-113)

(5) alkyl (e.g., A-10, 130)

(6) optionally substituted alknyl (e.g., A-18, 50, 51, 93, 98, 185, 186)

(7) optionally substituted carbamoyl, wherein the substituents on the N atom of carbamoyl together with the N atom may form a heterocycle, preferably 5- to 7-membered (e.g., A-54).

$R^A$:—C(=O)—$R^7$
$R^7$:hydroxy, methoxy, optionally substituted heterocyleoxy, preferably being 5- to 7-membered ring containing at leat one atom of N or O (e.g., A-80, 82, 83, 124), alkyl optionally substituted with alkoxy (e.g., A-160), alkyloxy optionally substituted with alkoxy (e.g., A-79)

$R^{28}$ or $R^{29}$ in other preferable embodiments is selected from Substituent Group A-2 as given below:

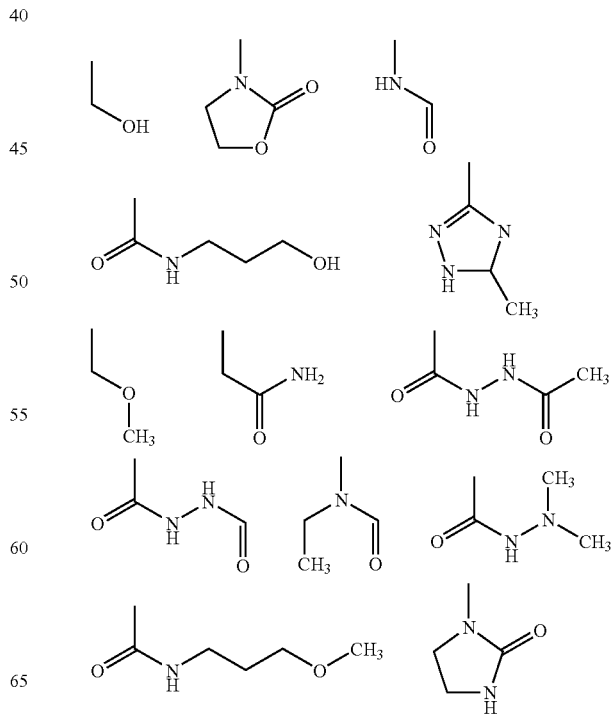

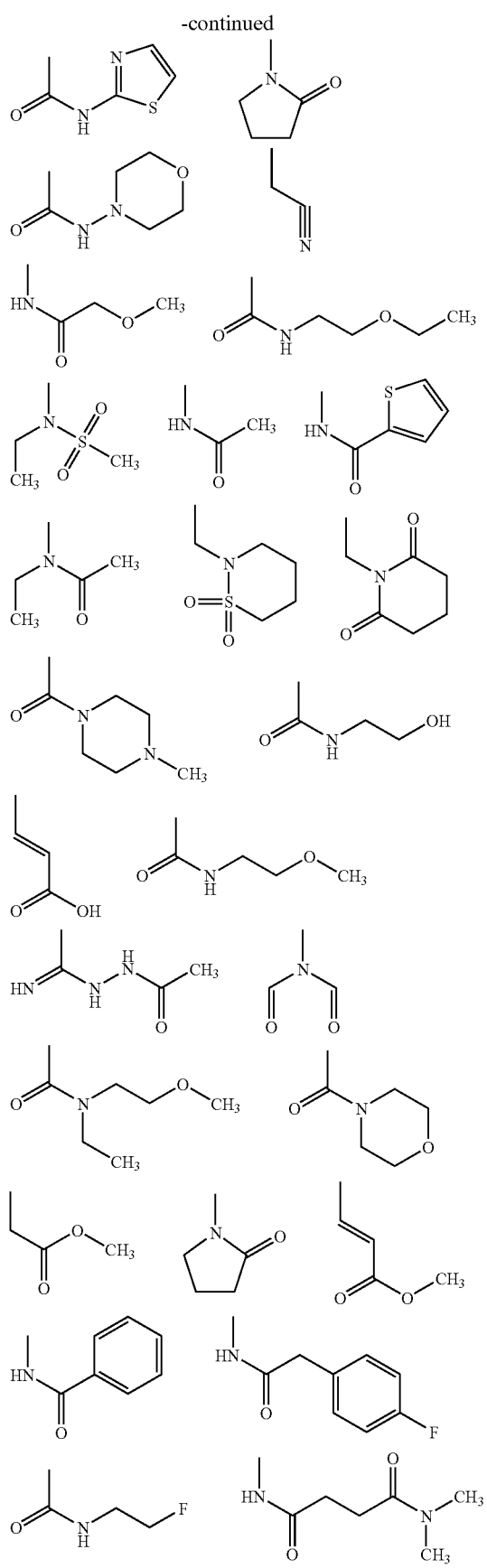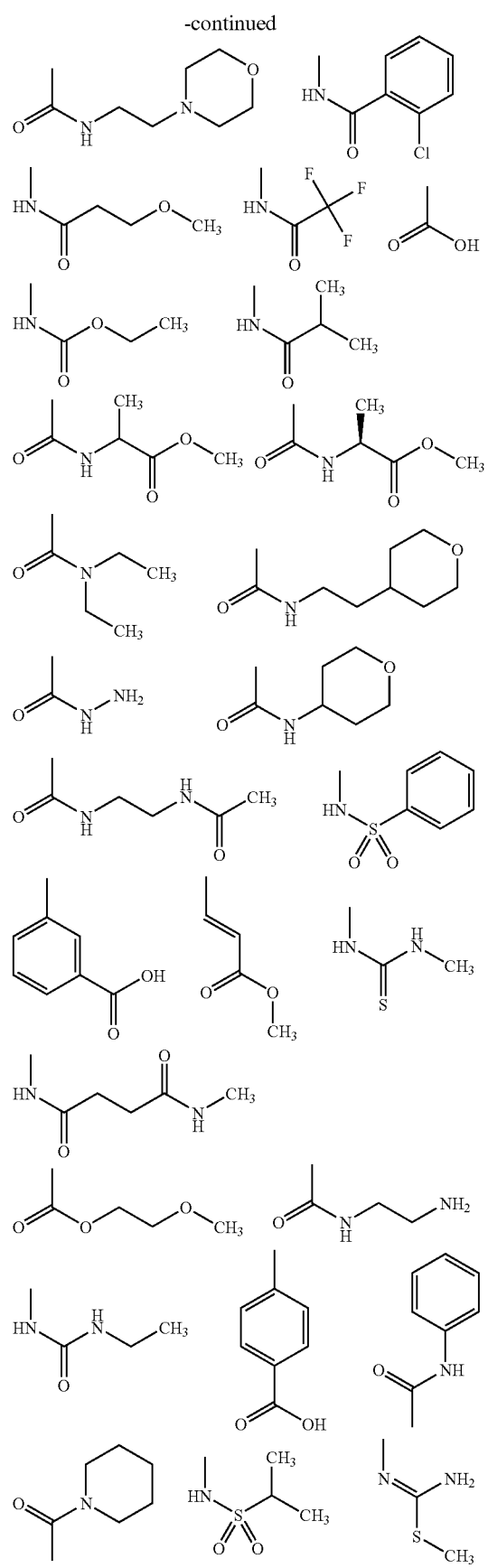

-continued

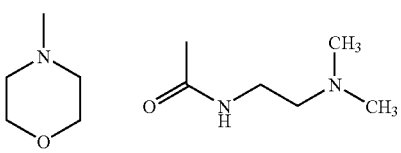

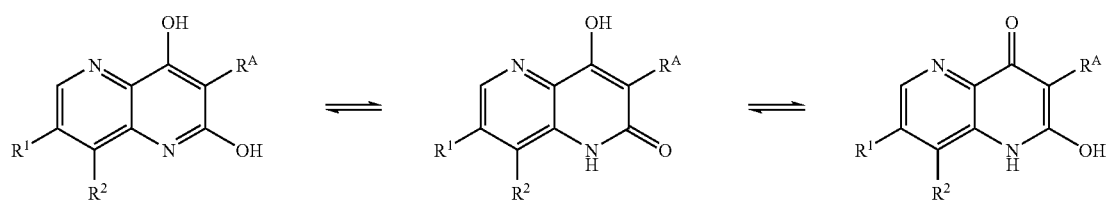

-continued

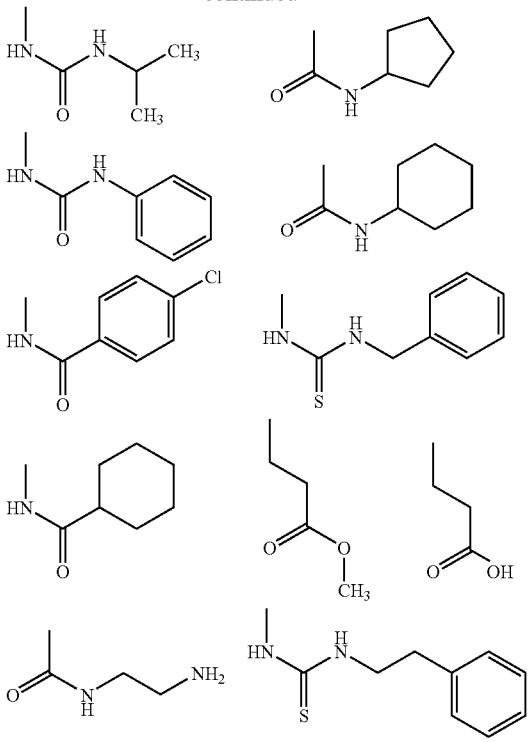

Preferable embodiments of Compound (IV-2) are shown below.

Y=OH; X=O; $R^1$=optionally substituted benzyl; $R^2$=hydrogen; $R^4$=hydrogen;

$R^A$=carboxy optionally substituted alkoxycarbonyl or optionally substituted carbamoyl wherein the substituents of carbamoyl include optionally substituted alkyl (Examples of substituent:optionally substituted amino), optionally substituted aryl (Examples of substituent:halogen), and optionally substituted aralkyl (Examples of substituent:halogen).

The present invention includes a compound, its prodrug, a pharmaceutically acceptable salt or a solvate thereof. All of the theoretical possible tautomers and geometrical isomers of a compound of the present invention are also within the scope of the present invention. For Example, a compound of the formula (I) (a keto form) wherein Y is oxo, thioxo or imino is also included in the present invention, as far as it is a tautomer of a compound (an enol form) wherein Y is hydroxy, mercapto or amino.

A prodrug is a derivative of a compound of the present invention having a group which can be decomposed chemically or metabolically, and such a prodrug is converted to a pharmaceutically active compound of the present invention by means of solvolysis or by placing the compound in vivo under a physiological condition. Method for selecting and preparing an appropriate prodrug derivative is described in the literature such as Design of Prodrugs, Elsevier, Amsterdam 1985.

It is known that HIV multiplies vigorously in a lymph node even in the asymptomatic term. Thus, a prodrug of a compound of the present invention is preferably a lymph-directed one. The diseases caused by HIV include an AIDS-associated encephalopathy. Thus, a preferable prodrug of a compound of the present invention is a brain-directed one. As these lymph-directed prodrug and brain-directed prodrug, the following prodrugs with higher lipophilicity are preferable.

When a compound of the present invention has a carboxyl group, an ester derivative prepared by reacting an original acid compound with a suitable alcohol or an amide derivative prepared by reacting an original acid compound with a suitable amine is exemplified as a prodrug. An especially preferred ester derivative as an prodrug is methylester, ethylester, n-propylester, isopropylester, n-butylester, isobutylester, tert-butylester, morpholinoethylester or N,N-diethylglycolamidoester.

When a compound of the present invention has a hydroxy group, an acyloxy derivative prepared by reacting a compound having a hydroxyl group with a suitable acylhalide or a suitable acid anhydride is exemplified as a prodrug. An especially preferred acyloxy derivative as a prodrug is —O(=O)—$CH_3$, —OC(=O)—$C_2H_5$, —OC(=O)-(tert-Bu), —OC(=O)—$C_{15}H_{31}$, —OC(=O)-(m-COONa-Ph), —OC(=O)—$CH_2CH_2$COONa, —O(C=O)—CH($NH_2$)$CH_3$ or —OC(=O)—$CH_2$—N($CH_3$)$_2$.

When a compound of the present invention has an amino group, an amide derivative prepared by reacting a compound having amino with a suitable acid halide or a suitable mixed anhydride is exemplified as a prodrug. An especially preferred amide derivative as a prodrug is —NHC(=O)—($CH_2$)$_2$O$CH_3$ or —NHC(=O)—CH($NH_2$)$CH_3$.

Especially in the case of a compound of the present invention, a prodrug can be produced by the chemical modification of Y, a substituent on B ring. For Example, Y is substituted with acyl and it is examined whether or not the prodrug is converted to a compound of the present invention by means of solvolysis or by placing the compound under a physiological condition. Therefore, even if Y is a substituent except for hydroxy, mercapto or amino, a compound wherein Y is converted to hydroxy, mercapto or amino by means of solvolysis or by placing the compound under a physiological condition is the prodrug of the present invention and is contained in the present invention. For Example, a compound converted to a compound of the present invention in phosphate buffer (pH7.4)-ethanol or plasma is a prodrug compound of the present invention.

Pharmaceutically acceptable salts of a compound of the present invention include, as basic salts, for Example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine; aralkyl amine salts such as N,N-dibenzylethylenediamine salts, benetamine salts; heterocyclic aromatic amine salts such as pyridin salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for Example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararic acid salts, malates, citrates salts, or ascorbates; sulfonates such as methanesulfonates, isethionates, benzenesulfonates, or p-toluenesulfonates; and acidic amino acid salts such as aspartates or glutamates.

Furthermore, various solvates of a compound of the present invention, for Example, monosolvate, disolvate, monohydrate or dihydrate are also within the scope of the present invention.

The term "inhibit" means that a compound of the present invention suppresses the action of integrase.

The term "pharmaceutically acceptable" means harmless with respect to the prevention and the treatment.

The preferable compound of the present invention exhibit a potent inhibitory activity against integrase in either in vitro and/or in vivo experiments.

In Compound (III) or Compound (V), the presence of $R^1$ and the binding position thereof, and/or the kinds of the $R^A$ and $R^B$ are one of the important factors for exhibiting the integrase inhibitory activity. Besides, the kinds of the substituents for $R^{28}$ and $R^{29}$ are also important.

General and representative processes for preparing the compounds of the present invention are shown below.

The presented representative production processes are not intended to limit the process for preparing the compounds of the present invention. Other process can give the compounds of the present invention.

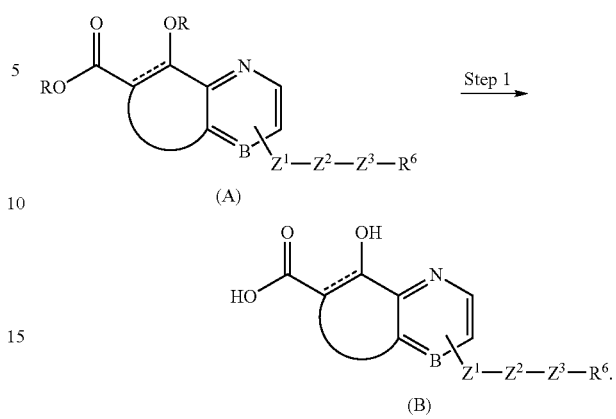

Step 1

This step is to prepare Compound (B) from Compound (A) by deprotecting a carboxyl or phenolic hydroxylprotective group.

This step can be carried out by heating with trialkylsilyl halide in the presence of alkali metal iodide in a reaction solvent.

The trialkylsilyl halide can be trimethylsilyl chloride.

The alkali metal iodide can be NaI or KI.

The reaction temperature may be from room temperature to 100° C., preferably from 70 to 90° C.

The reaction solvent may be a polar solvent, e.g., acetonitrile.

Step 1 can be carried out with hydrogen bromide in acetic acid at elevated temperature. The reagent can be preferably 47% hydrogen bromide in acetic acid.

Alternatively, the reaction may be carried out with $BBr_3$ at 0° C. to room temperature or with pyridinium chloride at 150° C. to 220° C.

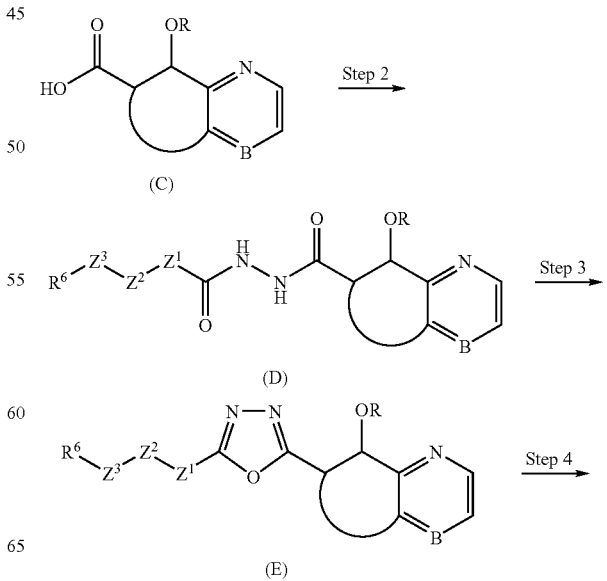

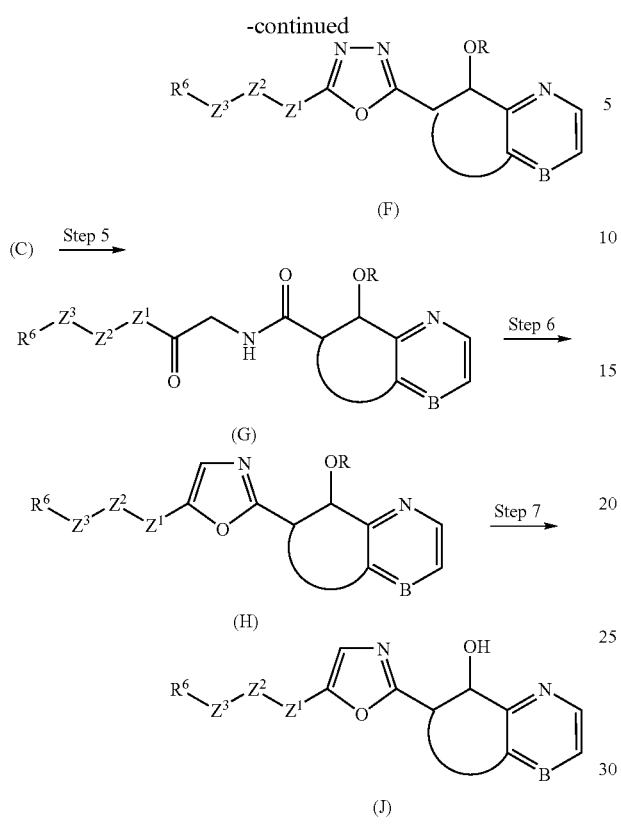

Step 2

This step converts Compound (C) into Compound (D) by transforming carboxylic acid to diacyl hydrazine. This step may be carried out by treating a carboxylic acid and monoacylhydrazine in the presence of condensing reagent in a suitable solvent.

The condensing reagent can be dicyclohexylcarbodiimide, 1-ethyl-3-(3-dimethylaminopropyl) carbodiimide hydrochloride. If required, a reagent e.g., 1-hydroxybenzotriazole, N-hydroxysuccinimide may be added.

The reaction temperature is from 0 to 100° C., preferably 20 to 30° C. The preferable reaction solvent is an aprotic solvent in general, e.g., tetrahydrofuran, N,N-dimethylformamide, etc.

Step 3

This step converts Compound (D) into Compound (E) by cyclizing diacylhydrazine to form an oxadiazole ring.

This step may be carried out by treating diacylhydrazine with phosphorus oxychloride or thionyl chloride at elevated temperature. The reaction temperature is 50 to 100° C., preferably 80 to 100° C. This Step may also be carried out using dibromotriphenylphosphorane in the presence of a base, e.g. triethylamine, where the reaction temperature is 0 to 100° C., preferably 0 to 30° C. The reaction solvent preferably is dichloromethane, tetrahydrofuran.

Step 4

This step converts Compound (E) to Compound (F) that can be carried out in a manner similar to that of Step 1.

Step 5

This step converts Compound (F) to Compound (G) by condensing a carboxylic acid and alpha-aminoketone to prepare an amide. This step may be carried out by treating the carboxylic acid and alpha-aminoketone in the presence of a condensing reagent in a suitable solvent.

The condensing reagent can be dicyclohexylcarbodiimide, 1-ethyl-3-(3-dimethylaminopropyl)carbodiimide hydrochloride. If necessary, a reagent e.g., 1-hydroxybenzotriazole or N-hydroxysuccinimide may be added. The reaction temperature is 0 to 100° C., preferably 20 to 30° C. The reaction solvent is preferably an aprotic solvent in general, e.g., tetrahydrofuran, N,N-dimethylformamide, etc.

Step 6

This step converts Compound (G) into Compound (H) in a manner similar to that of Step 3.

Step 7

This step converts Compound (H) into Compound (J) in a manner similar to that of Step 1.

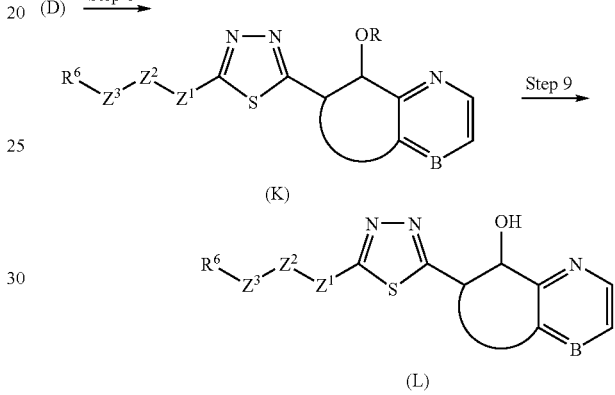

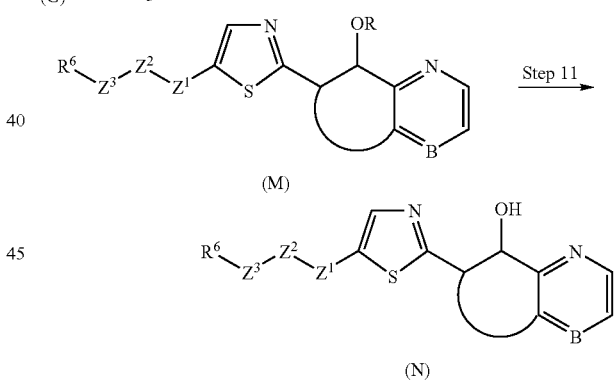

Step 8

This step converts Compound (D) into Compound (K) by cyclizing diacylhydrazine into a thiadizole ring. This step may be carried out by heating diacylhydrazine with phosphorus pentasulfide or a Lawson reagent. The reaction temperature is 50 to 150° C., preferably from 80 to 100° C. The reaction solvent is preferably toluene, tetrahydrofuran, etc.

Step 9

This step converts Compound (K) into Compound (L) in a manner similar to that of Step 1.

Step 10

This step converts Compound (G) into Compound (M) in a manner similar to that of Step 8.

Step 11

This step converts Compound (M) into Compound (N) in a manner similar to that of Step 1.

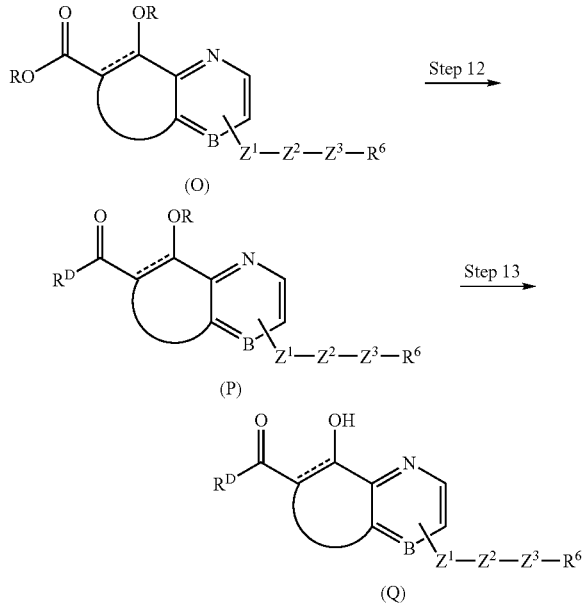

wherein $R^D$ is alkyl, aryl, heteroaryl, etc.

Step 12

This step converts Compound (O) into Compound (P) to form ketone from ester.

This step may be carried out by treating ester and an organometalic reagent in a suitable solvent.

The organometalic reagent can be alkyllithium, aryllithium, heteroaryllitium, a Grignard reagent, etc. The reaction temperature is −70° C. to room temperature, preferably −70° C. to 0° C.

The reaction solvent may be an ether type solvent, e.g., tetrahydrofuran, diethyl ether, etc.

Step 13

This step converts Compound (P) into Compound (O) in a manner similar to that of Step 1.

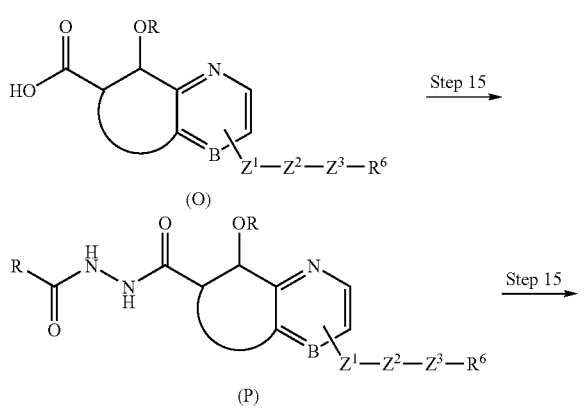

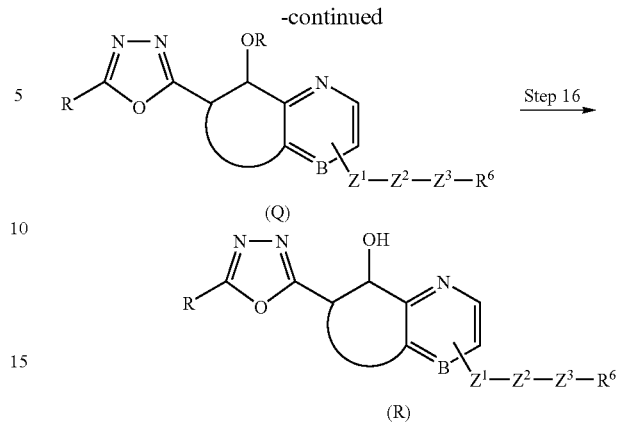

Step 14

This step converts Compound (R) into Compound (S) in a manner similar to that of Step 2.

Step 15

This step converts Compound (S) into Compound (T) in a manner similar to that of Step 3.

Step 16

This step converts Compound (T) into Compound (U) in a manner similar to that of Step 1.

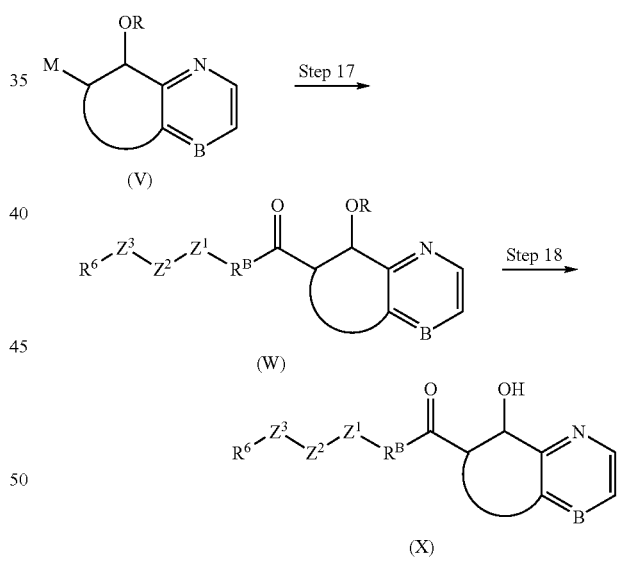

Step 17

This step converts Compound (V) into Compound (W) to prepare a ketone body from a halogen compound (X=Cl, Br, I). This step can be carried out by converting a halogen compound (X=Cl, Br, I) into the corresponding organometallic compound (M=metal) with an organometallic reagent, and then by treating it with a carboxylic acid chloride or a reactive ester in a suitable solvent. The organometallic reagent can be alkyllitium, aryllithium, etc. The reaction temperature may be −70° C. to room temperature, preferably −70 to 0° C. The reaction solvent may be an ether type solvent, e.g., tetrahydrofuran, diethyl ether, etc.

Step 18

This step converts Compound (W) into Compound (X) in a manner similar to that of Step 1.

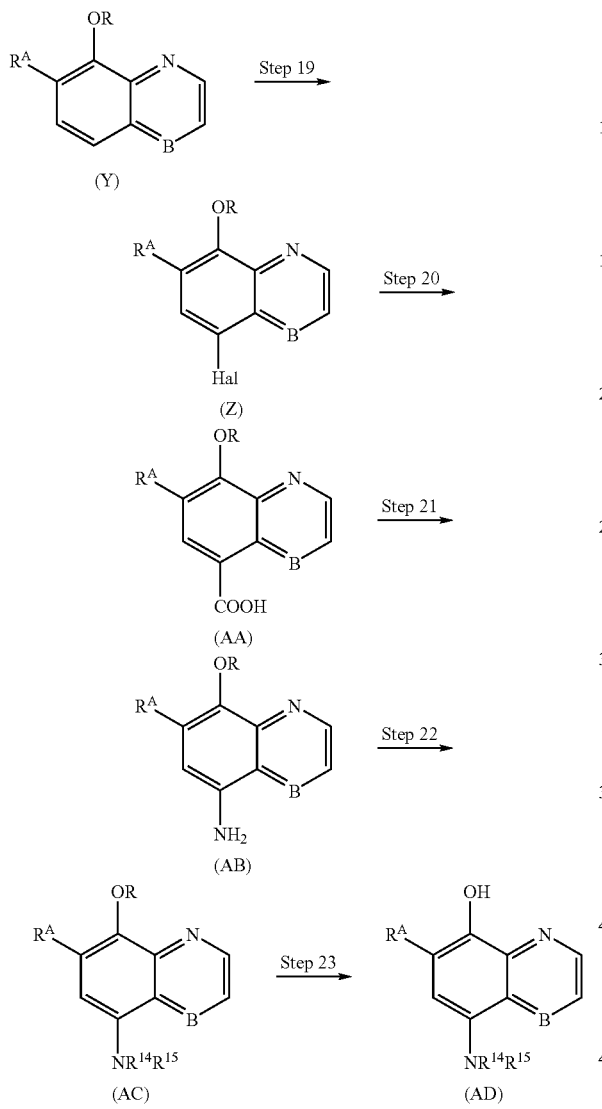

Step 19

This step converts Compound (Y) into Compound (Z). The step may be carried out by reacting Compound (Y) with bromine in acetic acid solvent in the presence of sodium acetate.

Step 20

This Step converts Compound (Z) into Compound (AA) by introducing carbon monoxide. This Step may be carried out by reacting Compound (Z) with carbon monoxide in a solvent e.g., dimethyl sulfoxide, etc in the presence of palladium acetate (II), 1,3-bis(diphenylphosphino)propane, triethylamine, and water.

Step 21

This Step converts Compound (AA) into Compound (AB) by the Curtius rearrangement reaction, etc. This Step may be carried out by treating Compound (AA) with diphenylphosphoric acid azide and triethylamine in a solvent, e.g., dimethylformamide.

Step 22

This Step converts Compound (AB) into Compound (AC) by conventional N-alkylation, N-acylation, N-sulfonylation, etc.

Step 23

This Step converts Compound (AC) into Compound (AD) in a manner similar to that of Step 1.

Further preferable process for preparing Compounds (III) and (III-1) of the present invention or intermediates thereof is exemplified below:

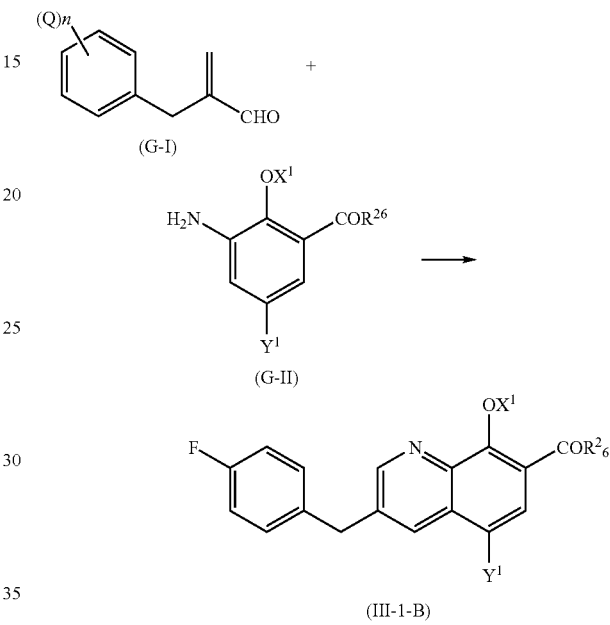

wherein Q is halogen; n is an integer 0 to 3; $X^1$ is hydrogen or a phenolic hydroxy protective group; $R^{26}$ is hydroxy, alkoxy, alkyl, alkoxyalkyl, cycloalkyl, optionally substituted aryl, optionally substituted heteroaryl or optionally substituted heterocycleoxy or —N($R^8$)($R^9$) wherein $R^8$ and $R^9$ is each independently is hydrogen, alkyl or alkoxy;

$Y^1$ is hydrogen,
halogen,
carboxy,
alkoxycarbonyl,
optionally substituted carbamoyl,
—N($R^{14}$)($R^{15}$) wherein $R^{14}$ and $R^{15}$ each independently is
hydrogen,
alkyl,
cycloalkyl,
—(CH$_2$)$_{1-3}$OR$^{16}$ wherein $R^{16}$ is hydrogen, alkyl, acyl or aryl,
—C(=O)R$^{17}$ wherein $R^{17}$ is hydrogen, hydroxy, optionally substituted alkoxy, optionally substituted alkyl, haloalkyl, optionally substituted aryl, optionally substituted heteroaryl, optionally substituted aralkyl, optionally substituted heteroaralkyl or optionally substituted amino,
—C(=S)R$^{17}$ wherein $R^{17}$ is as defined above,
—SO$_2$R$^{21}$ wherein $R^{21}$ is alkyl or optionally substituted amino, or
$R^{14}$ and $R^{15}$ combine to form optionally substituted thioamidino group or $R^{14}$ and $R^{15}$ combined together with the adjacent nitrogen to form optionally substituted nitrogen containing heterocycle, optionally possessing nitrogen, sulfur and/or oxygen in its ring, —$(CH_2)_{0-3}OR^{18}$ wherein $R^{18}$ is hydrogen, alkyl, acyl or aryl, —$(CH_2)_{1-3}CONHR^{19}$ wherein $R^{19}$ is hydrogen, alkyl, acyl or aryl, —$SO_3R^{20}$ wherein $R^{20}$ is alkyl or hydroxy, —$SO_2R^{21}$ wherein $R^{21}$ is alkyl or optionally substituted amino,

—$PO(OH)_2$,

—$PO(OH)(R^{22})$ wherein $R^{22}$ is alkyl, haloalkyl,

—$(CH_2)_{1-3}COR^{23}$ wherein $R^{23}$ is alkyl or optionally substituted aryl,

—$(CH_2)_{0-3}CN$,

—$R^{41}$—$COOR^{42}$ wherein $R^{41}$ is alkenyl and $R^{42}$ is hydrogen or alkyl, —$(CH_2)_{1-3}R^{40}$ wherein $R^{40}$ is optionally substituted aryl or optionally substituted heteroaryl, optionally substituted aryl or optionally substituted heteroaryl.

This reaction is to prepare quinoline compound (III-1-B) from an aniline derivative, Compound (G-I), and an acrolein derivative, Compound (G-II), by condensing preferably in the presence of a catalyst, especially an acid catalyst, in the presence or absence of solvent. Compound (III-1-B) is useful as an integrase inhibitor or a synthetic intermediate for preparing efficiently a integrase inhibitor in less steps under mild reaction condition. Thus this process is useful for industrial production of integrase inhibitors. Compound (G-I) and Compound (G-II) are known or easily available for those skilled in the art.

Q is an identical or different group selected from substituent for the aryl as defined above, and preferably a halogen, especially F; n is an integer of 0 to 3, preferably 1; $(Q)_n$ is preferably F, especially 4-F.

The protective group of phenolic hydroxyl in $X^1$ can be for Example those efficient to the synthetic reactions, preferably an ether type protective group (e.g., alkyl (e.g., methyl, ethyl), aralkyl (e.g., benzyl)) or ester type protective group (e.g., acyl (e.g., acetyl), mesyl, aroyl (e.g., benzoyl)), etc.

Quinoline compound (III-1-B) whereine $X^1$ is a protective group of phenolic hydroxy can easily be converted into the compound where $X^1$ is hydrogen.

$R^{26}$ is preferably alkoxy, especially methoxy.

$Y^1$ is preferably $R^{28}$ as defined above or is hydrogen, halogen, carboxy, alkoxycarbonyl, optionally substituted amino, optionally substituted alkyl or optionally substituted carbamoyl, and more preferably is hydrogen, halogen (e.g., Br), carboxy, alkoxycarbonyl (e.g., methoxycarbonyl).

The acid catalyst is preferably inorganic acid (e.g., hydrochloric acid, sulfuric acid, nitric acid, phosphoric acid, polyphosphoric acid, boric acid), carboxylic acid (e.g., acetic acid, trifluoroacetic acid, trichloroacetic acid, propionic acid), sulfonic acid (e.g., methanesulfonic acid, benzenesulfonic acid, tosylic acid, trifluoromethanesulfonic acid), and Lewis acid (e.g., boron trifluoride ether complex, boron trichloride, aluminum trichloride, titanium tetrachloride, titanium tetraisopropoxide, ferrous tribromide), etc.

This reaction is preferably carried out in the presence of an oxidizing reagent. The oxidizing reagent can be, for Example, oxygen in the air, m-nitrobenzenesulfonic acid or salts thereof (e.g., alkali metal salt), iron oxide, ferric sulfate, o-nitrophenol, iodine, etc. Among them, oxygen in the air, m-nitrobenzenesulfonic acid or salts thereof (e.g., Na salt) is preferable.

This reaction temperature can be from room temperature to about 200° C., preferably from about 50° C. to 150° C., more preferably from about 70 to about 120° C.

The reaction solvent can be a protic solvent (e.g., n-butanol, methanol, isopropyl alcohol, n-propanol, ethanol, ethyleneglycol, diethyleneglycol, monoglyme) or an aprotic solvent (e.g., tetrahydrofuran, dioxane, dimethoxyethane, diethylenglycol dimethyl ether, chlorobenzene, carbon tetrachloride, chloroform, butyl acetate, N,N-dimethylformamide, acetonitrile), and is preferably acetonitrile or the like. Acetic acid, that is an acidic catalyst, is also useful as a solvent.

Reaction time is usually from several tens of minutes to several tens of hours, preferably from about 1 to 10 hours.

Ratio of Compound (G-II) to Compound (G-I) to be used is usually ca. 0.5~5 molar equivalents, preferably about 1 to 2 molar equivalents.

Method for use of the compound of the present invention is explained below.

The compound of the present invention is useful as a medicine such as an antiviral agent. The compound of the present invention has an outstanding inhibitory activity against integrase of viruses. Therefore, the compound of the present invention is expected to prevent or treat various diseases caused by viruses producing integrase to grow in animal cells upon infection, and is useful as, for Example, an integrase inhibitor against retroviruses (e.g., HIV-1, HIV-2, HTLV-1, SIV or FIV), especially, an anti-HIV agent.

The compound of the present invention can be used in a combination therapy with an anti-HIV agent possessing other inhibitory mechanism such as a reverse transcriptase inhibitory agent and/or a protease inhibitory agent. Since any integrase inhibitor has not been on sale yet, it is useful to use the compound of the present invention in combination therapy with a reverse transcriptase inhibitory agent and/or a protease inhibitory agent.

Further, the compound of the present invention can be used not only as an anti-HIV mixture but also as a concomitant agent enhancing the activity of the other anti-HIV agent in a cocktail therapy.

The compound of the present invention can be used in the gene therapy using a retrovirus vector derived from HIV or MLV to suppress the spread of the retrovirus infection over non-target tissues. Specifically, in the case that cells infected in vitro with such a vector are put back in a body, a previous administration of the compound of the present invention prevents an unnecessary infection.

The compounds of the present invention can be administered orally or parenterally. For oral administration, the compound of the present invention can be used in any form of usual formulations, for Example, solid formulations such as tablets, powders, granules, capsules; aqueous formulations; oleaginous suspensions; or solutions such as syrup or elixir. For parenteral administration, the compound of the present invention can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives or stabilizers can be optionally used. And as an anti-HIV agent, oral agents are especially preferable.

The formulation according to the present invention may be manufactured by combining (for Example, admixing) a curatively effective amount of a compound of the present invention with a pharmaceutically acceptable carrier or diluent. The formulation of the present invention may be manufactured with well-known and easily available ingredients in accordance with a known method.

In the case of manufacturing a pharmaceutical composition according to the present invention, an active ingredient is admixed or diluted with a carrier, or they are contained in a carrier in the form of capsule, sacheier, paper, or another container. In case a carrier functions as a diluent, the carrier is a solid, semi-solid, or liquid material, which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier well known to those skilled in the art may be used for the formulation. In such formulation, a carrier is in the form of solid, liquid or a mixture thereof. For instance, a compound of the present invention is dissolved in 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator or capsule. A tablet for oral administration contains a suitable excipient such as calcium carbonate, sodium carbonate and lactose, calcium phosphate together with a disintegrator such as corn starch and alginic acid and/or a binder such as gelatin and acacia, and a lubricant such as magnesium stearate, stearic acid and talc.

In a powder medicine, a carrier is a finely pulverized solid, which is blended with finely pulverized active ingredients. In a tablet, active ingredients are admixed with a carrier having required binding power in a suitable ratio, and it is solidified in a desired shape and size. Powder medicine and tablet contain as the active ingredient about 1 to about 99% by weight of novel compounds of the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

A liquid formulation contains suspending agent, emulsifier, syrup agent or elixir agent. Active ingredients may be dissolved or suspended into a pharmaceutically acceptable carrier such as sterile water, a sterile organic solvent or a mixture thereof. Active ingredients may be dissolved frequently into a suitable organic solvent such as propylene glycol aqueous solution. When finely pulverized active ingredients are dispersed into aqueous starch, sodium carboxylmethylcellulose solution or suitable oil, the other compositions can be prepared.

Although an appropriate dosage of the compound of the present invention varies depending on the administration route, age, body weight, conditions of the patient, and kind of disease, in the case of oral administration, the daily dosage for an adult can be between approximately 0.05-3000 mg, preferably approximately 0.1-1000 mg, if necessary, in divisions. In the case of parenteral administration, the daily dosage for an adult can be between approximately 0.01-1000 mg, preferably approximately 0.05-500 mg.

EXAMPLE

Examples of the present invention are described below. Reactions were usually carried out under nitrogen atmosphere, and reaction solvents dried over molecular sieves were used. Extracts were dried over sodium sulfate or magnesium sulfate.

(Reagent)

n-Butyllithium=1.5 mol/l hexane solution

Sodium hydride=60% oil suspension (Abbreviation)

Et=ethyl; MeOH=methanol; EtOH=ethanol; DMF=N,N-dimethylformamide; THF=tetrahydrofuran; DMSO=dimethylsulfoxide; HOBt=1-hydroxybenzotriazole; WSCD=1-ethyl-3-(3-dimethylaminopropyl)carbodiimide hydrochloride, Me=methyl; iPr=isopropyl; c-Pr=cyclopropyl; Ph=phenyl; Bn=benzyl; c-hex=cyclohexyl; Ac=acetyl Reference Example 1

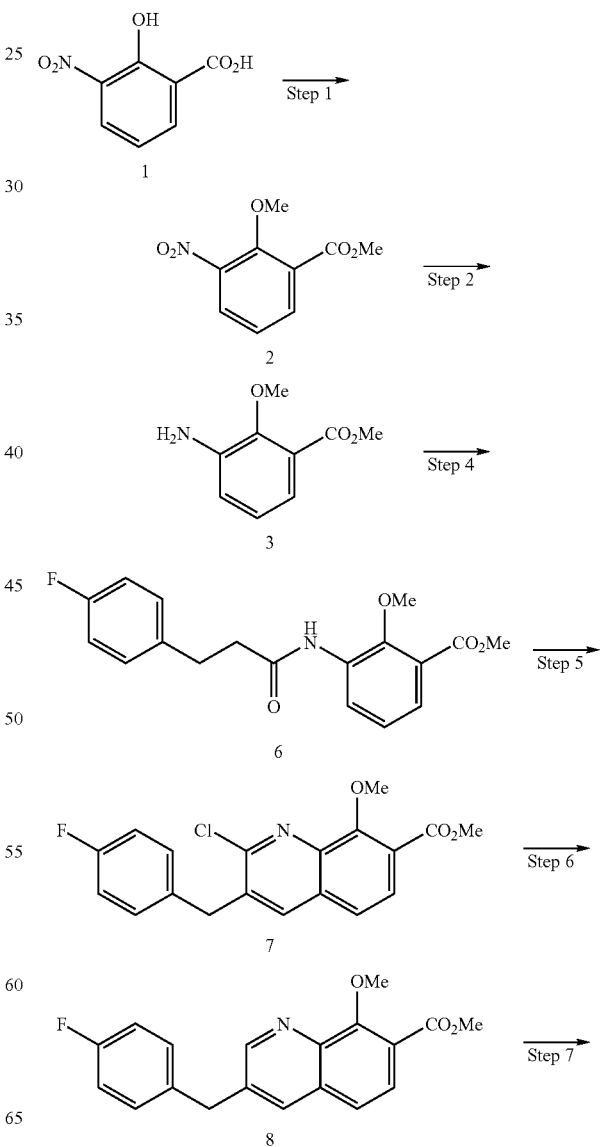

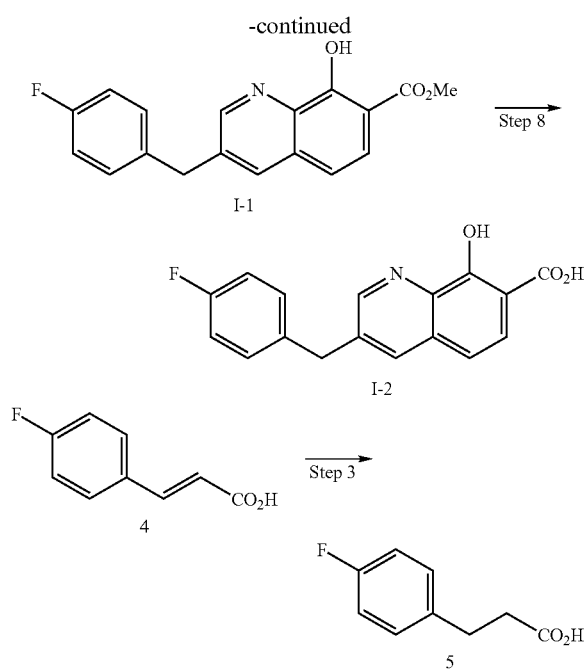

Step 1

Potassium carbonate (77 g) was added to a solution of Compound 1, i.e. 3-nitrosalicylic acid (51 g, 279 mmol) in DMF (250 ml), and dimethyl sulfate (58 ml) was added dropwise to the mixture with cooling on a water bath (25° C.). The reaction mixture was stirred at room temperature overnight. Then, the mixture was treated with aqueous ammonium chloride, and extracted with ethyl acetate. The extract was washed with water and brine, and was dried over magnesium sulfate. The solvent was evaporated in vacuo to give crude Compound 2 (56.3 g) as colorless crystals.

Step 2

To a solution of the crude Compound 2 (56.3 g) in a mixture of ethanol (200 ml), dioxane (200 ml) and water (40 ml) was added a suspension of 10% palladium carbon (2.82 g) in water (20 ml). The reaction mixture was stirred for 5.5 hours under hydrogen atmosphere at 1 atm. The reaction mixture was filtered through Celite and the filtrate was evaporated in vacuo. Obtained residue was treated with water (300 ml), and extracted twice with ether. The extract was washed with water and brine, and dried over magnesium sulfate. The solvent was evaporated in vacuo to give crude Compound 3 (48.4 g, 266 mmol) as an oil.

Step 3

To a solution of Compound 4, i.e. 4-fluorocinnamic acid (50 g, 300 mmol) in DMF (500 ml) was added 10% palladium-carbon (10 wt %) under ice-cooling, and the mixture was stirred for 6.5 hours under hydrogen atmosphere at 1 atm. The reaction mixture was filtered through Celite and the filtrate was evaporated in vacuo. The residue was dissolved in ethyl acetate (300 ml), and the solution was filtered again through Celite. The filtrate was concentrated in vacuo to give crude Compound 5 (61.8 g) as colorless crystals.

Step 4

To a solution of Compound 5 (47.0 g, 279 mmol) in methylene chloride (350 ml) were added 1-ethyl 3-(3-dimethylaminopropyl)carbodiimide hydrochloride (69.2 g, 360 mmol) and 1-hydroxybenzotriazole (4.07 g, 31 mmol) at room temperature, and the mixture was stirred for 60 minutes. A solution of the crude Compound 3 (48.4 g, 266 mmol) in methylene chloride (30 ml) was added dropwise to the solution, and the mixture was stirred for 2 hours at room temperature. The reaction mixture was treated with ice water, stirred, and methylene chloride layer was separated. Aqueous layer was extracted with methylene chloride. The organic layers were combined, washed with 1N hydrochloric acid, saturated aqueous sodium hydrogen carbonate and brine, and dried over magnesium sulfate. Removal of solvent in vacuo gave the crystalline residue, which were washed with diisopropyl ether to give Compound 6 (78.5 g, 237.0 mmol) as colorless crystals. Yield: 89.1% from Compound 1. m.p. 90-92° C.

Step 5

DMF (2.74 g, 37.5 mmol) was added dropwise to phosphorus oxychloride (31 g, 200 mmol) under ice-cooling, and the mixture was stirred for 30 minutes. To the mixture was added Compound 6 (78.0 g, 235 mmol), and the reaction mixture was warmed to room temperature, stirred for 30 minutes, and then stirred at 75° C. for 18 hours. Remaining phosphorus oxychloride was removed in vacuo, and ice water (50 ml) was added to the residue. Resulting resinous material was extracted with ethyl acetate, washed with brine, saturated aqueous sodium hydrogen carbonate, and dried over magnesium sulfate. The solvent was evaporated in vacuo to give crystals, which were washed with cold ethyl acetate to give Compound 7 (24.2 g, 67.3 mmol) as colorless crystals. Yield: 28.5%. m.p.: 126-127° C.

Step 6

To a solution of Compound 7 (23.9 g, 66.4 mmol) in a mixture of ethyl acetate (200 ml) and ethanol (400 ml) were added 5% palladium carbon (10 wt %) and triethylamine (12.3 g, 122 mmol) under ice-cooling. After warming to room temperature, the mixture was stirred for 2 hours under hydrogen atmosphere of 1 atm. Reaction mixture was filtered through Celite and the filtrate was concentrated in vacuo. The residue was dissolved in a mixture of ethyl acetate (250 ml) and water (150 ml), and the organic layer was separated. Aqueous layer was extracted with ethyl acetate. The organic layers were combined, washed with brine, and dried over magnesium sulfate. The solvent was evaporated in vacuo to give Compound 8 (19.3 g, 59.3 mmol) as colorless crystals. Yield: 89.2%; m.p.: 60-60.5° C.

Step 7

To a solution of sodium iodide (276 mg, 1.84 mmol) in acetonitrile (5 ml) was added trimethylsilyl chloride (234 μl, 1.84 mmol) under ice-cooling, and the mixture was stirred for 10 minutes at room temperature. This mixture was cooled again with iced water, and suspension of Compound 8 (120 mg, 0.369 mmol) in acetonitrile (1.5 ml) was added to the mixture, and then the reaction mixture was refluxed for 3.5 hours. The reaction mixture was cooled to room temperature and treated with 10% aqueous sodium hydrogen sulfite (13 ml). The precipitated crystals were collected by filtration, washed with water, and dried at 70° C. to give Compound I-1 of the title (100 mg, 0.321 mmol) as colorless crystals in 87% yield. The product was recrystallized from aqueous 80% methanol to give 52 mg of Compound I-1 of the title as colorless crystals; m.p.: 147.5-148.5° C. (from 80% methanol-water).

NMR (DMSO-$d_6$) δ: 3.92 (3H, s), 4.20 (2H, s), 7.12-7.18 (2H, m), 7.34-7.39 (3H, m), 7.81 (1H, d, J=8.7 Hz), 8.16 (1H, d, J=2.4 Hz), 8.87 (1H, d, J=2.4 Hz), 11.28 (1H, brs).

Elemental Analysis: $C_{18}H_{14}FNO_3$ Calcd. (%): C, 69.45; H, 4.53; F, 6.10; N, 4.50. Found (%): C, 69.43; H, 4.32; F, 5.90; N, 4.43.

Step 8

To a solution of Compound I-1 (129 mg, 0.414 mmol) in 1,4-dioxane (9 ml) at room temperature was added 1N-lithium hydroxide (6 ml), and the mixture was refluxed for 3 hours. After cooling to room temperature, 1N-hydrochloric acid (9 ml) was added to the reaction mixture. The precipitated crystals were collected by filtration, washed with water, and dried at 70° C. to give Compound I-2 of the title (122 mg, 0.410 mmol) as yellow crystals in 99% yield. This product was recrystallized from methanol to give Compound I-2 of the title (96 mg) as yellow crystals; m.p.: 236-237° C. (from methanol).

NMR (DMSO-$d_6$) δ: 4.22 (2H, s), 7.13-7.19 (2H, m), 7.27 (1H, d, J=8.7 Hz), 7.36-7.41 (2H, m), 7.86 (1H, d, J=8.7 Hz), 8.31 (1H, brs), 8.86 (1H, brs).

Elemental Analysis: $C_{17}H_{12}FNO_3$ Calcd. (%): C, 68.68; H, 4.07; F, 6.39; N, 4.71. Found (%): C, 68.54; H, 4.08; F, 6.25; N, 4.68.

Example 1

I-3

3-(4-Fluorobenzyl)-8-hydroxy-quinoline-5,7-dicarboxylic acid 7-methylester

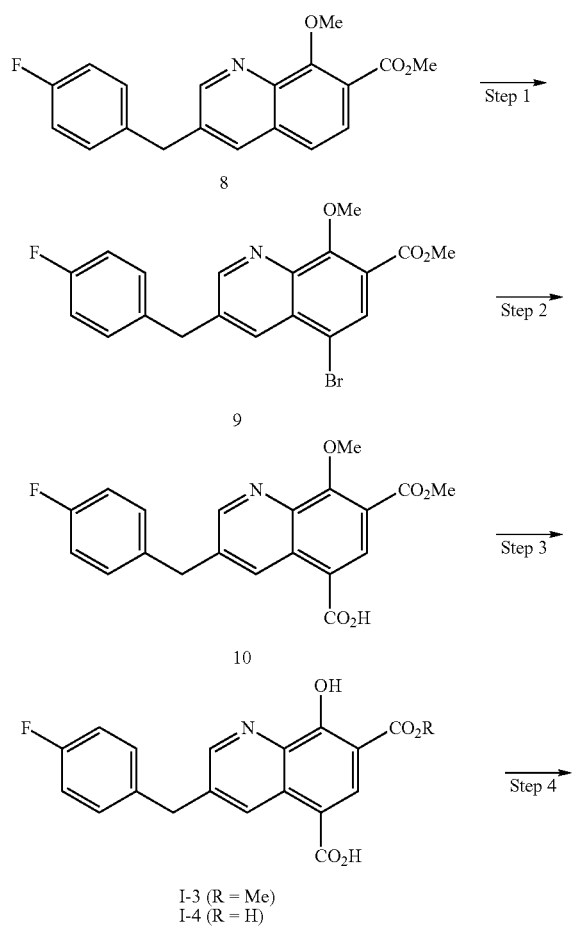

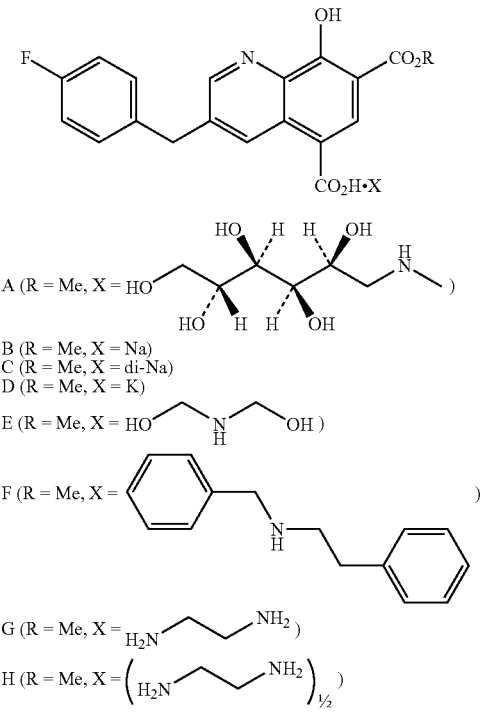

Step 1.

To a solution of Compound 8 (32.3 g, 99.2 mmol; obtained from Step 6 of Reference Example 1) in acetic acid (400 ml) was added sodium acetate (10.4 g, 127 mmol), and then a solution of bromine (5.62 ml, 109 mmol) in acetic acid (10 ml) was added dropwise to the mixture over 15 minutes. After stirring for 100 minutes at room temperature, additional amount of sodium acetate (10.4 g, 127 mmol) and a solution of bromine (5.62 ml, 109 mmol) in acetic acid (10 ml) were added. After stirring for 1.5 hour, sodium acetate (20.4 g, 249 mmol) was added to the reaction mixture under ice-cooling. The reaction mixture was treated with aqueous 10% sodium hydrogen sulfite (260 ml) and water (250 ml), and the mixture was stirred at the same temperature for 30 minutes. The precipitated crystals were collected by filtration and washed with water. The crystals were dissolved in ethyl acetate (600 ml), and the solution was washed successively with aqueous 10% sodium hydrogen sulfite, aqueous sodium hydrogen carbonate and water, and dried over magnesium sulfate. The solvent was evaporated in vacuo, and remaining residue was recrystallized from acetone-n-hexane to give Compound 9 (37.4 g, 92.5 mmol) as pale yellow crystals. Yield: 93.2%; m.p.: 110-111° C.

Step 2.

To a suspension of Compound 9 (3.05 g, 7.55 mmol), palladium (II) acetate (339 mg, 1.51 mmol) and 1,3-bis(diphenylphosphino)propane (781 mg, 1.89 mmol) in dimethyl sulfoxide (60 ml) were successively added triethylamine (10.5 ml, 75.3 mmol) and water (15 ml) at room temperature. The mixture was stirred for 30 minutes at room temperature, and then stirred under carbon monoxide atmosphere of 1 atm at room temperature for 1 hour and then at 70° C. for 2 hours. The reaction mixture was treated with ethyl acetate (120 ml) and water (120 ml), filtered through Celite, and was washed with ethyl acetate (60 ml) and water (60 ml). The filtrate was concentrated in vacuo to remove ethyl acetate, and obtained residue was treated with aqueous 10% citric acid (60 ml). The precipitated crystals were collected by filtration, washed with water, and recrystallized from ethyl acetate-methanol (1:1 v/v) to give Compound 10 (2.16 g, 58.5 mmol) as pale brown crystals. Yield: 78%.

Step 3.

To a solution of Compound 10 (150 mg, 0.406 mmol) in methylene chloride (10 ml) was added aluminum chloride (271 mg, 2.03 mmol) under ice-cooling. The reaction mixture was warmed to room temperature, stirred for 1.5 hours, and treated with 1N-hydrochloric acid (10 ml). Layers were separated and the aqueous layer was washed with chloroform. Crystals precipitated from the aqueous layer were collected by filtration, washed with water, and dried at 70° C. to give Compound I-3 (71 mg, 0.20 mmol) of the title as colorless crystals in 49% yield. This product was recrystallized from methanol to afford Compound I-3 of the title as colorless crystals (59 mg); m.p.: 237-239° C. (from methanol).

NMR (DMSO-$d_6$) δ: 3.92 (3H, s), 4.26 (2H, s), 7.13-7.19 (2H, m), 7.33-7.38 (2H, m), 8.63 (1H, s), 8.91 (1H, d, J=2.1 Hz), 9.25 (1H, d, J=2.1 Hz), 12.76 (1H, brs).

Elemental Analysis: $C_{19}H_{14}FNO_5$ Calcd. (%): C, 64.23; H, 3.97; F, 5.35; N, 3.94. Found (%): C, 63.83; H, 3.85; F, 5.27; N, 3.90.

Compound I-4

3-(4-Fluorobenzyl)-8-hydroxyquinoline-5,7-dicarboxylic acid

To a solution of Compound 10 (150 mg, 0.406 mmol) in methylene chloride (30 ml) was added a solution of 1M-boron tribromide in methylene chloride (4 ml, 4.0 mmol) under ice-cooling. The reaction mixture was warmed to room temperature and stirred for 2 days. The reaction mixture was treated with water and stirred for 30 minutes at room temperature. The precipitated crystals were collected by filtration, washed with ethyl acetate, and recrystallized from methanol to give Compound I-4 of the title (38 mg, 0.11 mmol) as yellow crystals; m.p.: 279-282° C. (from methanol). Yield: 26%.

NMR (DMSO-$d_6$) δ: 4.34 (2H, s), 7.15-7.21 (2H, m), 7.36-7.40 (2H, m), 8.76 (1H, s), 8.89 (1H, brs), 9.76 (1H, brs), 12.77 (1H, brs).

Elemental Analysis: $C_{18}H_{12}FNO_5$ MeOH Calcd. (%): C, 61.13; H, 4.32; F, 5.09; N, 3.75. Found (%): C, 60.45; H, 4.33; F, 4.87; N, 3.78.

Step 4

Compound I-3-A 3-(4-Fluorobenzyl)-8-hydroxyquinoline-5,7-dicarboxylic acid 7-methyl ester meglumine salt A suspension of compound I-3 (3.0 g, 8.4 mmol) obtained by Step 3 of Example 1 and megulumine (1.98 g, 10.14 mmol) in MeOH (60 mL) was stirred at 50° C. for 5 min. The resulting yellow solution was cooled to room temperature with stirring and stirred for 60 min. To the resulting slurry was added dropwise MeCN (150 mL) during 30 min. After stirring for 3 hr, the resulting solids were collected by filtration and washed with MeCN (60 mL). The solids were dried in vacuo at 100° C. for 3 hr to give compound I-3-A (4.24 g, 91.3%) as pale yellow crystals.

m.p.: 173.5° C. (from methanol-acetonitrile)

NMR (CD$_3$OD) δ: 2.70 (3H, s), 3.16 (2H, d, J=6.0 Hz), 3.61-3.84 (5H, m), 4.01-4.06 (1H, m), 4.03 (3H, s), 4.22 (2H, s), 7.00-7.05 (2H, m), 7.29-7.38 (2H, m), 8.43 (1H, s), 8.71 (1H, d, J=2.1 Hz), 9.18 (1H, d, J=2.1 Hz).

Elemental analysis for $C_{26}H_{31}FN_2O_{10}$ Calcd. (%): C, 56.72; H, 5.68; F, 3.45; N, 5.09. Found. (%): C, 56.51; H, 5.73; F, 3.53; N, 5.12.

The X-ray diffraction peaks were at 2□=6.06, 6.84, 12.04, 13.64, 16.88, 18.10, 19.86, 20.20, 21.04, 22.40, 22.74, 25.30, 27.28, 30.18 and 34.48.

Compound I-3-B 3-(4-Fluorobenzyl)-8-hydroxyquinoline-5,7-dicarboxylic acid 7-methyl ester sodium salt To a suspension of I-3 (735 mg, 2.069 mmol) in methanol (300 ml), was added 1M sodium methoxyde solution (2.02 ml, 2.066 mmol) at room temperature and the mixture was stirred for 1.5 hr, then evaporated. The residue was washed with eter (25 ml×2) to give compound I-3-B (746 mg, 1.977 mmol) as a pale yellow solid in 96% yield.

m.p.: >208-209° C.

NMR (DMSO-$d_6$) δ: 3.75 (3H, s), 4.11 (2H, s), 7.10-7.16 (2H, m), 7.27-7.32 (2H, m), 8.48 (1H, s), 8.60 (1H, s), 9.32 (1H, s).

Elemental analysis for $C_{19}H_{13}FNNaO_5H_2O$ Calcd. (%): C, 57.73; H, 3.82; F, 4.81; N, 3.54; Na, 5.82. Found. (%): C, 57.17; H, 3.82; F, 4.56; N, 3.68; Na, 5.17.

Compound I-3-C 3-(4-Fluorobenzyl)-8-hydroxyquinoline-5,7-dicarboxylic acid 7-methyl ester disodium salt According to the synthesis method of compound I-3-B, I-3 (200 mg, 0.563 mmol) was reacted and purified to give I-3-C (141 mg, 0.353 mmol) as yellow solid in 63%.

NMR (DMSO-$d_6$) δ: 3.69 (3H, s), 4.04 (2H, s), 7.09-7.15 (2H, m), 7.25-7.30 (2H, m), 8.28 (1H, s), 8.49 (1H, s), 9.76 (1H, brs).

Elemental analysis for $C_{19}H_{12}FNNa_2O_5 1.5H_2O$ Calcd. (%): C, 53.53; H, 3.55; F, 4.46; N, 3.29; Na, 10.79. Found. (%): C, 53.12; H, 3.53; F, 4.23; N, 3.37; Na, 10.32.

Compound I-3-D 3-(4-Fluorobenzyl)-8-hydroxyquinoline-5,7-dicarboxylic acid 7-methyl ester potassium salt According to the synthesis method of compound I-3-B, I-3 (50 mg, 0.141 mmol) was reacted, then purified to give I-3-D (54 mg, 0.137 mmol) as yellow solid in 97% yield.

NMR (DMSO-$d_6$) δ: 3.72 (3H, s), 4.07 (2H, s), 7.09-7.15 (2H, m), 7.26-7.31 (2H, m), 8.45 (1H, s), 8.56 (1H, s), 9.42 (1H, brs).

Elemental analysis for $C_{19}H_{13}FKNO_5$ Calcd. (%): C, 58.01; H, 3.33; F, 4.83; K, 9.94; N, 3.56. Found. (%): C, 53.02; H, 3.56; F, 4.25; K, 10.58; N, 3.39.

Compound I-3-E 3-(4-Fluorobenzyl)-8-hydroxyquinoline-5,7-dicarboxylic acid 7-methyl ester diethanol amine salt According to the synthesis method of compound I-3-A, I-3 (300 mg, 0.844 mmol) was reacted, then crystallized to give I-3-E (345 mg, 0.749 mmol) as colorless crystals in 89% yield.

M.p.: 160° C. (from methanol-acetonitrile)

NMR (CD$_3$OD) δ: 3.13 (4H, t, J=5.4 Hz), 3.80 (4H, t, J=5.4 Hz), 4.03 (3H, s), 4.22 (2H, s), 7.00-7.06 (2H, m), 7.29-7.34 (2H, m), 8.44 (1H, s), 8.72 (1H, d, J=2.1 Hz), 9.19 (1H, d, J=2.1 Hz).

Elemental analysis for C$_{23}$H$_{25}$FN$_2$O$_7$ Calcd. (%): C, 59.99; H, 5.47; F, 4.13; N, 6.08. Found. (%): C, 59.79; H, 5.49; F, 4.28; N, 6.06.

The X-ray diffraction peaks were at 2θ=6.66, 11.18, 13.28, 16.78, 22.04, 22.42, 22.92, 24.06, 25.50, 26.54, 27.68 and 33.90.

Compound I-3-F 3-(4-Fluorobenzyl)-8-hydroxyquinoline-5,7-dicarboxylic acid 7-methyl ester benzylphenetyl amine salt According to the synthesis method of I-3-A, I-3 (300 mg, 0.844 mmol) was reacted, then crystallized to give I-3-F (419 mg, 0.739 mmol) as colorless crystals in 88% yield.

M.p.: 160° C. (from methanol-acetonitrile) NMR, (CD$_3$OD) δ: 2.95-3.01 (2H, m), 3.20-3.25 (2H, m), 4.02 (3H, s), 4.18 (2H, s), 4.20 (2H, s), 6.99-7.05 (2H, m), 7.22-7.32 (7H, m), 7.41-7.47 (5H, m), 8.45 (1H, s), 8.71 (1H, d, J=2.1 Hz), 9.19 (1H, d, J=2.1 Hz).

Elemental analysis for C$_{34}$H$_{31}$FN$_2$O$_5$ Calcd. (%): C, 72.07; H, 5.51; F, 3.35; N, 4.94. Found. (%): C, 72.02; H, 5.62; F, 3.50; N, 4.98.

The X-ray diffraction peaks were at 2□=6.50, 9.70, 16.16, 17.60, 19.40, 20.62 and 22.66.

Compound I-3-G 3-(4-Fluorobenzyl)-8-hydroxyquinoline-5,7-dicarboxylic acid 7-methyl ester ethylenediamine salt According to the synthesis method of compound I-3-A, I-3 (300 mg, 0.844 mmol) was reacted, then crystallized to give I-3-G (324 mg, 0.780 mmol) as yellow crystals in 92% yield. m.p.: 164° C. (from methanol-acetonitrile)

NMR (CD$_3$OD) δ: 2.95 (4H, s), 3.24 (1H, brs), 4.02 (3H, s), 4.20 (2H, s), 4.86 (1H, brs), 7.00-7.06 (2H, m), 7.28-7.33 (2H, m), 8.43 (1H, s), 8.70 (1H, s), 9.19 (1H, s).

Elemental analysis for C$_{21}$H$_{22}$FN$_3$O$_5$ Calcd. (%): C, 60.72; H, 5.34; F, 4.57; N, 10.12. Found. (%): C, 59.04; H, 5.41; F, 4.62; N, 9.85.

The X-ray diffraction peaks were at 2θ=5.96, 16.46, 17.18, 17.84, 19.66, 22.06, 23.92, 24.42, 25.22, 26.22 and 27.22.

Compound I-3-H 3-(4-Fluorobenzyl)-8-hydroxyquinoline-5,7-dicarboxylic acid 7-methyl ester 0.5 ethylenediamine salt According to the synthesis method of compound I-3-A, I-3 (300 mg, 0.844 mmol) was reacted, then crystallized to I-3-H (201 mg, 0.522 mmol) as pale yellow crystals in 62% yield. M.p.: 137.5-138.5° C. (from methanol-acetonitrile)

NMR (CD$_3$OD) δ: 3.11 (2H, s), 4.02 (3H, s), 4.20 (2H, s), 7.00-7.06 (2H, m), 7.29-7.32 (2H, m), 8.55 (1H, s), 8.72 (1H, s), 9.26 (1H, s).

Elemental analysis for C$_{20}$H$_{18}$FN$_2$O$_5$ Calcd. (%): C, 62.33; H, 4.71; F, 4.93; N, 7.27. Found. (%): C, 60.08; H, 4.95; F, 4.84; N, 6.98.

The X-ray diffraction peaks were at 2θ=7.26, 9.22, 19.70 and 26.42.

Example 2

I-5

3-(4-Fluorobenzyl)-8-hydroxy-5-(2-hydroxyethylcarbamoyl)quinoline-7-carboxylic acid methylester

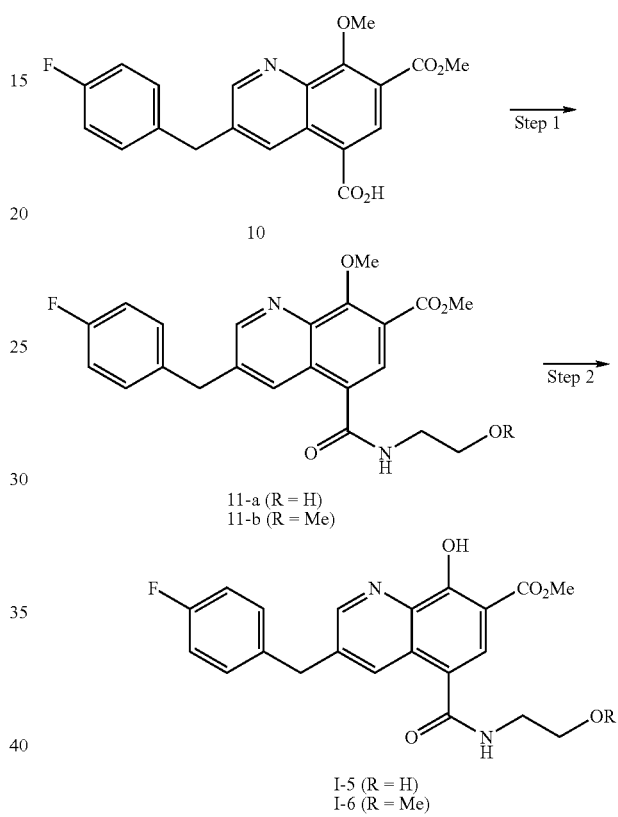

Step 1

To a suspension of Compound 10 (400 mg, 1.08 mmol; obtained from Step 2 of Example 1) and 1-hydroxybenzotriazole (15 mg, 0.11 mmol) in DMF (2 ml) were added successively 2-aminoethanol (79 μl, 1.3 mmol) and 1-ethyl-3-(3-dimethylaminopropyl) carbodiimide hydrochloride (228 mg, 1.19 mmol) at room temperature, and the mixture was stirred for 1 hour and left standing for 13 hours at room temperature. Water (10 ml) was added dropwise to the reaction mixture at room temperature. The precipitated crystals were collected by filtration, washed with water, and dried at 70° C. to give Compound 11-a (419 mg, 1.02 mmol) as colorless crystals in 94% yield.

In a manner similar to above procedure, Compound 10 (900 mg, 2.44 mmol) gave Compound 11-b (952 mg, 2.23 mmol) as colorless crystals in 92% yield.

Step 2

Compound I-5

To a solution of Compound 11-a (200 mg, 0.486 mmol) in methylene chloride (10 ml) was added aluminum chloride (324 mg, 2.43 mmol) under ice-cooling. The reaction mixture was warmed to room temperature, stirred for 1 hour, and treated with water (30 ml), and extracted with ethyl acetate. The extract was washed with 1N-hydrochloric acid, aqueous 10% sodium hydrogen carbonate and brine, and the extract was dried over sodium sulfate. The solvent was evaporated in vacuo to give Compound I-5 of the title as crude crystals (57 mg), which were recrystallized from acetone-ethyl ether to give Compound I-5 of the title (31 mg, 0.078 mmol) as colorless crystals in 16% yield; m.p.: 207-208° C. (from acetone-ethyl ether).

NMR (CDCl$_3$) δ: 3.67-3.72 (2H, m), 3.89-3.92 (2H, m), 4.05 (3H, s), 4.16 (2H, s), 6.53 (1H, brs), 6.97-7.03 (2H, m), 7.15-7.20 (2H, m), 8.10 (1H, s), 8.67 (1H, d, J=2.1 Hz), 8.82 (1H, d, J=2.1 Hz), 11.81 (1H, brs).

Elemental Analysis: C$_{21}$H$_{19}$FN$_2$O$_5$ Calcd. (%): C, 63.31; H, 4.81; F, 4.77; N, 7.03. Found (%): C, 62.96; H, 4.75; F, 4.61; N, 6.87.

Compound I-6

The crude crystals of Compound I-6 of the title (100 mg) were synthesized from Compound 11-b (200 mg, 0.469 mmol) in a manner similar to the steps 2 of Example 2, which were recrystallized from ethyl acetate-ethyl ether to give Compound I-6 of the title (60 mg, 0.15 mmol) as pale yellowish green crystals in 31% yield; m.p.: 152-154° C. (from ethyl acetate-ethyl ether).

NMR (CDCl$_3$) δ: 3.41 (3H, s), 3.60-3.63 (2H, m), 3.68-3.72 (2H, m), 4.05 (3H, s), 4.16 (2H, s), 6.40 (1H, brs), 6.97-7.02 (2H, m), 7.16-7.21 (2H, m), 8.10 (1H, s), 8.69 (1H, d, J=2.1 Hz), 8.84 (1H, d, J=2.1 Hz), 11.88 (1H, brs).

Elemental Analysis: C$_{22}$H$_{21}$FN$_2$O$_5$ 0.1HCl Calcd. (%): C, 63.51; H, 5.11; Cl, 0.85; F, 4.57; N, 6.73. Found (%): C, 61.58; H, 4.99; Cl, 0.69; F, 4.33; N, 6.60.

Example 3

I-7

5-Carbamoyl-3-(4-fluorobenzyl)-8-hydroxyquinoline-7-carboxylic acid

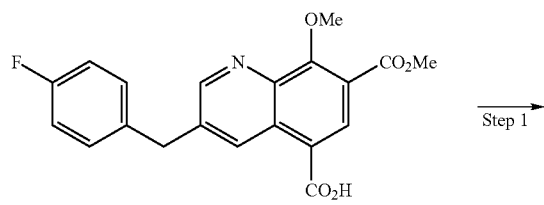

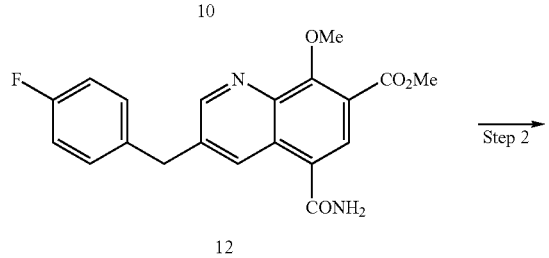

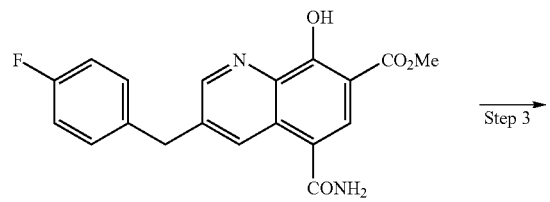

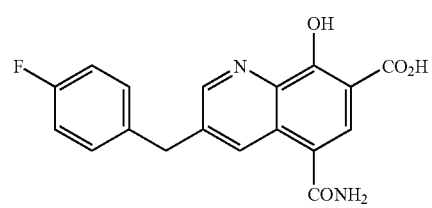

Step 1

In a manner similar to Step 1 of Example 2, Compound 10 (735 mg, 1.99 mmol) obtained from Step 2 of Example 1 gave crude crystals of Compound 12, which were recrystallized from ethyl acetate to give Compound 12 (491 mg, 1.33 mmol) as colorless crystals in 67% yield.

Step 2.

In a manner similar to Step 7 of Reference Example 1, Compound 12 (1.00 g, 2.72 mmol) gave crude crystals of Compound 13, which were recrystallized from 90% methanol-water to give Compound 13 (724 mg, 2.04 mmol) as colorless crystals in 75% yield.

Step 3.

Compound I-7

In a manner similar to Step 8 of Reference Example 1, Compound 13 (231 mg, 0.652 mmol) gave crude crystals of Compound I-7 of the title, which were recrystallized from methanol to give Compound I-7 of the title (138 mg, 0.406 mmol) as yellow crystals in 62% yield; m.p.: 265-266° C. (from methanol).

NMR (DMSO-d$_6$) δ: 4.28 (2H, s), 7.13-7.19 (2H, m), 7.33 (1H, brs), 7.34-7.39 (2H, m), 8.05 (1H, brs), 8.28 (1H, s), 8.86 (1H, d, J=1.8 Hz), 9.23 (1H, d, J=1.8 Hz).

Elemental Analysis: C$_{18}$H$_{13}$FN$_2$O$_4$ Calcd. (%): C, 63.53; H, 3.85; F, 8.23; N, 5.58. Found (%): C, 61.64; H, 3.86; F, 8.00; N, 5.30.

Example 4

I-8

5-Amino-3-(4-fluorobenzyl)-8-hydroxyquinoline-7-carboxylic acid methyl ester

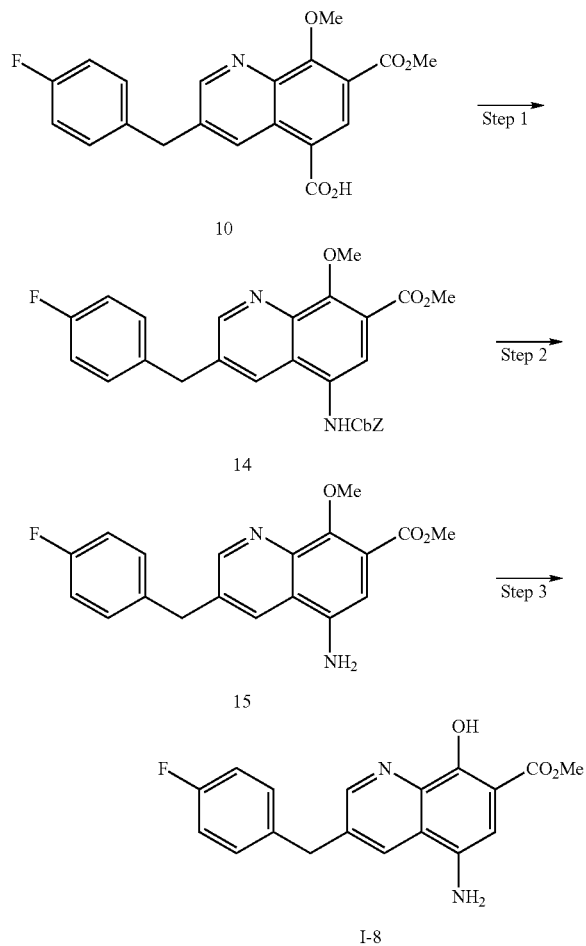

Step 1

To a solution of Compound 10 (7.500 g, 20.31 mmol; obtained in Step 2 of Example 1) in DMF (140 ml) were added dropwise a solution of diphenylphosphoric acid azide (7.27 g, 26.4 mmol) in DMF (5 ml) and a solution of triethylamine (7.93 ml, 56.9 mmol) in DMF (5 ml) successively at room temperature. The mixture was stirred at room temperature for 45 minutes, treated with benzyl alcohol (60 ml), stirred at 100° C. for 45 minutes, cooled, and poured into water (600 ml). After stirring at room temperature for 1 hour, the precipitated crystals were collected by filtration, washed with water and diisopropyl ether, and dried at 70° C. to give Compound 14 (7.694 g, 16.22 mmol) as colorless crystals. Yield 79.8%.

Step 2.

10% Palladium carbon (385 mg, 5 wt %) and a suspension of Compound 14 (7.694 g, 16.22 mmol) in ethyl acetate (100 ml) were added to ethyl acetate (50 ml) under ice-cooling. After warming to room temperature, 99.5% ethanol (150 ml) was added to the mixture. The mixture was stirred for 2 hours under hydrogen atmosphere of 1 atm. The reaction mixture was filtered through Celite, and the filtrate was concentrated in vacuo to give crude Compound 15 (5.695 g) as yellow oil.

Step 3

Compound I-8

In a manner similar to Step 7 of Reference Example 1, Compound 15 (100 mg, 0.295 mmol) gave crude crystals of Compound I-8 of the title, which were recrystallized from ethyl acetate-ethyl ether to give Compound I-8 of the title (44 mg, 0.13 mmol) as pale brown crystals in 46% yield; m.p.: 114-115° C. (from ethyl acetate-ethyl ether).

NMR (CDCl$_3$) δ: 3.71 (2H, brs), 4.00 (3H, s), 4.18 (2H, s), 6.99-7.04 (2H, m), 7.16-7.21 (2H, m), 7.19 (1H, s), 7.88 (1H, d, J=2.4 Hz), 8.86 (1H, d, J=2.4 Hz), 11.27 (1H, brs).

Elemental Analysis: C$_{18}$H$_{15}$FN$_2$O$_3$ 0.1HCl Calcd. (%): C, 65.52; H, 4.61; Cl, 1.07; F, 5.76; N, 8.49. Found (%): C, 62.75; H, 4.34; Cl, 1.36; F, 5.20; N, 8.40.

Example 5

I-9

5-Ethoxycarbonylamino-3-(4-fluorobenzyl)-8-hydroxyquinoline-7-carboxylic acid methyl ester

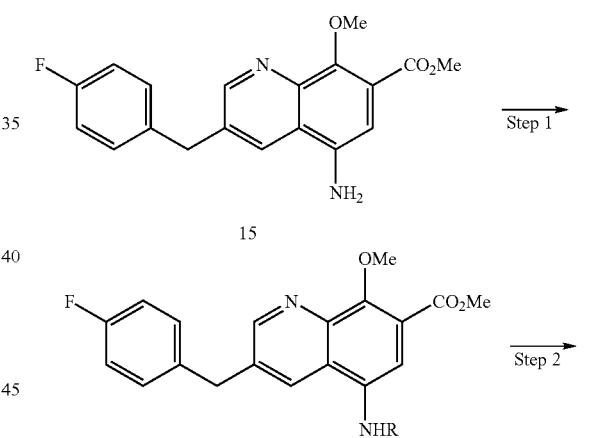

16-a (R = CO$_2$Et)
16-b (R = COMe)
16-c (R = COCF$_3$)
16-d (R = SO$_2$Me)

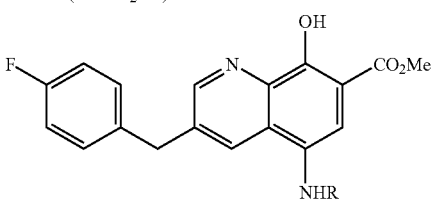

I-9 (R = CO$_2$Et)
I-10 (R = COMe)
I-11 (R = COCF$_3$)
I-12 (R = SO$_2$Me)

Step 1

To a suspension of Compound 15 (196 mg, 0.576 mmol; obtained from Step 2 of Example 4) in pyridine (5 ml) was added ethyl chloroformate (165 micro-liter, 1.73 mmol) under ice-cooling. The mixture was stirred for 1.5 hours. 0.25N-Hydrochloric acid (20 ml) was added to this reaction mixture, and the mixture was extracted with ethyl acetate. The extract was washed twice with each of 0.25N-hydrochloric acid, aqueous 10% sodium hydrogen carbonate and brine, dried over sodium sulfate. The solvent was concentrated in vacuo to give crude crystals of Compound 16-a (234 mg), which were recrystallized from diisopropyl ether to give Compound 16-a (179 mg, 0.434 mmol) as colorless crystals in 74% yield.

In a manner similar to above procedure, Compounds 16-b to Compound 16-d were prepared. Specifically, Compound 15 (205 mg, 0.602 mmol) gave Compound 16-b (196 mg, 0.513 mmol) as colorless crystals in 85% yield. Compound 15 (200 mg, 0.588 mmol) gave Compound 16-c (178 mg, 0.408 mmol) as pale pink crystals in 85% yield. Compound 15 (189 mg, 0.555 mmol) gave Compound 16-d (176 mg, 0.421 mmol) as pale orange crystals in 76% yield.

Step 2

In a manner similar to Step 7 of Reference Example 1, Compound 16-a (150 mg, 0.364 mmol) gave crude crystals of Compound I-9 of the title (76 mg). The crystals were subjected to silica gel column chromatography and was eluted with a mixture of chloroform, methanol and water (32:6:0.5 v/v). Fractions containing the desired compound were concentrated in vacuo to give residue, which was dissolved in chloroform, washed twice with each of 1N-hydrochloric acid and water, and dried over sodium sulfate. The solvent was evaporated in vacuo and the residue was recrystallized from ethyl ether to give Compound I-9 of the title (18 mg, 0.045 mmol) as colorless crystals in 12% yield; m.p.: 205-206° C. (from chloroform-ethyl ether).

NMR (DMSO-$d_6$) δ: 1.73 (3H, brs), 3.92 (3H, s), 4.12 (2H, brq, J=6.7 Hz), 4.22 (2H, s), 7.12-7.18 (2H, m), 7.35-7.40 (2H, m), 7.84 (1H, brs), 8.21 (1H, brs), 8.88 (1H, d, J=2.1 Hz), 9.39 (1H, brs), 11.14 (1H, brs).

Compound I-10

5-Acetylamino-3-(4-fluorobenzyl)-8-hydroxyquinoline-7-carboxylic acid methylester In a manner similar to Step 7 of Reference Example 1, Compound 16-b (150 mg, 0.392 mmol) gave crude crystals of Compound I-10 of the title (71 mg). The crystals were subjected to silica gel column chromatography and was eluted with chloroform-methanol-water (32:6:0.5 v/v). Fractions containing the desired compound were concentrated in vacuo to give residue, which was dissolved in chloroform, washed twice with each of 1N hydrochloric acid and water, and dried over sodium sulfate. The solvent was evaporated in vacuo, and the resulting residue was recrystallized from ethyl ether to give Compound I-10 of the title (49 mg, 0.13 mmol) as colorless crystals in 34% yield; m.p.: 243-245° C. (from chloroform-ethyl ether).

NMR (DMSO-$d_6$) δ: 2.13 (3H, s), 3.91 (3H, s), 4.22 (2H, s), 7.12-7.18 (2H, m), 7.33-7.37 (2H, m), 7.87 (1H, s), 8.22 (1H, d, J=2.1 Hz), 8.86 (1H, d, J=2.1 Hz), 9.83 (1H, s), 11.13 (1H, brs).

Elemental Analysis: $C_{20}H_{17}FN_2O_4$ Calcd; (%): C, 65.21; H, 4.65; F, 5.16; N, 7.60. Found (%): C, 64.93; H, 4.66; F, 5.01; N, 7.43.

Compound I-11

3-(4-Fluorobenzyl)-8-hydroxy-5-(2,2,2-trifluoroacetylamino)quinoline-7-carboxylic acid methyl ester In a manner similar to Step 7 of Reference Example 1, Compound 16-C (175 mg, 0.401 mmol) gave a crude Compound I-11 of the title, which was recrystallized from ethyl acetate-ethyl ether to give Compound I-11 of the title (94 mg, 0.22 mmol) as pale brown crystals in 55% yield; m.p.: 191-192° C. (from ethyl acetate-ethyl ether).

NMR (DMSO-$d_6$) δ: 3.92 (3H, s), 4.26 (2H, s), 7.13-7.19 (2H, m), 7.32-7.37 (2H, m), 7.82 (1H, s), 7.96 (1H, d, J=2.1 Hz), 8.93 (1H, d, J=2.1 Hz), 11.33 (1H, brs).

Elemental Analysis: $C_{20}H_{14}F_4N_2O_4$ Calcd. (%): C, 56.88; H, 3.34; F, 17.99; N, 6.63. Found (%): C, 56.88; H, 3.34; F, 17.39; N, 6.33.

Compound I-12

3-(4-Fluorobenzyl)-8-hydroxy-5-methanesulfonylaminoquinoline-7-carboxylic acid methyl ester In a manner similar to Step 7 of Reference Example 1, Compound 16-d (169 mg, 0.404 mmol) gave a crude Compound I-12 of the title, which was subjected to silica gel column chromatography and was eluted with chloroform-methanol-water (32:6:0.5 v/v). Fractions containing the desired compound were concentrated in vacuo to give a residue, which was treated with chloroform, washed twice with each of 1N-hydrochloric acid and water, and dried over sodium sulfate. The solvent was evaporated in vacuo, and the residue was recrystallized from ethyl ether to give Compound I-12 of the title (82 mg, 0.20 mmol) as pale pink crystals in 50% yield; m.p.: 189.5-190.5° C. (from chloroform-ethyl ether).

NMR (DMSO-$d_6$) δ: 2.94 (3H, s), 3.92 (3H, s), 4.25 (2H, s), 7.12-7.17 (2H, m), 7.34-7.39 (2H, m), 7.78 (1H, s), 8.42 (1H, d, J=2.1 Hz), 8.89 (1H, d, J=2.1 Hz), 9.57 (1H, brs), 11.16 (1H, brs).

Elemental Analysis: $C_{19}H_{17}FN_2O_5S$ Calcd. (%): C, 56.43; H, 4.24; F, 4.70; N, 6.93; S, 7.93. Found (%): C, 55.48; H, 4.19; F, 4.52; N, 6.53; S, 7.74.

Example 6

I-13

3-(4-Fluorobenzyl)-5-formylamino-8-hydroxyquinoline-7-carboxylic acid methyl ester

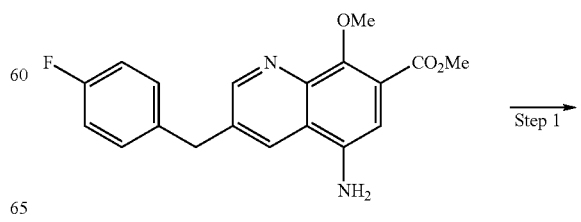

15

-continued

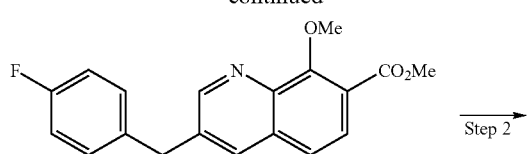

17

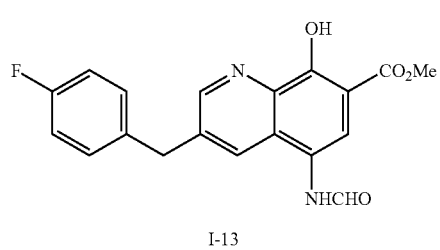

I-13

Step 1

A mixture of 98% formic acid (3.75 g, 79.8 mmol) and acetic anhydride (8.5 g, 83.3 mmol) was stirred for 1 hour at 50° C., and then cooled to room temperature. To a fraction (2 ml) of this solution transferred to a flask, Compound 15 (209 mg, 0.614 mmol; obtained in Step 2 of Example 4) was added and the mixture was stirred at room temperature for 1.5 hours. Ice-cooled reaction mixture was treated with aqueous 10% sodium hydrogen carbonate and the mixture was extracted with ethyl acetate. The extract was washed with water, dried over sodium sulfate, and concentrated to remove the solvent. The residue was subjected to silica gel column chromatography and was eluted with n-hexane-ethyl acetate (1:2 v/v). Fractions containing the desired compound were concentrated in vacuo to give Compound 17 (159 mg, 0.432 mmol) as colorless crystals in 70% yield.

Step 2

Compound I-13

In a manner similar to Step 7 of Reference Example 1, Compound 17 (140 mg, 0.380 mmol) gave a crude Compound I-1 of the title, which was subjected to silica gel column chromatography and was eluted with chloroform-methanol-water (32:6:0.5 v/v). Fractions containing the desired compound were concentrated in vacuo to give a residue, which was dissolved in chloroform and washed twice with each of 1N-hydrochloric acid and water, and dried over sodium sulfate. After removing the solvent in vacuo, the residue was recrystallized from ethyl ether to give Compound I-13 of the title (61 mg, 0.17 mmol) as colorless crystals in 61% yield; m.p.: 217-219° C. (from chloroform-ethyl ether).

NMR (DMSO-$d_6$) δ: 3.92 (3H, s), 4.22 (2H, s), 7.12-7.18 (2H, m), 7.34-7.39 (2H, m), 8.15 (1H, s), 8.32 (1H, brs), 8.42 (1H, d, J=1.8 Hz), 8.90 (1H, d, J=1.8 Hz), 11.21 (1H, brs).

Elemental Analysis: $C_{19}H_{15}FN_2O_4$ Calcd. (%): C, 64.40; H, 4.27; F, 5.36; N, 7.91. Found (%): C, 64.18; H, 4.41; F, 4.95; N, 7.46.

Example 7

I-14

3-(4-Fluorobenzyl)-8-hydroxy-5-isopropylamino-quinoline-7-carboxylic acid methylester

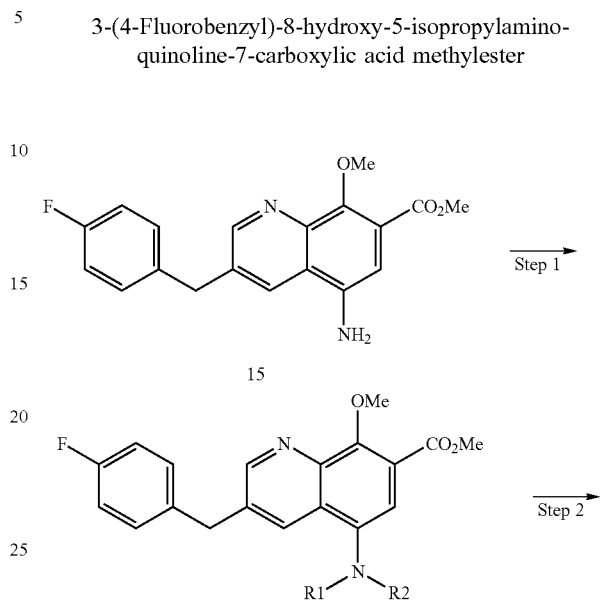

15

18-a (R1 = H R2 = iPr)
18-b (R1 = H R2 = cyclohexyl)
18-c (R1 = R2 = Me)

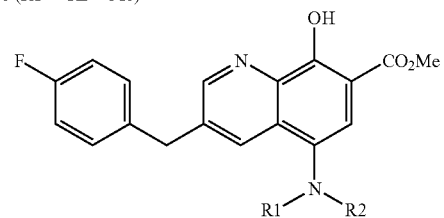

I-14 (R1 = H R2 = iPr)
I-15 (R1 = H R2 = cyclohexyl)
I-16 (R1 = R2 = Me)

Step 1

To a solution of Compound 15 (273 mg, 0.803 mmol; obtained from Step 2 of Example 4) in methylene chloride (10 ml) were added acetone (71 μl, 1.9 mmol), sodium triacetoxyborohydride (255 mg, 1.20 mmol) and acetic acid (138 μl, 2.41 mmol) under ice-cooling. The mixture was warmed to room temperature and stirred for 1.5 hours. After additional acetone (71 μl, 1.9 mmol) was added and stirring for 3 hours at room temperature, and the mixture was left standing for 15 hours. The reaction mixture was treated with ethyl acetate, and the mixture was washed with brine, and dried over sodium sulfate. Evaporation of the solvent in vacuo gave a residue, which was subjected to silica gel column chromatography and was eluted with n-hexane-ethyl acetate (1:1 v/v). Fractions containing the desired compound were concentrated in vacuo to give Compound 18-a (181 mg, 0.473 mmol) as yellow oil in 59% yield.

In a manner similar to above procedure, Compound 18-b and Compound 18-c were obtained. Specifically, Compound 15 (395 mg, 1.16 mmol) gave Compound 18-b (277 mg, 0.656 mmol) as yellow green crystals in 57% yield. Compound 15 (199 mg, 0.585 mmol) gave Compound 18-c (212 mg, 0.575 mmol) as a yellow oil in 98% yield.

Step 2

In a manner similar to Step 7 of Reference Example 1, Compound 18-a (175 mg, 0.458 mmol) gave a crude Compound I-14 of the title, which was subjected to silica gel column chromatography and was eluted with chloroform-methanol-water (32:6:0.5 v/v). Fractions containing the desired compounds were concentrated in vacuo to give a residue, which was dissolved in chloroform and washed twice with each of 1N-hydrochloric acid and water, and washed again with twice each of aqueous 10% sodium hydrogen carbonate and brine, and dried over sodium sulfate. The solvent was evaporated in vacuo and the residue was recrystallized from ethyl ether-diisopropyl ether to give Compound I-14 of the title (32 mg, 0.087 mmol) as yellow crystals in 19% yield; m.p.: 121-122° C. (ethyl ether-diisopropyl ether).

NMR (CDCl$_3$) δ: 1.29 (6H, d, J=6.3 Hz), 3.69 (1H, septet, J=6.3 Hz), 4.01 (3H, s), 4.18 (2H, s), 6.98-7.04 (2H, m), 7.01 (1H, s), 7.15-7.19 (2H, m), 7.92 (1H, d, J=1.8 Hz), 8.83 (1H, d, J=1.8 Hz), 11.26 (1H, s).

Elemental Analysis: $C_{21}H_{21}FN_2O_3$ Calcd. (%): C, 68.47; H, 5.75; F, 5.16; N, 7.60. Found (%): C, 67.99; H, 5.69; F, 4.95; N, 7.50.

Compound I-15

5-Cyclohexylamino-3-(4-fluorobenzyl)-8-hydroxyquinoline-7-carboxylic acid methylester In a manner similar to Step 7 of Reference Example 1, Compound 18-b (410 mg, 0.970 mmol) gave a crude Compound I-15 of the title, which was subjected to silica gel column chromatography and was eluted with ethyl acetate. Fractions containing the desired compound were concentrated in vacuo to give residue, which was recrystallized from 33% acetonitrile-water to give Compound I-15 of the title (82.5 mg, 0.202 mmol) as yellow crystals in 21% yield; m.p.: 75.5-77.5° C. (from 33% acetonitrile-water).

NMR (CDCl$_3$) δ: 1.23-1.82 (8H, m), 2.08-2.12 (2H, m), 3.25-3.32 (1H, m), 4.02 (3H, s), 4.18 (2H, s), 6.98-7.04 (2H, m), 7.01 (1H, s), 7.15-7.20 (2H, m), 7.90 (1H, d, J=1.8 Hz), 8.83 (1H, d, J=1.8 Hz), 11.24 (1H, s).

Elemental Analysis: $C_{24}H_{25}FN_2O_3$ Calcd. (%): C, 70.57; H, 6.17; F, 4.65; N, 6.87. Found (%): C, 67.56; H, 6.33; F, 4.18; N, 6.21.

Compound I-16

5-Dimethylamino-3-(4-fluorobenzyl)-8-hydroxyquinoline-7-carboxylic acid methylester In a manner similar to Step 7 of Reference Example 1, Compound 18-c (209 mg, 0.567 mmol) gave a crude Compound I-16 of the title, which was subjected to silica gel column chromatography and was eluted with chloroform-methanol-water (32:6:0.5 v/v). Fractions containing the desired compound were concentrated in vacuo to give a residue, which was dissolved in chloroform and washed with twice each of 1N-hydrochloric acid and water, washed again with twice each of aqueous 10% sodium hydrogen carbonate and brine, and dried over sodium sulfate. Evaporation of solvent in vacuo gave a residue, which was recrystallized from diisopropyl ether to give Compound I-16 of the title (77 mg, 0.22 mmol) as brown crystals in 38% yield.

m.p.: 62-63° C. (from chloroform-diisopropyl ether).

NMR (CDCl$_3$) δ: 2.76 (6H, s), 4.02 (3H, s), 4.18 (2H, s), 6.98-7.04 (2H, m), 7.16-7.21 (2H, m), 7.43 (1H, s), 8.26 (1H, d, J=2.1 Hz), 8.83 (1H, d, J=2.1 Hz), 11.55 (1H, brs).

Elemental Analysis: $C_{20}H_{19}FN_2O_3$ Calcd. (%): C, 67.79; H, 5.40; F, 5.36; N, 7.90. Found (%): C, 64.37; H, 5.56; F, 4.93; N, 7.41.

Example 8

I-17

5-(3-Ethylureido)-3-(4-fluorobenzyl)-8-hydroxyquinoline-7-carboxylic acid methylester

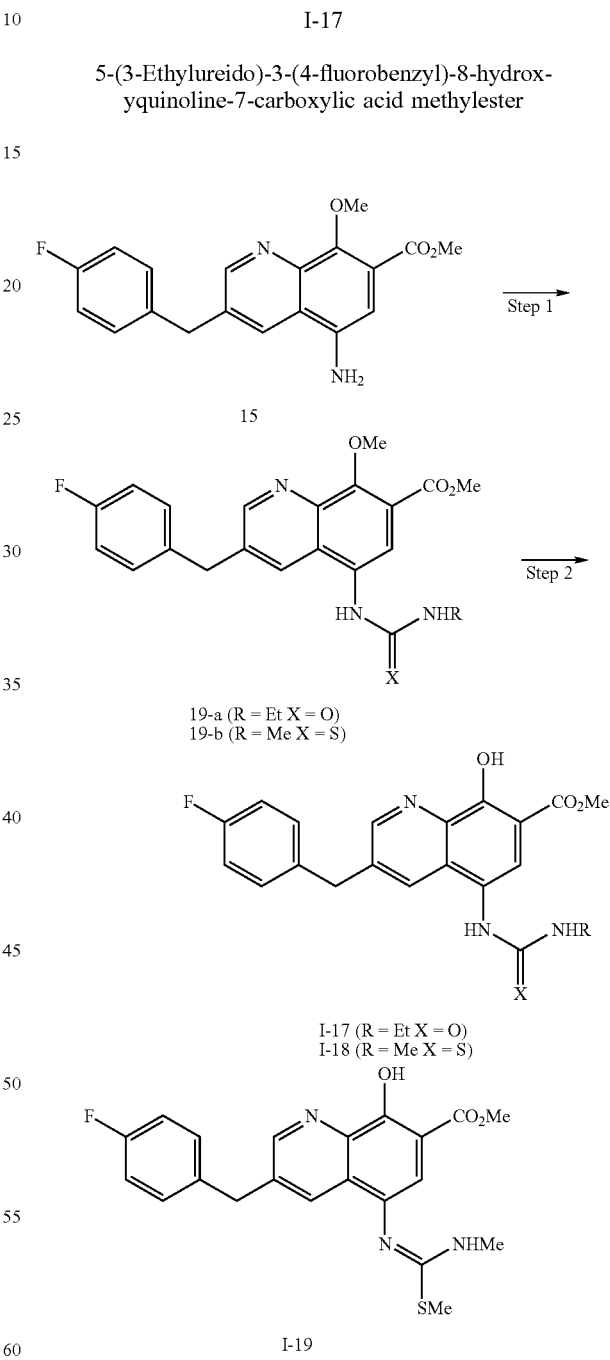

19-a (R = Et X = O)
19-b (R = Me X = S)

I-17 (R = Et X = O)
I-18 (R = Me X = S)

I-19

Step 1

To a solution of Compound 15 (230 mg, 0.676 mmol; obtained in Step 2 of Example 4) in tetrahydrofuran (6 ml) were added ethyl isocyanate (161 μl, 2.03 mmol) and bis(tri-N-butyltin) oxide (2 drops) under ice-cooling, and the mixture was warmed to room temperature and stirred for 2.5 hours. Additional amount of ethyl isocyanate (161 μl, 2.03 mmol) was added to the mixture and, the mixture was stirred for 2 hours at room temperature. After standing for 12 hours at room temperature, the solvent was evaporated in vacuo and the residue was recrystallized from ethyl ether to give Compound 19-a (185 mg, 0.450 mmol) as colorless crystals in 67% yield.

In a manner similar to above procedure, Compound 15 (240 mg, 0.705 mmol) gave Compound 19-b (209 mg, 0.505 mmol) as colorless crystals in 72% yield.

Step 2

To a solution of Compound 19-a (185 mg, 0.450 mmol) in methylene chloride (12 ml) was added aluminum chloride (300 mg, 2.25 mmol) under ice-cooling. The reaction mixture was warmed to room temperature and stirred for 1 hour. To the mixture were added an aqueous 10% citric acid (12 ml) and ethyl acetate (36 ml), and the precipitated crystals were collected by filtration. The crystals were dissolved in chloroform and washed with twice each of aqueous 10% citric acid and brine, and dried over sodium sulfate. After evaporating the solvent in vacuo, ethyl acetate was treated to the residue for recrystallizing to give Compound I-17 of the title (62 mg, 0.16 mmol) as pale yellow crystals in 35% yield. m.p.: 280-282° C. (from chloroform-ethyl acetate).

NMR (DMSO-$d_6$) δ: 1.06 (3H, t, J=7.2 Hz), 3.07-3.16 (2H, m), 3.92 (3H, s), 4.22 (2H, s), 6.31 (1H, t, J=5.4 Hz), 7.12-7.18 (2H, m), 7.31-7.36 (2H, m), 8.00 (1H, s), 8.19 (1H, d, J=1.8 Hz), 8.26 (1H, s), 8.85 (1H, d, J=1.8 Hz), 10.96 (1H, brs).

Elemental Analysis: $C_{21}H_{20}FN_3O_4$ Calcd. (%): C, 63.47; H, 5.07; F, 4.78; N, 10.57. Found (%): C, 62.71; H, 5.01; F, 4.64; N, 10.27.

Compound I-18

3-(4-Fluorobenzyl)-8-hydroxy-5-(3-methylthioureido)quinoline-7-carboxylic acid methylester In a manner similar to Step 2 of Example 8, Compound 19-b (91 mg, 0.22 mmol) gave a crude Compound I-18 of the title, which was recrystallized from ethyl acetate to give Compound I-18 (12 mg, 0.030 mmol) as pale yellow crystals in 14% yield. m.p.: 189-191° C. (from ethyl acetate).

NMR (CDCl$_3$) δ: 3.06 (3H, d, J=4.5 Hz), 4.04 (3H, s), 4.15 (2H, s), 5.70 (1H, m), 6.97-7.04 (2H, m), 7.13-7.17 (2H, m), 7.52 (1H, s), 7.88 (1H, s), 8.03 (1H, d, J=2.1 Hz), 8.84 (1H, d, J=2.1 Hz), 11.96 (1H, brs).

Compound I-19

5-(2,3-Dimethylisothioureido)-3-(4-fluorobenzyl)-8-hydroxyquinoline-7-carboxylic acid methylester In a manner similar to Step 7 of Reference Example 1, Compound 19-b (206 mg, 0.498 mmol) gave a crude Compound I-19 of the title (158 mg), which was recrystallized from ethyl acetate to give Compound I-19 of the title (97 mg, 0.24 mmol) as yellow crystals in 49% yield; m.p.: 198.5-199.5° C. (from ethyl acetate).

NMR (CDCl$_3$) δ: 2.27 (3H, brs), 2.99 (3H, brs), 3.99 (3H, s), 4.15 (2H, s), 4.61 (1H, brs), 6.96-7.03 (2H, m), 7.14-7.18 (2H, m), 7.35 (1H, s), 7.99 (1H, d, J=2.4 Hz), 8.80 (1H, d, J=2.4 Hz), 11.53 (1H, brs).

Elemental Analysis: $C_{21}H_{20}FN_3O_3S$ Calcd.(%): C, 61.00; H, 4.88; F, 4.59; N, 10.16; S, 7.75. Found (%): C, 60.84; H, 4.76; F, 4.45; N, 9.88; S, 7.55.

Example 9

I-20

3-(4-Fluorobenzyl)-5-formyl-8-hydroxyquinoline-7-carboxylic acid methylester

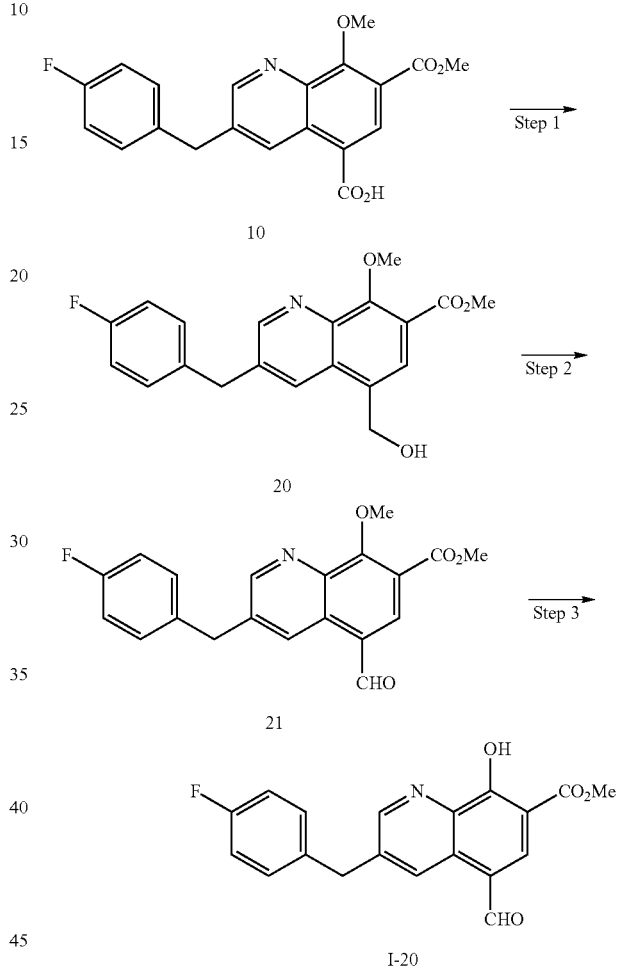

Step 1

To a solution of Compound 10 (450 mg, 1.22 mmol; obtained from Step 2 of Example 1) in tetrahydrofuran (15 ml) was added a solution of 1,1'-carbonyldiimidazole (296 mg, 1.83 mmol) in tetrahydrofuran (3 ml) at room temperature. The mixture was refluxed for 5 minutes and cooled to room temperature. The reaction mixture was treated with a solution of sodium borohydride (47 mg, 1.2 mmol) in water (3.6 ml), and the mixture was stirred at room temperature for 10 minutes. The reaction mixture was treated with aqueous 10% sodium hydrogen carbonate (18 ml) and extracted with ethyl acetate. The extract was washed with brine, dried over sodium sulfate, and concentrated in vacuo. The resulting residue was subjected to silica gel column chromatography and was eluted with n-hexane-ethyl acetate (1:1 v/v). Fractions containing the desired compound were concentrated in vacuo to give Compound 20 (342 mg, 0.962 mmol) as colorless oil in 79% yield.

Step 2

To a solution of Compound 20 (342 mg, 0.962 mmol) in chloroform (20 ml) was added manganese (IV) oxide (1.25 g, 14.4 mmol) at room temperature and the mixture was refluxed for 22 hours. The mixture was cooled to room temperature, filtered through Celite, and the filtrate was concentrated in vacuo to give a residue, which was subjected to silica gel column chromatography and was eluted with n-hexane-ethyl acetate (2:1 v/v). Fractions containing the desired compound were concentrated in vacuo to give Compound 21 (149 mg, 0.422 mmol) as colorless crystals in 44% yield.

Step 3

To a suspension of Compound 21 (213 mg, 0.603 mmol) and sodium iodide (723 mg, 4.82 mmol) in acetonitrile (10 ml) was added a solution of trimethylsilyl chloride (612 μl, 4.82 mmol) in acetonitrile (2.5 ml) under ice-cooling, and the mixture was stirred for 15 minutes. The reaction mixture was treated with a suspension of sodium hydrogen carbonate (405 mg, 4.82 mmol) in acetonitrile (2.5 ml), and the mixture was stirred for 15 minutes while warming to room temperature. Then, the mixture was refluxed for 1 hour, cooled to room temperature, and treated with aqueous 10% sodium hydrogen sulfite (30 ml). The precipitated crystals were collected by filtration, washed with water, and dried at 70° C. to give Compound I-20 of the title as yellow crystals (112 mg). The crystals were recrystallized from methanol-ethyl acetate to give Compound I-20 of the title (54.5 mg, 0.161 mmol) as pale yellow crystals in 27% yield; m.p.: 301-302° C. (from methanol ethyl acetate).

NMR (DMSO-$d_6$) δ: 3.70 (3H, s), 4.10 (2H, s), 7.10-7.16 (2H, m), 7.27-7.32 (2H, m), 8.21 (1H, brs), 8.43 (1H, brs), 9.36 (1H, brs), 9.57 (1H, brs).

Elemental Analysis: $C_{19}H_{14}FNO_4$ Calcd. (%): C, 67.25; H, 4.16; F, 5.60; N, 4.13. Found (%): C, 61.23; H, 3.57; F, 5.00; N, 3.94.

Example 10

I-21

5-Bromo-3-(4-fluorobenzyl)-8-hydroxyquinoline-7-carboxylic acid methylester

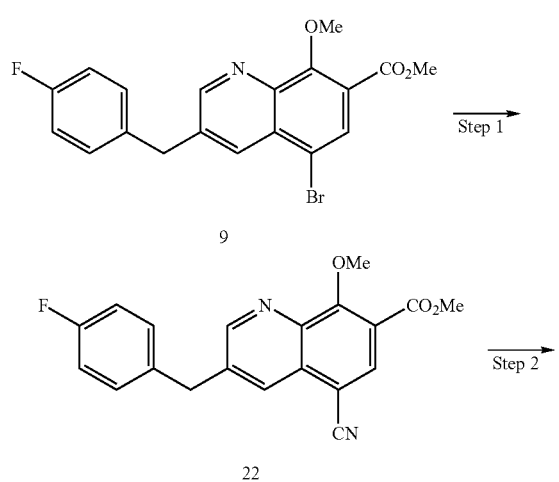

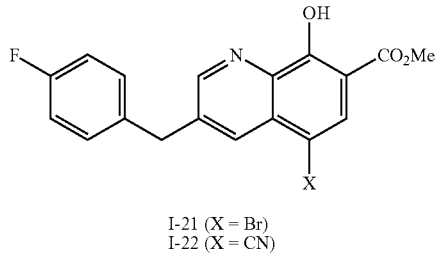

I-21 (X = Br)
I-22 (X = CN)

Step 1

A solution of Compound 9 (800 mg, 1.98 mmol; obtained from Step 1 of Example 1), cupper cyanide (709 mg, 7.92 mmol), tetraethylammonium cyanide (310 mg, 1.98 mmol), tris(dibenzylideneacetone)dipalladium (72.5 mg, 0.079 mmol), 1,1'-bis(diphenylphosphino)ferrocene (176 mg, 0.317 mg) in dioxane (10 ml) was refluxed for 1.5 hours. Tris(dibenzylideneacetone)dipalladium (72.5 mg, 0.079 mmol), and 1,1'-bis(diphenylphosphino)ferrocene (176 mg, 0.317 mg) were added and the mixture was refluxed for 4 hours. The reaction mixture was cooled to room temperature, treated with ethyl acetate (80 ml), and stirred for 20 minutes. The reaction mixture was filtered through Celite. The filtrate was washed with aqueous 10% sodium hydrogen carbonate and brine, and dried over sodium sulfate. The solution was concentrated in vacuo to give a residue, which was subjected to silica gel column chromatography and was eluted with n-hexane-ethyl acetate (3:1 v/v). Fractions containing the desired compound were concentrated in vacuo and recrystallized from diisopropyl ether to give Compound 22 (502 mg, 1.43 mmol) as pale pink crystals in 73% yield.

Step 2

In a manner similar to Step 3 of Example 9, Compound 9 (150 mg, 0.371 mmol; obtained from Step 1 of Example 1) gave Compound I-21 of the title (143 mg, 0.367 mmol) as colorless crystals in 99% yield; m.p.: 152° C. (from 33% acetonitrile-water).

NMR (DMSO-$d_6$) δ: 3.91 (3H, s), 4.30 (2H, s), 7.14-7.20 (2H, m), 7.37-7.42 (2H, m), 8.08 (1H, s), 8.24 (1H, d, J=2.1 Hz), 8.94 (1H, d, J=2.1 Hz), 11.31 (1H, brs).

Elemental Analysis: $C_{18}H_{13}BrFNO_3$ Calcd. (%): C, 55.41; H, 3.36; Br, 20.48; F, 4.87; N, 3.59. Found (%): C, 54.91; H, 3.41; Br, 19.73; F, 5.05; N, 3.65.

Compound I-22

5-Cyano-3-(4-fluorobenzyl)-8-hydroxyquinoline-7-carboxylic acid methylester

In a manner similar to Step 3 of Example 9, Compound 22 (150 mg, 0.428 mmol) gave crude crystals of Compound I-22 of the title, which were recrystallized from ethyl acetate-ethyl ether to afford Compound I-22 of the title (112 mg, 0.333 mmol) as pale pink crystals in 78% yield; m.p.: 178-179° C. (from ethyl acetate-ethyl ether).

NMR (DMSO-$d_6$) δ: 3.91 (3H, s), 4.32 (2H, s), 7.14-7.20 (2H, m), 7.39-7.44 (2H, m), 8.25 (1H, brs), 8.40 (1H, brs), 9.01 (1H, brs).

Elemental Analysis: $C_{19}H_{13}FN_2O_3$ Calcd. (%): C, 67.85; H, 3.90; F, 5.65; N, 8.33. Found (%): C, 67.09; H, 3.95; F, 5.47; N, 8.16.

Example 11

I-23

5-Butyl carbamoyl-3-(4-fluorobenzil)-8-hydroxyquinoline-7-carboxylic acid methyl ester

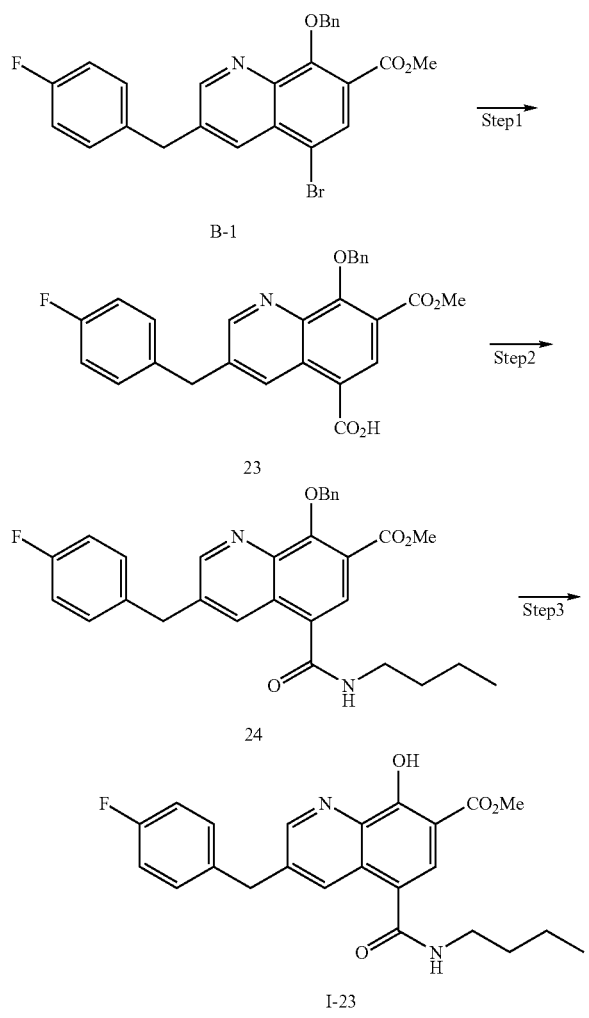

NMR (DMSO-$d_6$) δ: 3.84 (3H, s), 4.26 (2H, s), 5.52 (2H, s), 7.14-7.20 (2H, m), 7.34-7.42 (5H, m), 7.53-7.55 (2H, m), 8.46 (1H, s), 9.02 (1H, d, J=1.8 Hz), 9.20 (1H, m).

Step 2

In a manner similar to Step 1 of Example 2, Compound 23 (250 mg, 0.56 mmol) gave Compound 24 (245 mg, 0.49 mmol) as colorless crystals in 88% yield.

NMR (CDCl$_3$) δ: 0.98 (3H, t, J=7.3 Hz), 1.43 (2H, q, J=7.2 Hz), 1.58-1.68 (2H, m), 3.47 (2H, q, J=6.8 Hz), 3.86 (3H, s), 4.15 (2H, s), 5.49 (2H, s), 6.20 (1H, brs), 6.98-7.03 (2H, m), 7.18-7.22 (2H, m), 7.35-7.40 (3H, m), 7.55-7.57 (2H, m), 7.96 (1H, s), 8.64 (1H, s), 8.83 (1H, s).

Step 3

In a manner similar to Step 7 of Reference Example 1, Compound 24 (245 mg, 0.49 mmol) gave crude of Compound I-23, which were recrystallized from ethanol to give Compound I-23 of the title (143 mg, 0.35 mmol) as colorless crystal in 79% yield.

m.p.: 189-191° C. (from ethanol)

NMR (DMSO-$d_6$) δ: 0.92 (3H, t, J=7.2 Hz), 1.28-1.40 (2H, m), 1.46-1.55 (2H, m), 3.23-3.30 (2H, m), 3.93 (3H, s), 4.22 (2H, s), 7.12-7.18 (2H, m), 7.31-7.36 (2H, m), 7.99 (1H, s), 8.53-8.56 (1H, m), 8.54 (1H, s), 8.90 (1H, d, J=2.0 Hz).

Elemental Analysis: $C_{23}H_{23}FN_2O_4$ Calcd. (%): C, 67.31; H, 5.65; F, 4.63; N, 6.83. Found. (%): C, 67.19; H, 5.38; F, 4.56; N, 6.86.

In a manner similar to Example 11, Compound I-24~I-46 of the title were synthesized.

I-24 ~ I-46

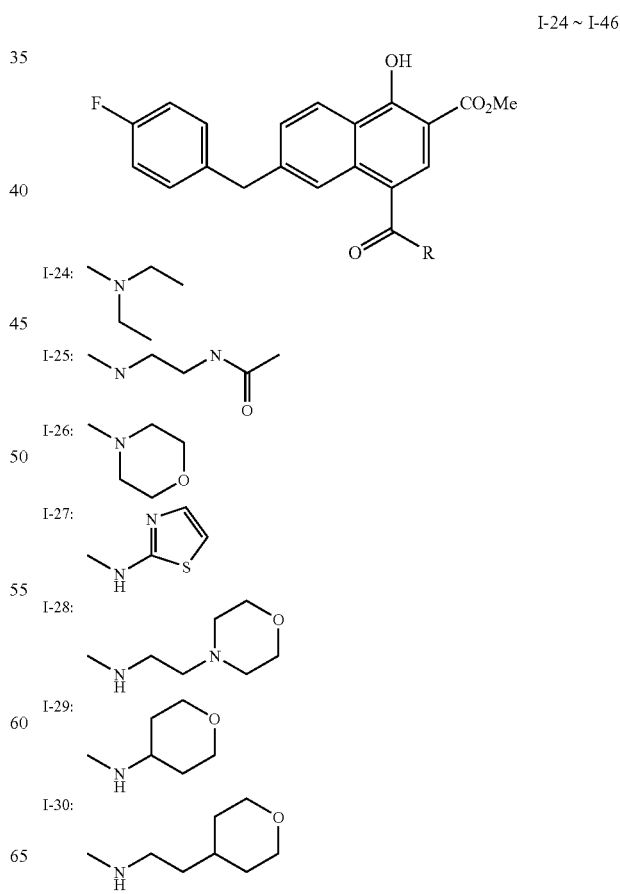

Step 1

To a suspension of the above Compound B-1 (29.25 g, 60.9 mmol), paradium acetete (II) (2.73 g, 12.2 mmol) and 1,3-bis(diphenylphosphino)propane (6.28 g, 15.2 mmol) in dimetylsulphoxide (293 ml) were added triethylamine and water at room temperature. After stirring for 30 minutes at room temperature, the mixture was stirred for an hour under CO atmosphere at 1 atm at room temperature and for 20 hours at 70° C. The reaction mixture was filtered through Celite and the obtained residue was washed with ethylacetate (300 ml). The filtrate was poured into aqueous citric acid and extracted with acetete ethyl. The extract was washed with water twice, brine and dried over anhydrous sodium sulufate. The obtained residue was concentrated in vacuo and washed with methanol and dried at 50° C. to give Compound 23 (20.08 g, 45.1 mmol) as colorless crystal in 74% yield.

-continued

I-31: 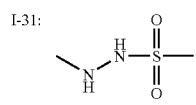

I-32: 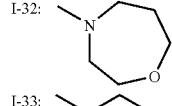

I-33: 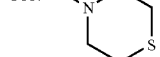

I-34: 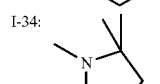

I-35: 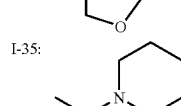

I-36: 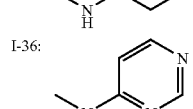

I-37: 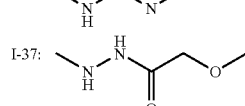

I-38: 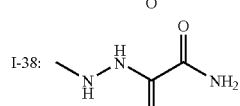

I-39: 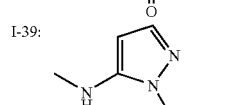

I-40: 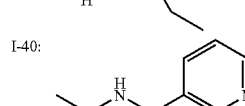

I-41: 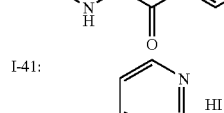

I-42: 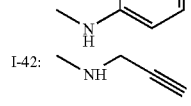

I-43: 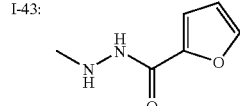

I-44: 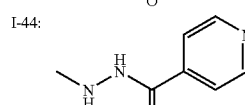

I-45: 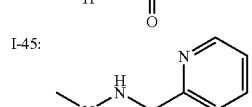

I-46: 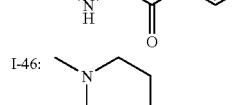

I-24

5-Diethyl carbamoyl-3-(4-fluorobenzyl)-8-hydroxyquinoline-7-carboxylic acid methylester m.p.: 130-131° C. (from ethanol)
NMR (DMSO-$d_6$) δ: 0.85 (3H, brs), 1.09 (3H, brs), 2.99 (2H, brs), 3.46 (2H, brs), 3.91 (3H, s), 4.24 (2H, s), 7.13-7.19 (2H, m), 7.31-7.36 (2H, m), 7.67 (1H, s), 7.69 (1H, d, J=2.2 Hz), 8.94 (1H, d, J=2.0 Hz).
Elemental Analysis: $C_{23}H_{23}FN_2O_4(H_2O)_{0.6}$ Calcd. (%): C, 65.58; H, 5.79; F, 4.51; N, 6.65. Found. (%): C, 65.60; H, 5.37; F, 4.50; N, 6.71.

I-25

5-(2-Acetylaminoethylcarbamoyl)-3-(4-fluorobenzyl)-8-hydroxy-quinoline-7-carboxylic acid methylester m.p.: 251-253° C. (from methanol)
NMR (DMSO-$d_6$) δ: 2.69 (3H, s), 3.93 (3H, s), 4.22 (2H, s), 7.17-7.23 (2H, m), 7.38-7.42 (2H, m), 8.02-8.05 (1H, m), 8.11 (1H, s), 8.63-8.67 (1H, m), 8.70 (1H, d, J=2.0 Hz), 8.94 (1H, d, J=2.0 Hz).
Elemental Analysis: $C_{23}H_{22}FN_3O_5(H_2O)_{0.1}$ Calcd. (%): C, 62.61; H, 5.07; F, 4.31; N, 9.52. Found (%): C, 62.69; H, 4.92; F, 4.27; N, 9.53.

I-26

(4-Fluorobenzyl)-8-hydroxy-5-(morpholine-4-carbonyl)quinoline-7-carboxylic acid methyl ester m.p.: 187-189° C. (from 2-propanol-diisopropyleter)
NMR (DMSO-$d_6$) δ: 3.91 (3H, s), 4.25 (2H, s), 7.14-7.20 (2H, m), 7.35-7.40 (2H, m), 7.75 (1H, s), 7.92 (1H, d, J=1.1 Hz), 8.93 (1H, d, J=1.6 Hz).
Elemental Analysis: $C_{23}H_{21}FN_2O_5$ Calcd. (%): C, 65.09; H, 4.99; F, 4.48; N, 6.60. Found (%): C, 65.07; H, 4.99; F, 4.38; N, 6.60.

I-27

3-(4-Fluorobenzyl)-8-hydroxy-5-(thiazole-2-ylcarbamoyl)quinoline-7-carboxylic acid methyl ester m.p.: 258-259° C. (from ethanol)
NMR (DMSO-$d_6$) δ: 3.94 (3H, s), 4.26 (2H, s), 7.11-7.17 (2H, m), 7.30-7.38 (3H, m), 7.57 (1H, d, J=3.6 Hz), 8.37 (1H, s), 8.75 (1H, s), 8.92 (1H, d, J=2.1 Hz), 12.66 (1H, brs).
Elemental Analysis: $C_{22}H_{16}FN_3O_4S$ Calcd. (%): C, 60.40; H, 3.69; F, 4.34; N, 9.61; S, 7.33. Found (%): C, 60.37; H, 3.78; F, 4.19; N, 9.30; S, 7.07.

I-28

3-(4-Fluorobenzyl)-8-hydroxy-5-(2-morpholine-4-yl-ethyl carbamoyl)-quinoline-7-carboxylic acid methyl ester m.p.: 198-199° C. (from ethanol)
NMR (DMSO-d6) δ: 2.42-2.45 (4H, m), 2.47-2.51 (2H, m), 3.36-3.43 (2H, m), 3.56-3.59 (4H, m), 3.92 (3H, s), 4.22 (2H, s), 7.12-7.18 (2H, m), 7.31-7.36 (2H, m), 8.03 (1H, s), 8.50 (1H, t, J=5.6 Hz), 8.59 (1H, d, J=2.1 Hz), 8.89 (1H, d, J=2.1 Hz).

Elemental Analysis: $C_{25}H_{26}FN_3O_5(H_2O)_{0.3}$ Calcd. (%): C, 63.50; H, 5.67; F, 4.02; N, 8.89. Found (%): C, 63.49; H, 5.56; F, 3.88; N, 8.90.

I-29

3-(4-Fluorobenzyl)-8-hydroxy-5-(tetrahydro-pyran-4-yl carbamoyl)quinoline-7-carboxylic acid methyl ester m.p.: 246-247° C. (from ethanol)

NMR (DMSO-d6) δ: 1.45-1.58 (2H, m), 1.76-1.81 (2H, m), 3.30-3.43 (2H, m), 3.86-3.89 (2H, m), 3.93 (3H, s), 3.96-4.03 (1H, m), 4.22 (2H, s), 7.12-7.18 (2H, m), 7.31-7.37 (2H, m), 7.97 (1H, s), 8.49 (1H, d, J=2.2 Hz), 8.52 (1H, d, J=7.5 Hz), 8.90 (1H, d, J=2.0 Hz).
Elemental Analysis: $C_{24}H_{23}FN_2O_5(H_2O)_{0.1}(EtOH)_{0.1}$ Calcd. (%): C, 65.34; H, 5.39; F, 4.27; N, 6.30. Found (%): C, 65.40; H, 5.32; F, 4.16; N, 6.39.

I-30

3-(4-Fluorobenzyl)-8-hydroxy-5-[2-(tetrahydropyran-4-yl)-ethyl carbamoyl]-quinoline-7-carboxylic acid methyl ester m.p.: 198-199° C. (from ethanol)
NMR (DMSO-d6) δ: 1.16-1.25 (2H, m), 1.44-1.64 (5H, m), 3.21-3.34 (4H, m), 3.81-3.86 (2H, m), 3.91 (3H, s), 4.21 (2H, s), 7.11-7.17 (2H, m), 7.30-7.35 (2H, m), 8.00 (1H, s), 8.52 (1H, t, J=5.8 Hz), 8.56 (1H, d, J=2.2 Hz), 8.86 (1H, d, J=1.9 Hz).
Elemental Analysis: $C_{26}H_{27}FN_2O_5(H_2O)_{0.1}(EtOH)_{0.1}$ Calcd. (%): C, 66.54; H, 5.93; F, 4.02; N, 5.92. Found (%): C, 66.60; H, 5.85; F, 3.85; N, 6.02.

I-31

5-(N'-Methanesulfonylhydrazinocarbonyl)-3-(4-fluorobenzyl)-8-hydroxy-quinoline-7-carboxylic acid methyl ester m.p.: >250° C. (from ethanol)
NMR (DMSO-d6) δ: 3.04 (3H, m), 3.94 (3H, s), 4.23 (2H, s), 7.13-7.18 (2H, m), 7.32-7.36 (2H, m), 8.12 (1H, s), 8.54 (1H, s), 8.94 (1H, d, J=1.9 Hz), 9.69 (1H, d, J=2.7 Hz), 10.79 (1H, d, J=2.7 Hz).
Elemental Analysis: $C_{20}H_{18}FN_3O_6S(H_2O)_{0.2}(EtOH)_{0.2}$ Calcd. (%): C, 53.24; H, 4.29; F, 4.13; N, 9.13; S, 6.97. Found (%): C, 53.26; H, 4.01; F, 4.08; N, 8.99; S, 6.82.

I-32

3-(4-Fluorobenzyl)-8-hydroxy-5-([1,4]oxazepane-4-carbonyl)-quinoline-7-carboxylic acid methyl ester m.p.: 136-137° C. (from 2-propanol)
NMR (DMSO-d6) δ: 1.50 (1H, brs), 1.86-1.91 (1H, m), 3.23-3.26 (3H, m), 3.55 (1H, brs), 3.66-3.69 (1H, m), 3.77 (3H, s), 3.91 (3H, s), 4.24 (2H, s), 7.13-7.19 (2H, m), 7.33-7.37 (2H, m), 7.73 (1H, d, J=4.7 Hz), 7.88 (1H, d, J=16.4 Hz), 8.94 (1H, d, J=2.2 Hz).
Elemental Analysis: $C_{24}H_{23}FN_2O_5(H_2O)_{0.2}(iPrOH)_{0.2}$ Calcd. (%): C, 65.07; H, 5.55; F, 4.18; N, 6.17. Found (%): C, 65.17; H, 5.47; F, 4.14; N, 6.16.

I-33

3-(4-Fluorobenzyl)-8-hydroxy-5-(thiomorpholine-4-carbonyl)-quinoline-7-carboxylic acid methyl ester m.p.: 184-185° C. (from 2-propanol)
NMR (DMSO-d6) δ: 2.20-2.37 (2H, m), 2.69 (2H, brs), 3.78-4.07 (2H, m), 3.91 (3H, s), 4.26 (2H, s), 7.14-7.19 (2H, m), 7.35-7.40 (2H, m), 7.75 (1H, s), 7.88 (1H, d, J=2.0 Hz), 8.94 (1H, d, J=2.1 Hz).
Elemental Analysis: $C_{23}H_{21}FN_2O_4S(H_2O)_{0.1}$ Calcd. (%): C, 62.46; H, 4.83; F, 4.30; N, 6.33; S, 7.25. Found (%): C, 62.42; H, 4.62; F, 4.11; N, 6.23; S, 7.22.

I-34

5-(4,4-Dimethyl-oxazolidine-3-carbonyl)-3-(4-fluoro-benzyl)-8-hydroxy-quinoline-7-carboxylic acid methyl ester m.p.: 149-150° C. (from 2-propanol)
NMR (DMSO-d6) δ: 1.47 (6H, s), 3.76 (2H, s), 3.91 (3H, s), 4.26 (2H, s), 4.49 (1H, brs), 7.15-7.21 (2H, m), 7.33-7.38 (2H, m), 7.76 (2H, s), 8.94 (1H, d, J=1.7 Hz).
Elemental Analysis: $C_{24}H_{23}FN_2O_5(H_2O)_{0.2}(iPrOH)_{0.1}$ Calcd. (%): C, 65.14; H, 5.44; F, 4.24; N, 6.23. Found (%): C, 65.14; H, 5.30; F, 4.08; N, 6.23.

I-35

3-(4-Fluoro-benzyl)-8-hydroxy-5-(piperidine-1-yl-carbamoyl)-quinoline-7-carboxylic acid methyl ester m.p.: 233-234° C. (from ethanol)
NMR (DMSO-d6) δ: 1.32-1.44 (1H, m), 1.56-1.68 (2H, m), 2.72-2.84 (2H, m), 3.92 (3H, s), 4.23 (2H, s), 7.12-7.18 (2H, m), 7.33-7.37 (2H, m), 7.90 (1H, s), 8.39 (1H, s), 8.91 (1H, d, J=1.9 Hz), 9.43 (1H, s).

I-36

3-(4-Fluorobenzyl)-8-hydroxy-5-(pyrimidine-4-yl-carbamoyl)-quinoline-7-carboxylic acid methyl ester m.p.: 241-242° C. (from ethanol)
NMR (DMSO-$d_6$) δ: 3.94 (3H, s), 4.24 (2H, s), 7.10-7.16 (2H, m), 7.33-7.38 (2H, m), 8.21 (1H, dd, J=1.7, 5.8 Hz), 8.29 (1H, s), 8.63 (1H, d, J=1.8 Hz), 8.74 (1H, d, J=5.8 Hz), 8.95 (1H, d, J=2.1 Hz), 11.5 (1H, s).
Elemental Analysis: $C_{23}H_{17}FN_4O_4$ Calcd. (%): C, 63.89; H, 3.96; F, 4.39; N, 12.96. Found (%): C, 63.73; H, 4.35; F, 4.24; N, 12.88.

I-37

3-(4-Fluorobenzyl)-8-hydroxy-5-[N'-(2-methoxy-acetyl)-hydrazinocarbonyl]-quinoline-7-carboxylic acid methyl ester m.p.: 181-182° C. (from ethanol-ether)
NMR (DMSO-d6) δ: 3.94 (3H, s), 4.01 (2H, s), 4.22 (2H, s), 7.12-7.18 (2H, m), 7.32-7.36 (2H, m), 8.15 (1H, s), 8.68 (1H, d, J=1.8 Hz), 8.92 (1H, d, J=2.0 Hz), 9.98 (1H, s), 10.38 (1H, s).

I-38

5-(N'-Aminooxalylhydrazinocarbonyl)-3-(4-fluorobenzyl)-8-hydroxyquinoine-7-carboxylic acid methyl ester m.p.: 233-234° C. (from ethanol-ether)

NMR (DMSO-d6) δ: 3.94 (3H, s), 4.22 (2H, s), 7.12-7.18 (2H, m), 7.32-7.35 (2H, m), 7.94 (1H, s), 8.15 (1H, s), 8.24 (1H, s), 8.68 (1H, d, J=2.0 Hz), 8.92 (1H, d, J=2.0 Hz), 10.51 (1H, s), 10.67 (1H, s).

Elemental Analysis: $C_{21}H_{17}FN_4O_6(H_2O)_{0.4}(EtOH)_{0.3}$ Calcd. (%): C, 56.23; H, 4.28; F, 4.12; N, 12.14. Found (%): C, 56.19; H, 3.95; F, 4.16; N, 11.88.

I-39

5-(2-Ethyl-2H-pyrazole-3-yl-carbamoyl)-3-(4-fluorobenzyl)-8-hydroxyquinoine-7-carboxylic acid methyl ester m.p.: 219-220° C. (from ethanol)

NMR (DMSO-$d_6$) δ: 1.30 (3H, t, J=7.2 Hz), 3.95 (3H, s), 4.03 (2H, q, J=7.2 Hz), 4.24 (2H, s), 6.29 (1H, s), 7.12-7.18 (2H, m), 7.33-7.38 (2H, m), 7.44 (1H, d, J=2.1 Hz), 8.27 (1H, s), 8.59 (1H, d, J=1.8 Hz), 8.95 (1H, d, J=1.8 Hz), 11.57 (1H, brs).

Elemental Analysis: $C_{24}H_{21}FN_4O_4$ Calcd. (%): C, 64.28; H, 4.72; F, 4.24; N, 12.49. Found (%): C, 64.24; H, 4.49; F, 4.11; N, 12.63.

I-40

3-(4-Fluorobenzyl)-8-hydroxy-5-[N'-(pyridine-3-carbonyl)-hydrazinocarbonyl]-quinoline-7-carboxylic acid methyl ester m.p.: 184-185° C. (from ethanol-ether)

NMR (DMSO-d6) δ: 3.96 (3H, s), 4.24 (2H, s), 7.12-7.18 (2H, m), 7.33-7.38 (2H, m), 7.71-7.76 (1H, m), 8.25 (1H, s), 8.44-8.47 (1H, m), 8.73 (1H, d, J=2.0 Hz), 8.82-8.92 (1H, m), 8.96 (1H, d, J=2.0 Hz), 9.14-9.21 (1H, m), 10.70 (1H, s), 10.95 (1H, s).

I-41

3-(4-Fluoro-benzyl)-8-hydroy-5-(pyridine-4-ylcarbamoyl)quinoline-7-carboxylic acid methyl ester m.p.: 266-267° C. (from ethanol)

NMR (DMSO-d6) δ: 3.94 (3H, s), 4.25 (2H, s), 7.12-7.18 (2H, m), 7.34-7.37 (2H, m), 8.20 (2H, d, J=7.2 Hz), 8.38 (1H, s), 8.66 (1H, d, J=2.1 Hz), 8.76 (2H, d, J=7.2 Hz), 8.98 (1H, d, J=2.1 Hz), 11.74 (1H, s).

Elemental Analysis: $C_{24}H_{19}F_1N_3O_4$ Calcd. (%): C, 51.54; H, 3.42; F, 3.40; N, 7.51. Found (%): C, 51.33; H, 3.54; F, 2.80; N, 7.69.

I-42

3-(4-Fluorobenzyl)-8-hydroxy-5-prop-2-ynylcarbamoylquinoline-7-carboxylic acid methyl ester m.p.: 192-193° C. (from ethanol)

NMR (DMSO-d6) δ: 3.18 (1H, t, J=2.4 Hz), 3.94 (3H, s), 4.09 (2H, q, J=2.7 Hz), 4.22 (2H, s), 7.12-7.18 (2H, m), 7.32-7.35 (2H, m), 8.07 (1H, s), 8.66 (1H, d, J=2.0 Hz), 8.91 (1H, d, J=2.1 Hz), 9.04-9.08 (1H, m).

Elemental Analysis: $C_{22}H_{17}FN_2O_4(H_2O)_{1.2}$ Calcd. (%): C, 63.83; H, 4.72; F, 4.59; N, 6.77. Found (%): C, 63.66; H, 4.16; F, 4.99; N, 6.75.

I-43

3-(4-Fluorobenzyl)-5-[N'-(furan-2-carbonyl)-hydrazinocarbonyl]-8-hydroxyquinoline-7-carboxylic acid methyl ester m.p.: 207-210° C. (from 85% acetone/water)

NMR (DMSO-$d_6$) δ: 3.95 (3H, s), 4.23 (2H, s), 6.71 (1H, s), 7.12-7.18 (2H, m), 7.29-7.37 (3H, m), 7.96 (1H, s), 8.20 (1H, s), 8.70 (1H, d, J=2.1 Hz), 8.94 (1H, d, J=2.1 Hz).

Elemental Analysis: $C_{24}H_{18}FN_{36}(H_2O)_{0.25}$ Calcd. (%): C, 61.60; H, 3.99; F, 4.06; N, 8.98. Found (%): C, 61.72; H, 3.99; F, 3.80; N, 8.61.

I-44

3-(4-Fluorobenzyl)-8-hydroxy-5-[N'-(pyridine-4-carbonyl)-hydrazinocarbonyl]-quinoline-7-carboxylic acid methyl ester (from ethyl acetate-ethyl ether)

NMR (DMSO-$d_6$) δ: 3.96 (3H, s), 4.24 (2H, s), 7.12-7.18 (2H, m), 7.32-7.37 (2H, m), 7.86 (2H, dd, J=4.5 Hz, 1.5 Hz), 8.24 (1H, s), 8.71 (1H, d, J=2.1 Hz), 8.81 (2H, dd, J=4.5 Hz, 1.5 Hz), 8.95 (1H, d, J=2.1 Hz), 10.69 (1H, s), 11.94 (1H, s).

I-45

3-(4-Fluorobenzyl)-8-hydroxy-5-[N'-(pyridine-2-carbonyl)-hydrazinocarbonyl]-quinoline-7-carboxylic acid methyl ester m.p.: 164-166° C. (from 85% acetone/water)

NMR (DMSO-$d_6$) δ: 3.96 (3H, s), 4.23 (2H, s), 7.11-7.17 (2H, m), 7.32-7.38 (2H, m), 7.67-7.71 (1H, m), 8.04-8.12 (2H, m), 8.21 (1H, s), 8.74 (2H, s), 8.93 (1H, d, J=1.8 Hz), 10.61 (1H, s), 10.70 (1H, s).

Elemental Analysis: $C_{25}H_{19}FN_4O_5(H_2O)_{0.5}$ Calcd. (%): C, 62.11; H, 4.17; F, 3.93; N, 11.59. Found (%): C, 62.01; H, 4.04; F, 3.80; N, 11.31.

I-46

5-(4-Carbamoylpiperidine-1-carbonyl)-3-(4-fluorobenzyl)-8-hydroxyquinoline-7-carboxylic acid methyl ester m.p.: 235-238° C. (from ethyl acetate)

NMR (DMSO-$d_6$) δ: 1.53 (2H, brs), 1.83 (1H, brs), 2.35 (1H, brs), 2.87 (2H, brs), 3.27 (2H, brs), 3.91 (3H, s), 4.24 (2H, s), 4.52 (1H, brs), 6.86 (1H, brs), 7.13-7.19 (2H, m), 7.31 (1H, m), 7.38 (2H, brs), 7.71 (1H, brs), 7.89 (1H, s), 8.94 (1H, s), 11.45 (1H, brs).

---

Elemental Analysis: $C_{22}H_{20}FN_3O_6(H_2O)_{0.1}$ Calcd. (%): C, 59.62; H, 4.59; F, 4.29; N, 9.48. Found (%): C, 59.55; H, 4.37; F, 4.26; N, 9.43.

Elemental Analysis: $C_{25}H_{24}FN_3O_5(H_2O)_{0.5}$ Calcd. (%): C, 63.28; H, 5.31; F, 4.00; N, 8.86. Found (%): C, 63.14; H, 5.24; F, 3.88; N, 8.74.

Example 12

I-47

3-(4-Fluorobenzyl)-8-hydroxy-5-(2,2,2-trifluoroethylcarbamoyl)quinoline-7-carboxylic acid methyl ester

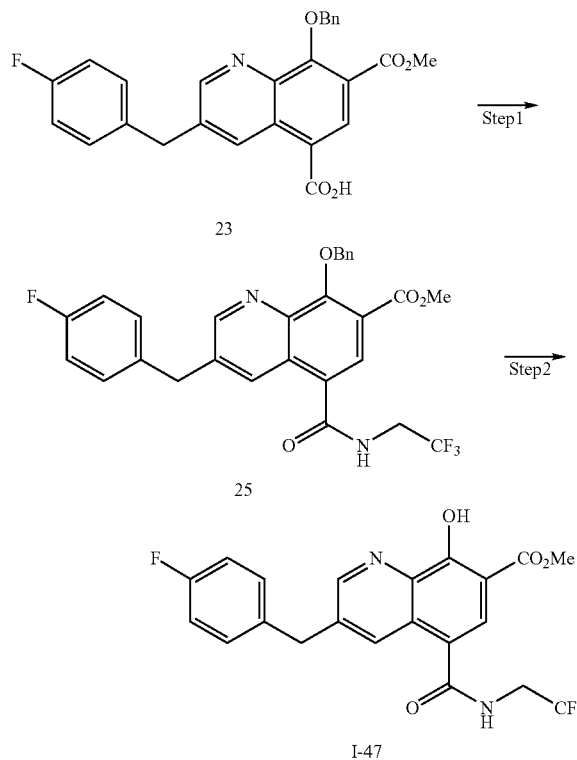

Step 1

In a manner similar to Step 1 of Example 2, Compound 23 (300 mg, 0.67 mmol) gave Compound 25 (237 mg, 0.45 mmol) as colorless crystals in 67% yield.

NMR (CDCl$_3$) δ: 3.86 (3H, s), 3.94-4.05 (2H, m), 4.12 (2H, s), 5.45 (2H, s), 6.74-6.78 (1H, m), 6.99-7.04 (2H, m), 7.18-7.23 (2H, m), 7.32-7.42 (3H, m), 7.53-7.56 (2H, m), 7.95 (1H, s), 8.51 (1H, d, J=2.3 Hz), 8.77 (1H, d, J=2.1 Hz).

Step 2

To a suspension of Compound 25 (237 mg, 0.45 mmol) in methanol (12 ml)-ethyl acetate, 10% Palladium carbon (23 mg) was added and stirred under ice-cooling for 2 hours under hydrogen atomosphere at 1 atm. The reaction mixture is filtered through Celite and the filtrate was concentrated in vacuo. The residue was recrystallized from ethanol to give Compound I-101 (118 mg, 0.27 mmol) of the title as colorless crystals in 61% yield.

m.p.: 211-212° C. (from ethanol)

NMR (DMSO-d$_6$) δ: 3.93 (3H, s), 4.06-4.17 (2H, m), 4.22 (2H, s), 7.12-7.18 (2H, m), 7.31-7.36 (2H, m), 8.11 (1H, s), 8.57 (1H, d, J=2.0 Hz), 8.92 (1H, d, J=2.1 Hz), 9.25 (1H, t, J=6.5 Hz).

Elemental Analysis: $C_{21}H_{16}F_4N_2O_4(H_2O)_{0.1}$ Calcd. (%): C, 57.56; H, 3.73; F, 17.34; N, 6.39. Found. (%): C, 57.65; H, 3.72; F, 17.32; N, 6.63.

In a manner similar to Example 12, Compound I-48~I-83 of the title were synthesized.

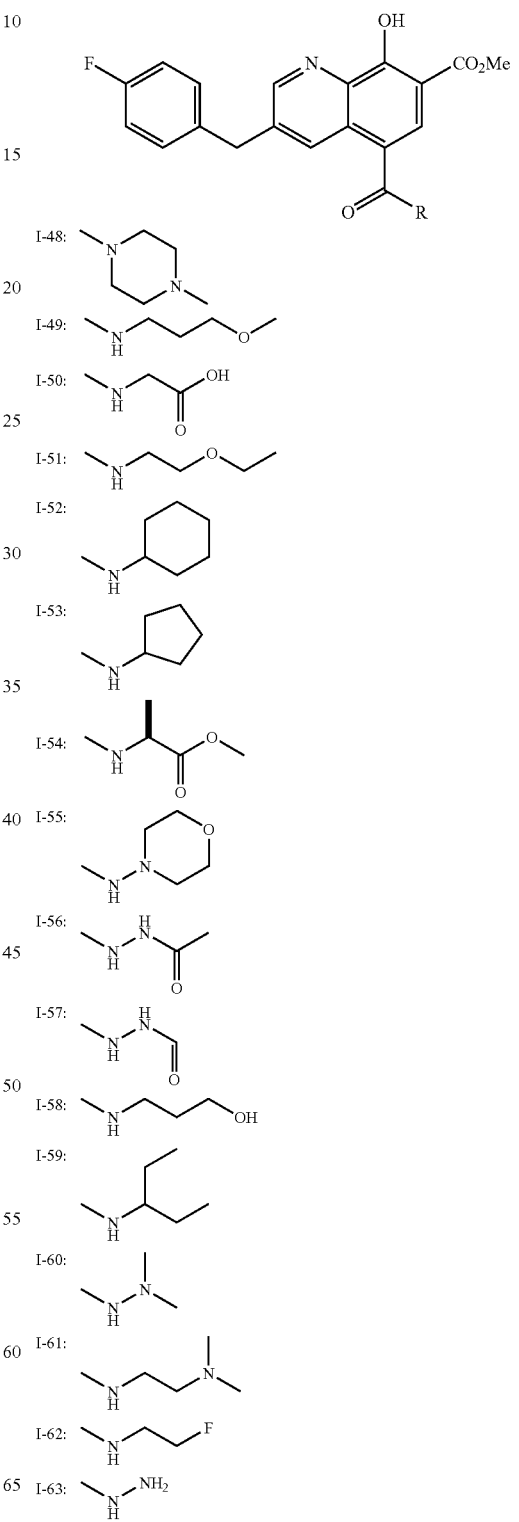

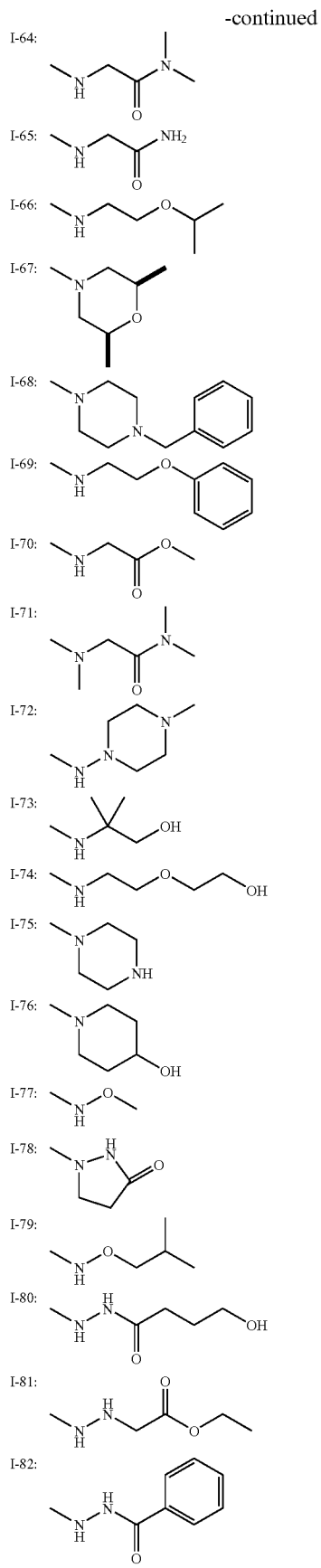

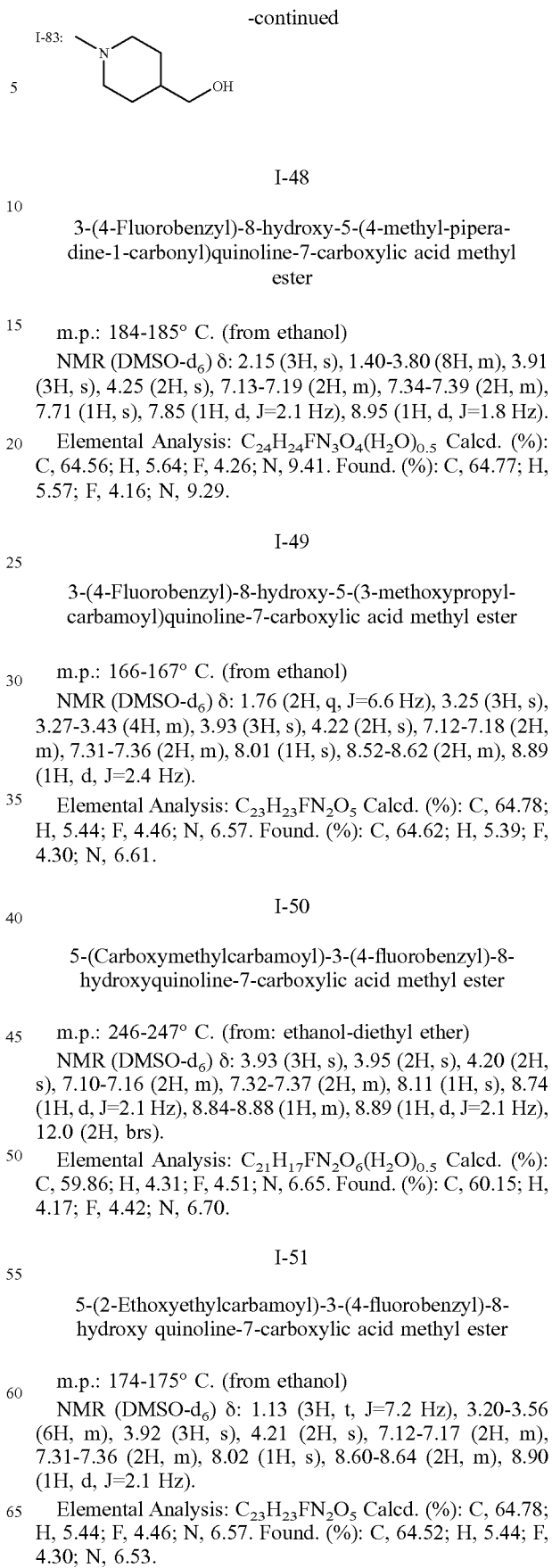

I-48

3-(4-Fluorobenzyl)-8-hydroxy-5-(4-methyl-piperadine-1-carbonyl)quinoline-7-carboxylic acid methyl ester m.p.: 184-185° C. (from ethanol)

NMR (DMSO-$d_6$) δ: 2.15 (3H, s), 1.40-3.80 (8H, m), 3.91 (3H, s), 4.25 (2H, s), 7.13-7.19 (2H, m), 7.34-7.39 (2H, m), 7.71 (1H, s), 7.85 (1H, d, J=2.1 Hz), 8.95 (1H, d, J=1.8 Hz).

Elemental Analysis: $C_{24}H_{24}FN_3O_4(H_2O)_{0.5}$ Calcd. (%): C, 64.56; H, 5.64; F, 4.26; N, 9.41. Found. (%): C, 64.77; H, 5.57; F, 4.16; N, 9.29.

I-49

3-(4-Fluorobenzyl)-8-hydroxy-5-(3-methoxypropylcarbamoyl)quinoline-7-carboxylic acid methyl ester m.p.: 166-167° C. (from ethanol)

NMR (DMSO-$d_6$) δ: 1.76 (2H, q, J=6.6 Hz), 3.25 (3H, s), 3.27-3.43 (4H, m), 3.93 (3H, s), 4.22 (2H, s), 7.12-7.18 (2H, m), 7.31-7.36 (2H, m), 8.01 (1H, s), 8.52-8.62 (2H, m), 8.89 (1H, d, J=2.4 Hz).

Elemental Analysis: $C_{23}H_{23}FN_2O_5$ Calcd. (%): C, 64.78; H, 5.44; F, 4.46; N, 6.57. Found. (%): C, 64.62; H, 5.39; F, 4.30; N, 6.61.

I-50

5-(Carboxymethylcarbamoyl)-3-(4-fluorobenzyl)-8-hydroxyquinoline-7-carboxylic acid methyl ester m.p.: 246-247° C. (from: ethanol-diethyl ether)

NMR (DMSO-$d_6$) δ: 3.93 (3H, s), 3.95 (2H, s), 4.20 (2H, s), 7.10-7.16 (2H, m), 7.32-7.37 (2H, m), 8.11 (1H, s), 8.74 (1H, d, J=2.1 Hz), 8.84-8.88 (1H, m), 8.89 (1H, d, J=2.1 Hz), 12.0 (2H, brs).

Elemental Analysis: $C_{21}H_{17}FN_2O_6(H_2O)_{0.5}$ Calcd. (%): C, 59.86; H, 4.31; F, 4.51; N, 6.65. Found. (%): C, 60.15; H, 4.17; F, 4.42; N, 6.70.

I-51

5-(2-Ethoxyethylcarbamoyl)-3-(4-fluorobenzyl)-8-hydroxy quinoline-7-carboxylic acid methyl ester m.p.: 174-175° C. (from ethanol)

NMR (DMSO-$d_6$) δ: 1.13 (3H, t, J=7.2 Hz), 3.20-3.56 (6H, m), 3.92 (3H, s), 4.21 (2H, s), 7.12-7.17 (2H, m), 7.31-7.36 (2H, m), 8.02 (1H, s), 8.60-8.64 (2H, m), 8.90 (1H, d, J=2.1 Hz).

Elemental Analysis: $C_{23}H_{23}FN_2O_5$ Calcd. (%): C, 64.78; H, 5.44; F, 4.46; N, 6.57. Found. (%): C, 64.52; H, 5.44; F, 4.30; N, 6.53.

I-52

5-Cyclohexylcarbamoyl-3-(4-fluorobenzyl)-8-hydroxyquinoline-7-carboxylic acid methyl ester m.p.: 212-213° C. (from ethanol)

NMR (DMSO-$d_6$) δ: 1.02-1.85 (8H, m), 3.32 (2H, s), 3.68-3.84 (1H, m), 3.92 (3H, s), 4.22 (2H, s), 7.12-7.18 (2H, m), 7.31-7.36 (2H, m), 7.94 (1H, s), 8.39 (1H, d, J=7.8 Hz), 8.45 (1H, d, J=2.1 Hz), 8.89 (1H, d, J=1.8 Hz), 11.38 (1H, brs).

Elemental Analysis: $C_{25}H_{25}FN_2O_4$ Calcd. (%): C, 68.79; H, 5.77; F, 4.35; N, 6.42. Found. (%): C, 68.77; H, 5.76; F, 4.22; N, 6.55.

I-53

5-Cyclopentylcarbamoyl-3-(4-fluorobenzyl)-8-hydroxyquinoline-7-carboxylic acid methyl ester m.p.: 221-222° C. (from ethanol)

NMR (DMSO-$d_6$) δ: 1.42-1.74 (6H, m), 1.82-1.96 (2H, m), 3.93 (3H, s), 4.22 (2H, s), 4.15-4.31 (1H, m), 7.12-7.18 (2H, m), 7.32-7.37 (2H, m), 7.95 (1H, s), 8.48-8.51 (2H, m), 8.90 (1H, d, J=1.8 Hz), 11.34 (1H, brs).

Elemental Analysis: $C_{24}H_{23}FN_2O_4$ Calcd. (%): C, 68.23; H, 5.49; F, 4.50; N, 6.63. Found. (%): C, 68.25; H, 5.50; F, 4.36; N, 6.75.

I-54

(4-Fluorobenzyl)-8-hydroxy-5-(1-methoxycarbonylethylcarbamoyl)quinoline-7-carboxylic acid methyl ester m.p.: 157-158° C. (from ethanol)

NMR (DMSO-$d_6$) δ: 1.39 (3H, d, J=7.4 Hz), 3.67 (3H, s), 3.93 (3H, s), 4.21 (2H, s), 4.44-4.53 (1H, m), 7.11-7.17 (2H, m), 7.31-7.36 (2H, m), 8.08 (1H, s), 8.58 (1H, d, J=2.0 Hz), 8.90 (1H, d, J=2.2 Hz), 8.98 (1H, d, J=6.9 Hz).

Elemental Analysis: $C_{23}H_{21}FN_2O_6$ Calcd. (%): C, 62.72; H, 4.81; F, 4.31; N, 6.36. Found. (%): C, 62.06; H, 4.87; F, 4.35; N, 6.27.

I-55

3-(4-Fluorobenzyl)-8-hydroxy5-(morpholine-4-ylcarbamoyl)quinoline-7-carboxylic acid methyl ester m.p.: >250° C. (from ethanol)

NMR (DMSO-d6) δ: 2.60 (4H, brs), 3.42 (4H, brs), 3.59 (3H, s), 3.92 (2H, s), 6.89-6.95 (2H, m), 7.09 (2H, m), 7.74 (1H, s), 8.23 (1H, s), 8.43 (1H, brs), 9.03 (1H, brs).

I-56

5-(N'-Acetyl-hydrazinocarbonyl)-3-(4-fluorobenzyl)-8-hydroxyquinoline-7-carboxylic acid methyl ester m.p.: 208-209° C. (from methanol-ethyl acetate)

NMR (DMSO-d6) δ: 1.95 (3H, s), 3.94 (3H, s), 4.21 (2H, s), 7.12-7.18 (2H, m), 7.32-7.35 (2H, m), 8.13 (1H, s), 8.68 (1H, d, J=1.7 Hz), 8.92 (1H, d, J=2.1 Hz), 9.97 (1H, s), 10.32 (1H, s).

Elemental Analysis: $C_{21}H_{18}FN_3O_5(H_2O)_{0.6}$ Calcd. (%): C, 59.74; H, 4.58; F, 4.50; N, 9.95. Found. (%): C, 59.70; H, 4.20; F, 4.32; N, 10.07.

I-57

5-(N'-Formylhydrazinocarbonyl)-3-(4-fluorobenzyl)-8-hydroxyquinoline-7-carboxylic acid methyl ester m.p.: 249-250° C. (from ether)

NMR (DMSO-d6) δ: 3.94 (3H, s), 4.22 (2H, s), 7.11-7.17 (2H, m), 7.32-7.37 (2H, m), 8.15 (1H, s), 8.12-8.18 (1H, m), 8.65 (1H, s), 8.93 (1H, d, J=1.9 Hz), 10.15 (1H, s), 10.48 (1H, s).

Elemental Analysis: $C_{20}H_{16}FN_3O_5(H_2O)_{0.3}$ Calcd. (%): C, 59.64; H, 4.15; F, 4.72; N, 10.43. Found. (%): C, 59.55; H, 3.91; F, 4.47; N, 10.48.

I-58

3-(4-Fluorobenzyl)-8-hydroxy-5-(3-hydroxypropylcarbamoyl)quinoline-7-carboxylic acid methyl ester m.p.: 167-168° C. (from ethanol)

NMR (DMSO-$d_6$) δ: 1.69 (2H, quin, J=6.9 Hz), 3.10-3.60 (4H, m), 3.93 (3H, s), 4.22 (2H, s), 4.50 (1H, s), 7.12-7.18 (2H, m), 7.32-7.37 (2H, m), 8.01 (1H, s), 8.55 (1H, t, J=5.4 Hz), 8.59 (1H, d, J=1.8 Hz), 8.89 (1H, d, J=1.8 Hz), 11.60 (1H, brs).

Elemental Analysis: $C_{23}H_{23}FN_2O_4$ Calcd. (%): C, 64.07; H, 5.13; F, 4.61; N, 6.79. Found. (%): C, 63.96; H, 4.96; F, 4.44; N, 6.99.

I-59

5-Dimethylcarbamoyl-3-(4-fluorobenzyl)-8-hydroxyquinoline-7-carboxylic acid methyl ester m.p.: 219-220° C. (from ethanol)

NMR (DMSO-$d_6$) δ: 0.87 (6H, t, J=7.2 Hz), 1.32-1.62 (4H, m), 3.70-3.84 (1H, m), 3.93 (3H, s), 4.22 (2H, s), 7.11-7.17 (2H, m), 7.30-7.35 (2H, m), 7.94 (1H, s), 8.22 (1H, d, J=8.7 Hz), 8.38 (1H, d, J=2.1 Hz), 8.91 (1H, d, J=2.1 Hz), 11.45 (1H, brs).

Elemental Analysis: $C_{24}H_{25}FN_2O_4$ Calcd. (%): C, 67.91; H, 5.94; F, 4.48; N, 6.60. Found. (%): C, 67.86; H, 6.31; F, 4.37; N, 6.71.

I-60

5-(N',N'-Dimethylhydrazinocarbonyl)-3-(4-fluorobenzyl)-8-hydroxyquinoline-7-carboxylic acid methyl ester m.p.: 198-199° C. (from 2-propanol)

NMR (DMSO-d6) δ: 2.57 (6H, s), 3.93 (3H, s), 4.24 (2H, s), 7.13-7.19 (2H, m), 7.33-7.38 (2H, m), 7.92 (1H, s), 8.42 (1H, s), 8.91 (1H, d, J=2.1 Hz), 9.46 (1H, s).

Elemental Analysis: $C_{21}H_{20}FN_3O_4(H_2O)_{0.1}(iPrOH)_{0.1}$ Calcd. (%): C, 63.13; H, 5.22; F, 4.69; N, 10.37. Found. (%): C, 63.22; H, 5.09; F, 4.61; N, 10.42.

I-61

5-(2-Dimethylaminoethylcarbamoyl)-3-(4-fluorobenzyl)-8-hydroxyquinoline-7-carboxylic acid methyl ester m.p.: 115-116° C. (from ethyl acetate)

NMR (DMSO-d6) δ: 2.79 (6H, s), 3.22-3.25 (2H, m), 3.63 (2H, q, J=5.6 Hz), 3.93 (3H, s), 4.23 (2H, s), 7.11-7.19

(2H, m), 7.32-7.37 (2H, m), 8.15 (1H, s), 8.70 (1H, d, J=2.1 Hz), 8.80-8.84 (1H, m), 8.91 (1H, d, J=2.1 Hz).

Elemental Analysis: $C_{23}H_{24}FN_3O_4(HCl)_{0.9}(H_2O)_{1.2}$ Calcd. (%): C, 57.56; H, 5.73; F, 3.96; N, 8.76; Cl, 6.65. Found. (%): C, 57.57; H, 5.63; F, 3.75; N, 8.82; Cl, 6.81.

I-62

3-(4-Fluorobenzyl)-5-(fluoroethylcarbamoyl)-8-hydroxyquinoline-7-carboxylic acid methyl ester m.p.: 216-217° C. (from ethanol)

NMR (DMSO-d6) δ: 3.54 (1H, q, J=5.2 Hz), 3.63 (1H, q, J=5.2 Hz), 3.93 (3H, s), 4.22 (2H, s), 4.49 (1H, t, J=5.1 Hz), 4.65 (1H, t, J=5.1 Hz), 7.12-7.19 (2H, m), 7.32-7.37 (2H, m), 8.06 (1H, s), 8.63 (1H, d, J=2.0 Hz), 8.81-8.85 (1H, m), 8.90 (1H, d, J=2.1 Hz).

Elemental Analysis: $C_{21}H_{18}F_2N_2O_4(H_2O)_{0.1}$ Calcd. (%): C, 62.71; H, 4.56; F, 9.45; N, 6.97. Found. (%): C, 62.78; H, 4.53; F, 9.33; N, 6.98.

I-63

3-(4-Fluorobenzyl)-5-hydrazinocarbonyl-8-hydroxyquinoline-7-carboxylic acid methyl ester m.p.: 156-157° C. (from ethanol)

NMR (DMSO-d6) δ: 3.92 (3H, s), 4.22 (2H, s), 7.11-7.19 (2H, m), 7.30-7.36 (2H, m), 8.00 (1H, s), 8.61 (1H, d, J=2.0 Hz), 8.90 (1H, d, J=2.0 Hz), 9.76 (1H, brs).

Elemental Analysis: $C_{19}H_{16}FN_3O_4(EtOH)_{0.1}$ Calcd. (%): C, 61.67; H, 4.47; F, 5.08; N, 11.24. Found. (%): C, 62.18; H, 4.51; F, 4.96; N, 10.83.

I-64

5-(Dimethylcarbamoylmethylcarbamoyl)-3-(4-fluorobenzyl)-8-hydroxyquinoline-7-carboxylic acid methyl ester m.p.: 198-199° C. (from etanol)

NMR (DMSO-$d_6$) δ: 2.89 (3H, s), 3.03 (3H, s), 3.93 (3H, s), 4.13 (2H, d, J=5.7 Hz), 4.20 (2H, s), 7.11-7.17 (2H, m), 7.33-7.37 (2H, m), 8.12 (1H, s), 8.63 (1H, t, J=6.0 Hz), 8.75 (1H, d, J=2.1 Hz), 8.89 (1H, d, J=2.1 Hz), 11.49 (1H, brs).

Elemental Analysis: $C_{23}H_{22}FN_3O_5$ Calcd. (%): C, 62.86; H, 5.05; F, 4.32; N, 9.56. Found. (%): C, 62.80; H, 4.95; F, 4.25; N, 9.65.

I-65

5-(Carbamoylmethylcarbamoyl)-3-(4-fluorobenzyl)-8-hydroxyquinoline-7-carboxylic acid methyl ester m.p.: 247-248° C. (from ethanol)

(DMSO-$d_6$) δ: 3.85 (2H, d, J=6.0 Hz), 3.93 (3H, s), 4.21 (2H, s), 7.10 (1H, s), 7.11-7.17 (2H, m), 7.33-7.37 (2H, m), 7.47 (1H, s), 8.14 (1H, s), 8.73 (1H, t, J=6.0 Hz), 8.78 (1H, d, J=2.1 Hz), 8.89 (1H, d, J=2.1 Hz).

Elemental Analysis: $C_{21}H_{18}FN_3O_5(H_2O)_{0.25}$ Calcd. (%): C, 60.65; H, 4.48; F, 4.57; N, 10.10. Found. (%): C, 60.57; H, 4.42; F, 4.49; N, 10.23.

I-66

3-(4-Fluorobenzyl)-8-hydroxy-5-(2-isopropoxyethylcarbamoyl)quinoline-7-carboxylic acid methyl ester m.p.: 175-176° C. (from ethanol)

(DMSO-$d_6$) δ: 1.10 (6H, d, J=6.1 Hz), 3.39 (2H, q, J=6.3 Hz), 3.51 (2H, t, J=6.3 Hz), 3.59 (1H, sept, J=6.1 Hz), 3.92 (3H, s), 4.22 (2H, s), 7.11-7.17 (2H, m), 7.31-7.36 (2H, m), 8.03 (1H, s), 8.59-8.60 (2H, m), 8.89 (1H, d, J=2.1 Hz).

Elemental Analysis: $C_{24}H_{25}FN_2O_5$ Calcd. (%): C, 65.44; H, 5.72; F, 4.31; N, 6.36. Found. (%): C, 65.16; H, 5.76; F, 4.28; N, 6.50.

I-67

5-(2,6-Dimethylmorphone-4-carbonyl)-3-(4-fluorobenzyl)-8-hydroxyquinoline-7-carboxylic acid methyl ester m.p.: 183-184° C. (from ethanol)

(DMSO-$d_6$) δ: 0.60-1.50 (4H, m), 2.42-4.42 (8H, m), 3.90 (3H, s), 4.24 (2H, s), 7.13-7.19 (2H, m), 7.33-7.38 (2H, m), 7.73 (1H, s), 7.85 (1H, s), 8.93 (1H, s), 11.35 (1H, brs).

Elemental Analysis: $C_{23}H_{23}FN_2O_4$ Calcd. (%): C, 66.36; H, 5.57; F, 4.20; N, 6.19. Found. (%): C, 66.06; H, 5.76; F, 4.11; N, 6.33.

I-68

5-(4-Methylpiperadine-1-carbonyl)-3-(4-fluorobenzyl)-8-hydroxyquinoline-7-carboxylic acid methyl ester m.p.: 148-149° C. (from ethanol)

(DMSO-$d_6$) δ: 3.44 (2H, s), 3.91 (3H, s), 4.25 (2H, s), 7.16-7.40 (9H, m), 7.71 (1H, s), 7.85 (1H, d, J=2.1 Hz), 8.95 (1H, d, J=2.1 Hz), 11.07 (1H, brs).

Elemental Analysis: $C_{30}H_{28}FN_3O_4(H_2O)_{0.5}$ Calcd. (%): C, 68.95; H, 5.59; F, 3.64; N, 8.04. Found. (%): C, 68.57; H, 5.72; F, 3.68; N, 8.27.

I-69

3-(4-Fluorobenzyl)-8-hydroxy-5-(2-phenoxyethylcarbamoyl)quinoline-7-carboxylic acid methyl ester m.p.: 194-195° C. (from ethanol)

(DMSO-$d_6$) δ: 3.66 (2H, q, J=5.7 Hz), 3.91 (3H, s), 4.15 (2H, t, J=5.7 Hz), 4.19 (2H, s), 6.94-6.99 (3H, m), 7.09-7.15 (2H, m), 7.27-7.33 (4H, m), 8.05 (1H, s), 8.62 (1H, d, J=2.1 Hz), 8.80 (1H, t, J=5.1 Hz), 8.88 (1H, d, J=2.1 Hz).

Elemental Analysis: $C_{27}H_{23}FN_2O_5$ Calcd. (%): C, 68.35; H, 4.89; F, 4.00; N, 5.90. Found. (%): C, 68.38; H, 4.93; F, 3.94; N, 5.76.

I-70

3-(4-Fluorobenzyl)-8-hydroxy-5-(methoxycarbonylmethylcarbamoyl)quinoline-7-carboxylic acid methyl ester m.p.: 209-210° C. (from ethanol)

(DMSO-$d_6$) δ: 3.69 (3H, s), 3.93 (3H, s), 4.04 (2H, d, J=5.7 Hz), 4.21 (2H, s), 7.11-7.17 (2H, m), 7.31-7.36 (2H, m), 8.12 (1H, s), 8.67 (1H, d, J=2.1 Hz), 8.90 (1H, d, J=2.1 Hz), 9.03 (1H, t, J=5.7 Hz), 11.40 (1H, brs).

I-71

5-(Dimethylcarbamoylmethylmethylcarbamoyl)-3-(4-fluorobenzyl)-8-hydroxyquinoline-7-carboxylic acid methyl ester m.p.: 99-100° C. (from ethanol-diethyl ether)

(DMSO-$d_6$) δ: 2.72 (3H, s), 2.95 (3H, s), 3.04 (3H, s), 3.92 (3H, s), 4.19 (2H, s), 7.10-7.16 (2H, m), 7.34-7.41 (2H, m), 7.76 (1H, s), 8.60 (1H, s), 8.93 (1H, s), 11.38 (1H, brs).

Elemental Analysis: $C_{24}H_{24}FN_3O_5$ Calcd. (%): C, 63.57; H, 5.33; F, 4.19; N, 9.27. Found. (%): C, 62.52; H, 5.53; F, 3.93; N, 9.13.

I-72

3-(4-Fluorobenzyl)-8-hydroxy-5-(4-methylpiperadine-1-ylcarbamoyl)quinoline-7-carboxylic acid methyl ester m.p.: 228-229° C. (from ethanol)

(DMSO-$d_6$) δ: 2.19 (3H, s), 2.43 (4H, brs), 2.84 (4H, brs), 3.92 (3H, s), 4.23 (2H, s), 7.13-7.19 (2H, m), 7.33-7.38 (2H, m), 7.92 (1H, s), 8.41 (1H, s), 8.91 (1H, d, J=2.1 Hz), 9.46 (1H, s).

Elemental Analysis: $C_{24}H_{25}FN_4O_4$ Calcd. (%): C, 63.71; H, 5.57; F, 4.20; N, 12.38. Found. (%): C, 63.66; H, 5.74; F, 4.08; N, 12.39.

I-73

3-(4-Fluorobenzyl)-8-hydroxy-5-(2-hydroxy-1,1-dimethylethyl carbamoyl)quinoline-7-carboxylic acid methyl ester m.p.: 204-205° C. (from ethanol)

(DMSO-d6) δ: 1.29 (6H, s), 3.53 (2H, s), 3.93 (3H, s), 4.22 (2H, s), 4.90 (1H, brs), 7.13-7.20 (2H, m), 7.32-7.37 (2H, m), 7.84 (1H, s), 7.90 (1H, s), 8.39 (1H, d, J=2.0 Hz), 8.89 (1H, d, J=2.1 Hz).

Elemental Analysis: $C_{23}H_{23}FN_2O_5(EtOH)_{0.1}$ Calcd. (%): C, 64.64; H, 5.52; F, 4.41; N, 6.50. Found. (%): C, 64.64; H, 5.52; F, 4.31; N, 6.61.

I-74

3-(4-Fluorobenzyl)-8-hydroxy-5-[2-(2-hydroxyethoxy)ethylcarbamoyl]-quinoline-7-carboxylic acid methyl ester m.p.: 162-163° C. (from ethanol)

(DMSO-$d_6$) δ: 3.40-3.60 (8H, m), 3.93 (3H, s), 4.22 (2H, s), 4.60 (1H, brs), 7.12-7.18 (2H, m), 7.32-7.35 (2H, m), 8.03 (1H, s), 8.61 (1H, d, J=2.1 Hz), 8.89 (1H, d, J=2.1 Hz).

Elemental Analysis: $C_{23}H_{23}FN_2O_6$ Calcd. (%): C, 62.44; H, 5.24; F, 4.29; N, 6.33. Found. (%): C, 62.47; H, 5.32; F, 4.11; N, 6.52.

Elemental Analysis: $C_{22}H_{19}FN_2O_6$ Calcd. (%): C, 61.97; H, 4.49; F, 4.46; N, 6.57. Found. (%): C, 61.90; H, 4.26; F, 4.30; N, 6.79.

I-75

3-(4-Fluorobenzyl)-8-hydroxy-5-(piperadine-1-carbonyl)quinoline-7-carboxylic acid methyl ester m.p.: 184-185° C. (from ethanol-dimethyl formamide)

(DMSO-$d_6$) δ: 2.57-3.34 (8H, m), 3.89 (3H, s), 4.24 (2H, s), 7.14-7.20 (2H, m), 7.33-7.38 (2H, m), 7.70 (1H, s), 7.85 (1H, d, J=1.8 Hz), 8.90 (1H, d, J=1.8 Hz).

Elemental Analysis: $C_{23}H_{22}FN_3O_4$ Calcd. (%): C, 60.12; H, 5.70; F, 4.13; N, 9.15. Found. (%): C, 60.10; H, 5.84; F, 3.90; N, 9.09.

I-76

3-(4-Fluorobenzyl)-8-hydroxy-5-(4-hydroxypiperidine-1-carbonyl)quinoline-7-carboxylic acid methyl ester m.p.: 196-197° C. (from ethanol)

(DMSO-$d_6$) δ: 1.20-4.20 (8H, m), 3.69 (1H, m), 3.91 (3H, s), 4.24 (2H, s), 4.79 (1H, s), 7.13-7.19 (2H, m), 7.33-7.38 (2H, m), 7.70 (1H, s), 7.84 (1H, s), 8.93 (1H, d, J=2.1 Hz), 11.45 (1H, brs).

Elemental Analysis: $C_{24}H_{23}FN_2O_5$ Calcd. (%): C, 65.74; H, 5.28; F, 4.33; N, 6.39. Found. (%): C, 65.48; H, 5.48; F, 4.14; N, 6.42.

I-77

3-(4-Fluorobenzyl)-8-hydroxy-5-methoxycarbamoylquinoline-7-carboxylic acid methyl ester m.p.: 200-201° C. (from: ethanol-diethyl ether)

(DMSO-$d_6$) δ: 3.74 (3H, s), 3.93 (3H, s), 4.24 (2H, s), 7.13-7.19 (2H, m), 7.33-7.38 (2H, m), 8.51 (1H, s), 8.92 (1H, d, J=2.1 Hz), 11.71 (1H, s).

I-78

3-(4-Fluorobenzyl)-8-hydroxy-5-(3-oxopiperidine-1-carbonyl)quinoline-7-carboxylic acid methylester m.p.: 228-229° C. (from ethanol)

(DMSO-$d_6$) δ: 2.61 (2H, m), 3.87 (2H, m), 3.91 (3H, s), 4.23 (2H, s), 7.11-7.17 (2H, m), 7.33-7.38 (2H, m), 7.93 (1H, s), 8.23 (1H, s), 8.91 (1H, d, J=2.1 Hz), 11.35 (1H, brs).

Elemental Analysis: $C_{22}H_{18}FN_3O_5(H_2O)_{0.5}$ Calcd. (%): C, 61.75; H, 4.36; F, 4.44; N, 9.82. Found. (%): C, 61.92; H, 4.42; F, 4.15; N, 9.86.

I-79

3-(4-Fluorobenzyl)-8-hydroxy-5-isobutylcarbamoylquinoline-7-carboxylic acid methyl ester m.p.: 178-179° C. (from: ethanol-diethyl ether)

(DMSO-$d_6$) δ: 0.94 (6H, d, J=6.7 Hz), 1.93 (1H, sept, J=6.7 Hz), 3.68 (2H, d, J=6.7 Hz), 3.92 (3H, s), 4.24 (2H, s), 7.12-7.18 (2H, m), 7.33-7.37 (2H, m), 7.97 (1H, s), 8.47 (1H, s), 8.91 (1H, d, J=2.0 Hz).

Elemental Analysis: $C_{23}H_{23}FN_2O_5(H_2O)_{0.2}$ Calcd. (%): C, 64.24; H, 5.48; F, 4.42; N, 6.51. Found. (%): C, 64.17; H, 5.45; F, 4.21; N, 6.67.

I-80

3-(4-Fluorobenzyl)-8-hydroxy-5-[N'-(4-hydroxybutylyl)hydrazinocarbonyl]-quinoline-7-carboxylic acid methyl ester m.p.: 224-225° C. (from ethanol)

(DMSO-$d_6$) δ: 1.68-1.78 (2H, m), 2.26 (2H, t, J=6.9 Hz), 3.44-3.46 (2H, m), 3.94 (3H, s), 4.21 (2H, s), 4.50 (1H, s), 7.11-7.17 (2H, m), 7.32-7.36 (2H, m), 8.14 (1H, s), 8.68 (1H, d, J=1.8 Hz), 8.92 (1H, d, J=2.1 Hz), 11.50 (1H, brs).

Elemental Analysis: $C_{23}H_{22}FN_3O_6$ Calcd. (%): C, 60.66; H, 4.87; F, 4.17; N, 9.23. Found. (%): C, 60.52; H, 4.94; F, 4.02; N, 9.30.

I-81

5-(N'-Ethoxycarbonylmethylhydrazinocarbonyl)-3-(4-fluorobenzyl)-8-hydroxyquinoline-7-carboxylic acid methyl ester m.p.: 184-185° C. (from ethanol)

(DMSO-$d_6$) δ: 1.22 (3H, t, J=7.0 Hz), 3.66 (2H, s), 3.92 (3H, s), 4.13 (2H, q, J=7.0 Hz), 4.21 (2H, s), 5.53 (1H, s), 7.12-7.17 (2H, m), 7.32-7.37 (2H, m), 7.98 (1H, s), 8.57 (1H, s), 8.89 (1H, d, J=2.0 Hz), 10.08 (1H, s).

Elemental Analysis: $C_{23}H_{22}FN_3O_6$ Calcd. (%): C, 60.66; H, 4.87; F, 4.17; N, 9.23. Found. (%): C, 60.54; H, 4.75; F, 4.07; N, 9.28.

I-82

5-(N'-Benzoylhydrazinocarbonyl)-3-(4-fluorobenzyl)-8-hydroxyquinoline-7-carboxylic acid methyl ester m.p.: 227-229° C. (from ethyl acetate-ethyl ether)

(DMSO-$d_6$) δ: 3.96 (3H, s), 4.23 (2H, s), 7.12-7.17 (2H, m), 7.32-7.37 (2H, m), 7.52-7.63 (3H, m), 7.96 (2H, dd, J=7.2 Hz, 2.1 Hz), 8.24 (1H, s), 8.74 (1H, d, J=2.1 Hz), 8.94 (1H, d, J=2.1 Hz), 10.55 (1H, s), 10.60 (1H, s).

Elemental Analysis: $C_{26}H_{20}FN_3O_5(H_2O)_{0.5}$ Calcd. (%): C, 64.73; H, 4.39; F, 3.94; N, 8.71. Found. (%): C, 65.00; H, 4.34; F, 3.88; N, 8.64.

I-83

3-(4-Fluorobenzyl)-8-hydroxy-5-(4-hydroxymethylpiperidine-1-carbonyl)quinoline-7-carboxylic acid methyl ester m.p.: 161-162° C. (from ethanol)

(DMSO-$d_6$) δ: 1.14-1.19 (1H, m), 1.38-1.79 (2H, m), 2.74-3.06 (6H, m), 3.92 (3H, s), 4.24 (2H, s), 7.13-7.19 (2H, m), 7.34-7.38 (2H, m), 7.70 (1H, brs), 7.84 (1H, s), 8.94 (1H, s).

Elemental Analysis: $C_{25}H_{25}FN_2O_5(H_2O)_{0.4}$ Calcd. (%): C, 65.32; H, 5.66; F, 4.13; N, 6.09. Found. (%): C, 65.36; H, 5.55; F, 3.99; N, 6.30.

Example 13

I-84

3-(4-Fluorobenzyl)-8-hydroxy-5-(N'-methylhydrazinocarbonyl)quinoline-7-carboxylic acid methyl ester

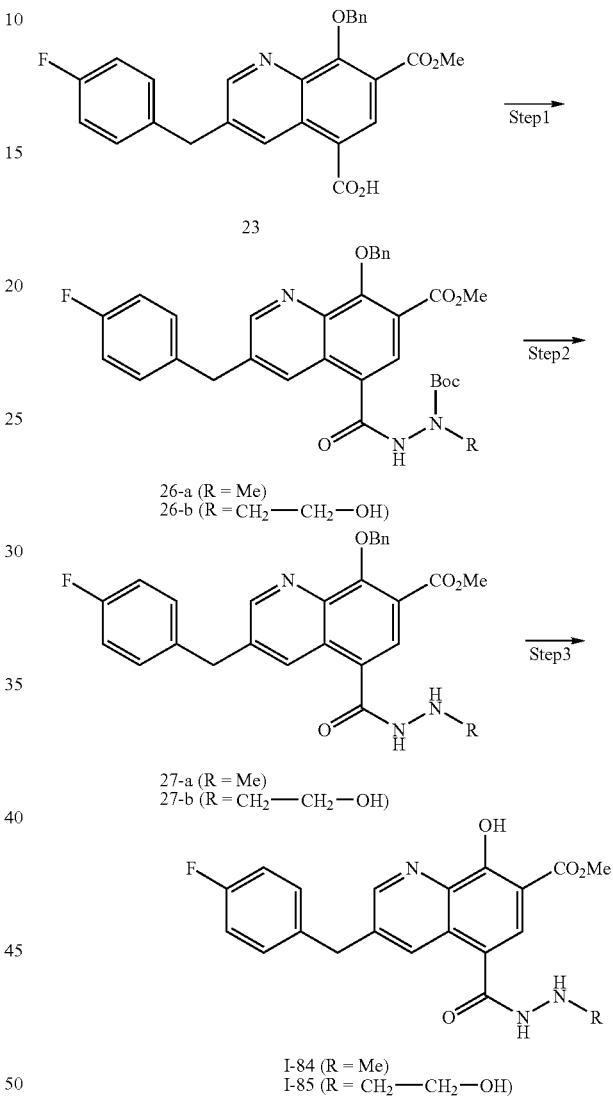

Step 1

In a manner similar to the step 1 of Example 2, Compound 23 (350 mg, 0.79 mmol) and N-methyl-hydrazine carboxylic acid tert-butyl ester (Ref. J. Org. Chem., 2002, 67, 8962-8969: 115 mg, 0.79 mmol) gave Compound 26 (366 mg, 0.64 mmol) as colorless oil in 81% yield.

NMR (CDCl$_3$) δ: 1.47 (9H, s), 3.24 (3H, m), 3.85 (3H, s), 4.14 (2H, s), 5.50 (2H, s), 6.97-7.03 (2H, m), 7.18-7.23 (2H, m), 7.28-7.40 (3H, m), 7.53-7.56 (2H, m), 8.06 (1H, s), 8.16 (1H, s), 8.63 (1H, s), 8.82 (1H, s).

Step 2

Compound 26 (360 mg, 0.63 mmol) was mixed with 4N HCl-ethyl acetate solution (15 ml) and was stirred for 2 hours at room temperature. The reaction mixture was evaporated in vacuo and obtained residue was mixed with saturated aqueous sodium hydrogen carbonate and extracted with ethyl acetate under ice-cooling. The extract was washed with brine and dried over sodium sulfuric anhydride and evaporated in vacuo. Obtained residue was washed with diisopropylether to give Compound 27 (270 mg, 0.57 mmol) as colorless crystal in 91% yield.

NMR (CDCl$_3$) δ: 2.77 (3H, brs), 3.87 (3H, s), 4.17 (2H, s), 5.53 (2H, s), 6.99-7.05 (2H, m), 7.19-7.23 (2H, m), 7.33-7.41 (3H, m), 7.55-7.57 (2H, m), 8.00 (1H, s), 8.62 (1H, s), 8.67 (1H, s).

Step 3

In a manner similar to Step 2 of Example 12, Compound 27 (265 mg, 0.56 mmol) gave crude crystals of Compound I-84 of the title, which were recrystallized from ethyl acetate-hexane to give Compound I-84 (95 mg, 0.25 mmol) of the title as colorless crystal in 44% yield.

m.p.: 188-189° C. (from ethyl acetate-hexane)

(DMSO-d$_6$) δ: 2.55 (3H, s), 3.93 (3H, s), 4.23 (2H, s), 7.12-7.18 (2H, m), 7.32-7.36 (2H, m), 7.98 (1H, s), 8.54 (1H, d, J=2.0 Hz), 8.91 (1H, d, J=2.0 Hz).

In a manner similar to Example 13, the Compound I-85 of the title was synthesized.

I-85

(4-Fluorobenzyl)-8-hydroxy-5-[N'-(2-hydroxyethyl)hydrazinocarbonyl)quinoline-7-carboxylic acid methyl ester m.p.: 193-194° C. (from ethanol)

(DMSO-d$_6$) δ: 2.88 (2H, t, J=5.6 Hz), 3.53 (2H, t, J=5.6 Hz), 3.92 (3H, s), 4.22 (2H, s), 4.60 (1H, s), 7.12-7.18 (2H, m), 7.32-7.37 (2H, m), 8.00 (1H, s), 8.56 (1H, d, J=1.8 Hz), 8.90 (1H, d, J=2.0 Hz), 10.09 (1H, s).

Elemental Analysis: $C_{21}H_{20}FN_3O_5(H_2O)_{0.2}$ Calcd. (%): C, 60.49; H, 4.93; F, 4.56; N, 10.08. Found. (%): C, 60.38; H, 4.76; F, 4.40; N, 10.14.

Example 14

I-86

5-(4-Acetylpiperadine-1-carbonyl)-3-(4-fluorobenzyl)-8-hydroxyquinoline-7-carboxylic acid methyl ester

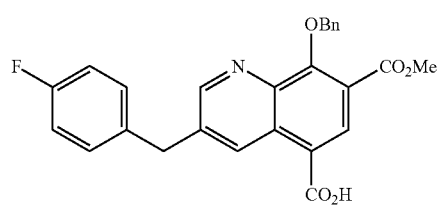

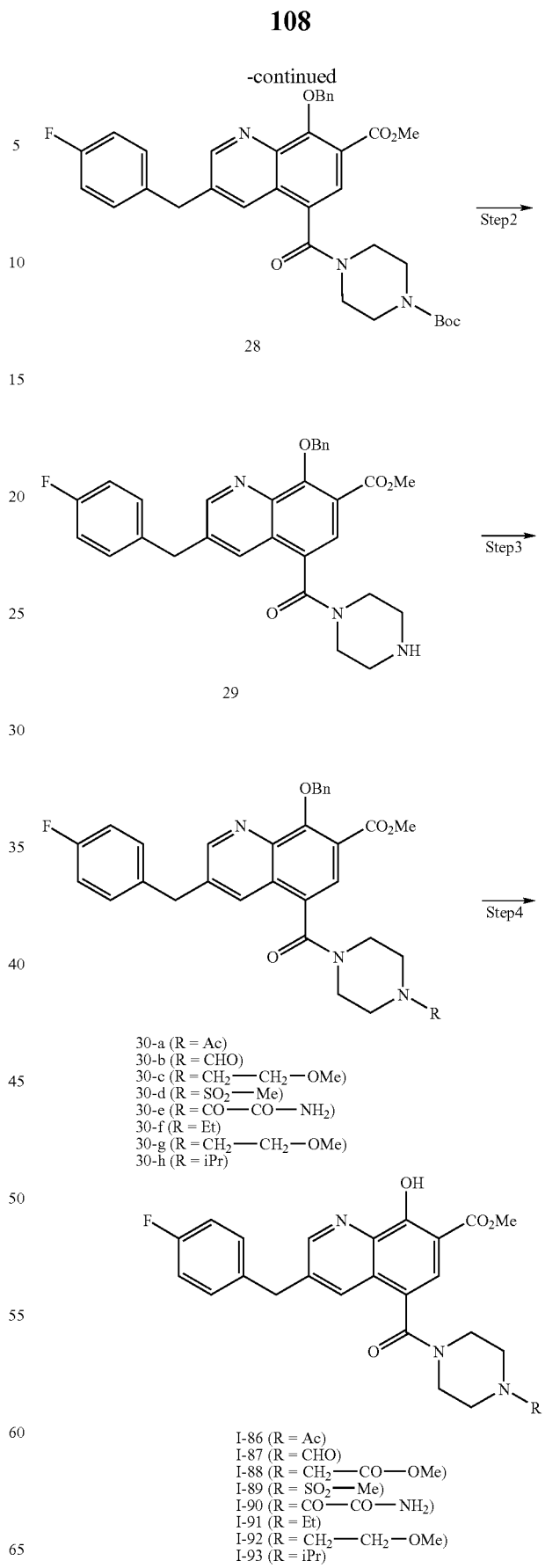

Step 1

In a manner similar to the step 1 of Example 2, the Compound 23 (1.22 g, 2.74 mmol) and tert-butyl 1-piperadine carboxyrate (562 mg, 3.02 mmol) gave crystal of Compound 28 (1.43 g, 2.33 mmol) as colorless oil in 85% yield.

m.p.: 196-197° C. (from ethanol)

(CDCl$_3$) δ: 1.48 (9H, s), 2.88-3.95 (8H, m), 3.87 (3H, s), 4.16 (2H, s), 5.52 (2H, s), 6.99-7.05 (2H, m), 7.16-7.21 (2H, m), 7.33-7.42 (3H, m), 7.56-7.61 (2H, m), 7.81 (1H, s), 7.86 (1H, s), 8.92 (1H, s).

Step 2

Compound 28 (1.43 g, 2.33 mmol) was mixed with 4N HCl-ethylacetate solution (15 ml) and the mixture was stirred for 1 hour at room temperature. The reaction mixture was evaporated in vacuo and obtained residue was mixed with saturated aqueous sodium hydrogen carbonate and extracted with ethylacetate under ice-cooling. The extract was washed with water and brine and dried over sodium sulfuric anhydride. The solvent was evaporated in vacuo to give crude Compound 29 (1.12 g) as yellow oil.

NMR (CDCl$_3$) δ: 2.58-3.23 (5H, m), 3.80-4.01 (3H, m), 3.87 (3H, s), 4.16 (2H, s), 5.52 (2H, s), 7.00-7.07 (2H, m), 7.16-7.22 (2H, m), 7.28-7.41 (3H, m), 7.59-7.61 (2H, m), 7.81 (1H, s), 7.89 (1H, d, J=2.1 Hz), 8.89 (1H, d, J=2.1 Hz).

Step 3

To a solution of Compound 29 (280 mg, 0.55 mmol) in chloroform (3 ml), triethylamine (91 ul, 0.65 mmol) at room temperature and acetylchloride (43 ul, 0.60 mmol) under ice-cooling, was added. The mixture was stirred for 1 hour at room temperature. To reaction mixture was added saturated aqueous sodium hydrogen carbonate and extracted with ethylacetate. The extract was washed with water and brine and dried over anhydrous sodium sulfate. The solvent was evaporated and the obtained residue was subjected to silica gel column chromatography to give Compound 30-a (267 mg, 0.48 mmol) as colorless oil in 87% yield.

NMR (CDCl$_3$) δ: 2.17 (3H, s), 2.82-4.11 (8H, s), 3.87 (3H, s), 4.17 (2H, s), 5.54 (2H, s), 7.00-7.05 (2H, m), 7.16-7.23 (2H, m), 7.31-7.42 (3H, m), 7.57-7.61 (2H, m), 7.77 (1H, s), 7.82 (1H, s), 8.93 (1H, d, J=2.1 Hz).

Step 4

Compound I-86

In a manner similar to Step 7 of Reference Example 1, Compound 30-a (262 mg, 0.47 mmol) gave crude crystals of Compound I-86 of the title, which were recrystallized from ethanol-water to give Compound Compound I-86 (85 mg, 0.18 mmol) of the title as colorless crystal in 39% yield.

m.p.: 196-197° C. (from ethanol)

(CDCl$_3$) δ: 2.07-2.16 (3H, m), 2.94-4.04 (8H, m), 4.04 (3H, s), 4.19 (2H, s), 6.99-7.06 (2H, m), 7.18-7.23 (2H, m), 7.49 (1H, s), 7.80 (1H, brs), 7.88 (1H, s), 8.90 (1H, s).

Elemental Analysis: C$_{25}$H$_{24}$FN$_3$O$_5$(H$_2$O)$_{0.1}$(EtOH)$_{0.1}$ Calcd. (%): C, 64.14; H, 5.30; F, 4.03; N, 8.90. Found. (%): C, 64.18; H, 5.19; F, 3.98; N, 8.82.

In a manner simmilar to Example 14, Compound I-87 to I-93 of the title were synthesized.

I-87

5-(4-Formylpiperadine-1-carbonyl)-3-(4-fluorobenzyl)-8-hydroxyquinoline-7-carboxylic acid methyl ester m.p.: 190-191° C. (from ethanol)

(CDCl$_3$) δ: 2.80-3.97 (8H, m), 4.04 (3H, s), 4.18 (2H, s), 6.99-7.06 (2H, m), 7.15-7.20 (2H, m), 7.82 (1H, s), 7.88 (1H, s), 8.09 (1H, s), 8.92 (1H, s).

Elemental Analysis: C$_{24}$H$_{22}$FN$_3$O$_5$(H$_2$O)$_{0.1}$ Calcd. (%): C, 63.60; H, 4.94; F, 4.19; N, 9.27. Found. (%): C, 63.59; H, 4.57; F, 4.07; N, 9.33.

I-88

3-(4-Fluorobenzyl)-8-hydroxy-5-(4-methoxycarbonylmethylpiperadine-1-carbonyl)quinoline-7-carboxylic acid methyl ester m.p.: 195-196° C. (from ethanol)

(CDCl$_3$) δ: 3.08-4.20 (10H, m), 4.03 (3H, s), 4.17 (2H, s), 6.99-7.04 (2H, m), 7.15-7.20 (2H, m), 7.75 (1H, brs), 7.87 (1H, s), 8.90 (1H, d, J=1.9 Hz).

Elemental Analysis: C$_{26}$H$_{26}$FN$_3$O$_6$ Calcd. (%): C, 63.02; H, 5.29; F, 3.83; N, 8.48. Found. (%): C, 63.46; H, 5.24; F, 3.78; N, 8.60.

I-89

3-(4-Fluorobenzyl)-8-hydroxy-5-(4-methanesulfonylpiperadine-1-carbonyl)quinoline-7-carboxylic acid methyl ester m.p.: 231-232° C. (from ethanol)

(DMSO-d$_6$) δ: 2.60-4.00 (8H, m), 2.90 (3H, s), 3.92 (3H, s), 4.25 (2H, s), 7.13-7.19 (2H, m), 7.33-7.38 (2H, m), 7.81 (1H, s), 7.98 (1H, d, J=2.1 Hz), 8.92 (1H, d, J=2.1 Hz), 11.37 (1H, brs).

Elemental Analysis: C$_{24}$H$_{24}$FN$_3$O$_6$S(H$_2$O)$_{0.25}$ Calcd. (%): C, 56.96; H, 4.88; F, 3.75; N, 8.30; S, 6.34. Found. (%): C, 57.11; H, 4.94; F, 3.44; N, 8.32; S, 5.96.

I-90

5-(4-Aminooxarylpiperadine-1-carbonyl)-3-(4-fluorobenzyl)-8-hydroxyquinoline-7-carboxylic acid methyl ester m.p.: 159-160° C. (from ethanol)

(DMSO-d$_6$) δ: 2.50-4.00 (8H, m), 3.90 (3H, s), 4.24 (2H, s), 7.12-7.17 (2H, m), 7.34-7.38 (2H, m), 7.73 (1H, s), 7.80 (1H, s), 7.99 (1H, s), 8.09 (1H, s), 8.89 (1H, d, J=2.1 Hz), 11.47 (1H, brs).

Elemental Analysis: C$_{25}$H$_{23}$FN$_4$O$_6$(H$_2$O)$_{1.0}$ Calcd. (%): C, 58.59; H, 4.92; F, 3.71; N, 10.93. Found. (%): C, 58.89; H, 4.74; F, 3.73; N, 11.03.

I-91

5-(4-Ethylpiperadine-1-carbonyl)-3-(4-fluorobenzyl)-8-hydroxyquinoline-7-carboxylic acid methyl ester m.p.: 171-172° C. (from ethanol-water)

(DMSO-d$_6$) δ: 0.97 (3H, t, J=6.9 Hz), 1.74-3.94 (8H, m), 2.29 (2H, q, J=7.2 Hz), 3.91 (3H, s), 4.24 (2H, s), 7.12-7.18

(2H, m), 7.34-7.38 (2H, m), 7.71 (1H, s), 7.86 (1H, d, J=2.1 Hz), 8.95 (1H, d, J=1.8 Hz), 11.35 (1H, brs).

Elemental Analysis: $C_{25}H_{26}FN_3O_4(H_2O)_{1.0}$ Calcd. (%): C, 63.95; H, 6.01; F, 4.05; N, 8.95. Found. (%): C, 64.04; H, 5.94; F, 3.87; N, 8.86.

I-92

3-(4-Fluorobenzyl)-8-hydroxy-5-[4-(2-methoxyethyl)-piperadine-1-carbonyl]-quinoline-7-carboxylic acid methyl ester m.p.: 119-120° C. (from ethanol-diethyl ether)

(DMSO-$d_6$) δ: 1.80-4.00 (8H, m), 3.05 (2H, brs), 3.22 (3H, s), 3.41 (2H, t, J=5.4 Hz), 3.91 (3H, s), 4.25 (2H, s), 7.13-7.18 (2H, m), 7.34-7.39 (2H, m), 7.71 (1H, s), 7.87 (1H, s), 8.94 (1H, d, J=1.8 Hz), 11.40 (1H, brs).

Elemental Analysis: $C_{26}H_{28}FN_3O_5(H_2O)_{0.5}$ Calcd. (%): C, 63.66; H, 5.96; F, 3.87; N, 8.57. Found. (%): C, 63.45; H, 5.86; F, 3.80; N, 8.59.

I-93

3-(4-Fluorobenzyl)-8-hydroxy-5-(4-isopropylpiperadine-1-carbonyl)quinoline-7-carboxylic acid methyl ester m.p.: 229° C. (from ethanol-diethyl ether)

(DMSO-$d_6$) δ: 1.26-1.28 (6H, m), 2.60-4.00 (8H, m), 3.92 (3H, s), 4.25 (2H, s), 7.14-7.20 (2H, m), 7.34-7.39 (2H, m), 7.92 (1H, brs), 8.08 (1H, d, J=1.5 Hz), 8.92 (1H, d, J=1.8 Hz), 10.94 (1H, brs).

Example 15

I-94

5-(1-Acetyl-piperidine-4-ylcarbamoyl)-3-(4-fluorobenzyl)-8-hydroxyquinoline-7-carboxylic acid methyl ester

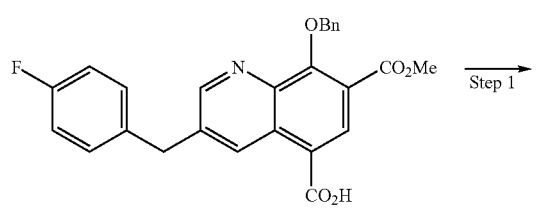

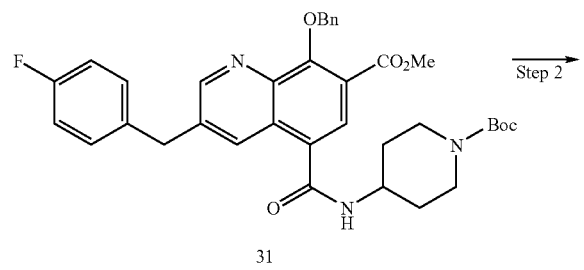

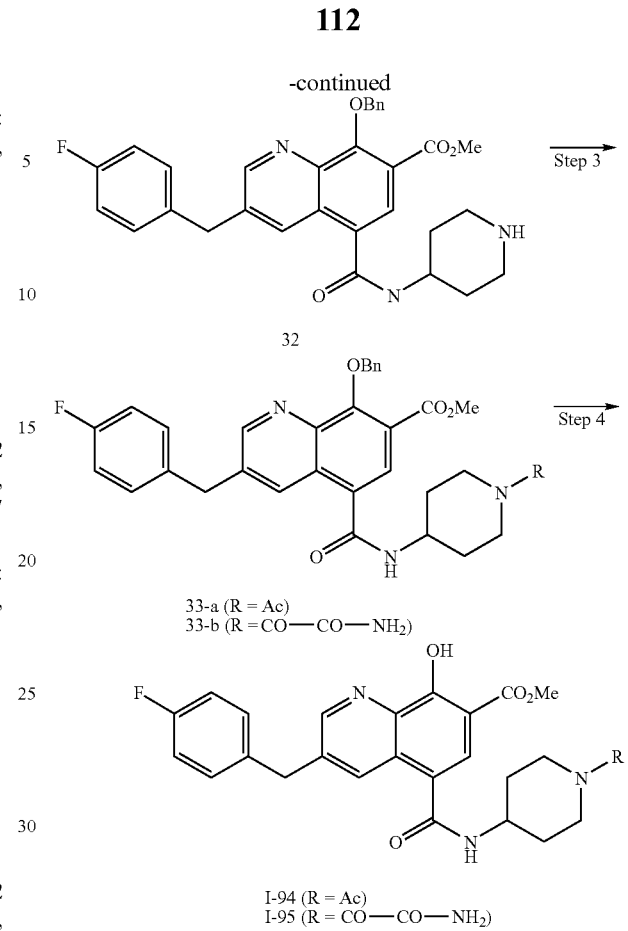

Step 1

In a manner similar to the Step 1 of Example 2, Compound 23 (2.5 g, 5.61 mmol) and 4-amino-1-N-boc-piperidine (1.35 g, 6.73 mmol) gave Compound 31 (2.88 g, 4.60 mmol) of the title as colorless crystals in 82% yield.

Step 2

In a manner similar to the Step 2 of Example 14, Compound 31 (2.80 g, 4.47 mmol) gave Compound 32 (1.23 g, 2.19 mmol) as colorless crystals in 49% yield.

Step 3.

In a manner similar to Step 3 of Example 14, Compound 32 (264 mg, 0.47 mmol) gave Compound 33 (277 mg, 0.46 mmol) as colorless crystals in 97% yield.

Step 4

In a manner similar to Step 2 of Example 12, Compound 33 (277 mg, 0.46 mmol) gave crude crystals of Compound I-94 of the title, which were recrystallized from ethanol-water to give Compound I-94 (152 mg, 0.30 mmol) of the title as colorless crystal in 65% yield.

m.p.: 214-215° C. (from ethanol-water)

(DMSO-$d_6$) δ: 1.30-1.50 (2H, m), 1.86 (2H, t, J=15.0 Hz), 2.02 (3H, s), 2.72 (1H, t, J=12.0 Hz), 3.16 (1H, t, J=11.7 Hz), 3.81 (1H, d, J=13.8 Hz), 3.90-4.20 (1H, m), 3.93 (3H, s), 4.23 (2H, s), 4.31 (1H, d, J=13.8 Hz), 7.13-7.19 (2H, m), 7.32-7.37 (2H, m), 7.98 (1H, s), 8.49 (1H, d, J=1.8 Hz), 8.52 (1H, d, J=7.5 Hz), 8.91 (1H, d, J=2.1 Hz), 11.44 (1H, brs).

Elemental Analysis: $C_{26}H_{26}FN_3O_5(H_2O)_{0.5}$ Calcd. (%): C, 64.52; H, 5.52; F, 3.93; N, 8.68. Found. (%): C, 64.67; H, 5.44; F, 3.83; N, 8.81.

In a manner similar to Example 15, Compound I-95 of the title was synthesized.

I-95

5-(1-Aminooxaryl-piperidine-4-ylcarbamoyl)-3-(4-fluorobenzyl)-8-hydroxyquinoline-7-carboxylic acid methyl ester m.p.: 261-263° C. (from ethanol)

(DMSO-$d_6$) δ: 1.30-1.58 (2H, m), 1.90 (2H, d, J=9.9 Hz), 2.88 (1H, t, J=10.5 Hz), 3.21 (2H, t, 11.7 Hz), 3.79 (1H, d, J=13.8 Hz), 3.89 (3H, s), 4.00-4.16 (1H, m), 4.22 (2H, s), 7.12-7.18 (2H, m), 7.32-7.37 (2H, m), 7.66 (1H, s), 7.98 (1H, s), 8.09 (1H, s), 8.49 (1H, d, J=2.1 Hz), 8.57 (1H, d, J=7.2 Hz), 8.89 (1H, d, J=2.1 Hz), 11.30 (1H, brs).

Elemental Analysis: $C_{26}H_{25}FN_4O_6(H_2O)_{0.5}$ Calcd. (%): C, 60.34; H, 5.06; F, 3.67; N, 10.83. Found. (%): C, 60.77; H, 5.03; F, 3.69; N, 10.90.

Example 16

I-96

3-(4-Fluorobenzyl)-8-hydroxy-5-(piperidine-4-yl carbamoyl)quinoline-7-carboxylic acid methyl ester

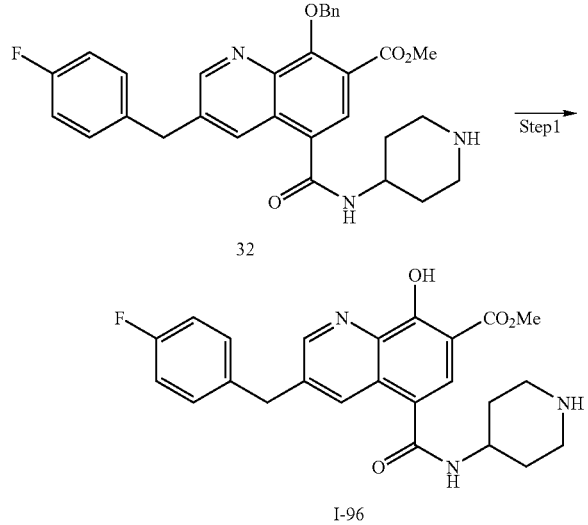

Step 1

In a manner similar to Step 2 of Example 12, Compound 32 (250 mg, 0.45 mmol) gave crude crystals of Compound I-96 of the title, which were recrystallized from ethanol to give Compound I-96 (127 mg, 0.27 mmol) of the title as pale yellow crystals in 61% yield.

m.p.: 232-233° C. (from ethanol)

(Acetone-$d_6$) δ: 1.80-2.35 (4H, m), 3.20-3.40 (2H, m), 3.55-3.70 (4H, m), 4.12 (3H, s), 4.25-4.37 (1H, m), 4.62 (2H, s), 7.12-7.19 (2H, m), 7.52-7.57 (2H, m), 8.54 (1H, s), 9.45 (1H, d, J=2.1 Hz), 9.52 (1H, d, J=2.1 Hz).

Elemental Analysis: $C_{24}H_{24}FN_3O_4(H_2O)_{0.5}$ Calcd. (%): C, 64.56; H, 5.64; F, 4.26; N, 9.41. Found. (%): C, 64.15; H, 5.49; F, 4.08; N, 9.31.

Example 17

I-97

3-(4-Fluorobenzyl)-8-hydroxy-5-(N'-methylcarbamoylmethyl-hydrazino arbonyl)quinoline-7-carboxylic acid methyl ester

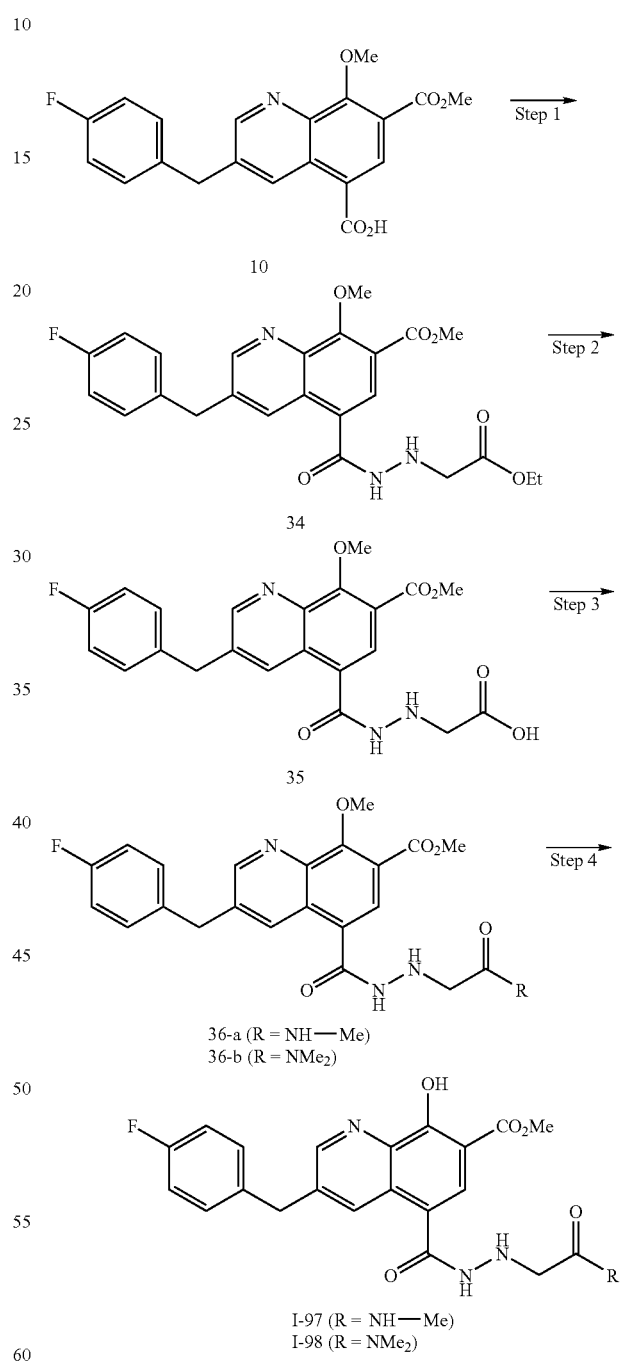

Step 1

In a manner similar to the Step 1 of Example 2, Compound 10 (1.0 g, 2.71 mmol) and ethyl hydrazino acetate hydrochloride (461 mg, 2.98 mmol) gave crude of Compound 34 (3.48 g).

Step 2

To a solution of crude Compound 34 (3.48 g) in dioxane (20 ml), 2N HCl (10 ml) was added and was stirred for 3 hours at 60° C. The reaction mixture was diluted with ethyl acetate, which were washed with water twice and dried over sodium sulfuric anhydride. The solvent was evaporated in vacuo to give Compound 35 (690 mg, 1.56 mmol) as colorless crystals in 58% yield.

Step 3

In a manner similar to the Step 1 of Example 2, Compound 35 (230 mg, 0.52 mmol) gave Compound 36-a (128 mg, 0.28 mmol) as colorless crystal in 54% yield.

Step 4

In a manner similar to Step 2 of Example 12, Compound 36-a (123 mg, 0.27 mmol) gave crude of Compound I-97 of the title, which were recrystallized from 90% methanol-water to give Compound I-97 (71 mg, 0.16 mmol) of the title as colorless crystal in 59% yield.

m.p.: 168-170° C. (from 90% methanol-water)

(DMSO-$d_6$) δ: 2.65 (3H, d, J=4.5 Hz), 3.42 (2H, s), 3.93 (3H, s), 4.22 (2H, s), 5.58 (1H, brs), 7.12-7.18 (2H, m), 7.32-7.37 (2H, m), 7.99 (1H, s), 8.08 (1H, brs), 8.55 (1H, d, J=2.1 Hz), 8.92 (1H, d, J=2.1 Hz), 10.03 (1H, brs).

Elemental Analysis: $C_{22}H_{21}FN_4O_5(H_2O)_{1.0}$ Calcd. (%): C, 57.64; H, 5.06; F, 4.14; N, 12.22. Found. (%): C, 57.45; H, 4.93; F, 4.00; N, 11.48.

In a manner similar to Example 17, Compound I-98 of the title was synthesized.

I-98

5-(N'-Dimethylcarbamoylmethylhydrazinocarbonyl)-3-(4-fluorobenzyl)-8-hydroxyquinoline-7-carboxylic acid methyl ester m.p.: 170-172° C. (from 90% methanol-water)

(DMSO-$d_6$) δ: 2.87 (3H, s), 2.96 (3H, s), 3.69 (2H, s), 3.93 (3H, s), 4.22 (2H, s), 5.41 (1H, brs), 7.12-7.18 (2H, m), 7.34-7.38 (2H, m), 8.00 (1H, s), 8.62 (1H, s), 8.90 (1H, s), 10.04 (1H, brs).

Elemental Analysis: $C_{23}H_{23}FN_4O_5(H_2O)_{0.5}$ Calcd. (%): C, 59.61; H, 5.22; F, 4.10; N, 12.09. Found. (%): C, 59.67; H, 4.96; F, 4.12; N, 11.47.

Example 18

I-99

3-(4-Fluorobenzyl)-8-hydroxy-quinoline-5,7-dicarboxylic acid 7-ethyl ester

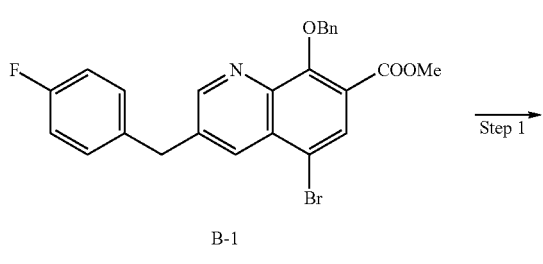

Ex 1B-1 compound B-1

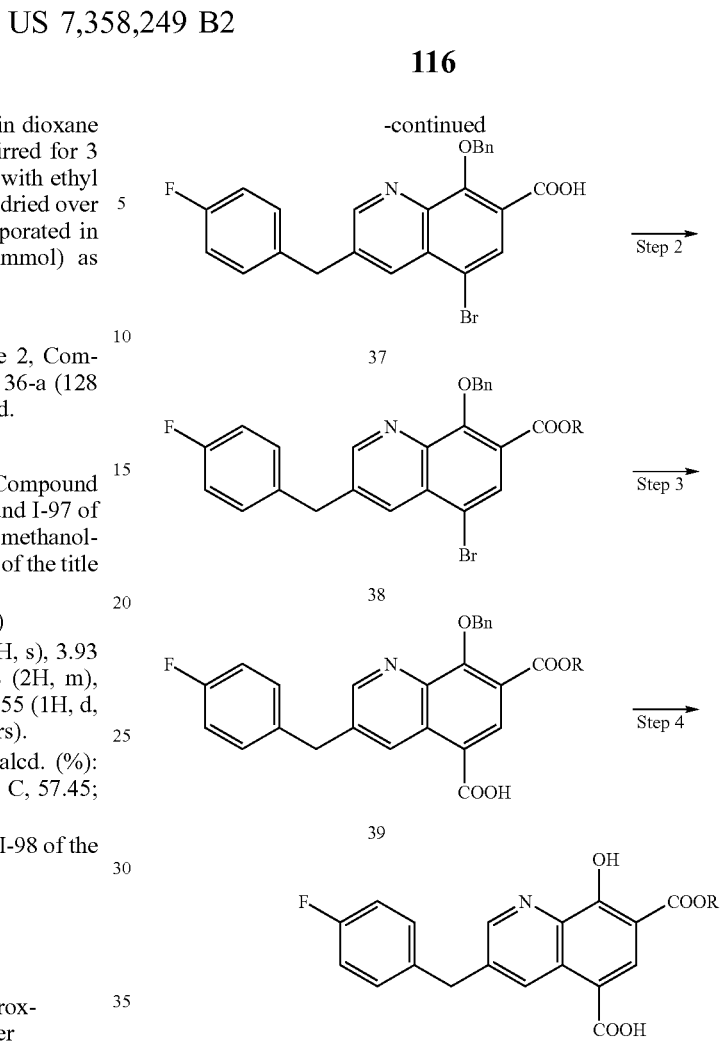

I-99 (R = Et)
I-100 (R = $^i$Pr)
I-101 (R = $^n$Pr)
I-102 (R = —CH$_2$CH$_2$OMe)

Step 1

Compound B-1 (obtained from Example 1B-1; 5.47 g, 11.39 mmol) was dissolved in tetrahydrofuran (27 ml) and methanol (27 ml), which was mixed with 2 N sodium hydroxide (6.85 ml) with stirring under nitrogen atomosphere at room temperature and refluxed with stirring in oil bath at 100° C. After 15 minutes, the reaction solution was mixed with 2 N hydrochloric acid (7.33 ml) and water (540 ml) and stirred under ice-cooling for 30 min. The pricipitated crystals were filtered and washed with water. The resulting crystals were dissolved in chloroform (100 ml), washed with water once, dried over anhydrous sodium sulfate and evaporated in vacuo to give Compound 37 (5.428 g, 100%) as beige crystals.

m.p.: 155-156° C.

Step 2

Compound 37 (obtained from Step 1; 466 mg, 11.0 mmol) was dissolved in dichloro methane (12 ml). The solution was mixed mixed with 1-ethyl-3-(3-dimethylaminopropyl)-carbodiimide hydrochloric acid (230 mg, 1.2 mmol), and hydrooxy benztriazole (162 mg, 1.2 mmol) with stirring under ice-cooling under nitrogen atomospher and stirred at room temperature. After 2 hours, ethanol (7.7 ml, 136 mmol) and triethyl amine (0.17 ml, 1.2 mmol) were added and the mixture was refluxed under stirring in oil bath at 70° C. After 2 hours, the reaction solution was evaporated in vacuo and the obtained residue was mixed with iced water (30 ml) and a small amount of diethylether to give crystals, which were stirred on ice for 30 minutes. The pricipitated crystals were filered and washed with water to give Compound 38 (95.7%) as beige crystal.

m.p.: 81 (wetness)-92-93° C.

Step 3

Compound 38 (obtained from Step 2; 467 mg, 0.945 mmol), acetic acid Palladium (II) (43 mg, 0.189 mmol) and 1,3-bis(diphenyl phosphino)propane (98 mg, 0.236 mmol) were mixed with dimethyl sulfoxide (4.5 ml), water (1.13 ml, 62.7 mmol) and triethylamine (1.32 ml, 9.46 mmol). The reaction flask was degassed three times and substituted with carbon monoxide, stirred with heating in oil bath at 70° C. for 19 hours. To the reaction mixture, 10% citric acid (9 ml) and ethyl acetate ester (10 ml) were added and stirred for 30 minutes at room temperature, filtered through Celite in Kiriyama type funnel, washed with ethylacetateester, transferred into a separatory funnel with water (10 ml), extracted with ethylacetate twice, washed with 10% citric acid (6 ml) and water, dried over anhydrous sodium sulfate and evaporated in vacuo to give Compound 3 as crude (343 mg, 79%). Obtained crude (343 mg) was subjected to silica gel chromatography (Kiesel gel 60, 70-230 mesh, 10 g) (chloroform-methanol: 98:2 solution) and recrystallized to give Compound 39 (118 mg, 27.2%) as colorless crystal.

m.p.: 195-196° C.

Step 4

Iodide sodium (300 mg, 2.0 mmol) was poured into acetonitrile (5 ml) and, was mixed with trimethyl sillyl chloride (0.254 ml, 2.0 mmol) under nitrogen atomosphere and ice-cooling, which and the mixture was stirred at room temperature for 10 min. The mixture was mixed with sodium hydrogen carbonate (168 mg, 2.0 mmol) under ice-cooling and stirred at room temperature for 10 minutes, then which was mixed with Compound 39 (R=Et) (obtained in Step 3; 115 mg, 0.250 mmol) as crystals with acetonitrile (4 ml) and stirred for 6 hours. The reaction mixture was refluxed in oil bath at 100° C. for 10 hours and after cooling to room temperature, mixed with 10% acidic $Na_2SO_4$ (11 ml) and $H_2O$(10 ml). After 50 min, the precipitated crystals were filtered to give crude of Compound 4 (54 mg, 58.7%), which were recrystallized from tetrahydrofuran and methanol to give Compound I-99 (45 mg, 48.9%) of the title.

m.p.: 238-239° C. (from: tetrahydrofuran-methanol)

(DMSO-$d_6$) δ: 1.36 (3H, t, J=7.2 Hz), 4.25 (2H, s), 4.39 (2H, q, J=7.2 hz), 7.13-7.18 (2H, m), 7.33-7.37 (2H, m), 8.61 (1H, s), 8.90 (1H, d, J=2.1 Hz), 9.25 (1H, d, J=2.1 Hz).

Elemental Analysis: $C_{20}H_{16}FNO_5$ Calcd. (%): C, 65.04; H, 4.37; F, 5.14; N, 3.79. Found. (%): C, 64.97; H, 4.57; F, 4.80; N, 3.72

Compounds I-100 to I-102 were synthesized from Compound 37 in a manner similar to the Step 1 of Compound I-99.

These Compounds of physical properties are as follows:

I-100

3-(4-Fluorobenzyl)-8-hydroxyquinoline-5,7-dicarboxylic acid 7-isopropylester m.p.: 249-251° C.(dec) (from: tetrahydrofuran-methanol)

(DMSO-$d_6$) δ: 1.38 (6H, d, J=6 Hz), 4.25 (2H, s), 5.24 (1H, m), 7.13-7.19 (2H, m), 7.33-7.38 (2H, m), 8.59 (1H, s), 8.91 (1H, d, J=2.1 Hz), 9.24 (1H, d, J=2.1 Hz).

Elemental Analysis: $C_{21}H_{18}FNO_5$ Calcd. (%): C, 65.18; H, 4.797; F, 4.91; N, 3.62. Found. (%): C, 65.01; H, 4.73; F, 4.72; N, 3.63.

I-101

3-(4-Fluorobenzyl)-8-hydroxyquinoline-5,7-dicarboxylic acid 7-propylester m.p.: 249-251° C.(dec) (from tetrahydrofuran-methanol)

(DMSO-$d_6$) δ: 1.38 (6H, d, J=6 Hz), 4.25 (2H, s), 5.24 (1H, m), 7.13-7.19 (2H, m), 7.33-7.38 (2H, m), 8.59 (1H, s), 8.91 (1H, d, J=2.1 Hz), 9.24 (1H, d, J=2.1 Hz).

Elemental Analysis: $C_{21}H_{18}FNO_5$ Calcd. (%): C, 65.18; H, 4.797; F, 4.91; N, 3.62. Found. (%): C, 65.01; H, 4.73; F, 4.72; N, 3.63.

I-102

3-(4-Fluorobenzyl)-8-hydroxyquinoline-5,7-dicarboxylic acid 7-(2-methoxyethyl) ester m.p.: 234-235° C.(dec) (from tetrahydrofuran-methanol)

(CDCl$_3$-CD$_3$OD) δ: 3.47 (3H, s), 3.80-3.83 (2H, m), 4.20 (2H, s), 4.60-4.63 (2H, m), 6.98-7.04 (2H, m), 7.18-7.23 (2H, m), 8.81 (1H, d, J=2.1 Hz), 8.85 (1H, s), 9.32 (1H, d, J=2.1 Hz).

Elemental Analysis: $C_{21}H_{18}FNO_6$ Calcd. (%): C, 63.16; H, 4.54; F, 4.76; N, 3.51. Found. (%): C, 62.98; H, 4.59; F, 4.61; N, 3.52.

Example 19

I-103

7-Acetyl-3-(4-fluorobenzyl)-8-hydroxyquinoline-5-carboxylic acid

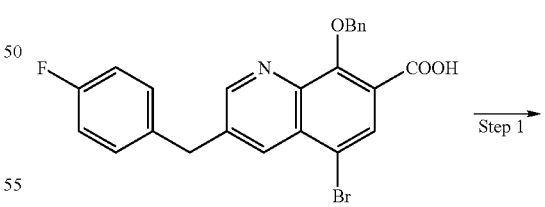

37

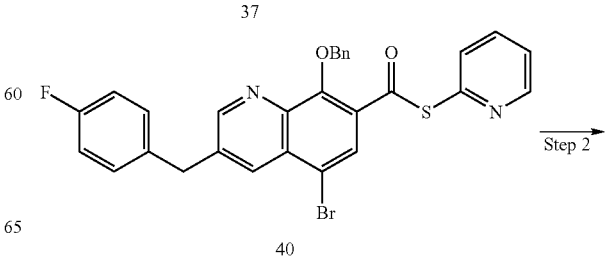

40

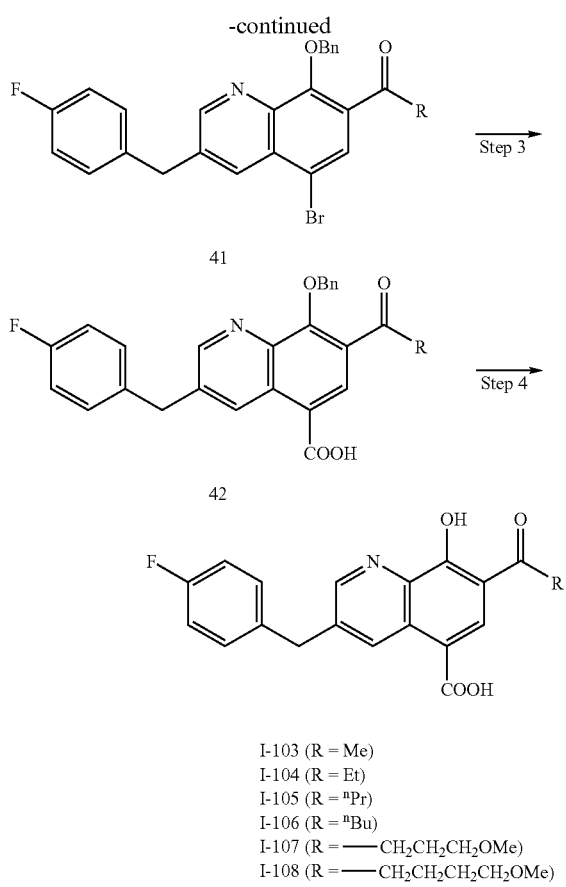

I-103 (R = Me)
I-104 (R = Et)
I-105 (R = ⁿPr)
I-106 (R = ⁿBu)
I-107 (R = ―CH₂CH₂CH₂OMe)
I-108 (R = ―CH₂CH₂CH₂CH₂OMe)

Step 1

Compound 37 (3.264 g, 7 mmol) and 2,2-dipyridyl disulfide (1.848 g, 8.39 mmol) were dissolved in THF (50 ml) and stirred under N₂ at room temperature and mixed with tri-n-butyl phosphine (2.1 ml, 8.43 mmol) immediately, followed by stirring. After 1 hour, the reaction solution was evaporated in vacuo and the obtained residue (6.9 g) was subjected to silica gel chromatography (toluene-acetone:49:1) in Lobar(R) columnB to give Compound 40 (3.703 g, 94.6%) as yellow viscous oil.

Step 2

Compound 40 (505 mg, 0.903 mmol) was dissolved in THF (9 ml) under N₂ underdry ice-acetone cooling, followed by adding dropwise a CH₃MgBr-THF solution (1 mol) (0.95 ml, 0.95 mmol) within 10 min and the mixture was stirred under cooling. After 1 hour, a CH₃MgBr-THF solution (1 mol) (0.81 ml, 0.81 mmol) was added and the mixture was additionally reacted for 1 hour. The resulting mixture was mixed with a saturated solution of NH₄Cl (10 ml), stirred at room temperature, extracted with ethyl acetate, washed with brine, dried over Na₂SO₄ and evaporated in vacuo. The resulting redidue (516 mg) was subjected to column chromatography (n-hexan:acetone=9:1, v/v) in Lobar® column B to give Compound 41 (363 mg, 86.6%) as colorless crystals. m.p.: 87-88° C.

Step 3

Compound 41 (360 mg, 0.775 mmol), acetic acid Palladium(II) (35 mg, 0.155 mmol) and 1,3-bis(diphenyl phosphino)propane (80 mg, 0.194 mmol) were mixed with DMSO(7 ml), H₂O(1.75 ml, 96.9 mmol) and triethyl amine (1.08 ml, 7.75 mmol), succecively. The reaction flask was degassed 3 times and substituted with CO and refluxed in the presence of CO at 70° C. in oil bath. After 24 hours, the reaction mixture was mixed with ethyl acetate (12 ml), stirred under ice-cooling, mixed with 10% citric acid (8 ml), stirred at room temperature for 30 min, filtered through Celite in Kiriyama funnel and washed with ethyl acetate and H₂O. The filtrate was transferred to a separatory funnel, mixed with ethyl acetate and H₂O, extracted, washed with 10% citric acid and H₂O, dried over Na₂SO₄ and evaporated in vacuo. The obtained residue was recrystallized from THF and methanol to give Compound 42 (239 mg, 71.8%) as greenish brown crystals.

m.p.: 186-190° C.

Step 4

Compound 42 (238 mg, 0.554 mmol) was dissolved in dioxane (29 ml), mixed with the 10% suspension of Palladium-carbon (48 mg) and H₂O (2 ml) and at normal pressure reduced by catalytic reduction. After 2.5 hours, to the reduced solution, tetrahydrofuran was added and its pricipitate was dissolved, filtered through Celite in KIRIYAMA funnel and evaporated into vacuo. The obtained crystals were recrystallized from tetrahydrofuran-methanol to give the title Compound I-103 (159 mg, 84.6%) as yellow crystals.

m.p.: 239-242° C. (from tetrahydrofuran-methanol)

(DMSO-d₆) δ: 2.73 (3H, s), 4.26 (2H, s), 7.13-7.19 (2H, m), 7.33-7.38 (2H, m), 8.63 (1H, s), 8.90 (1H, d, J=2.1 Hz), 9.26 (1H, d, J=2.1 Hz).

Elemental Analysis: C₁₉H₁₄FNO₄.0.2H₂O Calcd. (%): C, 66.55; H, 4.23; F, 5.54; N, 4.08. Found. (%): C, 66.53; H, 4.09; F, 5.15; N, 4.09.

Compounds I-104 to I-108 were synthesized from Compound 40 obtained in Step 1 of Compound I-103. The physical properties are as follows:

I-104

3-(4-Fluorobenzyl)-8-hydroxy-7-propionyl-quinoline-5-carboxylic acid m.p.: 235-237° C. (from tetrahydrofuran-methanol)

(DMSO-d₆) δ: 1.12(3H, t, J=7.2 Hz), 3.20 (2H, q, J=7.2 Hz), 4.26 (2H, s), 7.13-7.19 (2H, m), 7.33-7.38 (2H, m), 8.65 (1H, s), 8.90 (1H, d, J=2.1 Hz), 9.26 (1H, d, J=2.1 Hz).

Elemental Analysis: C₂₀H₁₆FNO₄.0.3H₂O Calcd. (%): C, 66.96; H, 4.66; F, 5.30; N, 3.90. Found. (%): C, 67.03; H, 4.57; F, 4.93; N, 3.95.

I-105

7-Butyryl-3-(4-fluorobenzyl)-8-hydroxyquinoline-5-carboxylic acid m.p.: 232-234° C. (from tetrahydrofuran-methanol)

(DMSO-d₆) δ: 0.95(3H, t, J=7.2 Hz), 1.62-1.74(2H, m), 3.14(2H, t, J=7.2 Hz), 4.26(2H, s), 7.13-7.19(2H, m), 7.33-7.38(2H, m), 8.63(1H, s), 8.90(1H, d, J=1.8 Hz), 9.26(1H, d, J=1.8 Hz).

Elemental Analysis: C₂₁H₁₈FNO₄.0.5H₂O Calcd. (%): C, 67.01; H, 5.09; F, 5.05; N, 3.72. Found. (%): C, 67.01; H, 4.97; F, 4.62; N, 3.75.

121

I-106

3-(4-Fluorobenzyl)-8-hydroxy-7-pentanoyl-quinoline-5-carboxylic acid m.p.: 227-229° C. (from tetrahydrofuran-methanol)
(DMSO-$d_6$) δ: 0.91(3H, t, J=7.2 Hz), 1.33-1.424(2H, m), 1.59-1.69(2H, m), 3.17 (2H, t, J=7.2 Hz), 4.26(2H, s), 7.13-7.19(2H, m), 7.33-7.38(2H, m), 8.63(1H, s), 8.90 (1H, d, J=1.8 Hz), 9.26(1H, d, J=1.8 Hz).

Elemental Analysis: $C_{22}H_{20}FNO_4 \cdot 0.4H_2O$ Calcd. (%): C, 68.00; H, 5.40; F, 4.89; N, 3.60. Found. (%): C, 68.01; H, 5.20; F, 4.54; N, 3.70.

I-107

3-(4-Fluorobenzyl)-8-hydroxy-7-(4-methoxy-butyryl)quinoline-5-carboxylic acid m.p.: 226-228° C. (from tetrahydrofuran-methanol)
(CDCl$_3$-CD$_3$OD) δ: 2.06-2.14(2H, m), 3.28(2H, t, J=7.2 Hz), 3.37(3H, s), 3.54(2H, t, J=6.0 Hz), 4.20(2H, s), 6.97-7.04(2H, m), 7.18-7.23(2H, m), 8.80(1H, d, J=1.8 Hz), 8.82(1H, s), 9.33(1H, d, J=1.8 Hz).

Elemental Analysis: $C_{22}H_{20}FNO_5 \cdot 0.4H_2O$ Calcd. (%): C, 65.31; H, 5.18; F, 4.70; N, 3.46. Found. (%): C, 65.27; H, 5.35; F, 4.33; N, 3.49.

I-108

3-(4-Fluorobenzyl)-8-hydroxy-7-(5-methoxypentanoyl)quinoline-5-carboxylic acid m.p.: 216-218° C. (from tetrahydrofuran-methanol)
(CDCl$_3$-CD$_3$OD) δ: 1.68-1.77(2H, m), 1.85-1.94(2H, m), 3.21(2H, d, J=7.2 Hz), 3.35(3H, s), 3.47(2H, d, J=6.0 Hz), 4.19(2H, s), 6.98-7.04(2H, m), 7.18-7.23(2H, m), 8.78(1H, s), 8.80(1H, d, J=1.8 Hz), 9.32(1H, d, J=1.8 Hz).

FABMS: m/z 412[M+H]$^+$, 823[2M+H]$^+$

Example 20

I-109

3-(4-Fluorobenzyl)-8-hydroxy-6-methylquinoline-7-carboxylic acid methyl

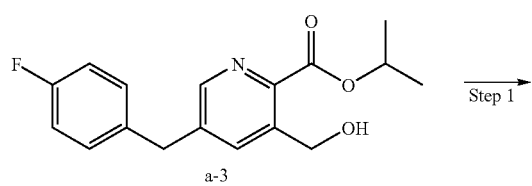

a-3

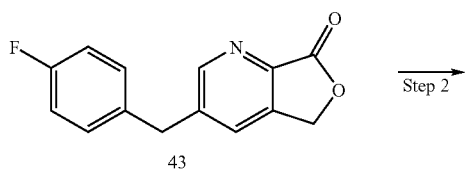

43

122

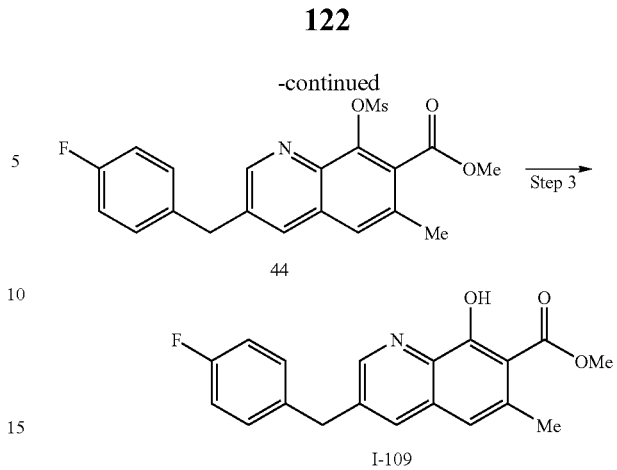

Step 1

Compound a-3(15.3 g, 50.4 mmol) of Example A-1 was dissolved in methanol (120 ml) and mixed with sodium hydride (60%) (100 mg, 2.50 mmol), and the mixtuer was stirred for 30 mins at room temperature. After cooling to 0° C., the pricipitate was filtered out to give Compound 43(11.9 g, 48.9 mmol) as colorless crystal in 97% yield.

NMR (CDCl$_3$) δ: 4.12(2H, s), 5.32(2H, s), 7.00-7.07(2H, m), 7.13-7.18 (2H, m), 7.60(1H, d, J=1.8 Hz), 8.77(1H, d, J=1.8 Hz).

Step 2

1.0M Lithium hexamethyl disilazide in a tetrahydrofuran solution (2.2 ml, 2.20 mmol) was cooled to −78° C., then the above Compound 43(242 mg, 1.00 mmol) in a dichloromethane (5 ml) solution was added and the mixture was stirred for 30 min at the same temperature. Crotonic acid methyl (0.16 ml, 1.70 mmol) was added and the mixture was stirred for 30 min at the same temperature and 1 hour at 0° C. A saturated NH$_4$Cl aq. was added to the reaction solution and extracted with ethyl acetate. The extract was washed and dried and the solvent was evaporated in vacuo. The obtained residue was dissolved in THF (5 ml) without purification and after cooling to 0° C., triethylamine (0.45 ml, 3.20 mmol) and methanesulfonyl chloride (0.16 ml, 2.10 mmol) were added and the mixture was stirred for 1 hour at the same temperature. Methanesulfonyl chloride (0.08 ml, 1.0 mmol) was added and the mixture was stirred for 1 hour at room temperature. To the reaction mixture, 2N HCl was added, and extracted with etyl acetate. The extract was washed and dried and the solvent was evaporated in vacuo and the obtained residue was purified by silicagel column chromatography (toluene:acetone=10:1, v/v) to give Compound 44 (125 mg, 0.250 mmol) obtained in 25% yield.

NMR (CDCl$_3$) δ:2.51(3H, d, J=0.9 Hz), 3.71(3H, s), 4.03(3H, s), 4.14(2H, s), 6.99-7.07(2H, m), 7.14-7.21(2H, m), 7.51(1H, s), 7.78(1H, d, J=2.1 Hz), 8.77 (1H, d, J=2.1 Hz).

Step 3

The above Compound 44(120 mg, 0.240 mmol) was dissolved in THF(1.5 ml) and methanol (1.5 ml), to which was added 28% sodium methoxide in methanol (0.3 ml), and the mixture was stirred for 4 hr at room temperature. To the reaction solution, a saturated NH$_4$Cl solution and water were added and the pricipitate was filtered out to give crude crystal (73 mg). It was recrystallized from acetone-methanol to give the title Compound I-109(38 mg, 0.117 mmol) as colorless crystals in 49% yield.

m.p.: 111-112° C.

(CDCl$_3$) δ: 2.59(3H, s), 4.02(3H, s), 4.13(2H, s), 6.98-7.05(3H, m), 7.14-7.20(2H, m), 7.68(1H, s), 8.72(1H, d, J=2.0 Hz).

The following compounds were obtained as well as the above.

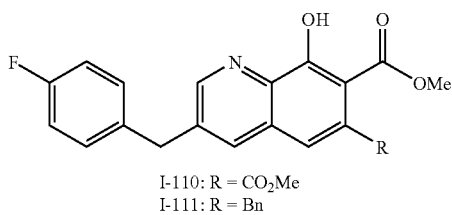

I-110: R = CO$_2$Me
I-111: R = Bn

Compound I-110

3-(4-Fluorobenzyl)-8-hydroxyquinoline-6,7-dicarboxylic acid dimethyl m.p.: 128-129° C.

(CDCl$_3$) δ: 3.93(3H, s), 4.00(3H, s), 4.18(2H, s), 7.69-7.07(2H, m), 7.14-7.21(2H, m), 7.71(1H, s), 7.88(1H, d, J=2.1 Hz), 8.82(1H, d, J=2.1 Hz).

Compound I-111

6-Benzyl-3-(4-fluorobenzyl)-8-hydroxyquinoline-7-carboxylic acid methyl m.p.: 83-84° C.

(CDCl$_3$) δ: 3.82(3H, s), 4.13(2H, s), 4.31(2H, s), 6.98-7.05(3H, m), 7.08-7.13(2H, m), 7.14-7.23(3H, m), 7.24-7.30 (2H, m), 7.71(1H, d, J=2.1 Hz), 8.72(1H, d, J=2.1 Hz).

Example 21

I-112

3-(4-Fluorobenzyl)-8-hydroxy-6-methoxycarbonylquinoline-7-carboxylic acid methyl

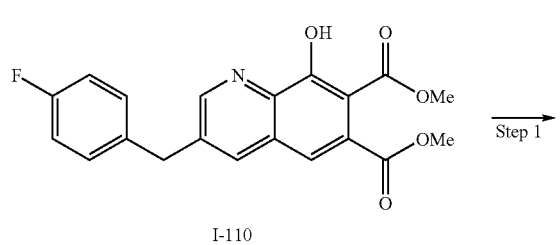

Step 1

The above Compound I-110(200 mg, 0.541 mmol) was dissolved in DMSO (10 ml) and 1N LiOH solution (2.1 ml, 2.10 mmol), and the mixture was stirred for 2 days at room temperature. To the reaction solution, 0.5M citric acid aqueous solution and water was added and the mixture was extracted with ethyl acetate. The extract was washed and dried and the solvent was evaporated under reduced pressure to give crude crystals (207 mg). The title Compound I-112 (26 mg) was crystallized from methanol. Additionally, the crystal crystallized from the mother liquor residue by ethyl acetate, was recrystallized from ethyl acetate to give the title Compound I-112 (54 mg). Totally, the title Compound I-112(80 mg, 0.225 mmol) was obtained in 42% yield.

m.p.: 215-220° C.

(DMSO-d$_6$) δ: 3.78(3H, s), 4.21(2H, s), 7.11-7.19(2H, m), 7.33-7.40 (2H, m), 7.99(1H, s), 8.34(1H, d, J=1.8 Hz), 8.93(1H, d, J=1.8 Hz), 10.59(1H, br s), 13.31(1H, br s).

Example 22

I-113

3-(4-Fluorobenzyl)-9-hydroxy-6,7-dihydrocyclopenta[g]quinoline-8-one

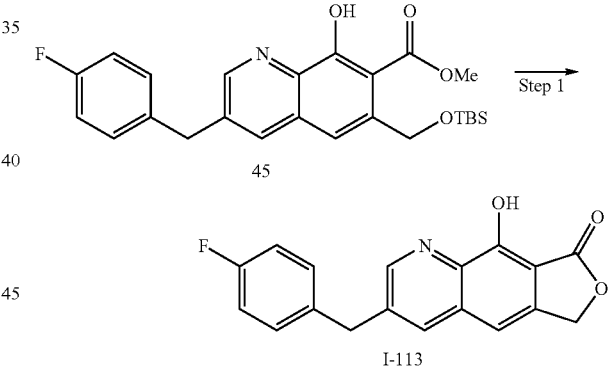

Step 1

Compound 45(82 mg, 0.180 mmol) obtained in a manner similar to Example 20 was poured into THF(1 ml) and after cooling to 0° C., 1.0M tetrabutyl ammonium fluoride in THF solution (0.37 ml, 0.370 mmol) was added thereto and the mixture was stirred for 1 hour at the same temperature and allowed to stand overnight at room temperature. To the reaction mixture, a saturated NH$_4$Cl aq. and water was added and the pricipitated crystal was filtered and obtained crude crystals (34 mg) were recrystallized from acetone-methanol to give Compound I-113 of the title (22 mg, 0.0711 mmol) in 40% yield.

m.p.: 195-197° C.

(CDCl$_3$) δ: 4.19(2H, s), 5.42(2H, s), 7.00-7.08(2H, m), 7.16-7.24(3H, m), 7.89(1H, s), 8.76(1H, d, J=2.1 Hz).

Example 23

I-114

5-Acetyl-3-(4-fluorobenzyl)-8-hydroxyquinoline-7-carboxylic acid methyl ester

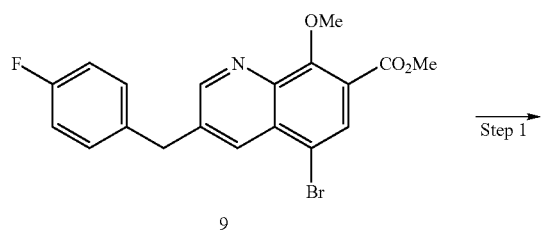

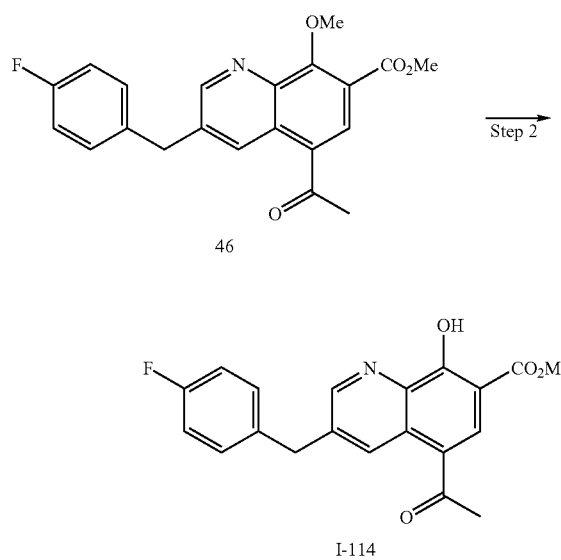

Step 1

To a suspension of Compound 9 (200 mg, 0.495 mmol obtained from Step 1 of Example 1) and tetrakis(triphenylphosphine)Palladium (0) (17 mg, 0.015 mmol) in toluene, tributyl(1-ethoxyvinyl)tin (0.335 ml, 0.992 mmol) was added at room temperature and the mixture was refluxed for 1 hour, which was concentrated in vacuo. The resulting residue was mixed with THF (2 ml) and 10% HCl (1 ml) and stirred for 1 hour at room temperature. The reaction mixture was mixed with ethyl acetate and filtrated through Celite for exclusion of insoluble material. The extract was washed with brine, dried over sodiun sulfate anhydrous, and concentrated in vacuo. The resultng residue was subjected to silicagel column chromatography and eluted with n-hexan-ethyl acetate (3:1, v/v). Fractions containing the desired compound were concentrated in vacuo to give Compound 46 (141 mg, 0.384 mmol) as yellow oil in 77% yield.

Step 2

In a manner similar to Step 3 of Example 9, Compound 46 (140 mg, 0.381 mmol) gave crude crystals of Compound I-114 of the title, which were recrystallized from ethylacetate-ethylether to give Compound I-114 (89 mg, 0.252 mmol) of the title as pale yellow crystals in 66% yield.

m.p.: 166-168° C. (from: ethyl acetate-ethyl ether)

(DMSO-$d_6$) δ: 2.66 (3H, s), 3.92 (3H, s), 4.24 (2H, s), 7.13-7.19 (2H, m), 7.33-7.38 (2H, m), 8.55 (1H, s), 8.91 (1H, d, J=2.1 Hz), 9.19 (1H, d, J=2.1 Hz).

Elemental Analysis: $C_{20}H_{16}FNO_4$ Calcd. (%): C, 67.98; H, 4.56; F, 5.38; N, 3.96. Found. (%): C, 67.57; H, 4.45; F, 5.11; N, 3.87.

Example 24

Compound I-115

3-(4-Fluorobenzyl)-5-guanidino-8-hydroxyquinoline-7-carboxylic acid methyl ester hydrochloride

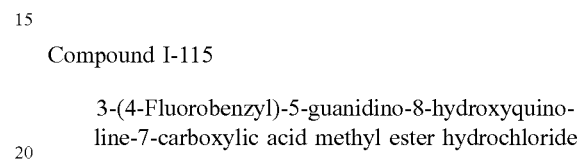

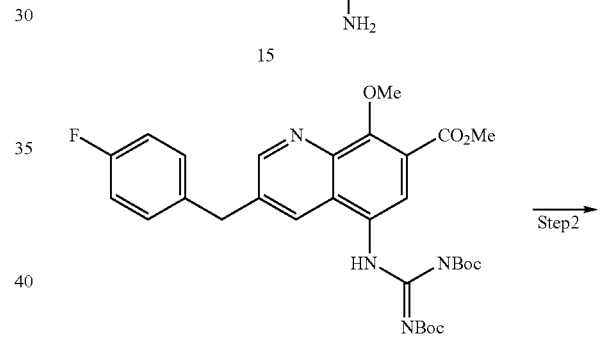

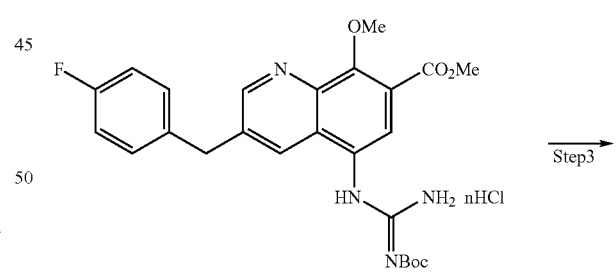

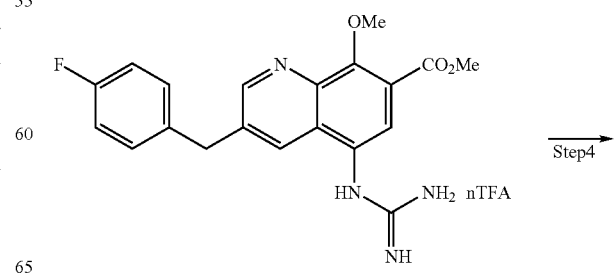

-continued

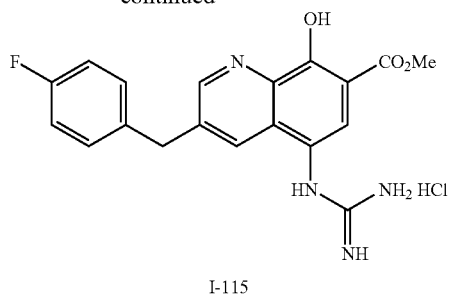

I-115

Step 1

To Compound 15 (obtained from in Step 2 of Ex 4; 500 mg, 1.47 mmol) in DMF(6 ml) solution, 1,3-di-tert-butoxycarbonyl-2-thio urea (447 mg, 1.62 mmol) and 1-ethyl-3-(3-dimethylaminopropyl)carbodiimide hydurochloride (310 mg, 1.62 mmol) were added and the mixture was stirred for 6 hours at room temperature. Water (24 ml) was added to the reaction solution and extracted with ethyl acetate. The extract was washed with brine, dried over sodiun sulfate anhydrous and concentrated in vacuo. The resulting residue was subjected to silicagel column chromatography and eluted with n-hexan-ethyl acetate (4:1, v/v). Fractions containing the desired compound were concentrated in vacuo to give Compound 47 (492 mg, 0.865 mmol) as colorless oil in 59% yield.

Step 2

Compound 47 (490 mg, 0.862 mmol) in 4N HCl ethyl acetate (12 ml) solution was stirred for 24 hours at room temperature. The solvent was evaporated in vacuo to give crude Compound 48 as crystalline residue.

Step 3

Compound 48 (388 mg) in trifluoroacetic acid (4 ml) was stirred for 4 days at room temperature. The solvent was evaporated in vacuo to give crude Compound 49 (690 mg) as red oil.

Step 4

In a manner similar to Step 2 of Example 12, Compound 49 (crude 690 mg) gave crude of Compound I-115 of the title, which was recrystallized from methanol to give Compound I-115 (154 mg, 0.380 mmol) of the title as colorless crystals.

m.p.: 261.5-262.5° C. (from: methanol)

(DMSO-$d_6$) δ: 3.92 (3H, s), 4.27 (2H, s), 7.12-7.18 (2H, m), 7.34-7.39 (2H, m), 7.39 (3H, brs), 7.74 (1H, s), 8.08 (1H, d, J=2.1 Hz), 8.94 (1H, d, J=2.1 Hz), 9.71 (1H, s).

Elemental Analysis: $C_{19}H_{17}FN_4O_3$·HCl Calcd. (%): C, 56.37; H, 4.48; Cl, 8.76; F, 4.69; N, 13.84, Found. (%): C, 54.71; H, 4.57; Cl, 8.55; F, 4.42; N, 13.19.

Example 25

I-116

3-(4-Fluorobenzyl)-5-diformylamino-8-hydroxyquinoline-7-carboxylic acid methyl ester

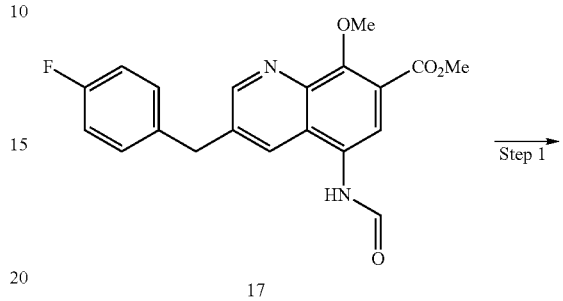

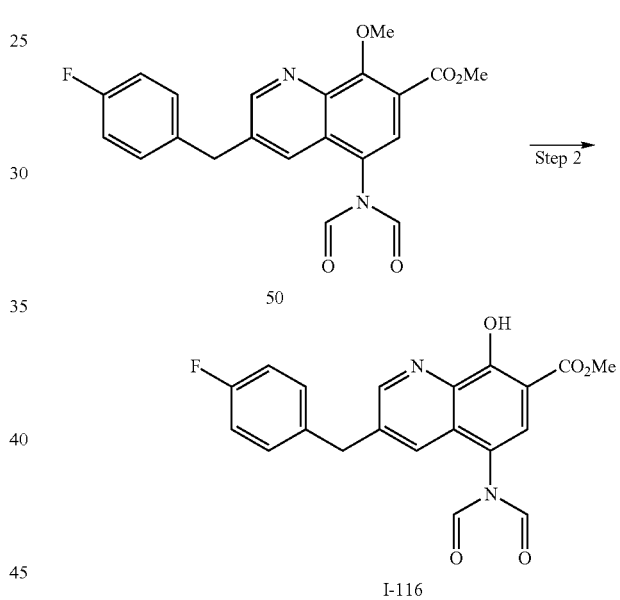

I-116

Step 1

In a manner similar to Step 1 of Ex. 6, Compound 17 (obtained from Step 1 of Ex. 6; 150 mg, 0.407 mmol) gave crude of Compound 50, which were recrystallized from diisopropylether to give Compound 50 (127 mg, 0.320 mmol) of the title as colorless crystals in 79% yield.

Step 2

In a manner similar to Step 3 of Ex. 9, Compound 50 (125 mg, 0.315 mmol) gave the crude Compound I-116 of the title, which were recrystallized from methanol to give Compound I-116 of the title (28.5 mg, 0.075 mmol) as colorless crystals in 24% yield.

m.p.: 243-245° C. (from: methanol)

(DMSO-$d_6$) δ: 3.90 (3H, s), 4.16 (2H, s), 7.10-7.16 (2H, m), 7.29-7.34 (2H, m), 7.75 (1H, s), 8.15 (1H, d, J=2.1 Hz), 8.87 (1H, d, J=2.1 Hz), 9.31 (2H, s).

Example 26

I-117

3-(4-Fluorobenzyl)-8-hydroxy-5-hydroxymethylquinoline-7-carboxylic acid methyl ester

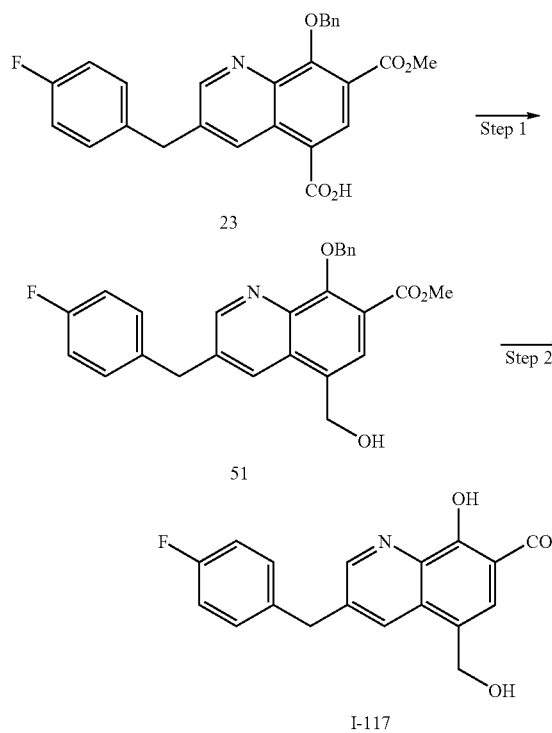

Step 1

To THF solution (50 ml) of Compound 23 (obtained from Step 1 of Ex. 11: 1.300 g, 2.918 mmol), 1,1'-carbonyldiimidazole (710 mg, 4.38 mmol) was added and the mixture was stirred for 15 min at 50° C. The reaction solution was cooled to room temperature and the water solution (10 ml) of sodium borohydride (113 mg, 2.99 mmol) was added dropwise for 30 min, then stirred for 15 min. To the reaction solution, 10% aqueous sodium hydrogen carbonate (50 ml) was added and extracted with ethylacetate (50 ml) twice. The extract was washed with brine (20 ml), dried over sodiun sulfate anhydrous and concentrated in vacuo. The resulting residue was subjected to silicagel column chromatography and eluted with n-hexan-ethyl acetate (2:1, v/v). Fractions containing the desired compound were concentrated in vacuo to give Compound 51 (1.085 g, 2.515 mmol) as colorless crystals in 86.2% yield.

Step 2

To a suspension (2 ml) of 10% Palladium-carbon (10 mg) in ethylacetate, under ice-cooling a solution of Compound 51 (100 mg, 0.232 mmol) in ethanol (2 ml) was added and the mixture was stirred for 1 hour under hydrogen atomosphere at 1 atm at room temperature. To the reaction solution, ethylacetate was added, and the mixture was filtered through Celite, washed with brine and dried over anhydrous sodium sulfate. The solvent was evaporated in vacuo and the obtained crude was recrystallized from 30% aqueous acetonitorile to give Compound I-117 of the title (53.5 mg, 0.157 mmol) as pale yellow-green crystals in 68% yield.

m.p.: 142-143° C. (from: 30% acetonitrile water)

(DMSO-$d_6$) δ: 3.92 (3H, s), 4.22 (2H, s), 4.81 (2H, d, J=5.1 Hz), 5.30 (1H, t, J=5.1 Hz), 7.11-7.17 (2H, m), 7.35-7.40 (2H, m), 7.83 (1H, s), 8.36 (1H, d, J=2.1 Hz), 8.86 (1H, d, J=2.1 Hz), 11.13 (1H, brs).

Elemental Analysis: $C_{19}H_{16}FNO_4$ Calcd. (%): C, 66.86; H, 4.72; F, 5.57; N, 4.10. Found. (%): C, 65.83; H, 4.79; F, 5.22; N, 3.94.

Example 27

I-118

3-(4-Fluorobenzyl)-8-hydroxy-5-methoxymethylquinoline-7-carboxylic acid methyl ester

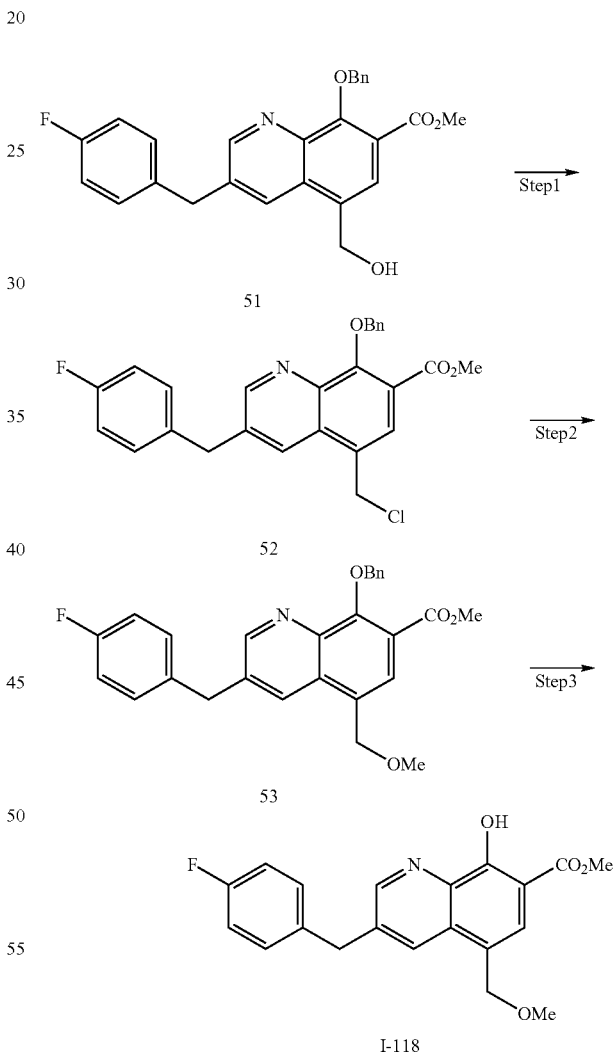

Step 1

To a solution of potassium cyanide (90 mg, 1.38 mmol) and 18-crown-6 (18 mg, 0.068 mmol) in acetonitorile (3 ml), under ice-cooling, a solution of Compound 51 (148 mg, 0.343 mmol) and tri-n-butyl phosphine (0.188 ml, 0.76 mmol) in acetonitrile (3 ml) and a solution of carbon tetrachloride (0.074 ml, 0.76 mmol) in acetonitrile (2 ml) were added and the mixture was stirred for 6 hours at room temperature. 10% citric water was added to the reaction solution and extracted with ethylacetate. The extract was washed with brine, dried over sodiun sulfate anhydrous and concentrated in vacuo. The resulting residue was subjected to silicagel column chromatography and eluted with n-hexan-ethylacetate (3:1, v/v). Fractions containing the desired compound were concentrated in vacuo to give Compound 52 (82 mg, 0.183 mmol) as colorless in 53% yield.

Step 2

To a suspension of Compound 52 (82 mg, 0.183 mmol) in methanol (4 ml), under ice-cooling, a solution of 28% sodium methoxidomethanol (212 mg, 1.10 mmol) was added and the mixture was stirred for 2 hours at 60° C. 10% citric water was added to the reaction solution and extracted with ethyl acetate. The extract was washed with brine, dried over sodiun sulfate anhydrous and concentrated in vacuo. The resulting residue was subjected to silica gel column chromatography and eluted with n-hexan-ethyl acetate (3:1, v/v). Fractions containing the desired compound were concentrated in vacuo to give Compound 53 (46 mg, 0.103 mmol) as colorless in 56% yield.

Step 3

In a manner similar to Step 2 in Ex. 26, Compound 53 (46 mg, 0.103 mmol) gave Compound I-118 of the title (24 mg, 0.068 mmol) as yellow-green crystals in 66% yield.

m.p.: 110-111° C. (from: 30% acetonitrile water)

(DMSO-$d_6$) δ: 3.28 (3H, s), 3.91 (3H, s), 4.23 (2H, s), 4.72 (2H, s), 7.12-7.18 (2H, m), 7.35-7.40 (2H, m), 7.82 (1H, s), 8.27 (1H, d, J=2.1 Hz), 8.86 (1H, d, J=2.1 Hz), 11.23 (1H, brs).

Example 28

I-119

5-(Ethyl-2-methoxyethylcarbamoyl)-3-(4-fluorobenzyl)-8-hydroxyquinoline-7-carboxylic acid methyl ester

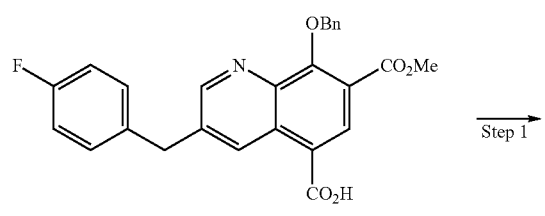

23

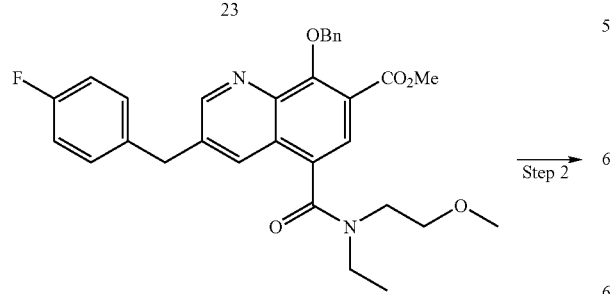

54

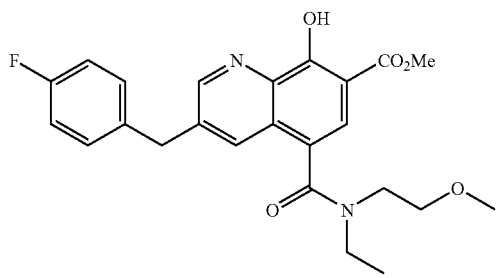

I-119

Step 1

In a manner similar to Step 1 in Ex. 2 Compound 23 (obtained from Step 1 of Ex. 11:90 mg, 0.202 mmol) was reacted. To the reaction solution, water was added and extracted with ethyl acetate. The extract was washed with brine and dried over anhydrous sodium sulfate. The solvent was evaporated in vacuo to give Compound 54 (98 mg, 0.185 mmol) as yellow oil in 91% yield.

Step 2

In a manner similar to Step 2 of Example 27, Compound 54 (97 mg, 0.183 mmol) gave crude crystals of Compound I-119 of the title, which were recrystallized from diisopropylether to give Compound I-119 (35.5 mg, 0.081 mmol) of the title as colorless crystals in 44% yield.

m.p.: 90-91° C. (from: diisopropylether)

(CDCl$_3$) δ: 0.96 (3H, t, J=6.9 Hz), 3.17 (2H, q, J=6.9 Hz), 3.41 (3H, s), 3.69 (4H, brs), 4.03 (3H, s), 4.15 (2H, s), 6.97-7.03 (2H, m), 7.14-7.19 (2H, m), 7.87 (1H, s), 7.92 (1H, d, J=2.1 Hz), 8.85 (1H, d, J=2.1 Hz), 11.95 (1H, brs).

Example 29

I-120

5-(Acetyl-ethylamino)-3-(4-fluorobenzyl)-8-hydroxyquinoline-7-carboxylic acid methyl ester

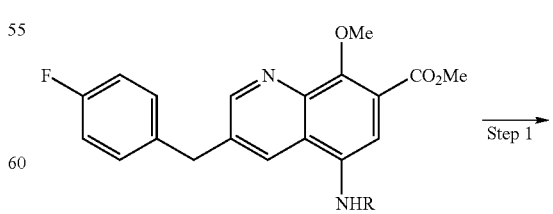

16-b (R = COMe)
17  (R = CHO)
16-d (R= SO$_2$Me)

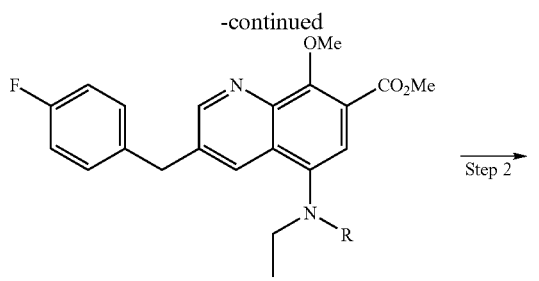

55-a (R = COMe)
55-b (R = CHO)
55-c (R = SO₂Me)

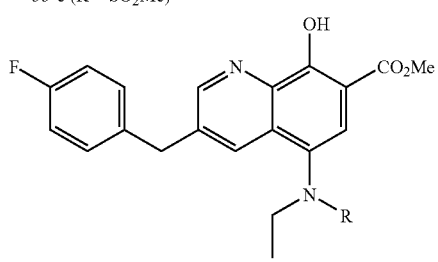

I-120 (R = COMe)
I-121 (R = CHO)
I-122 (R = SO₂Me)

Step 1

To a suspension of sodium hydride (30 mg, 0.75 mmol) in THF (5 ml), under ice-cooling, Compound 16-b (240 mg, 0.628 mmol; obtained from Step 1 of Ex. 5) was added and the mixture was stirred for 30 min. Then, ethyl bromide (0.14 ml, 1.88 mmol) was added at room temperature for 2 hours. The reaction solution was added to 10% citric water solution (50 ml) and extracted with ethyl acetate. The extract was washed with water twice, dried over sodiun sulfate anhydrous and concentrated in vacuo. The resulting residue was subjected to silicagel column chromatography and eluted with n-hexan-ethyl acetate (1:1, v/v). Fractions containing the desired compound were concentrated in vacuo to give Compound 55-a (111 mg, 0.270 mmol) as pale yellow crystal in 43% yield. In a manner similar to the above procedure, Compound 55-b, 55-c were obtained. Compound 17 (obtained from Step 1 of Ex. 6; 300 mg, 0.814 mmol) gave Compound 55-b (123 mg, 0.310 mmol) as yellow oil in 38% yield. Compound 16-d (obtained from Step 1 of Ex. 5; 270 mg, 0.645 mmol) gave Compound 55-c (176 mg, 0.394 mmol) as yellow crystals in 61% yield.

Step 2

In a manner similar to Step 3 of Example 9, Compound 55-a (111 mg, 0.270 mmol) gave crude crystals of Compound I-120 of the title, which were recrystallized from 90% aqueous methanol to give Compound I-I-120 (31.5 mg, 0.079 mmol) of the title as colorless crystals in 29% yield.

m.p.: 177-178° C. (from: 90% aqueous methanol)

(CDCl₃) δ: 1.11 (3H, t, J=7.2 Hz), 1.72 (3H, s), 3.40 (2H, m, J=7.2 Hz), 4.05 (3H, s), 4.17 (2H, s), 6.98-7.04 (2H, m), 7.12-7.17 (2H, m), 7.74 (1H, s), 7.82 (1H, d, J=2.1 Hz), 8.90 (1H, d, J=2.1 Hz), 11.98 (1H, brs).

In a manner similar to the Step 3 of Example 9, Compound 55-b (123 mg, 0.310 mmol) gave Compound I-121 (92 mg, 0.241 mmol) as yellowish-brown crystals in 78% yield.

I-121

5-(Ethylformylamino)-3-(4-fluorobenzyl)-8-hydroxyquinoline-7-carboxylic acid methyl ester m.p.: 90-91° C. (from: 30% aqueous acetonitrile)

(CDCl₃) δ: 1.11 (3H, t, J=7.2 Hz), 3.39-3.66 (2H, m), 4.05 (3H, s), 4.17 (2H, s), 6.99-7.05 (2H, m), 7.13-7.20 (2H, m), 7.75 (1H, s), 7.81 (1H, d, J=2.1 Hz), 8.17 (1H, s), 8.90 (1H, d, J=2.1 Hz), 11.98 (1H, brs).

Elemental Analysis: $C_{21}H_{19}FN_2O_4H_2O$ Calcd. (%): C, 62.99; H, 5.29; F, 4.74; N, 7.00. Found. (%): C, 63.73; H, 5.23; F, 4.77; N, 6.97.

In a manner similar to Step 3 of Example 9, Compound 55-c (174 mg, 0.390 mmol) gave crude of Compound I-122 of the title, which were recrystallized from methanol-ethylether to give Compound I-122 (28 mg, 0.065 mmol) of the title as colorless crystals in 17% yield.

I-122

5-(Ethylmethanesulfonylamino)-3-(4-fluorobenzyl)-8-hydroxyquinoline-7-carboxylic acid methyl ester m.p.: 149-150° C. (from: methanol-ethylether)

(CDCl₃) δ: 1.07 (3H, t, J=6.9 Hz), 2.99 (3H, s), 3.63-3.70 (1H, m), 3.80-3.87 (1H, m), 4.04 (3H, s), 4.20 (2H, s), 6.98-7.04 (2H, m), 7.15-7.20 (2H, m), 7.84 (1H, s), 8.22 (1H, d, J=2.1 Hz), 8.85 (1H, d, J=2.1 Hz), 11.88 (1H, brs).

Example 30

I-123

3-(4-Fluorobenzyl)-8-hydroxyquinoline-5,7-dicarboxylic acid 5-benzyl ester 7-methyl ester

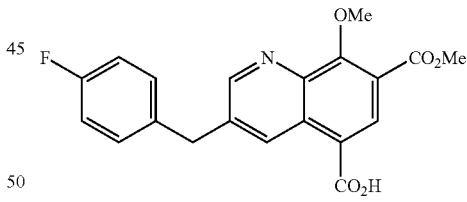

10

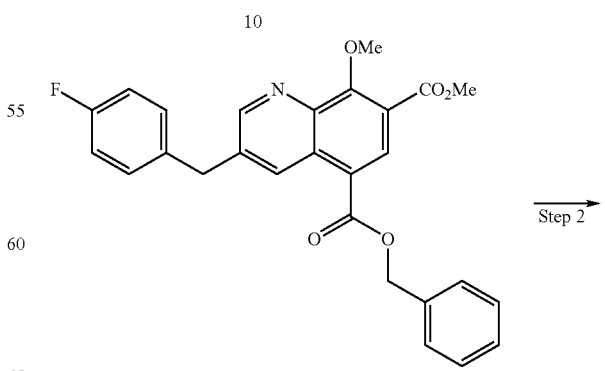

56

-continued

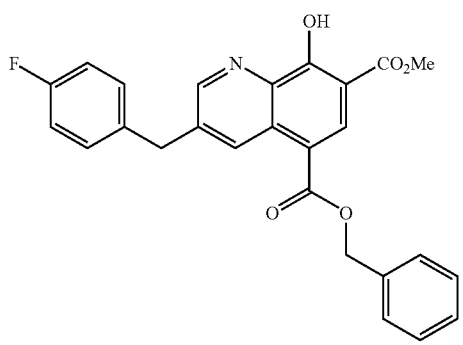

I-123

Step 1

A solution of 2M trimethylsilildiazomethane in hexane (0.609 ml, 1.22 mmol) was diluted with THF (4 ml) and cooled to −20° C. A solution of Compound 10 (obtained from Step 2 of Example 1; 300 mg, 0.812 mmol) in thionylchloride solution (5 ml) was refluxed for 1.5 hours and evaporated in vacuo. The resulting residue was added dropwise to the aboved reaction mixture under −10° C. After stirring for 1.5 hours, the reaction mixture was added to 10% aqueous sodium hydrogen carbonate (36 ml) under ice-cooling and extracted with ethyl acetate. The extract was washed with 10% aqueous sodium hydrogen carbonate and brine, and dried over sodium anhydrous, then evaporated in vacuo. To the residue, benzylalchol (5 ml) and 2,4,6-collidine (2.5 ml) were added and stirred for 20 mins at 150° C. The reaction solution was cooled to room temperature and 10% aqueous citric acid (50 ml) was added and extracted with ethylacetate. The extract was washed with 10% aqueous citric acid, 10% aqueous sodium hydrogencarbonate and brine, dried over sodiun sulfate anhydrous, and concentrated in vacuo. The resulting residue was subjected to silicagel column chromatography and eluted with n-hexan-ethyl acetate (1:1, v/v). Fractions containing the desired compound were concentrated in vacuo to give Compound 56 (128 mg, 0.279 mmol) as yellow oil in 34% yield.

Step 2

In a manner similar to the Step 3 of Example 9, Compound 56 (128 mg, 0.279 mmol) gave title Compound I-123 (81.5 mg, 0.183 mmol) as colorless crystals in 66% yield.

m.p.: 131-133° C. (from: 30% aqueous acetonitrile)

(CDCl$_3$) δ: 4.05 (3H, s), 4.16 (2H, s), 5.42 (2H, s), 6.96-7.02 (2H, m), 7.14-7.19 (2H, m), 7.37-7.49 (5H, m), 8.79 (1H, s), 8.84 (1H, d, J=2.1 Hz), 9.27 (1H, d, J=2.1 Hz).

Elemental Analysis: C$_{26}$H$_{20}$FNO$_5$ Calcd. (%): C, 70.11; H, 4.53; F, 4.27; N, 3.14. Found. (%): C, 69.62; H, 4.46; F, 4.23; N, 3.23.

Example 31

I-124

5-(2-Aminoethylcarbamoyl)-3-(4-fluorobenzyl)-8-hydroxyquinoline-7-carboxylic acid methyl ester

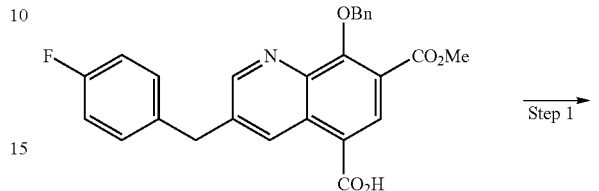

23

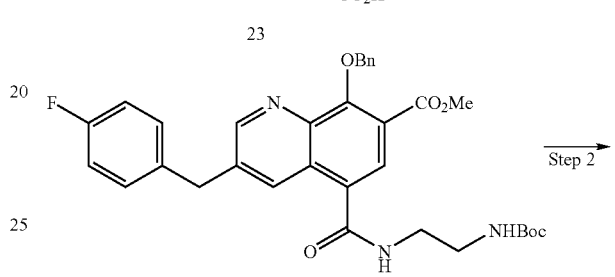

57

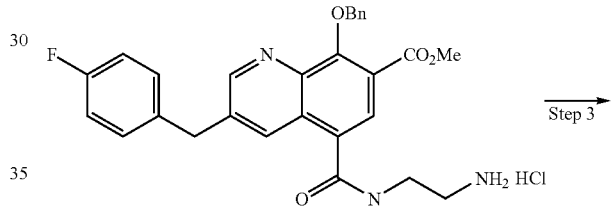

58

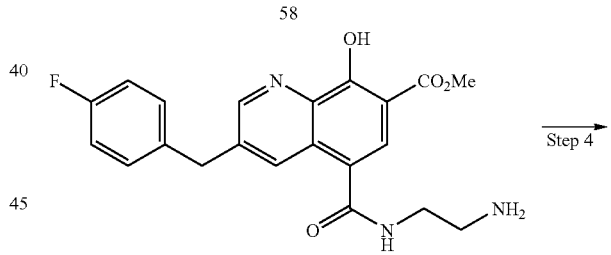

I-124

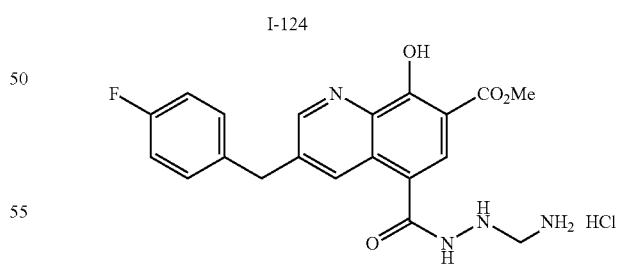

I-125

Step 1

In a manner similar to Step 1 of Ex. 2, Compound 23 (obtained from Step 1 of Example. 11; 300 mg, 0.674 mmol) was reacted. To the reaction solution, water was added and extracted with ethyl acetate. The extract was washed with brine, dried over sodium sulfate anhydrous and concentrated in vacuo. The resulting residue was subjected to silicagel column chromatography and eluted with n-hexan-ethyl acetate (1:1, v/v). Fractions containing the desired compound were concentrated in vacuo to give Compound 57 (306 mg, 0.521 mmol) as colorless crystals in 77% yield.

Step 2

A solution of Compound 57 (248 mg, 0.422 mmol) in 4N HCl ethylacetate (4 ml) was stirred for 45 mins at room temperature. The solvent was evaporated in vacuo to give crude Compound 58 (237 mg) as crystalline residue.

Step 3

In a manner similar to the Step 3 of Example 9, Compound 58 (237 mg) gave Compound I-124 of the title (82 mg) as yellow crystal.

m.p.: 229-230° C. (from: 30% aqueous acetonitrile)

(DMSO-$d_6$+DCl) δ: 3.03 (2H, brs), 3.57 (2H, brs), 3.96 (3H, s), 4.28 (2H, s), 7.14-7.20 (2H, m), 7.35-7.40 (2H, m), 8.27 (1H, s), 8.35 (1H, brs), 8.92 (1H, d, J=2.1 Hz), 9.00 (1H, d, J=2.1 Hz).

Step 4

I-125 5-(2-Aminoethylcarbamoyl)-3-(4-fluorobenzyl)-8-hydroxyquinoline-7-carboxylic acid methyl ester hydrochloride To a suspencion of Compound I-124 (82 mg, 0.206 mmol) in ethylacetate (2 ml), 4N HCl ethyl acetate solution (0.5 ml) was added at room temperature and the mixture was stirred for 15 min. The pricipitated crystals were washed with ethylacetate to give Compound I-125 (88 mg) of the title as blackish brown crystals.

m.p.: 225-227° C. (from: ethylacetate)

(DMSO-$d_6$) δ: 2.99-3.05 (2H, m), 3.93 (3H, s), 4.22 (2H, s), 7.13-7.19 (2H, m), 7.32-7.37 (2H, m), 7.96 (2H, brs), 8.19 (1H, s), 8.72 (1H, d, J=2.1 Hz), 8.74 (1H, brs), 8.92 (1H, d, J=2.1 Hz).

Elemental Analysis: $C_{21}H_{20}FN_3O_4 \cdot 1.5H_2O \cdot 1.5HCl$ Calcd. (%): C, 52.64; H, 5.15; Cl, 11.10; F, 3.97; N, 8.77 Found. (%): C, 49.12; H, 5.10; Cl, 11.03; F, 3.30; N, 8.05.

Example 32

I-126 bis[3-(4-Fluorobenzyl)-8-hydroxy-7-methoxycarbonylquinoline-5-yl]methane

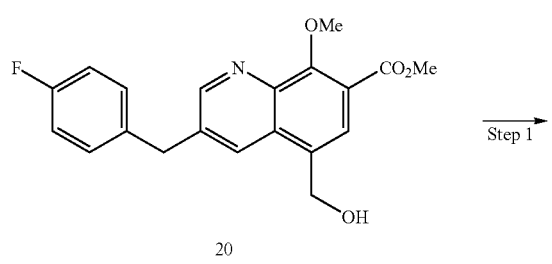

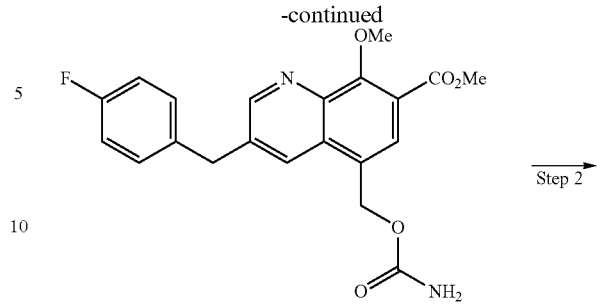

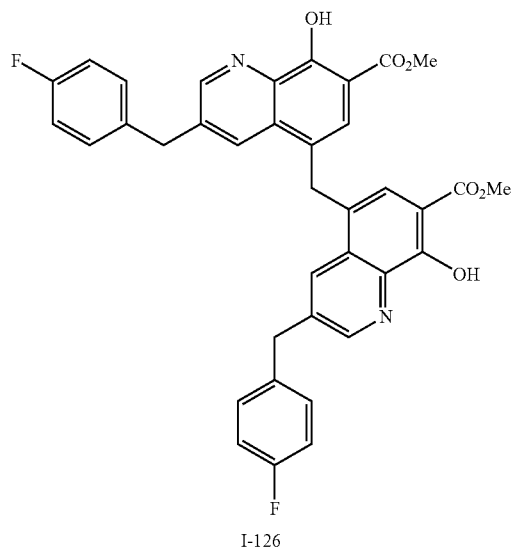

Step 1

To a THF solution (2 ml) of Compound 20 (obtained from Step 1 of Ex. 9: 200 mg, 0.563 mmol), trichloro acetyl isocyanate (0.101 ml, 0.847 mmol) was added at −78° C. and the mixture was stirred for 15 mins with warming gradually. At 0° C., water (0.6 ml) and triethylamine (0.3 ml) were added and the mixture was stirred for 1.5 hours at room temperature. Water was added to the reaction mixture and extracted with ethylacetate. The extract was washed with brine, dried over sodiun sulfate anhydrous and concentrated in vacuo. The resulting residue was subjected to silicagel column chromatography and eluted with ethylacetate. Fractions containing the desired compound were concentrated in vacuo to give Compound 59 (172 mg, 0.432 mmol) as colorless crystals in 77% yield.

Step 2

In a manner similar to Step 3 of Example 9, Compound 59 (170 mg, 0.427 mmol) gave crude crystal of Compound I-126, which was recrystallized from ethylacetate to give Compound I-126 (84 mg, 0.132 mmol) as yellowish-brown in 31% yield.

m.p.: 244-245° C. (from: ethylacetate)

(DMSO-$d_6$) δ: 3.80 (6H, s), 4.14 (4H, s), 4.64 (2H, s), 6.95-7.01 (4H, m), 7.18-7.22 (4H, m), 7.42 (2H, s), 8.26 (2H, s), 8.89 (2H, s), 11.13 (2H, brs).

Example 33

I-127

5-(1,1-Dioxide-1,2-thiazinane-2-yl)methyl-3-(4-fluorobenzyl)-8-hydroxy quinoline-7-carboxylic acid methyl ester

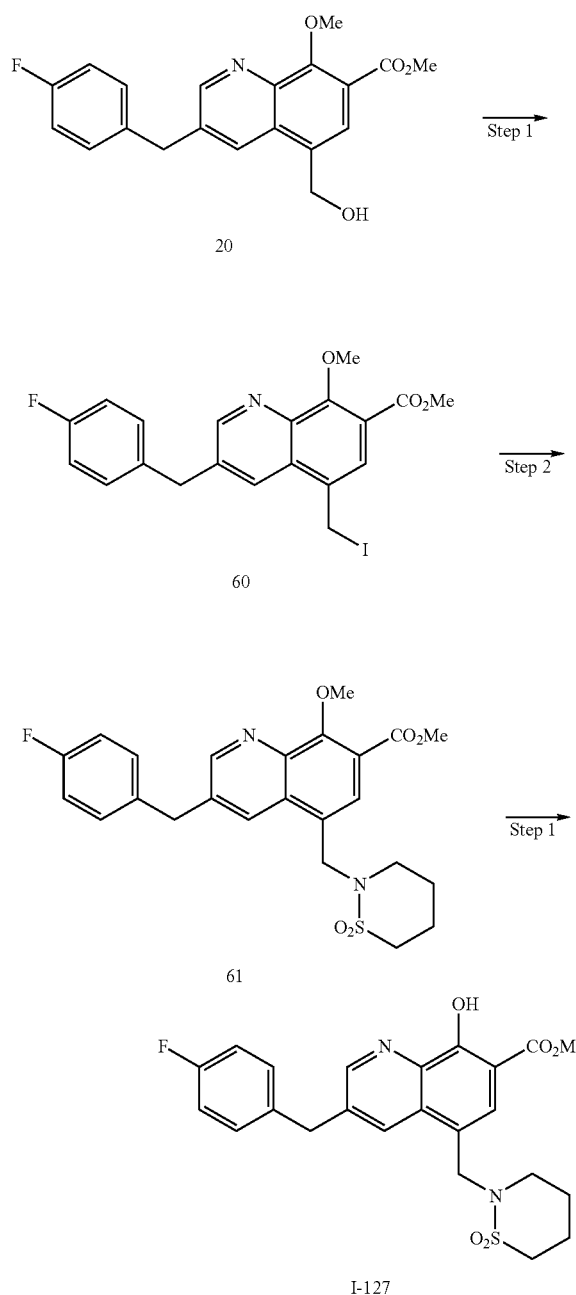

Step 1

To a suspension of Compound 20 (1.000 g, 2.814 mmol; obtained from Step 1 of Example 9) and sodium iodide (2.11 g, 14.1 mmol) in acetonitrile (40 ml), trimethylsilane chrolide (1.79 ml, 14.1 mmol) was added under ice-cooling. While warming to room temperature, the mixture was stirred for 30 mins and additional 30 mins at 50° C. It was cooled to room temperature and mixed with 10% sodium hydrogensulfate (40 ml). The pricipitate crystals were filtered and subjected to silicagel column chromatography and eluted with n-hexan-ethyl acetate (1:1, v/v). Fractions containing the desired compound were concentrated in vacuo to give Compound 60 (977 mg, 2.100 mmol) as colorless crystals in 74.6% yield.

Step 2

1,1-Dioxide-1,2-thiazinane (52 mg, 0.38 mmol) prepared in a manner similar to that described in WO02/309301 was added to a suspension of sodium hydride (15 mg, 0.38 mmol) in THF (5 ml) under ice-cooling and the mixture was stirred for 15 min. Then Compound 60 (150 mg, 0.322 mmol) was added and the mixture was stirred for 1 hour while warming to room temperature and for additonal 1.5 hours at 50° C. The reaction solution was cooled to room temperature and 10% citric water solution (15 ml) was added and the mixture was extracted with ethylacetate. The extract was washed with water, dried over sodiun sulfate anhydrous, and concentrated in vacuo. The resulting residue was subjected to silicagel column chromatography and eluted with n-hexan-ethyl acetate (1:2, v/v). Fractions containing the desired compound were concentrated in vacuo to give Compound 61 (141 mg, 0.298 mmol) as colorless crystals in 93% yield.

Step 3

In a manner similar to Step 3 of Example 9, Compound 61 (127 mg, 0.269 mmol) gave crude crystals of Compound I-127, which was recrystallized from chloroform-ethylether to give Compound I-127 (73 mg, 0.159 mmol) as yellow crystals in 59% yield.

m.p.: 159-161° C. (from: chloroform-ethylether)

(CDCl$_3$) δ: 1.43-1.54 (2H, m), 2.10-2.22 (2H, m), 2.95 (2H, t, J=6.0 Hz), 3.11 (2H, t, J=6.0 Hz), 4.03 (3H, s), 4.17 (2H, s), 4.53 (2H, s), 6.98-7.03 (2H, m), 7.21-7.26 (2H, m), 7.72 (1H, s), 8.47 (1H, d, J=1.8 Hz), 8.90 (1H, d, J=1.8 Hz).

Elemental Analysis: $C_{23}H_{23}FN_2O_5S$ Calcd. (%): C, 60.25; H, 5.06; F, 4.14; N, 6.11; S, 6.99. Found. (%): C, 60.33; H, 4.94; F, 4.28; N, 5.95; S, 6.61.

Example 34

I-128

5-(2,6-Dioxopiperidine-1-yl)methyl-3-(4-fluorobenzyl)-8-hydroxyquinoline-7-carboxylic acid methyl ester

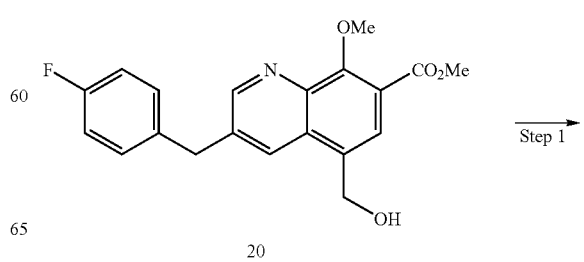

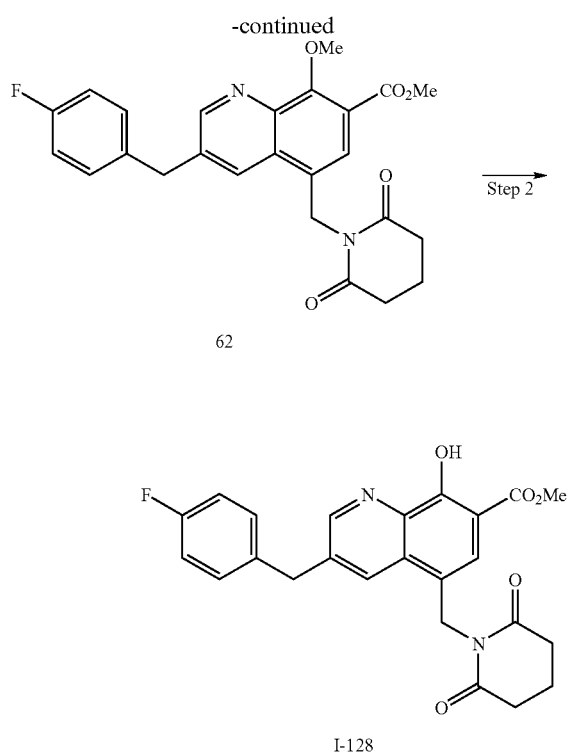

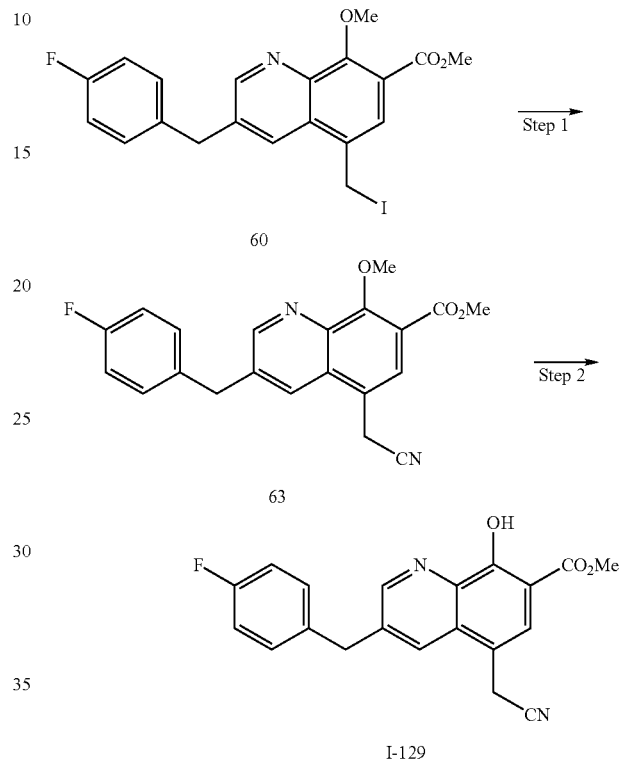

Example 35

I-129

5-Cyanomethyl-3-(4-fluorobenzyl)-8-hydroxyquinoline-7-carboxylic acid methyl ester

Step 1

To a solution (5 ml) of Compound 20 (140 mg, 0.394 mmol; obtained from Step 1 of Ex. 9) and piperidine-2,6-dione (53.5 mg, 0.473 mmol) in THF, tri-n-butylphosphine (0.147 ml, 0.590 mmol) and diisopropylazodi carboxyrate (0.116 ml, 0.589 mmol) were added under ice-cooling and the mixture was stirred for 1 hour while warming to room temperature. Ethyl acetate was added and the mixture was washed with water, dried over sodiun sulfate anhydrous and concentrated in vacuo. The resulting residue was subjected to silicagel column chromatography and eluted with toluene-ethyl acetate (1:1, v/v). Fractions containing the desired compound were concentrated in vacuo to give Compound 62 (92 mg, 0.204 mmol) as colorless crystals in 52% yield.

Step 2

In a manner similar to Step 2 of Ex. 2, Compound 62 (138 mg, 0.306 mmol) gave crude Compound I-314 of the title, which was subjected to silicagel column chromatography, eluted with chloroform-methanol-water (32:6:0.5, v/v) and concentrated at reduced pressure. The obtained residue was dissolved in chloroform and the solution was washed with 1N hydrochloric acid and water twice and dried over sodium sulfate anhydrous. The solvent was concentrated under reduced pressure, mixed with ethyl acetate-ethylether and recrystallized to give Compound I-128 of the title (21 mg, 0.048 mmol) as colorless crystals in 16% yield.

m.p.: 154-156° C. (from: ethylacetate-ethylether)

(CDCl$_3$) δ: 1.89 (2H, quintet, J=6.6 Hz), 2.66 (4H, t, J=6.6 Hz), 4.01 (3H, s), 4.17 (2H, s), 5.23 (2H, s), 6.98-7.04 (2H, m), 7.20-7.25 (2H, m), 7.89 (1H, s), 8.34 (1H, d, J=2.1 Hz), 8.85 (1H, d, J=2.1 Hz), 11.79 (1H, brs).

Step 1

Under ice-cooling, potassium cyanide (184 mg, 2.83 mmol) was added to a solution of Compound 60 (656 mg, 1.41 mmol) in DMF (10 ml) and the mixture was stirred for 1 hour while warming to room temperature. Then water (40 ml) was added to the reaction solution and stirred for 1 hour. The precipitated crystal was filtered and subjected to silicagel column chromatography and eluted with n-hexan-ethyl acetate (1:1, v/v). Fractions containing the desired compound were concentrated in vacuo to give Compound 63 (326 mg, 0.895 mmol) as colorless crystal in 64% yield.

Step 2

In a manner similar to Step 2 of Ex. 2, Compound 63 (120 mg, 0.329 mmol) gave crude Compound I-129 of the title, which was subjected to silica gel column chromatography and eluted with chloroform-methanol-water (32:6:0.5, v/v). Fractions containing the desired compound were concentrated in vacuo. The obtained residue was dissolved in chloroform, washed with 1N hydrochloric acid and water twice and dried over sodium sulfate anhydrous. The solvent was concentrated in vacuo and recrystallized from ethylacetate-ethylether to give Compound I-129 of the title (66 mg, 0.188 mmol) as colorless crystals in 57% yield.

m.p.: 173-175° C. (from: ethylacetate-ethylether)

(CDCl$_3$) δ: 3.94 (3H, s), 4.05 (2H, s), 4.22 (2H, s), 7.01-7.06 (2H, m), 7.17-7.22 (2H, m), 7.86 (1H, d, J=2.1 Hz), 7.96 (1H, s), 8.92 (1H, d, J=2.1 Hz).

Elemental Analysis: $C_{20}H_{15}FN_2O_3$ Calcd. (%): C, 68.57; H, 4.32; F, 5.42; N, 8.00. Found. (%): C, 68.46; H, 4.02; F, 5.35; N, 7.98.

Example 36

I-130

5-Carbamoylmethyl-3-(4-fluorobenzyl)-8-hydroxyquinoline-7-carboxylic acid methyl ester

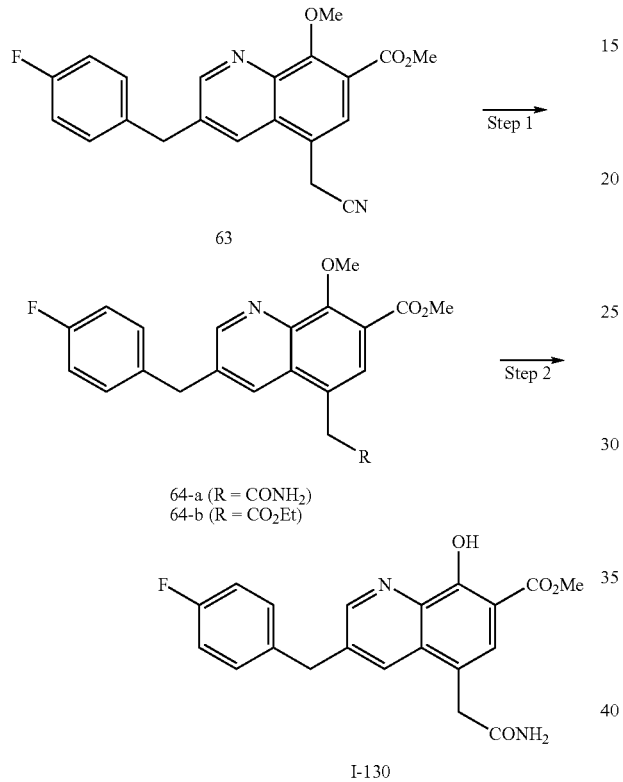

Step 1

A suspension of Compound 63 (465 mg, 1.28 mmol) in 4N HCl ethyl acetate (7 ml) was stirred for 2 hours under ice-cooling and allowed to stand for 2 days in a refrigarator. The solvent was evaporated in vacuo and water (35 ml) was added to the obtained residue, which was extracted with chloroform three times. The extract was washed with brine, dried over sodiun sulfate anhydrous, and concentrated in vacuo. The resulting residue (512 mg) was subjected to silicagel column chromatography and eluted with ethyl acetate. Fractions containing the desired compound were concentrated in vacuo to give Compound 64-a (85 mg, 0.222 mmol) as colorless crystals in 79% yield. After additional elution with ethyl acetate, fractions containing the desired compound were concentrated in vacuo to give Compound 64-a (85 mg, 0.222 mmol) as colorless crystals in 17% yield.

Step 2.

In a manner similar to Step 3 of Example 9, Compound 64-a (85 mg, 0.22 mmol) gave crude of Compound I-130 of the title, which was recrystallized from 85% aqueous acetone to give Compound I-130 (60 mg, 0.16 mmol) as colorless crystals in 74% yield.

m.p.: 209-211° C. (from: 85% aqueous acetone)
(DMSO-$d_6$) δ: 3.76 (2H, s), 3.92 (3H, s), 4.20 (2H, s), 6.99 (1H, brs), 7.11-7.16 (2H, m), 7.34-7.39 (2H, m), 7.56 (1H, brs), 7.75 (1H, s), 8.37 (1H, d, J=1.8 Hz), 8.84 (1H, d, J=1.8 Hz), 11.10 (1H, brs).
Elemental Analysis: $C_{20}H_{17}FN_2O_4 \cdot 0.75H_2O$ Calcd. (%): C, 62.90; H, 4.88; F, 4.97; N, 7.34. Found. (%): C, 63.09; H, 4.88; F, 4.79; N, 7.25.

Example 37

I-131

3-(4-Fluorobenzyl)-8-hydroxy-5-methoxycarbonylmethylquinoline-7-carboxylic acid methyl ester

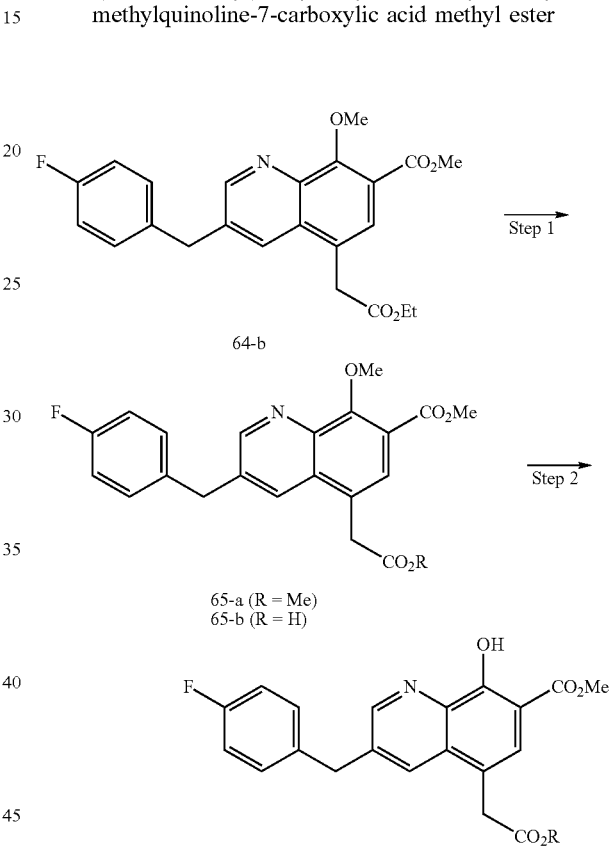

Step 1

To a suspension of Compound 64-b (155 mg, 0.377 mmol) in methanol (2 ml), 1M sodium methooxide methanol solution (4 ml) was added at room temperature and the mixture was stirred at 40° C. for 30 min. The reaction solution was cooled to room temperature and mixed with 2N hydrochloric acid (20 ml) and extracted with ethyl acetate. The extract was washed with water, dried over sodium sulfate anhydrous and concentrated in vacuo. The resulting residue was subjected to silicagel column chromatography and eluted with n-hexan-ethyl acetate (1:1, v/v). Fractions containing the desired compound were concentrated in vacuo to give Compound 65-a (70 mg, 0.176 mmol) as colorless crystals in 47% yield. 2N hydrochloric acid (1.6 ml) was added to a suspension of Compound 64-b (128 mg, 0.311 mmol) in 1,4-dioxane (8 ml) at room temperature and refluxed for 1 hour. The reaction solution was cooled to room temperature and extracted with ethylacetate twice. The extract was washed with water twice and saturated aqueous sodium hydrogen carbonate three times. The Obtained residue was poured into 12N hydrochloric acid and crystallized by neutralization to give Compound 65-b (114 mg, 0.297 mmol) as colorless crystals in 96% yield.

Step 2

In a manner similar to Step 3 of Ex. 9, Compound 65-a (69 mg, 0.17 mmol) gave crude of Compound I-131, which was subjected to silica gel column and eluted with chloroform-methanol-water (32:6:0.5, v/v). Fractions containing the desired compounds were concentrated in vacuo. The resulting residue was dissolved in chloroform, washed with 1N hydrochloric acid and water each twice and dried over anhydrous sodium sulfate. The solvent was concentrated in vacuo and recrystallized from ethylether to give Compound I-131 (12 mg, 0.031 mmol) of the title as pale yellow crystals in 18% yield.

m.p.: 168-169° C. (from: chloroform-ethylether)

(CDCl$_3$) δ: 3.62 (3H, s), 3.88 (2H, s), 4.02 (3H, s), 4.18 (2H, s), 6.99-7.05 (2H, m), 7.16-7.20 (2H, m), 7.80 (1H, s), 7.95 (1H, s), 8.87 (1H, brs), 11.80 (1H, brs).

I-132

5-Carboxymethyl-3-(4-fluorobenzyl)-8-hydroxyquinoline-7-carboxylic acid methyl ester In a manner similar to Step 2 of Ex. 2, Compound 65-b (114 mg, 0.297 mmol) gave the crude Compound I-132 of the title, which was recrystallized from acetone-ethyleter to give Compound I-132 of the title (68 mg, 0.184 mmol) as colorless crystals in 62% yield.

m.p.: 218-220° C. (from: acetone-ethyleter)

(DMSO-d$_6$) δ: 3.92 (3H, s), 3.97 (2H, s), 4.21 (2H, s), 7.10-7.16 (2H, m), 7.34-7.39 (2H, m), 7.75 (1H, s), 8.26 (1H, d, J=2.1 Hz), 8.86 (1H, d, J=2.1 Hz), 11.11 (1H, brs), 12.37 (1H, brs).

Elemental Analysis: C$_{20}$H$_{16}$FNO$_5$0.5H$_2$O Calcd. (%): C, 63.49; H, 4.53; F, 5.02; N, 3.70. Found. (%): C, 63.37; H, 4.35; F, 4.72; N, 3.63.

Example 38

I-133

5-(N'-Acetylhydrazinoiminomethyl)-3-(4-fluorobenzyl)-8-hydroxyquinoline-7-carboxylic acid methyl ester

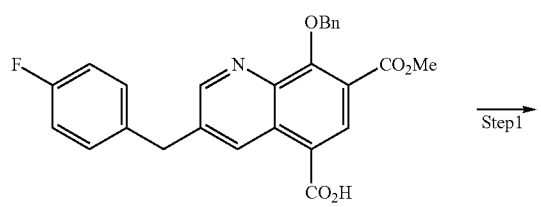

23

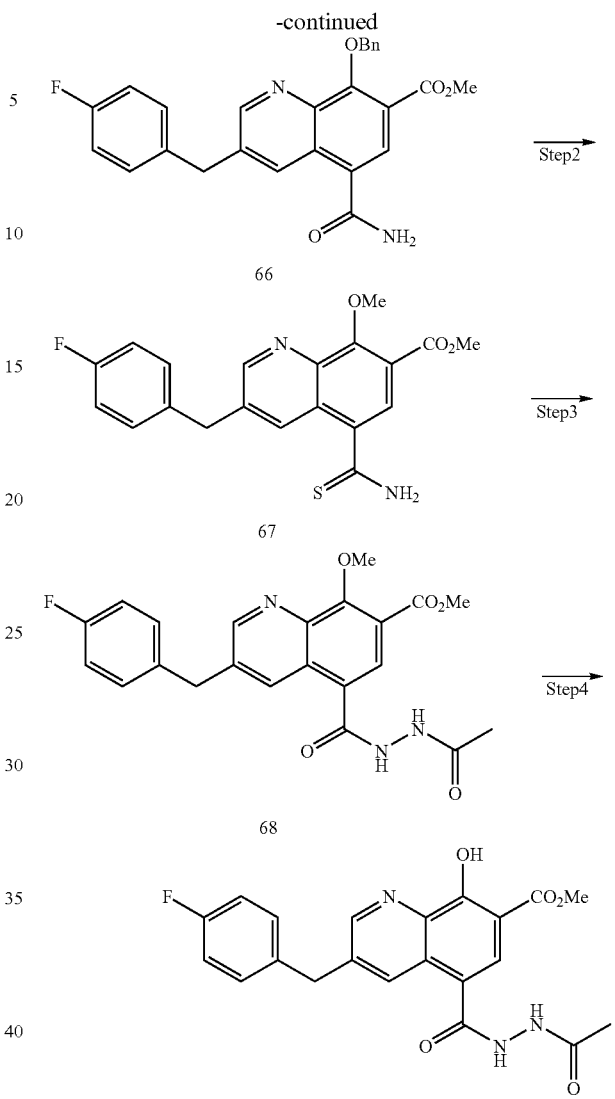

Step 1

In a manner similar to Step 1 of Ex. 2, Compound 23 (3.00 g, 6.74 mmol, obtained from Step 1 of Example 11) gave Compound 66 (2.83 g, 6.37 mmol) as colorless crystals in 94.5% yield.

Step 2

To a solution of Compound 66 (2.37 g, 5.33 mmol) in THF (120 ml), phosphorus pentasulfide (3.56 g, 8.01 mmol) was added at room temperature and the mixture was stirred for 1.5 hours at 40° C. The reaction solution was cooled to room temperature and mixed with saturated aqueous sodium hydrogen carbonate and ethylacetate. The obtained residue was filtered through Celite and the filtrate was extracted with ethylacetate. The extract was washed with brine, dried over sodiun sulfate anhydrous and concentrated in vacuo. The resulting residue was subjected to silicagel column chromatography and eluted with n-hexan-ethyl acetate (3:2, v/v). Fractions containing the desired compound were concentrated in vacuo to give Compound 67 (1.08 g, 2.35 mmol) as pale crystals in 44% yield.

Step 3

To a solution (15 ml) of Compound 67 (766 mg, 1.66 mmol) in methylenechloride, triethyloxonium tetrafluoro borate (366 mg, 1.93 mmol) was added under ice-cooling and the mixture was stirred for 30 mins while warming to room temperature. The reaction solution was ice-cooled and a solution (1.5 ml) of acetohydrazide (247 mg, 3.33 mmol) in methanol was added and the mixture was stirred for 1.5 hours while warming to room temperature. To the reaction solution, 10% aqueous sodium hydrogen carbonate (50 ml) was added and the mixture was extracted with ethylacetate twice. The extract was washed with saturated aqueous sodium hydrogen carbonate and brine and dried over sodium sulfate anhydrous. The residue obtained by evaporation in vacuo was washed with ethylether to give Compound 68 (632 mg, 1.26 mmol) as pale yellow crystals in 75.9% yield.

Step 4

In a manner similar to Step 7 of Ex. 1, Compound 68 (200 mg, 0.40 mmol) gave Compound I-133 (73 mg, 0.18 mmol) as colorless crystals in 45% yield.

Step 2 m.p.: 179-181° C. (from: 30% aqueous acetonitrile)

(DMSO-$d_6$) δ: 1.90 (3H, s), 3.92 (3H, s), 4.22 (2H, s), 6.56 (2H, s), 7.10-7.16 (2H, m), 7.32-7.40 (2H, m), 7.96 (1H, s), 8.61 (1H, s), 8.90 (1H, s), 9.70 (1H, s), 11.13 (1H, brs).

Elemental Analysis: $C_{21}H_{19}FN_4O_4 \cdot 1.5H_2O$ Calcd. (%): C, 57.66; H, 5.07; F, 4.34; N, 12.81. Found. (%): C, 57.65; H, 4.94; F, 4.34; N, 12.72.

Example 39

I-134

3-(4-Fluorobenzyl)-8-hydroxy-5-(5-methyl-1H-[1,2,4]triazole-3-yl)quinoline-7-carboxylic acid methyl ester

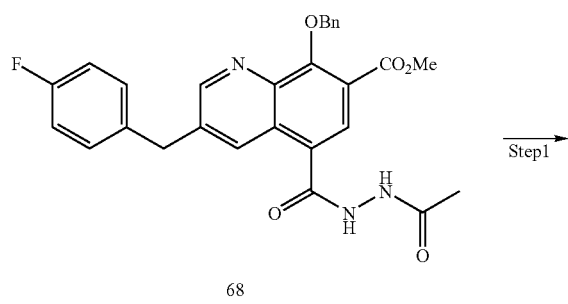

68

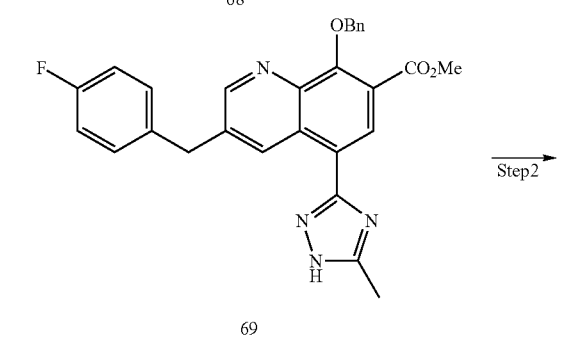

69

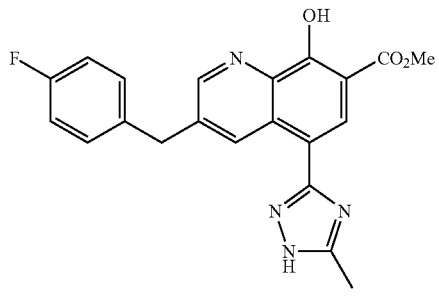

I-134

Step 1

A solution of Compound 68 (180 mg, 0.36 mmol) in diglyme (6 ml) was stirred in 45 mins at 160° C. The reaction mixture was cooled to room temperature and the residue obtained by evaporation in vacuo was subjected to silica gel column chromatography and eluted with ethylacetate. Fractions containing the desired compound were concentrated in vacuo and the obtained residue was dissolved in ethylacetate (150 ml). The solution was washed with water (50 ml×3) and dried over sodium sulfate anhydrous. The solvent was evaporated in vacuo to give the crude of Compound 69 as yellow oil.

Step 2

In a manner similar to Step 2 of Ex. 26, Compound 69 (208 mg as crude) gave crude Compound I-134 of the title, which was recrystallized from ethylether to give Compound I-134 of the title (84 mg, 0.214 mmol) as colorless crystals.

m.p.: 200-202° C. (from: 1,4-dioxane-ethylether)

(CDCl$_3$) δ: 2.59 (3H, s), 4.02 (3H, s), 4.19 (2H, s), 6.96-7.02 (2H, m), 7.16-7.20 (2H, m), 8.56 (1H, s), 8.84 (1H, d, J=1.8 Hz), 9.20 (1H, d, J=1.8 Hz), 10.80 (1H, brs), 11.90 (1H, brs).

Elemental Analysis: $C_{21}H_{17}FN_4O_3$ Calcd. (%): C, 64.28; H, 4.37; F, 4.84; N, 14.28. Found. (%): C, 62.72; H, 4.29; F, 4.63; N, 13.33.

Example 40

I-135

7-Carbamoyl-3-(4-fluorobenzyl)-8-hydroxyquinoline-5-carboxylic acid

B-1 ($R_1$ = Bn)
9  ($R_1$ = Me)

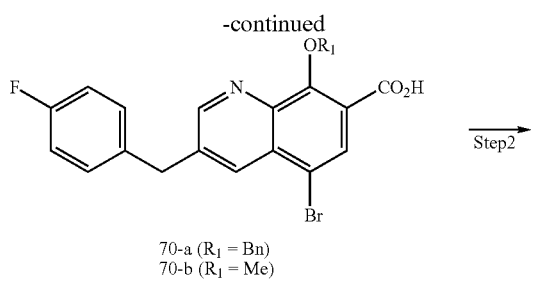

70-a (R₁ = Bn)
70-b (R₁ = Me)

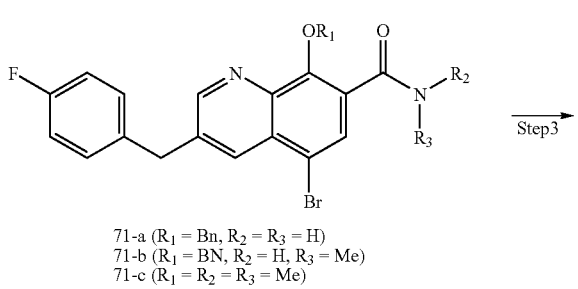

71-a (R₁ = Bn, R₂ = R₃ = H)
71-b (R₁ = BN, R₂ = H, R₃ = Me)
71-c (R₁ = R₂ = R₃ = Me)

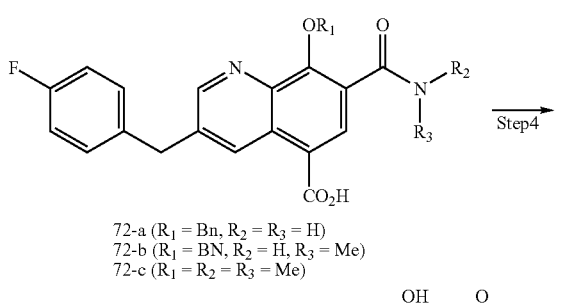

72-a (R₁ = Bn, R₂ = R₃ = H)
72-b (R₁ = BN, R₂ = H, R₃ = Me)
72-c (R₁ = R₂ = R₃ = Me)

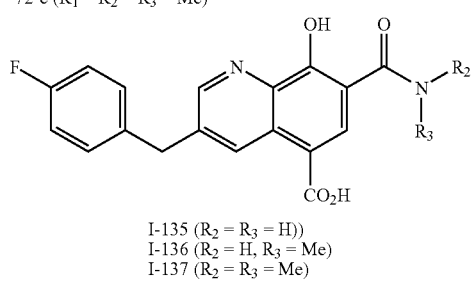

I-135 (R₂ = R₃ = H))
I-136 (R₂ = H, R₃ = Me)
I-137 (R₂ = R₃ = Me)

Step 1

In a manner similar to Step 8 of Reference Example 1, Compound B-1 (1.513 g, 3.150 mmol) gave Compound 70-a (1.425 g, 3.056 mmol) as colorless crystals in 97.0% yield. To a solution of Compound 9 (10.00 g, 24.74 mmol) in THF (50 ml)-methanol (50 ml), 2N sodium hydroxide aqueous solution (14.9 ml, 29.8 mmol) was added at room temperature and the mixture was refluxed for 20 mins. The reaction mixture was cooled to room temperature and mixed with 2N hydrochloric acid (16 ml, 32 mmol), water (400 ml) and stirred for 2 hr at room temperature. The pricipitated crystals were filtered and washed with methanol and isopropanol to give Compound 70-b (9.500 g, 24.35 mmol) as colorless crystals in 98.4% yield.

m.p.: 204-205° C.

Step 2

In a manner similar to Step 1 of Example 2, Compound 70-a (212 mg, 0.455 mmol) gave crystals of Compound 71-a (191 mg, 0.410 mmol) as colorless crystals in 90% yield. In a manner similar to Step 1 of Example 2, Compound 70-a (240 mg, 0.455 mmol) gave crystals of Compound 71-b (230 mg, 0.480 mmol) as colorless crystals in 93% yield.

In a manner similar to Step 1 of Example 2, Compound 70-b (1.520 g, 3.895 mmol) gave crystals of Compound 71-c (1.558 g, 3.734 mmol) as pale yellow crystals in 95.9% yield.

Step 3

In a manner similar to Step 2 of Example 1, Compound 71-a (189 mg, 0.406 mmol) gave crystals of Compound 72-a (108 mg, 0.251 mmol) as yellow crystals in 62% yield. In a manner similar to Step 2 of Example 1, Compound 71-b (230 mg, 0.480 mmol) gave crystals of Compound 72-b (86 mg, 0.193 mmol) as yellow crystals in 40% yield. In a manner similar to Step 2 of Example 1, Compound 71-c (1.47 g, 3.52 mmol) gave crystals of Compound 72-c (1.38 g, 3.61 mmol) as pale yellow crystals in 95.9% yield quantitatively.

Step 4

In a manner similar to Step 2 of Example 26, Compound 72-a (107 mg, 0.249 mmol) gave crude Compound I-135 of the title, which was recrystallized from DMF-acetone to give Compound I-135 (41 mg, 0.120 mmol) of the title as yellow crystals in 49% yield.

m.p.: 212-213° C. (from: DMF-acetone)

(DMSO-$d_6$) δ: 4.24 (2H, s), 7.13-7.19 (2H, m), 7.32-7.37 (2H, m), 7.83 (1H, brs), 8.80 (2H, s), 8.92 (1H, brs), 9.31 (1H, s), 12.52 (1H, brs).

I-136

3-(4-Fluorobenzyl)-8-hydroxy-7-methylcarbamoylquinoline-5-carboxylic acid

In a manner similar to Step 2 of Example 26, Compound 72-b (90 mg, 0.202 mmol) gave crude Compound I-136 of the title, which was recrystallized from DMF-methanol to give Compound I-136 (90 mg, 0.202 mmol) of the title as yellow crystals in 55% yield.

m.p.: 203-205° C. (from: DMF-methanol)

(DMSO-$d_6$) δ: 2.87 (3H, d, J=4.2 Hz), 4.22 (2H, s), 7.12-7.18 (2H, m), 7.31-7.36 (2H, m), 8.74 (1H, s), 8.81 (1H, s), 9.34 (1H, s), 9.64 (1H, brs), 12.44 (1H, brs).

I-137

7-Dimethylcarbamoyl-3-(4-fluorobenzyl)-8-hydroxyquinoline-5-carboxylic acid

In a manner similar to Step 7 of Example. 1, Compound 72-c (186 mg, 0.486 mmol) gave crude Compound I-137 of the title, which was recrystallized from ethylacetate-ethylether to give Compound I-137 (152 mg, 0.413 mmol) of the title as yellow crystals in 85% yield.

m.p.: 214.5-215.5° C. (from: ethylacetate-ethylether)

(DMSO-$d_6$) δ: 2.92 (3H, brs), 3.01 (3H, brs), 4.25 (2H, s), 7.12-7.18 (2H, m), 7.32-7.37 (2H, m), 8.09 (1H, s), 8.88 (1H, d, J=2.1 Hz), 9.25 (1H, d, J=2.1 Hz), 12.92 (1H, brs).

Elemental Analysis: $C_{20}H_{17}FN_2O_4 \cdot 0.5H_2O$ Calcd. (%): C, 63.66; H, 4.81; F, 5.03; N, 7.42. Found. (%): C, 63.18; H, 4.72; F, 4.43; N, 6.88.

Example 41

I-138

3-(4-Fluorobenzyl)-8-hydroxyquinoline-5,7-dicarboxylic acid diamide

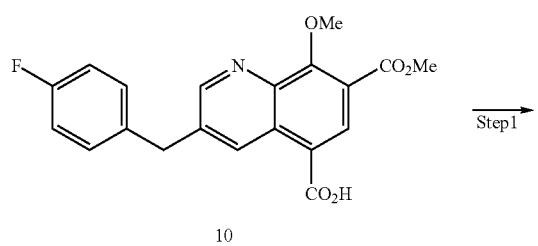

10

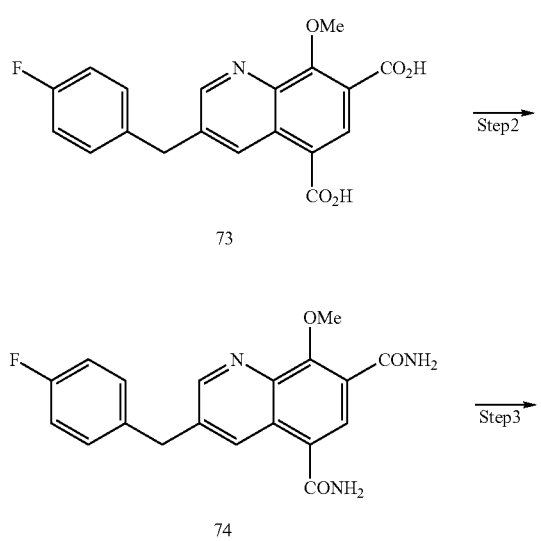

73

74

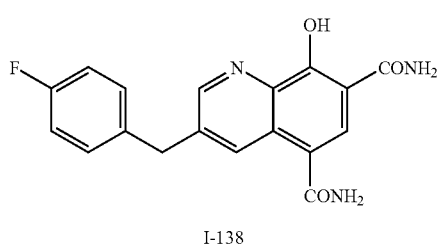

I-138

Step 1

In a manner similar to Step 8 of Reference Example 1, Compound 10 (891 mg, 2.412 mmol; obtained in Step 2 of Example 1) gave Compound 73 (653 mg, 1.838 mmol) as gray crystals in 76.3% yield.

Step 2

In a manner similar to Step 1 of Example 2, Compound 73 (325 mg, 0.915 mmol) gave crude Compound 74, which was recrystallized from methanol-ethylacetate to give Compound 74 (218 mg, 0.617 mmol) as colorless crystals in 67% yield.

Step 3

In a manner similar to Step 7 of Example 1, Compound 74 (215 mg, 0.608 mmol) gave Compound I-138 of the title (174 mg, 0.513 mmol) as colorless crystals in 84% yield.

m.p.: 214.5-215.5° C. (from: 30% aqueous acetonitrile)

(DMSO-$d_6$) δ: 4.21 (2H, s), 7.12-7.18 (2H, m), 7.31-7.36 (2H, m), 7.47 (1H, brs), 7.88 (1H, brs), 8.06 (1H, brs), 8.25 (1H, s), 8.45 (1H, brs), 8.70 (1H, d, J=2.1 Hz), 8.85 (1H, d, J=2.1 Hz).

Elemental Analysis: $C_{18}H_{14}FN_3O_3H_2O$ Calcd. (%): C, 60.50; H, 4.51; F, 5.32; N, 11.76. Found. (%): C, 60.00; H, 3.85; F, 4.98; N, 11.70.

Example 42

I-139

3-(4-Fluorobenzyl)-8-hydroxyquinoline-5,7-dicarboxylic acid 5-dimethyl amide 7-methyl amide

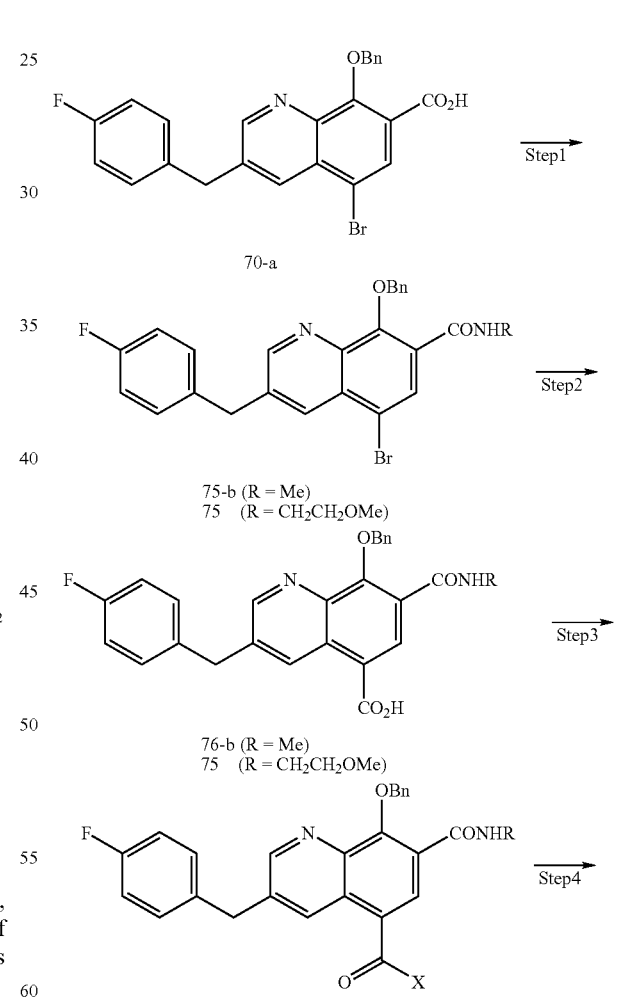

70-a 75-b (R = Me)
75  (R = CH₂CH₂OMe)

76-b (R = Me)
75  (R = CH₂CH₂OMe)

77-a (R = Me, X = NMe₂)
77-b (R = Me, X = NHCH₂CH₂OMe)
77-c (R = Me, X = OMe)
77-d (R = Me, X = OCH₂CH₂OMe)
77-e (R = CH₂CH₂OMe, X = OMe)

-continued

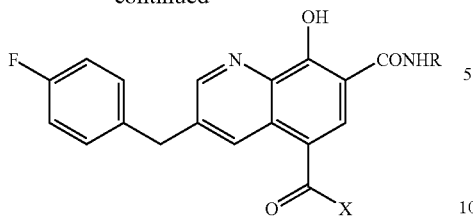

I-139 (R = Me, X = NMe$_2$)
I-140 (R = Me, X = NHCH$_2$CH$_2$OMe)
I-141 (R = Me, X = OMe)
I-142 (R = Me, X = OCH$_2$CH$_2$OMe)
I-143 (R = CH$_2$CH$_2$OMe, X = OMe)

Step 1

In a manner similar to Step 1 of Example 2, Compound 70-a (500 mg, 1.072 mmol) gave crude Compound 75 (851 mg) as yellow oil.

Step 2

In a manner similar to Step 2 of Example 1, crude Compound 75 (851 mg) gave crude crystals of Compound 76 (620 mg).

Step 3

In a manner similar to Step 1 of Example 2, Compound 76-b (123 mg, 0.277 mmol) gave crude of Compound 77-a (118 mg) as yellow oil.

In a manner similar to Step 1 of Example 2, Compound 76-b (210 mg, 0.473 mmol) gave crude Compound 77-b (308 mg) as yellow oil.

In a manner similar to Step 1 of Example 2, Compound 76-b (329 mg) gave crude of Compound 77-c (214 mg) as yellow oil.

To a solution of Compound 76-b (210 mg, 0.473 mmol) and 4-dimethyl aminopyridine (58 mg, 0.48 mmol) in DMF (10 ml) were added 2-methoxyethanol (0.097 ml, 1.23 mmol) and 1-ethyl-3-(3-dimethylaminopropyl)carbodiimide hydrochloride (127 mg, 0.662 mmol) under ice-cooling and the mixture was stirred for 5 hours while warming to room temperature. The reaction mixture was mixed with 1N hydrochloric acid (40 ml) and extracted with ethylacetate twice. The extract was washed with water three times, dried over sodium sulfate anhydrous and concentrated in vacuo. The resulting residue was subjected to silicagel column chromatography and eluted with n-hexan-ethyl acetate (1:2, v/v). Fractions containing the desired compound were concentrated in vacuo to give Compound 77-d (119 mg, 0.237 mmol) as colorless oil in 50% yield.

In a manner similar to Step 1 of Example 2, crude Compound 76 (620 mg) gave crude Compound 77-e (69 mg, 0.14 mmol) as colorless crystals.

Step 4

In a manner similar to Step 2 of Example 26, crude Compound 77-a (117 mg) gave crude Compound I-139 of the title, which was recrystallized from 1,4-dioxane-ethylether to give Compound I-139 (72 mg, 0.19 mmol) of the title as yellow crystals.

m.p.: 216-218° C. (from: 1,4-dioxane-ethylether)

(DMSO-d$_6$) δ: 2.73 (3H, brs), 2.87 (3H, d, J=4.5 Hz), 4.05 (3H, brs), 4.21 (2H, s), 7.12-7.18 (2H, m), 7.32-7.37 (2H, m), 7.90 (1H, d, J=1.8 Hz), 7.91 (1H, s), 8.85 (1H, d, J=1.8 Hz), 8.94 (1H, brs).

Elemental Analysis: C$_{21}$H$_{20}$FN$_3$O$_3$ Calcd. (%): C, 66.13; H, 5.29; F, 4.98; N, 11.02. Found. (%): C, 65.55; H, 5.37; F, 4.95; N, 10.94.

I-140

3-(4-Fluorobenzyl)-8-hydroxyquinoline-5,7-dicarboxylic acid 5-(2-methoxy ethyl)amide 7-methyl amide In a manner similar to Step 2 of Example 26, crude Compound 77-b (307 mg) gave crude Compound I-140 of the title, which was recrystallized from DMF-ethylacetate to give Compound I-140 (105 mg, 0.255 mmol) of the title as orange crystals.

m.p.: 237-239° C. (from: DMF-ethyl acetate)

(DMSO-d$_6$) δ: 2.88 (3H, d, J=4.2 Hz), 3.29 (3H, s), 3.43-3.50 (4H, m), 4.19 (2H, s), 7.12-7.18 (2H, m), 7.31-7.36 (2H, m), 8.16 (1H, s), 8.47 (1H, brs), 8.60 (1H, s), 8.82 (1H, s), 9.04 (1H, brs).

Elemental Analysis: C$_{22}$H$_{22}$FN$_3$O$_4$ Calcd. (%): C, 64.22; H, 5.39; F, 4.62; N, 10.21. Found. (%): C, 63.15; H, 5.08; F, 4.70; N, 10.22.

I-141

3-(4-Fluorobenzyl)-8-hydroxy-7-methoxycarbamoylquinoline-5-carboxylic acid methyl ester In a manner similar to Step 2 of Example 26, crude Compound 77-c (214 mg) gave crude Compound I-141 of the title, which was recrystallized from ethylacetate-ethylether to give Compound I-141 (5.5 mg, 0.015 mmol) of the title as yellow crystals.

m.p.: 186-188° C. (from: ethylacetate-ethylether)

(DMSO-d$_6$) δ: 2.89 (3H, brs), 3.86 (3H, s), 4.28 (2H, brs), 7.14-7.20 (2H, m), 7.34-7.39 (2H, m), 8.84 (2H, brs), 9.34 (2H, brs).

I-142

3-(4-Fluorobenzyl)-8-hydroxy-7-methoxycarbamoylquinoline-5-carboxylic acid 2-methoxyethyl ester In a manner similar to Step 2 of Example 26, Compound 77-d (108 mg, 0.215 mmol) gave crude Compound I-142 of the title, which was recrystallized from 1,4-dioxane-ethyl acetate to give Compound I-142 (75.8 mg, 0.184 mmol) of the title as orange crystals in 86% yield.

m.p.: 166-168° C. (from: 1,4-dioxane-ethyl acetate)

(DMSO-d$_6$) δ: 2.89 (3H, d, J=4.5 Hz), 3.32 (3H, s), 3.67-3.70 (2H, m), 4.27 (2H, s), 4.40-4.43 (2H, m), 7.14-7.20 (2H, m), 7.35-7.40 (2H, m), 8.84 (1H, s), 8.86 (1H, d, J=1.8 Hz), 9.34 (1H, d, J=1.8 Hz), 9.37 (1H, brs).

Elemental Analysis: C$_{22}$H$_{21}$FN$_2$O$_5$ Calcd. (%): C, 64.07; H, 5.13; F, 4.61; N, 6.79. Found. (%): C, 63.74; H, 4.96; F, 4.72; N, 6.93.

I-143

3-(4-Fluorobenzyl)-8-hydroxy-7-(2-methoxyethylcarbamoyl)quinoline-5-carboxylic acid methyl ester In a manner similar to Step 2 of Example 26, Compound 77-e (69 mg, 0.14 mmol) gave crude Compound I-143 of the title, which was recrystallized from 1,4-dioxane-ethylacetate to give Compound I-143 of the title (39.5 mg, 0.096 mmol) as yellow crystals in 70% yield.

m.p.: 165-167° C. (from: 1,4-dioxane-ethylacetate)

(DMSO-$d_6$) δ: 3.30 (3H, s), 3.48-3.56 (4H, m), 3.85 (3H, s), 4.29 (2H, s), 7.15-7.21 (2H, m), 7.36-7.41 (2H, m), 8.84 (1H, d, J=2.1 Hz), 8.89 (1H, s), 9.45 (1H, d, J=2.1 Hz), 9.73 (1H, brs).

Example 43

I-144

3-(4-Fluorobenzyl)-8-hydroxy-5-(2-methoxycarbonylvinyl)quinoline-7-carboxylic acid methyl ester

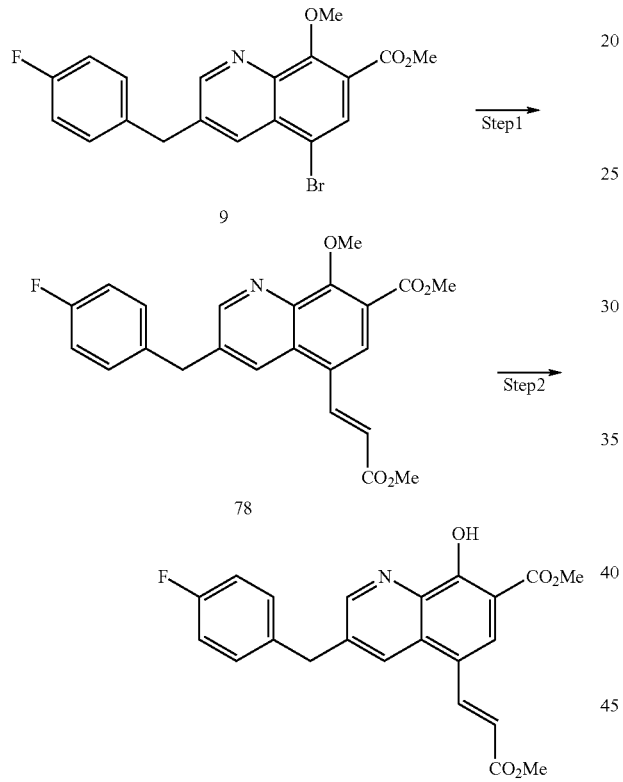

Step 1

A mixture of Compound 9 (2.000 g, 4.948 mmol; obtained in Step 1 of Example 1), acetic acid Palladium (II) (56 mg, 0.25 mmol), tris(2-methyl phenyl)phosphine (151 mg, 0.496 mmol), triethylamine (2.76 ml, 19.8 mmol) and methyl acrylate (1.34 ml, 14.9 mmol) was stirred for 24 hours at 110° C. in an autoclave. The reaction mixture was cooled to room temperature and mixed with water (100 ml) and 2N hydrochloric acid (30 ml), and extracted wuth ethylacetate (200 ml). The extract was washed with water twice, dried over sodiun sulfate anhydrous and concentrated in vacuo. The resulting residue was subjected to silicagel column chromatography and eluted with n-hexan-ethyl acetate (2:1, v/v). Fractions containing the desired compound were concentrated in vacuo to give Compound 78 (1.222 g, 2.985 mmol) as yellow oil in 60.3% yield.

Step 2

In a manner similar to Step 3 of Example 9, Compound 78 (122 mg, 0.298 mmol) gave crude Compound I-144, which was recrystallized from ethylacetate-ethylether to give Compound I-144 of the title (73 mg, 0.185 mmol) as flesh color crystals in 62% yield.

m.p.: 139-141° C. (from: ethylacetate-ethylether)

(CDCl$_3$) δ: 3.86 (3H, s), 4.06 (3H, s), 4.21 (2H, s), 6.51 (1H, d, J=15.6 Hz), 6.99-7.05 (2H, m), 7.16-7.21 (2H, m), 8.20-8.27 (3H, m), 8.88 (1H, d, J=1.8 Hz).

Elemental Analysis: $C_{22}H_{18}FNO_5$ Calcd. (%): C, 66.83; H, 4.59; F, 4.81; N, 3.54. Found. (%): C, 66.14; H, 4.55; F, 4.60; N, 3.63.

Example 44

I-145

5-(2-Carboxyvinyl)-3-(4-fluorobenzyl)-8-hydroxyquinoline-7-carboxylic acid methyl ester

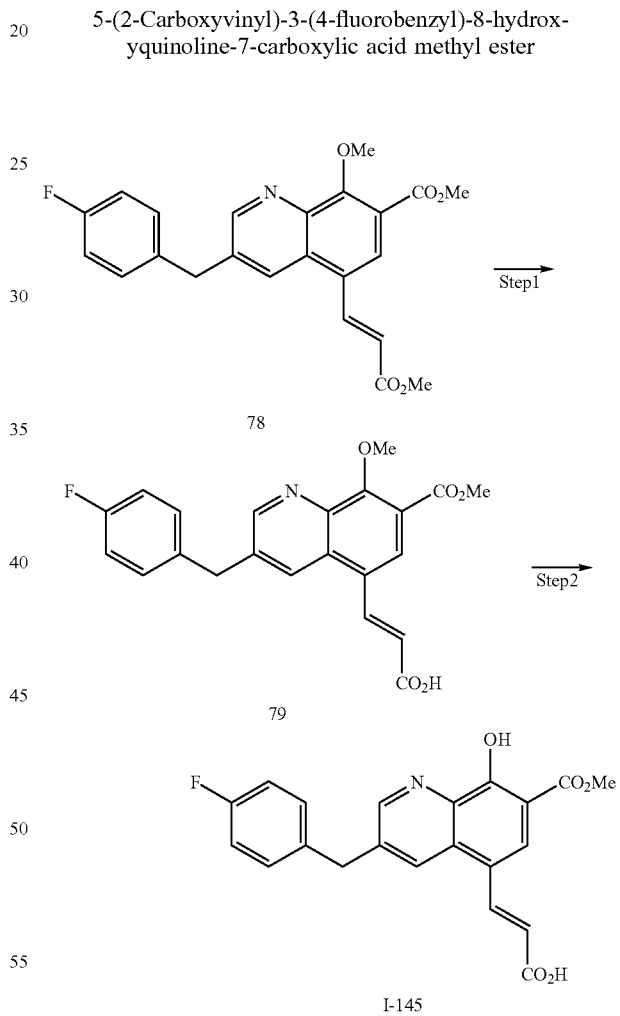

Step 1

To a solution of Compound 78 (464 mg, 1.133 mmol) in 1,4-dioxane (28 ml), 2N hydrochloric acid (5.6 ml) was added at room temperature and the mixture was refluxed for 1.5 hours. The mixture was cooled to room temperature and extracted with ethylacetate. The extract was washed with water and extracted with saturated aqueous sodium hydrogen carbonate three times. The mixture was mixed with 12N hydrochloric acid and neutralized to give Compound 79 (91 mg, 0.230 mmol) as colorless crystals in 15% yield.

Step 2

In a manner similar to Step 2 of Example 2, Compound 79 (90 mg, 0.228 mmol) gave crude Compound I-145, which was recrystallized from 85% aqueous acetone to give Compound I-145 of the title (56.5 mg, 0.148 mmol) as colorless crystals in 65% yield.

m.p.: 235-237° C. (from: 85% aqueous acetone)

(DMSO-$d_6$) δ: 3.93 (3H, s), 4.27 (2H, s), 6.51 (1H, d, J=15.6 Hz), 7.11-7.17 (2H, m), 7.39-7.44 (2H, m), 8.23 (1H, s), 8.24 (1H, d, J=15.6 Hz), 8.60 (1H, s), 8.89 (1H, s), 12.43 (1H, brs).

Elemental Analysis: $C_{21}H_{16}FNO_5$ Calcd. (%): C, 66.14; H, 4.23; F, 4.98; N, 3.67. Found. (%): C, 66.41; H, 4.44; F, 4.48; N, 3.52.

Example 45

I-146

5-(2-Carboxyethyl)-3-(4-fluorobenzyl)-8-hydroxyquinoline-7-carboxylic acid methyl ester

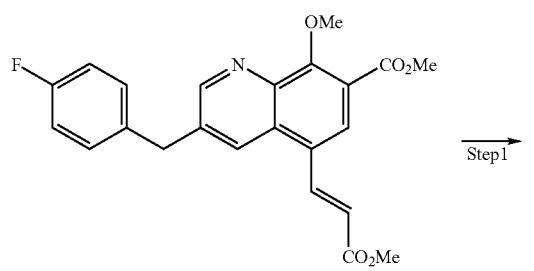

78

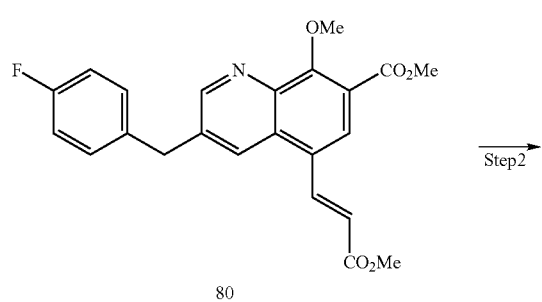

80

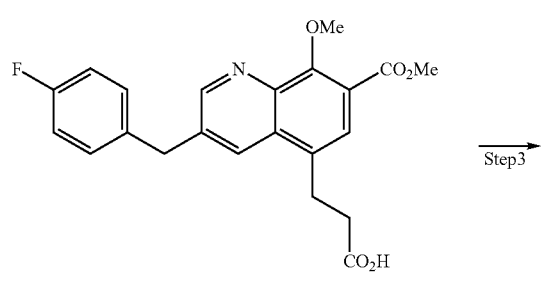

81

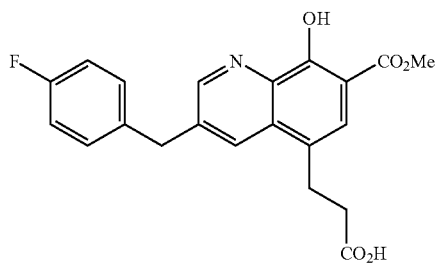

I-146

Step 1

To a solution of Compound 78 (1.22 g, 2.98 mmol) in ethylacetate (15 ml), 10% Palladium-Carbon (150 mg) was added under ice-cooling and the mixture was stirred for 12 hours at room temperature under hydrogen atmosphere at 1 atm. The mixture was mixed with ethylacetate, filtered through Celite, and the filtrate was concentrated in vacuo. The obtained residue was subjected to silicagel column chromatography and eluted with n-hexan-ethyl acetate (1:1, v/v). Fractions containing the desired compound were concentrated in vacuo to give Compound 80 (192 mg, 0.467 mmol) as yellow oil in 16% yield.

Step 2

In a manner similar to Step 1 of Example 44, Compound 80 (190 mg, 0.462 mmol) gave crude Compound 81, which was subjected to silicagel column chromatography and eluted with ethylacetate. Fractions containing the desired compound were concentrated in vacuo to give Compound 81 (73 mg, 0.184 mmol) as colorless crystals in 40% yield.

Step 3

In a manner similar to Step 2 of Example 2, Compound 81 (72 mg, 0.181 mmol) gave crude Compound I-146 of the title, which was recrystallized from ethylacetate to give Compound I-146 of the title (23.5 mg, 0.061 mmol) as colorless crystals in 34% yield.

m.p.: 254-256° C. (from: ethylacetate)

(DMSO-$d_6$) δ: 2.58 (2H, t, J=7.2 Hz), 3.17 (2H, t, J=7.2 Hz), 3.91 (3H, s), 4.24 (2H, s), 7.11-7.17 (2H, m), 7.37-7.42 (2H, m), 7.67 (1H, s), 8.38 (1H, d, J=2.1 Hz), 8.85 (1H, d, J=2.1 Hz), 11.03 (1H, brs), 12.24 (1H, brs).

Elemental Analysis: $C_{21}H_{18}FNO_5 \cdot 0.3H_2O \cdot 0.3EtOAc$ Calcd. (%): C, 64.22; H, 5.10; F, 4.58; N, 3.37. Found. (%): C, 64.24; H, 4.73; F, 3.97; N, 3.16.

Example 46

I-147

3-(4-Fluorobenzyl)-8-hydroxy-5-(2-methoxycarbonylethyl)-1,2,3,4-tetra hydroquinoline-7-carboxylic acid methyl ester

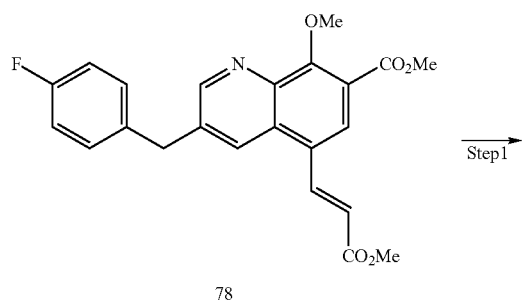

78

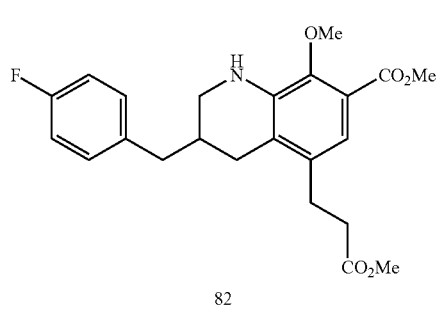

82

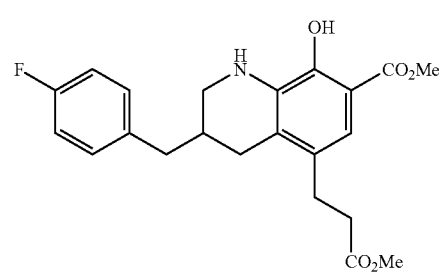

I-147

Step 1

In a manner similar to Step 1 of Example 44, Compound 78 (168 mg, 0.410 mmol) gave crude Compound 82, which was subjected to silicagel column chromatography and eluted with n-hexan-ethyl acetate (3:1, v/v). Fractions containing the desired compound were concentrated in vacuo to give 82 (108 mg, 0.260 mmol) as colorless oil in 63% yield.

Step 2

In a manner similar to Step 2 of Example 2, Compound 82 (108 mg, 0.260 mmol) gave crude Compound I-147 of the title, which was recrystallized from ethyl acetate-ethylether to give Compound I-147 of the title (66 mg, 0.164 mmol) as colorless crystals in 63% yield.

m.p.: 140-141° C. (from: ethyl acetate-ethylether)

(CDCl$_3$) δ: 2.23 (1H, brs), 2.38-2.85 (8H, m), 2.94-3.01 (1H, m), 3.30-3.34 (1H, m), 3.68 (3H, s), 3.91 (3H, s), 6.95 (1H, s), 6.96-7.02 (2H, m), 7.12-7.17 (2H, m), 10.74 (1H, s).

Elemental Analysis: C$_{22}$H$_{24}$FNO$_5$ Calcd. (%): C, 65.82; H, 6.03; F, 4.73; N, 3.49. Found. (%): C, 65.63; H, 6.03; F, 4.52; N, 3.46.

Example 47

I-148

5-(4-Carboxyphenyl)-3-(4-fluorobenzyl)-8-hydroxyquinoline-7-carboxylic acid methyl ester

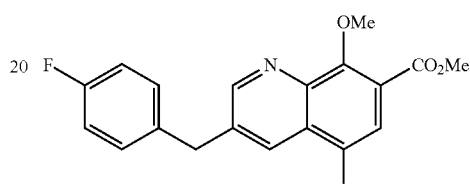

9

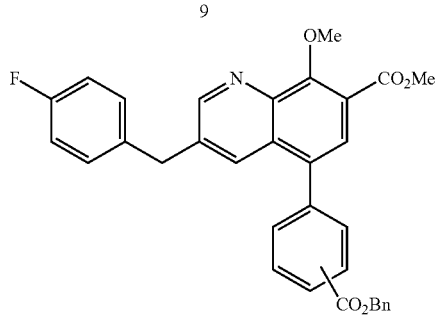

85-a (para)
85-b (meta)

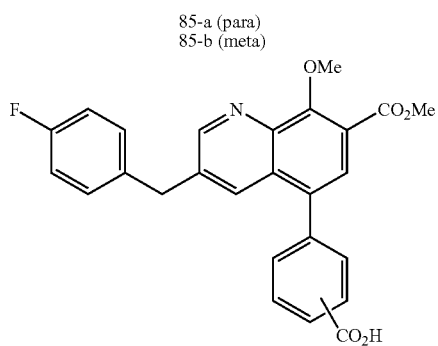

86-a (para)
86-b (meta)

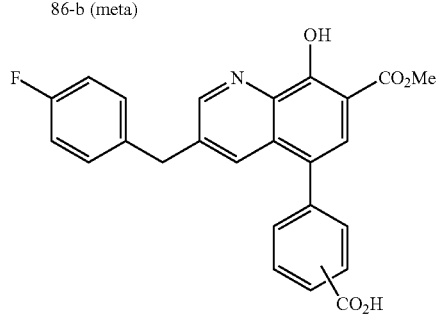

I-148 (para)
I-149 (meta)

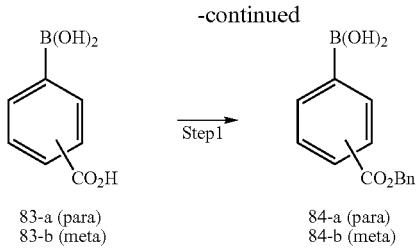

83-a (para)
83-b (meta)

84-a (para)
84-b (meta)

Step 1

To a suspension of Compound 83-a (1.000 g, 6.026 mmol) and potassium carbonate (2.75 g, 19.9 mmol) in DMF (10 ml), benzyl bromide was added under ice-cooling and the mixture was stirred while warming to room temperature for 2 hours. The reaction mixture was mixed with 2N hydr hydrochloric acid (30 ml) under ice-cooling and extracted with ethylacetate. The extract was washed with water three times and dried over sodium sulfate anhydrous. The solvent was evaporated in vacuo and the obtained residue was washed with n-hexan to give Compound 84-a (1.380 g, 5.389 mmol) as colorless crystals in 89.4% yield.

In a similar manner to above, Compound 83-b (1.000 g, 6.026 mmol) gave Compound 84-b (1.301 g, 5.081 mmol) as colorless crystals in 84.3% yield.

Step 2

A suspension of Compound 9 (250 mg, 0.619 mmol; obtained in Step 1 of Example 1), Compound 84-a (317 mg, 1.24 mmol), acetic acid Palladium (II) (28 mg, 0.12 mmol), tris(2-methyl phenyl)phosphine (47 mg, 0.15 mmol) and cesium carbonate (806 mg, 2.47 mmol) in 1,4-dioxane (15 ml) was refluxed for 8 hours. The reaction mixture was cooled to room temperature, mixed with saturated ammonium chrolide under ice-cooling and extracted with ethylacetate. The extract was washed with water, dried over sodiun sulfate anhydrous, and concentrated in vacuo. The resulting residue was subjected to silicagel column chromatography and eluted with toluen-ethyl acetate (3:1, v/v). Fractions containing the desired compound were concentrated in vacuo to give Compound 85-a (205 mg, 0.383 mmol) as yellow oil in 62% yield. In a similar manner to above, Compound (250 mg, 0.619 mmol; obtained in Step 1 of Example 1) and Compound 84-b (317 mg, 1.24 mmol) gave Compound 85-b (247 mg, 0.461 mmol) as yellow oil in 75% yield.

Step 3

To a solution of Compound 85-a (202 mg, 0.377 mmol) in 1,4-dioxane (7 ml), a suspension of 10% Palladium-Carbon (20 mg) in water (0.5 ml) was added and the mixture was stirred for 2.5 hours under hydrogen atomosphere at 1 atm at room temperature. The reaction mixture was mixed with ethylacetate, filtered through Celite, and the filtrate was concentrated in vacuo to give a residue. The resisue was recrystallized from acetone-toluene to give Compound 86-a (134 mg, 0.301 mmol) as colorless crystal in 80% yield. In a manner similar to the above procedure, Compound 85-b (247 mg, 0.461 mmol) gave Compound 86-b (148 mg, 0.332 mmol) as yellow oil in 72% yield.

Step 4

In a manner similar to Step 2 of Example 2, Compound 86-a (132 mg, 0.296 mmol) gave crude Compound I-148 of the title, which was recrystallized from 85% aqueous acetone to give Compound I-148 of the title (122 mg, 0.283 mmol) as pale yellowish green crystals in 96% yield.

m.p.: 289-291° C. (from: 85% aqueous acetone)

(DMSO-$d_6$) δ: 3.92 (3H, s), 4.19 (2H, s), 7.09-7.14 (2H, m), 7.28-7.33 (2H, m), 7.57 (2H, d, J=7.8 Hz), 7.78 (1H, s), 8.03 (1H, s), 8.07 (2H, d, J=7.8 Hz), 8.90 (1H, s), 11.28 (1H, brs), 13.07 (1H, brs).

Elemental Analysis: $C_{25}H_{18}FNO_5$ Calcd. (%): C, 69.60; H, 4.21; F, 4.40; N, 3.25. Found. (%): C, 69.88; H, 4.37; F, 4.07; N, 3.28

I-149

5-(3-Carboxyphenyl)-3-(4-fluorobenzyl)-8-hydroxyquinoline-7-carboxylic acid methyl ester In a manner similar to Step 2 of Example 2, Compound 86-b (146 mg, 0.328 mmol) gave crude Compound I-149 of the title, which was recrystallized from 85% aqueous acetone to give Compound I-148 of the title (121 mg, 0.280 mmol) as colorless crystals in 86% yield.

m.p.: 265-267° C. (from: 85% aqueous acetone)

(DMSO-$d_6$) δ: 3.93 (3H, s), 4.19 (2H, s), 7.07-7.13 (2H, m), 7.29-7.34 (2H, m), 7.62-7.72 (2H, m), 7.77 (1H, s), 7.95-8.04 (3H, m), 8.92 (1H, s), 11.27 (1H, brs), 13.16 (1H, brs).

Elemental Analysis: $C_{25}H_{18}FNO_5$ Calcd. (%): C, 69.60; H, 4.21; F, 4.40; N, 3.25. Found. (%): C, 69.62; H, 4.23; F, 4.25; N, 3.31

Example 48

I-150

5-(2-Formylphenyl)-3-(4-fluorobenzyl)-8-hydroxyquinoline-7-carboxylic acid methyl ester

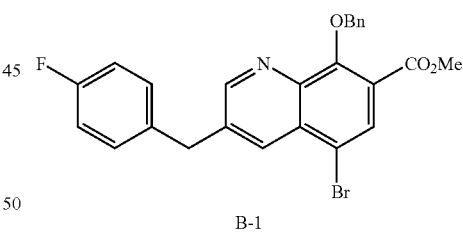

B-1

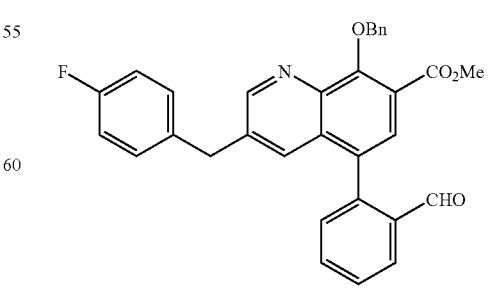

87

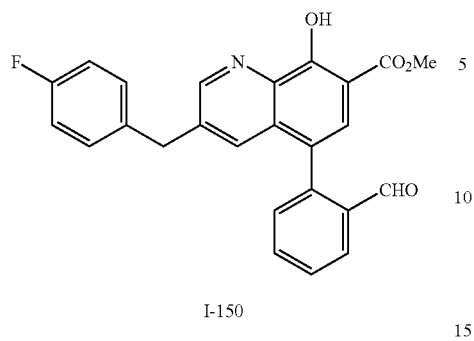

I-150

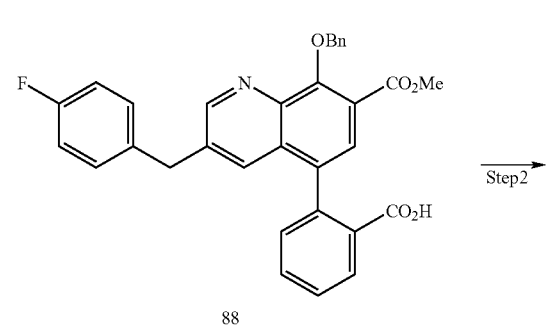

88

Step 1

In a manner similar to the Step 2 of Example 47, Compound B-1 (1.200 g, 2.498 mmol) gave Compound 87 (920 mg, 1.820 mmol) as yellow oil in 72.9% yield.

Step 2

In a manner similar to Step 2 of Example 2, Compound 87 (152 mg, 0.300 mmol) gave crude Compound I-150 of the title, which was recrystallized from 85% aqueous acetone to give Compound I-150 of the title (123 mg, 0.296 mmol) as pale yellow crystals in 98% yield.

m.p.: 73-75° C. (from: 85% aqueous acetone)

(DMSO-$d_6$) δ: 3.90 (3H, s), 4.12 (2H, s), 7.05-7.11 (2H, m), 7.20-7.24 (2H, m), 7.48 (1H, d, J=7.2 Hz), 7.60 (1H, d, J=2.1 Hz), 7.67-7.72 (2H, m), 7.78-7.83 (1H, m), 8.00 (1H, dd, J=7.2 Hz, J=1.2 Hz), 8.88 (1H, d, J=2.1 Hz), 9.62 (1H, s), 11.34 (1H, brs).

Elemental Analysis: $C_{25}H_{18}FNO_4 \cdot 2.5H_2O$ Calcd. (%): C, 65.21; H, 5.03; F, 4.13; N, 3.04. Found. (%): C, 64.82; H, 4.18; F, 3.68; N, 2.38.

Example 49

I-151

5-(2-Carboxyphenyl)-3-(4-fluorobenzyl)-8-hydroxyquinoline-7-carboxylic acid methyl ester

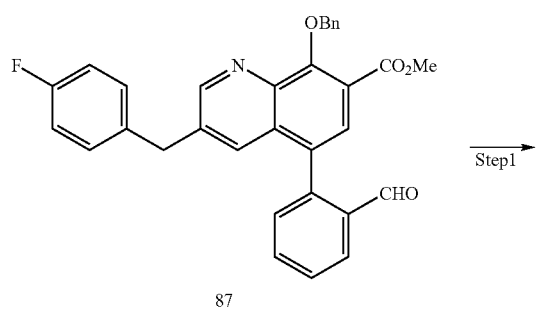

87

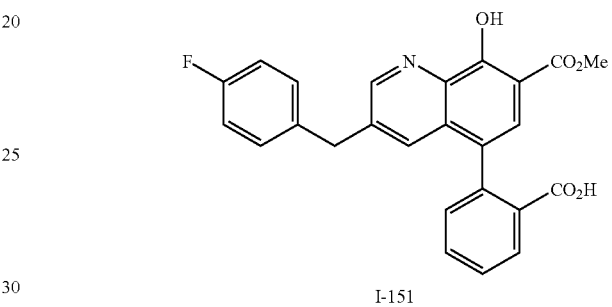

I-151

Step 1

To a solution of Compound 87 (260 mg, 0.514 mmol), 2,2,6,6-tetramethyl piperidine-1-oxyl (96 mg, 0.614 mmol) in ethyl acetate (8.6 ml), a sodium hydrogencarbonate aqueous solution (5.2 ml) was added, and 10% aqueous sodium hypochlorite (1.92 ml, 2.58 mmol) was added under ice-cooling and the mixture was stirred intensively for 2 hours while warming to room temperature. To the reaction mixture, 2N hydrochloric acid (5 ml) was added and extracted with ethyl acetate. The extract was washed with water twice, dried over sodiun sulfate anhydrous and concentrated in vacuo. The resulting residue was subjected to silicagel column chromatography and eluted with acetate-methanol (10:1, v/v). Fractions containing the desired compound were concentrated in vacuo to give Compound 88 (96 mg, 0.184 mmol) as colorless crystals in 36% yield.

Step 2

In a manner similar to Step 2 of Example 2, Compound 88 (95 mg, 0.182 mmol) gave crude Compound I-151 of the title, which was recrystallized from 85% aqueous acetone to give Compound I-151 (42 mg, 0.097 mmol) of the title as colorless crystals in 54% yield.

m.p.: 250-252° C. (from: 85% aqueous acetone)

(DMSO-$d_6$) δ: 3.90 (3H, s), 4.12 (2H, s), 7.05-7.11 (2H, m), 7.20-7.24 (2H, m), 7.48 (1H, d, J=7.2 Hz), 7.60 (1H, d, J=2.1 Hz), 7.67-7.72 (2H, m), 7.78-7.83 (1H, m), 8.00 (1H, dd, J=7.2 Hz, J=1.2 Hz), 8.88 (1H, d, J=2.1 Hz), 9.62 (1H, s), 11.34 (1H, brs).

Elemental Analysis: $C_{25}H_{18}FNO_5$ Calcd. (%): C, 69.60; H, 4.21; F, 4.40; N, 3.25. Found. (%): C, 70.98; H, 5.03; F, 3.62; N, 2.86.

Example 50

I-152

3-(4-Fluorobenzyl)-8-hydroxy-5-oxalylquinoline-7-carboxylic acid methyl ester

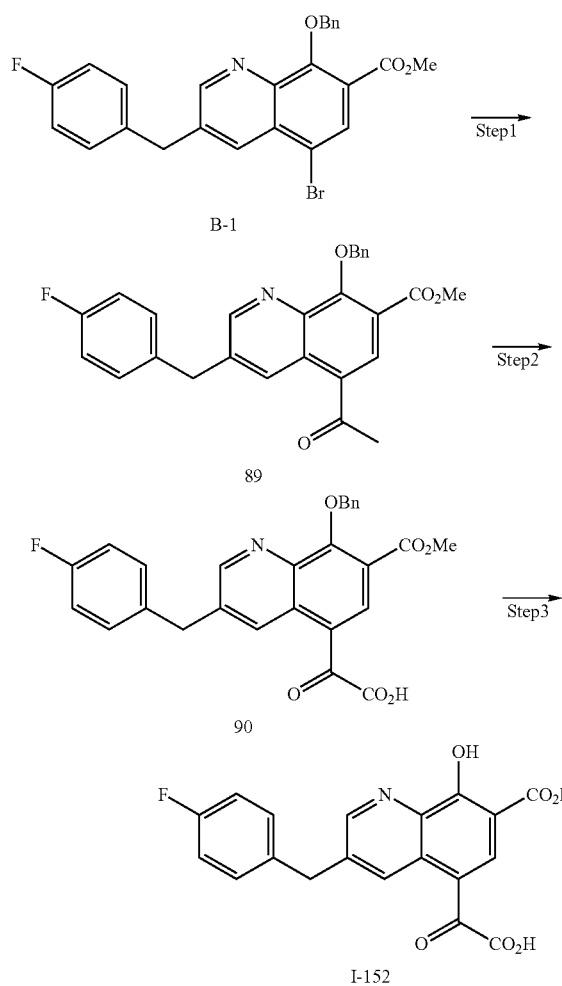

Step 1

In a manner similar to the Step 1 of Example 23, Compound B-1 (1.500 g, 3.123 mmol) gave Compound 89 (1.342 g, 3.026 mmol) as yellow oil in 96.9% yield.

Step 2

A suspension of Compound 89 (1.310 g, 2.954 mmol) and selenium dichloride (787 mg, 7.09 mmol) in pyridine (6 ml) was stirred at 100° C. The reaction mixture was mixed with 2N hydrochloric acid (74 ml) and extracted with ethylacetate. The extract was filtered through Celite and washed with water twice, mixed with saturated aqueous sodium hydrogen carbonate (100 ml), stirred intensively for 1 hour at room temperature. The precipitated crystals were filtered and the filtrate was washed with water and ethyl acetate. To a suspension of the crystals in water, 12N hydrochloric acid was added and neutralized to give Compound 90 (626 mg, 1.322 mmol) as colorless crystals in 45% yield.

Step 3

In a manner similar to the Step 7 of Example 1, Compound 90 (120 mg, 0.254 mmol) gave Compound I-152 (33 mg, 0.086 mmol) as colorless crystals in 34% yield.

m.p.: 231-233° C. (from: acetone-ethylether) IR (Nujol): 1720, 1667, 1617, 1603 cm$^{-1}$ (DMSO-d$_6$) δ: 3.88 (3H, s), 4.30 (2H, s), 7.14-7.20 (2H, m), 7.36-7.40 (2H, m), 8.46 (1H, s), 8.94 (1H, s), 9.42 (1H, s).

Example 51

I-153

5-Aminooxalyl-3-(4-fluorobenzyl)-8-hydroxyquinoline-7-carboxylic acid methyl ester

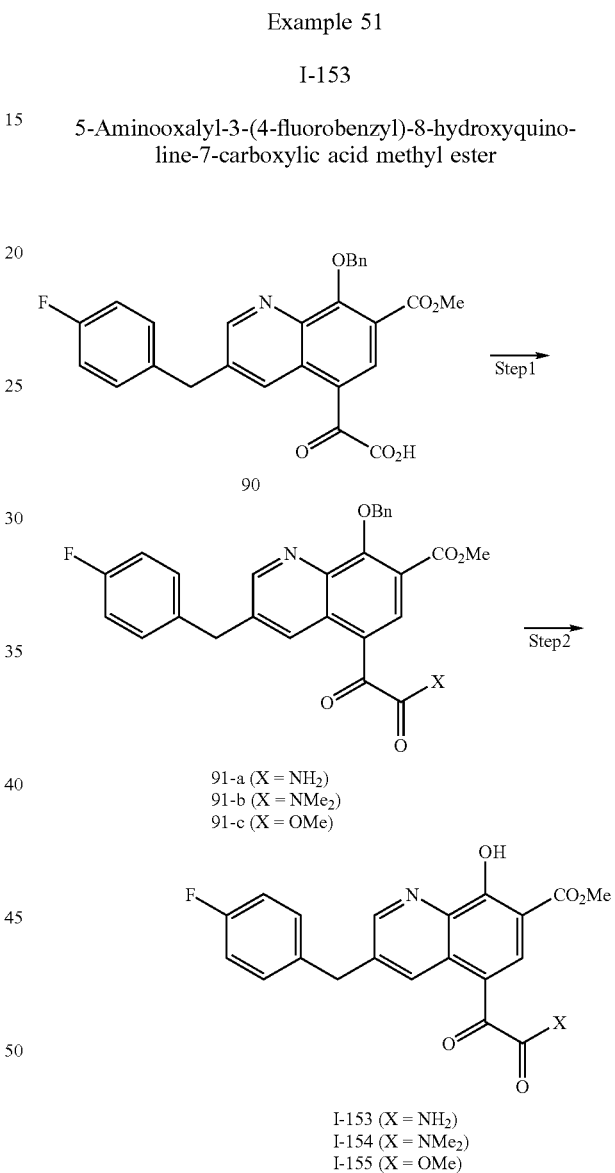

Step 1

In a manner similar to the Step 1 of Example 2, Compound 90 (120 mg, 0.254 mmol) gave Compound 91-a (35 mg, 0.074 mmol) as colorless crystals in 29% yield.

In a manner similar to the Step 1 of Example 2, Compound 90 (120 mg, 0.254 mmol) gave Compound 91-b (71 mg, 0.142 mmol) as colorless oil in 56% yield.

In a manner similar to the Step 1 of Example 2, Compound 90 (120 mg, 0.254 mmol) gave a crude Compound 91-c as yellow oil.

Step 2

In a manner similar to Step 2 of Example 2, Compound 91-a (35 mg, 0.074 mmol) gave crude Compound I-153 of the title, which was recrystallized from 85% aqueous acetone to give Compound I-153 of the title (16 mg, 0.042 mmol) as colorless crystals in 57% yield.

m.p.: 214-219° C. (from: 85% aqueous acetone)

(DMSO-$d_6$) δ: 3.90 (3H, s), 4.29 (2H, s), 7.14-7.20 (2H, m), 7.35-7.39 (2H, m), 7.97 (1H, brs), 8.31 (1H, brs), 8.57 (1H, s), 8.96 (1H, s), 9.32 (1H, s).

I-154 5-Dimethyl amino oxalyl3-(4-fluoro benzyl)-8-hydroxy quinoline-7-carboxylic acid methyl ester In a manner similar to Step 2 of Example 2, Compound 91-b (71 mg, 0.142 mmol) gave crude Compound I-154 of the title, which was recrystallized from ethyl acetate-ethylether to give Compound I-154 (18 mg, 0.044 mmol) of the title as yellow crystals in 31% yield.

m.p.: 187-189° C. (from: ethylacetate-ethylether)

(CDCl$_3$) δ: 3.03 (3H, s), 3.17 (3H, s), 4.05 (3H, s), 4.22 (2H, s), 6.99-7.05 (2H, m), 7.18-7.23 (2H, m), 8.41 (1H, s), 8.89 (1H, d, J=2.1 Hz), 9.49 (1H, d, J=2.1 Hz).

I-155

3-(4-Fluorobenzyl)-8-hydroxy-5-methoxyoxalylquinoline-7-carboxylic acid methyl ester In a manner similar to Step 2 of Example 2, crude Compound 91-c (280 mg) gave crude Compound I-155 of the title, which was recrystallized from 85% aqueous acetone to give Compound I-155 (29 mg, 0.073 mmol) of the title as yellow crystals.

m.p.: 156-158° C. (from: 85% aqueous acetone)

(CDCl$_3$) δ: 4.03 (3H, s), 4.07 (3H, s), 4.21 (2H, s), 6.99-7.05 (2H, m), 7.18-7.23 (2H, m), 8.54 (1H, s), 8.90 (1H, s), 9.34 (1H, s).

Example 52

I-156

8-Acetoxy-5-carbamoyl-3-(4-fluorobenzyl)quinoline-7-carboxylic acid methyl ester

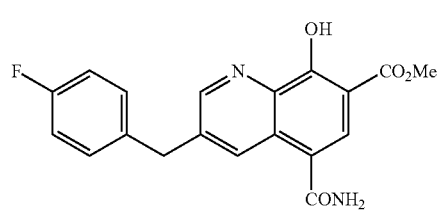

13

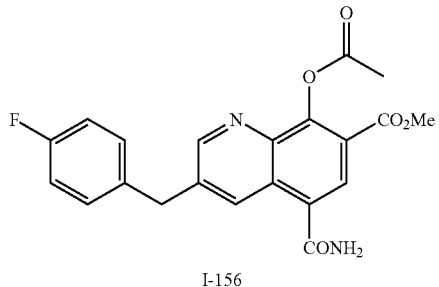

I-156

Step 1

To a solution of Compound 13 (100 mg, 0.282 mmol; obtained in Step 2 of Example 3) and 4-dimethylaminopyridine (3.5 mg, 0.029 mmol) in THF (4 ml), anhydrous acetic acid (0.096 ml, 1.02 mmol) was added under ice-cooling and the mixture was stirred at room temperature for 1 hour. The reaction mixture was under ice-cooling poured into 10% aqueous citric acid (20 ml) and extracted with ethyl acetate. The extract was washed with 10% citric acid and brine, dried over sodium sulfate anhydrous. The solvent was evaporated in vacuo and the resulting residue was recrystallized from 30% aqueous acetonitorile to give Compound I-156 (77.5 mg, 0.196 mmol) of the title as colorless crystals in 69% yield.

m.p.: 206° C. (from: 30% acetonitrile water)

(CDCl$_3$) δ: 2.54 (3H, s), 3.98 (3H, s), 4.17 (2H, s), 5.84 (1H, brs), 6.14 (1H, brs), 6.97-7.04 (2H, m), 7.14-7.20 (2H, m), 8.34 (1H, s), 8.74 (1H, d, J=2.1 Hz), 8.85 (1H, d, J=2.1 Hz).

Elemental Analysis: $C_{21}H_{17}FN_2O_5$ Calcd. (%): C, 63.63; H, 4.32; F, 4.79; N, 7.07. Found. (%): C, 63.36; H, 4.21; F, 4.67; N, 7.14.

Example 53

I-157

5-Carbamoyl-3-(4-fluorobenzyl)-8-hydroxy-5-methoxyoxalylquinoline-7-carboxylic acid methyl ester sodium salt

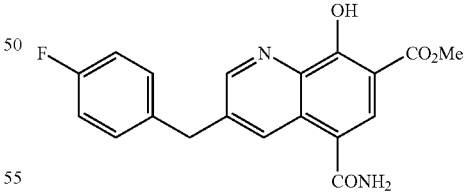

13

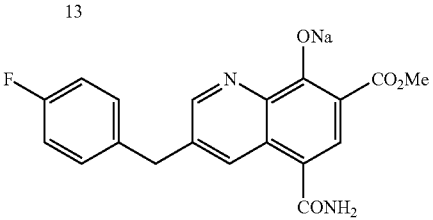

I-157

Step 1

To a solution of Compound 13 (848 mg, 2.39 mmol; obtained in Step 2 of Example 3) in methanol (340 ml), a solution of 1M sodium methoxide in methanol (2.34 ml, 2.39 mmol) was added and the mixture was stirred at 50° C. for 1 hour. The solvent was evaporated in vacuo and the resulting residue was washed with ethanol (50 ml×2) to give Compound I-157 (741 mg, 1.97 mmol) of the title as yellow solid in 82% yield.

m.p.: >300° C.

(DMSO-$d_6$) δ: 3.67 (3H, s), 4.05 (2H, s), 7.09-7.15 (2H, m), 7.25-7.30 (2H, m), 8.14 (1H, s), 8.34 (1H, d, J=2.1 Hz), 8.82 (1H, d, J=2.1 Hz).

Elemental Analysis: $C_{19}H_{14}FN_2NaO_4H_2O$ Calcd. (%): C, 57.87; H, 4.09; F, 4.82; N, 7.10; Na, 5.83. Found. (%): C, 58.26; H, 3.52; F, 4.54; N, 7.17; Na, 5.62.

Example 54

I-158

5-Benzenesulfonylamino-3-(4-fluorobenzyl)-8-hydroxyquinoline-7-carboxylic acid methyl

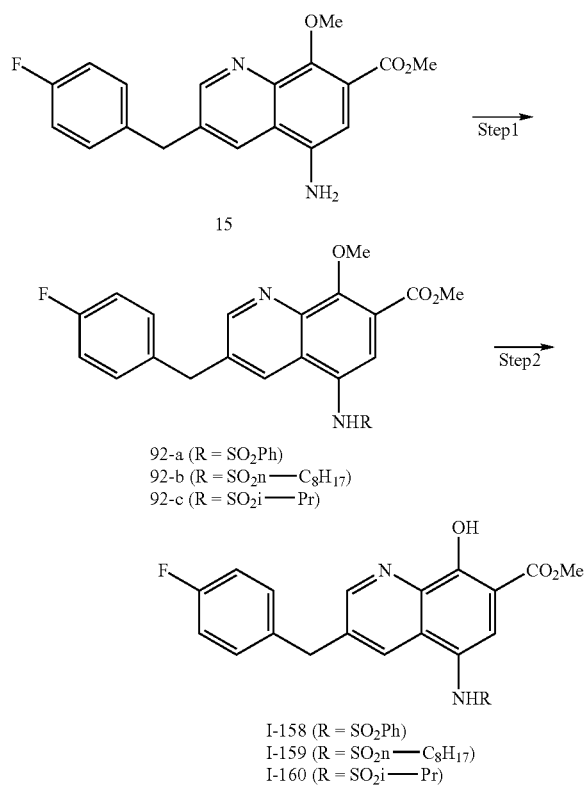

Step 1

To a solution of Compound 15 (200 mg, 0.588 mmol; obtained in Step 2 of Example 4) and pyridine (0.142 ml, 1.76 mmol) in methylene chloride (6 ml), under ice-cooling, benzene sulfonyl chloride (0.090 ml, 0.71 mmol) was added and the mixture was stirred for 1 hour. After stirred at room temperature for 2 hours, the reaction mixture was mixed with 1 N hydrochloric acid (10 ml) and extracted with water (20 ml) and brine (10 ml), dried over sodium sulfate anhydrous. The solvent was evaporated in vacuo and the resulting crystallic residue was recrystallized from ethyl acetate-hexan to give Compound 92-a (240 mg) as colorless crystals in 85% yield.

In a manner similar to the above procedure, Compound 92-b and Compound 92-c were obtained. Compound 15 (199 mg, 0.585 mmol) gave Compound 92-b (262 mg) as pale brown oil in 87% yield. Compound 15 (199 mg, 0.585 mmol) gave Compound 92-c (137 mg) as pale yellow oil in 53% yield.

Step 2

In a manner similar to Step 7 of Reference Example 1, Compound 92-a (197 mg, 0.410 mmol) gave crude Compound I-158 of the title, which was recrystallized from methanol to give Compound I-158 (122 mg) of the title as colorless crystals in 64% yield.

m.p.: 230-233° C. (from: methanol)

(DMSO-$d_6$) δ: 3.86 (3H, s), 4.07 (2H, s), 7.17 (2H, m), 7.25 (2H, m), 7.43-7.50 (3H, m), 7.55-7.62 (3H, m), 8.03 (1H, d, J=2.1 Hz), 8.79 (1H, d, J=2.1 Hz), 11.21 (1H, brs).

Elemental Analysis: $C_{24}H_{19}FN_2O_5S$ Calcd. (%): C, 61.79; H, 4.11; F, 4.07; N, 6.01; S, 6.87. Found. (%): C, 61.56; H, 4.01; F, 4.25; N, 6.07; S, 7.00.

I-159

3-(4-Fluorobenzyl)-8-hydroxy-5-(octane-1-sulfonylamino)quinoline-7-carboxylic acid methyl In a manner similar to Step 7 of Reference Example 1, Compound 92-b (260 mg, 0.503 mmol) gave crude crystals of Compound I-159 of the title, which were recrystallized from isopropanol to give Compound I-159 (156 mg) of the title as colorless crystals in 62% yield.

m.p.: 135-136° C. (from: isopropanol)

(DMSO-$d_6$) δ: 0.83 (3H, t, J=6.8 Hz), 1.12-1.34 (10H, m), 1.63 (2H, m), 2.99 (2H, m), 3.92 (3H, s), 4.24 (2H, s), 7.14 (2H, m), 7.36 (2H, m), 7.77 (1H, s), 8.43 (1H, d, J=1.8 Hz), 8.91 (1H, d, J=1.8 Hz), 9.61 (1H, s), 11.22 (1H, brs).

Elemental Analysis: $C_{26}H_{31}FN_2O_5S(H_2O)_{0.3}$ Calcd. (%): C, 61.47; H, 6.27; F, 3.74; N, 5.51; S, 6.31. Found. (%): C, 61.60; H, 6.18; F, 3.88; N, 5.46; S, 6.42.

Compound I-160

3-(4-Fluorobenzyl)-8-hydroxy-5-(propane-2-sulfonylamino)quinoline-7-carboxylic acid methyl In a manner similar to Step 7 of Reference Example 1, Compound 92-c (135 mg, 0.302 mmol) gave crude crystals of Compound I-160 of the title, which were recrystallized from isopropanol to give Compound I-160 (53.4 mg) of the title as blackish brown crystals in 41% yield.

m.p.: 179-181° C. (from: isopropanol)

(DMSO-$d_6$) δ: 1.20 (6H, d, J=6.6 Hz), 3.17 (1H, m), 3.92 (3H, s), 4.25 (2H, s), 7.17 (2H, m), 7.36 (2H, m), 7.78 (1H, s), 8.38 (1H, s), 8.93 (1H, s), 9.58 (1H, s), 11.21 (1H, brs).

Elemental Analysis: $C_{21}H_{21}FN_2O_5S(H_2O)_{0.3}$ Calcd. (%): C, 57.60; H, 4.97; F, 4.34; N, 6.40; S, 7.32. Found. (%): C, 57.54; H, 4.89; F, 4.44; N, 6.33; S, 7.42.

Example 55

I-161

5-(3-Benzylthioureido)-3-(4-fluorobenzyl)-8-hydroxyquinoline-7-carboxylic acid methyl

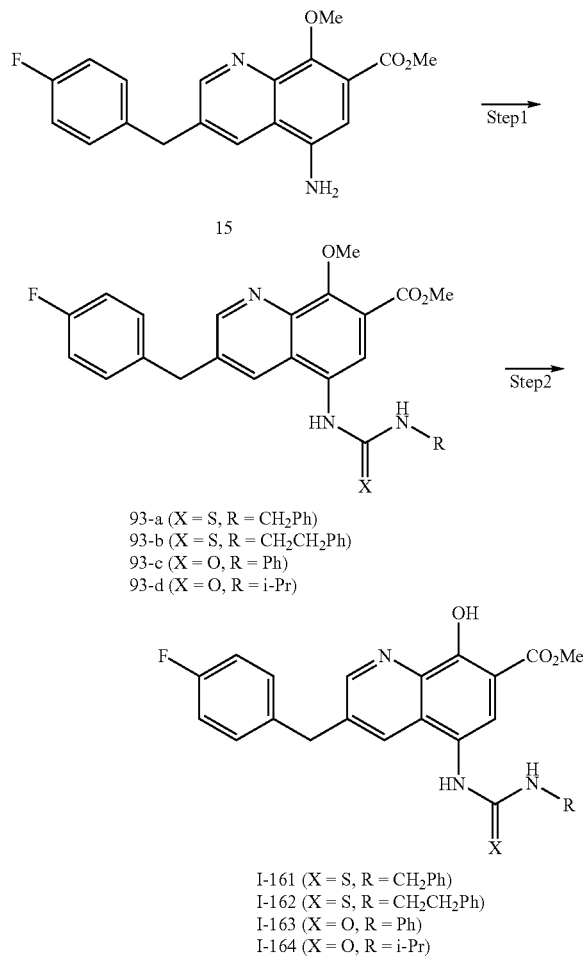

Step 1

A solution of Compound 15 (199 mg, 0.585 mmol; obtained in Step 2 of Example 4), benzylisothiocyanate (0.440 ml, 3.32 mmol) and bis(tri-n-butylstannoic)ooxide (0.030 ml, 0.059 mmol) in acetonitrile (5 ml) was refluxed for 12 hours. The reaction mixture was ice-cooled and the pricipitated crystals were filtered, washed with acetonitrile and evaporated in vacuo to give Compound 93-a (186 mg) as colorless crystals in 67% yield.

In a manner similar to the above procedure, Compound 92-b, Compound 92-c and Compound 92-d were obtained. Compound 15 (204 mg, 0.599 mmol) gave Compound 93-b (262 mg) as colorless crystals in 59% yield. Compound 15 (201 mg, 0.591 mmol) gave Compound 93-c (224 mg) as colorless crystals in 83% yield. Compound 15 (201 mg, 0.591 mmol) gave Compound 93-d (183 mg) as colorless crystals in 73% yield.

Step 2

To a solution of Compound 93-a (184 mg, 0.376 mmol) in methylene chloride (15 ml), a solution of boron tribromide in 1 M methylene chloride (1.50 ml, 1.50 mmol) was added under ice-cooling and stirred for 20 min. The mixture was mixed with water (15 ml) and methylene chloride, and evaporated in vacuo. The pricipitated crystals were filtered and the filtrate was washed with water to give crude crystals of the title Compound I-161, which were recrystallized from methanol to give Compound I-161 (120 mg) of the title as colorless crystals in 67% yield.

m.p.: 201-203° C. (from: methanol)

(DMSO-$d_6$) δ: 3.92 (3H, s), 4.20 (2H, s), 4.65 (2H, d, J=5.7 Hz), 7.13 (2H, m), 7.18-7.34 (7H, m), 7.66 (1H, s), 7.97 (1H, brs), 8.03 (1H, brs), 8.87 (1H, d, J=1.8 Hz), 9.59 (1H, brs), 11.27 (1H, brs).

Elemental Analysis: $C_{26}H_{22}FN_3O_3S(H_2O)_{0.2}$ Calcd. (%): C, 65.18; H, 4.71; F, 3.97; N, 8.77; S, 6.69. Found. (%): C, 65.20; H, 4.35; F, 3.93; N, 8.76; S, 6.44.

I-162

3-(4-Fluorobenzyl)-8-hydroxy-5-(3-phenethylthioureido)quinoline-7-carboxylic acid methyl In a manner similar to the syntheses of Compound I-161, Compound 93-b (176 mg, 0.349 mmol) gave crude crystals of Compound I-162, which were recrystallized from methanol to give Compound I-162 (118 mg) as pale blackish brown crystals in 69% yield.

m.p.: 203-206° C. (from: methanol)

(DMSO-$d_6$) δ: 2.71 (2H, m), 3.57 (2H, m), 3.92 (3H, s), 4.22 (2H, s), 7.06-7.35 (9H, m), 7.52 (1H, brs), 7.60 (1H, s), 7.92 (1H, d, J=1.8 Hz), 8.89 (1H, d, J=1.8 Hz), 9.48 (1H, brs), 11.25 (1H, brs).

Elemental Analysis: $C_{27}H_{24}FN_3O_3S$ Calcd. (%): C, 66.24; H, 4.94; F, 3.88; N, 8.58; S, 6.55. Found. (%): C, 66.03; H, 4.43; F, 3.77; N, 8.56; S, 6.41.

I-163

3-(4-Fluorobenzyl)-8-hydroxy-5-(3-phenylureido)quinoline-7-carboxylic acid methyl In a manner similar to the syntheses of Compound I-161, Compound 93-c (240 mg, 0.522 mmol) gave crude crystals of Compound I-163, which were recrystallized from dimethylformamide-water-methanol to give Compound I-163 (160 mg) as colorless crystals in 69% yield.

m.p.: 267-271° C. (from: dimethylformamide-water-methanol)

(DMSO-$d_6$) δ: 3.93 (3H, s), 4.25 (2H, s), 6.98 (1H, m), 7.12 (2H, m), 7.29 (2H, m), 7.34 (2H, m), 7.47 (2H, m), 8.06 (1H, s), 8.27 (1H, s), 8.53 (1H, s), 8.86 (1H, s), 8.88 (1H, d, J=1.8 Hz), 11.07 (1H, brs).

Elemental Analysis: $C_{25}H_{20}FN_3O_4(H_2O)_{0.4}$ Calcd. (%): C, 66.34; H, 4.63; F, 4.20; N, 9.28. Found. (%): C, 66.27; H, 4.51; F, 4.18; N, 9.41.

I-164

3-(4-Fluorobenzyl)-8-hydroxy-5-(3-isopropylureido)quinoline-7-carboxylic acid methyl In a manner similar to the syntheses of Compound I-161, Compound 93-d (183 mg, 0.430 mmol) gave crude crystals of Compound I-164 of the title, which were recrystallized from dimethyl formamide-water-methanol to give Compound I-164 (160 mg) of the title as pale brown amorphous in 78% yield.

m.p.: 251-256° C. (from: dimethyl formamide-water-methanol)

(DMSO-$d_6$) δ: 1.16 (6H, d, J=6.6 Hz), 3.80 (1H, m), 3.97 (3H, s), 4.28 (2H, s), 6.27 (1H, d, J=7.5 Hz), 7.20 (2H, m), 7.39 (2H, m), 8.10 (1H, s), 8.22 (2H, s), 8.91 (1H, d, J=2.1 Hz), 11.03 (1H, brs).

Elemental Analysis: $C_{22}H_{22}FN_3O_4(H_2O)_{0.2}$ Calcd. (%): C, 63.67; H, 5.44; F, 4.58; N, 10.12. Found. (%): C, 63.59; H, 5.37; F, 4.56; N, 10.41.

Example 56

I-165

3-(4-Fluorobenzyl)-8-hydroxy-5-(3-methylcarbamoylpropionylamino)quinoline-7-carboxylic acid methyl

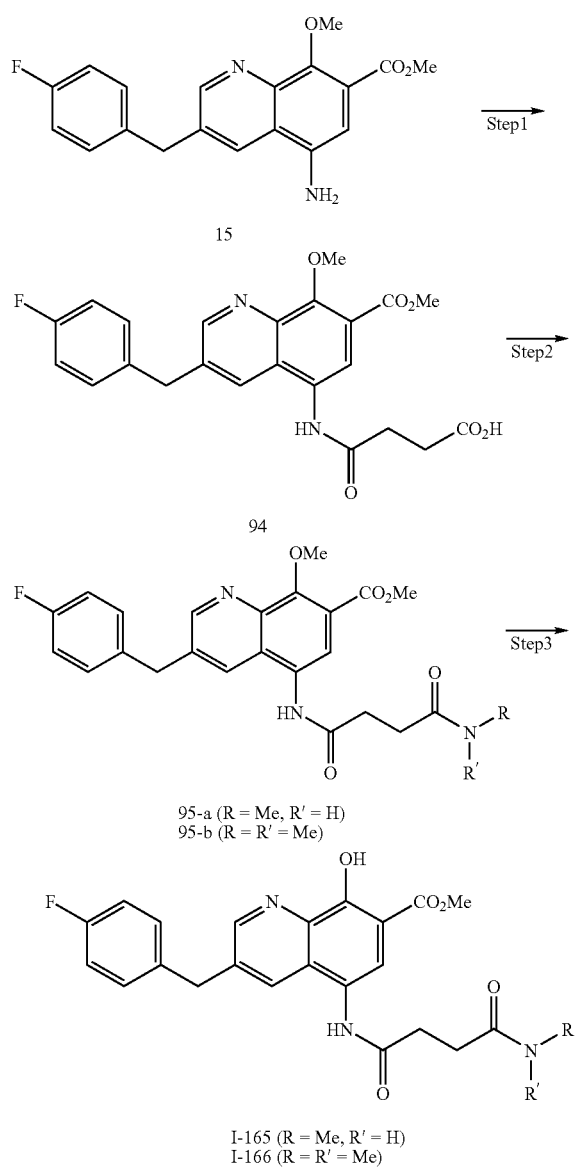

Step 1

A solution of Compound 15 (962 mg, 2.83 mmol; obtained in Step 2 of Example 4) and succinic anhydrous (313 mg, 3.13 mmol) in THF (20 ml) was refluxed for 24 hours with heating. The reaction mixture was mixed with diethylether (20 ml) under ice-cooling and the pricipitated crystals were filtered, washed with diethylether and evaporated in vacuo to give Compound 94 (1.21 g) as colorless crystals in 97% yield.

Step 2

To a solution of Compound 94 (198 mg, 0.450 mmol) and 1-hydroxybenzotriazole (74.2 mg, 0.549 mmol) in dimethyl formamide (2 ml), a solution of methylamine in 2.0M THF (0.460 ml, 0.920 mmol) and 1-ethyl-3-(3-dimethylamino propyl)carbodiimide hydrochloride (131 mg, 0.683 mmol) were added and the mixture was stirred for 23 hours. The reaction mixture was mixed with water (10 ml) and methanol (5 ml), and the pricipitated crystals were filtered, washed with water and evaporated in vacuo to give Compound 95-a (154 mg) as colorless crystals in 76% yield. In a manner similar to the above procedure, Compound 94 (149 mg, 0.338 mmol) gave Compound 95-b (150 mg) as colorless crystals in 95% yield.

Step 3

In a manner similar to the Step 7 of Reference Example 1, Compound 95-a (152 mg, 0.335 mmol) gave Compound I-165 (129 mg) of the title as colorless crystals in 88% yield.

m.p.: 248-250° C.

(DMSO-$d_6$) δ: 2.45 (2H, t, J=7.0 Hz), 2.60 (3H, d, J=4.5 Hz), 2.65 (2H, t, J=7.0 Hz), 3.91 (3H, s), 4.20 (2H, s), 7.14 (2H, m), 7.38 (2H, m), 7.82 (1H, s), 7.83 (1H, m), 8.32 (1H, d, J=2.0 Hz), 8.86 (1H, d, J=2.0 Hz), 9.86 (1H, s), 11.12 (1H, brs).

Elemental Analysis: $C_{23}H_{22}FN_3O_5(H_2O)_{0.5}$ Calcd. (%): C, 61.60; H, 5.17; F, 4.24; N, 9.37. Found. (%): C, 61.66; H, 4.95; F, 4.34; N, 9.42.

I-166

5-(3-Dimethylcarbamoylpropionylamino)-3-(4-fluorobenzyl)-8-hydroxyquinoline-7-carboxylic acid methyl In a manner similar to the Step 7 of Reference Example 1, Compound 95-b (150 mg, 0.321 mmol) gave Compound I-166 (123 mg) of the title as pale brown crystals in 85% yield.

m.p.: 230-232° C.

(DMSO-$d_6$) δ: 2.66 (4H, m), 2.85 (3H, s), 3.01 (3H, s), 3.91 (3H, s), 4.19 (2H, s), 7.13 (2H, m), 7.38 (2H, m), 7.79 (1H, is), 8.38 (1H, d, J=1.8 Hz), 8.86 (1H, d, J=1.8 Hz), 9.87 (1H, s), 11.13 (1H, brs).

Elemental Analysis: $C_{24}H_{24}FN_3O_5$ Calcd. (%): C, 63.57; H, 5.33; F, 4.19; N, 9.27. Found. (%): C, 63.16; H, 5.37; F, 4.14; N, 8.97.

Example 57

I-167

3-(4-Fluorobenzyl)-8-hydroxy-5-(5-oxo-4,5-dihydro[1,2,4]oxadiazole-3-yl) quinoline-7-carboxylic acid methyl

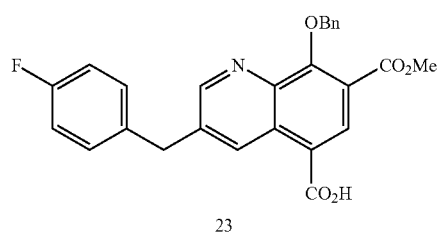
23

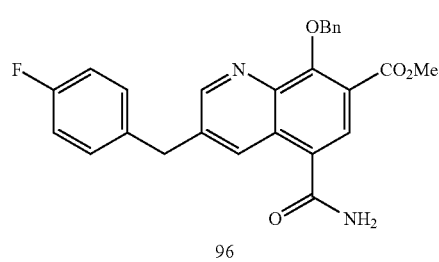
96

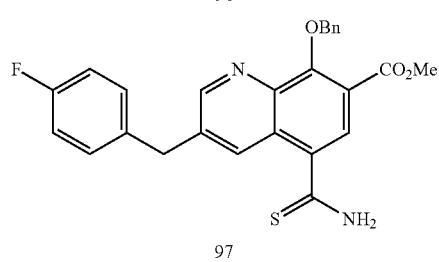
97

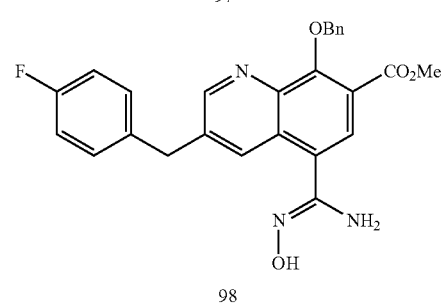
98

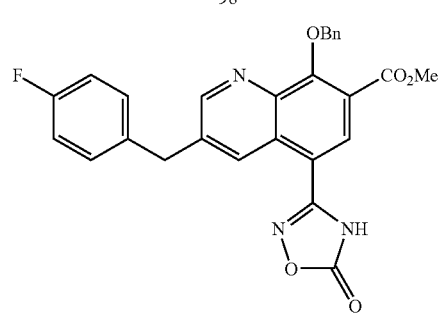
99

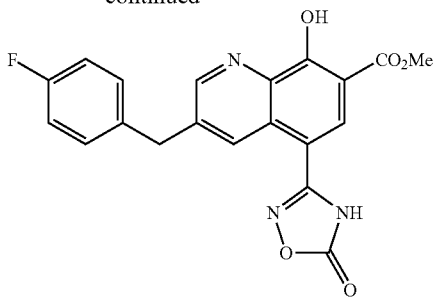
I-167

Step 1

To a solution of Compound 23 (1.00 g, 2.24 mmol; obtained in Example 11), ammonium chloride and 1-hydroxybenzotriazole (338 mg, 2.50 mmol) in dimethyl formamide (10 ml), diisopropylethylamine (1.60 ml, 9.19 mmol) and 1-ethyl-3-(3-dimethyl aminopropyl)carbodiimide hydrochloride (539 mg, 2.81 mmol) were added at room temperature, and the mixture was stirred for 66 hours and refluxed for 1 hour. The reaction mixture was mixed with water (40 ml) and the pricipitated crystals were filtered, washed with water and evaporated in vacuo to give Compound 96 (921 mg) as colorless crystals in 92% yield.

Step 2

To a solution of Compound 96 (921 mg, 2.07 mmol) in THF (50 ml), phosphorus pentasulfide (938 mg, 2.11 mmol) was added at room temperature and the mixture was stirred for 1 hour and refluxed with heating for 2 hours. The reaction mixture was mixed with disodium hydrogen phosphate.12hydrate (6.05 g) and water (50 ml) and extracted with chloroform. The extract was dried over sodiun sulfate anhydrous and concentrated in vacuo. The resulting residue was subjected to silicagel column chromatography and eluted with n-hexan-ethyl acetate (4:1, v/v). Fractions containing the desired compound were concentrated in vacuo to give Compound 97 (501 mg) as yellow crystals in 53% yield.

Step 3

To a solution of Compound 97 (499 mg, 1.08 mmol) in methylene chloride (10 ml), triethyloxonium tetrafluoroborate (95%, 249 mg, 1.25 mmol) was added under ice-cooling and the mixture was stirred at room temperature for 30 mins. The mixture was mixed with a solution of hydroxylamine in 1M methanol (5 ml), then stirred for 40 hours. The mixture was mixed with acueous sodium hydrogencarbonate (30 ml) and extracted with chloroform three times. The extract was washed with saturated acueous sodium hydrogencarbonate (20 ml) and water (20 ml), dried over sodium sulfate anhydrous and evaporated in vacuo. The resulting residue was subjected to silicagel column chromatography and eluted with n-hexan-ethyl acetate (1:2, v/v). Fractions containing the desired compound were concentrated in vacuo to give Compound 98 (371 mg) as colorless crystals in 75% yield.

Step 4

To a solution of Compound 98 (350 mg, 0.762 mmol) and pyridine (0.0740 ml, 0.915 mmol) in dimethylformamide (3.5 ml), ethyl chlorocarbonate (0.080 ml, 0.837 mmol) was added under ice-cooling and the mixture was stirred for 30 min, which was mixed with water (14 ml) and extracted with ethylacetate. The extract was washed with water (20 ml) and brine (20 ml) and dried over sodium sulfate anhydrous. The solvent was evaporated in vacuo. The resulting residue was dissolved in xylen (5 ml) and refluxed with heating for 2 hours and evaporated in vacuo. The crystallic residue was recrystallized from ethyl acetate-diisopropyl ether to give Compound 99 (172 mg) as pale brown crystals on 47% yield.

Step 5

To a solution of Compound 99 (170 mg, 0.350 mmol) and sodium iodide (317 mg, 2.13 mmol) in acetonitrile-methylene chloride (1:1, v/v, 6 ml), chloro trimethyl silane (0.270 ml, 1.58 mmol) was added under ice-cooling, and the mixture was stirred for 4 hours at room temperature. The mixture was mixed with 10% aqueous sodium bisulfite (3 ml) and water (10 ml), extracted with chloroform twice and dried over sodium sulfate anhydrous. The solvent was evaporated in vacuo. The crystallic residue was recrystallized from methanol to give Compound I-167 of the title (113 mg) as colorless crystals on 82% yield.

m.p.: 212-214° C. (from: methanol)

NMR (DMSO-$d_6$) δ: 3.94 (3H, s), 4.26 (2H, s), 7.15 (2H, m), 7.36 (2H, m), 8.29 (1H, s), 8.87 (1H, d, J=2.1 Hz), 8.96 (1H, d, J=2.1 Hz), 12.89 (1H, brs).

Elemental Analysis: $C_{20}H_{14}FN_3O_5(MeOH)_{0.2}$ Calcd. (%): C, 60.39; H, 3.71; F, 4.73; N, 10.46. Found. (%): C, 60.33; H, 3.61; F, 4.58; N, 10.57.

Example 58

I-168

5-((1S)-1-Dimethylcarbamoylethylcarbamoyl)-3-(4-fluorobenzyl)-8-hydroxyquinolne-7-carboxylic acid methyl

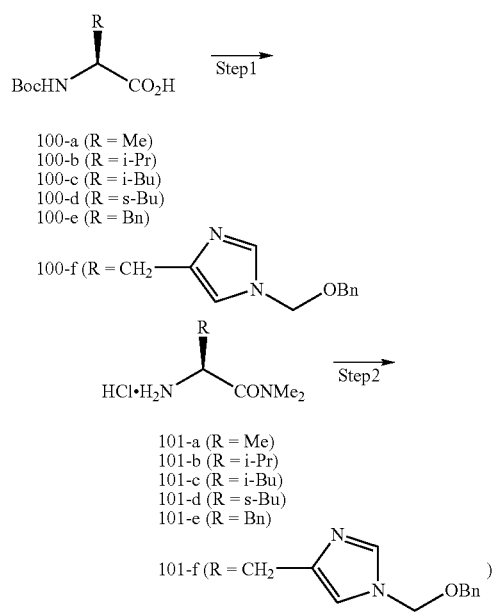

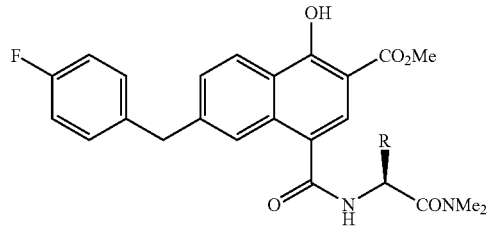

I-168 (R = Me)
I-169 (R = i-Pr)
I-170 (R = i-Bu)
I-171 (R = s-Bu)
I-172 (R = Bn)

I-173 (R = CH₂—[imidazole-CH₂OBn])

Step 1

To a solution of N-t-BOC-L-alanine 100-a (1.89 g, 9.99 mmol) and 1-hydroxybenzotriazole (270 mg, 2.00 mmol) in dimethylformamide (20 ml), a solution of dimethyl amine in 2.0 M tetrahydrofuran (7.50 ml, 15.0 mmol) and 1-ethyl-3-(3-dimethyl aminopropyl)-carbodiimide hydrochloride (2.30 g, 12.0 mmol) was added at room temperature and stirred for 4 hours. The mixture was mixed with water (50 ml) and extracted with ethyl acetate (100 ml). The extract was washed with water (20 ml) twice and brine (20 ml), and dried over sodium sulfate anhydrous. The residue, which was obtained from the mixture by evaporation in vacuo, was mixed with a solution of hydrogen chloride in 4M dioxane (25 ml, 100 mmol) and stirred for 45 min. The solvent was evaporated in vacuo to give a crude Compound 101-a, which was allowed to react without purification. In a manner similar to above, N-t-BOC-L-valine, N-t-BOC-L-leucine, N-t-BOC-L-isoleucine, N-t-BOC-L-phenylalanine and N□-t-BOC-N$^{im}$-(benzyloxymethyl)-L-histidine each gave crude Compounds, 101-b to 101-f, respectively.

Step 2

To a solution of Compound 23 (300 mg, 0.673 mmol; obtained in Example 11), a crude of the above Compound 101-a (208 mg) and 1-hydroxybenzotriazole (92.3 mg, 0.683 mmol) in dimethyl formamide (3 ml), triethyl amine (0.280 ml, 2.01 mmol) and 1-ethyl-3-(3-dimethylaminopropyl)carbodiimide hydrochloride (201 mg, 1.05 mmol) were added at room temperature and stirred for 6 hours. The mixture was mixed with 0.2N hydrochloric acid (10 ml) and extracted with ethyl acetate (60 ml).

The extract was washed with 1N hydrochloric acid (30 ml), water (30 ml), saturated aqueous sodium hydrogencarbonate (30 ml), water (30 ml) and brine (30 ml), and dried over sodiun sulfate anhydrous. The mixture was evaporated in vacuo. A suspension of the resulting residue and 10% Palladium carbon (50.2 mg) in ethylacetate-methanol (1:1, v/v, 30 ml) was stirred for 2 hours under hydrogen atomosphere at 1 atm at room temperature, which was filtered and concentrated in vacuo. The resulting crystalline residue was recrystallized from acetonitrile-methanol to give Compound I-168 (94.0 mg) of the title as colorless crystals in 31% yield.

m.p.: 139-140° C. (from: acetonitrile-methanol)

NMR (DMSO-$d_6$) δ: 1.28 (3H, d, J=7.2 Hz), 2.87 (3H, s), 3.08 (3H, s), 3.93 (3H, s), 4.21 (2H, s), 4.93 (1H, m), 7.14 (2H, m), 7.34 (2H, m), 8.04 (1H, s), 8.61 (1H, d, J=1.8 Hz), 8.74 (1H, d, J=7.5 Hz), 8.88 (1H, d, J=2.1 Hz).

Elemental Analysis: $C_{24}H_{24}FN_3O_5(H_2O)_{0.4}$ Calcd. (%): C, 62.57; H, 5.43; F, 4.12; N, 9.12. Found. (%): C, 62.53; H, 5.22; F, 4.17; N, 9.02.

I-169

5-((1S)-1-Dimethylcarbamoyl-2-methylpropylcarbamoyl)-3-(4-fluoro benzyl)-8-hydroxyquinoline-7-carboxylic acid methyl In a manner similar to the syntheses of Compound I-168, Compound 23 (300 mg, 0.673 mmol) gave crude crystals of Compound I-169 of the title, which were recrystallized from isopropanol to give Compound I-169 (167 mg) of the title as colorless crystals in 52% yield.

m.p.: 173-174° C. (from: isopropanol)

NMR (DMSO-$d_6$) δ: 0.90 (3H, d, J=6.6 Hz), 0.91 (3H, d, J=6.6 Hz), 2.09 (1H, m), 2.89 (3H, s), 3.14 (3H, s), 3.93 (3H, s), 4.21 (2H, s), 4.74 (1H, dd, J=8.1, 8.1 Hz), 7.14 (2H, m), 7.33 (2H, m), 7.96 (1H, s), 8.43 (1H, d, J=2.0 Hz), 8.68 (1H, d, J=8.1 Hz), 8.90 (1H, d, J=2.0 Hz), 11.52 (1H, brs).

Elemental Analysis: $C_{26}H_{28}FN_3O_5$ Calcd. (%): C, 64.85; H, 5.86; F, 3.95; N, 8.73. Found. (%): C, 64.59; H, 5.86; F, 3.89; N, 8.69.

I-170

5-((1S)-1-Dimethylcarbamoyl-3-methylbutylcarbamoyl)-3-(4-fluoro benzyl)-8-hydroxyquinoline-7-carboxylic acid methyl In a manner similar to the syntheses of Compound I-168, Compound 23 (300 mg, 0.673 mmol) gave crude crystals of Compound I-170 of the title, which were recrystallized from ethanol to give Compound I-170 (179 mg) of the title as colorless crystals in 54% yield.

m.p.: 192-193° C. (from: ethanol)

NMR (DMSO-$d_6$) δ: 0.89 (3H, d, J=6.3 Hz), 0.93 (3H, d, J=6.3 Hz), 1.41, (1H, m), 1.62 (2H, m), 2.88 (3H, s), 3.10 (3H, s), 3.93 (3H, s), 4.21 (2H, s), 4.96 (1H, m), 7.14 (2H, m), 7.33 (2H, m), 8.00 (1H, s), 8.51 (1H, d, J=2.4 Hz), 8.75 (1H, d, J=8.1 Hz), 8.91 (1H, d, J=2.4 Hz), 11.38 (1H, brs).

Elemental Analysis: $C_{27}H_{30}FN_3O_5$ Calcd. (%): C, 65.44; H, 6.10; F, 3.83; N, 8.48. Found. (%): C, 65.40; H, 6.19; F, 3.78; N, 8.44.

I-171

5-((1S,2S)-1-Dimethylcarbamoyl-2-methylbutylcarbamoyl)-3-(4-fluoro benzyl)-8-hydroxyquinoline-7-carboxylic acid methyl In a manner similar to the syntheses of Compound I-168, Compound 23 (300 mg, 0.673 mmol) gave crude crystals of Compound I-171 of the title, which were recrystallized from ethanol to give Compound I-171 (118 mg) of the title as colorless crystals in 35% yield.

m.p.: 172-173° C. (from: ethanol)

NMR (DMSO-$d_6$) δ: 0.83 (3H, t, J=7.2 Hz), 0.86 (3H, d, J=6.9 Hz), 1.16 (1H, m), 1.49 (1H, m), 1.90 (1H, m), 2.89 (3H, s), 3.16 (3H, s), 3.92 (3H, s), 4.21 (2H, s), 4.79 (1H, dd, J=8.7, 8.7 Hz), 7.14 (2H, m), 7.33 (2H, m), 7.95 (1H, s), 8.43 (1H, d, J=2.1 Hz), 8.72 (1H, d, J=8.7 Hz), 8.90 (1H, d, J=2.1 Hz), 11.39 (1H, brs).

Elemental Analysis: $C_{27}H_{30}FN_3O_5$ Calcd. (%): C, 65.44; H, 6.10; F, 3.83; N, 8.48. Found. (%): C, 65.34; H, 5.99; F, 3.71; N, 8.44.

I-172

5-((s)-1-Dimethylcarbamoyl-2-phenylethylcarbamoyl)-3-(4-fluorobenzyl)-8-hydroxyquinoline-7-carboxylic acid methyl In a manner similar to syntheses of Compound I-168, Compound 23 (300 mg, 0.673 mmol) gave crude crystals of Compound I-172 of the title, which were recrystallized from acetonitrile to give Compound I-172 (283 mg) of the title as pale blue crystals in 79% yield.

m.p.: 224-226° C. (from: acetonitrile)

NMR (DMSO-$d_6$) δ: 2.87 (3H, s), 2.92 (1H, dd, J=9.6, 13.8 Hz), 3.02 (3H, s), 3.04 (1H, dd, J=5.7, 13.8 Hz), 3.94 (3H, s), 4.15 (2H, s), 5.15 (1H, m), 7.14 (2H, m), 7.19-7.34 (7H, m), 7.95 (1H, s), 8.23 (1H, d, J=2.3 Hz), 8.84 (1H, d, J=2.3 Hz), 8.91 (1H, d, J=8.1 Hz), 11.34 (1H, brs).

Elemental Analysis: $C_{30}H_{28}FN_3O_5$ Calcd. (%): C, 68.04; H, 5.33; F, 3.59; N, 7.93. Found. (%): C, 67.81; H, 5.27; F, 3.52; N, 7.84.

I-173

5-[(1S)-2-(1-Benzyloxymethyl-1H-imidazole-4-yl)-1-dimethylcarbamoyl ethylcarbamoyl]-3-(4-fluorobenzyl)-8-hydroxyquinoline-7-carboxylic acid methyl In a manner similar to syntheses of Compound I-168, Compound 23 (300 mg, 0.673 mmol) gave crude crystalx of Compound I-173 of the title, which were recrystallized from ethanol to give Compound I-173 (128 mg) of the title as pale yellow crystals in 29% yield.

m.p.: 159-160° C. (from: ethanol)

NMR (DMSO-$d_6$) δ: 2.86 (3H, s), 2.94 (3H, s), 2.97 (1H, dd, J=9.0, 15.3 Hz), 3.08 (1H, dd, J=5.7, 15.3 Hz), 3.90 (3H, s), 4.16 (2H, s), 4.45 (1H, d, J=11.3 Hz), 4.51 (1H, d, J=11.3 Hz), 5.23 (1H, m), 5.48 (1H, d, J=11.1 Hz), 5.56 (1H, d, J=11.1 Hz), 6.78 (1H, s), 7.11 (2H, m), 7.27-7.37 (7H, m), 7.80 (1H, s), 7.99 (1H, s), 8.35 (1H, d, J=1.8 Hz), 8.81 (1H, d, J=1.8 Hz), 8.85 (1H, d, J=8.4 Hz).

Elemental Analysis: $C_{35}H_{34}FN_5O_6(H_2O)_{0.7}$ Calcd. (%): C, 64.45; H, 5.47; F, 2.91; N, 10.74. Found. (%): C, 64.38; H, 5.34; F, 2.83; N, 10.85.

Example. 59

I-174

3-(4-Fluorobenzyl)-8-hydroxy-5-isobutylaminoquinoline-7-carboxylic acid methyl ester

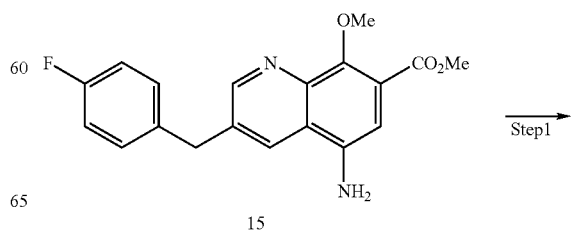

15

-continued

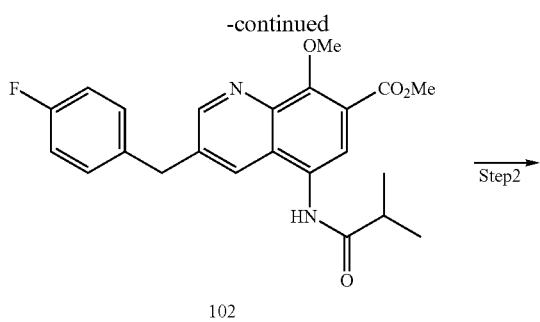

102

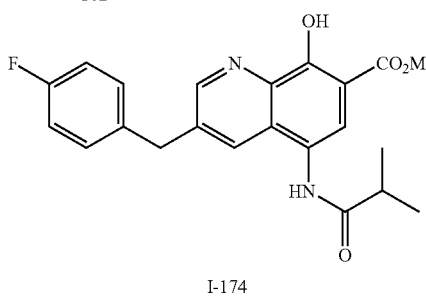

I-174

Step 1

Isobuthyl chloride (57.6 μl, 0.55 mmol) was added dropwise to a solution of Compound 15 (170.2 mg, 0.5 mmol; obtained in Step 2 of Example 2) and pyridine (51.0 μl, 0.63 mmol) in DMF (3.0 ml) at 0° C. The reaction mixture was stirred for 30 mins, mixed with ice-water and stirred for 15 mins. The pricipitate was filtered and washed with water, MeCN and isopropylether, which was dried in vacuo for 5 hours at 70° C. to give Compound 102 (179 mg, 0.45 mmol, 90.0%) as colorless crystals.

Step 2

To a solution of Compound 102 (150 mg, 0.380 mmol) in methylene chloride (7.0 ml), a solution of 1.0M BBr$_3$ (0.75 ml, 0.75 mmol) in methylene chloride was added dropwise at −20° C.

The reaction mixture was stirred for 10 min and warmed to room temperature. After cooling to −20° C. again, a solution of 1.0M BBr$_3$ (0.75 ml, 0.75 mmol) in methylene chloride was added dropwise to the reaction mixture, stirred for 10 min and mixed with ice-water. Then, the reaction mixture was extracted with ethyl acetate and the organic layer was washed with brine, saturated aqueous sodium bicarbonate and brine. The organic layer was dried over anhydrous sulfate sodium and evaporated in vacuo. The obtained residue was subjected to silica gel column chromatography and eluted with chloroform-aqueous methanol (32:6:0.5, v/v). The resulting pale yellow crystals were poured into ethyl acetate and washed with dilute hydrochloric acid, H$_2$O, brine and dried over anhydrous sodium sulfate. The solvent was evaporated in vacuo and recrystallized from isopropylether to give Compound I-174 (45 mg, 0.11 mmol, 31.0%) of the title as colorless crystals.

m.p.: 249-251° C. (from: i-Pr$_2$O)

NMR (CDCl$_3$) δ: 1.27 (6H, d, J=6.6 Hz), 2.61 (1H, m), 4.00 (3H, s), 4.17 (2H, s), 6.96-7.06 (2H, m), 7.10-7.20 (3H, m), 7.64-7.70 (1H, m), 7.92 (1H, s), 8.82-8.84(1H, m), 11.83 (1H,brs).

Elemental Analysis: C$_{22}$H$_{21}$FN$_2$O$_4$0.1H$_2$O Calcd. (%): C, 66.36; H, 5.37; F, 4.77; N, 7.03. Found. (%): C, 66.31; H, 5.14; F, 4.50; N, 7.11.

In a manner similar to Example 59 and Step 2 of Example 2, Compounds I-175 to I-182 were synthesised.

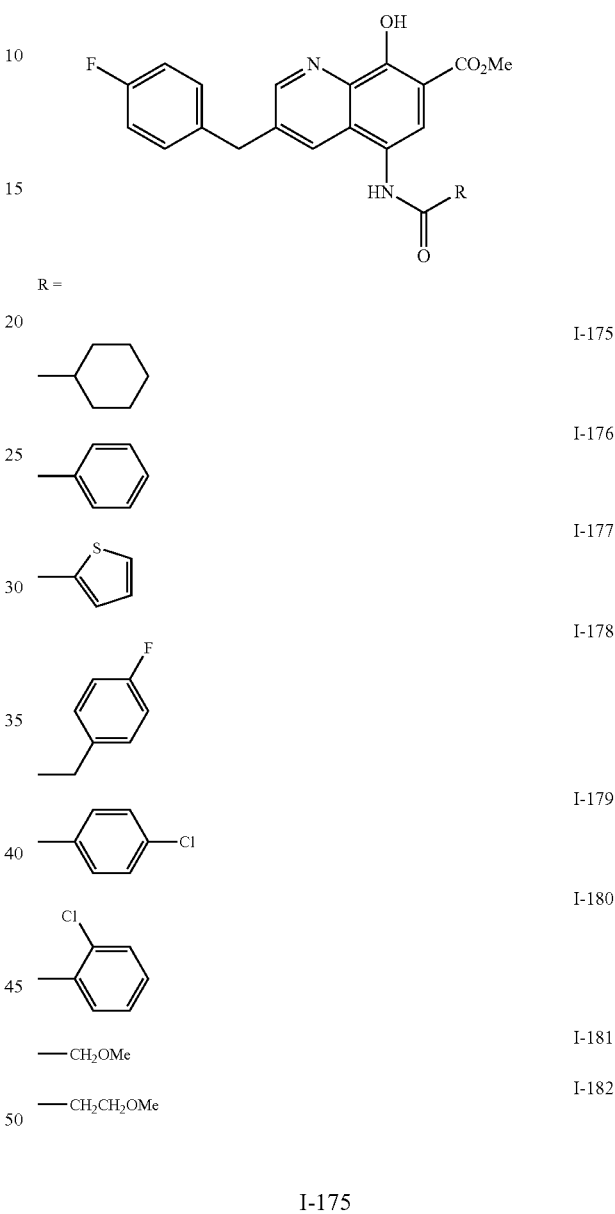

I-175

5-(Cyclohexancarbonylamino)-3-(4-fluorobenzyl)-8-hydroxyquinoline-7-carboxylic acid methyl ester m.p.: 250-251° C. (from: MeOH)

NMR (CDCl$_3$) δ:1.20-2.00 (10H, m), 2.24-2.40 (1H, m), 4.00 (3H, s), 4.17 (2H, s), 6.98-7.10 (3H, m), 7.12-7.20 (2H, m), 7.58-7.62 (1H, m), 7.90 (1H, s), 8.82-8.88(1H, m), 11.82 (1H, brs).

Elemental Analysis: C$_{25}$H$_{25}$FN$_2$O$_4$0.2H$_2$O Calcd. (%): C, 68.23; H, 5.82; F, 4.32; N, 6.37. Found. (%): C, 68.20; H, 5.64; F, 4.06; N, 6.41.

I-176

5-Benzoylamino-3-(4-fluorobenzyl)-8-hydroxyquinoline-7-carboxylic acid methyl ester m.p.: 247-249° C. (from: MeOH)

NMR (CDCl$_3$) δ: 4.02 (3H, s), 4.17 (2H, s), 6.86-7.06 (2H, m), 7.12-7.20 (2H, m), 7.50-7.66 (3H, m), 7.76-7.98 (4H, m), 8.09 (1H, s), 8.86-8.92 (1H, m).

Elemental Analysis: C$_{25}$H$_{19}$FN$_2$O$_4$0.4MeOH Calcd. (%): C, 68.83; H, 4.68; F, 4.29; N, 6.32. Found. (%): C, 69.03; H, 4.62; F, 3.97; N, 6.31.

I-177

3-(4-Fluorobenzyl)-8-hydroxy-5-[(thiophene-2-carbonyl)-amino]-quinoline-7-carboxylic acid methyl ester m.p.: 224-225° C. (from: MeOH)

NMR (CDCl$_3$) δ: 4.00 (3H, s), 4.16 (2H, s), 6.94-7.14 (2H, m), 7.10-7.20 (3H, m), 7.60 (1H, d, J=4.8 Hz), 7.64-7.74 (2H, m), 7.82-7.88 (1H, m), 8.06 (1H, s), 8.82-8.90 (1H, m).

Elemental Analysis: C$_{23}$H$_{17}$FN$_2$O$_4$S0.3H$_2$O Calcd. (%): C, 62.52; H, 4.01; F, 4.30; N, 6.34; S, 7.26. Found. (%): C, 62.81; H, 3.69; F, 4.05; N, 6.41; S, 6.97.

I-178

3-(4-Fluorobenzyl)-5-[2-(4-fluorophenyl)-acetylamino]-8-hydroxyquinoline-7-carboxylic acid methyl ester m.p.: 239-240° C. (from: MeOH)

NMR (CDCl$_3$) δ: 3.79 (2H, s), 4.00 (3H, s), 4.10 (2H, s), 6.96-7.18 (5H, m), 7.28-7.36 (2H, m), 7.38-7.44 (1H, m), 7.96 (1H, s), 8.80-8.86 (1H, m).

Elemental Analysis: C$_{26}$H$_{20}$F$_2$N$_2$O$_4$0.2MeOH0.1HCl Calcd. (%): C, 66.60; H, 4.46; F, 8.04; N, 5.92. Found. (%): C, 66.83; H, 4.34; F, 7.60; N, 5.95.

I-179

3-(4-Fluorobenzyl)-8-hydroxy-5-(2-methoxy-acetylamino)-quinoline-7-carboxylic acid methyl ester m.p.: 154-155° C. (from: MeOH)

NMR (CDCl$_3$) δ: 3.52 (3H, s), 4.01 (3H, s), 4.11 (2H, s), 4.20 (2H, s), 7.00-7.08 (2H, m), 7.14-7.22 (2H, m), 7.72-7.78 (1H, m), 8.15 (1H, s), 8.30 (1H, brs), 8.80-8.90 (1H, m), 11.87 (1H, brs).

Elemental Analysis: C$_{21}$H$_{19}$FN$_2$O$_5$ Calcd. (%): C, 63.31; H, 4.81; F, 4.77; N, 7.03. Found. (%): C, 63.06; H, 4.54; F, 4.59; N, 7.14.

I-180

5-(4-Chlorobenzoylamino)-3-(4-fluorobenzyl)-8-hydroxyquinoline-7-carboxylic acid methyl ester m.p.: 253-254° C. (from: MeOH)

NMR (DMSO-d$_6$) δ: 3.93 (3H, s), 4.23 (2H, s), 7.08-7.16 (2H, m), 7.30-7.36 (2H, m), 7.65 (2H, d, J=8.4 Hz), 7.86 (1H, s), 8.04 (1H, d, J=8.4 Hz), 8.10-8.14 (1H, m), 8.88-8.90 (1H, m).

I-181

5-(2-Chlorobenzoylamino)-3-(4-fluorobenzyl)-8-hydroxyquinoline-7-carboxylic acid methyl ester m.p.: 230-232° C. (from: MeOH)

NMR (DMSO-d$_6$) δ: 3.94 (3H, s), 4.25 (2H, s), 7.12-7.20 (2H, m), 7.30-7.40 (2H, m), 7.44-7.68 (4H, m), 7.93 (1H, s), 8.16-8.22 (1H, m), 8.92-8.96 (1H, m).

Elemental Analysis: C$_{25}$H$_{18}$FN$_2$O$_4$Cl Calcd. (%): C, 64.59; H, 3.90; F, 4.09; N, 6.03; Cl, 7.63. Found. (%): C, 64.33; H, 4.01; F, 4.03; N, 6.05; Cl, 7.52.

I-182

3-(4-Fluorobenzyl)-8-hydroxy-5-(3-methoxy-propionylamino)-quinoline-7-carboxylic acid methyl ester m.p.: 190-192° C. (from: MeOH)

NMR (DMSO-d$_6$) δ: 2.64 (2H, t, J=6.4 Hz), 3.29 (3H, s), 3.66 (2H, t, J=6.4 Hz), 3.91 (3H, s), 4.20 (2H, s), 7.10-7.20 (2H, m), 7.30-7.38 (2H, m), 7.83 (1H, s), 8.16-8.18 (1H, m), 8.84-8.90 (1H, m), 9.84 (1H, s), 11.63 (1H, brs).

Elemental Analysis: C$_{22}$H$_{21}$FN$_2$O$_5$ Calcd. (%): C, 64.07; H, 5.13; F, 4.61; N, 6.79. Found. (%): C, 63.80; H, 5.01; F, 4.42; N, 6.72.

Example 60

I-183

3-(4-Fluorobenzyl)-8-hydroxy-5-(2-oxo-oxazolidine-3-yl)-quinoline-7-carboxylic acid methyl ester

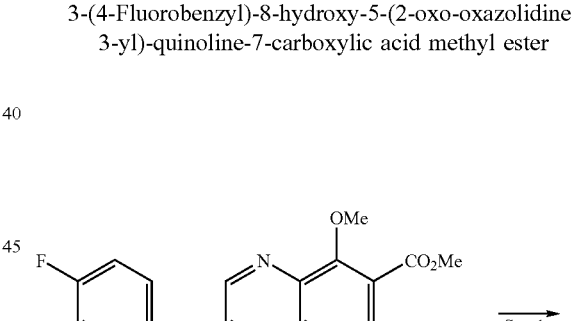

15

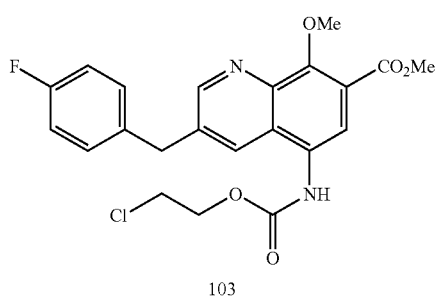

103

-continued

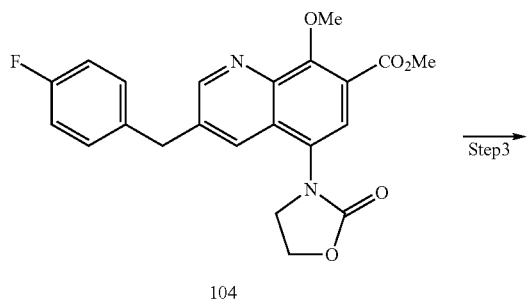

104

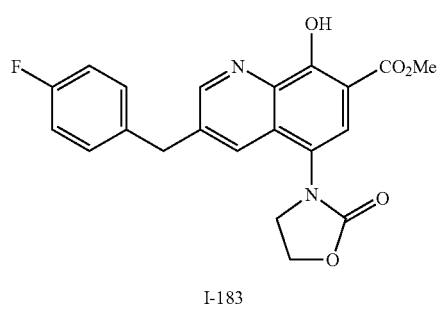

I-183

Step 1

To a solution of Compound 15 (170.2 mg, 0.5 mmol; obtained in Step 2 of Example 4) and pyridine (204.0 μl, 2.5 mmol) in DMF (3.0 ml), 2-chloro ethyl chloroformate (79 mg, 0.55 mmol) was added dropwise at 0° C. and stirred for 10 min, mixed with ice-water and stirred for 10 min. The pricipitate was filtered and washed with water, MeCN: isopropyl ether=1:1 (v/v), and isopropyl ether. The resulting residue was evaporated in vacuo for 5 hours at 70° C. to give Compound 103 (212 mg, 0.46 mmol, 92.0%) as colorless crystals.

Step 2

To a solution of Compound 103 (174 mg, 0.38 mmol) in THF (15 ml), under ice-cooling 60% NaH (18.0 mg, 0.45 mmol) was added. The reaction solution was stirred for 30 min at room temperature and mixed with ice-water. The reaction mixture was extracted with ethyl acetate and the organic layer was washed with water, brine and dried over magnesium sulfate. The obtained residue was washed with isopropylether to give Compound 104 (149 mg, 0.36 mmol, 95.5%) as colorless crystals.

Step 3

In a manner similar to the Step 2 of Example 2, Compound 104 (140 mg, 0.3 mmol) gave Compound I-183 (78 mg, 0.197 mmol, 65.6%) as colorless crystals.

m.p.: 152-153° C. (from: MeOH—CHCl$_3$-EtOAc)

NMR (CDCl$_3$) δ: 3.98-4.06 (2H, m), 4.02 (3H, s), 4.20 (2H, s), 4.56-4.64 (2H, m), (2H, s), 6.98-7.06 (2H, m), 7.14-7.20 (2H, m), 7.84-7.88 (1H, m), 7.92 (1H, s), 8.82-8.90 (1H, m).

Elemental Analysis: C$_{21}$H$_{17}$FN$_2$O$_5$·0.4H$_2$O Calcd. (%): C, 62.50; H, 4.45; F, 4.71; N, 6.94. Found. (%): C, 62.55; H, 4.24; F, 4.59; N, 6.95.

In a manner similar to Example 60, Compound I-184 was synthesized.

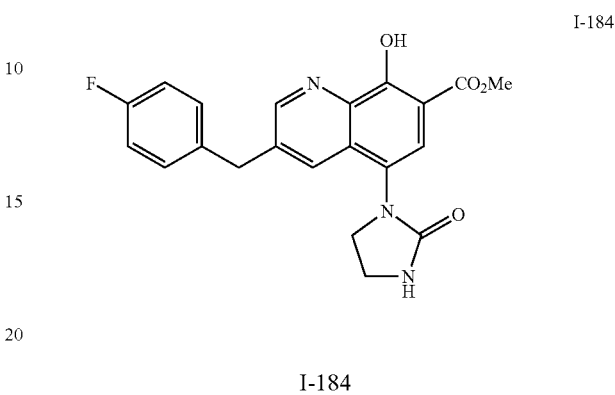

I-184

3-(4-Fluorobenzyl)-8-hydroxy-5-(2-oxo-imidazolidine-1-yl)-quinoline-7-carboxylic acid methyl ester m.p.: 248-250° C. (from: MeOH-EtOAc)

NMR (DMSO-d$_6$) δ: 3.45-3.55 (2H, m), 3.76-3.86 (2H, m), 3.92 (3H, s), 4.23 (2H, s), 6.90 (1H, brs), 7.10-7.20 (2H, m), 7.30-7.40 (2H, m), 7.70 (1H, s), 8.12-8.18 (1H, m), 8.82-8.86 (1H, s), 11.16 (1H, brs).

Elemental Analysis: C$_{21}$H$_{18}$FN$_3$O$_4$·0.2H$_2$O Calcd. (%): C, 63.22; H, 4.65; F, 4.76; N, 10.53. Found. (%): C, 63.02; H, 4.28; F, 4.68; N, 10.63.

Example. 61

I-185

3-(4-Fluorobenzyl)-8-hydroxy-5-morpholine-4-yl-quinoline-7-carboxylic acid methyl ester

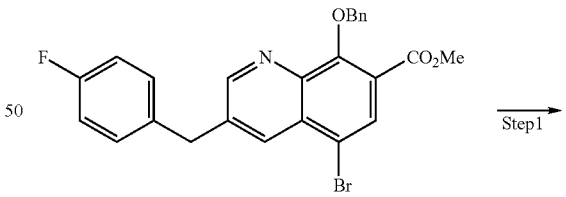

B-1

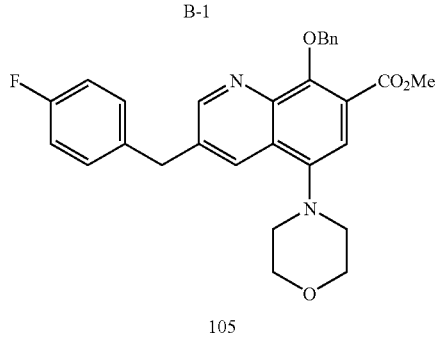

105

-continued

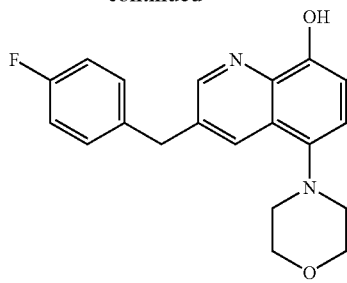

I-185

Step 1

A suspension of Compound B-1 (120 mg, 0.25 mmol; obtained in Example. B-1;), Tris(dibebzylidenacetone)-dipalladium(0)(9 mg, 0.01 mmol), 4,5-Bis(diphenyl phosphino)-9,9-dimethylxantthene (18 mg, 0.03 mmol), cesium carbonate (114 mg, 0.35 mmol) and morpholine (26 mg, 0.3 mmol) in dioxane (0.5 ml) was reacted with heating at 100° C. for 8 hours. The reaction solution was cooled to room temperature and mixed with cooled-aqueous citric acid. The reaction mixture was extracted with ethyl acetate and washed with water, brine and dried over sodium sulfate. The solvent was evaporated in vacuo and the resulting residue was subjected to silica gel column chromatography and eluted with n-hexan-ethyl acetate (1:2, v/v) to give Compound 105 (106 mg, 0.22 mmol, 87.0%) as pale yellow crystals.

Step 2

To a solution of Compound 105 (100 mg, 0.21 mmol) in ethyl acetate (2 ml)-ethanol (2 ml), 10% Pd—C (10 mg, 10 wt %) was added and reacted for 30 min at room temperature under hydrogen atomosphere. The reaction solution was filtered and the filtrate was concentrated in vacuo. The obtained residue was recrystallized from isopropylether-ethyl acetate to give Compound I-185 of the title (38 mg, 0.1 mmol, 46.0%) as pale green crystals.

m.p.: 119-120° C. (from: $^i$-Pr$_2$O-EtOAc)

NMR (CDCl$_3$) δ: 2.90-2.98 (4H, m), 3.80-3.90 (4H, m), 4.03 (3H, s), 4.20 (2H, s), 7.00-7.08 (2H, m), 7.16-7.24 (2H, m), 7.46 (1H, s), 8.14-8.18 (1H, m), 8.84-8.88 (1H, m), 11.05 (1H, s).

Elemental Analysis: C$_{22}$H$_{21}$FN$_2$O$_4$ Calcd. (%): C, 66.66; H, 5.34; F, 4.79; N, 7.07. Found. (%): C, 66.50; H, 5.28; F, 4.62; N, 7.02.

In a manner similar to Example 61, Compounds I-186 and I-187 were synthesized.

-continued

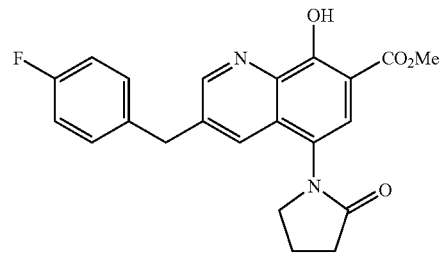

I-186

3-(4-Fluorobenzyl)-8-hydroxy-5-piperidine-1-yl-quinoline-7-carboxylic acid methyl ester m.p.: 133-134° C. (from: i-Pr$_2$O)

NMR (CDCl$_3$) δ: 1.40-1.80 (10H, m), 4.01 (3H, s), 4.19 (2H, s), 7.00-7.08 (2H, m), 7.16-7.24 (2H, m), 7.40 (1H, s), 8.10-8.18 (1H, m), 8.80-8.88 (1H, m), 11.57 (1H, m).

Elemental Analysis: C$_{23}$H$_{23}$FN$_2$O$_3$0.2H$_2$O Calcd. (%): C, 69.40; H, 5.93; F, 4.77; N, 7.04. Found. (%): C, 69.43; H, 5.78; F, 4.54; N, 6.96.

I-187

3-(4-Fluorobenzyl)-8-hydroxy-5-(2-oxo-pyroridine-1-yl)-quinoline-7-carboxylic acid methyl ester m.p.: 186-188° C. (from: EtOAc)

NMR (CDCl$_3$) δ: 2.20-2.32 (2H, m), 2.60-2.68 (2H, m), 3.72-3.80 (2H, m), 4.01 (3H, s), 4.18 (2H, s), 6.98-7.06 (2H, m), 7.12-7.20 (2H, m), 7.62-7.64 (2H, m), 8.84-8.88 (1H, m).

Elemental Analysis: C$_{22}$H$_{19}$FN$_2$O$_4$ Calcd. (%): C, 67.00; H, 4.86; F, 4.82; N, 7.10. Found. (%): C, 66.76; H, 4.86; F, 4.67; N, 7.11.

Example 62

I-188

1-[3-(4-Fluorobenzyl)-8-hydroxy-7-propionylquinoline-5-yl]-pyrrolidine-2-one

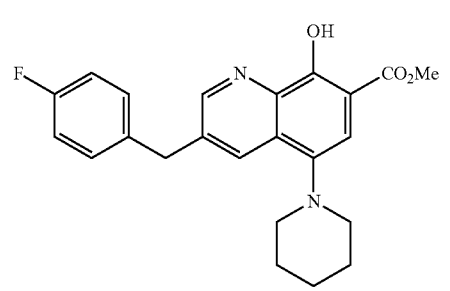

I-186

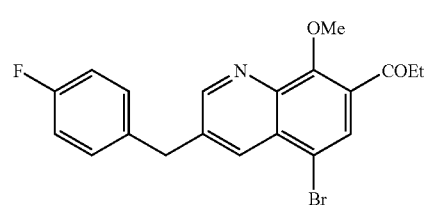

106

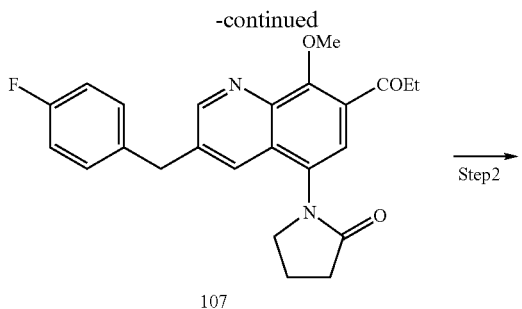

107

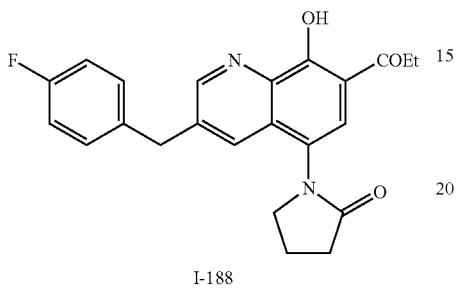

I-188

Step 1

In a manner similar to Example 61, Compound 106 (133 mg, 0.33 mmol; obtained in manner of WO02/70486) gave to Compound 107 (50 mg, 0.124 mmol, 36.4%).

Step 2

A mixture of Compound 107 (50 mg, 0.124 mmol) and pyridine hydrochloride (500 mg, 4.3 mmol) was stirred for 10 min at 180° C. The reaction solution was cooled to room temperature and mixed with ice water and stirred for 60 min. The pricipitated crystals were filtered and washed with water and dried under reduced pressure. The resulting residue was recrystallized from etyl acetate to give Compound I-188 of the title (30 mg, 0.076 mmol, 63.7%) as colorless crystals.

m.p.: 202-203° C. (from: EtOAc)

NMR (CDCl$_3$): 1.28 (3H, d, J=6.9 Hz), 2.22-2.34 (2H, m), 2.60-2.68 (2H, m), 3.13 (2H, q, J=6.9 Hz), 3.74-3.80 (2H, m), 4.18 (2H, s), 6.98-7.06 (2H, m), 7.12-7.20 (2H, m), 7.60-7.64 (1H, m), 7.73 (1H, s), 8.82-8.85 (1H, m).

Elemental Analysis: $C_{23}H_{21}FN_2O_3 \cdot 0.6H_2O$ Calcd. (%): C, 68.51; H, 5.55; F, 4.71; N, 6.95. Found. (%): C, 68.24; H, 5.54; F, 4.54; N, 6.76.

Example 63

I-189

5-(Dimethylaminooxalyl-amino)-3-(4-fluorobenzyl)-8-hydroxyquinoline-7-carboxylic acid methyl ester

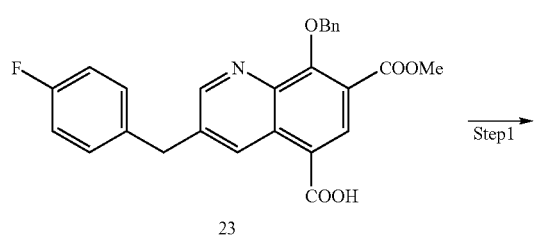

23

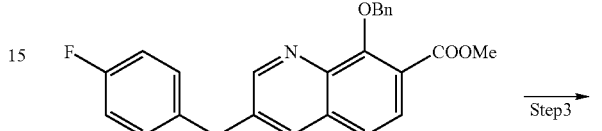

108

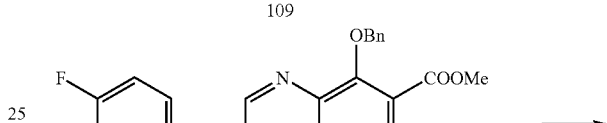

109

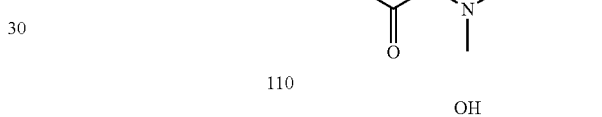

110

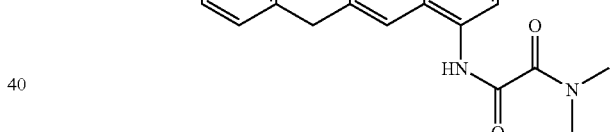

I-189

Step 1

To a solution of Compound 23 (obtained in Example 11; 8.0 g, 18 mmol) in THF (80 ml), triethyl amine (3.5 ml, 25.2 mmol), diphenyl azide phoshate (4.83 ml, 21.6 mmol) and 2-trimethyl sillyl ethanol (3.6 ml, 25.2 mmol) were added. The reaction solution was refluxed for 3 hours and cooled to room temperature. The solvent was evaporated in vacuo, mixed with ethyl acetate (300 ml) and water (100 ml), and separated. The organic layer was washed with 10% aqueous citric acid, brine, saturated aqueous sodium hydrogen carbonate and brine, and dried over magnesium sulfate. The solvent was evaporated in vacuo and the obtained residue was recrystallized from isopropylether to give Compound 108 (8.13 g, 14.5 mmol, in 80.5%) as pale yellow crystals.

Step 2

To a solution of Compound 108 (6.36 g, 11.3 mmol) in THF (35 ml), 1.0M tetrabutyl ammonium fluoride (17 ml, 17 mmol) in toluene and potassium fluoride (989 mg, 17 mmol) was added and stirred for 6 hours. The reaction solution was mixed with iced-water and extracted with ethyl acetate and the organic layer was washed with 10% aqueous citric acid,

Example 64

I-191

3-(4-Fluorobenzyl)-5-[(furan-2-carbonyl)-amino]-8-hydroxynoline-7-carboxylic acid methyl ester

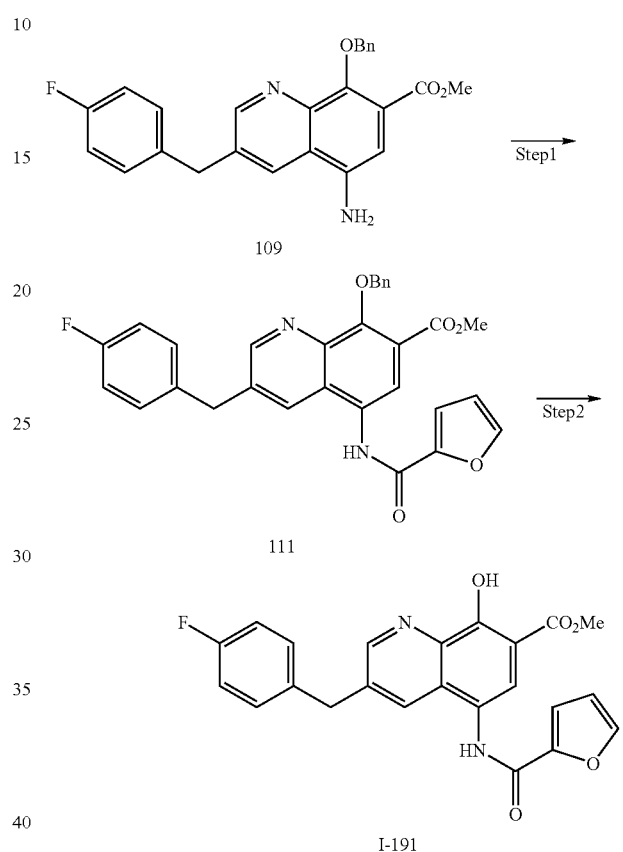

Step 1

In a manner similar to the Step 1 of Example 59, Compound 109 (208 mg, 0.5 mmol; obtained in Step 2 of Example 63) gave Compound 111 (170 mg, 0.33 mmol, 66.6%) as colorless crystals.

Step 2

In a manner similar to the Step 4 of Example 63, Compound 111 (160 mg, 0.31 mmol) gave Compound I-191 (90 mg, 0.21 mmol) of the title as pale green crystals in 68.4% yield.

m.p.: 232-233° C. (from: MeOH)

NMR (CDCl$_3$) δ: 4.02 (3H, s), 4.19 (2H, s), 6.60-6.64 (1H, m), 6.96-7.04 (2H, m), 7.12-7.20 (2H, m), 7.26-7.30 (1H, m), 7.58-7.59 (1H, m), 7.91 (1H, s), 8.07 (1H, s), 8.18 (1H, s), 8.88 (1H, s), 11.88 (1H, s).

Elemental Analysis: C$_{23}$H$_{17}$FN$_2$O$_5$ Calcd. (%): C, 65.71; H, 4.08; F, 4.52; N, 6.66. Found. (%): C, 65.51; H, 4.11; F, 4.38; N, 6.92

In a manner similar to Example 64, Compounds I-192 to I-194 were synthesized.

--- brine, saturated aqueous sodium hydrogen carbonate, and dried over magnesium sulfate and concentrated. The resulting residue was subjected to silica gel chromatography (n-hexan:ethyl acetate:chloroform=2:1:1, v/v) to give Compound 109 (4.8 g) as yellow crystals.

Step 3

To a solution of pyridine (101 µl, 1.25 mmol) and oxalyl chloride (95 µl, 1.0 mmol) in THF (7.0 ml), a solution of Compound 109 (208 mg, 0.5 mmol) in THF (3.0 ml) was dropwise added dropwise at −20° C. After stirring for 30 mins at this temperature, a solution of 2.0M dimethyl amine (2.5 ml, 5 mmol) in THF was dropwise added dropwise. The reaction solution was stirred for 30 mins and mixed with water (5.0 ml). Additionaly the reaction mixture was stirred for 30 min and filtered. The filtrate was extracted with ethyl acetate and the organic layer was washed with diluted hydrochloric acid, water, and brine. The organic layer was dried over sodium sulfate and evaporated in vacuo. The obtained oil was recrystallized from isopropylether to give Compound 110 (56 mg, 0.11 mmol, 21.7%) as colorless crystals.

Step 4

Compound 110 (120 mg, 0.23 mmol) was dissolved in ethyl acetate (3.0 ml)-methanol (3.0 ml)—THF (3.0 ml) and mixed with 10% Pd—C. The reaction mixture was stirred for 1.5 hours at room temperature under hydrogen atmosphere. The reaction solution was filtered and the filtrate was evaporated. The obtaained residue was recrystallized from methanolethyl acetate to give Compound I-189 of the title (60 mg, 0.14 mmol, 61.3%) as pale green crystals.

m.p.: 216-218° C. (from: $^i$-Pr$_2$O)

NMR (CDCl$_3$) δ: 3.15 (3H, s), 3.53 (3H, s), 4.03 (3H, s), 4.19 (2H, s), 6.98-7.04 (2H, m) 7.12-7.18 (2H, m), 7.92-7.96 (1H, m), 8.24 (1H, s), 8.86-8.90 (1H, m), 9.45 (1H, s).

Elemental Analysis: C$_{22}$H$_{20}$FN$_3$O$_5$0.1H$_2$O Calcd. (%): C, 61.85; H, 4.77; F, 4.45; N, 9.84. Found. (%): C, 61.68; H, 4.61; F, 4.22; N, 9.67.

In a manner similar to Example 63, Compound I-190 was synthesized.

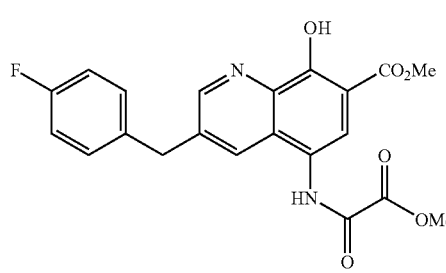

I-190

3-(4-Fluorobenzyl)-8-hydroxy-5-(methoxyoxalylamino)-quinoline-7-carboxylic acid methyl ester m.p.: 168-170° C. (from: MEOH-EtOAc)

NMR (CDCl$_3$) δ: 4.02 (3H, s), 4.03 (3H, s), 4.20 (2H, s), 6.98-7.06 (2H, m), 7.12-7.20 (2H, m), 7.82-7.86 (1H, m), 8.21 (1H, s), 8.86-8.94 (2H, m), 11.93 (1H, s).

Elemental Analysis: C$_{21}$H$_{17}$FN$_2$O$_6$1.11H$_2$O Calcd. (%): C, 58.36; H, 4.48; F, 4.30; N, 6.48. Found. (%): C, 58.13; H, 4.26; F, 4.18; N, 6.54.

193

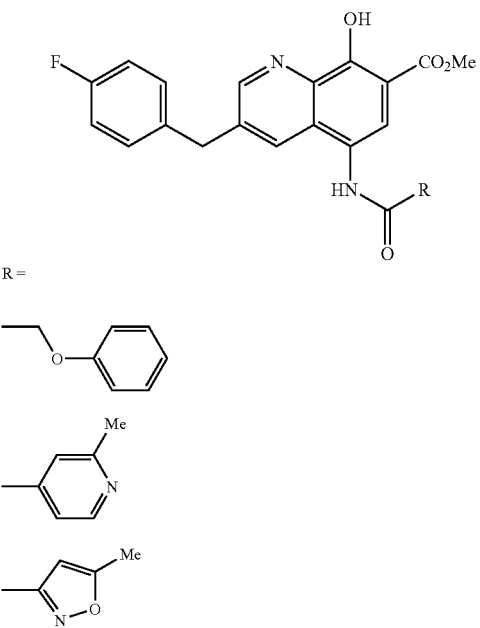

R =

- I-192  [ethoxyphenoxy group]
- I-193  [2-methylpyridine]
- I-194  [5-methylisoxazole]

I-192

3-(4-Fluorobenzyl)-8-hydroxy-5-(2-phenoxyacety-lamino)-quinoline-7-carboxylic acid methyl ester m.p.: 172-173° C. (from: MeOH-EtOAc)

NMR (CDCl$_3$) δ: 4.02 (3H, s), 4.11 (2H, s), 4.75 (2H, s), 6.96-7.06 (4H, m), 7.06-7.18 (3H, m), 7.32-7.44 (2H, m), 7.68 (1H, s), 8.15 (1H, s), 8.30 (1H, s), 8.86 (1H, s).

Elemental Analysis: $C_{26}H_{21}FN_2O_5$ Calcd. (%): C, 67.82; H, 4.60; F, 4.13; N, 6.08. Found. (%): C, 67.60; H, 4.55; F, 4.07; N, 6.07.

I-193

3-(4-Fluorobenzyl)-8-hydroxy-5-[(2-methylpyridine-4-carbonyl)-amino]-quinoline-7-carboxylic acid methyl ester m.p.: 229-230° C. (from: MeOH)

NMR (CDCl$_3$) δ: 2.69 (3H, s), 4.02 (3H, s), 4.17 (2H, s), 6.96-7.03 (2H, m), 7.10-7.18 (2H, m), 7.48-7.56 (1H, s), 7.63 (1H, s), 7.81 (1H, s), 8.02-8.10 (2H, m), 8.64-8.70 (1H, s), 8.84-8.88 (1H, s).

Elemental Analysis: $C_{25}H_{20}FN_3O_4$·1.0HCl Calcd. (%): C, 62.31; H, 4.39; F, 3.94; N, 8.72. Found. (%): C, 62.63; H, 4.17; F, 4.25; N, 9.56.

I-194 3-(4-Fluorobenzyl)-8-hydroxy-5-[(5-methyl-isoxazole-3-carbonyl)-amino]-quinoline-7-carboxylic acid methyl ester m.p.: 182-183° C. (from: MeOH)

NMR (CDCl$_3$) δ: 2.56 (3H, s), 4.02 (3H, s), 4.19 (2H, s), 6.55 (1H, s), 6.96-7.04 (2H, m), 7.10-7.20 (2H, m), 7.92-7.96 (1H, m), 8.22 (1H, s), 8.54 (1H, s), 8.86-8.90 (1H, m).

194

Example 65

I-195

3-(4-Fluorobenzyl)-8-hydroxy-quinoline-5,7-dicar-boxylic acid 7-(1-acetyl piperidine-4-yl)-ester

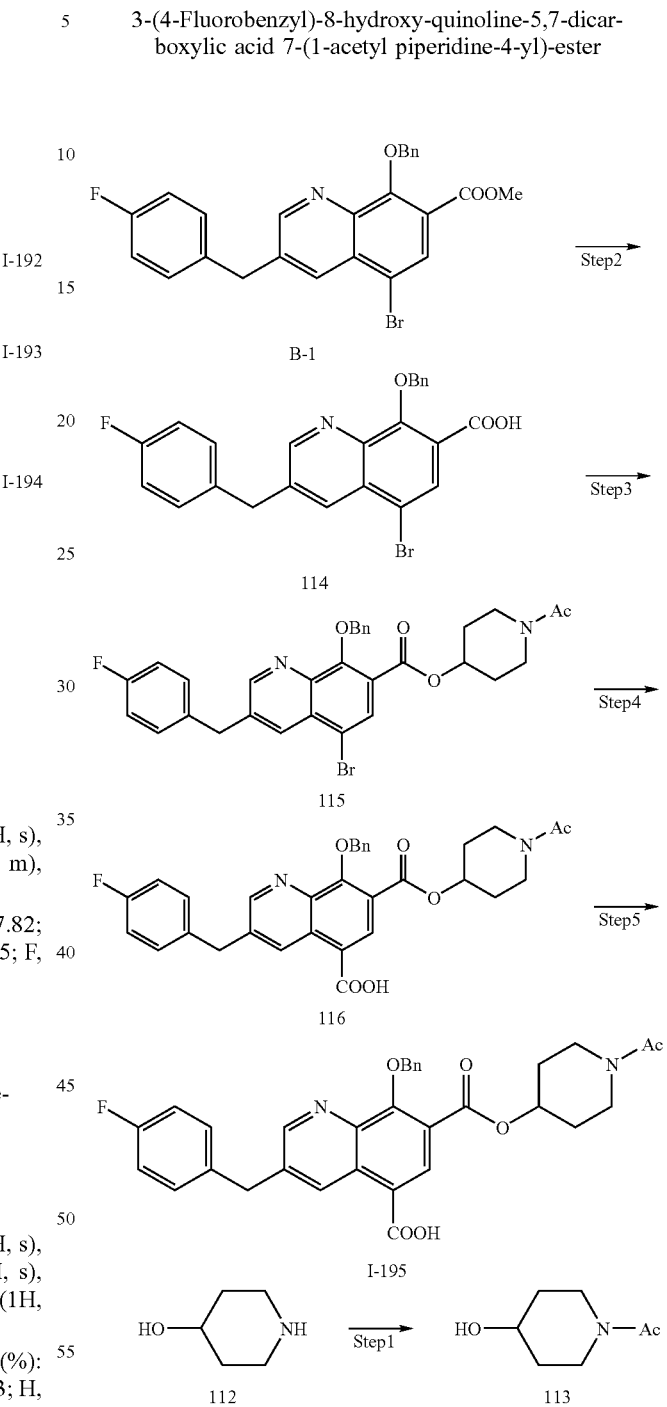

Step 1

To a solution of 4-hydroxypiperidine and Compound 112 (7.4 g, 73.2 mmol) in MeOH (20 ml), water (10 ml) and acetic anhydride (15.2 ml, 161 mmol) was added at room temperature and stirred for 2 hours. The reaction solvent was evaporated in vacuo and mixed with water (20 ml), evaporated in vacuo. Additionaly, toluene (20 ml) was added to the resisue and evaporated in vacuo. The obtained residue was mixed with n-hexan (30 ml) and crystallized under ice-cooling. The n-hexan was removed and, ether (30 ml) and n-hexan (30 ml) was added to the residue. After stirring for 10 minutes, the solvent was evaporated in vacuo and n-hexan (30 ml) was added, then the mixture was filtered to give Compound 113 (9.2 g, 64.2 mmol, 87.8%) as colorless crystals.

NMR (CDCl$_3$) δ: 1.40-1.60 (2H, m), 1.80-1.98 (2H, m), 2.80-3.30 (3H, m), 3.60-3.78 (1H, m), 3.88-3.98 (1H, m), 4.00-4.12 (1H, m).

Step 2

To a solution of Compound B-1 (1.5 g, 3.1 mmol; obtained in Example B-1) in dioxane (47 ml), 1N aqueous LiOH (31.0 ml, 31.0 mmol) was added at room temperature and reacted for 2 hours at 80° C. The reaction solution was cooled and 2N aqueous HCl (20.0 ml, 40.0 mmol) was added dropwise under ice-cooling and stirring. The reaction mixture was stirred for 2 hours and the pricipitated crystals were filtered out and washed with water. The crystals were evaporated in vacuo for 3 hours at 70° C. to give Compound 114 (1.35 g, 2.9 mmol, 93.4%) as colorless crystals.

Step 3

To a solution of Compound 114 (1.3 g, 2.8 mmol), triphenyl phosphine (1.47 g, 5.6 mmol) and Compound 113 (891 mg, 6.2 mmol; obtained in Example 65) in THF, a solution of azodic arboxylic acid diisopropyl ester (2.8 ml, 5.6 mmol) in toluene was added dropwise at 0° C. and reacted for 30 mins. The reaction mixture was mixed with water and extracted with ethyl acetate. The organic layer was washed with water and brine, dried over anhydrous sodiun sulfate, and concentrated in vacuo. The resulting residue was subjected to silicagel column chromatography and eluted with ethyl acetate, additionaly with toluene-acetone (5:1, v/v) to give Compound 115 (1.6 g, 2.71 mmol) in 96.6% yield.

Step 4

In a manner similar to Step 2 of Example 1, Compound 115 (1.6 g, 2.71 mmol) gave 116 (1.12 g, 2.0 mmol) as pale yellow crystals in 74.5% yield.

Step 5

In a manner similar to Step 4 of Example 63, Compound 116 (120 nmg, 0.22 mmol) gave Compound I-195 (79.0 g, 0.17 mmol) of the title as pale yellow crystals in 77% yield.

m.p.: 230-232° C. (from: MeOH-THF-$i$-Pr$_2$O)

NMR (DMSO-d$_6$) δ: 1.60-1.86 (4H, m), 2.04 (3H, s), 3.30-3.80 (4H, m), 4.26 (2H, s), 5.20-5.30 (1H, m), 7.10-7.20 (2H, m), 7.30-7.40 (2H, m), 8.62 (1H, s), 8.88-8.92 (1H, m), 9.22-9.28 (1H, m).

Elemental Analysis: C$_{25}$H$_{23}$FN$_2$O$_6$0.2H$_2$O Calcd. (%): C, 63.90; H, 5.02; F, 4.04; N, 5.96. Found. (%): C, 63.66; H, 5.03; F, 3.94; N, 5.89.

Example 66

I-196

3-(4-Fluorobenzyl)-8-hydroxy-5-(2-methoxyethyl-carbonyl)-quinoline-7-carboxylic acid

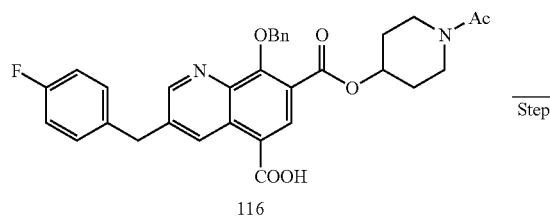

116

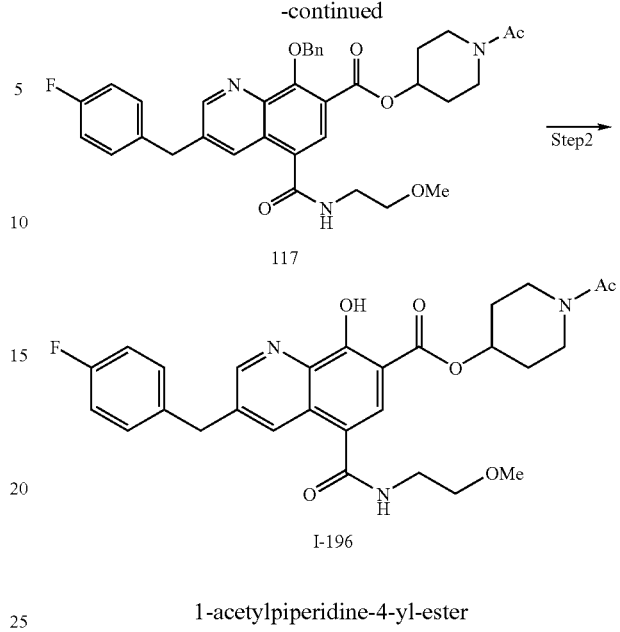

117

I-196

1-acetylpiperidine-4-yl-ester

Step 1

In a manner similar to Step 1 of Example 2, Compound 116 (150 g, 0.27 mmol obtained in Example. 65) gave Compound 117 (120 mg, 0.27 mmol) as pale yellow crystals in 72.6% yield.

Step 2

In a manner similar to Step 4 of Example 63, Compound 117 (120 nmg, 0.20 mmol) gave Compound I-196 (84.0 g, 0.16 mmol) of the title as pale yellow crystals in 81.6% yield.

m.p.: 110-112° C. (from: i-Pr$_2$O)

NMR (CDCl$_3$) δ: 1.80-1.96 (2H, m), 2.00-2.18 (5H, m), 3.40 (3H, s), 3.40-3.56 (2H, m), 3.58-3.66 (2H, m), 3.66-3.82 (3H, m), 4.00-4.10 (1H, m), 4.17 (2H, s), 5.32-5.40 (1H, m), 6.35-6.44 (1H, m), 6.96-7.04 (2H, m), 7.14-7.22 (2H, m), 8.06 (1H, s), 8.64-8.68 (1H, m), 8.82-8.86 (1H, m).

Elemental Analysis: C$_{28}$H$_{30}$FN$_3$O$_6$0.3H$_2$O Calcd. (%): C, 63.58; H, 5.83; F, 3.59; N, 7.94. Found. (%): C, 63.41; H, 5.83; F, 3.47; N, 8.02.

In a manner similar to Example 66, Compounds I-197 to I-199 were synthesized.

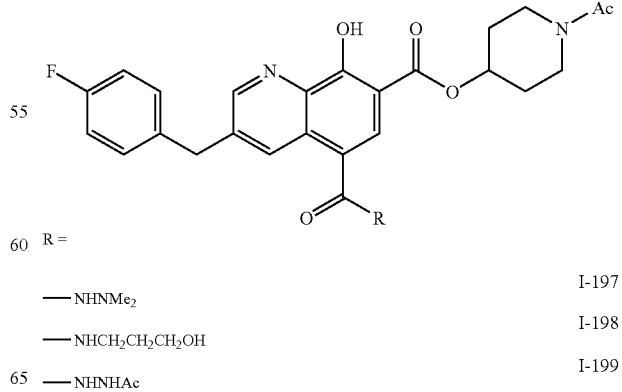

R =

| — NHNMe$_2$ | I-197 |
| — NHCH$_2$CH$_2$CH$_2$OH | I-198 |
| — NHNHAc | I-199 |

197

I-197

5-(N',N'-Dimethylhydrazinocarbonyl)-3-(4-fluorobenzyl)-8-hydroxyquinoline-7-carboxylic acid 1-acetylpiperidine-4-yl-ester m.p.: 92-93° C. (from: $^i$-Pr$_2$O)

NMR (CDCl$_3$) δ: 1.80-1.96 (2H, m), 2.00-2.20 (5H, m), 2.74 (6H, s), 3.36-3.50 (2H, m), 3.70-3.82 (1H, m), 4.00-4.18 (1H, m), 4.17 (2H, s), 5.30-5.40 (1H, m), 6.71 81H, s), 6.96-7.06 (2H, m), 7.14-7.24 (2H, m), 7.96 (1H, s), 8.49 (1H, s), 8.82-8.88 (1H, m).

Elemental Analysis: C$_{27}$H$_{29}$FN$_4$O$_5$0.5H$_2$O Calcd. (%): C, 62.66; H, 5.84; F, 3.67; N, 10.83. Found. (%): C, 62.70; H, 6.04; F, 3.38; N, 10.67.

I-198

3-(4-Fluorobenzyl)-8-hydroxy-5-(3-hydroxypropyl-carbamoyl)-quinoline-7-carboxylic acid 1-acetylpiperidine-4-yl-ester m.p. 97-99° C. (from: $^i$-Pr$_2$O)

NMR (CDCl$_3$) δ: 1.80-1.96 (4H, m), 1.96-2.18 (5H, m), 3.40-3.54 (2H, m), 3.60-3.80 (5H, m), 3.96-4.08 (1H, m), 4.17 (2H, s), 5.25-5.40 (1H, m), 6.64-6.76 (1H, m), 6.98-7.04 (2H, m), 7.16-7.22 (2H, m), 8.06 (1H, s), 8.64-8.68 (1H, m), 8.82-8.86 (1H, m).

Elemental Analysis: C$_{28}$H$_{30}$FN$_3$O$_6$ 1.0H$_2$O Calcd. (%): C, 62.10; H, 5.96; F, 3.51; N, 7.76. Found. (%): C, 62.36; H, 5.60; F, 3.44; N, 7.75.

I-199

5-(N'-Acetylhydrazinocarbonyl)-3-(4-fluorobenzyl)-8-hydroxyquinoline-7-carboxylic acid 1-acetylpiperidine-4-yl ester m.p.: 129-131° C. (from: ethyl acetate-ethylether)

NMR (CDCl$_3$) δ: 1.84-1.92 (2H, m), 2.03-2.11 (2H, m), 2.14 (3H, s), 2.17 (3H, s), 3.38-3.50 (2H, m), 3.76-3.81 (1H, m), 4.06-4.11 (1H, m), 4.17 (2H, s), 5.34-5.39 (1H, m), 6.97-7.04 (2H, m), 7.16-7.21 (2H, m), 8.18 (1H, s), 8.33 (1H, d, J=5.1 Hz), 8.67 (1H, d, J=2.1 Hz), 8.71 (1H, brs), 8.85 (1H, d, J=2.1 Hz).

Elemental Analysis: C$_{27}$H$_{27}$FN$_4$O$_6$ 2H$_2$O Calcd. (%): C, 58.06; H, 5.59; F, 3.40; N, 10.03. Found. (%): C, 58.29; H, 5.18; F, 3.56; N, 9.30.

198

Example 67

I-200

3-(4-Fluorobenzyl)-8-hydroxy-5-(3-methoxy-propionyl amino)-quinoline-7-carboxylic acid 1-acetylpiperidine-4-yl-ester

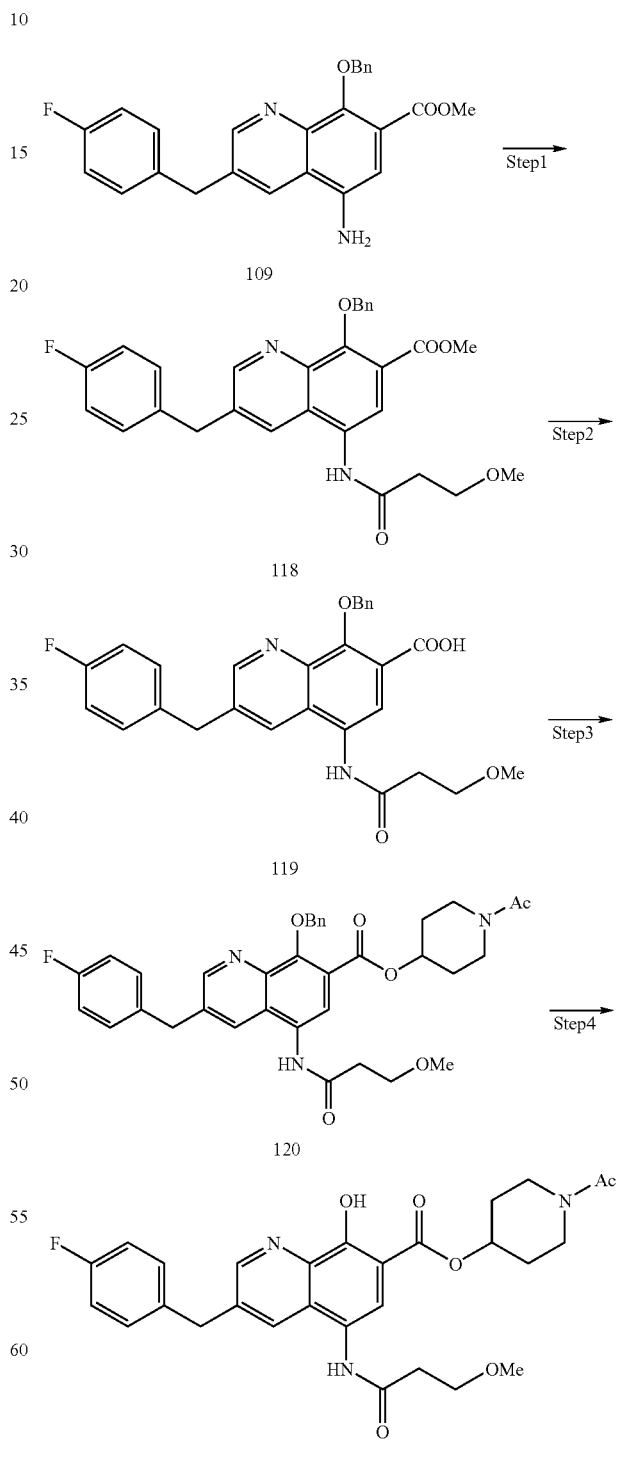

Step 1

In a manner similar to Step 1 of Example 59, Compound 109 (624 mg, 1.5 mmol obtained in Step. 2 of Example. 65) gave Compound 118 (300 mg, 0.6 mmol, 40.0%) as pale yellow crystals in 40.0% yield.

Step 2

To a solution of Compound 118 (300 mg, 0.6 mmol) in MeOH (5 ml)-THF (3 ml), 2N NaOH (0.5 ml, 1.0 mmol) was added at room temperature and reacted for 5 hours. Under ice-cooling, the reaction solution was mixed with 2N HCl (2.0 ml, 4.0 mmol) and stirred for 1 hour. The pricipitated crystals were filtered out and washed with water and evaporated for 3 hours at 70° C. to give Compound 119 (220 mg, 0.45 mmol, 75.1%) as colorless crystals.

Step 3

In a manner similar to the Step 2 of Example 66, Compound 119 (125 mg, 0.25 mmol) gave Compound 120 (130 mg, 0.21 mmol) as oil in 84% yield.

Step 4

In a manner similar to the Step 4 of Example 63, Compound 120 (130 nmg, 0.21 mmol) gave Compound I-200 of the title (72.0 g, 0.14 mmol) as pale green solid in 65.7% yield.

m.p.: 89-90° C.

NMR (CDCl$_3$) δ: 1.80-1.96 (2H, m), 1.94-2.10 (2H, m), 2.14 (3H, s), 2.70-2.76 (2H, m), 3.41 (3H, s), 3.41-3.52 (1H, m), 3.54-3.68 (1H, m), 3.70-3.80 (3H, m), 3.90-4.00 (1H, m), 4.19 (2H, s), 5.28-5.40 (1H, m), 6.96-7.06 (2H, m), 7.12-7.20 (2H, m), 7.84-7.88 (1H, m), 8.11 (1H, s), 8.36 (1H, s), 8.84-8.88 (1H, m).

Elemental Analysis: $C_{28}H_{30}FN_3O_6 \cdot 0.6H_2O$ Calcd. (%): C, 62.93; H, 5.89; F, 3.56; N, 7.86. Found. (%): C, 62.68; H, 5.86; F, 3.47; N, 7.83.

The following compounds having a 1,6-naphthylidine nucleus were synthesized:

Example A-1

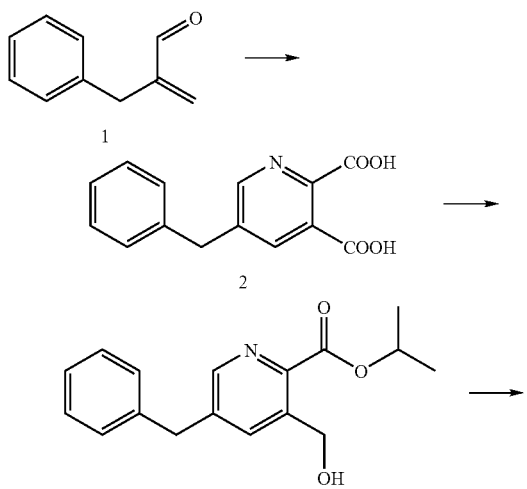

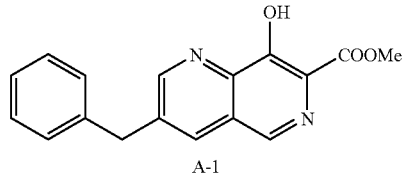

Compound A-1: Methyl 3-Benzyl-8-hydroxy-1,6-naphthylidine-7-carboxylate 1) 2-Benzyl-2-propenal 1 (27.78 g, 190 mmol) that is known and described in U.S. Pat. No. 4,973,695, and 2-aminobutanedicarboxylic acid diethyl ester (29.95 g, 160 mmol) that is known and described in Chem. Pharm. Bull., 1989, 37, 3236, were reacted in a manner similar to that described in Japanese Patent publication (Kokai) S64-16764/1989, and the product was subjected to alkaline hydrolysis using 4N-sodium hydroxide (160 ml, 640 mmol) to give 2-benzylpyridine-2,3-dicarboxylic acid 2 (23.22 g) in 56% yield.

NMR (DMSO-d$_6$) δ: 4.09 (2H, s) 7.20-7.35(5H, m), 8.03 (1H, d, J=2.1 Hz), 8.68 (1H, d, J=2.1 Hz).

2) Compound 2 (2.52 g, 9.80 mmol) was heated in acetic anhydride at 120° C. for 2 hours. The solvent was evaporated and the resulting acid anhydride was subjected to alcoholysis by isopropyl alcohol and then to reduction of the acid chloride by a method similar to that described in J. Med. Chem., 1989, 32, 827, so as to give isopropyl 5-benzyl-3-hydroxymethyl-pyridine-2-carboxylate 3 (560 mg) in 20% yield.

NMR (CDCl$_3$) δ: 1.44 (6H, d, J-6.3 Hz), 3.69 (1H, brt, J=6.9 Hz), 4.04(2H, s), 4.75(2H, d, J=6.3 Hz), 5.34(1H, seC, J=6.3 Hz), 7.15-7.33 (5H, m), 7.63 (1H, d, J=2.1 Hz), 8.56 (1H, d, J=2.1 Hz).

3) By using Compound 3 (550 mg, 1.93 mmol) and N-tosylglycine methyl ester, the Mitsunobu reaction was carried out, followed by a ring closure reaction by the action of 1M-sodium methoxide according to WO02/30930 so as to give Compound A-1 (557 mg) in 85% yield; m.p.: 174° C.

Elemental Analysis: $C_{17}H_{14}N_2O_3$ Calcd. (%): C, 69.38; H, 4.79; N, 9.52. Found (%): C, 69.40; H, 4.78; N, 9.34.

NMR (CDCl$_3$) δ: 4.12 (3H, s), 4.25 (2H, s), 7.22-7.39 (5H, m), 7.98 (1H, m), 8.76 (1H, s), 9.10 (1H, d, J=2.1 Hz), 11.76 (1H, s).

In a manner similar to that of Example A-1, Compounds A-2, 3 were synthesized:

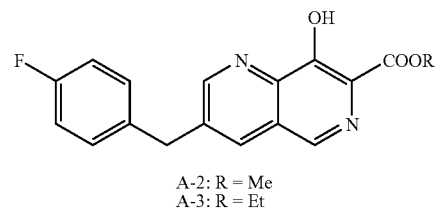

A-2: R = Me
A-3: R = Et

Example A-2

Compound A-2: Methyl 3-(4-fluorobenzyl)-8-hydroxy-1,6-naphthylidine-7-carboxylate;

m.p.: 218-219° C.
Elemental Analysis: $C_{17}H_{13}FN_2O_3$ Calcd. (%): C, 65.38; H, 4.20; N, 8.97. Found (%): C, 65.19; H, 4.19; N, 8.90.
NMR (CDCl$_3$) δ: 4.13 (3H, s), 4.23 (2H, s), 7.02-7.08 (2H, m), 7.17-7.23 (2H, m), 7.97 (1H, m), 8.77 (1H, s), 9.08 (1H, d, J=2.1 Hz), 11.77 (1H, s).

Example A-3

Compound A-3: Ethyl 3-(4-fluorobenzyl)-8-hydroxy-1,6-naphthylidine-7-carboxylate m.p.: 209-211° C.
Elemental Analysis: $C_{18}H_{15}FN_2O_3$ Calcd. (%): C, 66.25; H, 4.63; N, 8.58. Found (%): C, 66.03; H, 4.44; N, 8.47.
NMR (CDCl$_3$) δ: 1.53 (3H, t, J=7.1 Hz), 4.22 (2H, s), 4.60 (2H, q, J=7.2 Hz), 7.00-7.08 (2H, m), 7.18-7.22 (2H, m), 7.96 (1H, m), 8.77 (1H, s), 9.07 (1H, d, J=2.1 Hz), 11.93 (1H, s).

2-(4-Fluorobenzyl)-2-propenal 6 was synthesized by the following process:

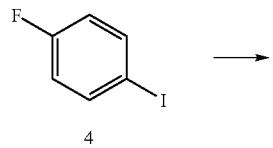

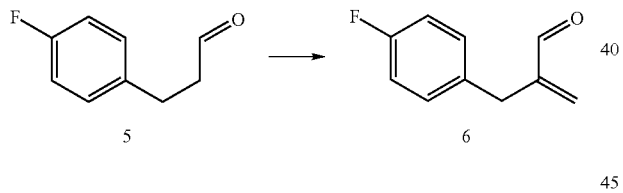

1) In a manner similar to that describe in Chem. Commun., 1984, 1287, 4-fluoroiodobenzene 4 (50 g, 225 mmol) and allyl alcohol (23 ml, 337 mmol) were subjected to Heck reaction in the presence of palladium acetate and the mixture was distilled in vacuo (94-96° C., 7 mmHg) to give 3-(4-fluorophenyl)propional 5 (27.5 g) in 80% yield.
NMR (CDCl$_3$) δ: 2.73-2.79 (2H, m), 2.93 (2H, t, J=7.4 Hz), 6.94-7.00 (2H, m), 7.12-7.17 (2H, m), 9.8.1 (1H, t, J=1.2 Hz).

2) Compound 5 (53 g, 348 mmol) and 37% formalin (31.2 ml) were heated in diethylamine hydrochloride (38.3 g) at 110° C. for 1 hour. The mixture was diluted with ether, washed three times with water. The extract was dried over magnesium sulfate, and distilled in vacuo (101-103° C., 8 mmHg) to give 2-(4-fluorobenzyl)-2-propenal 6 (45.3 g) in 79% yield.
NMR (CDCl$_3$) δ: 3.54 (2H, s), 6.07 (1H, d, J=0.6 Hz), 6.11 (1H, t, J=1.4 Hz), 6.94-7.01 (2H, m), 7.11-7.16 (2H, m), 9.59 (1H, s).

Example A-4

Compound A-4: 3-(4-fluorobenzyl)-8-hydroxy-1,6-naphthylidine-7-carboxylic acid

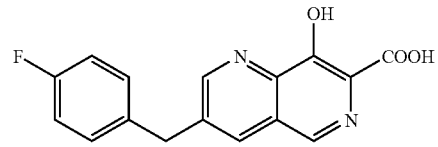

To a solution of Compound A-2 (156 mg, 0.5 mmol) in methanol-tetrahydrofuran (8 ml) was added 2N-sodium hydroxide (1 ml) and the mixture was refluxed for 1.5 hours. After cooling, the mixture was treated with 2N-hydrochloric acid and the solvent was evaporated off. The precipitated crystals were collected by filtration and washed with water and ether. The crystals were further washed with acetone to give Compound A-4 (72 mg) in 48% yield; m.p.: 257° C.
FABMS: m/z 299 (M+H)$^+$
NMR (DMSO-d$_6$) δ: 4.19 (2H, s), 7.12-7.18 (2H, m), 7.34-7.39 (2H, m), 8.21 (1H, d, J=2.1 Hz), 8.40 (1H, s), 8.88 (1H, d, J=2.1 Hz).

Example A-5

Compound A-5: Methyl 3-benzyl-5-chloro-8-hydroxy-1,6-naphthylidine-7-carboxylate

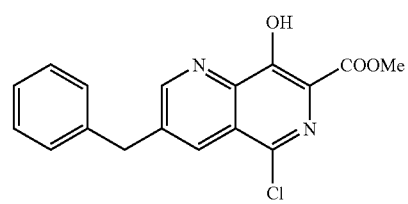

To a solution (10 ml) of Compound A-1 (118 mg, 0.4 mmol) in acetonitrile (10 ml) was added N-chlorosuccinimide (59 mg, 0.44 mmol), and the mixture was refluxed for 30 minutes. After cooling, the mixture was concentrated and treated with methanol. The precipitated crystals were collected by filtration and washed with methanol. Recrystallization of the crystals from methanol-chloroform mixture gave Compound A-5 (69 mg) in 52% yield; m.p.: 209-210° C.
Elemental Analysis: $C_{17}H_{13}ClN_2O_3$ Calcd. (%): C, 62.11; H, 3.99; N, 8.52. Found (%): C, 62.17; H, 3.90; N, 8.44.
NMR (CDCl$_3$) δ: 4.11 (3H, s), 4.28 (2H, s), 7.22-7.39 (5H, m), 8.34 (1H, dt, J=0.9, 2.1 Hz), 9.11 (1H, d, J=2.1 Hz), 11.78 (1H, s).

Example A-6

Compound A-6: Methyl 3-benzyl-5-bromo-8-hydroxy-1,6-naphthylidine-7-carboxylate

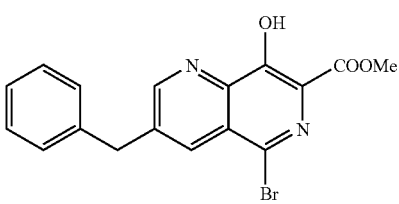

To a solution of Compound A-1 (106 mg, 0.36 mmol) in acetonitrile (10 ml) was added N-bromosuccinimide (71 mg, 0.4 mmol), and the mixture was stirred at room temperature for 1.5 hours. The reaction mixture was treated with aqueous 0.5M-sodium thiosulfate, and extracted twice with chloroform. The organic layer was washed three times with water, dried over sodium sulfate, and concentrated. The precipitated crystals were collected by filtration and washed with methanol. The resulting crystals were recrystallized from methanol-chloroform to give Compound A-6 (108 mg) in 81% yield. m.p.: 213-214° C.

Elemental Analysis: $C_{17}H_{13}BrN_2O_3$ Calcd. (%): C, 54.71; H, 3.51; N, 7.51. Found (%): C, 54.77; H, 3.35; N, 7.35.

NMR (CDCl$_3$) δ: 4.11 (3H, s), 4.29 (2H, s), 7.22-7.39 (5H, m), 8.30 (1H, dt, J=0.9, 2.1 Hz), 9.07 (1H, d, J=2.1 Hz), 11.77 (1H, s).

In a manner similar to Example A-6, Compounds A-7 and 8 were prepared.

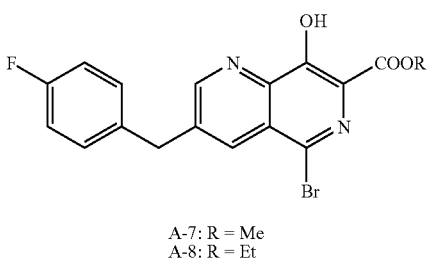

A-7: R = Me
A-8: R = Et

Example A-7

Compound A-7: Methyl 5-bromo-3-(4-fluorobenzyl)-8-hydroxy-1,6-naphthylidine-7-carboxylate; m.p.: 234-236° C.

Elemental Analysis: $C_{17}H_{12}BrFN_2O_3$ Calcd. (%): C, 52.19; H, 3.09; N, 7.16. Found (%): C, 52.29; H, 2.99; N, 7.05.

NMR (CDCl$_3$) δ: 4.11 (3H, s), 4.26 (2H, s), 7.02-7.09 (2H, m), 7.17-7.23 (2H, m), 8.28 (1H, dt, J=0.9, 2.1 Hz), 9.05 (1H, d, J=2.1 Hz), 11.78 (1H, s).

Example A-8

Compound A-8: Ethyl 5-bromo-3-(4-fluorobenzyl)-8-hydroxy-1,6-naphthylidine-7-carboxylae;

m.p.: 154-155° C.

Elemental Analysis: $C_{18}H_{14}BrFN_2O_3$ Calcd. (%): C, 53.35; H, 3.48; N, 6.91. Found (%): C, 53.42; H, 3.14; N, 6.91.

NMR (CDCl$_3$) δ: 1.51 (3H, t, J=7.1 Hz), 4.26 (2H, s), 4.59 (2H, q, J=7.2 Hz), 7.03-7.08 (2H, m), 7.18-7.23 (2H, m), 8.27 (1H, m), 9.04 (1H, d, J=2.1 Hz), 11.93 (1H, s).

Example A-9

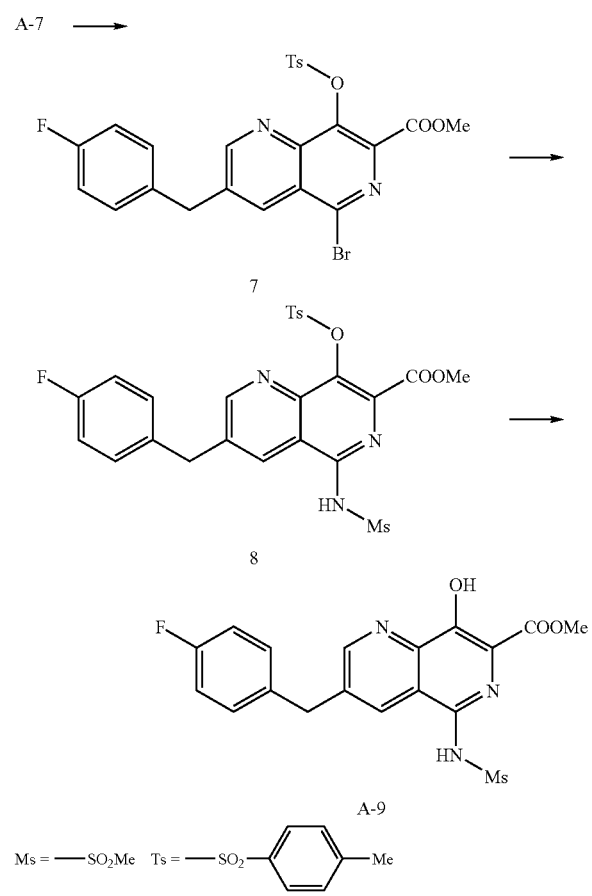

Ms = —SO$_2$Me   Ts = —SO$_2$—⟨⟩—Me

Compound A-9: Methyl 3-(4-fluorobenzyl)-8-hydroxy-5-methanesulfonylamino-1,6-naphthylidine-7-carboxylate 1) To a solution of Compound A-7 (3.28 g, 8.38 mmol) and triethylamine (1.67 ml, 12 mmol) in methylene chloride (60 ml) was added tosyl chloride (1.60 g, 8.4 mmol), and the mixture was stirred at room temperature overnight. Additional tosyl chloride (160 mg, 0.84 mmol) was added to the mixture, and the mixture was stirred for 2 hours. The resulting mixture was concentrated, diluted with ethyl acetate, washed with aqueous saturated ammonium chloride, water, aqueous saturated sodium hydrogen carbonate, dried over magnesium sulfate, and concentrated.

The residue was purified by silica gel column chromatography. The precipitated crystals were collected by filtration, and washed with isopropanol-acetone to give compound 7 (4.08 g) in 89% yield.

NMR (CDCl$_3$) δ: 2.44 (3H, s), 3.80 (3H, s), 4.22 (2H, s), 7.03-7.09 (2H, m), 7.16-7.20 (2H, m), 7.32 (2H, d, J=8.1 Hz), 7.84 (2H, d, J=8.4 Hz), 8.28 (1H, m), 8.88 (1H, d, J=2.1 Hz).

2) In a manner similar to that described in a literature (Org. Lett., 2000, 2, 1101.) under nitrogen atmosphere, a mixture of Compound 7 (613 mg, 1.12 mmol) and methane sulfonamide (127 mg, 1.34 mmol) was refluxed in the presence of palladium acetate (11 mg, 0.05 mmol), xantphos (43 mg, 0.075 mmol), and cesium carbonate (489 mg, 1.5 mmol) in dioxane for 2 hours to give Compound 8 (618 mg) in 98% yield.

NMR (CDCl$_3$) □: 2.43 (3H, s), 3.16 (3H, s), 3.85 (3H, s), 4.09 (2H, s), 6.99-7.05 (2H, m), 7.09-7.14 (2H, m), 7.31 (2H, d, J=7.8 Hz), 7.81 (2H, d, J=8.4 Hz), 8.56 (1H, m), 8.62 (1H, d, J=2.1 Hz), 12.23 (1H, s).

3) To a solution of Compound 8 (150 mg, 0.27 mmol) in tetrahydrofuran (3 ml) was added 1M-sodium methoxide (0.81 ml, 0.81 mmol) under ice-cooling, and the mixture was stirred at room temperature for 2 hours. The reaction mixture was neutralized with 1N-hydrochloric acid, and extracted twice with chloroform. The organic layer was washed with water, dried over sodium sulfate, and concentrated. The resulting crystals were collected by filtration and washed with ethyl acetate to give Compound A-9 (59 mg) in 54% yield; m.p.: 205-210° C. FABMS: m/z 406 (M+H)$^+$.

NMR (DMSO-d$_6$) δ: 3.53 (3H, s), 3.94 (3H, s), 4.26 (2H, s), 7.16 (2H, dd, J=8.9, 8.9 Hz), 7.39 (2H, dd, J=5.7, 8.7 Hz), 8.56 (1H, s), 9.14 (1H, d, J=1.8 Hz), 10.79 (1H, brs), 11.23 (1H, brs).

In a manner similar to that of Example A-9, following Compounds A-10 and A-11 were synthesized.

Example A-10

Compound A-10: Methyl 5-acetylamino-3-(4-fluorobenzyl)-8-hydroxy-1,6-naphthylidine-7-carboxylate

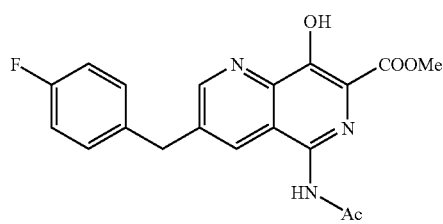

A-10 m.p.: 263-267° C. FABMS: m/z 370 (M+H)$^+$

NMR (DMSO-d$_6$) δ: 2.15 (3H, s), 3.93 (3H, s), 4.25 (2H, s), 7.15 (2H, dd, J=8.9, 8.9 Hz), 7.36 (2H, dd, J=5.7, 8.7 Hz), 8.18 (1H, d, J=1.8 Hz), 9.08 (1H, d, J=1.8 Hz), 10.51 (1H, s), 11.24 (1H, brs).

Example A-11

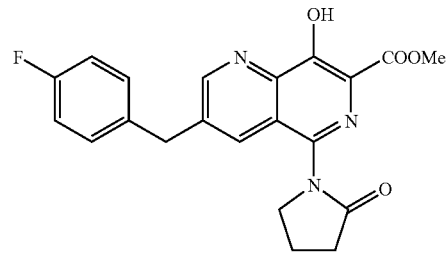

A-11

Compound A-11: Methyl 3-(4-fluorobenzyl)-8-hydroxy-5-(2-oxopyrrolidin-1-yl)-1,6-naphthylidine-7-carboxylate; m.p.: 260-262° C. FABMS: m/z 396 (M+H)$^+$ NMR (CDCl$_3$) δ: 2.31 (2H, tt, J=7.5, 7.5 Hz), 2.66 (2H, t, J=8.1 Hz), 4.08 (3H, s), 4.13 (2H, t, J=6.9 Hz), 4.21 (2H, s), 6.99-7.05 (2H, m), 7.16-7.21 (2H, m), 7.98 (1H, m), 9.00 (1H, d, J=2.1 Hz), 11.70 (1H, s).

Example A-12

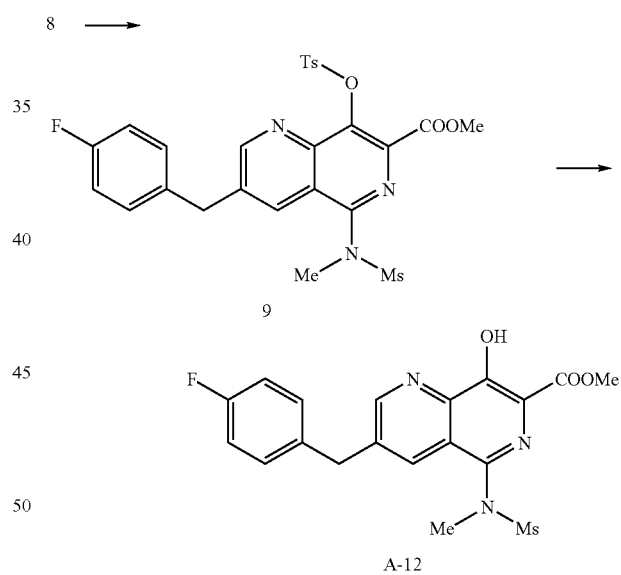

Compound A-12: Methyl 3-(4-fluorobenzyl)-8-hydroxy-5-(N-methyl)methanesulfonylamino-1,6-naphthylidine 7-carboxylate 1) To a solution of Compound 8 (306 mg, 0.55 mmol) in dimethylformamide (3 ml) were added cesium carbonate (176 mg, 0.54 mmol) and methyl iodide (0.034 ml, 0.54 mmol), and the mixture was stirred under nitrogen atmosphere at room temperature overnight. Additional amount of cesium carbonate (117 mg, 0.36 mmol) and methyl iodide (0.022 ml, 0.36 mmol) were added and the mixture was stirred for 3 days. The mixture was treated with diluted hydrochloric acid, and extracted twice with ethyl acetate. The organic layer was washed with water and brine, dried over magnesium sulfate, and concentrated. The resulting residue was purified by silica gel column chromatography to give Compound 9 (233 mg) in 74% yield.

NMR (CDCl$_3$) δ: 2.42(3H, s), 3.17(3H, s), 3.42(3H, s), 3.86(3H, s), 4.17(2H, s), 6.98-7.04(2H, m), 7.05-7.17(2H, m), 7.29(2H, d, J=7.8 Hz), 7.84(2H, d, J=8.4 Hz), 8.47(1H, m), 8.76(1H, d, J=2.1 Hz).

2) Compound A-12 was synthesized from Compound 9 by a method similar to that of Example A-9 (3); m.p.: 190-192° C.

Elemental Analysis: C$_{18}$H$_{18}$FN$_3$O$_5$S Calcd. (%): C, 54.41; H, 4.33; N, 10.02. Found (%): C, 54.13; H, 4.04; N, 9.84.

NMR (CDCl$_3$) δ: 3.20 (3H, s), 3.36 (3H, s), 4.07 (3H, s), 4.23 (2H, s), 6.99-7.05 (2H, m), 7.16-7.21 (2H, m), 8.46 (1H, d, J=2.1 Hz), 9.21 (1H, d, J=2.4 Hz), 11.81 (1H, s).

Example A-13

Compound A-13: Methyl 3-(4-fluorobenzyl)-8-hydroxy-5-(2-oxopiperidin-1-yl)-1,6-naphthylidine-7-carboxylate

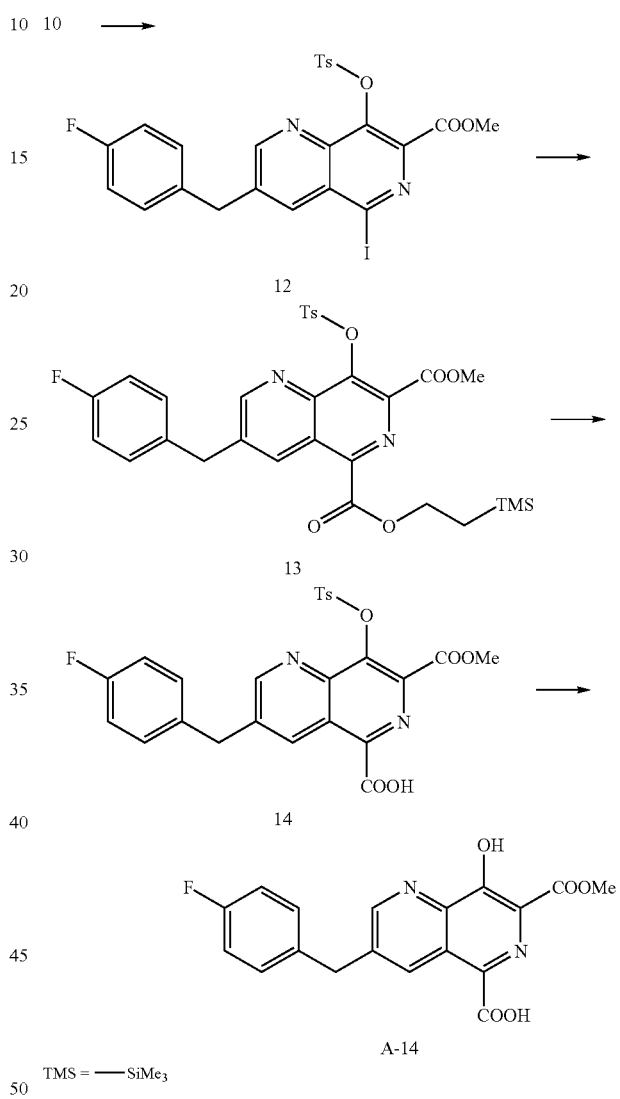

1) To a solution of Compound A-2 (3.56 g, 11.4 mmol) in dimethylformamide (200 ml) was added N-iodosuccinimide (3.06 g, 13.6 mmol) and the mixture was stirred at room temperature overnight. The reaction mixture was concentrated in vacuo and the residue was dissolved in chloroform. The solution was washed with aqueous 10% sodium hydrogen sulfite and water, dried over sodium sulfate, and concentrated. The precipitated crystals were collected by filtration and washed with methanol to give Compound 10 (4.97 g) in 99% yield.

NMR (CDCl$_3$) δ: 4.10 (3H, s), 4.27 (2H, s), 7.03-7.09 (2H, m), 7.18-7.23 (2H, m), 8.10 (1H, m), 8.99 (1H, d, J=1.8 Hz), 11.76 (1H, s).

2) Compound A-13 was synthesized from Compound 10 in a manner similar to that of Example 9; m.p.: 260-264° C.
FABMS: m/z 410 (M+H)$^+$ NMR (CDCl$_3$) δ: 1.99 (4H, brs), 2.53-2.58 (2H, m), 3.41 (1H, brs), 4.08 (3H, s), 4.21 (2H, s), 7.02-7.07 (2H, m), 7.15-7.20 (2H, m), 7.65 (1H, m), 9.01 (1H, d, J=2.1 Hz), 11.84 (1H, s).

Example A-14

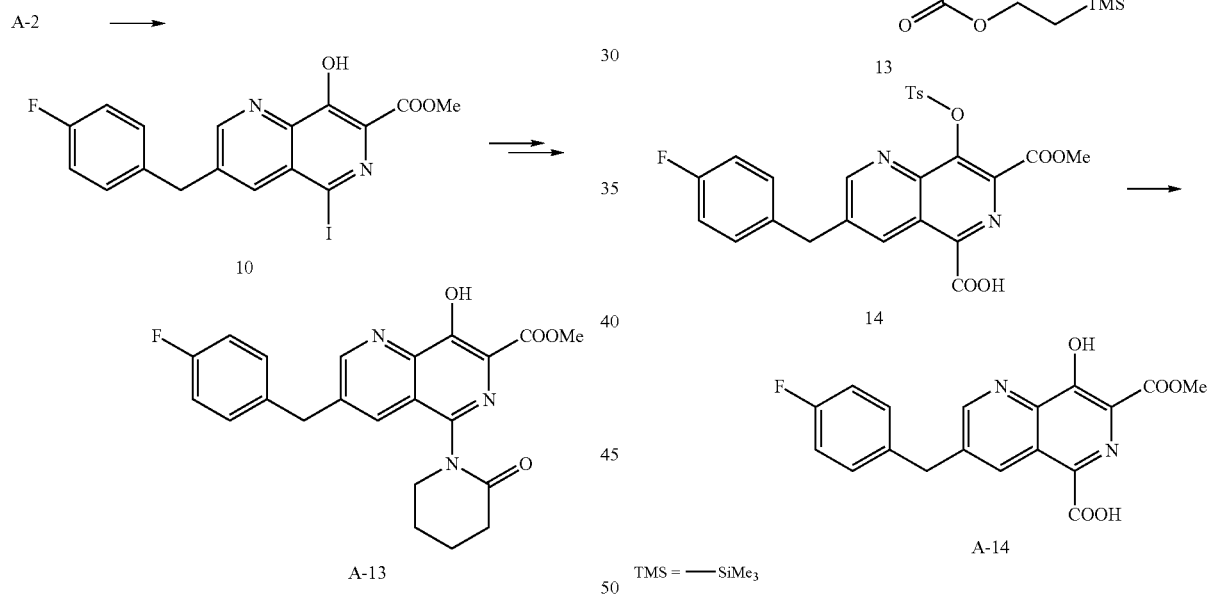

TMS = —SiMe$_3$

Compound A-14: 7-Methyl ester of 3-(4-fluorobenzyl)-8-hydroxy-1,6-naphthylidine-5,7-dicarboxylic acid 1) Compound 12 was synthesized from Compound 10 by a method similar to that of Example A-9, (1).

NMR (CDCl$_3$) □: 2.43 (3H, s), 3.79 (3H, s), 4.22 (2H, s), 7.03-7.08 (2H, m), 7.15-7.20 (2H, m), 7.31 (2H, d, J=7.8 Hz), 7.83 (2H, d, J=8.1 Hz), 8.10 (1H, m), 8.82 (1H, d, J=2.1 Hz).

2) To a solution of Compound 12 (592 mg, 1.0 mmol) in dimethylformamide (12 ml) were added diisopropylethylamine (0.52 ml, 3.0 mmol), 2-(trimethylsilyl)ethanol (1.43 ml, 10 mmol), and palladium acetate (11 mg, 0.05 mmol), and the mixture was stirred under carbon monoxide atmosphere at room temperature for 1 day. The reaction mixture was treated with dilute hydrochloric acid and extracted twice with ethyl acetate. The organic layer was washed twice with water and brine, dried over magnesium sulfate, and concentrated to give a residue, which was purified by silica gel column chromatography to give Compound 13 (490 mg) in 80% yield.

NMR (CDCl$_3$) δ: 0.11 (9H, s), 1.18-1.24 (2H, m), 2.43 (3H, s), 3.83 (3H, s), 4.19 (2H, s), 4.52-4.58 (2H, m), 7.01-7.07 (2H, m), 7.14-7.20 (2H, m), 7.31 (2H, d, J=7.8 Hz), 7.84 (2H, d, J=8.4 Hz), 8.87 (1H, d, J=2.1 Hz), 8.93 (1H, m).

3) To a solution of Compound 13 (480 mg, 0.79 mmol) in tetrahydrofuran (5 ml) was dropwise added 1M-tetrabutylammonium fluoride (1.0 ml) under ice cooling, and the mixture was stirred at room temperature. After 30 minutes, an additional amount of 1M-tetrabutylammonium fluoride (0.8 ml) was added dropwise to the mixture, and the mixture was stirred at room temperature for 30 minutes. The reaction mixture was treated with hydrochloric acid and extracted twice with ethyl acetate. The organic layer was washed with water and brine, dried over sodium sulfate, and concentrated to give Compound 14 (431 mg) as residue.

NMR (CDCl$_3$) δ: 2.43 (3H, s), 3.89 (3H, s), 4.21 (2H, s), 6.99-7.07 (2H, m), 7.13-7.19 (2H, m), 7.30 (2H, d, J=7.8 Hz), 7.81 (2H, d, J=8.7 Hz), 8.84 (1H, d, J=2.1 Hz), 9.66 (1H, m).

4) Compound A-14 was synthesized from Compound 14 by a method similar to that of Example A-9, (3); m.p.: 184-186° C.

Elemental Analysis: C$_{18}$H$_{13}$FN$_2$O$_5$ Calcd. (%): C, 60.68; H, 3.68; N, 7.86. Found (%): C, 60.46; H, 3.53; N, 7.87.

NMR (CDCl$_3$) δ: 4.14 (3H, s), 4.26 (2H, s), 7.00-7.06 (2H, m), 7.18-7.23 (2H, m), 9.09 (1H, d, J=2.1 Hz), 9.70 (1H, m), 11.04 (1H, brs), 12.06 (1H, brs).

Example A-15

Compound A-15: Dimethyl 3-(4-fluorobenzyl)-8-hydroxy-1,6-naphthylidine-5,7-dicarboxylate

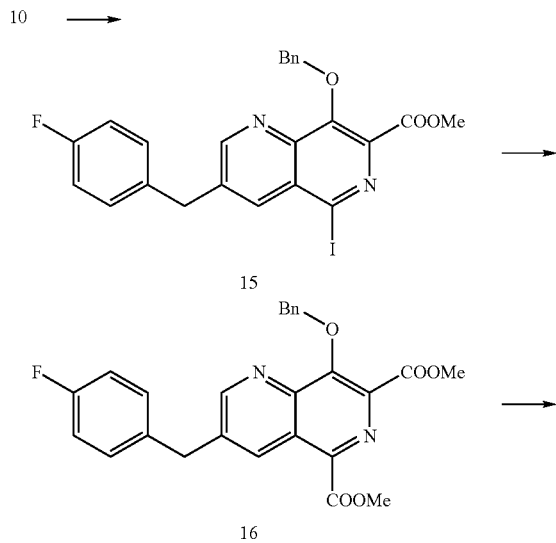

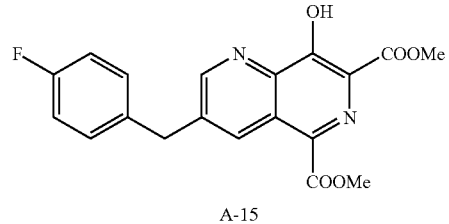

A-15

Bn = —CH$_2$C$_6$H$_5$

1) To a suspension of Compound 10 (8.76 g, 20 mmol) in dimethylformamide (80 ml) were added DBU (4.48 ml, 30 mmol) and benzyl bromide (3.56 ml, 30 mmol), and the mixture was stirred at room temperature for 5 hours. The reaction mixture was treated with aqueous 0.5M-citric acid and 10% sodium hydrogen sulfite, and extracted twice with ethyl acetate. The organic layer was washed with water, aqueous saturated sodium hydrogen carbonate and brine, dried over magnesium sulfate, and concentrated. The residue was purified by silica gel column chromatography. The precipitated crystals were collected by filtration and washed with diisopropyl ether to give Compound 15 (7.64 g) in 72% yield.

NMR (CDCl$_3$) δ: 3.94 (3H, s), 4.26 (2H, s), 5.54 (2H, s), 7.03-7.09 (2H, m), 7.19-7.26 (2H, m), 7.32-7.41 (3H, m), 7.55-7.57 (2H, m), 8.13 (1H, m), 8.97 (1H, d, J=2.1 Hz).

2) To a solution of Compound 15 (264 mg, 0.5 mmol) in dimethylformamide (5 ml) were added diisopropylethylamine (0.44 ml, 2.5 mmol), methanol (0.4 ml, 10 mmol) and palladium acetate (5.6 mg, 0.025 mmol), and the mixture was stirred at room temperature for 2 hours under carbon monoxide atmosphere. The reaction mixture was treated with dilute hydrochloric acid and extracted twice with ethyl acetate. The organic layer was washed twice with water and brine, dried over magnesium sulfate, and concentrated. The residue was purified by silica gel column chromatography and the precipitated crystals were collected by filtration and washed with diisopropyl ether to give Compound 16 (199 mg) in 87% yield.

NMR (CDCl$_3$) δ: 3.96 (3H, s), 4.06 (3H, s), 4.24 (2H, s), 5.70 (2H, s), 7.02-7.08 (2H, m), 7.20-7.25 (2H, m), 7.32-7.40 (3H, m), 7.55-7.57 (2H, m), 9.05 (1H, d, J=2.1 Hz), 9.18 (1H, m).

3) To a solution of Compound 16 (115 mg, 0.25 mmol) in methylene chloride (3 ml) was added trifluoroacetic acid (1 ml) under ice cooling, and the mixture was stirred at room temperature for 2 hours. The solvent was evaporated and the residue was treated with dilute aqueous sodium hydroxide to adjust the pH to 7.2. The mixture was extracted with chloroform and the organic layer was washed with a phosphate buffer of pH7.2. The solvent was evaporated and the precipitated crystals were recrystallized from methanol-chloroform to give Compound A-15 (69 mg) in 74% yield; m.p.: 191-194° C.

Elemental Analysis: C$_{19}$H$_{15}$FN$_2$O$_5$ Calcd. (%): C, 61.62; H, 4.08; N, 7.56. Found (%): C, 61.86; H, 3.92; N, 7.52.

NMR (CDCl$_3$) δ: 4.06 (3H, s), 4.14 (3H, s), 4.25 (2H, s), 7.01-7.07 (2H, m), 7.19-7.24 (2H, m), 9.07 (1H, d, J=2.1 Hz), 9.23 (1H, m), 12.16 (1H, brs).

Example A-16

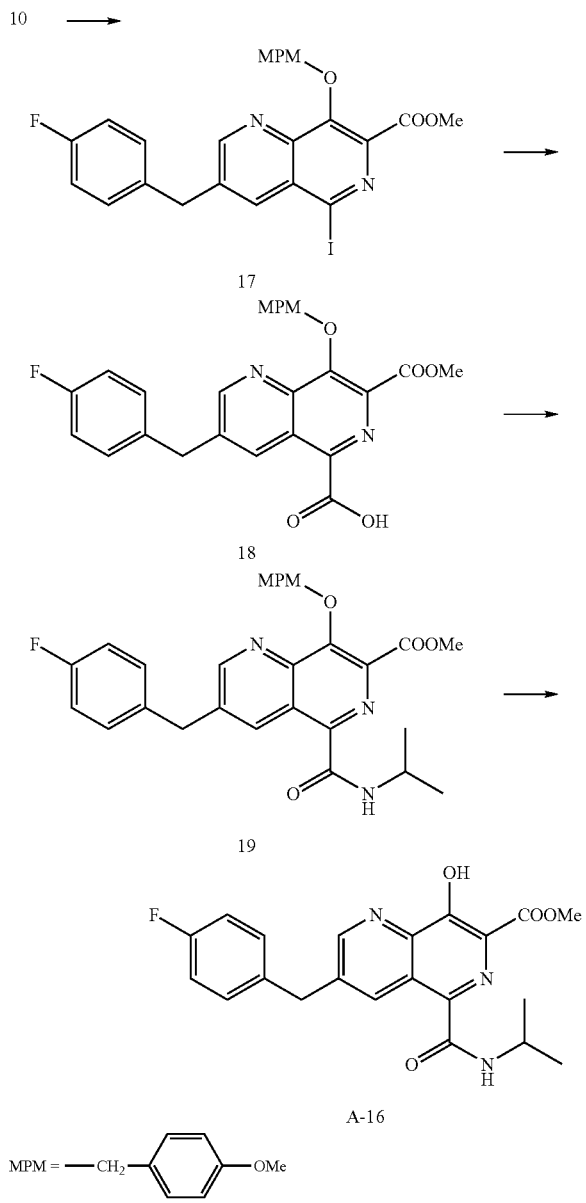

Compound A-16: Methyl 3-(4-fluorobenzyl)-8-hydroxy-5-(isopropylamino)carbonyl-1,6-naphthylidine-7-carboxylate 1) To a solution of Compound 10 (2.32 g, 5.29 mmol) in dimethylformamide (90 ml) were added 4-methoxybenzyl chloride (1.08 ml, 8.0 mmol) and cesium carbonate (2.82 g, 8.0 mmol), and the mixture was heated with stirring at 50° C. overnight. After cooling, the mixture was treated with aqueous ammonium chloride and extracted twice with ethyl acetate. The organic layer was washed twice with water and brine, dried over magnesium sulfate, and concentrated. The precipitated crystals were recrystallized from diisopropyl ether-methanol to give Compound 17 (1.75 g) in 59% yield.

NMR (CDCl$_3$) δ: 3.81 (3H, s), 3.95 (3H, s), 4.26 (2H, s), 5.48 (2H, s), 6.89 (2H, d, J=8.4 Hz), 7.04-7.10 (2H, m), 7.20-7.25 (2H, m), 7.48 (2H, d, J=8.7 Hz), 8.13 (1H, m), 8.98 (1H, d, J=2.4 Hz).

2) Compound 18 was synthesized from Compound 17 according to a method similar to that of (2), (3) in Example A-14.

NMR (CDCl$_3$) δ: 3.81 (3H, s), 3.96 (3H, s), 4.25 (2H, s), 5.76 (2H, s), 6.88 (2H, d, J=8.4 Hz), 7.01-7.07 (2H, m), 7.20-7.25 (2H, m), 7.44 (2H, d, J=8.7 Hz), 9.07 (1H, d, J=2.4 Hz), 9.73 (1H, m), 11.42 (1H, brs).

3) To a solution of Compound 18 (130 mg, 0.27 mmol) in methylene chloride (4 ml) were added diisopropylamine (0.026 ml, 0.3 mmol), WSCD hydrochloride (58 mg, 0.3 mmol) and HOBt (5 mg, 0.03 mmol), and the mixture was stirred at room temperature overnight. The reaction mixture was treated with hydrochloric acid and extracted twice with ethyl acetate. The organic layer was washed with aqueous saturated sodium hydrogen carbonate and brine, dried over magnesium sulfate, and concentrated. The precipitated crystals were washed with methanol to give Compound 19 (120 mg) in 85% yield.

NMR (CDCl$_3$) δ: 1.32 (6H, d, J=6.6 Hz), 3.80 (3H, s), 3.95 (3H, s), 4.20 (2H, s), 4.20-4.33 (1H, m), 5.58 (2H, s), 6.87 (2H, d, J=8.7 Hz), 6.98-7.04 (2H, m), 7.20-7.24 (2H, m), 7.44 (2H, d, J=8.7 Hz), 8.01 (1H, d, J=8.4 Hz), 9.00 (1H, d, J=2.1 Hz), 9.96 (1H, m).

4) Compound A-16 was synthesized from Compound 19 in a manner similar to that of Example A-15, (3); m.p.: 170-172° C.

Elemental Analysis: C$_{21}$H$_{20}$FN$_3$O$_4$ Calcd. (%): C, 63.47; H, 5.07; N, 10.57. Found (%): C, 63.18; H, 5.05; N, 10.52.

NMR (CDCl$_3$) δ: 1.34 (6H, d, J=6.3 Hz), 4.12 (3H, s), 4.21 (2H, s), 4.23-4.37 (1H, m), 6.97-7.03 (2H, m), 7.18-7.23 (2H, m), 7.91 (1H, d, J=8.1 Hz), 9.01 (1H, d, J=2.1 Hz), 9.94 (1H, m), 11.86 (1H, brs).

Example A-17

Compound A-17: Methyl 3-(4-fluorobenzyl)-8-hydroxy-5-(2-methoxyethyl)aminocarbonyl-1,6-naphthylidine-7-carboxylate

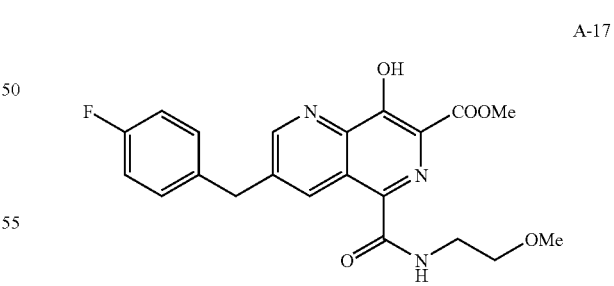

Compound A-17 was synthesized in a manner similar to that of Example A-16; m.p.: 145-146° C.

Elemental Analysis: C$_{21}$H$_{20}$FN$_3$O$_5$ Calcd. (%): C, 61.01; H, 4.88; N, 10.16. Found (%): C, 60.89; H, 4.87; N, 10.26.

NMR (CDCl$_3$) δ: 3.44 (3H, s), 3.61-3.73 (4H, m), 4.12 (3H, s), 4.22 (2H, s), 6.98-7.04 (2H, m), 7.18-7.22 (2H, m), 8.35 (1H, bRt), 9.02 (1H, d, J=2.1 Hz), 9.88 (1H, m), 11.91 (1H, brs).

Example A-18

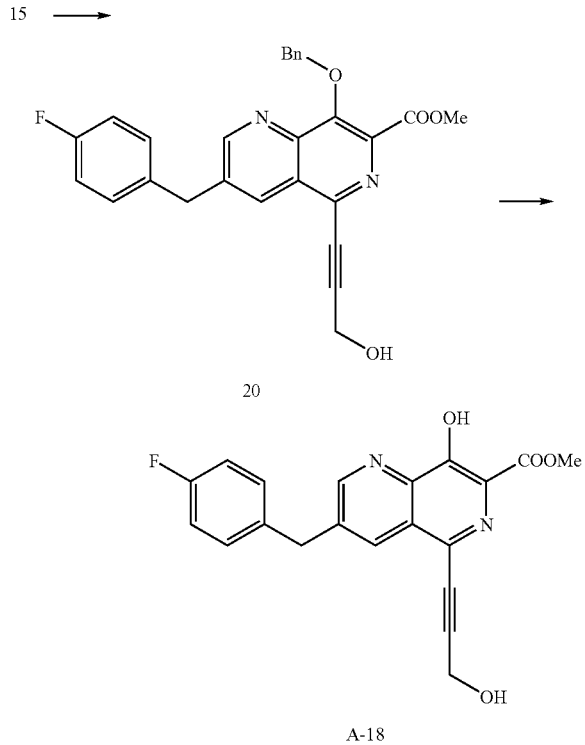

Compound A-18: Methyl 3-(4-fluorobenzyl)-8-hydroxy-5-(3-hydroxy-1-propynyl)-1,6-naphthylidine-7-carboxylate 1) To a solution of Compound 15 (528 mg, 1.0 mmol) in dimethylformamide (10 ml) were added propargyl alcohol (0.087 ml, 1.5 mmol), triethylamine (1.39 ml, 10 mmol), cuprous iodide (9.5 mg, 0.05 mmol) and $PdCl_2(PPh_3)_2$ (35 mg, 0.05 mmol) at room temperature under nitrogen atmosphere, and the mixture was stirred for 30 minutes. The reaction mixture was treated with aqueous 0.5M-citric acid and aqueous 10% sodium hydrogen sulfite, and extracted twice with ethyl acetate. The organic layer was washed with aqueous 0.5M-citric acid and water. After filtration, the mixture was evaporated to remove the solvent and the resulting residue was purified by silica gel column chromatography to give Compound 20 (410 mg) in 90% yield.

NMR (CDCl$_3$) δ: 3.94 (3H, s), 4.24 (2H, s), 4.62 (2H, s), 5.60 (2H, s), 7.02-7.08 (2H, m), 7.18-7.23 (2H, m), 7.32-7.41 (3H, m), 7.55-7.58 (2H, m), 8.39 (1H, m), 9.01 (1H, d, J=2.1 Hz).

2) Compound A-18 was synthesized from Compound 20 in a manner similar to that of Example A-15 (3); m.p.: 205-208° C.

Elemental Analysis: $C_{20}H_{15}FN_2O_4 \cdot 0.1H_2O$ Calcd. (%): C, 65.25; H, 4.16; N, 7.65. Found (%): C, 64.98; H, 3.99; N, 7.69.

NMR (CDCl$_3$) δ: 4.11 (3H, s), 4.25 (2H, s), 4.60 (2H, s), 7.02-7.07 (2H, m), 7.17-7.23 (2H, m), 8.37 (1H, m), 9.04 (1H, d, J=2.1 Hz), 11.97 (1H, s).

Example A-19

Compound A-19: 1-[3-(4-fluorobenzyl)-8-hydroxy-1,6-naphthylidin-7-yl]propan-1-one

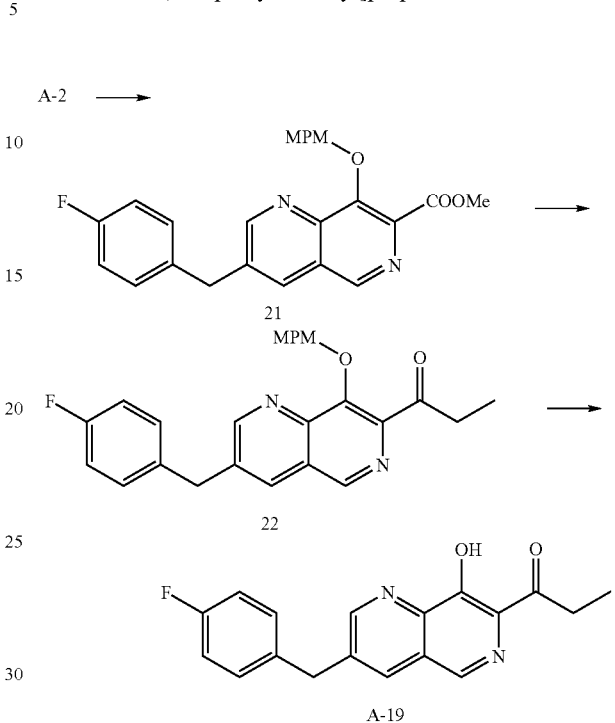

1) Compound 21 was synthesized from Compound A-2 in a manner similar to that of Example A-16 (1)

NMR (CDCl$_3$) δ: 3.81 (3H, s), 3.97 (3H, s), 4.22 (2H, s), 5.52 (2H, s), 6.90 (2H, d, J=9.0 Hz), 7.03-7.08 (2H, m), 7.19-7.23 (2H, m), 7.52 (2H, d, J=8.7 Hz), 8.01 (1H, m), 8.97 (1H, s), 9.07 (1H, d, J=2.1 Hz).

2) To a solution of Compound 21 (303 mg, 0.70 mmol) in tetrahydrofuran (6 ml) was added 1M-ethylmagnesium bromide (0.84 ml) under nitrogen stream under cooling with a dry-ice acetone bath, and the mixture was stirred at the same temperature for 4.5 hours. The reaction mixture was treated with aqueous ammonium chloride and the mixture was extracted twice with ethyl acetate. The organic layer was washed with water and brine, dried over magnesium sulfate, and concentrated to give a residue, which was purified by silica gel column chromatography to give Compound 22 (200 mg) in 66% yield.

NMR (CDCl$_3$) δ: 1.78 (3H, t, J=7.2 Hz), 3.06 (2H, q, J=7.2 Hz), 3.80 (3H, s), 4.22 (2H, s), 5.49 (2H, s), 6.88 (2H, d, J=8.7 Hz), 7.02-7.08 (2H, m), 7.19-7.23 (2H, m), 7.48 (2H, d, J=8.7 Hz), 7.99 (1H, m), 8.93 (1H, s), 9.06 (1H, d, J=2.1 Hz).

3) Compound A-19 was synthesized from Compound 22 in a manner similar to that of Example A-15 (3); m.p.: 159° C.

Elemental Analysis: $C_{18}H_{15}FN_2O_2$ Calcd. (%): C, 69.67; H, 4.87; N, 9.03. Found (%): C, 69.80; H, 4.81; N, 9.02.

NMR (CDCl$_3$) δ: 1.29 (3H, t, J=7.7 Hz), 3.38 (2H, q, J=7.5 Hz), 4.22 (2H, s), 7.02-7.08 (2H, m), 7.17-7.22 (2H, m), 7.95 (1H, m), 8.69 (1H, s), 9.06 (1H, d, J=2.4 Hz), 13.40 (1H, s).

Example A-20

Compound A-20: 3-(4-Fluorobenzyl)-8-hydroxy-1,6-naphthylidine-7-carboxylic acid (2-methoxyethyl) amide

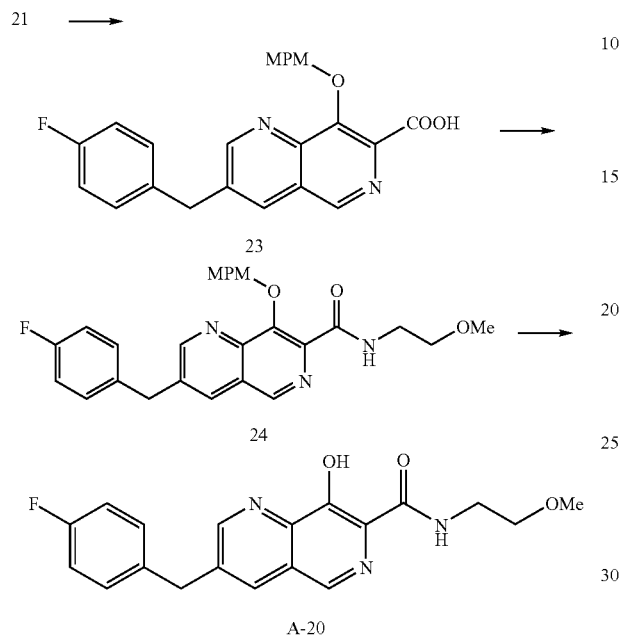

1) To a solution of Compound 21 (310 mg, 0.72 mmol) in tetrahydrofuran-methanol (4 ml) was added aqueous 2N-sodium hydroxide (0.5 ml) under ice cooling, and the mixture was stirred at room temperature for 1 hour. Additional aqueous 2N-sodium hydroxide (0.5 ml) was added, and the mixture was stirred at room temperature for 30 minutes. The reaction mixture was acidified with dilute hydrochloric acid and extracted with chloroform. The organic layer was washed with water, dried over sodium sulfate, and concentrated to give Compound 23 (319 mg) in quantitative yield.

NMR (CDCl$_3$) δ: 3.79 (3H, s), 4.25 (2H, s), 5.70 (2H, s), 6.86 (2H, d, J=8.7 Hz), 7.04-7.10 (2H, m), 7.19-7.24 (2H, m), 7.51 (2H, d, J=8.7 Hz), 8.03 (1H, m), 8.92 (1H, s), 9.12 (1H, d, J=2.1 Hz).

2) Compound 24 was synthesized from Compound 23 in a manner similar to that of Example A-16 (3)

NMR (CDCl$_3$) δ: 3.36 (3H, s), 3.56 (2H, t, J=5.1 Hz), 3.67 (2H, t, J=5.4 Hz), 3.80 (3H, s), 4.20 (2H, s), 5.52 (2H, s), 6.88 (2H, d, J=8.7 Hz), 7.03-7.09 (2H, m), 7.19-7.23 (2H, m), 7.55 (2H, d, J=8.7 Hz), 7.99 (1H, m), 8.20 (1H, brt), 8.96 (1H, s), 9.06 (1H, d, J=2.4 Hz).

3) Compound A-20 was synthesized from Compound 24 in a manner similar to that of Example A-15 (3); m.p.: 147-150° C.

Elemental Analysis: C$_{19}$H$_{18}$FN$_3$O$_3$ Calcd. (%): C, 64.22; H, 5.11; N, 11.82. Found (%): C, 63.82; H, 4.97; N, 11.65.

NMR (CDCl$_3$) δ: 3.43 (3H, s), 3.60-3.73 (4H, m), 4.21 (2H, s), 7.01-7.07 (2H, m), 7.17-7.21 (2H, m), 7.91 (1H, s), 8.34 (1H, brt), 8.57 (1H, s), 9.03 (1H, d, J=2.1 Hz), 13.35 (1H, s).

Example A-21

Compound A-21: Methyl 3-benzyl-5-(1,1-dioxido-1,2-thiazinan-2-yl)-8-hydroxy-1,6-naphthylidine-7-carboxylate

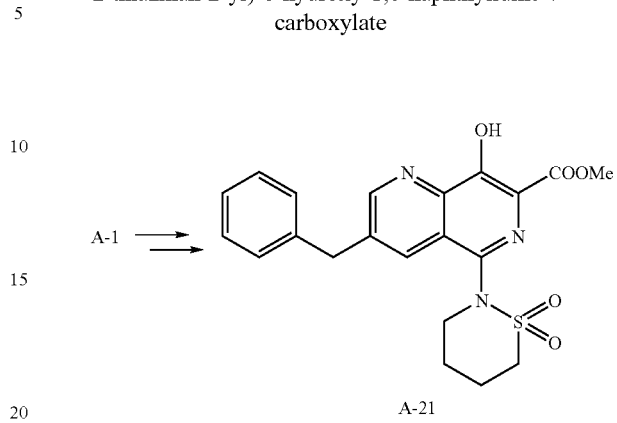

Compound A-21 was synthesized from Compound A-1 in three steps by a method similar to that described in WO 02/30930; m.p.: 186° C.

Elemental Analysis: C$_{21}$H$_{21}$N$_3$O$_5$S Calcd. (%): C, 59.00; H, 4.95; N, 9.80. Found (%): C, 58.85; H, 4.81; N, 9.84.

NMR (CDCl$_3$) δ: 2.41-2.58 (4H, m), 3.19-3.23 (1H, m), 3.65-3.65 (2H, m), 4.07 (3H, s), 4.11-4.19 (1H, m), 4.25 (2H, s), 7.21-7.35 (5H, m), 8.42 (1H, m), 9.02 (1H, d, J=2.1 Hz), 11.71 (1H, s).

Example A-22

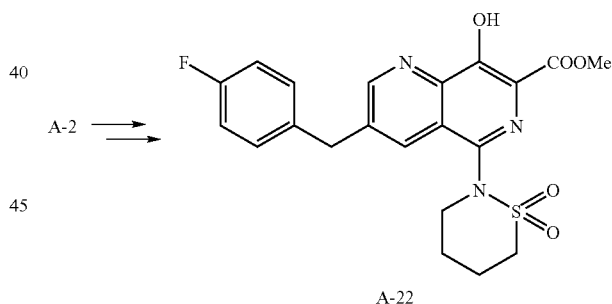

Compound A-22: Methyl 3-(4-fluorobenzyl)-5-(1,1-dioxido-1,2-thiazinan-2-yl)-8-hydroxy-1,6-naphthylidine-7-carboxylate Compound A-21 was synthesized from Compound A-2 in 3 steps by a method similar to that of WO02/30930; m.p.: 183-185° C.

Elemental Analysis: C$_{21}$H$_{20}$N$_3$O$_5$S Calcd. (%): C, 56.62; H, 4.53; N, 9.43; F, 4.26; S, 7.20. Found (%): C, 56.60; H, 4.33; N, 9.28; F, 4.33; S, 7.11.

NMR (CDCl$_3$) δ: 1.60-1.80 (1H, m), 2.30-2.70 (3H, m), 3.10-3.30 (1H, m), 3.50-3.90 (2H, m), 4.08 (3H, s), 4.1-4.3 (1H, m), 4.23 (2H, s), 6.95-7.10 (2H, m), 7.13-7.22 (2H, m), 8.38-8.42 (1H, m), 8.98-9.02 (1H, m), 11.03 (1H, s).

Example A-23

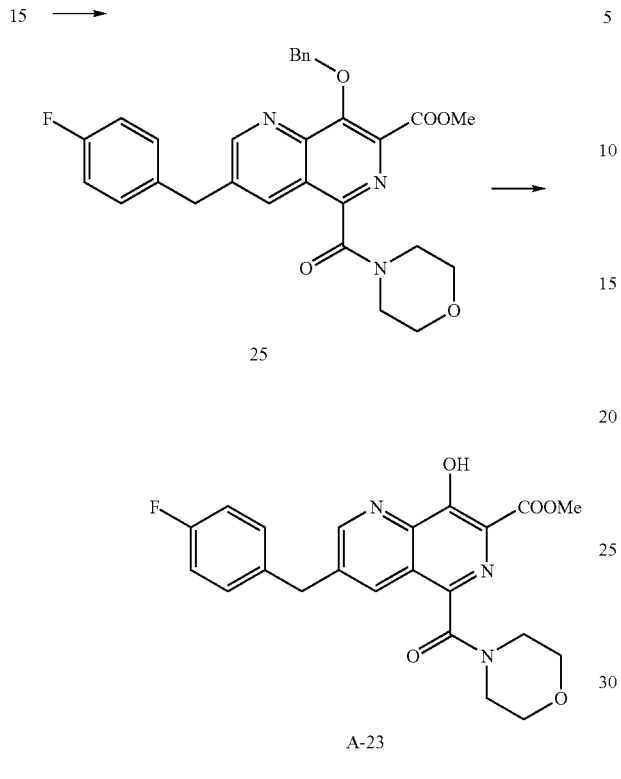

Compound A-22: Methyl 3-(4-fluorobenzyl)-8-hydroxy-5-(morpholinecarbonyl)-1,6-naphthylidine-7-carboxylate 1) To a solution of Compound 15 (264 mg, 0.5 mmol) in dimethyl formamide (5 ml) were added morpholine (0.44 ml, 5.0 mmol) and palladium acetate (11 mg, 0.05 mmol), and the mixture was stirred under carbon monoxide atmosphere at room temperature for 5 hours. The reaction mixture was treated with aqueous 0.5M-citric acid and aqueous 10% sodium hydrogen sulfite, and the mixture was extracted twice with ethyl acetate. The organic layer is washed twice with water, filtered, and concentrated. The precipitated crystals were washed with methanol to give Compound 25 (195 mg) in 76% yield.

NMR (CDCl$_3$) δ: 3.42-3.45 (2H, m), 3.62-3.65 (2H, m), 3.81-3.91 (4H, m), 3.93 (3H, s), 4.20 (2H, s), 5.61 (2H, s), 7.01-7.07 (2H, m), 7.18-7.22 (2H, m), 7.33-7.42 (3H, m), 7.55-7.58 (2H, m), 8.30 (1H, m), 9.03 (1H, d, J=2.4 Hz).

2) Compound A-23 was synthesized in a manner similar to that of Example A-15 (3); m.p.: 235-236° C.

Elemental Analysis: C$_{22}$H$_{20}$FN$_3$O$_5$ Calcd. (%): C, 62.11; H, 4.74; N, 9.88; F, 4.47. Found (%): C, 61.99; H, 4.66; N, 9.90; F, 4.66.

NMR (CDCl$_3$) δ: 3.42-3.46 (2H, m), 3.60-3.63 (2H, m), 3.80-3.83 (2H, m), 3.87-3.90 (2H, m), 4.10 (3H, s), 4.21 (2H, s), 7.00-7.07 (2H, m), 7.15-7.21 (2H, m), 8.28 (1H, s), 9.05 (1H, s), 11.94 (1H, brs).

Example A-24

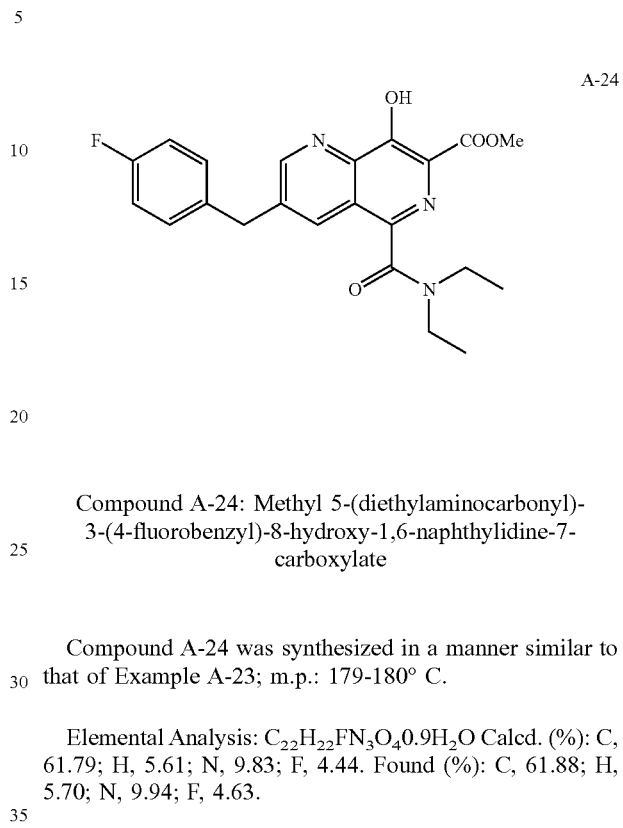

Compound A-24: Methyl 5-(diethylaminocarbonyl)-3-(4-fluorobenzyl)-8-hydroxy-1,6-naphthylidine-7-carboxylate Compound A-24 was synthesized in a manner similar to that of Example A-23; m.p.: 179-180° C.

Elemental Analysis: C$_{22}$H$_{22}$FN$_3$O$_4$·0.9H$_2$O Calcd. (%): C, 61.79; H, 5.61; N, 9.83; F, 4.44. Found (%): C, 61.88; H, 5.70; N, 9.94; F, 4.63.

NMR (CDCl$_3$) δ: 1.13 (3H, t, J=7.2 Hz), 1.27 (3H, t, J=7.2 Hz), 3.17 (2H, q, J=7.2 Hz), 3.61 (2H, q, J=7.2 Hz), 4.09 (3H, s), 4.20 (2H, s), 6.99-7.05 (2H, m), 7.14-7.20 (2H, m), 8.11 (1H, d, J=2.2 Hz), 9.05 (1H, d, J=2.1 Hz), 11.92 (1H, brs).

Example 25

Compound A-25: Methyl 3-(4-fluorobenzyl)-5-(4-fluorophenyl)-8-hydroxy-1,6-naphthylidine-7-carboxylate

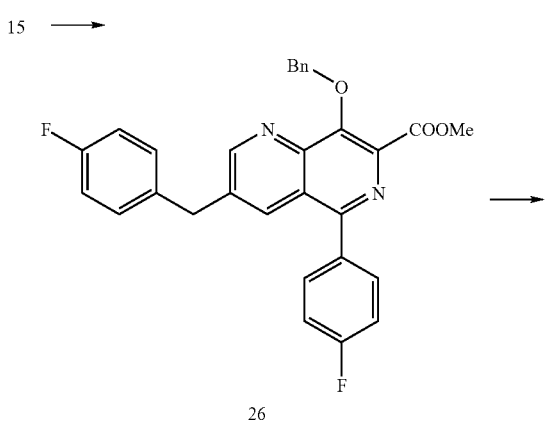

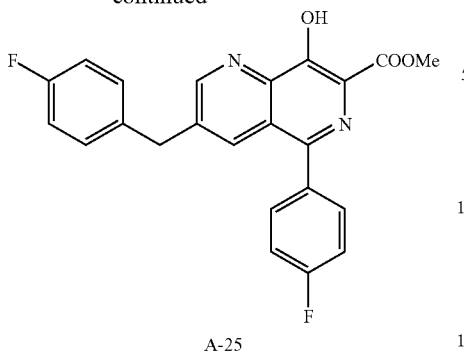

A-25

1) A mixture of compound 15 (264 mg, 0.5 mmol), 4-fluorophenylboronic acid (84 mg, 0.6 mmol), palladium acetate (5.6 mg, 0.025 mmol), xantphos (22 mg, 0.05 mmol), and cesium carbonate (244 mg, 0.75 mmol) in dioxane was heated under reflux for 4 hours. The reaction mixture was treated with aqueous 0.5M-citric acid and extracted twice with ethyl acetate. The organic layer was washed twice with water, filtered and concentrated. The residue was purified by silica gel column chromatography and recrystallization from methanol to give Compound 26 (171 mg) in 69% yield.

NMR (CDCl$_3$) δ: 3.95 (3H, s), 4.16 (2H, s), 5.59 (2H, s), 6.99-7.05 (2H, m), 7.13-7.24 (4H, m), 7.34-7.43 (2H, m), 7.60-7.64 (5H, m), 8.11 (1H, m), 9.04 (1H, d, J=2.1 Hz).

2) Compound A-25 was synthesized from Compound 26 in a manner similar to that of Example A-15 (3); m.p.: 195-196° C.

Elemental Analysis: C$_{23}$H$_{16}$F$_2$N$_2$O$_3$ Calcd. (%): C, 67.98; H, 3.97; N, 6.89; F, 9.35. Found (%): C, 68.06; H, 3.89; N, 7.08; F, 9.68.

NMR (CDCl$_3$) δ: 4.10 (3H, s), 4.16 (21H, s), 6.98-7.03 (2H, m), 7.10-7.23 (4H, m), 7.55-7.59 (2H, m), 8.05 (1H, d, J=2.0 Hz), 9.05 (1H, d, J=2.0 Hz), 11.82 (1H, s).

Example A-26

Compound A-26: Methyl 5-[(dimethylamino)sulfonyl]-amino-3-(4-fluorobenzyl)-8-hydroxy-1,6-naphthylidine-7-carboxylate

15 ⟶

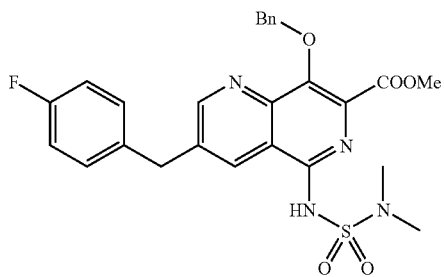

27

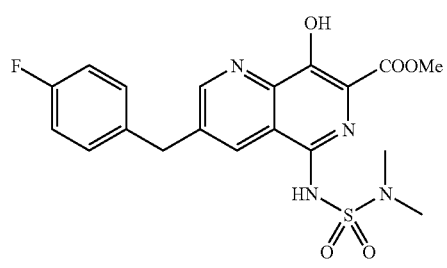

A-26

1) Compound 27 was synthesized from Compound 15 in a manner similar to that of Example A-9 (2).

NMR (CDCl$_3$) δ: 2.84 (6H, s), 3.94 (3H, s), 4.17 (2H, s), 5.33 (2H, s), 7.01-7.07 (2H, m), 7.16-7.21 (2H, m), 7.34-7.42 (3H, m), 7.53-7.55 (2H, m), 8.66 (1H, m), 8.97 (1H, d, J=2.4 Hz), 11.82 (1H, s).

2) Compound A-26 was synthesized from Compound 27 in a manner similar to that of Example A-15 (3); m.p.: 159-160° C.

Elemental Analysis: C$_{19}$H$_{19}$FN$_4$O$_5$S Calcd. (%): C, 52.53; H, 4.41; N, 12.90; F, 4.37; S, 7.38. Found (%): C, 52.56; H, 4.14; N, 12.94; F, 4.50; S, 7.49.

NMR (CDCl$_3$) δ: 2.82 (6H, s), 4.09 (3H, s), 4.17 (2H, s), 7.00-7.07 (2H, m), 7.14-7.19 (2H, m), 8.66 (1H, s), 8.98 (1H, s), 10.30 (1H, s), 11.53 (1H, s).

Example A-27

Compound A-27: 3-(4-fluorobenzyl)-8-hydroxy-5-(methanesulfonylamino)-1,6-naphthylidine-7-carboxylic acid methylamide

15 ⟶

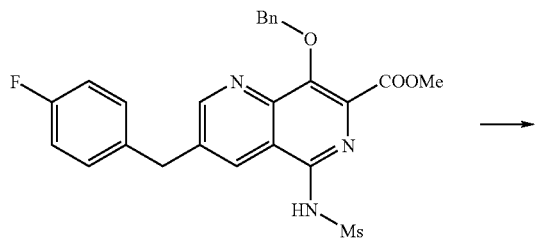

28

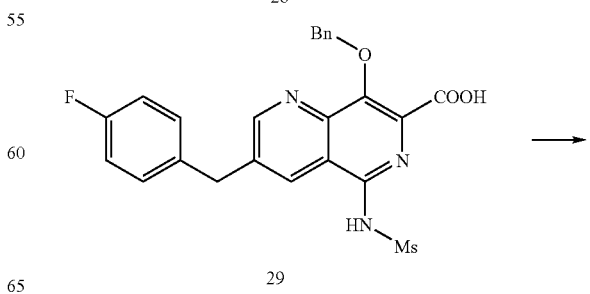

29

-continued

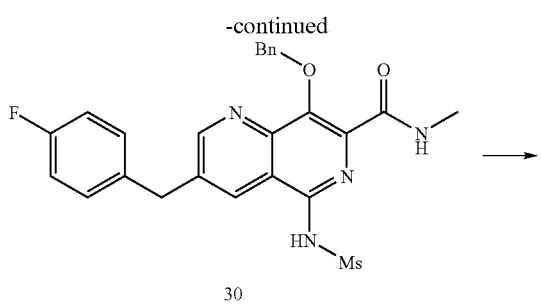

30

1) Compound 28 was synthesized from Compound 15 in a manner similar to that of Example A-9 (2);

NMR (CDCl₃) δ: 3.14 (3H, s), 3.95 (3H, s), 4.17 (2H, s), 5.35 (2H, s), 7.01-7.07 (2H, m), 7.16-7.21 (2H, m), 7.35-7.42 (3H, m), 7.52-7.55 (2H, m), 8.67 (1H, d, J=2.1 Hz), 8.99 (1H, d, J=2.1 Hz), 12.11 (1H, s).

2) To a solution of Compound 28 (1.49 g, 3.0 mmol) in a mixture of methanol, tetrahydrofuran and dimethyl sulfoxide (100 ml) was added 1N-sodium hydroxide (9 ml), and the reaction mixture was stirred overnight. The reaction mixture was concentrated in vacuo, treated with aqueous 0.5M-citric acid and 1N-hydrochloric acid, and extracted twice with ethyl acetate. The organic layer was washed twice with water, dried over sodium sulfate, and concentrated. The precipitated crystals were collected by filtration and washed with diisopropyl ether-acetone to give Compound 29 (1.31 g) in 91% yield.

NMR (CDCl₃) δ: 3.14 (3H, s), 4.19 (2H, s), 5.72 (2H, s), 7.02-7.08 (2H, m), 7.18-7.23 (2H, m), 7.41 (5H, brs), 8.71 (1H, d, J=2.1 Hz), 9.01(1H, d, J=2.1 Hz), 11.99 (1H, brs).

3) Compound 30 was synthesized from Compound 29 in a manner similar to that of Example A-16 (3);

NMR (CDCl₃) δ: 2.78 (3H, d, J=5.0 Hz), 3.12 (3H, s), 4.17 (2H, s), 5.48 (2H, s), 7.01-7.07(2H, m), 7.18-7.22 (2H, m), 7.43 (5H, s), 7.92 (1H, d, J=4.4 Hz), 8.72 (1H, d, J=2.3 Hz), 8.97 (1H, d, J=2.3 Hz), 12.36 (1H, s).

4) Compound A-27 was synthesized from Compound 30 in a manner similar to that of Example A-15 (3); m.p.: 234-235° C.

Elemental Analysis: $C_{18}H_{17}FN_4O_4S$ Calcd. (%): C, 53.46; H, 4.24; N, 13.85; F, 4.70; S, 7.93. Found (%): C, 53.51; H, 4.14; N, 13.87; F, 4.76; S, 7.87.

NMR (DMSO-d₆) δ: 2.95 (3H, d, J=4.9 Hz), 3.43 (3H, s), 4.25 (2H, s), 7.13-7.20 (2H, m), 7.35-7.41 (2H, m), 8.29 (1H, d, J=4.7 Hz), 8.54 (1H, d, J=1.8 Hz), 9.11 (1H, d, J=2.0 Hz), 10.70 (1H, brs), 12.05 (1H, s), 13.55 (1H, s).

Example A-28

Compound A-28: 3-(4-fluorobenzyl)-8-hydroxy-5-methanesulfonylamino-1,6-naphthylidine-7-carboxylic acid (2-methoxyethyl)amide

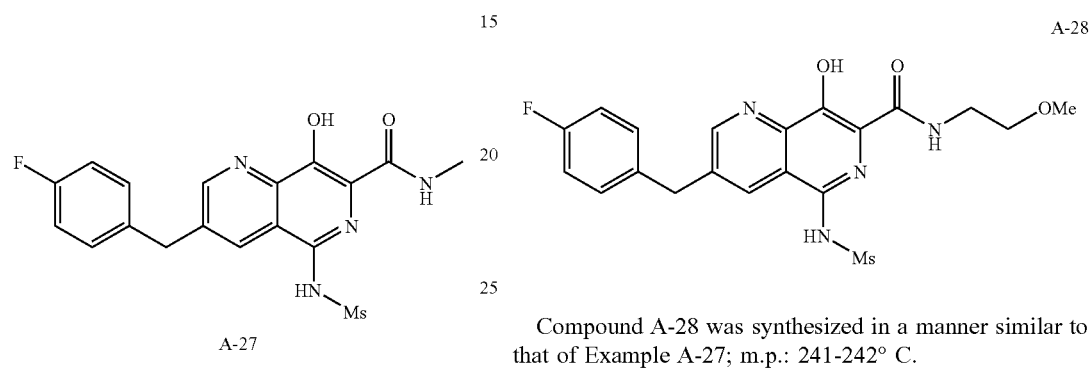

Compound A-28 was synthesized in a manner similar to that of Example A-27; m.p.: 241-242° C.

Elemental Analysis: $C_{20}H_{21}FN_4O_5S$ Calcd. (%): C, 53.56; H, 4.72; N, 12.49; F, 4.24; S, 7.15. Found (%): C, 53.59; H, 4.55; N, 12.55; F, 4.22; S, 7.12.

NMR (DMSO-d₆) δ: 3.33 (3H, s), 3.42 (3H, s), 3.47-3.59 (4H, m), 4.24 (2H, s), 7.13-7.20 (2H, m), 7.35-7.41 (2H, m), 8.26 (1H, t, J=5.5 Hz), 8.58 (1H, d, J=1.8 Hz), 9.12 (1H, d, J=2.0 Hz), 10.78 (1H, s), 13.13 (1H, s).

Example A-29

Compound A-29: 3-(4-fluorobenzyl)-8-hydroxy-5-methanesulfonyl-amino[1,6]naphthylidine-7-carboxylic acid isopropylamide

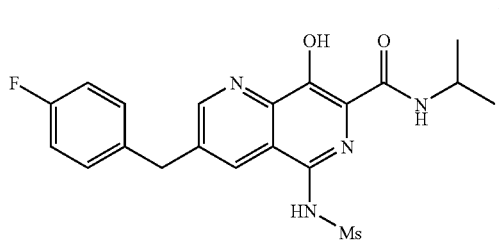

Compound A-29 was synthesized in a manner similar to that of Example A-27; m.p.: 167-168° C.

Elemental Analysis: $C_{20}H_{21}FN_4O_4S$ Calcd. (%): C, 55.54; H, 4.89; N, 12.96; F, 4.39; S, 7.41. Found (%): C, 55.53; H, 4.79; N, 12.87; F, 4.39; S, 7.44.

NMR (DMSO-d₆) δ: 1.26 (6H, d, J=6.6 Hz), 3.39 (3H, s), 4.07-4.17 (1H, m), 4.24 (2H, s), 7.13-7.20 (2H, m), 7.36-7.41 (2H, m), 7.87 (1H, d, J=8.4 Hz), 8.59 (1H, d, J=1.8 Hz), 9.11 (1H, d, J=2.1 Hz), 13.02 (1H, s).

Example A-30 to A-33

According to the method of Example A-26, compounds A-30 to A-33 were synthesized.

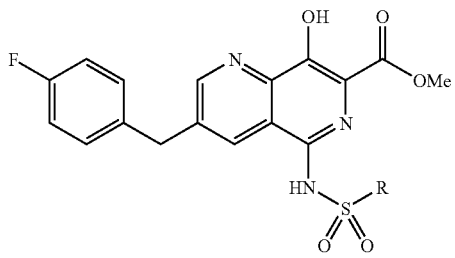

A-30: R = —i-Pr
A-31: R = —C$_6$H$_4$—(4-F)
A-32: R = —Et
A-33: R = —CH$_2$Ph

A-30. 3-(4-Fluorobenzyl)-8-hydroxy-5-(isopropylsulfonyl)amino[1,6]naphthylidine-7-carboxylic acid methyl ester mp: 138-139° C.
Elementary analysis for C$_{20}$H$_{20}$F$_1$N$_3$O$_5$S$_1$ Calculation (%): C, 55.42; H, 4.65; N, 9.69; F, 4.38; S, 7.40. Found (%): C, 55.48; H, 4.41; N, 9.77; F, 4.22; S, 7.21.
NMR(CDCl$_3$)δ: 1.43(6H, d, J=6.9 Hz), 3.30(1H, m), 4.09(3H, s), 4.18(2H, s), 7.00-7.06(2H, m), 7.14-7.19(2H, m), 8.62(1H, d, J=2.3 Hz), 8.99(1H, d, J=2.3 Hz), 10.36(1H, s), 11.87(1H, s).

A-31 3-(4-Fluorobenzyl)-8-hydroxy-5-[(4-fluorophenyl)sulfonyl]amino[1,6]naphthylidine-7-carboxylic acid methyl ester mp: 180-181° C.
Elementary analysis for C$_{23}$H$_{17}$F$_2$N$_3$O$_5$S$_1$ Calculation (%): C, 56.90; H, 3.53; N, 8.66; F, 7.83; S, 6.61. Found (%): C, 56.88; H, 3.38; N, 8.78; F, 7.60; S, 6.37.
NMR(CDCl$_3$)δ: 4.14(3H, s), 4.15(2H, s), 6.99-7.05(2H, m), 7.11-7.20(4H, m), 7.98-8.03(2H, m), 8.64(1H, d, J=2.0 Hz), 8.97(1H, d, J=2.3 Hz), 10.27(1H, s), 11.96(1H, s).

A-32 3-(4-Fluorobenzyl)-8-hydroxy-5-(ethylsulfonyl)amino[1,6]naphthylidine-7-carboxylic acid methyl ester mp: 197-198° C.
Elementary analysis for C$_{19}$H$_{18}$F$_1$N$_3$O$_5$S$_1$ Calculation (%): C, 54.41; H, 4.33; N, 10.02; F, 4.53; S, 7.64. Found (%): C, 54.41; H, 4.03; N, 10.09; F, 4.30; S, 7.45.
NMR(CDCl$_3$)δ: 1.43(3H, t, J=7.3 Hz), 3.20(2H, q, J=7.3 Hz), 4.10(3H, s), 4.17(2H, s), 7.00-7.07(2H, m), 7.14-7.19(2H, m), 8.65(1H, s), 9.00(1H, d, J=2.1 Hz), 10.35(1H, s), 11.87(1H, s).

A-33 3-(4-Fluorobenzyl)-8-hydroxy-5-(benzylsulfonyl)amino[1,6]naphthylidine-7-carboxylic acid methyl ester mp: 203-204° C.
Elementary analysis for C$_{24}$H$_{20}$F$_1$N$_3$O$_5$S$_1$ Calculation (%): C, 59.87; H, 4.19; N, 8.73; F, 3.95; S, 6.66. Found (%): C, 60.00; H, 4.00; N, 8.87; F, 3.77; S, 6.38.
NMR(CDCl$_3$): 4.04(3H, s), 4.18(2H, s), 4.40(2H, s), 7.03-7.34(9H, m), 8.66(1H, d, J=2.3 Hz), 8.99(1H, d, J=2.3 Hz), 10.22(1H, s), 11.44(1H, s).

Example A-34 to A-44

According to the method of Example A-26, compounds A-34 to A-44 were synthesized.

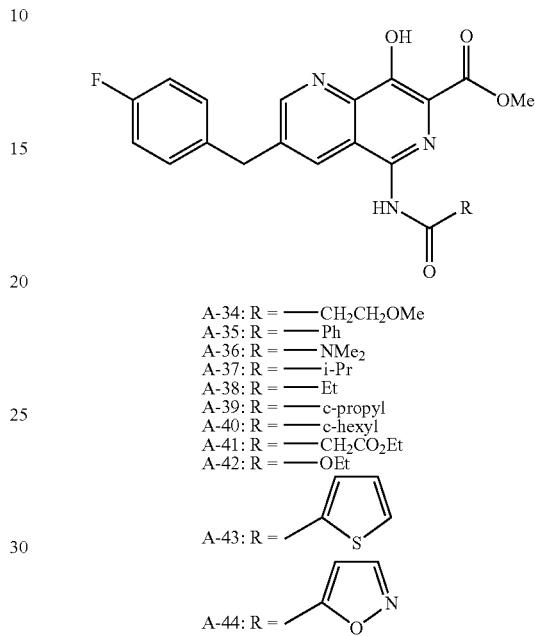

A-34: R = —CH$_2$CH$_2$OMe
A-35: R = —Ph
A-36: R = —NMe$_2$
A-37: R = —i-Pr
A-38: R = —Et
A-39: R = —c-propyl
A-40: R = —c-hexyl
A-41: R = —CH$_2$CO$_2$Et
A-42: R = —OEt A-43: R = thiophenyl A-44: R = isoxazolyl

A-34 3-(4-Fluorobenzyl)-8-hydroxy-5-(3-methoxy-1-propionyl)amino[1,6]naphthylidine-7-carboxylic acid methyl ester mp: 205-206° C.
NMR (CDCl$_3$) δ: 2.72 (2H, t, J=6.0 Hz), 3.42 (3H, s), 3.76 (2H, t, J=6.0 Hz), 4.09 (3H, s), 4.21 (2H, s), 6.98-7.08 (2H, m), 7.15-7.25 (2H, m), 8.00 (1H, s), 8.40 (1H, brs), 9.02 (1H, d, J=2.1 Hz), 11.69 (1H, brs).

A-35 5-Benzoylamino-3-(4-fluorobenzyl)-8-hydroxy[1,6]naphthylidine-7-carboxylic acid methyl ester mp: 209-210° C.
Elementary analysis for C$_{24}$H$_{18}$FN$_3$O$_4$ Calculation (%): C, 66.82; H, 4.21; N, 9.74; F, 4.40. Found (%): C, 66.91; H, 4.17; N, 9.69; F, 4.28.
NMR (CDCl$_3$) δ: 4.10 (3H, s), 4.20 (2H, s), 6.94-7.04 (2H, m), 7.12-7.22 (2H, m), 7.50-7.67 (3H, m), 7.90-8.60 (4H, m), 9.30 (1H, d, J=2.1 Hz), 11.66 (1H, brs).

A-36 5-(3,3-Dimethylureido)-3-(4-fluorobenzyl)-8-hydroxy[1,6]naphthylidine-7-carboxylic acid methyl ester mp: 244-245° C.
Elementary analysis for C$_{20}$H$_{19}$FN$_4$O$_4$ Calculation (%): C, 60.30; H, 4.81; N, 14.06; F, 4.77. Found (%): C, 60.01; H, 4.69; N, 13.76; F, 4.65.
NMR (DMSO-d$_6$) δ: 2.95 (6H, s), 3.92 (3H, s), 4.25 (2H, s), 7.12-7.22 (2H, m), 7.32-7.42 (2H, m), 7.97 (1H, s), 9.05 (1H, d, J=1.8 Hz), 9.06 (1H, s), 11.15 (1H, brs).

A-37 3-(4-Fluorobenzyl)-8-hydroxy-5-isobutylamino[1,6]naphthylidine-7-carboxylic acid methyl ester mp: 248-252° C.

NMR(DMSO-$d_6$)δ: 1.08(3H, d, J=6.9 Hz), 2.69(1H, sep, J=6.9 Hz), 3.92(3H, s), 4.27(2H, s), 7.13-7.20(2H, m), 7.33-7.37(2H, m), 7.73(1H, s), 9.12(1H, s), 10.40(1H, s), 11.26(1H, br s).

A-38 3-(4-Fluorobenzyl)-8-hydroxy-5-propionylamino[1,6]naphthylidine-7-carboxylic acid methyl ester mp: 232-235.5° C.

NMR(DMSO-$d_6$)δ: 1.09(3H, t, J=7.5 Hz), 2.43(2H, q, J=7.5 Hz), 3.92(3H, s), 4.26(2H, s), 7.12-7.19(2H, m), 7.32-7.38(2H, m), 8.01(1H, s), 9.10(1H, s), 10.43(1H, s), 11.23(1H, br s).

A-39 5-[(Cycropropanecarbonyl)amino]-38-(4-fluorobenzyl)-8-hydroxy[1,6]naphthylidine-7-carboxylic acid methyl ester mp: 253-256° C.

NMR(DMSO-$d_6$)δ: 0.75-0.84(4H, m), 1.92(1H, br s), 3.92(3H, s), 4.26(2H, s), 7.12-7.21(2H, m), 7.31-7.38(2H, m), 7.86(1H, s), 9.10(1H, s), 10.77(1H, s), 11.23(1H, br s).

A-40 5-[(Cycrohexanecarbonyl)amino]-3-(4-fluorobenzyl)-8-hydroxy[1,6]naphthylidine-7-carboxylic acid methyl ester mp: 254-258° C.

NMR(CDCl$_3$)δ: 1.24-1.39(3H, m), 1.40-1.55(2H, m), 1.68-1.76(1H, m), 1.80-1.96(4H, m), 2.33(1H, br s), 4.08 (3H, s), 4.21(2H, s), 7.00-7.09(2H, m), 7.16-7.24(2H, m), 7.74(1H, br s), 7.81(1H, br s), 9.05(1H, d, J=2.0 Hz), 11.65(1H, br s).

A-41 5-[[(Ethoxycarbonyl)acetyl]amino]-3-(4-fluorobenzyl)-8-hydroxy[1,6]naphthylidine-7-carboxylic acid methyl ester mp: 208-210.5° C.

NMR(DMSO-$d_6$)δ: 1.21(3H, t, J=7.0 Hz), 3.62(2H, s), 3.93(3H, s), 4.14(2H, q, J=7.0 Hz), 4.24(2H, s), 7.10-7.19 (2H, m), 7.31-7.38(2H, m), 8.28(1H, br s), 9.11(1H, d, J=2.0 Hz), 10.82(1H, s), 11.28(1H, br s).

A-42 5-[(Ethoxycarbonyl)amino]-3-(4-fluorobenzyl)-8-hydroxy[1,6]naphthylidine-7-carboxylic acid methyl ester mp: 247-249° C.

Elementary analysis for $C_{20}H_{18}FN_3O_5$ Calculation (%): C, 60.15; H, 4.54; N, 10.52; F, 4.76. Found (%): C, 60.03; H, 4.50; N, 10.55; F, 4.64.

NMR (DMSO-$d_6$) δ: 1.18 (3H, t, J=7.2 Hz), 3.92 (3H, s), 4.08 (2H, q, J=7.2 Hz), 4.27 (2H, s), 7.11-7.21 (2H, m), 7.32-7.42 (2H, m), 8.15 (1H, s), 9.11 (1H, d, J=1.8 Hz), 9.92 (1H, s), 11.24 (1H, brs).

A-43 3-(4-Fluorobenzyl)-8-hydroxy-5-[(thiophene-2-carbonyl)amino]-[1,6]naphthylidine-7-carboxylic acid methyl ester mp: 204-205° C.

Elementary analysis for $C_{22}H_{16}FN_3O_4S$ Calculation (%): C, 60.40; H, 3.69; N, 9.61; F, 4.34; S, 7.33. Found (%): C, 60.44; H, 3.75; N, 9.57; F, 4.21; S, 7.03.

NMR (DMSO-$d_6$) δ: 3.93 (3H, s), 4.26 (2H, s), 7.06-7.16 (2H, m), 7.25-7.38 (3H, m), 7.93 (1H, d, J=4.8 Hz), 8.12-8.18 (2H, m), 9.11 (1H, d, J=1.8 Hz), 11.04 (1H, s), 11.34 (1H, brs).

A-44 3-(4-Fluorobenzyl)-8-hydroxy-5-[(isoxazole-5-carbonyl)amino]-[1,6]naphthylidine-7-carboxylic acid methyl ester mp: 218-220° C.

Elementary analysis for $C_{21}H_{15}FN_4O_5$ Calculation (%): C, 59.72; H, 3.58; N, 13.26; F, 4.50. Found (%): C, 59.74; H, 3.71; N, 13.02; F, 4.30.

NMR (DMSO-$d_6$) δ: 3.93 (3H, s), 4.26 (2H, s), 7.07-7.17 (2H, m), 7.30-7.40 (3H, m), 8.32 (1H, s), 8.87 (1H, d, J=1.8 Hz), 9.12 (1H, d, J=1.8 Hz), 11.46 (1H, s).

Example A-45 to A-51

According to the method of Example A-18, compounds A-45 to A-51 were synthesized.

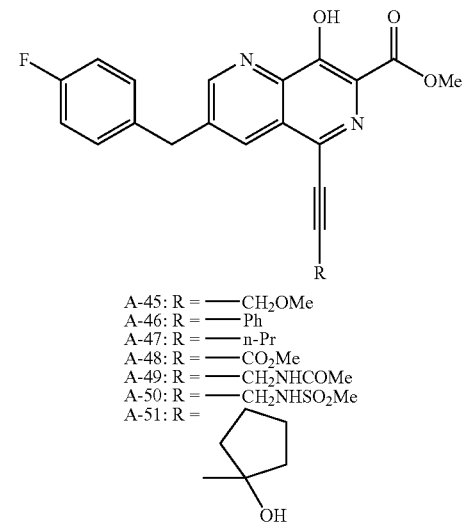

A-45: R = —CH$_2$OMe
A-46: R = —Ph
A-47: R = —n-Pr
A-48: R = —CO$_2$Me
A-49: R = —CH$_2$NHCOMe
A-50: R = —CH$_2$NHSO$_2$Me
A-51: R =

A-45 3-(4-Fluorobenzyl)-8-hydroxy-5-(3-methoxy-1-propynyl)-[1,6]naphthylidine-7-carboxylic acid methyl ester mp: 190-191° C.

Elementary analysis for $C_{21}H_{17}FN_2O_4$ Calculation (%): C, 66.31; H, 4.50; F, 4.99; N, 7.36. Found (%): C, 66.19; H, 4.37; F, 4.82; N, 7.38.

NMR($d_6$-DMSO) δ: 3.34(3H, s), 3.93(3H, s), 4.33(2H, s), 4.46(2H, s), 7.15-7.21(2H, m), 7.37-7.42(2H, m), 8.33(1H, m), 9.15(1H, d, J=2.1 Hz).

A-46 3-(4-Fluorobenzyl)-8-hydroxy-5-(phenylethynyl)-[1,6]-naphthylidine-7-carboxylic acid methyl ester mp: 238-239° C.

Elementary analysis for $C_{25}H_{17}FN_2O_3$ Calculation (%): C, 72.81; H, 4.15; F, 4.61; N, 6.79. Found (%): C, 71.88; H, 4.20; F, 4.60; N, 6.81.

NMR(CDCl$_3$)δ: 4.13(3H, s), 4.30(2H, s), 7.07-7.24(2H, m), 7.24-7.27(3H, m), 7.28-7.51 (4H, m), 8.34(1H, brs), 9.10(1H, d, J=2.1 Hz), 11.99(1H, s).

A-47 3-(4-Fluorobenzyl)-8-hydroxy-5-(pentyn-1-yl)-[1,6]-naphthylidine-7-carboxylic acid methyl ester mp: 197-198° C.

Elementary analysis for $C_{22}H_{19}FN_2O_3$ Calculation (%): C, 69.83; H, 5.06; F, 5.02; N, 7.40. Found (%): C, 69.67; H, 4.89; F, 4.82; N, 7.50.

NMR(CDCl$_3$) δ: 1.04(3H, t, J=7.2 Hz), 1.64(2H, m), 2.48(2H, t, J=7.2 Hz), 4.10(3H, s), 4.25(2H, s), 7.02-7.09 (2H, m), 7.19-7.27(2H, m), 8.28(1H, m), 9.05(1H, d, J=2.1 Hz), 11.89(1H, s).

A-48 3-(4-Fluorobenzyl)-8-hydroxy-5-[(methoxycarbonyl)ethynyl]-[1,6]-naphthylidine-7-carboxylic acid methyl ester mp: 171° C.

Elementary analysis for $C_{21}H_{15}FN_2O_5$ Calculation (%): C, 63.96; H, 3.83; F, 4.82; N, 7.10. Found (%): C, 63.93; H, 3.64; F, 4.69; N, 7.21.

NMR(CDCl$_3$) δ: 3.89(3H, s), 4.13(3H, s), 4.27(2H, s), 7.02-7.09(2H, m), 7.18-7.26(2H, m), 8.34(1H, m), 9.07(1H, d, J=2.1 Hz), 12.16(1H, s).

A-49 5-[3-(Acetylamino)propyn-1-yl]-3-(4-fluorobenzyl)-8-hydroxy[1,6]-naphthylidine-7-carboxylic acid methyl ester mp: 209-211° C.

Elementary analysis for $C_{22}H_{18}FN_3O_4$ Calculation (%): C, 64.86; H, 4.45; F, 4.66; N, 10.31. Found (%): C, 64.61; H, 4.42; F, 4.45; N, 10.38.

NMR(CDCl$_3$) δ: 2.34(3H, s), 4.12(3H, s), 4.21(2H, s), 4.50(2H, s), 6.55(1H, s), 7.05-7.09(2H, m), 7.15-7.27(2H, m), 8.05(1H, m), 9.06(1H, d, J=2.1 Hz), 11.81(1H, s).

A-50 3-(4-Fluorobenzyl)-8-hydroxy-5-[3-(methanesulfonyamino)propyn-1-yl][1,6]naphthylidine-7-carboxylic acid methyl ester mp: 223-225° C.

Elementary analysis for $C_{21}H_{18}FN_3O_5S_1$ Calculation (%): C, 56.88; H, 4.09; F, 4.28; N, 9.48; S, 7.23. Found (%): C, 56.71; H, 4.08; F, 4.21; N, 9.47; S, 7.35.

NMR(DMSO-d$_6$)δ: 3.04(3H, s), 3.93(3H, s), 4.24(2H, d, J=6.0 Hz), 4.30(2H, s), 7.13-7.19(2H, m), 7.37-7.42(2H, m), 7.81(1H, t, J=6.0 Hz), 8.57(1H, d, J=2.1 Hz), 9.13(1H, d, J=2.1 Hz).

A-51 3-(4-Fluorobenzyl)-8-hydroxy-5-[(1-hydroxycyclopentyl)ethynyl][1,6]naphthylidine-7-carboxylic acid methyl ester mp: 215-216° C.

Elementary analysis for $C_{24}H_{21}F_1N_4O_4$ Calculation (%): C, 68.56; H, 5.03; F, 4.52; N, 6.66. Found (%): C, 68.34; H, 4.97; F, 4.38; N, 6.76.

NMR(CDCl$_3$)δ: 1.76-2.05(8H, m), 4.15(3H, s), 4.26(2H, s), 7.03-7.11(2H, m), 7.19-7.27(2H, m), 8.18(1H, d, J=2.3 Hz), 9.07(1H, d, J=2.3 Hz), 11.96(1H, s).

Example A-52 a-15 ⟶

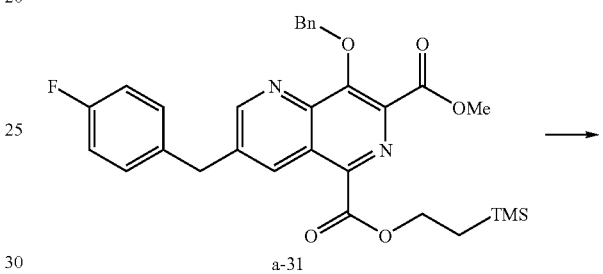

a-31

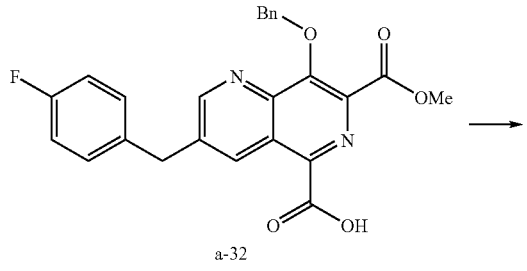

a-32

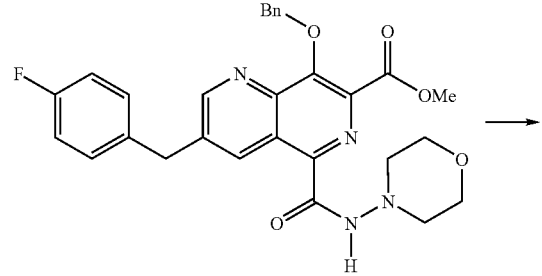

a-33

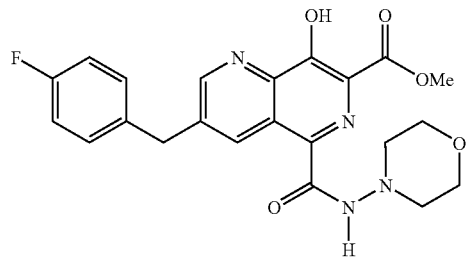

A-52

A-52 3-(4-Fluorobenzyl)-8-hydroxy-5-[(morpholine-4-yl)carbamoyl]-[1,6]naphthylidine-7-carboxylic acid methyl ester 1) According to the method of Example A-14 (2), compound a-31 was synthesized from compound a-15.

NMR (CDCl$_3$) δ: 1.22 (2H, m), 3.95 (3H, s), 4.23 (2H, s), 4.54 (2H, m), 5.67 (2H, s), 7.05 (2H, m), 7.22 (2H, m), 7.32-7.41 (3H, m), 7.54-7.59 (2H, m), 9.03 (1H, d, J=2.4 Hz), 9.08 (1H, m).

2) According to the method of Example A-14 (3), compound a-32 was synthesized from compound a-31.

NMR (CDCl$_3$) δ: 3.96 (3H, s), 4.26 (2H, s), 5.77 (2H, s), 7.04 (2H, m), 7.23 (2H, m), 7.33-7.42 (3H, m), 7.51-7.42 (2H, m), 9.07 (1H, d, J=2.1 Hz), 9.74 (1H, m), 11.4 (1H, s).

3) A solution containing compound a-32 (283 mg, 0.537 mmol), 4-aminomorpholine (0.069 ml, 0.72 mmol), 1-ethyl3-(3-dimethylaminopropyl)carbodiimide hydrochloride (150 mg, 0.783 mmol), and 1-hydroxybenzotoriazole (8 mg, 0.06 mmol) in dichloromethane (5 ml) was stirred at room temperature overnight, to which was added 10% citric acid aq. (10 ml) and the mixture was extracted with ethyl acetate 2 times. The organic layer was washed with citric acid aq. and water, dried over anhydrous sodium sulphate, and evaporated in vacuum. The obtained amorphous residue was purified with column chromatography, then the obtained white solid was washed with diisopropyleter to give compound a-33 as white solid (292 mg).

NMR (CDCl$_3$) δ: 3.01 (4H, t, J=4.5 Hz), 3.90 (4H, t, J=4.5 Hz), 3.95 (3H, s), 4.19 (2H, s), 5.66 (2H, s), 7.01 (2H, m), 7.22 (2H, m), 7.32-7.41 (3H, m), 7.50-7.54 (2H, m), 8.78 (1H, brs), 9.03 (2H, d, J=2.4 Hz), 9.84 (1H, m).

4) According to the method of Example A-15 (3), compound A-52 was synthesized from compound a-33.

mp: 229° C. (decompose)

Elementary analysis for $C_{22}H_{21}FN_4O_5$ Calculation (%): C, 60.00; H, 4.81; F, 4.31; N, 12.72. Found (%): C, 59.74; H, 4.73; F, 4.19; N, 12.45.

NMR (CDCl$_3$) δ: 3.04 (4H, t, J=4.5 Hz), 3.92 (4H, t, J=4.5 Hz), 4.13 (3H, s), 4.20 (2H, s), 7.00 (2H, m), 7.20 (2H, m), 8.73 (1H, brs), 9.04 (1H, d, J=2.1 Hz), 9.81 (1H, m), 11.91 (1H, brs).

Example A-53 to A-58

According to the method of Example A-52, compounds A-53 to A-58 were synthesized.

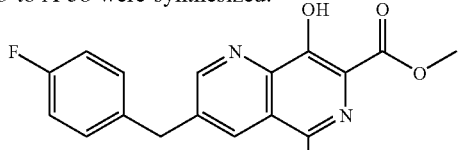

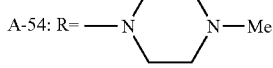
A-53: R = —NHNHCOCH$_3$

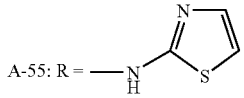
A-54: R = —N〔piperazine〕N—Me

A-55: R = —NH〔thiazole〕

A-56: R = —NHCH$_2$CONMe$_2$
A-57: R = —NH(CH$_2$)$_3$OCOCF$_3$
A-58: R = —NH(CH$_2$)$_3$OH

A-53 5-(N'-Acetyl-hydradinocarbonyl)-3-(4-fluorobenzyl)-8-hydroxy[1,6]naphthylidine-7-carboxylic acid methyl ester mp: 246-248° C.

Elementary analysis for $C_{20}H_{17}FN_4O_5$ Calculation (%): C, 58.25; H, 4.16; F, 4.61; N, 13.59. Found (%): C, 58.15; H, 4.06; F, 4.39; N, 13.45.

NMR (CDCl$_3$) δ: 2.18 (3H, s), 4.11 (3H, s), 4.22 (2H, s), 7.02 (2H, m), 7.20 (2H, m), 7.83 (1H, brd, J=4.5 Hz), 9.04 (1H, d, J=2.4 Hz), 9.64 (1H, m), 9.96 (1H, brd, J=4.5 Hz), 12.03 (1H, s).

A-54. 5-(4-Methylpiperadine-1-carbonyl)-3-(4-fluorobenzyl)-8-hydroxy[1,6]naphthylidine-7-carboxylic acid methyl ester mp: 226-227° C.

Elementary analysis for $C_{23}H_{23}FN_4O_4$ Calculation (%): C, 63.00; H, 5.29; F, 4.33; N, 12.78. Found (%): C, 62.95; H, 5.07; F, 4.19; N, 12.68.

NMR (CDCl$_3$) δ: 2.25 (2H, m), 2.31 (3H, s), 2.50 (2H, m), 3.37 (2H, m), 3.88 (2H, m), 4.10 (3H, s), 4.21 (2H, s), 7.03 (2H, m), 7.18 (2H, m), 8.20 (1H, m), 9.06 (1H, d, J=2.4 Hz), 11.96 (1H, brs).

A-55 5-[(Thiazole-2-yl)aminocarbonyl]-3-(4-fluorobenzyl)-8-hydroxy[1,6]naphthylidine-7-carboxylic acid methyl ester mp: 198° C.

Elementary analysis for $C_{21}H_{15}FN_4O_4S$ Calculation (%): C, 57.53; H, 3.45; F, 4.33; N, 12.78; S, 7.31. Found (%): C, 57.38; H, 3.28; F, 4.22; N, 12.62; S, 7.28.

NMR (CDCl$_3$) δ: 4.16 (3H, s), 4.27 (2H, s), 7.02 (2H, m), 7.10 (1H, d, J=3.5 Hz), 7.21 (2H, m), 7.59 (1H, d, J=3.5 Hz), 9.06 (1H, d, J=2.4 Hz), 9.91 (1H, m), 11.28 (1H, brs), 12.16 (1H, brs).

A-56 5-[[(Dimethylcarbamoyl)methyl]carbamoyl]-3-(4-fluorobenzyl)-8-hydroxy[1,6]naphthylidine-7-carboxylic acid methyl ester mp: 194-196° C.

Elementary analysis for $C_{22}H_{21}FN_4O_5$ Calculation (%): C, 60.00; H, 4.81; F, 4.31; N, 12.72. Found (%): C, 59.93; H, 4.64; F, 4.10; N, 12.49.

NMR (CDCl$_3$) δ: 3.06 (3H, s), 3.08 (3H, s), 4.13 (3H, s), 4.21 (2H, s), 4.29 (2H, d, J=4.5 Hz), 7.02 (2H, m), 7.20 (2H, m), 8.79 (1H, brt, J=4.5 Hz), 9.03 (1H, d, J=2.4 Hz), 9.45 (1H, m), 12.00 (1H, brs).

A-57 5-[3-(2,2,2-Trifluoroacetoxy)propylcarbamoyl]-3-(4-fluorobenzyl)-8-hydroxy[1,6]naphthylidine-7-carboxylic acid methyl ester mp: 133-134° C.

Elementary analysis for $C_{23}H_{19}F_4N_3O_6$ Calculation (%): C, 54.23; H, 3.76; F, 14.92; N, 8.25. Found (%): C, 54.20; H, 3.68; F, 12.62; N, 8.17.

NMR (CDCl$_3$) δ: 2.17 (2H, tt, J=6.3 Hz, 6.3 Hz), 3.64 (2H, dt, J=6.3 Hz, 6.3 Hz), 4.12 (3H, s), 4.22 (2H, s), 4.51 (2H, t, J=6.3 Hz), 7.01 (2H, m), 7.21 (2H, m), 8.26 (1H, brt, J=6.3 Hz), 9.02 (1H, d, J=2.4 Hz), 9.86 (1H, m), 11.88 (1H, brs).

A-58 5-[(3-Hydroxypropyl)carbamoyl]-3-(4-fluorobenzyl)-8-hydroxy[1,6]naphthylidine-7-carboxylic acid methyl ester mp: 184-185° C.

Elementary analysis for $C_{21}H_{20}FN_3O_5$ Calculation (%): C, 61.01; H, 4.88; F, 4.60; N, 10.16. Found (%): C, 60.94; H, 4.88; F, 4.42; N, 10.14.

NMR (CDCl$_3$) δ: 1.88 (2H, tt, J=5.7 Hz, 6.3 Hz), 3.08 (1H, br), 3.68 (2H, dt, J=6.3 Hz, 6.6 Hz), 3.73 (2H, dt, J=5.7 Hz, 5.7 Hz), 4.12 (3H, s), 4.23 (s, 2H), 7.01 (2H, m), 7.20 (2H, m), 8.36 (1H, brt, J=6.6 Hz), 9.02 (1H, d, J=2.1 Hz), 9.88 (1H, m), 11.87 (1H, br).

Example A-59

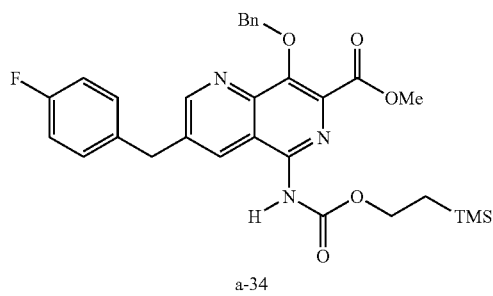

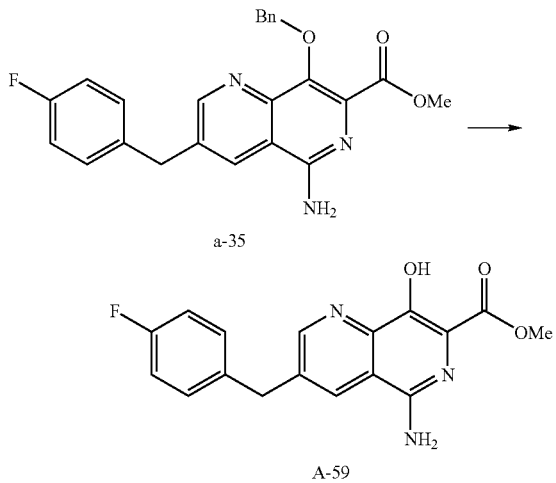

A-59 5-Amino-3-(4-fluorobenzyl)-8-hydroxy[1,6]naphthylidine-7-carboxylic acid methyl ester 1) A solution containing compound a-32 (9.49 g, 21.3 mmol), diphenylphosphoric acid azide (5.72 ml, 25.5 mmol), triethyl amine (4.14 ml, 29.7 mmol), and 2-(trimethylsilyl)etanol (4.26 ml, 29.7 mmol) in tetrahydrofuran (95 ml) was refluxed under heating under N$_2$ atomosphere for 3 hr. The reaction mixture was cooled to room temperature, to which was added 10% citric acid aq. and ethyl acetate and the mixture was extracted with ethyl acetate 3 times. The extract was washed with 10% citric acid aq., saturated sodium hydrogencarbonate aq., and water, dried over anhydrous sodium sulphate, and evapoarted to give crude compound a-34 (14.31 g) as oil, which was used in the next reaction without purification.

2) To a solution of crude compound a-34 (14.31 g) in tetrahydrofuran (95 ml), were added a solution of 1M tetrabutylammonium fluoride in tetrahydrofuran (32 ml) and KF (1.86 g) and the mixture was stirred at room temperature overnight. 10% citric acid aq. and ethyl acetate are added thereto and the mixture was extracted with ethyl acetate 3 times. The extract was washed with 10% citric acid aq., saturated sodium hydrogencarbonate aq., and water, dried over anhydrous sodium sulphated, and evaporated in vacuum. The residue was purified with silica gel column chromatography and recrystallized from ethyl acetate/diisopropyleter to give compound a-35 (7.48 g). Yield: 84% Further obtained was the second crystal 431 mg.

mp: 159-160° C.

NMR (CDCl$_3$) δ:3.91 (3H, s), 4.19 (2H, s), 5.28 (2H, br. s), 5.35 (2H, s), 7.03 (2H, t like, J=8.7 Hz), 7.16-7.24 (2H, m), 7.30-7.40 (3H, m), 7.56-7.63 (2H, m), 7.86 (1H, br.s), 9.01 (1H, d, J=2.1 Hz).

3) According to the method of Example A-15(3), compound A-59 was synthesized from compound a-35.

mp: 198-199° C.

Elementary analysis for $C_{17}H_{14}FN_3O_3$ Calculation (%): C, 62.38; H, 4.31; F, 5.80; N, 12.84. Found (%): C, 62.20; H, 4.36; F, 5.68; N, 12.75.

NMR (CDCl$_3$) δ: 4.07 (3H, s), 4.20 (2H, s), 4.85 (2H, brs), 7.04 (2H, m), 7.18 (2H, m), 7.82 (1H, m), 9.04 (1H, d, J=2.1 Hz), 11.22 (1H, s).

Example A-60

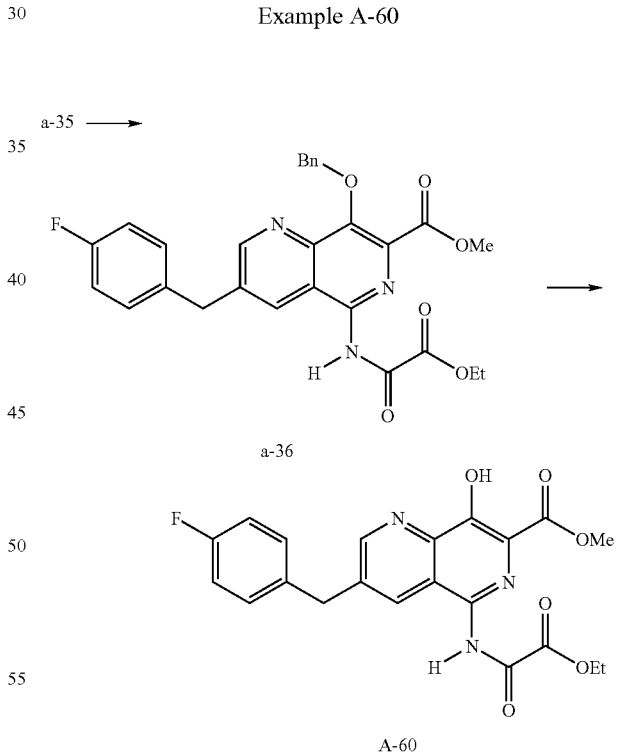

A-60 5-[(Ethoxyoxalyl)amino]-3-(4-fluorobenzyl)-8-hydroxy[1,6]naphthylidine-7-carboxylic acid methyl ester 1) To a solution of compound a-35 (250 mg, 0.60 mmol) and pyridine (0.072 ml) in methylene chloride (3 ml), was added chloroethoxyoxalyl (0.08 ml) under ice-cooling and the mixture was stirred under $N_2$ atomosphere for 40 min. 0.5M citric acid aq. was added thereto and the mixture was extracted with ethyl acetate. The extract was washed with sodium hydrogencarbonate aq. and saturated saline, ried over anhydrous magnesium sulphate, and evaporated in vacuum. The residue was purified with silica gel column chromatography to give compound a-36 (307 mg).
Yield: 99%
NMR(CDCl$_3$)δ: 1.46(3H, t, J=7.1 Hz), 3.94(3H, s), 4.20 (2H, s), 4.48(2H, q, J=7.1 Hz), 5.55(2H, s), 6.98-7.07(2H, m), 7.15-7.23(2H, m), 7.32-7.43(3H, m), 7.55-7.60(2H, m), 8.02(1H, s), 9.02(1H, d, J=2.1 Hz), 9.48(1H, br s).
2) According to the method of Example A-15 (3), compound A-60 was synthesized.
mp: 182-184° C.
NMR(CDCl$_3$)δ: 1.46(3H, t, J=7.2 Hz), 4.11(3H, s), 4.21 (2H, s), 4.47(2H, q, J=7.2 Hz), 6.98-7.06(2H, m), 7.13-7.20(2 h, m), 7.95(1H, d, J=2.0 Hz), 9.03(1H, d, J=2.0 Hz), 9.30(1H, br s).

Example A-61 to A-74

According to the method of Example A-60, compounds A-61 to A-74 were synthesized.

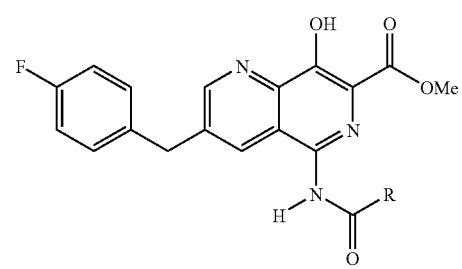

A-61: R = —CH$_2$OMe
A-62: R = —CH$_2$CH$_2$CO$_2$Et
A-64: R = —OMe

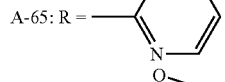

A-65: R =

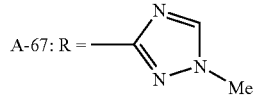

A-66: R =

A-67: R =

A-68: R = —O-i-Pr
A-69: R = —OCH$_2$CH$_2$OMe
A-70: R = —CH$_2$NHCOMe
A-71: R = —CH$_2$NHSO$_2$Me
A-72: R = —CH$_2$CONHMe
A-73: R = —CH$_2$CONMe$_2$
A-74: R = —CH$_2$CONH$_2$

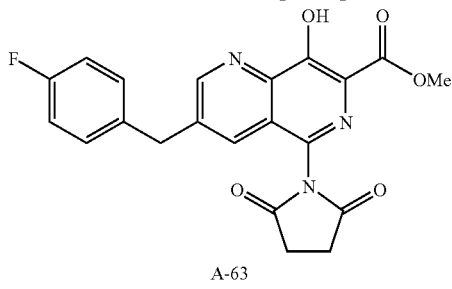

A-63

A-61 3-(4-Fluorobenzyl)-8-hydroxy-5-[(2-methoxyacetyl)amino][1,6]naphthylidine-7-carboxylic acid methyl ester mp: 208-209° C.
NMR(CDCl$_3$)δ: 3.53(3H, s), 4.11(5H, s), 4.21(2H, s), 6.98-7.06(2H, m), 7.14-7.21(2H, m), 7.97(1H, s), 8.81(1H, br s), 9.02(1H, d, J=2.0 Hz), 11.70(1H, br s).

A-62 5-[[3-(Ethoxycarbonyl)propionyl]amino]-3-(4-fluorobenzyl)-8-hydroxy[1,6]naphthylidine-7-carboxylic acid methyl ester mp: 214-215° C.
NMR(DMSO-d$_6$)δ: 1.18(3H, t, J=7.1 Hz), 2.60-2.67(2H, m), 2.69-2.76(2H, m), 3.92(3H, s), 4.07(2H, q, J=7.1 Hz), 4.22(2H, s), 7.10-7.18(2H, m), 7.31-7.38(2H, m), 8.18(1H, s), 9.09(1H, d, J=2.0 Hz), 10.63(1H, s), 11.24(1H, br s).

A-63 5-(2,5-Dioxopyrrolidine-1-yl)-3-(4-fluorobenzyl)-8-hydroxy[1,6]naphthylidine-7-carboxylic acid methyl ester mp: 214-125° C.
NMR(DMSO-d$_6$)δ: 3.00(4H, d, J=1.7 Hz), 3.93(3H, s), 4.25(2H, s), 7.11-7.19(2H, m), 7.29-7.36(2H, m), 8.48(1H, d, J=2.0 Hz), 9.13(1H, d, J=2.0 Hz), 11.69(1H, br s).

A-64 3-(4-Fluorobenzyl)-8-hydroxy-5-[(methoxycarbonyl)amino][1,6]naphthylidine-7-carboxylic acid methyl ester mp: 253-255° C.
Elementary analysis for $C_{19}H_{16}FN_3O_5$ Calculation (%): C, 59.22; H, 4.19; N, 10.90; F, 4.93. Found (%): C, 59.06; H, 4.03; N, 10.89; F, 4.78.
NMR (DMSO-d$_6$) δ: 3.63 (3H, s), 3.91 (3H, s), 4.27 (2H, s), 7.10-7.20 (2H, m), 7.32-7.42 (2H, m), 8.21 (1H, s), 9.10 (1H, d, J=2.1 Hz), 9.98 (1H, s), 11.25 (1H, brs).

A-65 3-(4-Fluorobenzyl)-8-hydroxy-5-(pyrimidine-2-carbonyl)amino[1,6]naphthylidine-7-carboxylic acid methyl ester mp: 236-237° C.
Elementary analysis for $C_{22}H_{16}FN_5O_4$ Calculation (%): C, 60.97; H, 3.72; N, 16.16; F, 4.38. Found (%): C, 61.04; H, 3.61; N, 16.09; F, 4.16.
NMR (DMSO-d$_6$) δ: 3.91 (3H, s), 4.26 (2H, s), 7.06-7.16 (2H, m), 7.30-7.40 (2H, m), 7.75-7.80 (1H, m), 8.30 (1H, s), 9.05 (2H, d, J=5.1 Hz), 9.12 (1H, d, J=1.8 Hz), 11.16 (1H, s), 11.18 (1H, brs).

A-66 3-(4-Fluorobenzyl)-5-(frane-2-carbonyl)amino-8-hydroxy[1,6]naphthylidine-7-carboxylic acid methyl ester mp: 200-202° C.
Elementary analysis for $C_{22}H_{16}FN_3O_5 \cdot 0.5H_2O$ Calculation (%): C, 61.40; H, 3.98; N, 9.76; F, 4.41. Found (%): C, 61.28; H, 3.76; N, 9.93; F, 4.24.
NMR (DMSO-d$_6$) δ: 3.93 (3H, s), 4.26 (2H, s), 7.06-7.16 (2H, m), 7.28-7.38 (2H, m), 7.47 (1H, d, J=3.3 Hz), 7.98 (1H, d, J=1.5 Hz), 8.19 (1H, d, J=2.1 Hz), 9.10 (1H, d, J=2.1 Hz), 10.87 (1H, s), 11.32 (1H, brs).

A-67 3-(4-Fluorobenzyl)-8-hydroxy-5-(1-methyl-1H-[1,2,4]-triazole-3-carbonyl)amino[1,6]naphthylidine-7-carboxylic acid methyl ester mp: 214-215° C.
Elementary analysis for $C_{21}H_{17}FN_6O_4 \cdot 0.6H_2O$ Calculation (%): C, 56.36; H, 4.19; N, 18.60; F, 4.20. Found (%): C, 56.35; H, 4.11; N, 18.65; F, 4.06.
NMR (DMSO-$d_6$) δ: 3.92 (3H, s), 4.01 (3H, s), 4.26 (2H, s), 7.07-7.17 (2H, m), 7.28-7.38 (2H, m), 8.19 (1H, d, J=2.1 Hz), 8.71 (1H, s), 9.11 (1H, d, J=2.1 Hz), 10.77 (1H, s), 11.28 (1H, brs).

A-68 3-(4-Fluorobenzyl)-8-hydroxy-5-[(isopropoxycarbonyl)amino][1,6]naphthylidine-7-carboxylic acid methyl ester mp: 257-258° C.
Elementary analysis for $C_{21}H_{20}FN_3O_5$ Calculation (%): C, 61.01; H, 4.88; N, 10.16; F, 4.60. Found (%): C, 60.98; H, 5.15; N, 10.17; F, 4.43.
NMR (DMSO-$d_6$) δ: 1.19 (1H, d, J=6.3 Hz), 3.91 (3H, s), 4.28 (2H, s), 4.75-4.86 (1H, m), 7.10-7.20 (2H, m), 7.32-7.42 (2H, m), 8.05 (1H, d, J=2.1 Hz), 9.11 (1H, d, J=2.1 Hz), 9.82 (1H, s), 11.25 (1H, brs).

A-69. 3-(4-Fluorobenzyl)-8-hydroxy-5-[[(2-methoxyethoxy)carbonyl]amino][1,6]naphthylidine-7-carboxylic acid methyl ester mp: 246-247° C.
Elementary analysis for $C_{21}H_{20}FN_3O_6$ Calculation (%): C, 58.74; H, 4.69; N, 9.79; F, 4.42. Found (%): C, 58.69; H, 4.69; N, 9.70; F, 4.26.
NMR (CDCl$_3$) δ: 3.41 (3H, s), 3.57-3.65 (2H, m), 4.10 (3H, s), 4.21 (2H, s), 4.27-4.35 (2H, m), 6.98-7.08 (2H, m), 7.14-7.24 (2H, m), 8.08 (1H, s), 9.02 (1H, d, J=2.4 Hz), 11.67 (1H, s).

A-70 5-[[2-(Acetylamino)acetyl]amino]-3-(4-fluorobenzyl)-8-hydroxy[1,6]naphthylidine-7-carboxylic acid methyl ester mp: 254-256° C.
NMR(DMSO-$d_6$) δ: 1.92(3H, s), 3.93(3H, s), 3.99(2H, d, J=5.6 Hz), 4.21(2H, s), 7.09-7.18(2H, m), 7.33-7.40(2H, m), 8.27-8.34(2H, m), 9.10(1H, d, J=1.9 Hz), 10.58(1H, s), 11.26(1H, s).

A-71 3-(4-Fluorobenzyl)-8-hydroxy-5-[[2-(methanesulfonyamino)acetyl]amino][1,6]naphthylidine-7-carboxylic acid methyl ester mp: 204-205° C.
NMR(DMSO-$d_6$)δ: 3.00(3H, s), 3.92(3H, s), 4.04(2H, d, J=5.9 Hz), 4.22(2H, s), 7.09-7.17(2H, m), 7.32-7.38(2H, m), 7.53(1H, t, J=5.9 Hz), 8.30(1H, s), 9.10(1H, d, J=2.2 Hz), 10.66(1H, s), 11.26(1H, br s).

A-72 3-(4-Fluorobenzyl)-8-hydroxy-5-[[2-(methylcarbamoyl)acetyl]amino][1,6]naphthylidine-7-carboxylic acid methyl ester mp: 249-250° C.
NMR(DMSO-$d_6$)δ: 2.66(3H, d, J=4.4 Hz), 3.37(2H, s), 3.93(3H, s), 4.21(2H, s), 7.08-7.16(2H, m), 7.33-7.39(2H, m), 8.06-8.09(1H, m), 8.41(1H, s), 9.09(1H, d, J=1.9 Hz), 10.67(1H, s), 11.27(1H, br s).

A-73 5-[[2-(Dimethylcarbamoyl)acetyl]amino]-3-(4-fluorobenzyl)-8-hydroxy[1,6]naphthylidine7-carboxylic acidmethyl mp: 239-241° C.
NMR(DMSO-$d_6$)δ: 2.89(3H, s), 3.02(3H, s), 3.62(2H, s), 3.92(3H, s), 4.21(2H, s), 7.09-7.17(2H, m), 7.33-7.42(2H, m), 8.54(1H, s), 9.10(1H, s), 10.66(1H, s), 11.25(1H, br s).

A-74 5-[[2-(Carbamoyl)acetyl]amino]-3-(4-fluorobenzyl)-8-hydroxy[1,6]naphthylidine-7-carboxylic acid methyl ester mp: 224-226° C.
NMR(DMSO-$d_6$)δ 3.37(2H, s), 3.93(3H, s), 4.20(2H, s), 7.09-7.18(2H, m), 7.21(1H, s), 7.33-7.40(2H, m), 7.60(1H, s), 8.47(1H, s), 9.10(1H, s), 10.66(1H, s), 11.26(1H, s).

Example A-75

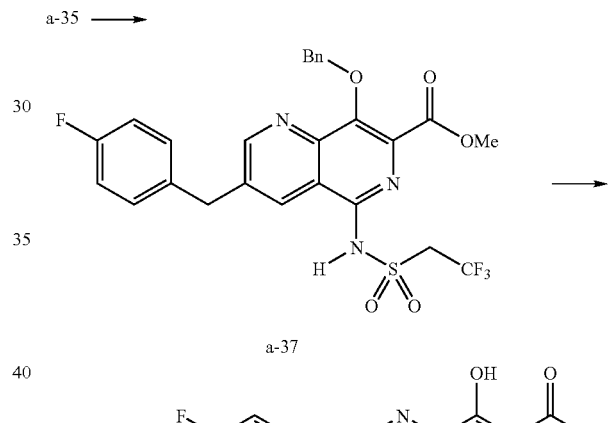

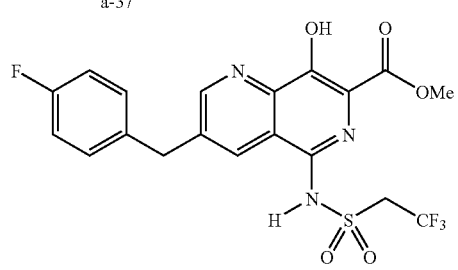

A-75

A-75 3-(4-Fluorobenzyl)-8-hydroxy5-[(1,1,1-trifluoroethyl)sulfonylamino]-[1,6]naphthylidine-7-carboxylic acid methyl ester 1) To a solution of compound a-35 (300 mg, 0.72 mmol) and triethylamine (182 mg, 1.8 mmol) in methylene chloride (3 ml), was added ice-cooled 2,2,2-trifluoroethane sulfonyl chloride (328 mg, 1.8 mmol) and the mixture was stirred under $N_2$ atomosphere for 40 min. 0.5M citric acid aq. was added therto and the mixture was extracted with chloroform. The extract was washed with water, dried over anhydrous magnesium sulphate, and evaporated in vacuum. The residue was purified with silica gel column chromatography to give compound a-37 (278 mg).

Yield: 69%

NMR (CDCl₃) δ: 3.95(2H, dd, J=9.2, 18.2 Hz), 3.96(3H, s), 4.19(2H, s), 5.39(2H, s), 7.02-7.06(2H, m), 7.17-7.26 (2H, m), 7.35-7.43(3H, m), 7.50-7.54(2H, m), 8.67(1H, d, J=2.3 Hz), 9.04(1H, d, J=2.3 Hz), 12.20(1H, s).

2) According to the method of Example A-15 (3), compound A-75 was synthesized from compound a-37.

mp: 219-220° C.

Elementary analysis for $C_{19}H_{15}F_4N_3O_5S_1 \cdot 0.2H_2O$ Calculation (%): C, 47.84; H, 3.25; N, 8.81; F, 15.93; S, 6.72. Found (%): C, 48.22; H, 3.10; N, 9.00; F, 15.53; S, 6.60.

NMR (CDCl₃) δ: 3.95(2H, dd, J=9.0, 18.0 Hz), 4.12(3H, s), 4.19(2H, s), 7.01-7.07(2H, m), 7.14-7.19(2H, m), 8.66 (1H, d, J=2.3 Hz), 9.04(1H, d, J=2.3 Hz), 10.36(1H, s), 11.94(1H, s).

Example A-76 to A-78

According to the method of Example A-75, compounds A-76 to A-78 were synthesized.

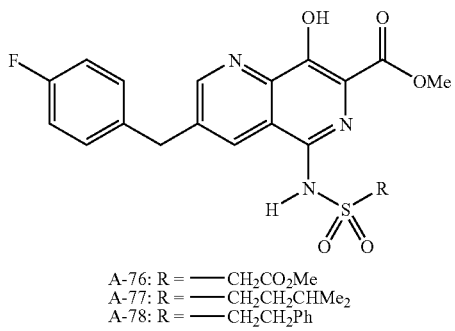

A-76: R = —CH₂CO₂Me
A-77: R = —CH₂CH₂CHMe₂
A-78: R = —CH₂CH₂Ph

A-76 3-(4-Fluorobenzyl)-8-hydroxy-5-[[(methoxycarbonyl)methanesulfonyl]amino][1,6]naphthylidine-7-carboxylic acid methyl ester mp: 197-199° C.

Elementary analysis for $C_{20}H_{18}F_1N_3O_7S_1$ Calculation (%): C, 51.83; H, 3.91; N, 9.07; F, 4.10; S, 6.92. Found (%): C, 51.91; H, 4.14; N, 9.10; F, 3.95; S, 6.97.

NMR (CDCl₃) δ: 3.68 (3H, s), 4.11 (3H, s), 4.18 (2H, s), 4.20 (2H, s), 7.00-7.07 (2H, m), 7.15-7.19 (2H, m), 8.68 (1H, s), 9.02 1H, d, J=2.0 Hz), 10.37 (1H, brs), 12.00 (1H, brs).

A-77 3-(4-Fluorobenzyl)-8-hydroxy-5-[[(3-methylbutane)-1-sulfonyl]amino]-[1,6]naphthylidine-7-carboxylic acid methyl ester mp: 171-173° C.

Elementary analysis for $C_{22}H_{24}F_1N_3O_5S_1$ Calculation (%): C, 57.25; H, 5.24; N, 9.10; F, 4.12; S, 6.95. Found (%): C, 57.36; H, 5.55; N, 9.14; F, 4.02; S, 7.22.

NMR (CDCl₃) δ: 0.92 6H, d, J=6.4 Hz), 1.67-1.73 (3H, m), 3.15-3.20 (2H, m), 4.09 (3H, s), 4.18 (2H, s), 7.00-7.06 (2H, m), 7.14-7.19 (2H, m), 8.62 (1H, s), 9.00 (1H, d, J=2.3 Hz), 10.35 (1H, brs), 11.84 (1H, brs).

A-78 3-(4-Fluorobenzyl)-8-hydroxy-5-[(2-phenylethane)sulfonylamino]-[1,6]naphthylidine-7-carboxylic acid methyl ester mp: 185-187° C.

Elementary analysis for $C_{25}H_{22}F_1N_3O_5S_1$ Calculation (%): C, 60.60; H, 4.48; N, 8.48; F, 3.83; S, 6.47. Found (%): C, 60.61; H, 4.77; N, 8.50; F, 3.72; S, 6.47.

NMR (CDCl₃) δ: 3.17-3.23 (2H, m), 3.48-3.52 (2H, m), 4.11 (3H, s), 4.15 (2H, s), 7.00-7.20 (9H, m), 8.49 (1H, s), 8.98 (1H, d, J=2.0 Hz), 10.33 (1H, brs), 11.84 (1H, brs).

Example A-79

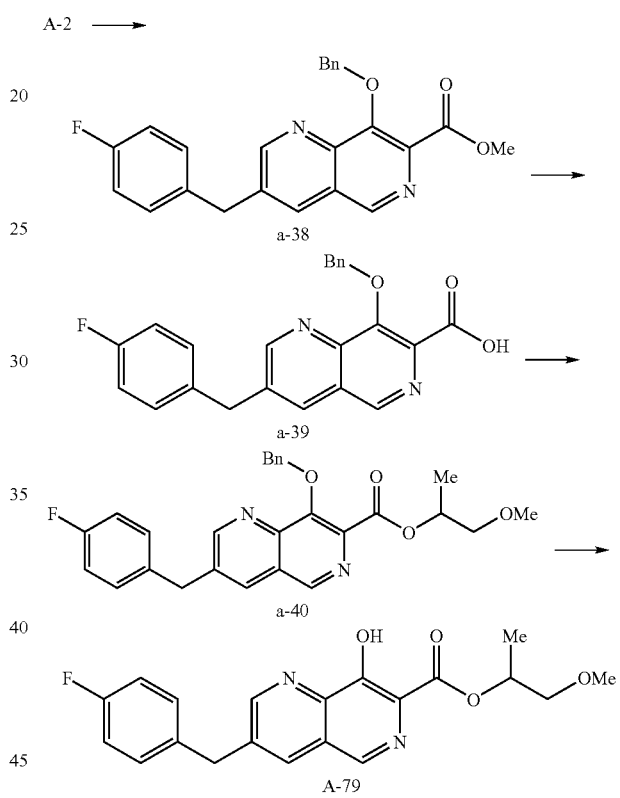

A-79 3-(4-Fluorobenzyl)-8-hydroxy[1,6]naphthylidine-7-carboxylic acid [2-(1-methoxy)propyl]ester 1) To a solution of compound A-2 (5.00 g, 16.0 mmol), benzyl alcohol (1.99 ml), and triphenylphosphine (5.04 g) in tetrahydrofuran (50 ml), was added dropwise an ice-cooled solution of diisopropyl azodicarboxylate in 40% toluene (10.4 ml) under N₂ atomsphere and the mixture was stirred at the same temperature for 20 min. While warming to room temperature, the mixture was further stirred for 2 hr and 45 min, then evaporated in vacuum. The residue was crystallized from methanol (40 ml)/water (10 ml) to give compound a-38 (4.83 g). Yield: 75% mp: 97-98° C.

NMR (CDCl₃) δ: 3.97 (3H, s), 4.22 (2H, s), 5.59 (2H, s), 7.06 (2H, t like, J=8.7 Hz), 7.18-7.28 (2H, m), 7.33-7.43 (2H, m), 7.58-7.64 (2H, m), 8.02 (1H, d, J=2.4 Hz), 8.99 (1H, s), 9.07 (1H, d, J=2.4 Hz).

2) To a solution of compound a-38 (4.83 g, 12.0 mmol) in tetrahydrofuran (25 ml)-methanol (25 ml), was added 2N NaOH aq. (7.8 ml) and the mixture was stirred at room temperature for 2 hr. 2N HCl aq. (7.8 ml) was added thereto and the organic solvent was evaporated in vacuum. The residue was extracted with ethyl acetate and the extract was washed with water and saturated saline, dried over anhydrous sodium sulphate, and evaporatde. The residue was crystallized from methanol/diisopropyl-eter to give compound a-39 (4.50 g). Yield: 97% mp: 124-125° C.

NMR (CDCl$_3$) δ: 4.25 (2H, s), 5.74 (2H, s), 7.07 (2H, t like, J=8.7 Hz), 7.18-7.27 (2H, m), 7.30-7.40 (2H, m), 7.60-7.66 (2H, m), 8.04 (1H, d, J=2.4 Hz), 8.92 (1H, s), 9.11 (1H, d, J=2.4 Hz).

3) To a suspension of compound a-39 (388 mg, 1.0 mmol), 1-methoxy-2-propanol (0.13 ml), and 4-(N,N-dimethylamino)pyridine (122 mg) in DMF (2 ml), was added WSCD hydrochloride (268 mg) and the mixture was stirred at room temperature for 4 hr. The reaction mixture was poured to ice water, to whichh was added 10% citric acid and 1N HCl aq. and the mixture was extracted with ethyl acetate. The extract was washed with sodium hydrogen carbonate aq. and water, dried over anhydrous sodium sulphate, and evaporatde. The residue was purified with silica gel column chromatography to give compound a-40 (236 mg). Yield: 51%

NMR (CDCl$_3$) δ: 1.37 (3H, d, J=6.3 Hz), 3.34 (3H, s), 3.47 (1H, dd, J=7.2 Hz, 4.5 Hz), 3.56 (1H, dd, J=7.2 Hz, 6.0 Hz), 4.22 (2H, s), 5.37-5.46 (1H, m), 5.59 (2H, s), 7.06 (2H, t like, J=8.7 Hz), 7.17-7.28 (2H, m), 7.32-7.42 (2H, m), 7.58-7.64 (2H, m), 8.02 (1H, d, J=2.1 Hz), 9.01 (1H, br. s), 9.05 (1H, d, J=2.1 Hz).

4) According to the method of Example A-15 (3), compound A-79 was synthesized from compound a-40.

mp: 130-131° C.

Elementary analysis for C$_{20}$H$_{19}$FN$_2$O$_4$ Calculation (%): C, 64.86; H, 5.17; F, 5.13; N, 7.56. Found (%): C, 64.84; H, 5.03; F, 4.93; N, 7.51.

NMR(CDCl$_3$)δ: 1.48(3H, d, J=6.6 Hz), 3.42(3H, s), 3.59 (1H, dd, J=3.9, 10.5 Hz), 3.76(1H, dd, J=6.9, 10.5 Hz), 4.22(2H, s), 5.54-5.61(1H, m), 7.03-7.08(2H, m), 7.18-7.22 (2H, m), 7.96(1H, d, J=2.1 Hz), 8.79(1H, s), 9.07(1H, d, J=2.1 Hz), 11.94(1H, bs).

Example A-80 to A-84

According to the method of Example A-79, compounds A-80 to A-84 were synthesized, provided that Example A-81 was prepared by esterification utilizing Mitsunobu Reaction.

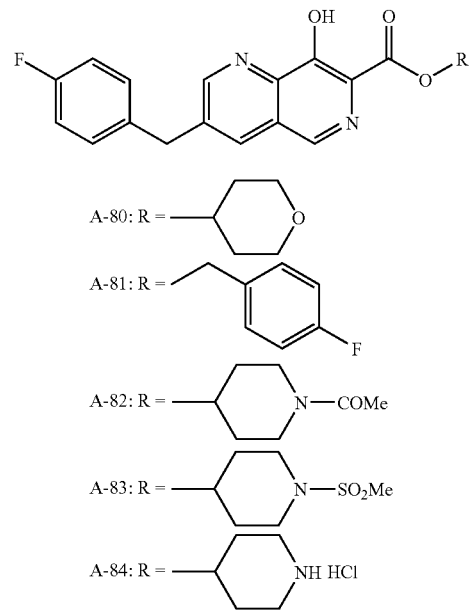

A-80 3-(4-fluorobenzyl)-8-hydroxy[1,6]naphthylidine-7-carboxylic acid tetrahydropyran-4-yl ester mp: 183-184° C.

Elementary analysis for C$_{21}$H$_{19}$FN$_2$O$_4$ Calculation (%): C, 65.96; H, 5.01; F, 4.97; N, 7.33. Found (%): C, 65.83; H, 4.89; F, 4.75; N, 7.25.

NMR(CDCl$_3$)δ: 2.02-2.15(4H, m), 3.56-3.64(2H, m), 4.05-4.12(2H, m), 4.23(2H, s), 5.33-5.39(1H, m), 7.03-7.08 (2H, m), 7.18-7.23(2H, m), 7.97(1H, d, J=2.1 Hz), 8.79(1H, s), 9.07(1H, d, J=2.1 Hz), 11.93(1H, bs).

A-81 3-(4-Fluorobenzyl)-8-hydroxy[1,6]naphthylidine-7-carboxylic acid 4-fluorobenzyl ester mp: 169-171° C.

Elementary analysis for C$_{23}$H$_{16}$F$_2$N$_2$O$_3$ Calculation (%): C, 67.98; H, 3.97; F, 9.35; N, 6.89. Found (%): C, 68.02; H, 4.01; F, 8.61; N, 6.91.

NMR(CDCl$_3$)δ: 4.22(2H, s), 5.52(2H, s), 7.02-7.11(4H, m), 7.17-7.22(2H, m), 7.52-7.56(2H, m), 7.95(1H, m), 8.76 (1H, s), 9.07(1H, d, J=2.4 Hz), 11.75(1H, bs).

A-82 3-(4-Fluorobenzyl)-8-hydroxy[1,6]naphthylidine-7-carboxylic acid 1-acetylpiperidine-4-yl ester mp: 163-165° C.

Elementary analysis for C$_{23}$H$_{22}$FN$_3$O$_4$ Calculation (%): C, 65.24; H, 5.24; F, 4.49; N, 9.92. Found (%): C, 65.11; H, 5.14; F, 4.33; N, 9.78.

NMR(CDCl$_3$)δ: 1.85-2.02(2H, m), 2.05-2.20(2H, m), 2.14(3H, s), 3.24-3.42(2H, m), 3.84-3.89(1H, m), 4.23-4.32(1H, m), 4.23(2H, s), 5.34-5.43(1H, m), 7.03-7.08(2H, m), 7.18-7.22(2H, m), 7.97(1H, d, J=2.1 Hz), 8.77(1H, s), 9.07(1H, d, J=2.1 Hz), 11.84(1H, bs).

A-83. 3-(4-Fluorobenzyl)-8-hydroxy[1,6]naphthylidine-7-carboxylic acid (1-methanesulfonypiperidine-4-yl ester mp: 184-185° C.
Elementary analysis for C$_{22}$H$_{22}$FN$_3$O$_5$S Calculation (%): C, 57.51; H, 4.83; F, 4.13; N, 9.14; S, 6.98. Found (%): C, 57.38; H, 4.74; F, 3.98; N, 9.05; S, 7.07.
NMR(CDCl$_3$)δ: 2.10-2.30(4H, m), 2.85(3H, s), 3.20-3.28(2H, m), 3.63-3.71(2H, m), 4.23(2H, s), 5.30-5.38(1H, m), 7.03-7.08(2H, m), 7.18-7.22(2H, m), 7.97(1H, d, J=2.1 Hz), 8.77(1H, s), 9.07(1H, d, J=2.1 Hz), 11.78(1H, bs).

A-84 3-(4-Fluorobenzyl)-8-hydroxy[1,6]naphthylidine-7-carboxylic acid piperidine-4-yl ester hydrochloride mp: 230-232° C.(dec)
Elementary analysis for C$_{21}$H$_{20}$FN$_3$O$_3$·1.4HCl·0.8H$_2$O Calculation (%): C, 56.44; H, 5.19; F, 4.25; N, 9.40; Cl, 11.11. Found (%): C, 56.38; H, 5.01; F, 4.11; N, 9.38; Cl, 10.90.
NMR(DMSO-d$_6$)δ: 1.90-2.00(2H, m), 2.10-2.25(2H, m), 4.27(2H, s), 5.25-5.35(1H, m), 7.15-7.20(2H, m), 7.38-7.42(2H, m), 8.38(1H, d, J=2.1 Hz), 8.71(2H, bs), 8.86(1H, s), 9.14(1H, d, J=2.1 Hz).

Example A-85 a-39 ⟶

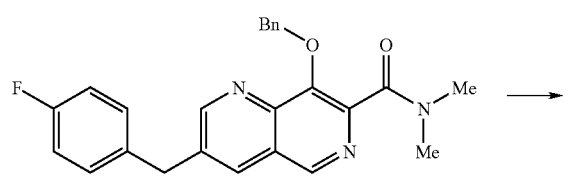

a-41

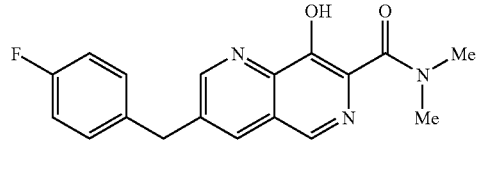

A-85

A-85 3-(4-Fluorobenzyl)-8-hydroxy[1,6]naphthylidine-7-carboxylic acid N,N-dimethyl amide 1) According to the method of Example A-16 (3), compound a-41 was synthesized from compound a-39.
NMR (CDCl$_3$) δ: 2.77(3H, s), 3.13(3H, s), 4.22(2H, s), 5.55(2H, s), 7.03-7.08(2H, m), 7.17-7.23(2H, m), 7.32-7.41(3H, m), 7.53-7.57(2H, m), 8.00(1H, d, J=2.3), 8.97(1H, s), 9.04(1H, d, J=2.1 Hz).

2) According to the method of Example A-15 (3), compound A-85 was synthesized from a-41.
mp: 180-181° C.
Elementary analysis for C$_{18}$H$_{16}$F$_1$N$_3$O$_2$ Calculation (%): C, 66.45; H, 4.96; N, 12.92; F, 5.84. Found (%): C, 66.48; H, 4.80; N, 12.88; F, 5.82.
NMR (CDCl$_3$) δ:3.00-3.80(6H, brs), 4.21(2H, s), 7.01-7.07(2H, m), 7.17-7.22(2H, m), 7.92(1H, d, J=2.2 Hz), 8.63(1H, s), 9.02(1H, d, J=2.1 Hz), 13.2(1H, brs).

Example A-86 to A-92

According to the method of Example A-85, compounds A-86 to A-92 were synthesized.

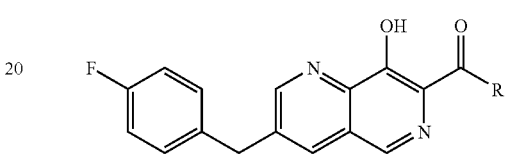

A-86: R = ——NHNHMe
A-87: R = ——NHNMe$_2$
A-88: R = ——NHOMe
A-89: R = ——NH$_2$
A-90: R = ——NHMe
A-91: R = ——NHEt
A-92: R = ——NHi-Pr

A-86 3-(4-Fluorobenzyl)-8-hydroxy[1,6]naphthylidine-7-carboxylic acid N'-methylhydrazide mp: 119-120° C.
Elementary analysis for C$_{17}$H$_{15}$F$_1$N$_4$O$_2$ Calculation (%): C, 62.57; H, 4.63; N, 17.17; F, 5.82. Found (%): C, 62.51; H, 4.48; N, 16.95; F, 6.04.
NMR (CDCl$_3$) δ:3.40(3H, brs), 4.22(2H, s), 7.02-7.07(2H, m), 7.17-7.22(2H, m), 7.93(1H, d, J=2.1 Hz), 8.62(1H, s), 9.05(1H, s).

A-87 3-(4-Fluorobenzyl)-8-hydroxy[1,6]naphthylidine-7-carboxylic acid N',N'-dimethylhydrazide mp: 138-139° C.
Elementary analysis for C$_{18}$H$_{17}$F$_1$N$_4$O$_2$ Calculation (%): C, 63.52; H, 5.03; N, 16.46; F, 5.58. Found (%): C, 63.53; H, 5.04; N, 16.34; F, 5.59.
NMR (CDCl$_3$) δ:2.79(6H, s), 4.21(2H, s), 7.02-7.08(2H, m), 7.17-7.22(2H, m), 7.91(1H, d, J=2.1 Hz), 8.54(1H, s), 9.05(1H, d, J=2.1 Hz).

A-88 3-(4-Fluorobenzyl)-8-hydroxy[1,6]naphthylidine-7-carboxylic acid methoxy amide mp: 196-197° C.
Elementary analysis for C$_{17}$H$_{14}$F$_1$N$_3$O$_3$ Calculation (%): C, 62.38; H, 4.31; N, 12.84; F, 5.80. Found (%): C, 62.39; H, 4.33; N, 12.68; F, 5.76.
NMR (CDCl$_3$) δ:3.97(3H, s), 4.22(2H, s), 7.02-7.08(2H, m), 7.17-7.22(2H, m), 7.92(1H, d, J=2.3 Hz), 8.54(1H, s), 9.06(1H, d, J=2.1 Hz).

A-89 3-(4-Fluorobenzyl)-8-hydroxy[1,6]naphthylidine-7-carboxylic acid amide mp: 267-270° C. (decomp.)

Elementary analysis for $C_{16}H_{12}FN_3O_2$ Calculation (%): C, 64.64; H, 4.07; F, 6.39; N, 14.13. Found (%): C, 64.33; H, 4.10; F, 6.63; N, 14.17.

NMR($d_6$-DMSO)δ: 4.25(2H, s), 7.13-7.21(2H, m), 7.36-7.41(2H, m), 8.28(1H, brs), 8.33(1H, d, J=2.1 Hz), 8.64(1H, brs), 8.80(1H, s), 9.09(1H, d, J=2.1 Hz), 14.09(1H, s).

A-90 3-(4-Fluorobenzyl)-8-hydroxy[1,6]-naphthylidine-7-carboxylic acid methyl amide mp: 259-260° C.

Elementary analysis for $C_{17}H_{14}FN_3O_2$ Calculation (%): C, 65.59; H, 4.53; F, 6.10; N, 13.50. Found (%) C, 65.37; H, 4.55; F, 6.14; N, 13.42.

NMR(CDCl$_3$)δ: 3.08(3H, t, J=2.7 Hz), 4.21(2H, s), 7.01-7.08(2H, m), 7.16-7.27(2H, m), 7.91(1H, m), 8.06(1H, brs), 8.56(1H, s), 9.04(1H, d, J=2.1 Hz), 13.40(1H, s).

A-91 3-(4-Fluorobenzyl)-8-hydroxy[1,6]-naphthylidine-7-carboxylic acid ethyl amide mp: 189-190° C.

Elementary analysis for $C_{18}H_{16}FN_3O_2$ Calculation (%): C, 66.45; H, 4.96; F, 5.84; N, 12.92. Found (%): C, 66.70; H, 4.99; F, 5.94; N, 12.95.

NMR(CDCl$_3$)δ: 1.33(3H, t, J=7.4 Hz), 4.49-3.60(2H, m), 4.21(2H, s), 7.01-7.08(2H, m), 7.16-7.27(2H, m), 7.91(1H, m), 8.05(1H, brs), 8.56(1H, s), 9.04(1H, d, J=2.1 Hz), 13.47(1H, s).

A-92 3-(4-Fluorobenzyl)-8-hydroxy[1,6]-naphthylidine-7-carboxylic acid isopropyl amide mp: 179-180° C.

Elementary analysis for $C_{19}H_{18}FN_3O_2$ Calculation (%): C, 67.24; H, 5.35; F, 5.60; N, 12.38. Found (%): C, 67.50; H, 5.33; F, 5.80; N, 12.47.

NMR(CDCl$_3$)δ: 1.34(6H, d, J=6.6 Hz), 4.21(2H, s), 4.33(1H, m), 7.02-7.08(2H, m), 7.17-7.22(2H, m), 7.91(2H, m), 8.56(1H, s), 9.04(1H, d, J=2.1 Hz), 13.54(1H, s).

Example A-93 a-20 ⟶

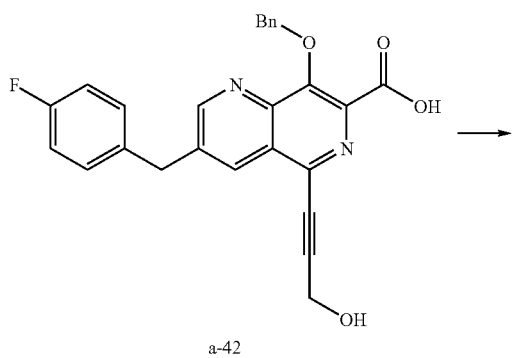

a-42

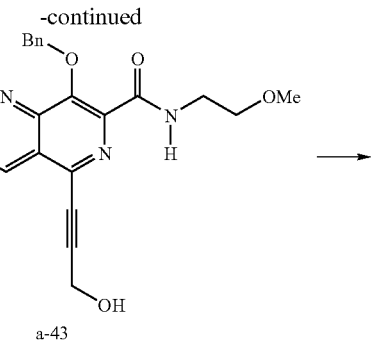

a-43

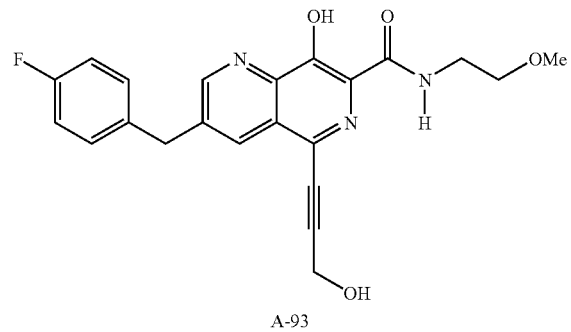

A-93

A-93 3-(4-Fluorobenzyl)-8-hydroxy-5-(3-hydroxylpropyn-1-yl)[1,6]naphthylidine-7-carboxylic acid 2-methoxyethyl amide 1) According to the method of Example A-79 (2), compound a-42 was synthesized from compound a-20.

NMR (CDCl$_3$) δ: 4.25(2H, s), 4.62(2H, s), 5.73(2H, s), 7.02-7.08(2H, m), 7.18-7.24(2H, m), 7.28-7.38(3H, m), 7.60-7.62(2H, m), 8.37(1H, s), 9.04(1H, brs).

2) According to the method of Example A-16 (3), compound a-43 was synthesized from a-42.

NMR (CDCl$_3$) δ: 3.34(3H, s), 3.57-3.61(2H, m), 3.65-3.70(2H, m), 4.15(2H, s), 4.60(2H, s), 5.54(2H, s), 6.98-7.04(2H, m), 7.15-7.20(2H, m), 7.31-7.40(3H, m), 7.63-7.66(2H, m), 8.21(1H, t, J=5.3 Hz), 8.26(1H, d, J=2.1 Hz), 8.91(1H, d, J=2.1 Hz).

3) According to the method of Example A-15 (3), compound A-93 was synthesized from a-43.

mp: 156-157° C.

Elementary analysis for $C_{22}H_{20}F_1N_3O_4 \cdot 0.2H_2O$ Calculation (%): C, 63.98; H, 4.98; N, 10.17; F, 4.60. Found (%): C, 63.99; H, 4.79; N, 10.13; F, 4.84.

NMR (CDCl$_3$) δ: 3.43(3H, s), 3.61-3.63(2H, m), 3.65-3.73(2H, m), 4.22(2H, s), 4.63(2H, s), 7.01-7.06(2H, m), 7.16-7.21(2H, m), 8.28(1H, d, J=2.3 Hz), 8.30(1H, brs), 8.99(1H, d, J=2.1 Hz), 13.63(1H, s).

Example A-94 to A-98

According to the method of Example A-93, compounds A-94 to A-98 were synthesized.

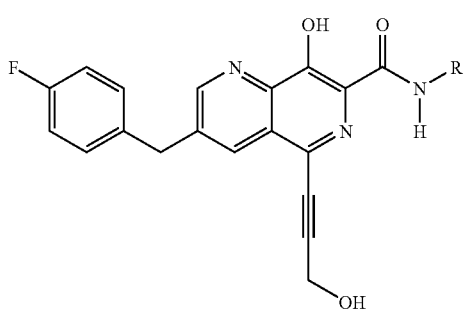

A-94: R = —H
A-95: R = —OMe
A-96: R = —i-Pr
A-97: R = —NMe₂
A-98: R = —Me

A-94 3-(4-Fluorobenzyl)-8-hydroxy-5-(3-hydroxy-1-propyn-1-yl)[1,6]naphthylidine-7-carboxylic acid amide mp: 241-242° C.
Elementary analysis for C₁₉H₁₄F₁N₃O₃0.3H₂O Calculation (%): C, 63.97; H, 4.13; N, 11.78; F, 5.33. Found (%): C, 63.88; H, 4.01; N, 11.67; F, 5.33.
NMR (CD₃OD) δ: 4.31(2H, s), 4.52(2H, s), 7.04-7.10 (2H, m), 7.31-7.36(2H, m), 8.55(1H, d, J=2.0 Hz), 8.96(1H, d, J=2.0 Hz).

A-95 3-(4-Fluorobenzyl)-8-hydroxy-5-(3-hydroxy-1-propyn-1-yl)[1,6]naphthylidine-7-carboxylic acid methoxy amide mp: 175-177° C.
Elementary analysis for C₂₀H₁₆F₁N₃O₄ Calculation (%): C, 62.99; H, 4.23; N, 11.02; F, 4.98. Found (%): C, 62.81; H, 4.32; N, 10.92; F, 4.82.
NMR (CDCl₃) δ: 3.96(3H, s), 4.24(2H, s), 4.63(2H, s), 7.02-7.07(2H, m), 7.16-7.21(2H, m), 8.30(1H, d, J=2.1 Hz), 9.02(1H, d, J=2.3 Hz), 10.19(1H, s), 12.88(1H, s).

A-96 3-(4-Fluorobenzyl)-8-hydroxy-5-(3-hydroxy-1-propyn-1-yl)-[1,6]naphthylidine-7-carboxylic acid isopropyl amide mp: 175-177° C.
Elementary analysis for C₂₂H₂₀FN₃O₃ Calculation (%): C, 67.17; H, 5.12; F, 4.83; N, 10.68. Found (%): C, 67.27; H, 5.12; F, 4.71; N, 10.61.
NMR (CDCl₃) δ: 1.34 (6H, d, J=6.6 Hz), 1.83 (1H, t, J=6.0 Hz), 4.23 (2H, s), 4.31 (1H, d×7, J=6.6 Hz, 8.4 Hz), 4.64 (2H, d, J=6.0 Hz), 7.04 (2H, m), 7.19 (2H, m), 7.85 (1H, brd, J=8.4 Hz), 8.30 (1H, m), 9.01 (1H, d, J=2.1 Hz), 13.86 (1H, s).

A-97 3-(4-Fluorobenzyl)-8-hydroxy-5-(3-hydroxy-1-propyn-1-yl)[1,6]naphthylidine-7-carboxylic acid N',N'-dimethylhydrazide mp: 115-117° C.
Elementary analysis for C₂₁H₁₉F₁N₄O₃0.2H₂O0.7C₃H₈O₁(I-PrOH) Calculation (%): C, 63.05; H, 5.73; N, 12.73; F, 4.32. Found (%): C, 62.99; H, 5.69; N, 12.79; F, 4.24.
NMR (CDCl₃) δ: 2.78(6H, s), 4.23(2H, s), 4.64(2H, s), 7.01-7.07(2H, m), 7.17-7.21(2H, m), 8.29(1H, d, J=2.1 Hz), 9.00(1H, d, J=2.3 Hz), 13.43(1H, brs).

A-98 3-(4-Fluorobenzyl)-8-hydroxy-5-(3-hydroxy-1-propyn-1-yl)-[1,6]naphthylidine-7-carboxylic acid methyl amide mp: 185° C.
Positive HR-FABMS for C₂₀H₁₆FN₃O₃+H Calculation (m/z): 366.1254. Found (m/z): 366.1250 (Int. 100%).
NMR (CDCl₃) δ: 3.07 (3H, d, J=5.4 Hz), 4.24 (2H, s), 4.63 (2H, s), 7.04 (2H, m), 7.19 (2H, m), 8.0 (1H, br), 8.30 (1H, m), 9.01 (1H, d, J=2.1 Hz), 13.68 (1H, s).

Example A-99 a-38 ⟶

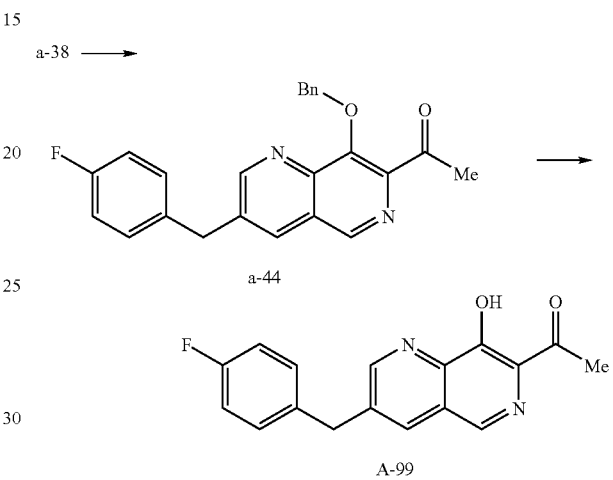

A-99 7-Acetyl-3-(4-fluorobenzyl)-8-hydroxy[1,6]naphthylidine

1) According to the method of Example A-19 (2), compound a-44 was synthesized from compound a-38.
NMR (CDCl₃) δ: 2.67(3H, s), 4.22(2H, s), 5.58(2H, s), 7.03-7.09(2H, m), 7.19-7.22(2H, m), 7.34-7.41(3H, m), 7.55-7.59(2H, m), 8.01(1H, d, J=2.1 Hz), 8.96(1H, s), 9.07 (1H, d, J=2.1 Hz).
2) According to the method of Example A-15 (3), compound A-99 was synthesized from compound a-44.
mp: 175-176° C.
Elementary analysis for C₁₇H₁₃F₁N₂O₃0.2H₂O Calculation (%): C, 68.08; H, 4.50; N, 9.34; F, 6.33. Found (%): C, 68.13; H, 4.65; N, 9.34; F, 6.40.
NMR (CDCl₃) δ: 2.86(3H, s), 4.23(2H, s), 7.03-7.08(2H, m), 7.18-7.22(2H, m), 7.96(1H, d, J=2.2 Hz), 8.70(1H, s), 9.06(1H, s), 13.34(1H, s).

Example A-100

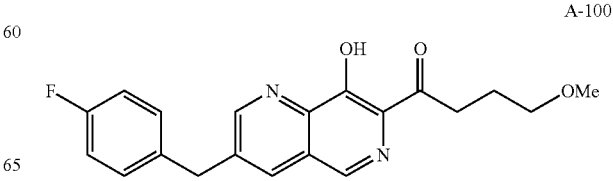

A-100

According to the method of Example A-99, compound A-100 was synthesized.

A-100 3-(4-fluorobenzyl)-8-hydroxy-7-(4-methoxy-butylyl)[1,6]naphthylidine mp: 117-118° C.

Elementary analysis for $C_{20}H_{19}F_1N_2O_3$ Calculation (%): C, 67.79; H, 5.40; N, 7.91; F, 5.36. Found (%): C, 67.69; H, 5.64; N, 7.96; F, 5.36.

NMR (CDCl$_3$) δ: 2.09(2H, m), 3.34(3H, s), 3.42-3.47(2H, m), 3.50-3.54(2H, m), 4.23(2H, s), 7.02-7.09(2H, m), 7.17-7.22(2H, m), 7.95(1H, d, J=2.2 Hz), 8.70(1H, s), 9.06(1H, d, J=2.1 Hz), 13.35(1H, s).

Example A-101 a-15 ⟶

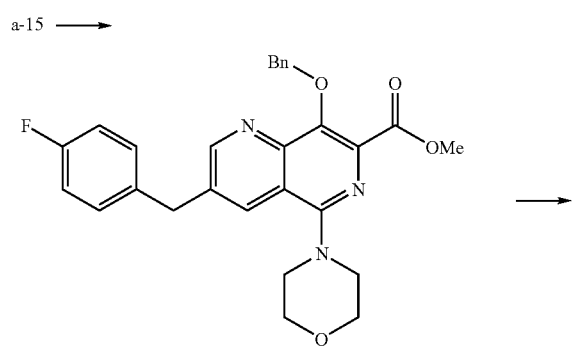

a-45

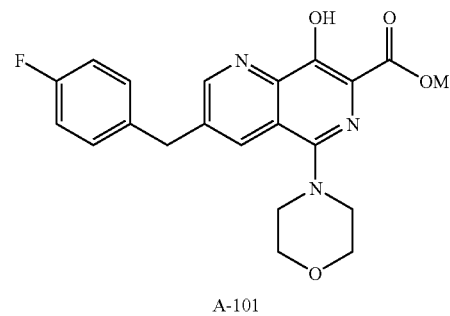

A-101

A-101 3-(4-Fluorobenzyl)-8-hydroxy-5-(morpho-line-4-yl)[1,6]naphthylidine-7-carboxylic acid methyl ester 1) According to the method of Example A-9 (2), compound a-45 was synthesized from compound a-15.

NMR (CDCl$_3$) δ: 3.33 (4H, t, J=4.5 Hz), 3.86 (4H, t, J=4.5 Hz), 3.91 (3H, s), 4.20 (2H, s), 5.41 (2H, s), 7.06 (2H, m), 7.15-7.22 (2H, m), 7.32-7.41 (3H, m), 7.56-7.61 (2H, m), 8.01 (1H, m), 8.98 (1H, d, J=2.1 Hz).

2) According to the method of Example A-15 (3), compound A-101 was synthesized from compound a-45.

mp: 185-187° C.

Positive HR-FABMS for $C_{21}H_{20}FN_3O_4$+H Calculation (m/z): 398.1516. Found (m/z): 398.1520 (Int. 100%).

NMR (CDCl$_3$) δ: 3.23 (4H, t, J=4.7 Hz), 3.85 (4H, t, J=4.7 Hz), 4.06 (3H, s), 4.21 (2H, s), 7.06 (2H, m), 7.19 (2H, m), 8.01 (1H, m), 9.01 (1H, d, J=2.1 Hz), 11.48 (1H, s).

Example A-102

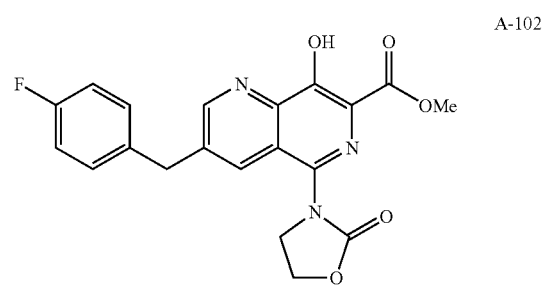

A-102

According to the method of Example A-101, compound A-102 was synthesized.

A-102 3-(4-Fluorobenzyl)-8-hydroxy-5-(2-oxo-oxazolidine-3-yl)-[1,6]naphthylidine-7-carboxylic acid methyl ester mp: 256° C. (decompose)

Elementary analysis for $C_{20}H_{16}FN_3O_5$ Calculation (%): C, 60.45; H, 4.06; F, 4.78; N, 10.57. Found (%): C, 60.19; H, 4.06; F, 4.63; N, 10.52.

NMR (CDCl$_3$) δ: 4.08 (3H, s), 4.22 (2H, s), 4.40 (2H, t, J=8.0 Hz), 4.65 (2H, t, J=8.0 Hz), 7.02 (2H, m), 7.19 (2H, m), 8.20 (1H, m), 9.02 (1H, d, J=2.1 Hz), 11.67 (1H, s).

Example A-103 a-15 ⟶

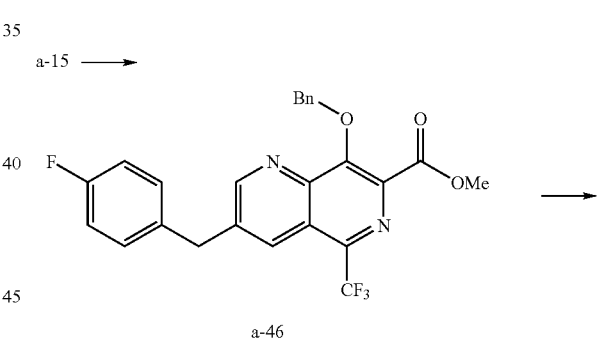

a-46

A-103

A-103 3-(4-Fluorobenzyl)-8-hydroxy-5-(trifluoromethyl)[1,6]naphthylidine-7-carboxylic acid methyl ester 1) CuI (95 mg, 0.50 mmol) and methyl fluorosulfonyl (difluoro)acetate (0.255 ml, 2.00 mmol) were added to HMPA (3 ml) under ice-cooling and the mixture was stirred at room temperature for 15 min. Compound a-15 (528 mg, 1.00 mmol) was added thereto and the mixture was stirred at 80° C. for 1 hr and 10 min. Water was added thereto, and the mixture was extracted with ethyl acetate. The extract was washed with water and saturated saline, dried over anhydrous magnesium sulphate, and evaporated in vacuum. The residue was crystallized from methanol/diisopropyleter to give compound a-46 (3.60 g). Yield: 76%

NMR (CDCl$_3$) δ: 3.96 (3H, s), 4.25 (2H, s), 5.67 (2H, s), 7.02-7.60 (9H, m), 8.34 (1H, s), 9.08 (1H, d, J=2.1 Hz).

2) According to the method of Example A-15 (3), compound A-103 was synthesized from compound a-46.

mp: 184-185° C.

Elementary analysis for $C_{18}H_{12}F_4N_2O$ Calculation (%): C, 56.85; H, 3.18; N, 7.37; F, 19.98. Found (%): C, 56.71; H, 3.23; N, 7.37; F, 20.35.

NMR (CDCl$_3$) δ: 4.14 (3H, s), 4.26 (2H, s), 7.01-7.10 (2H, m), 7.15-7.24 (2H, m), 8.29 (1H, s), 9.10 (1H, d, J=2.1 Hz), 12.18 (1H, s).

Example A-104

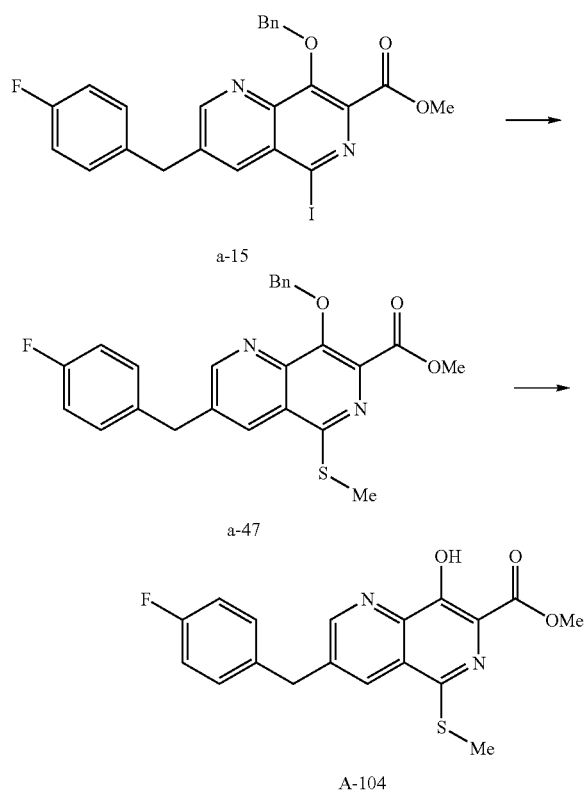

A-104 3-(4-Fluorobenzyl)-8-hydroxy-5-(methylthio) [1,6]naphthylidine-7-carboxylic acid methyl ester 1) To a solution of compound a-15 (3.17 g, 6.00 mmol) in N,N-dimethylformamide (30 ml) cooled to 0° C., was added sodium thiomethoxide (547 mg, 7.80 mmol) and the mixture was stirred at the same temperature for 2 hr. Sodium thiomethoxide (42 mg, 0.600 mmol) was further added and the mixture was stirred for 1 hr. Saturated ammonium chloride aq. and water were added thereto and the mixture was extracted with ethyl acetate. The extract was washed with water and saturated saline, dried over anhydrous magnesium sulphate, and evaporatde. The obtained crude crystal was washed with methanol to give compound a-47 (2.40 g, 5.35 mmol). Yield: 89%

NMR(CDCl$_3$)δ: 2.72(3H, s), 3.93(3H, s), 4.20(2H, s), 5.44(2H, s), 7.00-7.08(2H, m), 7.17-7.23(2H, m), 7.31-7.44 (3H, m), 7.55-7.61(2H, m), 8.25(1H, s), 9.10(1H, s).

2) According to the method of Example A-15 (3), compound A-104 was synthesized from compound a-47.

mp: 154-157° C.

NMR(CDCl$_3$)δ: 2.72(3H, s), 4.08(3H, s), 4.21(2H, s), 7.00-7.08(2H, m), 7.15-7.22(2H, m), 8.20(1H, d, J=2.0 Hz), 9.02(1H, d, J=2.0 Hz), 11.49(1H, s).

Example A-105

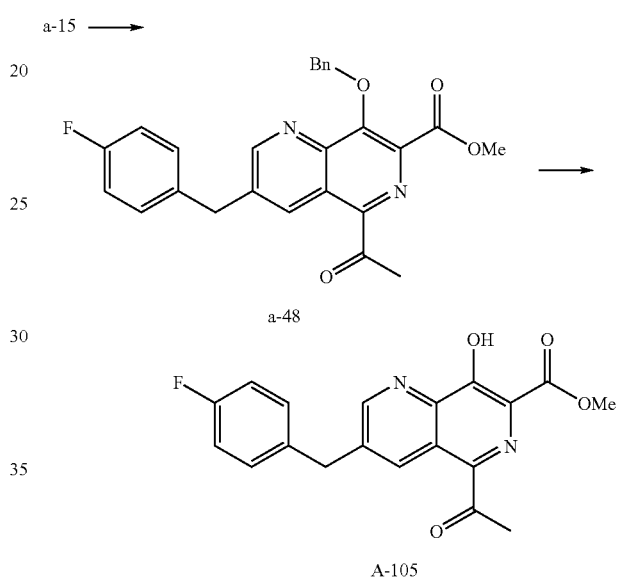

A-105. 5-Acetyl-3-(4-fluorobenzyl)-8-hydroxy[1,6] naphthylidine-7-carboxylic acid methyl ester 1) To a solution of compound a-15 ((264 mg, 0.50 mmol)) in toluene ((10 ml)), were added tetrakis triphenylphosphine paradium ((87 mg, 0.013 mmol)) and 1-ethoxyvinyl tri-n-butyl tin ((0.338 ml, 1.00 mmol)) at room temperature, and the mixture was stirred at 100° C. for 2 hr 30 min. To the mixture were added THF (10 ml) and 2N HCl aq. ((1.0 ml)), which was stirred at room temperature for 15 min. Water was added thereto and the mixture was extracted with ethyl acetate. The extract was washed with saturated saline, dried over anhydrous magnesium sulphate, and evaporatde. The residue was purified with silica gel column chromatography to give compound a-48 (213 mg) as oil. Yield: 96%

NMR (CDCl$_3$) δ: 2.84 (3H, s), 3.96 (3H, s), 4.21 (2H, s), 5.70 (2H, s), 7.00-7.60 (9H, m), 9.00 (1H, d, J=2.1 Hz), 9.33 (1H, d, J=2.1 Hz).

2) According to the method of Example A-15 (3), compound A-105 was synthesized from compound a-48.

mp: 154-155° C.

Elementary analysis for $C_{19}H_{15}FN_2O_4$ Calculation (%): C, 64.40; H, 4.27; N, 7.91; F, 5.36. Found (%): C, 64.19; H, 4.30; N, 7.90; F, 5.27.

NMR (CDCl$_3$) δ: 2.84 (3H, s), 4.13 (3H, s), 4.22 (2H, s), 6.98-7.07 (2H, m), 7.16-7.24 (2H, m), 9.02 (1H, d, J=2.1 Hz), 9.35 (1H, d, J=2.1 Hz), 12.18 (1H, brs).

Example A-106 a-32 ⟶

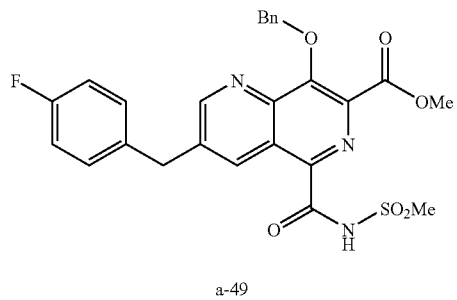

a-49

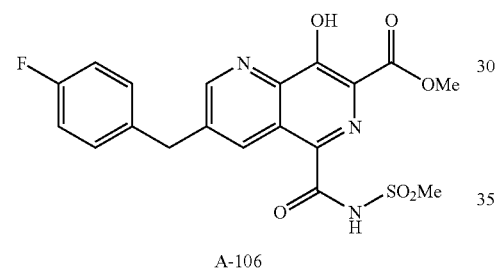

A-106

A-106 3-(4-Fluorobenzyl)-8-hydroxy-5-[(methanesulfonyamino)carbonyl]-[1,6]naphthylidine-7-carboxylic acid methyl ester 1) To a suspension containing compound a-32 (446 mg, 1.00 mmol), methanesulfonamide ((143 mg, 1.50 mmol)), and WSCD hydrochloride (288 mg, 1.50 mmol) in methylene chloride ((15 ml)), was added 4-(dimethylamino)pyridine (183 mg, 1.50 mmol) and the mixture was stirred at room temperature for 2 hr 30 min and refluxed under heating for 1 hr 30 min. Water and 2N HCl aq. (0.8 ml) were added thereto and the mixture was extracted with ethyl acetate. The extract was washed with water and saturated saline, dried over anhydrous magnesium sulphate, and evaporated in vacuum. The residue was purified with silica gel column chromatography to give compound a-49 (361 mg). Yield: 69%

NMR (CDCl$_3$) δ: 3.44 (3H, s), 3.96 (3H, s), 4.22 (2H, s), 5.77 (2H, s), 7.00-7.55 (9H, m), 9.05 (1H, d, J=2.1 Hz), 9.71 (1H, s), 10.58 (1H, s).

2) According to the method of Example A-15 (3), compound A-106 was synthesized from compound a-49.
mp: 234-235° C.
Elementary analysis for C$_{19}$H$_{16}$FN$_3$O$_6$S Calculation (%): C, 52.65; H, 3.72; N, 9.70; F, 4.38; S, 7.40. Found (%): C, 52.67; H, 3.84; N, 9.61; F, 4.31; S, 7.36.

NMR (CDCl$_3$) δ: 3.46 (3H, s), 4.14 (3H, s), 4.23 (2H, s), 6.99-7.09 (2H, m), 7.15-7.25 (2H, m), 9.07 (1H, d, J=2.1 Hz), 9.68 (1H, d, J=2.1 Hz), 10.42 (1H, s), 12.15 (1H, brs).

Example A-107 a-49 ⟶

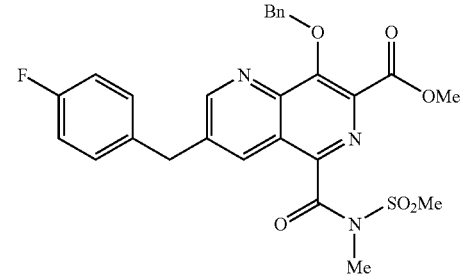

a-50

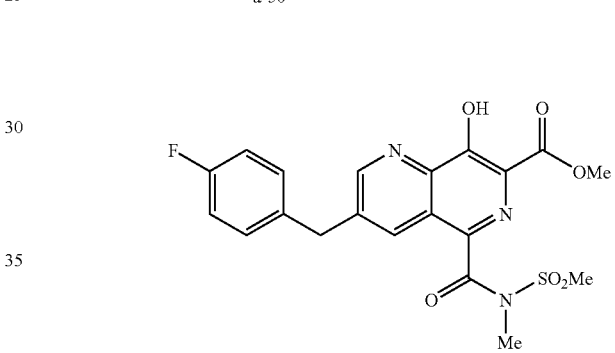

A-107

A-107 3-(4-Fluorobenzyl)-8-hydroxy-5-[[N-(methanesulfony)-N-methyl]aminocarbonyl]-[1,6]naphthylidine-7-carboxylic acid methyl ester 1) To a solution of compound a-49 ((134 mg, 0.26 mmol), methanol ((0.016 ml, 0.38 mmol), and triphenylphosphine ((100 mg, 0.38 mmol) in tetrahydrofuran ((5.0 ml), was added dropwise under ice-cooling a 40% solution of azodicarboxylic acid diisopropyl ester in toluene ((0.206 ml, 0.38 mmol) and the mixture was stirred at the same temperature for 2 hr 30 min, then evaporated in vacuum. The residue was purified with silica gel column chromatography to give compound a-50 ((77 mg). Yield: 56%.

NMR (CDCl$_3$) δ: 3.48 (3H, s), 3.59 (3H, s), 3.89 (3H, s), 4.20 (2H, s), 5.64 (2H, s), 7.00-7.56 (9H, m), 8.30 (1H, d, J=2.4 Hz), 9.01 (1H, d, J=2.4 Hz)

2) According to the method of Example A-15 (3), compound A-107 was synthesized from compound a-50.
mp: 155° C.
NMR (CDCl$_3$) δ: 3.48 (3H, s), 3.58 (3H, s), 4.08 (3H, s), 4.21 (2H, s), 6.99-7.08 (2H, m), 7.14-7.24 (2H, m), 8.29 (1H, d, J=2.1 Hz), 9.02 (1H, d, J=2.1 Hz), 11.85 (1H, brs).

Example A-108

According to the method of Example A-106, compound A-108 was synthesized.

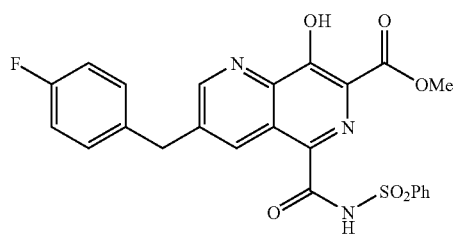

A-108 5-(Benzenesulfonylamino)carbonyl-3-(4-fluorobenzyl)-8-hydroxy[1,6]naphthylidine-7-carboxylic acid methyl ester mp: 228-229° C.

Elementary analysis for $C_{24}H_{18}FN_3O_6S$ Calculation (%): C, 58.18; H, 3.66; N, 8.48; F, 3.83; S, 6.47. Found (%): C, 58.31; H, 3.84; N, 8.35; F, 3.77; S, 6.33.

NMR (CDCl$_3$) δ: 4.16 (3H, s), 4.19 (2H, s), 6.96-7.06 (2H, m), 7.10-7.20 (2H, m), 8.22 (1H, d, J=7.8 Hz), 9.10 (1H, s), 9.61 (1H, s), 10.61 (1H, s), 12.17 (1H, brs).

Example A-109

A-109. 3-(4-Fluorobenzyl)-8-hydroxy-5-methane-sulfony[1,6]naphthylidine-7-carboxylic acid methyl ester 1) To a solution of compound a-47 (1.43 g, 3.19 mmol) in dichloromethane (20 ml) cooled to 0° C., m-chloroperbenzoic acid (1.38 g, 7.98 mmol) was added and the mixture was stirred at the same temperature for 2 hr. m-Chloroperbenzoic acid (442 mg, 2.55 mmol) was added thereto and the mixture was stirred for 2 hr. 0.5M sodium thiosulfate was added and the mixture was extracted with chloroform. The extract was washed with saturated hydrocarbonate aq. and saturated saline, dried over anhydrous magnesium sulphate, and evaporated in vaccum. The obtained residue was purified with silica gel column chromatography to give compound a-51 (1.52 g, 3.16 mmol) as crystals. Yield: 99%

NMR(CDCl$_3$)δ: 3.54(3H, s), 3.93(3H, s), 4.24(2H, s), 5.69(2H, s), 7.00-7.08(2H, m), 7.18-7.25(2H, m), 7.33-7.43 (3H, m), 7.51-7.56(2H, m), 9.05(1H, d, J=2.3 Hz), 9.08(1H, d, J=2.3 Hz).

2) According to the method of Example A-15 (3), compound A-109 was synthesized from compound a-51.

mp: 132-133° C.

NMR(CDCl$_3$)δ: 3.52(3H, s), 4.10(3H, s), 4.25(2H, s), 7.00-7.07(2H, m), 7.16-7.23(2H, m), 9.04-9.07(2H, m), 12.08(1H, br s).

Example A-110

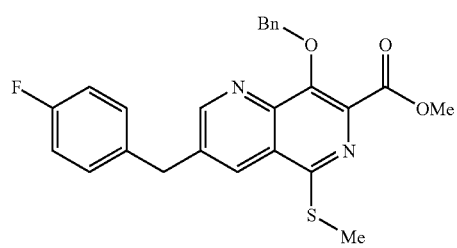

a-47

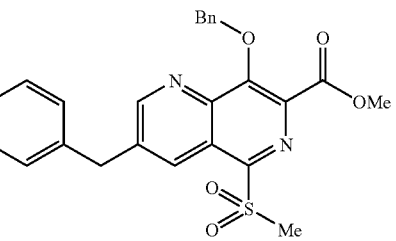

a-51

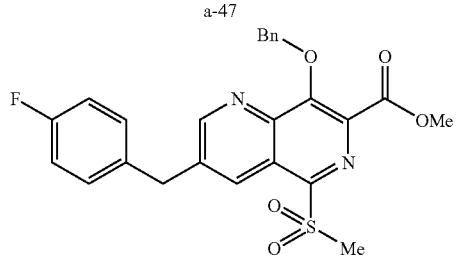

a-51

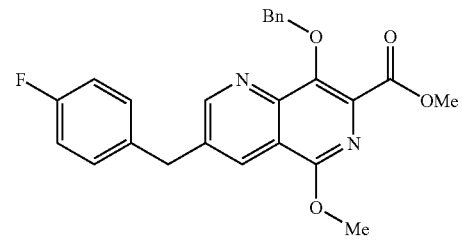

a-52

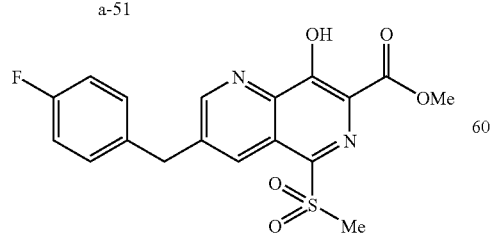

A-109

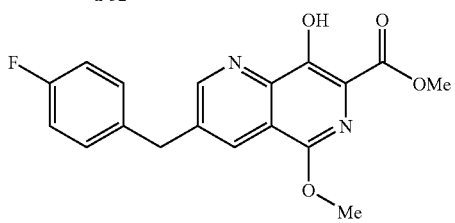

A-110

A-110 3-(4-Fluorobenzyl)-8-hydroxy-5-methoxy[1,6]naphthylidine-7-carboxylic acid methyl ester 1) To a solution of compound a-51 (480 mg, 1.00 mmol) in methanol cooled to 0° C., was added a 28% sodium methoxide-methanol solution (0.24 ml, 1.2 mmol) and the mixture was stirred at room temperature for 2 hr. Saturated ammonium chloride aq. was added thereto and the mixture was extracted with ethyl acetate. The extract was washed with water and saturated saline, dried over anhydrous magnesium sulphate, and evaporated in vaccum. The obtained residue was purified with silica gel column chromatography to give compound a-52 (230 mg, 0.532 mmol). Yield: 53%

NMR(CDCl$_3$)δ: 3.91(3H, s), 4.13(3H, s), 4.18(2H, s), 5.39(2H, s), 6.99-7.07(2H, m), 7.16-7.23(2H, m), 7.31-7.41 (3H, m), 7.56-7.61(2H, m), 8.28(1H, d, J=2.4 Hz), 9.00(1H, d, J=2.4 Hz).

2) According to the method of Example A-15 (3), compound A-110 was synthesized from compound a-52.

mp: 138-139° C.

NMR(CDCl$_3$)δ: 4.06(3H, s), 4.10(3H, s), 4.19(2H, s), 6.98-7.07(2H, m), 7.14-7.22(2H, m), 8.26(1H, d, J=1.9 Hz), 9.02(1H, d, J=1.9 Hz), 11.41(1H, s).

Example A-111, A-12

According to the method of Example A-110, compounds A-111 and A-112 were synthesized.

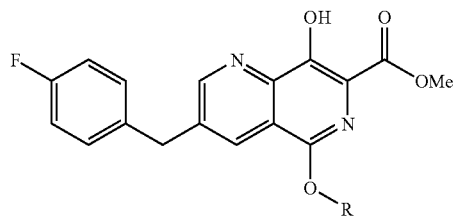

A-111: R = —CH$_2$CO$_2$Me
A-112: R = —CH$_2$CH$_2$OMe

A-111 3-(4-Fluorobenzyl)-8-hydroxy-5-[(methoxycarbonyl)methoxy][1,6]naphthylidine-7-carboxylic acid methyl ester mp: 125-127° C.

NMR(CDCl$_3$)δ: 3.80(3H, s), 4.02(3H, s), 4.20(2H, s), 5.05(2H, s), 6.99-7.07(2H, m), 7.15-7.23(2H, m), 8.35(1H, d, J=2.2 Hz), 9.04(1H, d, J=2.2 Hz), 11.40(1H, s).

A-112 3-(4-Fluorobenzyl)-8-hydroxy-5-(2-methoxyethoxy)[1,6]naphthylidine-7-carboxylic acid methyl ester mp: 117-118° C.

NMR(CDCl$_3$)δ: 3.45(3H, s), 3.82-3.86(2H, m), 4.05(3H, s), 4.19(2H, s), 4.64-4.69(2H, m), 6.98-7.06(2H, m), 7.13-7.20(2H, m), 8.34(1H, d, J=1.9 Hz), 9.00(1H, d, J=1.9 Hz), 11.39(1H, s).

Example A-113

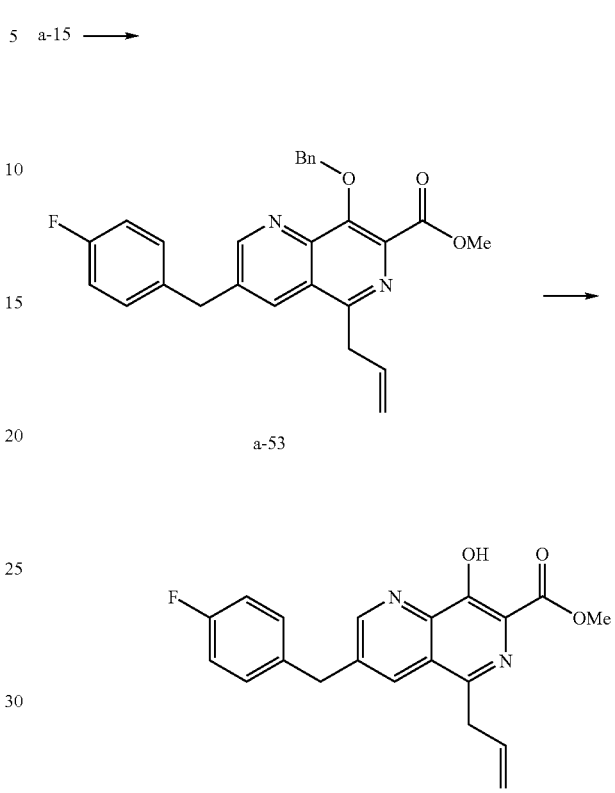

A-113 5-Allyl-3-(4-fluorobenzyl)-8-hydroxy[1,6]naphthylidine-7-carboxylic acid methyl ester 1) To a solution of compound a-15 ((528 mg, 1.00 mmol) in toluene ((10 ml), were added tetrakis triphenylphosphine paradium ((115 mg, 0.10 mmol) and allyl tri-n-butyl tin ((0.744 ml, 2.40 mmol) at room temperature and the mixture was refluxed under heating for 3 hr. Water was added thereto and the mixture was extracted with ethyl acetate. The extract was washed with water and saturated saline, dried over anhydrous magnesium sulphate, and evaporated in vaccum. The residue was purified with silica gel column chromatography and crystallized from methanol/diisopropyleter to give compound a-53 ((272 mg). Yield: 52%

NMR (CDCl$_3$) δ: 3.94 (3H, s), 4.00 (1H, d, J=6.3 Hz), 4.21 (2H, s), 4.97-5.16 (2H, m), 5.51 (2H, s), 5.98-6.14 (1H, m), 7.00-7.10 (2H, m), 7.15-7.25 (2H, m), 7.32-7.43 (3H, m), 7.59 (1H, d, J=6.3 Hz), 8.15 (1H, d, J=2.1 Hz), 9.03 (1H, d, J=2.1 Hz).

2) According to the method of Example A-15 (3), compound A-113 was synthesized from compound a-53.

mp: 154-155° C.

Elementary analysis for C$_{20}$H$_{17}$FN$_2$O$_3$ Calculation (%): C, 68.17; H, 4.86; N, 7.95; F, 5.39. Found (%): C, 67.68; H, 4.57; N, 7.90; F, 5.25.

NMR (CDCl$_3$) δ: 3.94 (1H, d, J=6.0 Hz), 4.11 (3H, s), 4.22 (2H, s), 4.93-5.13 (2H, m), 5.95-6.09 (1H, m), 7.02-7.12 (2H, m), 7.15-7.25 (2H, m), 8.10 (1H, s), 9.04 (1H, d, J=2.1 Hz), 11.73 (1H, s).

Example A-114

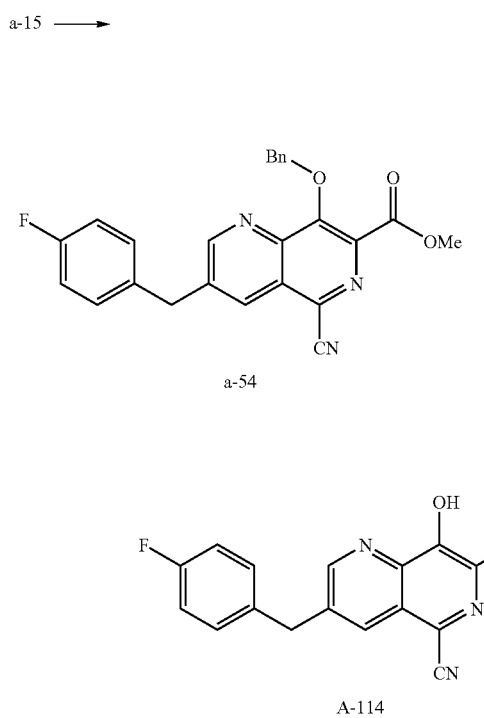

A-114 5-Cyano-3-(4-fluorobenzyl)-8-hydroxy[1,6]naphthylidine-7-carboxylic acid methyl ester 1) To a solution of compound a-15 ((264 mg, 0.50 mmol) in dioxane ((4 ml), were added tris(dibenzylideneacetone)diparadium (23 mg, 0.025 mmol), 1,1'-bisdiphenylphosphinoferrocene ((56 mg, 0.10 mmol), copper cyanide ((I) ((179 mg, 2.00 mmol), and tetraethylammonium cyanide (78 mg, 0.50 mmol)) at room temperature and the mixture was refluxed under heating for 3 hr. Water and a saturated sodium hydrogencarbonate aq. were added thereto and the mixture was extracted with ethyl acetate. The extract was washed with a saturated brine, dried over anhydrous magnesium sulphate, and evaporated in vaccum. The residue was purified with silica gel column chromatography and crystallized from acetone/diisopropyleter to give compound a-54 (108 mg)). Yield: 50%

NMR (CDCl$_3$) δ: 3.97 (3H, s), 4.27 (2H, s), 5.80 (2H, s), 7.02-7.56 (9H, m), 8.37 (1H, d, J=2.1 Hz), 9.04 (1H, d, J=2.1 Hz).

2) According to the method of Example A-15 (3), compound A-114 was synthesized from compound a-54.

mp: 239-240° C.

Elementary analysis for $C_{18}H_{12}FN_3O_3$ Calculation (%): C, 64.09; H, 3.59; N, 12.46; F, 5.63. Found (%): C, 64.39; H, 3.70; N, 12.25; F, 5.35.

NMR (CDCl$_3$) δ: 4.16 (3H, s), 4.29 (2H, s), 7.02-7.11 (2H, m), 7.17-7.25 (2H, m), 8.34 (1H, d, J=2.1 Hz), 9.13 (1H, d, J=2.1 Hz), 12.35 (1H, brs).

Example A-115

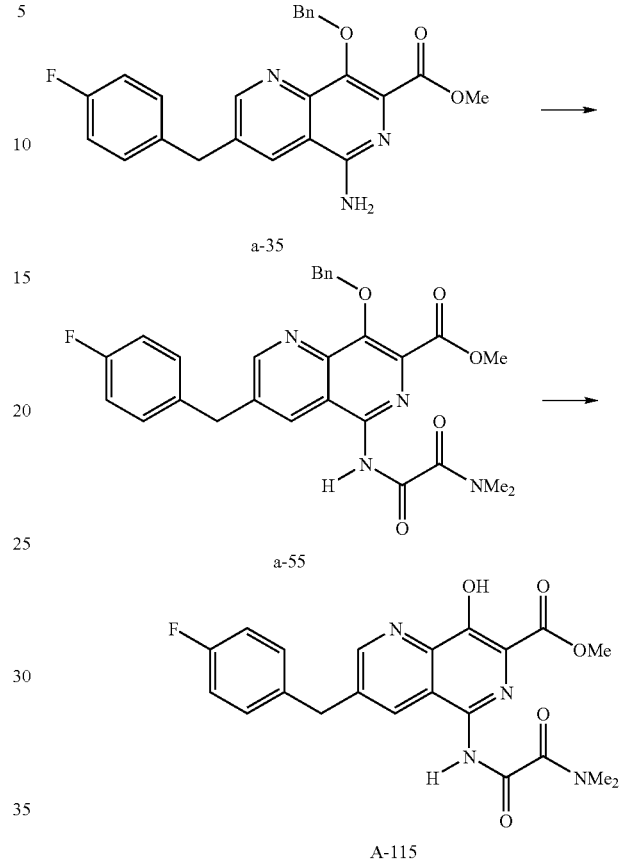

A-115 5-[[(Dimethylamino)oxalyl]amino]-3-(4-fluorobenzyl)-8-hydroxy[1,6]naphthylidine-7-carboxylic acid methyl ester 1) To a solution of compound a-35 (420 mg, 1.00 mmol) in tetrahydrofuran (10 ml) cooled to 0° C., were added pyridine (0.20 ml, 2.50 mmol) and oxalyl chloride (0.17 ml, 2.00 mmol) and the mixture was stirred at the same temperature for 20 min. A 2.0 M solution of dimethylamine in methanol (5 ml, 10.0 mmol) was added thereto and the mixture was stirred for 30 min. Water was added thereto and the mixture was extracted with ethyl acetate. The extract was washed with 0.5M citric acid aq., saturated sodium bicarbonate aq., and saturated saline and dried over anhydrous magnesium sulphate, then evaporated in vaccum. The obtained residue was purified with silica gel column chromatography to give compound a-55 (416 mg, 0.805 mmol). Yield: 80%

NMR(CDCl$_3$)δ: 3.09(3H, s), 3.36(3H, s), 3.92(3H, s), 4.20(2H, s), 5.52(2H, s), 6.98-7.06(2H, m), 7.16-7.23(2H, m), 7.30-7.42(3H, m), 7.55-7.61(2H, m), 8.06(1H, br s), 9.04(1H, d, J=1.8 Hz), 9.74(1H, br s).

2) According to the method of Example A-15 (3), compound A-115 was synthesized from compound a-55.

mp: 225-227° C.

NMR(DMSO-d$_6$)δ: 2.84(3H, s), 3.11(3H, s), 3.94(3H, s), 4.27(3H, s), 7.12-7.22(2H, m), 7.36-7.43(2H, m), 8.55(1H, br s), 9.16(1H, d, J=2.0 Hz), 11.18(1H, br s), 11.28(1H, br s).

Example A-116 to A-118

According to the method of Example A-115, compounds A-116 to A-118 were synthesized.

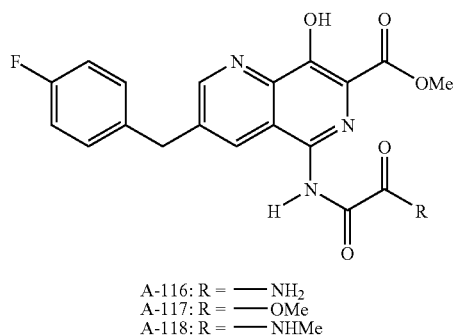

A-116: R = —NH$_2$
A-117: R = —OMe
A-118: R = —NHMe

A-116 5-[(Aminoxalyl)amino]-3-(4-fluorobenzyl)-8-hydroxy[1,6]naphthylidine-7-carboxylic acid methyl ester mp: 266-268° C.

NMR(DMSO-d$_6$)δ: 3.93(3H, s), 4.27(2H, s), 7.10-7.19 (2H, m), 7.32-7.39(2H, m), 8.02(1H, s), 8.21(1H, s), 8.26 (1H, s), 9.12(1H, s), 10.98(1H, s), 11.38(1H, br s).

A-117 3-(4-Fluorobenzyl)-8-hydroxy-5-[(methoxyoxalyl)amino][1,6]naphthylidine-7-carboxylic acid methyl ester mp: 115-117° C.

NMR(CDCl$_3$)δ: 4.02(3H, s), 4.11(3H, s), 4.21(2H, s), 6.97-7.06(2H, m), 7.12-7.20(2H, m), 7.95(1H, s), 9.04(1H, d, J=2.1 Hz), 9.31(1H, s), 11.76(1H, s).

A-118 3-(4-Fluorobenzyl)-8-hydroxy-5-[[(methylamino)oxalyl]amino][1,6]naphthylidine-7-carboxylic acid methyl ester mp: 253-254° C.

NMR(DMSO-d$_6$)δ: 2.77(3H, d, J=4.6 Hz), 3.92(3H, s), 4.26(2H, s), 7.10-7.18(2H, m), 7.32-7.38(2H, m), 8.22(1H, s), 8.88(1H, d, J=4.6 Hz), 9.11(1H, d, J=1.9 Hz), 11.00(1H, s), 11.37(1H, br s).

Example A-19

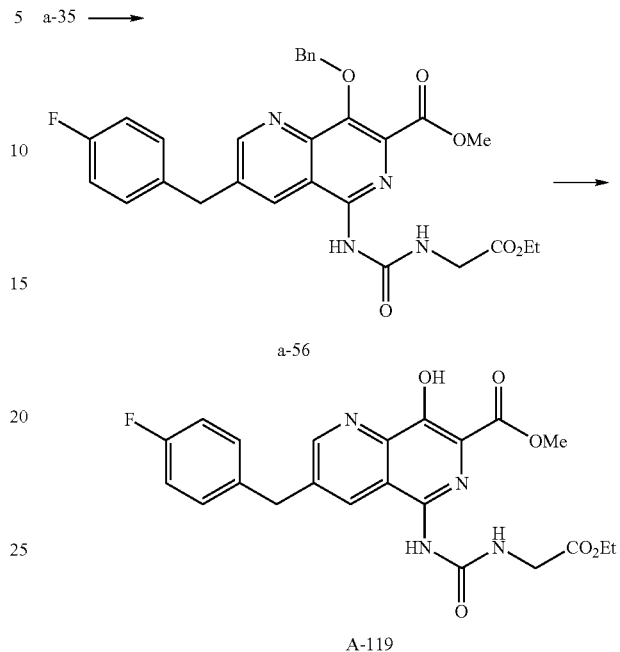

A-119 5-[3-[(Ethoxycarbonyl)methyl]ureido]-3-(4-fluorobenzyl)-8-hydroxy [1,6]naphthylidine-7-carboxylic acid methyl ester 1) To a solution of compound a-35 (208 mg, 0.50 mmol)) in tetrahydrofuran (4.0 ml), was added isocyanatoethyl acetate (0.067 ml, 0.60 mmol) under ice-cooling and the mixture was stirred at room temperature for 1 hr and 30 min. Isocyanatoethyl acetate (0.045 ml, 0.40 mmol) was added thereto and the mixture was refluxed under heating for 1 hr and 30 min. The mixture was allowed to stand for cooling, then diisopropyleter (8.0 ml) was added and the precipitated crystal was filtered off as compound a-56 (155 mg). Yield: 57%

NMR (CDCl$_3$) δ: 1.26 (3H, t, J=7.2 Hz), 3.94 (3H, s), 4.16-4.25 (4H, m), 5.40 (2H, s), 7.01-7.64 (9H, m), 8.37 (1H, s), 8.69 (1H, s), 9.05 (1H, d, J=1.8 Hz), 10.48 (1H, t, J=4.8 Hz).

2) According to the method of Example A-15 (3), compound A-119 was synthesized from compound a-56.

mp: 264-265° C.

Elementary analysis for C$_{22}$H$_{21}$FN$_4$O$_6$ Calculation (%): C, 57.89; H, 4.64; N, 12.28; F, 4.16. Found (%): C, 57.78; H, 4.49; N, 12.33; F, 4.05.

NMR (DMSO-d$_6$) δ: 1.22 (3H, t, J=6.9 Hz), 3.92 (3H, s), 4.09 (2H, d, J=5.7 Hz), 4.15 (2H, q, J=6.9 Hz), 4.20 (2H, s), 7.11-7.21 (2H, m), 7.37-7.47 (2H, m), 8.98 (1H, s), 9.11 (1H, d, J=1.5 Hz), 9.83 (1H, s), 10.02-10.12 (1H, m).

Example A-120

According to the method of Example A-119, compound A-120 was synthesized.

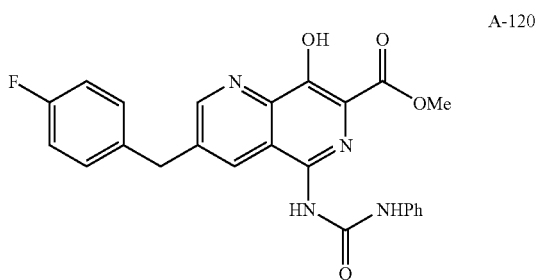

A-120 3-(4-Fluorobenzyl)-8-hydroxy-5-(3-phenylureido)-[1,6]naphthylidine-7-carboxylic acid methyl ester mp: 254-255° C.

Elementary analysis for $C_{24}H_{19}FN_4O_4$ Calculation (%): C, 64.57; H, 4.29; N, 12.55; F, 4.26. Found (%): C, 64.51; H, 4.30; N, 12.56; F, 4.02.

NMR (DMSO-$d_6$) δ: 4.02 (3H, s), 4.22 (2H, s), 7.03-7.21 (3H, m), 7.35-7.48 (4H, m), 7.70 (2H, d, J=7.5 Hz), 9.09 (1H, s), 9.15 (1H, d, J=1.8 Hz), 10.01 (1H, s), 12.69 (1H,

Example A-121

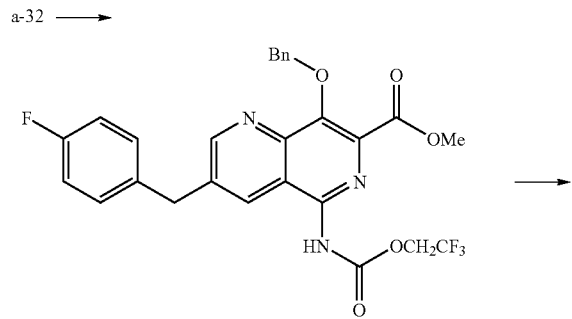

A-121 3-(4-Fluorobenzyl)-8-hydroxy-5-[[(2,2,2-trifluoroethoxy)carbonyl]amino][1,6]naphthylidine-7-carboxylic acid methyl ester 1) A solution of compound a-32 (223 mg, 0.50 mmol), diphenyl azidophosphate (0.129 ml, 0.60 mmol), triethyl amine (0.098 ml, 0.70 mmol), and 2,2,2-trifluoroethanol (0.091 ml, 1.25 mmol) in tetrahydrofuran (5.0 ml) was refluxed under heating under $N_2$ atomosphere for 4 hr and 30 min. The mixture was cooled to room temperature, and water was added thereto, which was extracted with ethyl acetate. The extract was washed with 0.5N citric acid aq., saturated sodium hydrogencarbonate aq., and water, then dried over anhydrous magnesium sulphate and evaporated in vaccum. The residue was purified with silica gel column chromatography and crystallized from methanol/diisopropyleter to give compound a-57 (99 mg). Yield: 36%

NMR (CDCl$_3$) δ: 3.83 (3H, s), 4.26 (2H, s), 4.80 (2H, q, J=9.0 Hz), 5.45 (2H, s), 7.12-7.22 (2H, m), 7.34-7.56 (7H, m), 8.33 (1H, s), 9.20 (1H, d, J=2.1 Hz), 11.75 (1H, brs).

2) According to the method of Example A-15 (3), compound A-121 was synthesized from compound a-57.

mp: 251-252° C.

NMR (DMSO-$d_6$) δ: 3.92 (3H, s), 4.27 (2H, s), 4.77 (2H, q, J=9.0 Hz), 7.10-7.20 (2H, m), 7.32-7.43 (2H, m), 8.18 (1H, s), 9.12 (1H, d, J=2.1 Hz), 10.50 (1H, s).

Example A-122 to A-125

According to the method of Example A-79, compounds A-122 to A-125 were synthesized.

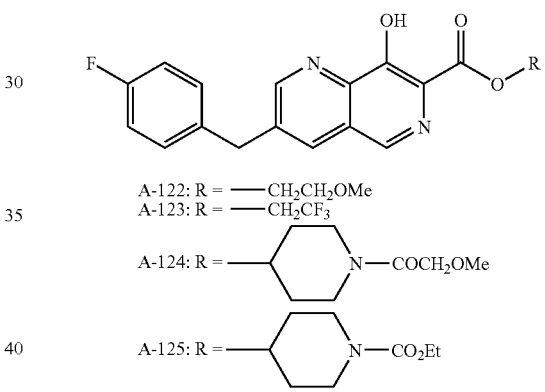

A-122 3-(4-Fluorobenzyl)-8-hydroxy[1,6]naphthylidine-7-carboxylic acid 2-methoxyethyl ester mp: 147-148° C.

Elementary analysis for $C_{19}H_{17}FN_2O_4$ Calculation (%): C, 64.04; H, 4.81; N, 7.86; F, 5.33. Found (%): C, 64.03; H, 4.89; N, 7.93; F, 5.05.

NMR (CDCl$_3$) δ: 3.44 (3H, s), 3.84 (2H, t like, J=4.8 Hz), 4.23 (2H, s), 4.69 (2H, t like, J=4.8 Hz), 7.05 (2H, t, J=8.7 Hz), 7.17-7.23 (2H, m), 7.96 (1H, d, J=2.1 Hz), 8.78 (1H, s), 9.07 (1H, d, J=2.1 Hz), 11.77 (1H, br. s).

A-123 3-(4-Fluorobenzyl)-8-hydroxy[1,6]naphthylidine-7-carboxylic acid 2,2,2-trifluoroethyl ester mp: 202-203° C.

Elementary analysis for $C_{18}H_{12}F_4N_2O_3$ Calculation (%): C, 56.85; H, 3.18; N, 7.37; F, 19.98. Found (%): C, 56.83; H, 3.20; N, 7.38; F, 19.70.

NMR (CDCl$_3$) δ: 4.24 (2H, s), 4.90 (2H, q, J=8.1 Hz), 7.06 (2H, t, J=8.7 Hz), 7.16-7.24 (2H, m), 7.98 (1H, d, J=2.1 Hz), 8.80 (1H, s), 9.08 (1H, d, J=2.1 Hz), 11.18 (1H, br. s).

A-124 3-(4-Fluorobenzyl)-8-hydroxy[1,6]naphthyridine-7-carboxylic acid [1-(2-methoxyacetyl)piperidin-4-yl]ester mp: 160-161° C.
Elementary analysis for $C_{24}H_{24}FN_3O_5$ Calculation (%): C, 63.57; H, 5.33; N, 9.27; F, 4.19. Found (%): C, 63.41; H, 5.29; N, 9.17; F, 3.82.
NMR (CDCl$_3$) δ: 1.89-2.10 (4H, m), 3.26-3.46 (2H, m), 3.44 (3H, s), 3.89-4.00 (1H, m), 4.13 & 4.15 (total 1H, each s), 4.18-4.32 (1H, m), 4.23 (2H, s), 5.35-5.45 (1H, m), 7.05 (2H, t, J=8.7 Hz), 7.16-7.24 (2H, m), 7.97 (1H, d, J=2.1 Hz), 8.77 (1H, s), 9.07 (1H, d, J=2.1 Hz), 11.83 (1H, br. s).

A-125 3-(4-Fluorobenzyl)-8-hydroxy[1,6]naphthyridine-7-carboxylic acid [1-(ethoxycarbonyl)piperidin-4-yl]ester mp: 147-148° C.
Elementary analysis for $C_{24}H_{24}FN_3O_5$ Calculation (%): C, 63.57; H, 5.33; N, 9.27; F, 4.19. Found (%): C, 63.45; H, 5.22; N, 9.23; F, 4.06.
NMR (CDCl$_3$) δ: 1.28 (3H, t, J=7.2 Hz), 1.88-2.18 (4H, m), 3.196-3.28 (2H, m), 3.99-4.11 (2H, m), 4.15 (2H, q, J=7.2 Hz), 4.23 (2H, s), 5.30-5.38 (1H, m), 7.05 (2H, t, J=8.7 Hz), 7.17-7.27 (2H, m), 7.96 (1H, d, J=2.1 Hz), 8.77 (1H, s), 9.07 (1H, d, J=2.1 Hz), 11.87 (1H, br. s).

Example A-126 a-39 ⟶

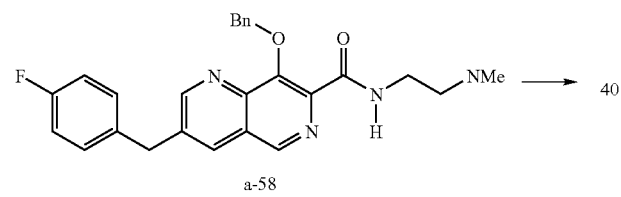
a-58

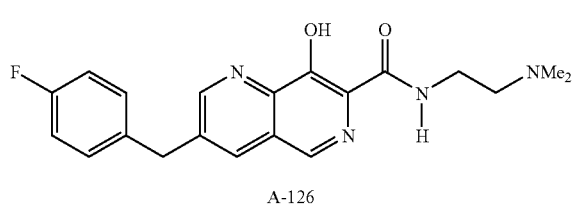
A-126

A-126 3-(4-Fluorobenzyl)-8-hydroxy[1,6]naphthyridine-7-carboxylic acid [2-(N,N-dimethylamino)ethyl]amide 1) According to the method of Example A-16 (3), compound a-58 was synthesized from compound a-39.
NMR (CDCl$_3$) δ: 2.22 (6H, s), 2.47 (2H, t, J=6.0 Hz), 3.56 (2H, q, J=6.0 Hz), 4.20 (2H, s), 5.57 (2H, s), 7.01-7.07 (2H, m), 7.17-7.22 (2H, m), 7.30-7.40 (3H, m), 7.62-7.67 (2H, m), 7.99 (1H, d, J=2.1 Hz), 8.18 (1H, br. s), 8.96 (1H, s), 9.03 (1H, d, J=2.1 Hz).

2) According to the method of Example A-15 (3), compound A-126 was synthesized from a-58.
mp: 151-152° C.
NMR (CDCl$_3$) δ:2.34 (6H, s), 2.60 (2H, t, J=6.0 Hz), 3.61 (2H, q, J=6.0 Hz), 4.20 (2H, s), 4.21(2H, s), 7.01-7.07(2H, m), 7.17-7.22(2H, m), 7.92(1H, d, J=2.1 Hz), 8.38(1H, br. s), 8.58 (1H, s), 9.03 (1H, d, J=2.1 Hz).

Example A-127 to A-142

According to the method of Example A-60, compounds A-127 to A-142 were synthesized.

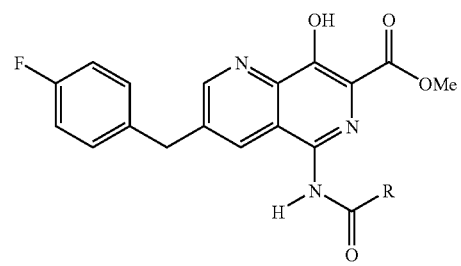

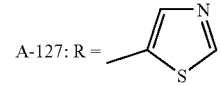
A-127: R =

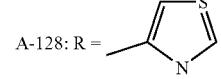
A-128: R =

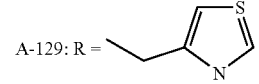
A-129: R =

A-130: R = —CMe$_3$

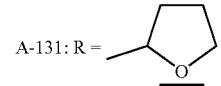
A-131: R =

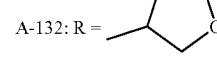
A-132: R =

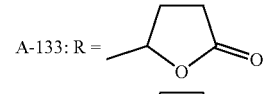
A-133: R =

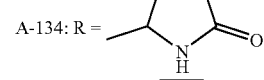
A-134: R =

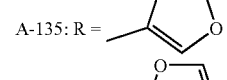
A-135: R =

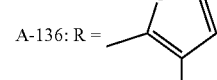
A-136: R =

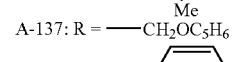
A-137: R = —CH$_2$OC$_5$H$_6$Me

A-138: R =

A-139: R =

-continued

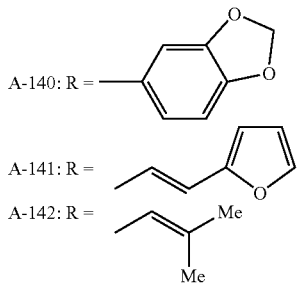

A-140: R = [benzo[1,3]dioxole]
A-141: R = [propenyl-furan]
A-142: R = [2-methylpropenyl, Me, Me]

A-127 3-(4-Fluorobenzyl)-8-hydroxy-5-[(thiazole-5-carbonyl)amino]-[1,6]naphthylidine-7-carboxylic acid methyl ester mp: 202-204° C. (dec)

Elementary analysis for $C_{21}H_{15}FN_4O_4S \cdot 0.4H_2O$ Calculation (%): C, 56.60; H, 3.57; F, 4.26; N, 12.57; S, 7.20. Found (%): C, 56.66; H, 3.45; F, 4.12; N, 12.52; S, 7.33.

NMR(DMSO-$d_6$)δ: 3.93(3H, s), 4.26(2H, s), 7.08-7.14 (2H, m), 7.33-7.36(2H, m), 8.20(1H, d, J=2.1 Hz), 8.81(1H, d, J=0.6 Hz), 9.11(1H, d, J=2.1 Hz), 9.37(1H, d, J=0.6 Hz), 11.29(2H, bs).

A-128 3-(4-Fluorobenzyl)-8-hydroxy-5-[(thiazole-4-carbonyl)-amino]-[1,6]naphthylidine-7-carboxylic acid methyl ester mp: 235-236° C. (dec)

Elementary analysis for $C_{21}H_{15}FN_4O_4S \cdot 0.3H_2O$ Calculation (%): C, 56.83; H, 3.54; F, 4.28; N, 12.62; S, 7.22. Found (%): C, 56.64; H, 3.30; F, 4.07; N, 12.47; S, 7.17.

NMR(DMSO-$d_6$)δ: 3.92(3H, s), 4.26(2H, s), 7.09-7.14 (2H, m), 7.31-7.36(2H, m), 8.20(1H, d, J=1.8 Hz), 8.55(1H, d, J=1.8 Hz), 9.11(1H, d, J=1.8 Hz), 9.31(1H, d, J=1.8 Hz), 10.75(1H, s), 11.36(1H, bs).

A-129 3-(4-Fluorobenzyl)-8-hydroxy-5-[(2-thiazole-4-yl)acetylamino][1,6]naphthylidine-7-carboxylic acid methyl ester mp: 227-228° C.(dec)

Elementary analysis for $C_{22}H_{17}FN_4O_4S$ Calculation (%): C, 58.40; H, 3.79; F, 4.20; N, 12.38; S, 7.09. Found (%): C, 58.47; H, 3.44; F, 4.21; N, 12.42; S, 7.08.

NMR(DMSO-$d_6$)δ: 3.90(3H, s), 3.97(2H, s), 4.19(2H, s), 7.08-7.14(2H, m), 7.27-7.32(2H, m), 7.50(1H, d, J=1.8 Hz), 8.16(1H, s), 9.06(1H, s), 9.08(1H, d, J=1.8 Hz), 10.71(1H, s)).

A-130 5-[(2,2-Dimethylpropionyl)amino]-3-(4-fluorobenzyl)-8-hydroxy[1,6]naphthylidine-7-carboxylic acid methyl ester mp: 238-239° C.(dec)

Elementary analysis for $C_{22}H_{22}FN_3O_4$ Calculation (%): C, 64.22; H, 5.39; F, 4.62; N, 10.21. Found (%): C, 64.25; H, 5.45; F, 4.52; N, 10.22.

NMR(DMSO-$d_6$)δ: 1.19(9H, s), 3.92(3H, s), 4.28(2H, s), 7.15-7.21(2H, m), 7.32-7.37(2H, m), 7.58(1H, d, J=2.1 Hz), 9.14(1H, d, J=2.1 Hz), 9.97(1H, s), 11.34(1H, bs).

A-131 3-(4-Fluorobenzyl)-8-hydroxy-5-[(tetrahydrofuran-2-carbonyl)amino][1,6]naphthylidine-7-carboxylic acid methyl mp: 181-183° C.

NMR(DMSO-$d_6$)δ: 1.80-1.94(3H, m), 2.15-2.28(1H, m), 3.78-3.87(1H, m), 2.91-4.00(1H, m), 3.92(3H, s), 4.29(2H, s), 4.44-4.49(1H, m), 7.14-7.23(2H, m). 7.31-7.38(2H, m), 7.77(1H, d, J=1.6 Hz), 9.14(1H, d, J=1.6 Hz), 10.23(1H, s), 11.30(1H, br s).

A-132 3-(4-Fluorobenzyl)-8-hydroxy-5-[(tetrahydrofuran3-carbonyl)amino][1,6]naphthylidine-7-carboxylic acid methyl ester mp: 240-241.5° C.

NMR(DMSO-$d_6$)δ: 1.95-2.16(2H, m), 3.23-3.33(1H, m), 3.67-3.77(3H, m), 3.92-3.99(1H, m), 3.92(3H, s), 4.27(2H, s), 7.13-7.20(2H, m), 7.32-7.38(2H, m), 7.84(1H, s), 9.12 (1H, d, J=1.8 Hz), 10.63(1H, s), 11.27(1H, br s).

A-133 3-(4-Fluorobenzyl)-8-hydroxy-5-[(5-oxotetrahydrofuran2-carbonyl)amino][1,6]naphthylidine-7-carboxylic acid methyl ester mp: 205-210° C.

NMR(DMSO-$d_6$)δ: 2.17-2.29(1H, m), 2.47-2.64(3H, m), 3.93(3H, s), 4.28(2H, s), 5.21-5.24(1H, m), 7.13-7.20(2H, m), 7.33-7.39(2H, m), 8.00(1H, s), 9.13(1H, d, J=2.0 Hz), 10.91(1H, s), 11.29(1H, br s).

A-134 3-(4-Fluorobenzyl)-8-hydroxy-5-[(5-oxopyrrolidine-2-carbonyl)amino][1,6]naphthylidine-7-carboxylic acid methyl ester mp: 217-219° C.

NMR(DMSO-$d_6$)δ: 1.89-2.01(1H, m), 2.15-2.22(2H, m), 2.31-2.45(1H, m), 3.92(3H, s), 4.27(2H, s), 4.31-4.37(1H, m), 7.12-7.21(2H, m), 7.32-7.39(2H, m), 7.92(1H, s), 7.95 (1H, s), 9.13(1H, d, J=2.0 Hz), 10.70(1H, s), 11.30(1H, br s).

A-135 3-(4-Fluorobenzyl)-5-[(furan-3-carbonyl)amino]-8-hydroxy[1,6]naphthylidine-7-carboxylic acid methyl ester mp: 106-108° C.

NMR(DMSO-$d_6$)δ: 3.93(3H, s), 4.26(2H, s), 7.04-7.06 (1H, m), 7.08-7.17(2H, m), 7.30-7.37(2H, m), 7.84(1H, t, J=1.7 Hz), 8.12(1H, d, J=1.9 Hz), 8.47(1H, s), 9.10(1H, d, J=1.9 Hz), 10.77(1H, s), 11.32(1H, br s).

A-136 3-(4-Fluorobenzyl)-8-hydroxy-5-[(3-methylfuran-2-carbonyl)amino][1,6]naphthylidine-7-carboxylic acid methyl ester mp: 213-215° C.

(DMSO-$d_6$)δ: 2.30(3H, s), 3.93(3H, s), 4.27(2H, s), 6.62 (1H, d, J=1.5 Hz), 7.07-7.16(2H, m), 7.32-7.38(2H, m), 7.83(1H, d, J=1.5 Hz), 8.17(1H, d, J=2.1 Hz), 9.12(1H, d, J=2.1 Hz), 10.58(1H, s), 11.33(1H, br s).

A-137 3-(4-Fluorobenzyl)-8-hydroxy-5-[(2-phenoxyacetyl)amino][1,6]naphthylidine-7-carboxylic acid methyl ester mp: 221-225° C.

(DMSO-$d_6$)δ: 3.93(3H, s), 4.21(2H, s), 4.90(2H, s), 6.97-7.17(5H, m), 7.29-7.39(4H, m), 8.21(1H, s), 9.10(1H, d, J=2.1 Hz), 10.74(1H, s), 11.28(1H, br s).

A-138 3-(4-Fluorobenzyl)-8-hydroxy-5-[(pyridine-4-carbonyl)amino][1,6]naphthylidine-7-carboxylic acid methyl ester mp: 215-220° C. (decomp.)

(DMSO-$d_6$)δ: 3.93(3H, s), 4.26(2H, s), 7.08-7.17(2H, m), 7.31-7.38(2H, m), 7.93-7.97(2H, m), 8.20(1H, d, J=1.9 Hz), 8.82-8.86(2H, m), 9.13(1H, d, J=1.9 Hz), 11.30(1H, s), 11.39(1H, br s).

A-139 3-(4-Fluorobenzyl)-8-hydroxy-5-[[(3,3,3-trifluoro)propionyl]amino][1,6]naphthylidine-7-carboxylic acid methyl ester mp: 246-248° C.

(DMSO-$d_6$) δ: 3.55-3.75 (2H, m), 3.92 (3H, s), 4.25 (2H, s), 7.10-7.20 (2H, m), 7.30-7.40 (2H, m), 8.04 (1H, s), 9.12 (1H, d, J=2.1 Hz), 10.92 (1H, s).

A-140 5-[(Benzo[1,3]dioxol-5-carbonyl)amino]-3-(4-fluorobenzyl)-8-hydroxy [1,6]naphthylidine-7-carboxylic acid methyl ester mp: 218-219° C.

(DMSO-$d_6$) δ: 3.93 (3H, s), 4.25 (2H, s), 6.16 (2H, s), 7.05-7.15 (3H, m), 7.27-7.37 (2H, m), 7.58 (1H, d, J=1.2 Hz), 7.63-7.71 (1H, m), 8.09 (1H, d, J=2.4 Hz), 9.10 (1H, d, J=2.4 Hz), 10.80 (1H, s), 11.34 (1H, brs).

A-141 3-(4-Fluorobenzyl)-5-[[(3-furan-2-yl)acryl]amino]-8-hydroxy[1,6]naphthylidine-7-carboxylic acid methyl ester mp: 247-249° C.

(DMSO-$d_6$) δ: 3.92 (3H, s), 4.25 (2H, s), 6.60-6.68 (1H, m), 6.75 (1H, d, J=15.3 Hz), 6.90 (1H, d, J=3.6 Hz), 7.07-7.17 (2H, m), 7.29-7.39 (2H, m), 7.43 (1H, d, J=15.3 Hz), 7.86 (1H, s), 8.11 (1H, d, J=1.5 Hz), 9.08 (1H, d, J=1.5 Hz), 10.80 (1H, s).

A-142 3-(4-Fluorobenzyl)-5-[(3,3-dimethylacryl)amino]-8-hydroxy[1,6]naphthylidine-7-carboxylic acid methyl ester mp: 229-230° C.

(DMSO-$d_6$) δ: 1.89 (3H, s), 2.09 (3H, s), 3.92 (3H, s), 4.25 (2H, s), 6.01 (1H, s), 7.08-7.18 (2H, m), 7.31-7.40 (2H, m), 8.00 (1H, d, J=2.1 Hz), 9.09 (1H, d, J=2.1 Hz), 10.37 (1H, s).

Example A-143

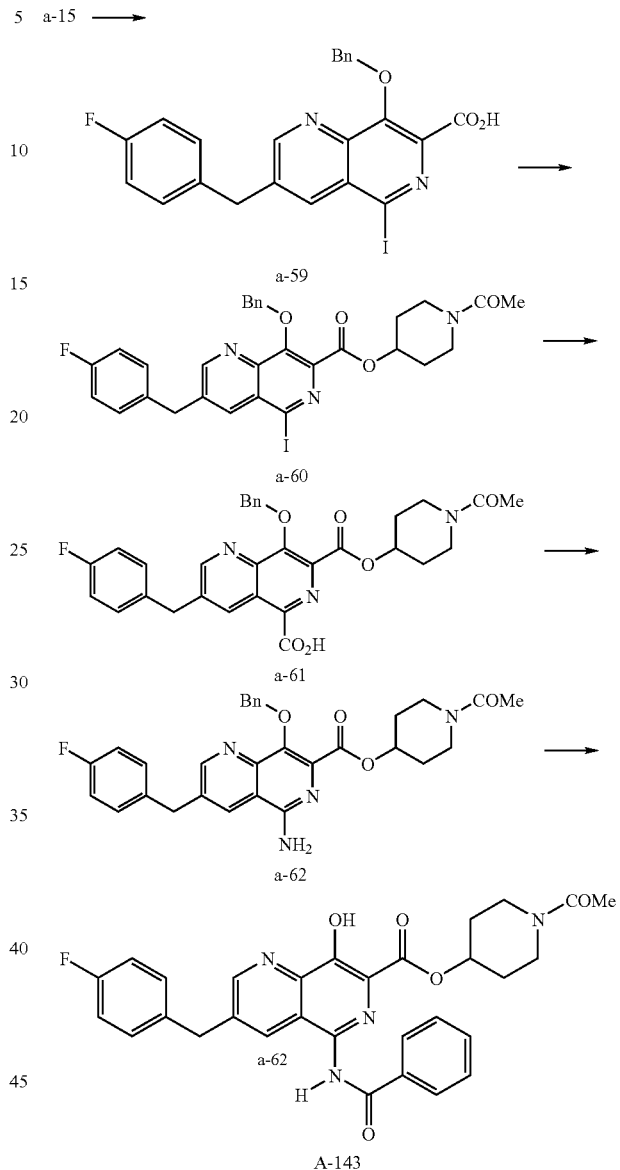

A-143 3-(4-Fluorobenzyl)-8-hydroxy-5-(benzoylamino)[1,6]naphthylidine-7-carboxylic acid (1-acetylpiperidine-4-yl) amide 1) To a suspension of the above compound a-15 (5.10 g, 9.65 mmol) in THF (25 ml)-methanol (25 ml), was added 2N NaOH aq. and the mixture was stirred at room temperature overnight. 2N HCl (12.5 ml) was added thereto and the mixture was evaporated in vaccum, then water was added, and extracted with ethyl acetate. The extract was washed with water and brine, then dried over anhydrous magnesium sulphate. The residue was crystallized from methanol (25 ml) to give compound a-59 (3.60 g) in 73% yield.

mp: 137-138° C.

(DMSO-d$_6$) δ: 4.28 (2H, s), 5.69 (2H, s), 7.08 (2H, t, J=8.7 Hz), 7.20-7.40 (5H, m), 7.58-7.62 (2H, m), 8.13 (1H, d, J=2.1 Hz), 9.03 (1H, d, J=2.1 Hz)

2) To a solution of the above compound a-59 (8.51 g, 16.6 mmol), N-acetyl-4-hydroxypiperidine (4.74 g, 33.1 mmol), and triphenylphosphine (8.69 g) in tetrahydrofuran (250 ml), was added dropwise, under N$_2$ atomosphere and ice-cooling, a solution of azodicarboxylic acid diisopropyl in 40% toluen (17.7 g) and the mixture was stirred at the same temperature for 2 hr. The residue obtained by evaporation in vaccum was purified with silica gel column chromatography. Crystallization from acetone/eter gave compound a-60 (10.32 g) in 98% yield.

mp: 141-143° C.

(CDCl$_3$) δ: 1.59-1.97 (4H, m), 2.07 (3H, s), 3.23-3.35 (1H, m), 3.43-3.60 (2H, m), 3.73-3.83 (1H, m), 4.26 (2H, s), 5.20-5.30 (1H, m), 5.57 (2H, s), 7.06 (2H, t like, J=8.7 Hz), 7.18-7.25 (2H, m), 7.33-7.72 (5H, m), 8.14 (1H, d, J=2.4 Hz), 8.96 (1H, J=2.4 Hz).

3) To a solution of the above compound a-60 (8.80 g, 13.8 mmol) in dimethylformamide (220 ml), were added triethylamine (5.8 ml, 41.6 mmol), allylalcohol (9.38 ml, 138 mmol) and palladium acetate (155 mg, 0.69 mmol), and the mixture was stirred at CO atomosphere and room temperature for 7.5 hr. Citric acid (9 g) and water (700 ml) were added thereto and the mixture was extracted with ethyl acetate (×2). The extract was washed with water, dried over anhydrous magnesium sulphate, and evaporated in vaccum. The residue was crystallized from THF-diisopropyleter to give a-61 (6.27 g) in 82% yield.

NMR (DMSO-d$_6$) δ: 1.40-1.98 (4H, m), 1.98 (3H, s), 3.18-3.80 (4H, m), 4.31 (2H, s), 5.10-5.20 (1H, m), 5.64 (2H, s), 7.18 (2H, t like, J=8.7 Hz), 7.34-7.67 (7H, m), 8.89 (1H, J=2.1 Hz), 9.23 (1H, d, J=2.1 Hz).

4) Compound a-62 was synthesized from above compound a-61 according to Example A-59, (1) and (2).
mp: 104-107° C.

(CDCl$_3$) δ: 1.60-2.00 (4H, m), 2.05 (3H, s), 3.21-3.60 (3H, m), 3.80-3.90 (1H, m), 4.19 (2H, s), 5.19-5.35 (3H, m), 5.36 (2H, s), 7.01-7.09 (2H, m), 7.15-7.42 (5H, m), 7.52-7.58 (2H, m), 7.88 (1H, br. s), 8.99 (1H, d, J=2.1 Hz).

5) Compound A-143 was synthesized from compound a-62 according to Example A-60, (1) and (2).
mp: 124-126° C.

(DMSO-d$_6$)δ: 1.58-2.02(4H, m), 2.02(3H, s), 3.10-3.50 (2H, m), 3.71-3.97(2H, m), 4.25(2H, s), 5.23-5.28(1H, m), 7.08-7.13(2H, m), 7.30-7.35(2H, m), 7.54-7.68(3H, m), 8.04-8.06(2H, m), 8.12(1H, d, J=2.1 Hz), 9.11(1H, d, J=2.1 Hz), 10.98(1H, s), 11.43(1H, bs).

Example A-144 to A-148

According to the method of Example A-143, Compound A-144 to A-148 were synthesized.

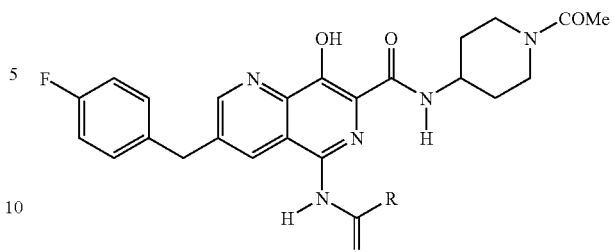

A-144: R = —OEt
A-145: R = —CONMe$_2$
A-146: R = —CONH$_2$
A-147: R = (2-thienyl)
A-148: R = (thiazol-4-yl)

A-144. 5-(Ethoxycarbonylamino)-3-(4-fluorobenzyl)-8-hydroxy[1,6]naphthylidine-7-carboxylic acid (1-acetylpiperidine-4-yl) ester NMR(CDCl$_3$)δ: 1.31(3H, t, J=7.2 Hz), 1.95-2.16(4H, m), 2.16(3H, s), 3.43-3.56(2H, m), 3.79-4.10(2H, m), 4.23(2H, q, J=7.2 Hz), 5.37-5.42(1H, m), 7.00-7.06(2H, m), 7.17-7.22 (2H, m), 8.29(1H, s), 9.05(1H, d, J=2.1 Hz).

A-145. 5-[[(Dimethylamino)oxalyl]amino]-3-(4-fluorobenzyl)-8-hydroxy[1,6]naphthylidine-7-carboxylic acid (1-acetylpiperidine-4-yl)ester NMR(CDCl$_3$)δ: 1.91-2.16(4H, m), 2.16(3H, s), 3.12(3H, s), 3.40(3H, s), 3.40-3.60(2H, m), 3.81-4.07(2H, m), 4.22 (2H, s), 5.36-5.41(1H, m), 7.00-7.09(2H, m), 7.17-7.21(2H, m), 7.95(1H, d, J=2.1 Hz), 9.05(1H, d, J=2.1 Hz), 11.66(1H, bs).

A-146. 5-[(Aminooxalyl)amino]-3-(4-fluorobenzyl)-8-hydroxy[1,6]naphthylidine7-carboxylic acid (1-acetylpiperidine4-yl)ester mp: 133-135° C.
(DMSO-d$_6$)δ:1.60-2.03(4H, m), 2.03(3H, s), 3.10-3.50 (2H, m), 3.70-3.93(2H, m), 4.27(2H, s), 5.23-5.28(1H, m), 7.12-7.18(2H, m), 7.33-7.38(2H, m), 8.01(1H, s), 8.19(1H, d, J=1.8 Hz), 8.26(1H, s), 9.11(1H, d, J=1.8 Hz), 10.98(1H, s), 11.35(1H, bs).

A-147. 3-(4-Fluorobenzyl)-8-hydroxy5-[(thiophene-2-carbonyl)amino][1,6]naphthylidine-7-carboxylic acid (1-acetylpiperidine-4-yl) ester mp: 135-137° C.
(DMSO-d$_6$)δ:1.58-2.02(4H, m), 2.02(3H, s), 3.10-3.50 (2H, m), 3.71-3.99(2H, m), 4.26(2H, s), 5.23-5.28(1H, m), 7.07-7.13(2H, m), 7.26-7.35(3H, m), 7.92(1H, m), 8.12-8.16 (2H, m), 9.10(1H, d, J=2.1 Hz), 11.05(1H, s), 11.41(1H, bs).

A-148. 3-(4-Fluorobenzyl)-8-hydroxy5-[(thiazole-4-carbonyl)amino][1,6]naphthylidine-7-carboxylic acid (1-acetylpiperidine-4-yl)ester NMR(CDCl$_3$)δ: 1.97-2.15(4H, m), 3.42-3.45(2H, m), 3.80-4.09(2H, m), 4.22(2H, s), 5.36-5.42(1H, m), 6.97-7.03 (2H, m), 7.15-7.20(2H, m), 8.15(1H, d, J=2.1 Hz), 8.34(1h, d, J=2.1 Hz), 8.91(1H, d, J=2.1 Hz), 9.04(1H, d, J=2.1 Hz).

Example A-149

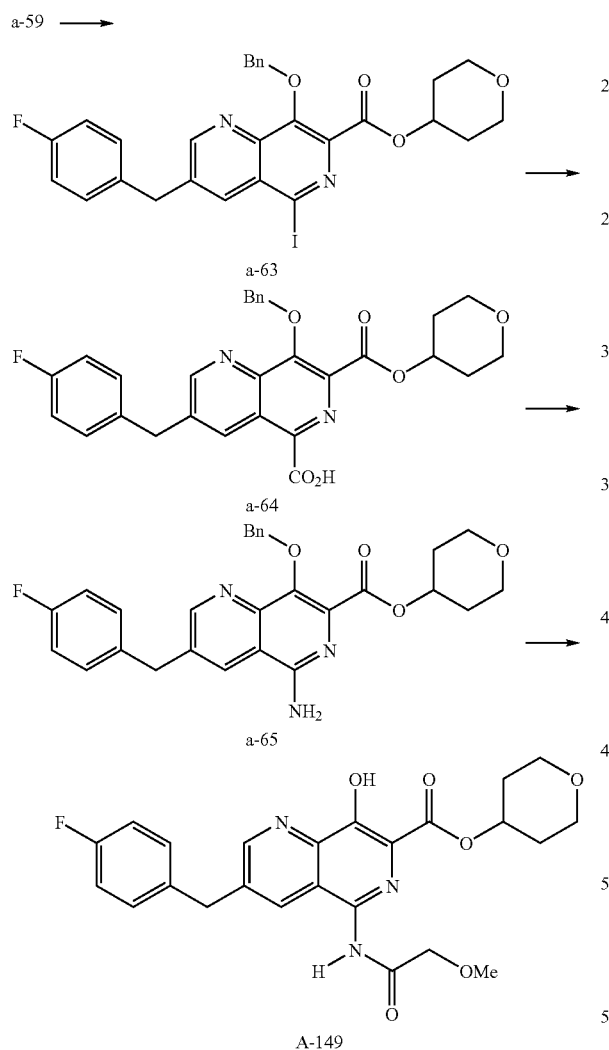

A-149

A-149. 3-(4-Fluorobenzyl)-8-hydroxy5-[(2-methoxyacetyl)amino][1,6]naphthylidine-7-carboxylic acid (tetorahydropyran-4-yl)ester 1) According to the method of Example A-143, compounds a-59 to a-63 were synthesized.

NMR (CDCl$_3$) δ:1.65-1.81(2H, m), 1.93-2.12(2H, m), 3.50-3.59(2H, m), 3.86-3.95(2H, m), 4.25(2H, s), 5.18-5.25 (1H, m), 5.55(2H, s), 7.03-7.10(2H, m), 7.19-7.40(5H, m), 7.50-7.55(2H, m), 8.14(1H, d, J=2.1 Hz), 8.95(1H, d, J=2.1 Hz)

2) According to the method of Example A-143, compounds a-63 to a-64 were synthesized.

NMR (CDCl$_3$) δ: 1.67-1.81(2H, m), 1.96-2.07(2H, m), 3.50-3.59(2H, m), 3.86-3.95(2H, m), 4.26(2H, s), 5.19-5.28 (1H, m), 5.80(2H, s), 7.00-7.08(2H, m), 7.19-7.41(5H, m), 7.48-7.54(2H, m), 9.05(1H, d, J=2.1 Hz), 9.74(1H, d, J=2.1 Hz), 11.39 (1H, br.s)

3) According to the method of Example A-143, compounds a-64 to a-65 were synthesized.

NMR (CDCl$_3$) δ:1.70-1.80(2H, m), 1.94-2.04(2H, m), 3.47-3.56(2H, m), 3.87-3.95(2H, m), 4.18(2H, s), 5.15-5.26 (1H, m), 5.29 (2H, br.s), 5.35(2H, s), 7.00-7.08(2H, m), 7.14-7.20(2H, m), 7.29-7.40(3H, m), 7.54-7.60(2H, m), 7.87 (1H, br.s), 8.99(1H, d, J=2.1 Hz)

4) According to the method of Example A-143, (5), compounds a-65 to Example A-149 were synthesized.

mp: 80-83° C.

(DMSO-d$_6$)δ: 1.65-1.78(2H, m), 1.97-2.06(2H, m), 3.38 (3H, s), 3.48-3.57(2H, m), 3.86-3.94(2H, m), 4.18(2H, s), 4.26(2H, s), 5.17-5.27(1H, m), 7.11-7.20(2H, m), 7.32-7.39 (2H, m), 8.12(1H, s), 9.10(1H, d, J=2.0 Hz), 10.41(1H, s), 11.35(1H, br s).

Example A-150 to A-152

According to the method of Example A-149, compounds A-150 to A-152 were synthesized.

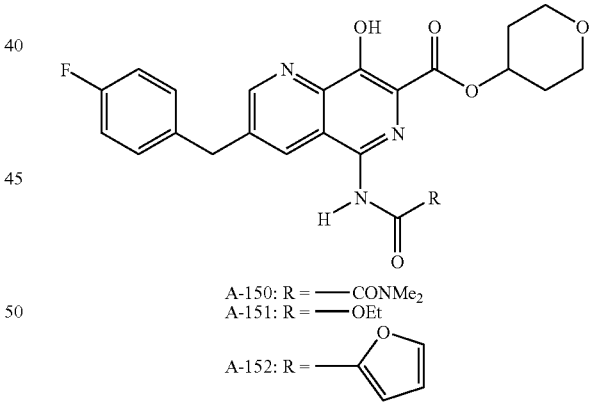

A-150: R = —CONMe$_2$
A-151: R = —OEt
A-152: R = (2-furyl)

A-150. 5-[[[(Dimethylamino)oxalyl]amino]-3-(4-fluorobenzyl)-8-hydroxy[1,6]naphthylidine-7-carboxylic acid (tetrahydropyrane-4-yl) ester mp: 118.5-121° C.

(CDCl$_3$)δ: 1.92-2.05(2H, m), 2.08-2.17(2H, m), 3.12(3H, s), 3.39(3H, s), 3.57-3.66(2H, m), 4.03-4.11(2H, m), 4.21 (2H, s), 5.27-5.37(1H, m), 6.98-7.07(2H, m), 7.15-7.22(2H, m), 7.94(1H, s), 9.04(1H, d, J=1.9 Hz), 9.60(1H, br s), 11.78(1H, s).

A-151. 5-[(Ethoxycarbonyl)amino]-3-(4-fluorobenzyl)-8-hydroxy[1,6]naphthylidine-7-carboxylic acid (tetrahydropyrane-4-yl) ester mp: 91-94° C.

(DMSO-$d_6$)δ: 1.15(3H, t, J=7.0 Hz), 1.62-1.76(2H, m), 1.94-2.05(2H, m), 3.46-3.56(2H, m), 3.84-3.93(2H, m), 4.05 (2H, q, J=7.0 Hz), 4.25(2H, s), 5.16-5.23(1H, m), 7.11-7.18 (2H, m), 7.33-7.39(2H, m), 8.10(1H, s), 9.10(1H, d, J=1.7 Hz), 9.90(1H, s), 11.29(1H, s).

A-152. 3-(4-Fluorobenzyl)-5-[(frane-2-carbonyl)amino]-8-hydroxy[1,6]naphthylidine-7-carboxylic acid (tetrahydropyrane-4-yl) ester mp: 107-110° C.

(DMSO-$d_6$)δ: 1.65-1.78(2H, m), 1.98-2.06(2H, m), 3.47-3.56(2H, m), 3.86-3.94(2H, m), 4.26(2H, s), 5.18-5.27(1H, m), 6.75(1H, dd, J=3.5, 1.7 Hz), 7.07-7.16(2H, m), 7.30-7.37(2H, m), 7.48(1H, d, J=3.5 Hz), 7.99(1H, t, J=0.9 Hz), 8.17(1H, d, J=2.0 Hz), 9.10(1H, d, J=2.0 Hz), 10.91(1H, s), 11.44(1H, br s).

Example A-153

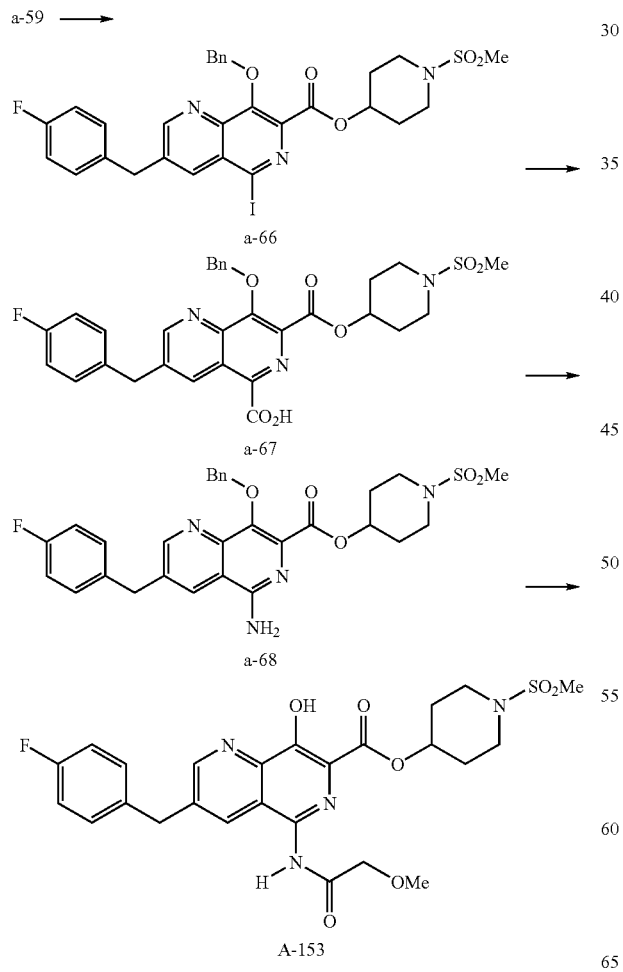

A-153. 3-(4-Fluorobenzyl)-8-hydroxy-5-[(2-methoxyacetyl)amino][1,6]naphthylidine-7-carboxylic acid [(1-methanesulfony)piperidine4-yl]ester 1) According to the method of Example A-143 (2), compounds a-59 to a-66 were synthesized.
NMR (CDCl$_3$) δ:1.81-2.08(4H, m), 2.71(3H, s), 3.20-3.30 (4H, m), 4.26(2H, s), 5.20-5.28(1H, m), 5.55(2H, s), 7.03-7.10(2H, m), 7.19-7.24(2H, m), 7.34-7.42(3H, m), 7.50-7.54 (2H, m), 8.14(1H, d, J=2.1 Hz), 8.97(1H, d, J=2.1 Hz)

2) According to the method of Example A-143 (3), compounds a-66 to a-67 were synthesized.
NMR (CDCl$_3$) δ:1.75-1.87(2H, m), 1.93-2.08(2H, m), 2.71(3H, s), 3.16-3.31(4H, m), 4.26(2H, s), 5.21-5.27(1H, m), 5.81(2H, s), 7.01-7.08(2H, m), 7.19-7.25(2H, m), 7.35-7.42(3H, m), 7.47-7.51(2H, m), 9.06(1H, d, J=2.3 Hz), 9.75(1H, d, J=2.1 Hz)

3) According to the method of Example A-143 (4), compounds a-67 to a-68 were synthesized.
NMR (CDCl$_3$) δ:1.80-2.03(4H, m), 2.63(3H, s), 3.13-3.29 (4H, m), 4.19(2H, s), 5.17-5.23(1H, m), 5.27(1H, s), 5.33 (2H, s), 7.01-7.07(2H, m), 7.16-7.21(2H, m), 7.33-7.41(3H, m), 7.54-7.57(2H, m), 7.87(1H, s), 8.99(1H, d, J=2.0 Hz)

4) According to the method of Example A-143 (5), compounds a-68 to Example A-153 were synthesized.
mp: 175-176° C.
Elementary analysis for $C_{25}H_{27}F_1N_4O_7S_1$ Calculation (%): C, 54.94; H, 4.98; N, 10.25; F, 3.48; S, 5.87. Found (%): C, 54.83; H, 4.90; N, 10.23; F, 3.54; S, 5.68.
(CDCl$_3$) δ:2.06-2.23(4H, m), 2.86(3H, s), 3.24-3.32(2H, m), 3.57(3H, s), 3.59-3.67(2H, m), 4.14(2H, s), 4.22(2H, s), 5.29-5.34(1H, m), 7.00-7.07(2H, m), 7.16-7.21(2H, m), 8.01 (1H, s), 9.01(1H, d, J=2.1 Hz), 11.48(1H, s)

Example A-154 to A-159

According to the method of Example A-153, compounds A-154 to A-159 were synthesized.

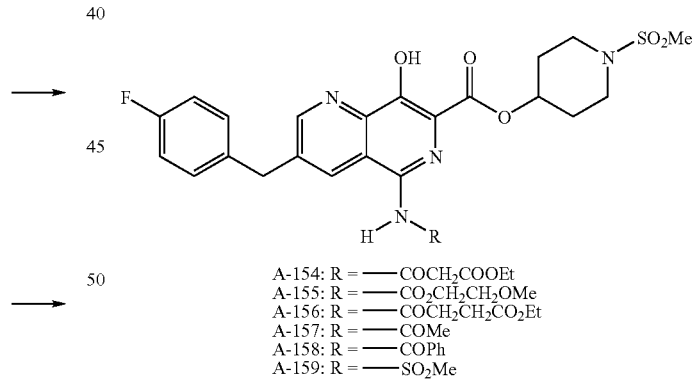

A-154: R = —COCH$_2$COOEt
A-155: R = —CO$_2$CH$_2$CH$_2$OMe
A-156: R = —COCH$_2$CH$_2$CO$_2$Et
A-157: R = —COMe
A-158: R = —COPh
A-159: R = —SO$_2$Me

A-154. 5-[[(2-Ethoxycarbonyl)acetyl]amino]-3-(4-fluorobenzyl)-8-hydroxy[1,6]naphthylidine-7-carboxylic acid [(1-methanesulfony)piperidine-4-yl] ester mp: 98-100° C.
Elementary analysis for $C_{27}H_{29}F_1N_4O_8S_1 0.3H_2O$ Calculation (%): C, 55.09; H, 4.97; N, 9.52; F, 3.23; S, 5.45. Found (%): C, 54.59; H, 5.02; N, 9.43; F, 3.20; S, 5.40.
(CDCl$_3$) δ:1.33(3H, t, J=7.0 Hz), 2.06-2.23(4H, m), 2.87 (3H, s), 3.30-3.40(2H, m), 3.50-3.60(2H, m), 3.64(2H, s), 4.22(2H, s), 4.27(2H, q, J=7.0 Hz), 5.30-5.40(1H, m), 7.00-7.07(2H, m), 7.16-7.21(2H, m), 8.14(1H, brs), 9.03(1H, d, J=2.0 Hz), 11.47(1H, s)

A-155. 3-(4-Fluorobenzyl)-8-hydroxy-5-[[(2-methoxyethoxy)carbonyl]amino][1,6]naphthylidine-7-carboxylic acid [(1-methanesulfony)piperidine-4-yl]ester mp: 115-116° C.

Elementary analysis for $C_{26}H_{29}F_1N_4O_8S_1 \cdot 0.3H_2O$ Calculation (%): C, 54.16; H, 5.07; N, 9.72; F, 3.29; S, 5.56. Found (%): C, 53.72; H, 5.19; N, 9.25; F, 3.12; S, 5.24.

(CDCl$_3$) δ:2.00-2.23(4H, m), 2.87(3H, s), 3.30-3.40(2H, m), 3.42(3H, s), 3.50-3.60(2H, m), 3.63-3.66(2H, m), 4.21(2H, s), 4.30-4.33(2H, m), 5.30-5.40(1H, m), 7.00-7.06(2H, m), 7.16-7.21(2H, m), 8.20(1H, brs), 9.01(1H, d, J=2.1 Hz), 11.39(1H, s)

A-156. 5-[[3-(Ethoxycarbonyl)propionyl]amino]-3-(4-fluorobenzyl)-8-hydroxy[1,6]naphthylidine-7-carboxylic acid [(1-methanesulfony)piperidine-4-yl]ester mp: 168-170° C.

Elementary analysis for $C_{28}H_{31}F_1N_4O_8S_1$ Calculation (%): C, 55.81; H, 5.18; N, 9.30; F, 3.15; S, 5.32. Found (%): C, 55.77; H, 5.07; N, 9.28; F, 3.12; S, 5.23.

(CDCl$_3$) δ: 1.26(3H, t, J=7.2 Hz), 2.00-2.23(4H, m), 2.70-2.93(7H, m), 3.18-3.30(2H, m), 3.50-3.65(2H, m), 4.14(2H, q, J=7.0 Hz), 4.21(2H, s), 5.23-5.38(1H, m), 7.00-7.06(2H, m), 7.16-7.21(2H, m), 8.20(1H, brs), 9.00(1H, d, J=2.1 Hz), 11.44(1H, s)

A-157. 5-(Acetylamino)-3-(4-fluorobenzyl)-8-hydroxy[1,6]naphthylidine-7-carboxylic acid [(1-methanesulfony)piperidine-4-yl]ester mp: 136-138° C.

Elementary analysis for $C_{24}H_{25}F_1N_4O_6S_1 \cdot 0.6H_2O$ Calculation (%): C, 54.66; H, 5.01; N, 10.62; F, 3.60; S, 6.08. Found (%): C, 54.75; H, 4.96; N, 10.04; F, 3.26; S, 5.76.

(CDCl$_3$) δ:2.00-2.23(4H, m), 2.36(3H, s), 2.85(3H, s), 3.18-3.30(2H, m), 3.50-3.65(2H, m), 4.23(2H, s), 5.23-5.38(1H, m), 7.00-7.06(2H, m), 7.16-7.21(2H, m), 8.02(1H, brs), 9.03(1H, s), 11.40(1H, s)

A-158. 5-(Benzoylamino)-3-(4-fluorobenzyl)-8-hydroxy[1,6]naphthylidine-7-carboxylic acid [(1-methanesulfony)piperidine-4-yl]ester mp: 159-163° C.

Elementary analysis for $C_{29}H_{27}F_1N_4O_6S_1 \cdot 0.3H_2O$ Calculation (%): C, 59.64; H, 4.76; N, 9.59; F, 3.25; S, 5.49. Found (%): C, 59.64; H, 4.68; N, 9.46; F, 3.21; S, 5.34.

(CDCl$_3$) δ:2.00-2.23(4H, m), 2.88(3H, s), 2.85(3H, s), 3.30-3.50(2H, m), 3.53-3.65(2H, m), 4.23(2H, s), 5.30-5.50(1H, m), 6.98-7.04(2H, m), 7.17-7.21(2H, m), 7.50-7.65(3H, m), 8.08(2H, d, J=7.3 Hz), 8.40(1H, brs), 9.03(1H, d, J=2.1 Hz), 11.20(1H, s)

A-159. 3-(4-Fluorobenzyl)-8-hydroxy-5-(methanesulfonyamino)[1,6]naphthylidine-7-carboxylic acid [(1-methanesulfony)piperidine-4-yl]ester mp: 257-259° C.

Elementary analysis for $C_{23}H_{25}F_1N_4O_7S_2$ Calculation (%): C, 49.99; H, 4.65; N, 10.14; F, 3.44; S, 11.61. Found (%): C, 49.89; H, 4.47; N, 9.86; F, 3.40; S, 11.22.

(CDCl$_3$) δ:2.00-2.20(4H, m), 2.90(3H, s), 3.12(3H, s), 3.20-3.35(2H, m), 3.60-3.70(2H, m), 4.18(2H, s), 5.52-5.60(1H, m), 7.00-7.04(2H, m), 7.17-7.21(2H, m), 8.64(1H, d, J=2.1 Hz), 9.01(1H, d, J=2.1 Hz), 11.95(1H, s)

Example A-160

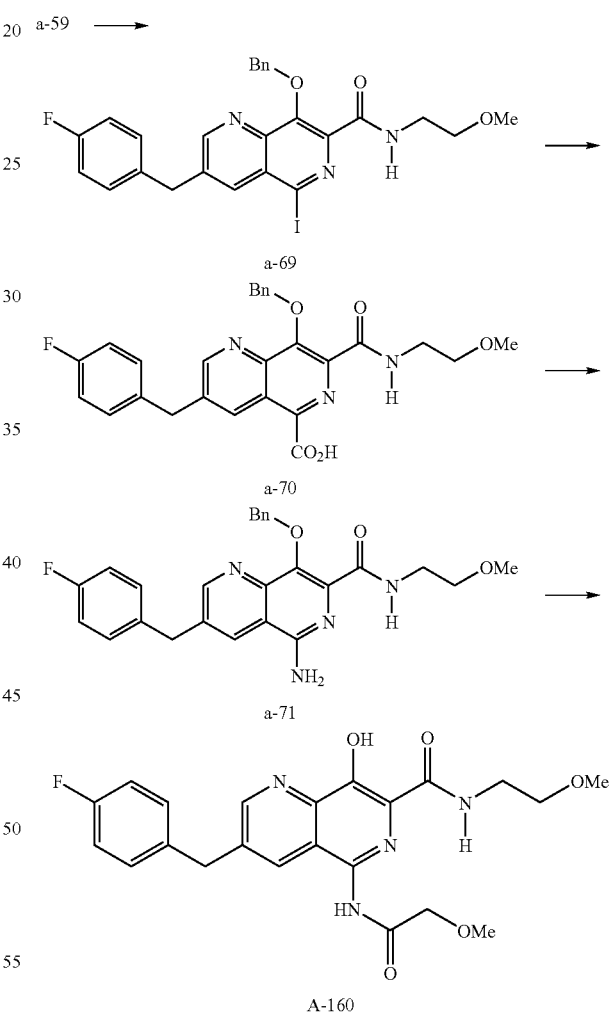

A-160. 3-(4-Fluorobenzyl)-8-hydroxy-5-[(2-methoxyacetyl)amino][1,6]naphthylidine-7-carboxylic acid (2-methoxyethyl)amide 2) According to the method of Example A-16 (3), compounds a-59 to a-69 were synthesized.

mp: 74-78° C.

(CDCl$_3$) δ: 3.38 (3H, s), 3.55-3.70 (4H, m), 4.25 (2H, s), 5.52 (2H, s), 7.06 (2H, t, J=8.7 Hz), 7.19-7.40 (5H, m), 7.62-7.68 (2H, m), 7.95-8.02 (1H, m), 8.10 (1H, d, J=2.1 Hz), 8.97 (1H, d, J=2.1 Hz)

3) According to the method of Example A-143 (3), compounds a-69 to a-70 were synthesized.

mp: 149-151° C.

(CDCl$_3$) δ: 3.29 (3H, s), 3.44-3.48 (2H, m), 3.58-3.64 (2H, m), 4.25 (2H, s), 5.79 (2H, s), 7.04 (2H, t, J=8.7 Hz), 7.19-7.27 (2H, m), 7.36-7.40 (3H, m), 7.49-7.54 (2H, m), 8.19-8.28 (1H, m), 9.05 (1H, d, J=2.1 Hz), 9.74 (1H, d, J=2.1 Hz)

4) According to the method of Example A-143 (4), compounds a-70 to a-71 were synthesized.

mp: 170-172° C.

(CDCl$_3$) δ: 3.30 (3H, s), 3.47-3.53 (2H, m), 3.56-3.64 (2H, m), 4.18 (2H, s), 5.33 (2H, s), 5.37 (2H, br. s), 7.04 (2H, t, J=8.7 Hz), 7.16-7.22 (2H, m), 7.32-7.40 (3H, m), 7.60-7.64 (2H, m), 8.88 (1H, br. s), 8.18-8.24 (1H, m), 8.99 (1H, d, J=2.1 Hz)

5) According to the method of Example A-143 (5), compound a-71 to compound A-160 were synthesized.

mp: 170° C.

(CDCl$_3$)δ: 3.43(3H, s), 3.59(3H, s), 3.59-3.64(2H, m), 3.66-3.73(2H, s), 4.20(2H, s), 6.98-7.06(2H, m), 7.14-7.20 (2H, m), 7.95(1H, br s), 8.06-8.12(1H, m), 8.64(1H, br s), 9.00(1H, d, J=2.2 Hz), 13.26(1H, br s).

Example A-161 to A-165

According to the method of Example A-160, compounds A-161 to A-165 were synthesized.

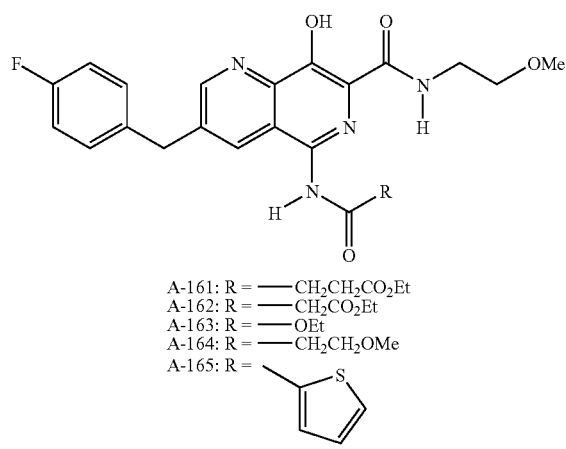

A-161: R = —CH$_2$CH$_2$CO$_2$Et
A-162: R = —CH$_2$CO$_2$Et
A-163: R = —OEt
A-164: R = —CH$_2$CH$_2$OMe
A-165: R = —(2-thienyl)

A-161. 5-[[3-(Ethoxycarbonyl)propionyl]amino]-3-(4-fluorobenzyl)-8-hydroxy[1,6]naphthylidine-7-carboxylic acid (2-methoxyethyl)amide mp: 190° C.

(DMSO-d$_6$)δ: 1.18(3H, t, J=7.1 Hz), 2.61-2.67(2H, m), 2.71-2.77(2H, m), 3.29(3H, s), 3.53(4H, s), 4.07(2H, q, J=7.1 Hz), 4.21(2H, s), 7.11-7.18(2H, m), 7.32-7.39(2H, m), 8.22(1H, s), 8.74(1H, br s), 9.08(1H, d, J=1.8 Hz), 10.52(1H, s), 13.58(1H, s).

A-162. 5-[[2-(Ethoxycarbonyl)acetyl]amino]-3-(4-fluorobenzyl)-8-hydroxy[1,6]naphthylidine-7-carboxylic acid (2-methoxyethyl)amide mp: 224-226° C.

(DMSO-d$_6$)δ: 1.19(3H, t, J=6.7 Hz), 3.29(3H, s), 3.54 (4H, s), 3.66(2H, s), 4.09-4.14(2H, m), 4.23(2H, s), 7.11-7.18(2H, m), 7.32-7.38(2H, m), 8.32(1H, s), 8.76(1H, br s), 9.09(1H, d, J=1.7 Hz), 10.69(1H, s), 13.61(1H, s).

A-163. 5-[(Ethoxycarbonyl)amino]-3-(4-fluorobenzyl)-8-hydroxy[1,6]naphthylidine-7-carboxylic acid (2-methoxyethyl)amide mp: 175° C.

(CDCl$_3$) δ: 1.30 (3H, t, J=7.2 Hz), 3.43 (3H, s), 3.59-3.72 (4H, m), 4.20 (3H, s), 4.18-4.27 (4H, m), 6.90 (1H, brs), 6.98-7.08 (2H, m), 7.14-7.24 (2H, m), 8.00-8.16 (2H, m), 9.00 (1H, d, J=2.1 Hz), 13.18 (1H, s).

A-164. 3-(4-Fluorobenzyl)-8-hydroxy-5-[(3-methoxypropionyl)amino][1,6]naphthylidine-7-carboxylic acid (2-methoxyethyl)amide mp: 164-165° C.

(CDCl$_3$) δ: 2.75 (2H, t, J=6.0 Hz), 3.43 (3H, s), 3.46 (3H, s), 3.57-3.76 (4H, m), 3.80 (2H, t, J=6.0 Hz), 4.20 (3H, s), 6.98-7.07 (2H, m), 7.14-7.24 (2H, m), 7.94 (1H, s), 8.13 (1H, brs), 8.45 (1H, brs), 8.99 (1H, d, J=2.4 Hz), 13.22 (1H, s).

A-165. 3-(4-Fluorobenzyl)-8-hydroxy-5-[(thiophene-2-carbonyl)amino][1,6]naphthylidine-7-carboxylic acid (2-methoxyethyl)amide mp: 188-189° C.

(CDCl$_3$) δ: 3.41 (3H, s), 3.55-3.73 (4H, m), 4.19 (3H, s), 6.94-7.04 (2H, m), 7.12-7.24 (3H, m), 7.64-7.68 (1H, m), 7.74-7.68 (1H, m), 8.00-8.20 (2H, m), 9.00 (1H, d, J=2.4 Hz), 13.26 (1H, brs).

Example A-166

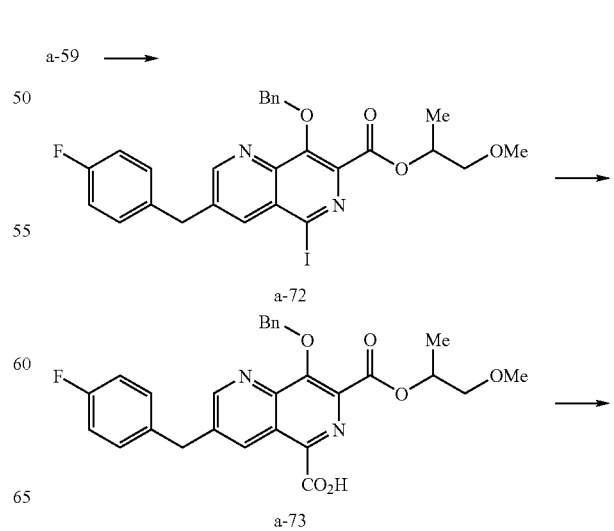

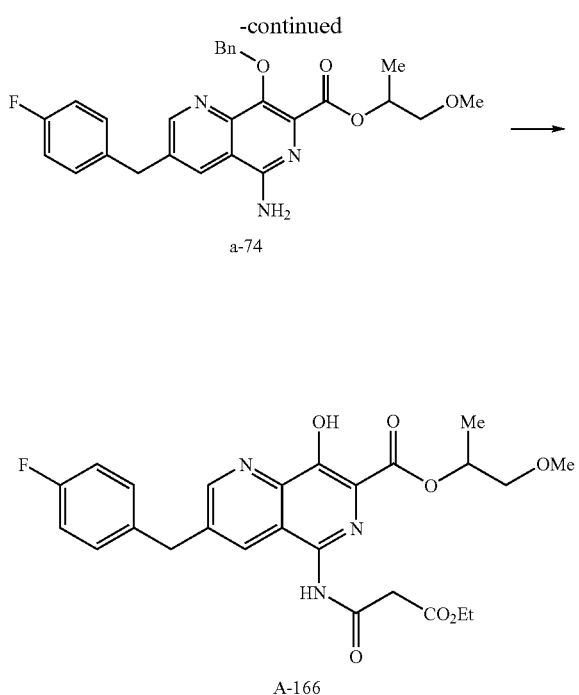

a-74

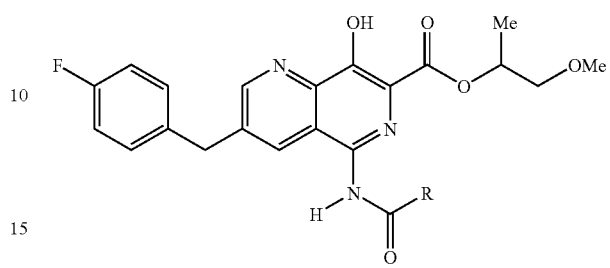

A-167: R = —OEt
A-168: R = —CH₂CH₂OMe

Example A-167, A-168

According to the method of Example A-166, compounds A-167 and A-168 were synthesized.

A-167. 5-[(Ethoxycarbonyl)amino]-3-(4-fluorobenzyl)-8-hydroxy[1,6]naphthylidine-7-carboxylic acid [2-(1-methoxy)propyl]ester NMR (CDCl$_3$) δ: 1.29 (3H, t, J=7.2 Hz), 1.48 (3H, t, J=6.6 Hz), 3.43 (3H, s), 3.55-3.76 (2H, m), 4.15 (2H, q, J=7.2 Hz), 4.21 (2H, s), 5.42-5.54 (1H, m), 6.98-7.08 (2H, m), 7.15-7.24 (2H, m), 8.13 (1H, s), 9.01 (1H, d, J=2.4H), 11.55 (1H, brs).

A-168. 3-(4-Fluorobenzyl)-8-hydroxy-5-[(3-methoxypropionyl)amino][1,6]naphthylidine-7-carboxylic acid [2-(1-methoxy)propyl]ester NMR (CDCl$_3$) δ: 1.45 (3H, t, J=6.3 Hz), 3.41 (3H, s), 3.42 (3H, s), 3.53-3.73 (4H, m), 4.20 (2H, s), 5.40-5.55 (1H, m), 6.99-7.08 (2H, m), 7.15-7.24 (2H, m), 8.02 (1H, s), 9.00 (1H, d, J=2.4H), 11.67 (1H, brs).

Example A-169

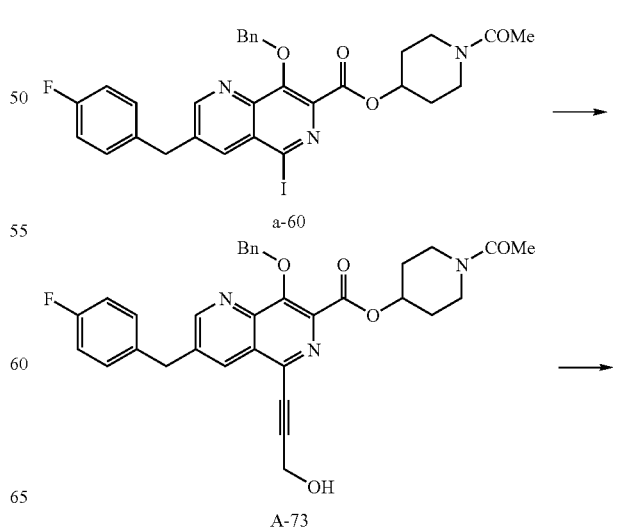

A-166

A-166. 5-[[(2-Ethoxycarbonyl)acetyl]amino]-3-(4-fluorobenzyl)-8-hydroxy [1,6]naphthylidine-7-carboxylic acid [2-(1-methoxy)propyl]ester 1) According to the method of Example A-143 (2), compounds a-59 to a-72 were synthesized.

NMR (CDCl$_3$) δ: 1.34 (3H, d, J=6.6 Hz), 3.33 (3H, s), 3.42-3.55 (2H, m), 4.25 (2H, s), 5.30-5.40 (1H, m), 5.54 (2H, s), 7.06 (2H, t like, J=8.7 Hz), 7.18-7.22 (2H, m), 7.33-7.40 (3H, m), 7.55-7.60 (2H, m), 8.12 (1H, d, J=2.1 Hz), 8.94 (1H, d, J=2.1 Hz)

2) According to the method of Example A-143 (3), compounds a-72 to a-73 were synthesized.

NMR (CDCl$_3$) δ: 1.33 (3H, d, J=6.6 Hz), 3.35 (3H, s), 3.43-3.55 (2H, m), 4.25 (2H, s), 5.35-5.43 (1H, m), 5.78 (2H, s), 7.04 (2H, t like, J=8.7 Hz), 7.19-7.24 (2H, m), 7.33-7.41 (3H, m), 7.53-7.58 (2H, m), 9.04 (1H, d, J=2.4 Hz), 9.73 (1H, d, J=2.4 Hz)

3) According to the method of Example A-143 (4), compounds a-73 to a-74 were synthesized.

NMR (CDCl$_3$) δ: 1.34 (3H, d, J=6.3 Hz), 3.31 (3H, s), 3.42-3.56 (2H, m), 4.18 (2H, s), 5.32-5.39 (1H, m), 5.34 (2H, s), 5.89 (2H, br.s), 7.03 (2H, t like, J=8.7 Hz), 7.16-7.40 (5H, m), 7.60-7.65 (2H, m), 7.95 (1H, br.s), 8.97 (1H, d, J=2.1 Hz)

4) According to the method of Example A-143 (5), compound A-166 was synthesized from a-74.

mp: 70-71° C.

(CDCl$_3$) δ: 1.33 (3H, t, J=7.2 Hz), 1.46 (3H, t, J=6.6 Hz), 3.43 (3H, s), 3.54-3.75 (4H, m), 4.21 (2H, s), 4.28 (2H, q, J=7.2 Hz), 5.42-5.55 (1H, m), 7.00-7.08 (2H, m), 7.16-7.25 (2H, m), 8.12 (1H, brs), 9.01 (1H, s), 11.68 (1H, brs).

-continued

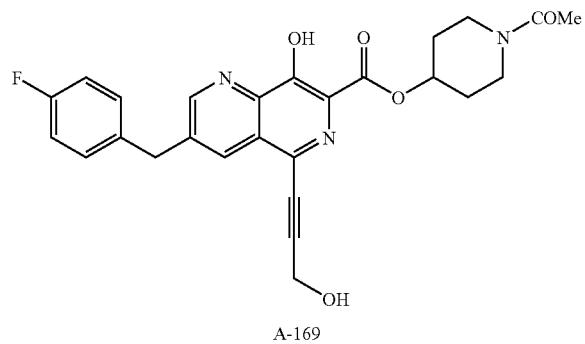

A-169

A-169. 3-(4-Fluorobenzyl)-8-hydroxy5-(3-hydroxyl-propynyl)[1,6]naphthylidine-7-carboxylic acid (1-acetylpiperidine-4-yl) ester According to the method of Example A-18 (1) and (2), compound A-169 was synthesized from compounda-60.

mp: 163-164° C.

(DMSO-$d_6$)δ: 1.61-2.03(4H, m), 2.03(3H, s), 3.10-3.50 (2H, m), 3.71-3.94(2H, m), 4.32(2H, s), 4.45(2H, d, J=5.4 Hz), 5.21-5.27(1H, m), 5.55(1H, t, J=5.4 Hz), 7.14-7.20(2H, m), 7.36-7.41(2H, m), 8.47(1H, d, J=1.2 Hz), 9.11(1H, d, J=1.2 Hz).

Example A-170

According to the method of Example A-169, compound A-170 was synthesized.

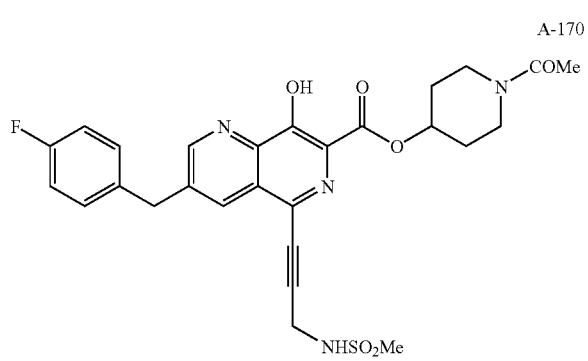

A-170

A-170. 3-(4-Fluorobenzyl)-8-hydroxy-5-[3-(methanesulfonyamino)-1-propynyl][1,6]naphthylidine-7-carboxylic acid (1-acetylpiperidine-4-yl) ester mp: 192-193° C.

(DMSO-$d_8$)δ: 1.61-2.03(4H, m), 2.03(3H, s), 3.04(3H, s), 3.20-3.50(2H, m), 3.69-3.91(2H, m), 4.24(2H, d, J=6.0 Hz), 4.30(2H, s), 5.20-5.27(1H, m), 7.14-7.20(2H, m), 7.38-7.42 (2H, m), 7.81(1H, t, J=6.0 Hz), 8.56(1H, d, J=2.1 Hz), 9.12(1H, d, J=2.1 Hz).

Example A-171 to A-172

According to the method of Example A-169, compound A-171 to A-172 was synthesized.

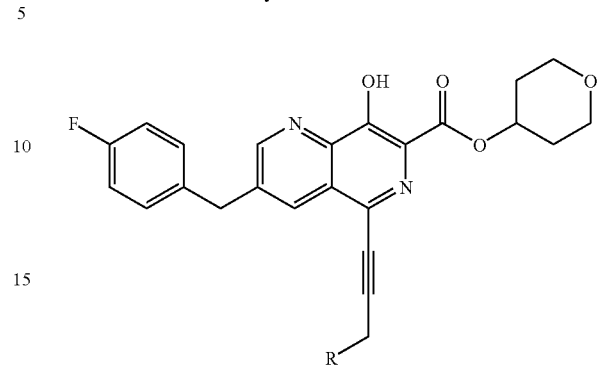

A-171: R = ―OH
A-172: R = ―NHSO$_2$Me

A-171. 3-(4-Fluorobenzyl)-8-hydroxy-5-(3-hydroxyl-propynyl)[1,6]naphthylidine-7-carboxylic acid (tetrahydropyrane-4-yl) ester mp: 210-212° C.

(DMSO-$d_6$)δ: 1.68-1.80(2H, m), 1.97-2.06(2H, m), 3.48-3.57(2H, m), 3.86-3.94(2H, m), 4.32(2H, s), 4.45(2H, d, J=4.9 Hz), 5.18-5.26(1H, m), 5.55(1H, t, J=5.6 Hz), 7.13-7.21(2H, m), 7.35-7.43(2H, m), 8.48(1H, d, J=1.8 Hz), 9.12(1H, d, J=1.8 Hz), 11.69(1H, br s).

A-172. 3-(4-Fluorobenzyl)-8-hydroxy5-[3-(methanesulfonyamino)-1-propynyl][1,6]naphthylidine-7-carboxylic acid (tetrahydropyrane-4-yl) ester mp: 216-218° C.

(DMSO-$d_6$)δ: 1.67-1.80(2H, m), 1.97-2.06(2H, m), 3.05 (3H, s), 3.48-3.63(2H, m), 3.85-3.94(2H, m), 4.25(2H, d, J=5.9 Hz), 4.31(2H, s), 5.17-5.26(1H, m), 7.13-7.21(2H, m), 7.37-7.43(2H, m), 7.82(1H, t, J=5.9 Hz), 8.58(1H, d, J=1.9 Hz), 9.14(1H, d, J=1.9 Hz), 11.70(1H, br s).

Example A-173

According to the method of Example A-169, compound A-173 was synthesized.

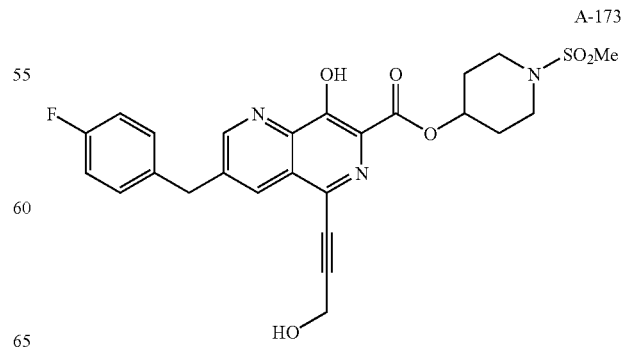

A-173

A-173. 3-(4-Fluorobenzyl)-8-hydroxy-5-(3-hydroxy-1-propynyl)-[1,6]naphthylidine-7-carboxylic acid (1-methanesulfonylpiperidine-4-yl) ester mp: 197-200° C.

Elementary analysis for $C_{25}H_{24}F_1N_3O_6S_1 \cdot 0.1CF_3COOH \cdot 0.8H_2O$ Calculation (%): C, 56.12; H, 4.80; N, 7.79; F, 4.58; S, 5.95. Found (%): C, 56.13; H, 4.59; N, 7.90; F, 4.29; S, 5.89.

($CDCl_3$) δ: 1.80-1.91(2H, m), 2.00-2.13(2H, m), 2.93(3H, s), 3.10-3.25(4H, m), 4.33(2H, s), 4.45(2H, s), 5.10-5.20 (1H, m), 5.56(1H, brs), 7.13-7.21(2H, m), 7.36-7.41(2H, m), 8.49(1H, d, J=2.1 Hz), 9.12(1H, d, J=2.1 Hz)

Example A-174

According to the method of Example A-60, compound A-174 was synthesized.

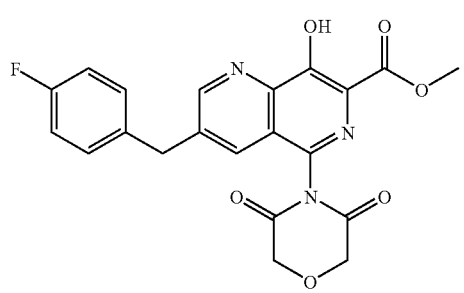

A-174. 5-(3,5-Dioxomorpholine-4-yl)-3-(4-fluorobenzyl)-8-hydroxy[1,6]naphthylidine-7-carboxylic acid methyl ester mp: 182-184° C.

Elementary analysis for $C_{21}H_{16}FN_3O_6$ Calculation (%): C, 59.30; H, 3.79; F, 4.47; N, 9.88. Found (%): C, 59.28; H, 3.75; F, 4.34; N, 9.72.

($CDCl_3$) δ: 4.11 (3H, s), 4.22 (2H, s), 4.56 (4H, s), 7.04 (2H, m), 7.14 (2H, m), 7.56 (1H, m), 9.05 (1H, d, J=2.1 Hz), 12.12 (1H, s).

Example A-175

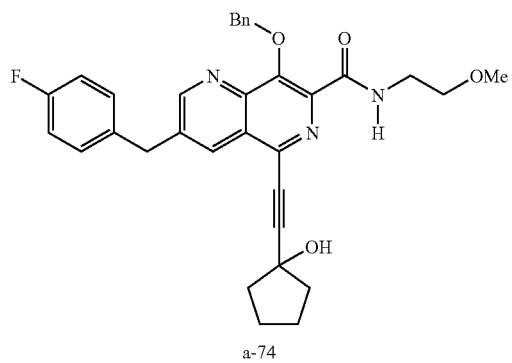

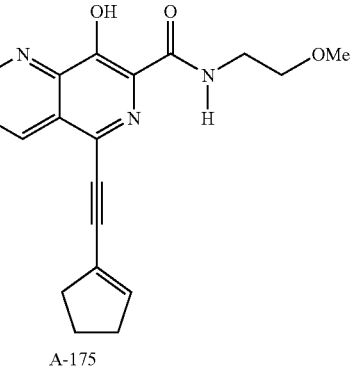

A-175. 5-[2-(1-Cyclopentenyl)thienyl]-3-(4-fluorobenzyl)-8-hydroxy[1,6]naphthylidine-7-carboxylic acid (2-methoxyethyl) amide 1) According to the method of Example A-18 (1), compound a-74 was synthesized from a-69.

NMR ($CDCl_3$) δ: 1.78-1.97 (4H, m), 1.99 (1H, s), 2.03-2.09 (4H, m), 3.36 (3H, s), 3.57 (2H, t, J=4.8 Hz), 3.67 (2H, brdt, J=4.8 Hz, 5.7 Hz), 4.24 (2H, s), 5.58 (2H, s), 7.07 (2H, m), 7.23 (2H, m), 7.30-7.39 (3H, m), 7.62-7.66 (2H, m), 8.02 (1H, brt, J=5.7 Hz), 8.18 (1H, m), 9.04 (1H, br).

2) According to the method of Example A-15 (3), Compound A-175 was synthesized from a-74, provided that the reaction was conducted overnight.

mp: 146° C.

Elementary analysis for $C_{26}H_{24}FN_3O_3$ Calculation (%): C, 70.10; H, 5.43; F, 4.26; N, 9.43. Found (%): C, 70.07; H, 5.45; F, 4.09; N, 9.37.

($CDCl_3$) δ: 2.02 (2H, tt, J=7.5 Hz, 7.5 Hz), 2.51-2.62 (4H, m), 3.42 (3H, s), 3.62 (2H, t, J=4.5 Hz), 3.70 (2H, m), 4.24 (2H, s), 6.29 (1H, m), 7.06 (2H, m), 7.22 (2H, m), 8.20 (1H, m), 8.30 (1H, brt, J=5.4 Hz), 9.03 (1H, d, J=2.4 Hz), 13.56 (1H, s).

Example A-176

According to the method of Example A-175, compound A-176 was synthesized.

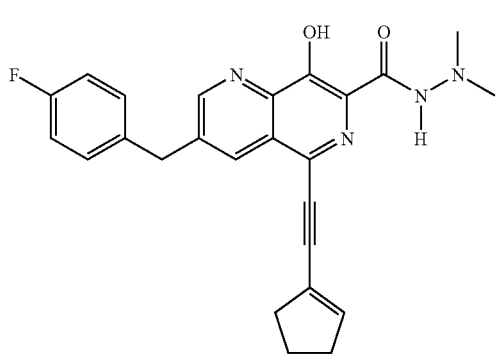

285

A-176. 5-[2-(1-Cyclopentenyl)ethynyl]-3-(4-fluorobenzyl)-8-hydroxy[1,6]naphthylidine-7-carboxylic acid N',N'-dimethylhydrazine mp: 206-207° C.

Elementary analysis for $C_{25}H_{23}FN_4O_2$ Calculation (%): C, 69.75; H, 5.39; N, 13.02; F, 4.41. Found (%): C, 69.63; H, 5.25; N, 12.87; F, 4.29.

(CDCl$_3$) δ: 2.02 (2H, tt, J=7.5 Hz, 7.5 Hz), 2.50-2.63 (4H, m), 2.77 (6H, s), 4.24 (2H, s), 6.30 (1H, m), 7.07 (2H, m), 7.22 (2H, m), 8.19 (1H, m), 8.67 (1H, brs), 9.04 (1H, d, J=2.4 Hz), 13.45 (1H, s).

Example A-177

According to the method of Example A-169, compound A-177 was synthesized.

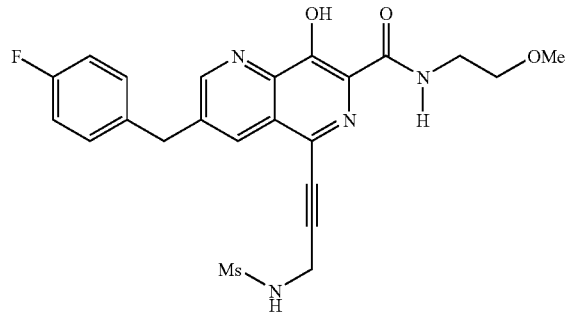

A-177

A-177. 3-(4-Fluorobenzyl)-8-hydroxy-5-[3-(methanesulfonyamino)-1-propynyl]-[1,6]naphthylidine-7-carboxylic acid (2-methoxyethyl) amide mp: 198° C.

Elementary analysis for $C_{23}H_{23}FN_4O_5S$ Calculation (%): C, 56.78; H, 4.77; F, 3.90; N, 11.52; S, 6.59. Found (%): C, 56.60; H, 4.72; F, 3.65; N, 11.38; S, 6.42.

(CDCl$_3$) δ: 3.12 (3H, s), 3.43 (3H, s), 3.62 (2H, t, J=4.8 Hz), 3.70 (2H, dt, J=4.8 Hz, 4.8 Hz), 4.23 (2H, s), 4.33 (2H, d, J=6.3 Hz), 4.67 (1H, brt, J=6.3 Hz), 7.05 (2H, m), 7.21 (2H, m), 8.23 (1H, brt, J=4.8 Hz), 8.31 (1H, m), 9.03 (1H, d, J=2.4 Hz), 13.68 (1H, s).

Example A-178

According to the method of Example A-169, compound A-178 was synthesized.

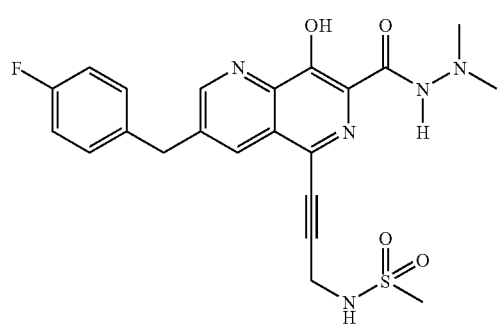

A-178

286

A-178. 3-(4-Fluorobenzyl)-8-hydroxy-5-[3-(methanesulfonyamino)-1-propynyl][1,6]naphthylidine-7-carboxylic acid N',N'-dimethylhydrazide mp: 229-230° C. (dec.)

Elementary analysis for $C_{22}H_{22}FN_5O_4S$ Calculation (%): C, 56.04; H, 4.70; N, 14.85; F, 4.03; S, 6.80. Found (%): C, 56.12; H, 4.53; N, 14.65; F, 3.95; S, 6.58.

(CDCl$_3$) δ: 2.78 (6H, s), 3.10 (3H, s), 4.23 (2H, s), 4.33 (2H, d, J=6.0 Hz), 4.76 (1H, brt, J=6.0 Hz), 7.05 (2H, m), 7.21 (2H, m), 8.31 (1H, m), 8.56 (1H, brs), 9.03 (1H, d, J=2.1 Hz), 13.51 (1H, s).

Example A-179

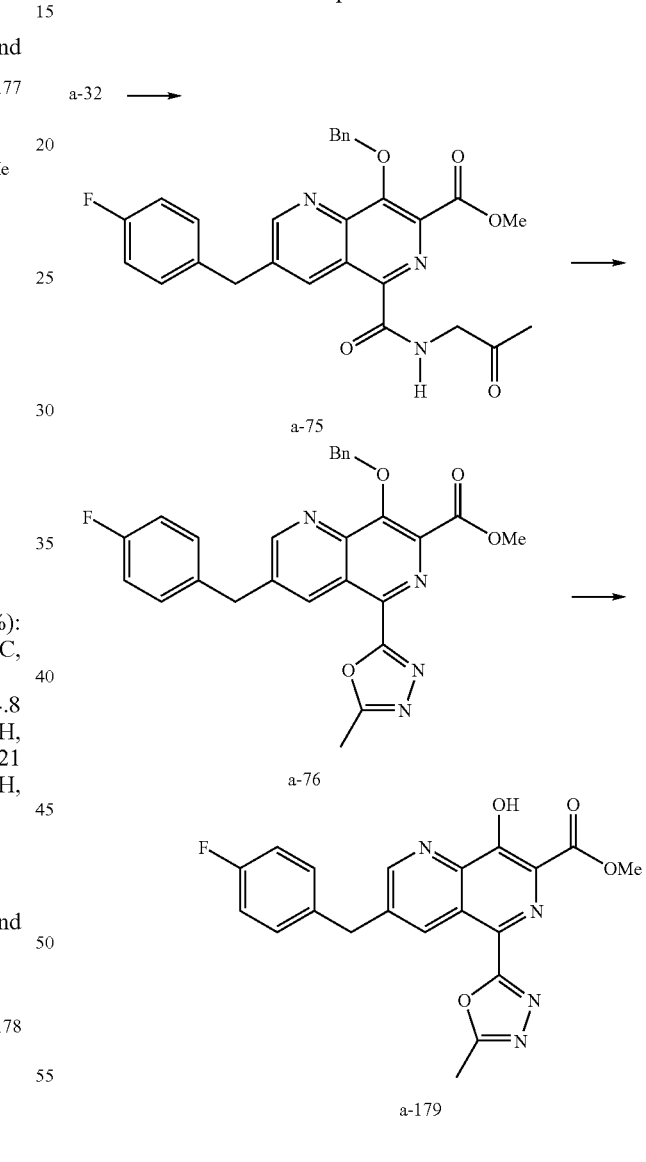

A-179. 3-(4-Fluorobenzyl)-8-hydroxy-5-(5-methyl[1,3,4]oxadiazole-2-yl)-[1,6]naphthylidine-7-carboxylic acid methylester 1) According to the method of Example A-52 (3), compound a-75 was synthesized from a-32.

NMR (CDCl$_3$) δ: 2.16 (3H, s), 3.93 (3H, s), 4.21 (2H, s), 5.69 (2H, s), 7.03 (2H, m), 7.21 (2H, m), 7.32-7.40 (3H, m), 7.51-7.55 (2H, m), 7.94 (1H, brd, J=4.5 Hz), 9.02 (1H, d, J=2.1 Hz), 9.67 (1H, m), 9.99 (1H, brd, J=4.4 Hz).

2) To a solution of triphenylphosphine (315 mg) in dichloromethane (10 mL), was added dropwise 1 M solution of bromide in dichloromethane (1.2 mL) under ice-cooling and the mixture was stirred at room temperature for 30 min, to which was added dropwise under ice-cooling triethylamine (0.35 mL). A solution of compound a-75 (502 mg) in dichloromethane (10 mL) was added dropwise and the mixture was stirred at room temperature for 30 min. Water was added thereto, extracted with chloroform (×3), and the chloroform layer was washed with brine, ried over anhydrous sodium sulphate, and evaporated. The obtained oil product was purified with column chromatography and the obtained white solid was washed with ethyl acetate to give a-76 as a white solid (383 mg) in 79% yield.

NMR (CDCl$_3$) δ: 2.72 (3H, s), 3.98 (3H, s), 4.28 (2H, s), 5.72 (2H, s), 7.04 (2H, m), 7.24 (2H, m), 7.32-7.41 (3H, m), 7.54-7.58 (2H, m), 9.08 (1H, d, J=2.4 Hz), 9.74 (1H, m).

3) According to the method of Example A-15 (3), compound A-179 was synthesized from compound a-76.

mp: 220° C.

Elementary analysis for C$_{20}$H$_{15}$FN$_4$O$_4$ Calculation (%): C, 60.91; H, 3.83; N, 14.21; F, 4.82. Found (%): C, 60.75; H, 3.74; N, 14.17; F, 4.70.

(CDCl$_3$) δ: 2.73 (3H, s), 4.16 (3H, s), 4.28 (2H, s), 7.02 (2H, m), 7.22 (2H, m), 9.10 (1H, d, J=2.1 Hz), 9.71 (1H, m), 12.08 (1H, brs).

Example A-180

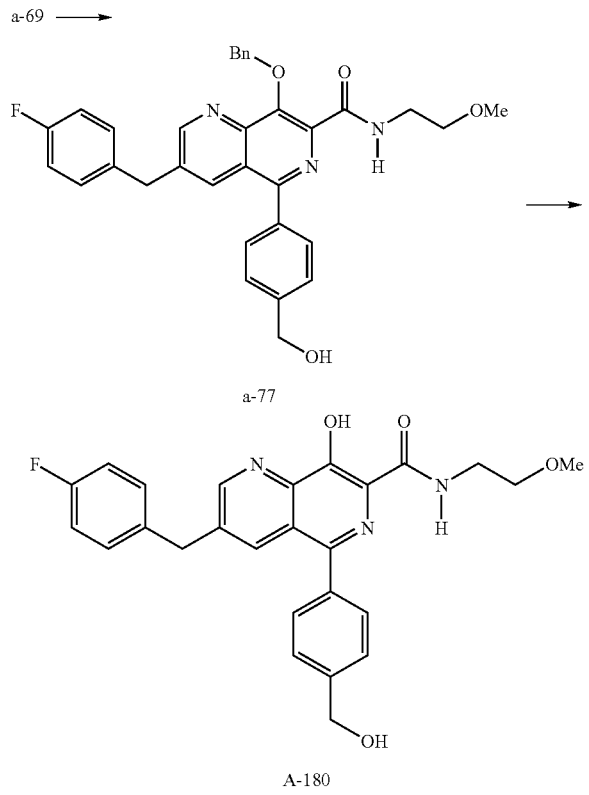

A-180. 3-(4-Fluorobenzyl)-8-hydroxy-5-[4-(hydroxymethyl)phenyl]-[1,6]naphthylidine-7-carboxylic acid (2-methoxyethyl) amide 1) A solution of compound a-69 (285 mg, 0.499 mmol), tetrakistriphenylphosphine palladium (29 mg), 4-(hydroxymethyl)phenyl boric acid (91 mg) in 1M sodium carbonate aq. (1 mL) and dioxane (5 mL) was stirred in N$_2$ atomosphere at 100° C. for 6 hr. The mixture was cooled to room temperature, then water and chloroform were added thereto with stirring, extracted with chloroform (3×). The combined chloroform layer was washed with saline, dried over anhydrous sodium sulphate, and evaporated. The oily residue was purified with column chromatography and crystallized with isopropyl alcohol. The obtained yellow solid was washed with isopropyl alcohol and diisopropyleter to give a-77 as white solid (177 mg) in 64% yield.

NMR (CDCl$_3$) δ: 1.84 (1H, t, J=5.7 Hz), 3.35 (3H, s), 4.14 (2H, s), 4.84 (2H, d, J=5.7 Hz), 5.56 (2H, s), 7.01 (2H, m), 7.14 (2H, m), 7.29-7.42 (3H, m), 7.54 (2H, m), 7.65 (2H, m), 7.73 (2H, m), 8.16 (1H, m), 8.22 (1H, brt, J=5.4 Hz), 9.03 (1H, d, J=2.4 Hz).

2) According to the method of Example A-15 (3), compound A-180 was synthesized from compounda-77.

mp: 151-153° C.

(CDCl$_3$) δ: 1.77 (1H, t, J=5.7 Hz), 3.39 (3H, s), 3.60 (2H, t, J=5.1 Hz), 3.70 (2H, dt, J=5.1 Hz, 5.7 Hz), 4.14 (2H, s), 4.84 (2H, d, J=5.7 Hz), 6.99 (2H, m), 7.11 (2H, m), 7.52-7.60 (4H, m), 8.10 (1H, m), 8.36 (1H, brt, J=5.7 Hz), 9.01 (1H, d, J=2.1 Hz), 13.33 (1H, s).

Example A-181

According to the method of Example A-180, compound A-181 was synthesized.

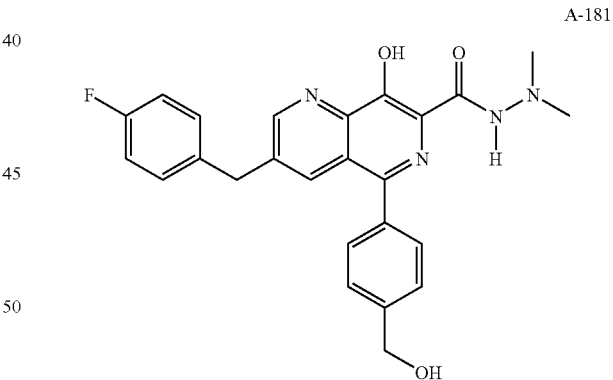

A-181. 3-(4-Fluorobenzyl)-8-hydroxy-5-[4-(hydroxymethyl)phenyl][1,6]naphthylidine-7-carboxylic acid N',N'-dimethylhydrazide mp: 219-221° C.

Elementary analysis for C$_{25}$H$_{23}$FN$_4$O$_3$ Calculation (%): C, 67.25; H, 5.19; N, 12.55; F, 4.26. Found (%): C, 67.26; H, 5.11; N, 12.39; F, 4.14.

(CDCl$_3$) δ: 1.82 (1H, brt, J=5.1 Hz), 2.75 (6H, s), 4.14 (2H, s), 4.85 (2H, d, J=5.1 Hz), 6.99 (2H, m), 7.11 (2H, m), 7.57 (4H, m), 8.07 (1H, m), 8.70 (1H, brs), 9.02 (1H, d, J=2.1 Hz), 13.18 (1H, s).

Example A-182 a-15 →

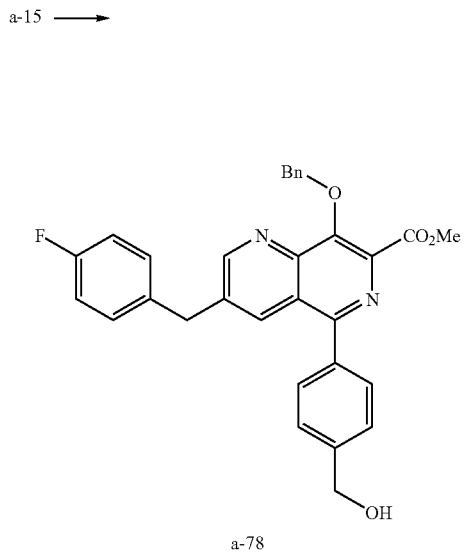

a-78

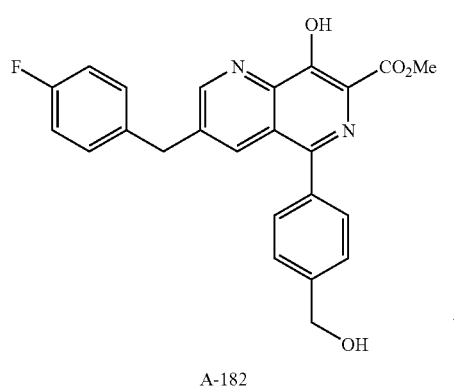

A-182

A-182 3-(4-Fluorobenzyl)-8-hydroxy-5-[4-(hydroxymethyl)phenyl][1,6]naphthylidine-7-carboxylic acidmethylester 1) According to the method of Example A-25 (1), a-78 was synthesized from compound a-15.

NMR (CDCl$_3$) δ: 3.94 (3H, s), 4.15(2H, s), 4.81(2H, s), 5.59 (2H, s), 6.98-7.04 (2H, m), 7.12-7.17 (2H, m), 7.34-7.43 (3H, m), 7.51-7.53 (2H, m), 7.63-7.65(4H, m), 8.17 (1H, d, J=2.3 Hz), 9.03(1H, d, J=2.1 Hz).

2) According to the method of Example A-15 (3), A-182 was synthesized from compound a-78.

mp: 183-185° C.

Elementary analysis for $C_{24}H_{19}F_1N_2O_4$ Calculation (%): C, 68.89; H, 4.58; N, 6.70; F, 4.54. Found (%): C, 68.60; H, 4.56; N, 6.78; F, 4.44.

(CDCl$_3$) δ: 4.09(3H, s), 4.15(2H, s), 4.81(2H, s), 6.97-7.03(2H, m), 7.07-7.14(2H, m), 7.50(2H, d, J=8.5 Hz), 7.60(2H, d, J=8.1 Hz), 8.11(1H, d, J=2.3 Hz), 9.04(1H, d, J=2.1 Hz), 11.82(1H, s)

Example A-183 a-78 →

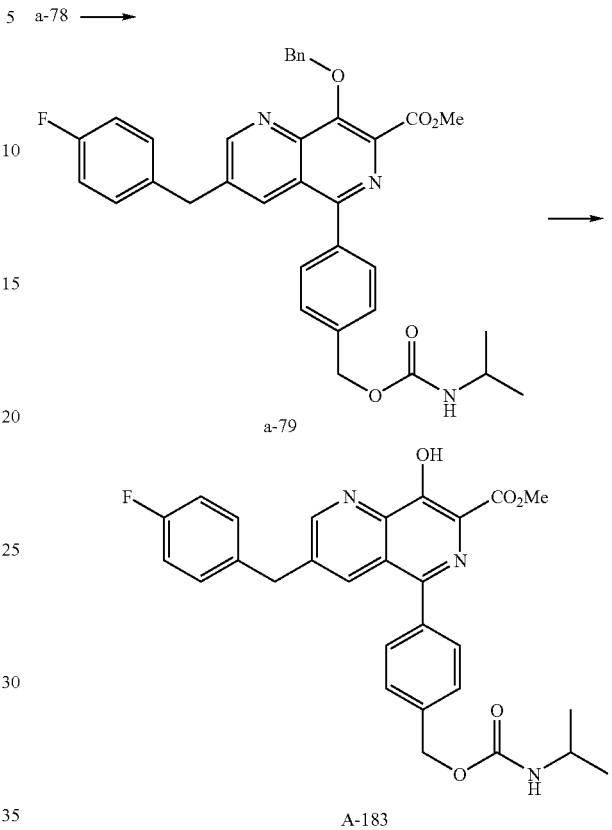

a-79

A-183

A-183. 3-(4-Fluorobenzyl)-8-hydroxy-5-[4-[[(isopropylcarbamoyl)oxy]methyl]phenyl][1,6]naphthylidine-7-carboxylic acid methyl ester To a solution of compound a-78 (200 mg, 0.39 mmol) and triethylamine (47 mg, 0.47 mmol) in methylene chloride (3 ml), was added isopropylisocyanate (40 mg, 0.47 mmol) and a drop of bis(tributyltin)oxide. The mixture was stirred at room temperature for 30 min and water was added thereto to terminate the reaction. The mixture was extracted with chloroform, washed with water, dried, and evaporated. The residue was purified with silica gel chromatography and a portion eluted with hexane-ethyl acetate (2:1) was evaporated to give a-79 (213 mg, 92%).

NMR (CDCl$_3$) δ: 1.19(6H, d, J=6.6 Hz), 3.80-4.00(1H, m), 3.94(3H, s), 4.15(2H, s), 5.19(2H, s), 5.58(2H, s), 6.98-7.04(2H, m), 7.12-7.17(2H, m), 7.34-7.43(3H, m), 7.51 (2H, d, J=7.9 Hz), 7.64 (2H, d, J=7.9 Hz), 8.17(1H, d, J=2.1 Hz), 9.03(1H, d, J=2.3 Hz)

4) According to the method of Example A-15 (3), Example A-183 was synthesized from a-79.

mp: 210-212° C.

Elementary analysis for $C_{28}H_{26}F_1N_3O_5$ Calculation (%): C, 66.79; H, 5.20; N, 8.35; F, 3.77. Found (%): C, 66.70; H, 5.22; N, 8.45; F, 3.63.

(CDCl$_3$) δ: 1.19(6H, d, J=6.6 Hz), 3.80-3.92(1H, m), 4.09(3H, s), 4.15(2H, s), 5.18(2H, s), 6.97-7.03(2H, m), 7.10-7.14(2H, m), 7.49(2H, d, J=8.1 Hz), 7.58(2H, d, J=8.1 Hz), 8.11(1H, d, J=2.1 Hz), 9.04(1H, d, J=2.1 Hz), 11.82 (1H, s)

Example A-184

According to the method of Example A-75, Example A-184 was synthesized from a-35.

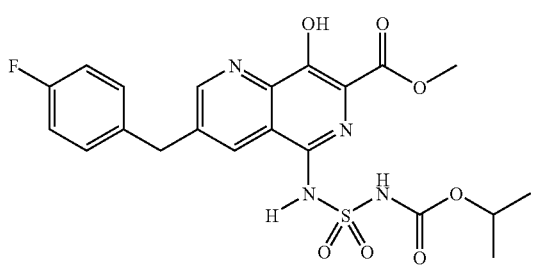

A-184

A-184. 3-(4-Fluorobenzyl)-8-hydroxy-5-[[[(isopropyloxy)carbamoyl]sulfonyl]amino][1,6]naphthylidine-7-carboxylic acid methyl ester mp: 170-172° C.

Elementary analysis for $C_{21}H_{21}F_1N_4O_7S_1$ Calculation (%): C, 51.22; H, 4.30; N, 11.38; F, 3.86; S, 6.51. Found (%): C, 51.24; H, 4.22; N, 11.42; F, 3.65; S, 6.73.

(CDCl$_3$) δ: 1.18(6H, d, J=6.3 Hz), 4.12(3H, s), 4.18(2H, s), 4.83-4.92(1H, m), 6.99-7.06(2H, m), 7.13-7.20(2H, m), 7.45(1H, s), 8.75(1H, d, J=2.0 Hz), 9.02(1H, d, J=2.1 Hz), 10.44(1H, s), 12.13(1H, s)

Example A-185, A-186

According to the method of compound A-185, A-186 was synthesized from A-169.

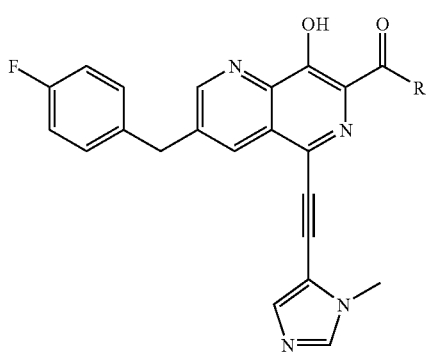

A-185: R = OMe
A-186: R = NH(CH$_2$)$_2$OMe

A-185. 3-(4-Fluorobenzyl)-8-hydroxy-5-[(3-methyl-3H-imidazole-4-yl)thienyl][1,6]naphthylidine-7-carboxylic acid methyl ester mp: 230° C. (decomposition)

(CDCl$_3$) δ: 3.67 (3H, s), 4.13 (3H, s), 4.28 (2H, s), 7.07 (2H, m), 7.23 (2H, m), 7.45 (1H, br), 7.54 (1H, br), 8.26 (1H, m), 9.11 (1H, d, J=2.1 Hz), 12.01 (1H, s).

A-186. 3-(4-Fluorobenzyl)-8-hydroxy-5-[(3-methyl-3H-imidazole-4-yl)thienyl][1,6]naphthylidine-7-carboxylic acid (2-methoxyethyl) amide mp: 244-245° C.

(CDCl$_3$) δ: 3.44 (3H, s), 3.64 (2H, m), 3.69 (3H, s), 3.73 (2H, m), 4.26 (2H, s), 7.07 (2H, m), 7.23 (2H, m), 7.48 (1H, br), 7.55 (1H, br), 8.21 (1H, m), 8.31 (1H, brt), 9.07 (1H, d, J=2.1 Hz), 13.69 (1H, s).

Example A-187, A-188

According to the method of Example A-143, compound A-187 and A-188 were synthesized.

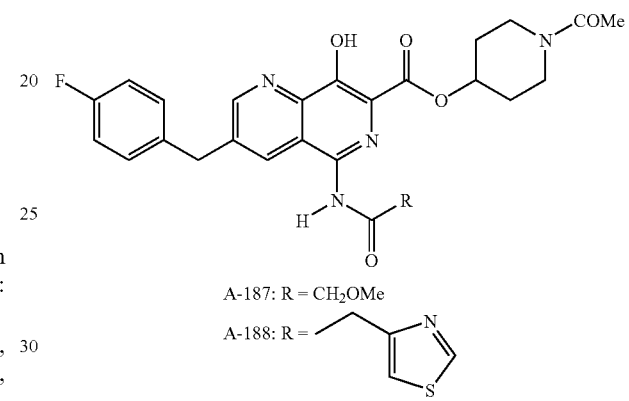

A-187: R = CH$_2$OMe

A-188: R =

A-187. 3-(4-Fluorobenzyl)-8-hydroxy-5-[(2-methoxyacetyl)amino][1,6]naphthylidine-7-carboxylic acid (1-acetylpiperidine4-yl) ester

NMR (CDCl$_3$) δ: 1.91-2.14(4H, m), 2.14(3H, s), 3.39-3.49(2H, m), 3.57(3H, s), 3.78-3.87(1H, m), 4.13-4.16(1H, m), 4.13(2H, s), 4.21(2H, s), 5.34-5.40(1H, m), 7.00-7.05 (2H, m), 7.16-7.21(2H, m), 7.99(1H, d, J=2.1 Hz), 8.80(1H, bs), 9.01(1H, d, J=2.1 Hz), 11.60(1H, bs).

A-188. 3-(4-Fluorobenzyl)-8-hydroxy-5-[(2-thiazole-4-yl)acetylamino][1,6]naphthylidine-7-carboxylic acid (1-acetylpiperidine-4-yl) ester

NMR (CDCl$_3$) δ: 1.90-2.14(4H, m), 2.14(3H, s), 3.39-3.51(2H, m), 3.76-3.85(1H, m), 4.07-4.13(1H, m), 4.07(2H, s), 4.20(2H, s), 5.34-5.39(1H, m), 6.99-7.05(2H, m), 7.15-7.20(2H, m), 7.29(1H, d, J=2.1 Hz), 8.02(1H, s), 8.85(1H, d, J=2.1 Hz), 9.00(1H, d, J=2.1 Hz), 11.54(1H, bs).

The present invention includes the following compounds. These can be synthesized in a manner similar to those disclosed in the working Examples.

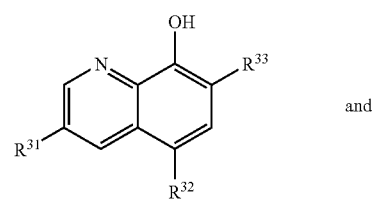

and

-continued

[Structure: bicyclic pyridine with OH, R³¹, R³², R³³ substituents]

Substituents R³¹, R³² and R³³ of the compounds may be exemplified by the followings:

R³¹ =

(31A) 4-fluorobenzyl (31B) 4-fluorophenoxy (31C) 4-fluorophenylthio (31D) 4-fluorophenylsulfinyl (31E) 4-fluorophenylsulfonyl (31F) (4-fluorobenzyl)oxy

R³² =

(32A) 2-oxopyrrolidin-1-yl (32B) 2,5-dioxopyrrolidin-1-yl (32C) 1,1-dioxoisothiazolidin-2-yl (32D) 2-oxopiperidin-1-yl (32E) 2,6-dioxopiperidin-1-yl (32F) 1,1,3-trioxo-1,2-thiazinan-2-yl (32G) N-acyl-N-propionylamino (32H) N-methyl-methanesulfonamido (32J) N-methylacetamido R³³=COOMe (33A), COOEt (33B), COOiPr (33C), COEt (33D), COCH₂CH₂CH₂OMe (33E)

Preferable combinations of substituents (as shown in the order of (R³¹, R³², R³³)) include the followings:
(31A, 32A, 33A), (31A, 32A, 33B), (31A, 32A, 33C), (31A, 32A, 33D), (31A, 32B, 33A), (31A, 32B, 33B), (31A, 32B, 33C), (31A, 32B, 33D), (31A, 32B, 33E), (31A, 32C, 33A), (31A, 32C, 33B), (31A, 32C, 33C), (31A, 32C, 33D), (31A, 32C, 33E), (31A, 32D, 33A), (31A, 32D, 33B), (31A, 32D, 33C), (31A, 32D, 33D), (31A, 32D, 33E), (31A, 32E, 33A), (31A, 32E, 33B), (31A, 32E, 33C), (31A, 32E, 33D), (31A, 32E, 33E), (31A, 32F, 33A), (31A, 32F, 33B), (31A, 32F, 33C), (31A, 32F, 33D), (31A, 32F, 33E), (31A, 32G, 33A), (31A, 32G, 33B), (31A, 32G, 33C), (31A, 32G, 33D), (31A, 32G, 33E), (31A, 32H, 33A), (31A, 32H, 33B), (31A, 32H, 33C), (31A, 32H, 33D), (31A, 32H, 33E), (31A, 32J, 33A), (31A, 32J, 33B), (31A, 32J, 33C), (31A, 32J, 33D), (31A, 32J, 33E), (31B, 32A, 33A), (31B, 32A, 33B), (31B, 32A, 33C), (31B, 32A, 33D), (31B, 32A, 33E), (31B, 32B, 33A), (31B, 32B, 33B), (31B, 32B, 33C), (31B, 32B, 33D), (31B, 32B, 33E), (31B, 32C, 33A), (31B, 32C, 33B), (31B, 32C, 33C), (31B, 32C, 33D), (31B, 32C, 33E), (31B, 32D, 33A), (31B, 32D, 33B), (31B, 32D, 33C), (31B, 32D, 33D), (31B, 32D, 33E), (31B, 32E, 33A), (31B, 32E, 33B), (31B, 32E, 33C), (31B, 32E, 33D), (31B, 32E, 33E), (31B, 32F, 33A), (31B, 32F, 33B), (31B, 32F, 33C), (31B, 32F, 33D), (31B, 32F, 33E), (31B, 32G, 33A), (31B, 32G, 33B), (31B, 32G, 33C), (31B, 32G, 33D), (31B, 32G, 33E), (31B, 32H, 33A), (31B, 32H, 33B), (31B, 32H, 33C), (31B, 32H, 33D), (31B, 32H, 33E), (31B, 32J, 33A), (31B, 32J, 33B), (31B, 32J, 33C), (31B, 32J, 33D), (31B, 32J, 33E), (31C, 32A, 33A), (31C, 32A, 33B), (31C, 32A, 33C), (31C, 32A, 33D), (31C, 32A, 33E), (31C, 32B, 33A), (31C, 32B, 33B), (31C, 32B, 33C), (31C, 32B, 33D), (31C, 32B, 33E), (31C, 32C, 33A), (31C, 32C, 33B), (31C, 32C, 33C), (31C, 32C, 33D), (31C, 32C, 33E), (31C, 32D, 33A), (31C, 32D, 33B), (31C, 32D, 33C), (31C, 32D, 33D), (31C, 32D, 33E), (31C, 32E, 33A), (31C, 32E, 33B), (31C, 32E, 33C), (31C, 32E, 33D), (31C, 32E, 33E), (31C, 32F, 33A), (31C, 32F, 33B), (31C, 32F, 33C), (31C, 32F, 33D), (31C, 32F, 33E), (31C, 32G, 33A), (31C, 32G, 33B), (31C, 32G, 33C), (31C, 32G, 33D), (31C, 32G, 33E), (31C, 32H, 33A), (31C, 32H, 33B), (31C, 32H, 33C), (31C, 32H, 33D), (31C, 32H, 33E), (31C, 32J, 33A), (31C, 32J, 33B), (31C, 32J, 33C), (31C, 32J, 33D), (31C, 32J, 33E), (31D, 32A, 33A), (31D, 32A, 33B), (31D, 32A, 33C), (31D, 32A, 33D), (31D, 32A, 33E), (31D, 32B, 33A), (31D, 32B, 33B), (31D, 32B, 33C), (31D, 32B, 33D), (31D, 32B, 33E), (31D, 32C, 33A), (31D, 32C, 33B), (31D, 32C, 33C), (31D, 32C, 33D), (31D, 32C, 33E), (31D, 32D, 33A), (31D, 32D, 33B), (31D, 32D, 33C), (31D, 32D, 33D), (31D, 32D, 33E), (31D, 32E, 33A), (31D, 32E, 33B), (31D, 32E, 33C), (31D, 32E, 33D), (31D, 32E, 33E), (31D, 32F, 33A), (31D, 32F, 33B), (31D, 32F, 33C), (31D, 32F, 33D), (31D, 32F, 33E), (31D, 32G, 33A), (31D, 32G, 33B), (31D, 32G, 33C), (31D, 32G, 33D), (31D, 32G, 33E), (31D, 32H, 33A), (31D, 32H, 33B), (31D, 32H, 33C), (31D, 32H, 33D), (31D, 32H, 33E), (31D, 32J, 33A), (31D, 32J, 33B), (31D, 32J, 33C), (31D, 32J, 33D), (31D, 32J, 33E), (31E, 32A, 33A), (31E, 32A, 33B), (31E, 32A, 33C), (31E, 32A, 33D), (31E, 32A, 33E), (31E, 32B, 33A), (31E, 32B, 33B), (31E, 32B, 33C), (31E, 32B, 33D), (31E, 32B, 33E), (31E, 32C, 33A), (31E, 32C, 33B), (31E, 32C, 33C), (31E, 32C, 33D), (31E, 32C, 33E), (31E, 32D, 33A), (31E, 32D, 33B), (31E, 32D, 33C), (31E, 32D, 33D), (31E, 32D, 33E), (31E, 32E, 33A), (31E, 32E, 33B), (31E, 32E, 33C), (31E, 32E, 33D), (31E, 32E, 33E), (31E, 32F, 33A), (31E, 32F, 33B), (31E, 32F, 33C), (31E, 32F, 33D), (31E, 32F, 33E), (31E, 32G, 33A), (31E, 32G, 33B), (31E, 32G, 33C), (31E, 32G, 33D), (31E, 32G, 33E), (31E, 32H, 33A), (31E, 32H, 33B), (31E, 32H, 33C), (31E, 32H, 33D), (31E, 32H, 33E), (31E, 32J, 33A), (31E, 32J, 33B), (31E, 32J, 33C), (31E, 32J, 33D), (31E, 32J, 33E), (31F, 32A, 33A), (31F, 32A, 33B), (31F, 32A, 33C), (31F, 32A, 33D), (31F, 32A, 33E), (31F, 32B, 33A), (31F, 32B, 33B), (31F, 32B, 33C), (31F, 32B, 33D), (31F, 32B, 33E), (31F, 32C, 33A), (31F, 32C, 33B), (31F, 32C, 33C), (31F, 32C, 33D), (31F, 32C, 33E), (31F, 32D, 33A), (31F, 32D, 33B), (31F, 32D, 33C), (31F, 32D, 33D), (31F, 32D, 33E), (31F, 32E, 33A), (31F, 32E, 33B), (31F, 32E, 33C), (31F, 32E, 33D), (31F, 32E, 33E), (31F, 32F, 33A), (31F, 32F, 33B), (31F, 32F, 33C), (31F, 32F, 33D), (31F, 32F, 33E), (31F, 32G, 33A), (31F, 32G, 33B), (31F, 32G, 33C), (31F, 32G, 33D), (31F, 32G, 33E), (31F, 32H, 33A), (31F, 32H, 33B), (31F, 32H, 33C), (31F, 32H, 33D), (31F, 32H, 33E), (31F, 32J, 33A), (31F, 32J, 33B), (31F, 32J, 33C), (31F, 32J, 33D), (31F, 32J, 33E)

For exmple: ($R^{31}$, $R^{32}$, $R^{33}$)=(31A, 32A, 33A) means a compound wherein $R^{31}$ is 31A; $R^{32}$ is 32A and $R^{33}$ is 33A. Other combinations are also shown in a similar manner.

The present invention also includes the following compounds.

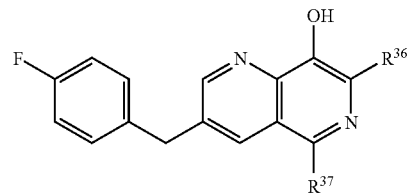

wherein $R^{36}$ is —$CO_2Me$, —$CO_2Et$, —$CO_2CH_2CH_2OMe$, —$CONHNMe_2$, —$CONHOMe$, —$CONHCH_2CH_2OMe$, —$CONH_2$, —$CONHMe$, —$CONHEt$, —$CONHiPr$, —$COEt$, —$COMe$ or —$COCH_2CH_2CH_2OMe$; $R^{37}$ is —H, —$NHCOMe$, —$NHCOEt$, —$NHCOiPr$, —$NHCOPh$, —$NHCOCH_2CH_2OMe$, —$NHCOCH_2CF_3$, —$NHCONMe_2$, —$NHCO_2Et$, —$NHCOCH_2CO_2Et$, —NHCO-cycloPr, —NHCO-cycloHex, —$NMeCOMe$, —$NHSO_2Me$, —$NHSO_2Et$, —$NHSO_2iPr$, —$NHSO_2CH_2CF_3$, —$NHSO_2Ph-4F$, —$NHSO_2Bn$, —$NHSO_2NH_2$, —$NHSO_2NHMe$, —$NHSO_2NMe_2$, —$NHSO_2CH_2CH_2OMe$, —$NMeSO_2Me$, -morpholine, —NHiBu, -piperidine-4-OH, —NHBn, —OMe, —$OCH_2CH_2OMe$, —$OCH_2COOH$, —$OSO_2Me$, —$OSO_2NH_2$, —SMe, —$SO_2Me$, —$SO_2NH_2$, —$SO_2NHMe$, —C≡$CCH_2OH$, —C≡$CCH_2OMe$, —C≡$CCO_2H$, —C≡$CCO_2Me$, —C≡$CCONH_2$, —C≡CNPr, —C≡CPh, —$C_6H_4$-4-F, —$C_6H_4$-4-COOH, —$CO_2H$, —$CO_2Me$, —$CONH_2$, —$CONHCH_2CH_2OMe$, —CONHiPr, —CO-morpholinyl, —COMe or —$CF_3$.

The present invention further includes the following compounds. These compounds may be synthesized in a manner similar to that of the above Examples.

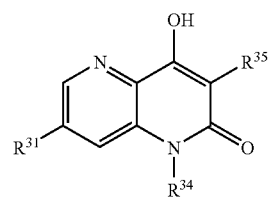

The substituents of $R^{31}$, $R^{34}$ and $R^{35}$ on the above compounds are exemplified by the following substituents:

$R^{31}$ =

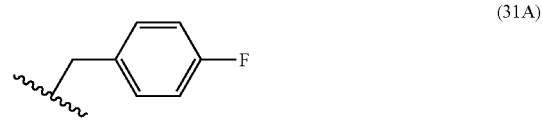

(31A)

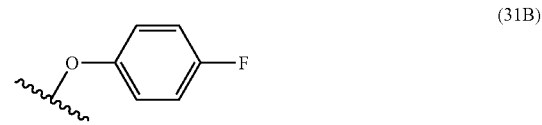

(31B)

-continued

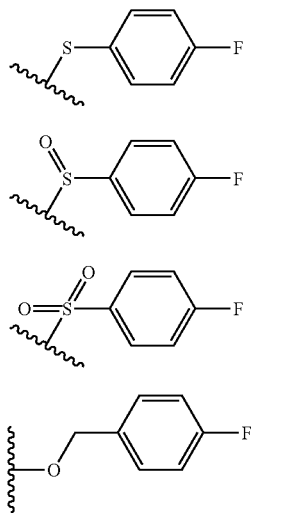

(31C)

(31D)

(31E)

(31F)

$R^{34}$=Me (34A), Et (34B), Pr (34C), COMe (34D), SO$_2$Me (34E)

$R^{35}$=COOMe (35A), COOEt (35B), COOiPr (35C), COEt (35D), COCH$_2$CH$_2$CH$_2$OMe (35E), CONHMe (35F), CONHEt (35G), CONHCH2CH2OMe (35H)

Preferable combinations of substituents (shown in the order of ($R^{31}$, $R^{34}$, $R^{35}$)) include the following combinations:

(31A, 34A, 35A), (31A, 34A, 35B), (31A, 34A, 35C), (31A, 34A, 35D), (31A, 34A, 35F), (31A, 34A, 35G), (31A, 34A, 35H), (31A, 34B, 35A), (31A, 34B, 35B), (31A, 34B, 35C), (31A, 34B, 35D), (31A, 34B, 35E), (31A, 34B, 35F), (31A, 34B, 35G), (31A, 34B, 35H), (31A, 34C, 35A), (31A, 34C, 35B), (31A, 34C, 35C), (31A, 34C, 35D), (31A, 34C, 35E), (31A, 34C, 35F), (31A, 34C, 35G), (31A, 34C, 35H), (31A, 34D, 35A), (31A, 34D, 35B), (31A, 34D, 35C), (31A, 34D, 35D), (31A, 34D, 35E), (31A, 34D, 35F), (31A, 34D, 35G), (31A, 34D, 35H), (31A, 34E, 35A), (31A, 34E, 35B), (31A, 34E, 35C), (31A, 34E, 35D), (31A, 34E, 35E), (31A, 34E, 35F), (31A, 34E, 35G), (31A, 34E, 35H), (31B, 34A, 35A), (31B, 34A, 35B), (31B, 34A, 35C), (31B, 34A, 35D), (31B, 34A, 35E), (31B, 34A, 35F), (31B, 34A, 35G), (31B, 34A, 35H), (31B, 34B, 35A), (31B, 34B, 35B), (31B, 34B, 35C), (31B, 34B, 35D), (31B, 34B, 35E), (31B, 34B, 35F), (31B, 34B, 35G), (31B, 34B, 35H), (31B, 34C, 35A), (31B, 34C, 35B), (31B, 34C, 35C), (31B, 34C, 35D), (31B, 34C, 35E), (31B, 34C, 35F), (31B, 34C, 35G), (31B, 34C, 35H), (31B, 34D, 35A), (31B, 34D, 35B), (31B, 34D, 35C), (31B, 34D, 35D), (31B, 34D, 35E), (31B, 34D, 35F), (31B, 34D, 35G), (31B, 34D, 35H), (31B, 34E, 35A), (31B, 34E, 35B), (31B, 34E, 35C), (31B, 34E, 35D), (31B, 34E, 35E), (31B, 34E, 35F), (31B, 34E, 35G), (31B, 34E, 35H), (31C, 34A, 35A), (31C, 34A, 35B), (31C, 34A, 35C), (31C, 34A, 35D), (31C, 34A, 35E), (31C, 34A, 35F), (31C, 34A, 35G), (31C, 34A, 35H), (31C, 34B, 35A), (31C, 34B, 35B), (31C, 34B, 35C), (31C, 34B, 35D), (31C, 34B, 35E), (31C, 34B, 35F), (31C, 34B, 35G), (31C, 34B, 35H), (31C, 34C, 35A), (31C, 34C, 35B), (31C, 34C, 35C), (31C, 34C, 35D), (31C, 34C, 35E), (31C, 34C, 35F), (31C, 34C, 35G), (31C, 34C, 35H), (31C, 34D, 35A), (31C, 34D, 35B), (31C, 34D, 35C), (31C, 34D, 35D), (31C, 34D, 35E), (31C, 34D, 35F), (31C, 34D, 35G), (31C, 34D, 35H), (31C, 34E, 35A), (31C, 34E, 35B), (31C, 34E, 35C), (31C, 34E, 35D), (31C, 34E, 35E), (31C, 34E, 35F), (31C, 34E, 35G), (31C, 34E, 35H), (31D, 34A, 35A), (31D, 34A, 35B), (31D, 34A, 35C), (31D, 34A, 35D), (31D, 34A, 35E), (31D, 34A, 35F), (31D, 34A, 35G), (31D, 34A, 35H), (31D, 34B, 35A), (31D, 34B, 35B), (31D, 34B, 35C), (31D, 34B, 35D), (31D, 34B, 35E), (31D, 34B, 35F), (31D, 34B, 35G), (31D, 34B, 35H), (31D, 34C, 35A), (31D, 34C, 35B), (31D, 34C, 35C), (31D, 34C, 35D), (31D, 34C, 35E), (31D, 34C, 35F), (31D, 34C, 35G), (31D, 34C, 35H), (31D, 34D, 35A), (31D, 34D, 35B), (31D, 34D, 35C), (31D, 34D, 35D), (31D, 34D, 35E), (31D, 34D, 35F), (31D, 34D, 35G), (31D, 34D, 35H), (31D, 34E, 35A), (31D, 34E, 35B), (31D, 34E, 35C), (31D, 34E, 35D), (31D, 34E, 35E), (31D, 34E, 35F), (31D, 34E, 35G), (31D, 34E, 35H), (31E, 34A, 35A), (31E, 34A, 35B), (31E, 34A, 35C), (31E, 34A, 35D), (31E, 34A, 35E), (31E, 34A, 35F), (31E, 34A, 35G), (31E, 34A, 35H), (31E, 34B, 35A), (31E, 34B, 35B), (31E, 34B, 35C), (31E, 34B, 35D), (31E, 34B, 35E), (31E, 34B, 35F), (31E, 34B, 35G), (31E, 34B, 35H), (31E, 34C, 35A), (31E, 34C, 35B), (31E, 34C, 35C), (31E, 34C, 35D), (31E, 34C, 35E), (31E, 34C, 35F), (31E, 34C, 35G), (31E, 34C, 35H), (31E, 34D, 35A), (31E, 34D, 35B), (31E, 34D, 35C), (31E, 34D, 35D), (31E, 34D, 35E), (31E, 34D, 35F), (31E, 34D, 35G), (31E, 34D, 35H), (31E, 34E, 35A), (31E, 34E, 35B), (31E, 34E, 35C), (31E, 34E, 35D), (31E, 34E, 35E), (31E, 34E, 35F), (31E, 34E, 35G), (31E, 34E, 35H), (31F, 34A, 35A), (31F, 34A, 35B), (31F, 34A, 35C), (31F, 34A, 35D), (31F, 34A, 35E), (31F, 34A, 35F), (31F, 34A, 35G), (31F, 34A, 35H), (31F, 34B, 35A), (31F, 34B, 35B), (31F, 34B, 35C), (31F, 34B, 35D), (31F, 34B, 35E), (31F, 34B, 35F), (31F, 34B, 35G), (31F, 34B, 35H), (31F, 34C, 35A), (31F, 34C, 35B), (31F, 34C, 35C), (31F, 34C, 35D), (31F, 34C, 35E), (31F, 34C, 35F), (31F, 34C, 35G), (31F, 34C, 35H), (31F, 34D), 35A), (31F, 34D, 35B), (31F, 34D, 35C), (31F, 34D, 35D), (31F, 34D, 35E), (31F, 34D, 35F), (31F, 34D, 35G), (31F, 34D, 35H), (31F, 34E, 35A), (31F, 34E, 35B), (31F, 34E, 35C), (31F, 34E, 35D), (31F, 34E, 35E), (31F, 34E, 35F), (31F, 34E, 35G), (31F, 34E, 35H)

For Example: ($R^{31}$, $R^{34}$, $R^{35}$)=(31A, 34A, 35A) means a compound wherein $R^{31}$ is 31A; $R^{34}$ is 34A and $R^{35}$ is 35A. Other combinations are also shown in a similar manner.

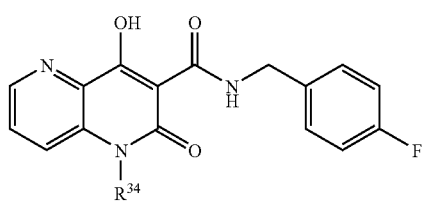

The substituent of $R^{34}$ on the above compound includes the following:

$R^{34}$=Me (34A), Et (34B), Pr (34C), COMe (34D), SO$_2$Me (34E)

The present invention includes the following compounds. These compounds may be synthesized in a manner similar to that of above Examples.

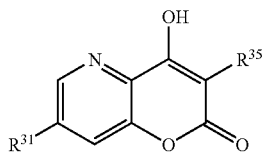

The substituents of $R^{31}$ and $R^{35}$ on the above compounds are exemplified by the following substituents:

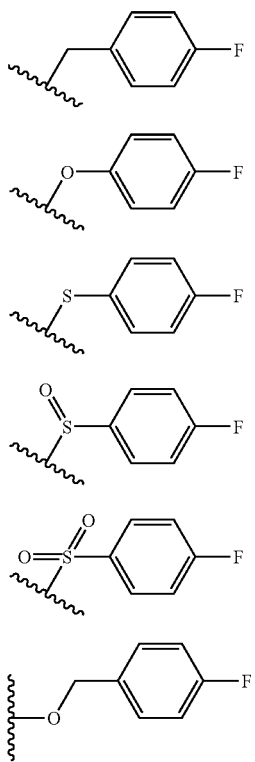

$R^{35}$=COOMe (35A), COOEt (35B), COOiPr (35C), COEt (35D), COCH$_2$CH$_2$CH$_2$OMe (35E), CONHMe (35F), CONHEt (35G), CONHCH2CH2OMe (35H)

The preferable combinations of substituents (shown in the order of ($R^{31}$, $R^{35}$)) involve the followings:
(31A, 35A), (31A, 35B), (31A, 35C), (31A, 35D), (31A, 35E), (31A, 35F), (31A, 35G), (31A, 35H), (31B, 35A), (31B, 35B), (31B, 35C), (31B, 35D), (31B, 35E), (31B, 35F), (31B, 35G), (31B, 35H), (31C, 35A), (31C, 35B), (31C, 35C), (31C, 35D), (31C, 35E), (31C, 35F), (31C, 35G), (31C, 35H), (31D, 35A), (31D, 35B), (31D, 35C), (31D, 35D), (31D, 35E), (31D, 35F), (31D, 35G), (31D, 35H), (31E, 35A), (31E, 35B), (31E, 35C), (31E, 35D), (31E, 35E), (31E, 35F), (31E, 35G), (31E, 35H), (31F, 35A), (31F, 35B), (31F, 35C), (31F, 35D), (31F, 35E), (31F, 35F), (31F, 35G), (31F, 35H)

For Examples: ($R^{31}$, $R^{35}$)=(31A, 35A) means a compound wherein $R^{31}$ is 31A; and $R^{35}$ is 35A. Other combinations are also shown in a similar manner.

The present invention includes the following compounds. Following compounds can be synthesized in a manner similar to that in above Examples.

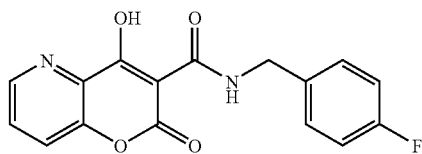

Reference Example B-1

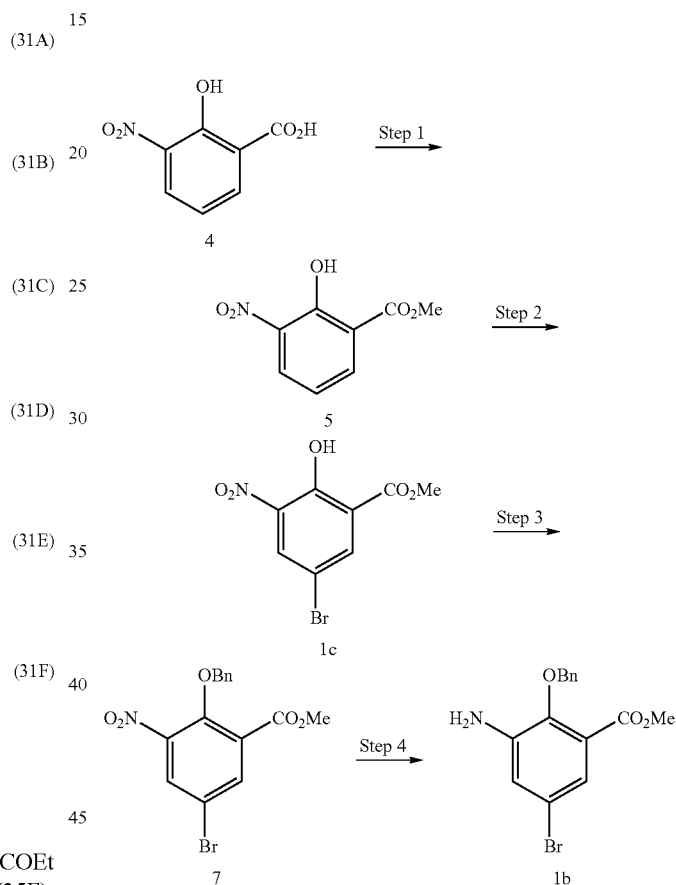

(Me=methyl, Bn=benzyl)

Step 1

To a suspension of Compound 4 (3-nitrosalicylic acid, 38.2 g, 209 mmol) in acetone (400 ml) were added potassium hydrogen carbonate (22.9 g) and dimethyl sulfate (21.7 ml), and the mixture was refluxed for 21 hours. The reaction mixture was filtered through Celite, and the filtrate was concentrated in vacuo. To the residue was added diluted hydrochloric acid and the acidified mixture was extracted with chloroform. The extract was washed with water and saturated saline, dried over magnesium sulfate, and concentrated in vacuo. The residue was dissolved in methanol (200 ml), and the solution was refluxed for 10 minutes, and cooled with ice water. The precipitated crystals were collected by filtration to give Compound 5 (36.3 g, 88.4%); mp: 129-130° C.

NMR (CDCl$_3$) δ: 4.02 (3H, s), 7.01 (1H, t, J=8.1 Hz), 8.15 (2H, dt, J=1.8 Hz, 8.1 Hz), 12.00 (1H, s).

Step 2

To a solution of Compound 5 (22.3 g, 113 mmol) in DMF (200 ml) was added N-bromosuccinimide (20.1 g) under ice cooling in nitrogen atmosphere. The mixture was stirred at the same temperature for 30 minutes, diluted with water, and the precipitated crystals were collected by filtration. The crystals were washed with water and methanol and dried to give Compound 1c (28.0 g, 89.7%); m.p.: 146-147° C.

NMR (CDCl$_3$) δ: 4.03 (3H, s), 8.24 (1H, d, J=2.4 Hz), 8.27 (2H, d, J=2.4 Hz), 11.90 (1H, s).

Step 3

To a solution of Compound 1c (10.3 g, 37.3 mmol) in DMF (200 ml) were added potassium carbonate (7.74 g) and benzyl bromide (5.3 ml) under nitrogen atmosphere, and the mixture was stirred at room temperature. 1.5 hours and 3 hours later, additional amounts of potassium carbonate (2.58 g) and benzyl bromide (2.2 ml) were each added, and the mixture was stirred overnight. The reaction mixture was diluted with water and extracted with ethyl acetate. The extract was washed with water and saturated saline, dried over magnesium sulfate, and concentrated in vacuo. The residue was purified by silica gel column chromatography (n-hexane-ethyl acetate=8:1-6:1) to give Compound 7 (11.9 g, 87.1%) as crystals.

NMR (CDCl$_3$) δ: 3.90 (3H, s), 5.16 (2H, s), 7.35-7.41 (3H, m), 7.43-7.49 (21H, m), 8.05 (1H, d, J=2.4 Hz), 8.17 (1H, d, J=2.4 Hz).

Step 4

A mixture of Compound 7 (10.3 g, 28.1 mmol), powdered iron (9.43 g), aqueous saturated ammonium chloride (50 ml) and toluene (50 ml) was stirred under nitrogen atmosphere at 90° C. for 5 hours. The reaction mixture was cooled to room temperature and the precipitated solid was removed by filtration. The filtrate was treated with water and extracted with ethyl acetate. The extract was washed with water and saturated saline, dried over magnesium sulfate, and concentrated in vacuo to give crude crystals of Compound 1b (9.58 g, quantitative yield).

NMR (CDCl$_3$) δ: 3.88 (3H, s), 4.96 (2H, s), 7.03 (1H, d, J=2.6 Hz), 7.33 (1H, d, J=2.6 Hz), 7.35-7.43 (3H, m), 7.45-7.50 (2H, m).

Step 1

To a suspension of Compound 8 (4-hydroxyisophthalic acid, 6.71 g, 36.8 mmol) in acetone (140 ml) were added potassium hydrogen carbonate (8.10 g) and dimethyl sulfate (7.0 ml), and the mixture was refluxed for 21 hours. The reaction mixture was filtered through Celite and the filtrate was concentrated in vacuo. The residue was diluted with water and extracted with chloroform. The extract was washed with saturated saline, dried over magnesium sulfate, and concentrated in vacuo. The residue was crystallized from methanol (50 ml) to give Compound 9 (6.44 g, 83.2%).

NMR (CDCl$_3$) δ: 3.91 (3H, s), 3.99 (3H, s), 7.02 (1H, d, J=8.7 Hz), 8.12 (1H, dd, J=8.7 Hz, 2.1 Hz), 8.56 (1H, d, J=2.1 Hz), 11.19 (1H, s).

Step 2

To a solution of Compound 9 (3.57 g, 17.0 mmol) in concentrated sulfuric acid (10 ml) cooled under an ice-methanol bath, was dropwise added a mixture of fuming nitric acid (0.85 ml) and concentrated sulfuric acid (1.5 ml) with keeping a temperature lower than 5° C. After the addition, the bath was replaced by an ice water bath, and the mixture was stirred for 35 minutes. The reaction mixture was poured into an ice (50 g)-water (50 g) under vigorous stirring and the mixture was extracted with ethyl acetate. The extract was washed with water and saturated saline, dried over magnesium sulfate, and concentrated in vacuo. The residue was crystallized from ethyl acetate (10 ml)-methanol (30 ml) to give Compound 10 (3.20 g, 73.8%); m.p.: 103.5-104.5° C.

NMR (CDCl$_3$) δ: 3.97 (3H, s), 4.07 (3H, s), 8.80 (2H, s), 12.45 (1H, s).

Step 3

To a solution of Compound 10 (1.42 g, 5.56 mmol) in a mixture of 1,4-dioxane (15 ml) and ethanol (10 ml) were added 10% palladium-carbon (140 mg) and water (5 ml), and the mixture was stirred under hydrogen atmosphere for 2 hours. The catalyst was filtered off, and the filtrate was concentrated in vacuo to give crude crystals of Compound 1d (1.18 g, 94%).

NMR (CDCl$_3$) δ: 3.88 (3H, s), 3.97 (3H, s), 7.53 (1H, d, J=2.0 Hz), 8.00 (1H, d, J=2.0 Hz), 11.34 (1H, s).

Reference Example B-2

Reference Example B-3

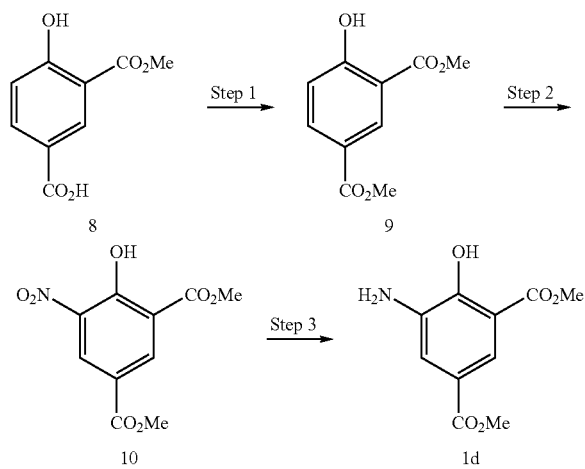

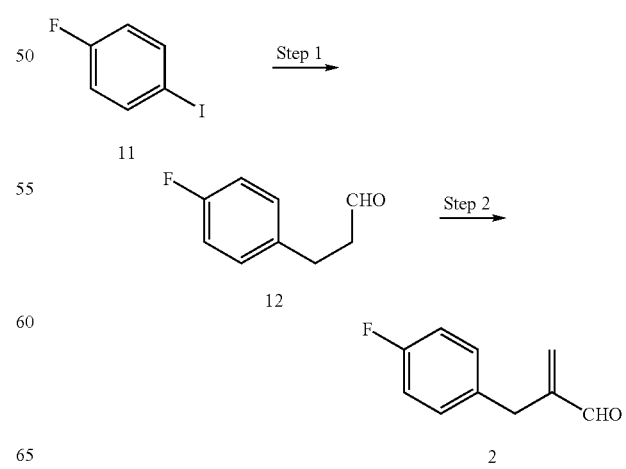

Step 1

To a mixture of Compound 11 (4-fluoroiodobenzene, 250 g, 1.13 mmol), benzyltriethylammonium chloride (256 g), sodium hydrogen carbonate (236 g), allyl alcohol (115 ml) and DMF (250 ml) was added palladium acetate (2.5 g) under nitrogen atmosphere, and the mixture was stirred at 45-50° C. for 5 hours. The reaction mixture was allowed to cool to room temperature, treated with water (1 liter) and ether (800 ml), and filtered through Celite. The filtrate was extracted with ether. The extract was washed with water, washed with saturated saline, dried over magnesium sulfate, and concentrated in vacuo to give a crude product of Compound 12 (170 g). This product was used in the next step without further purification.

NMR (CDCl$_3$) δ: 2.73-2.79 (2H, m), 2.93 (2H, t, J=7.4 Hz), 6.94-7.00 (2H, m), 7.12-7.17 (2H, m), 9.81 (1H, t, J=1.2 Hz).

Step 2

A mixture of the crude product of Compound 12 (170 g), diethylamine hydrochloride (123 g), and 37% formalin (103 ml) was stirred under nitrogen atmosphere at 110° C. for 2 hours. The reaction mixture was cooled to room temperature and diluted with water (500 ml), and extracted with ethyl acetate. The extract was washed with water and saturated saline, dried over magnesium sulfate, and concentrated in vacuo. The residue was concentrated in vacuo to give Compound 2 (136.5 g, 73.7%, Overall yield of two steps) as oil. This was used in the next step without further purification; boiling point: 93-97° C. (3 mmHg).

NMR (CDCl$_3$) δ: 3.54 (2H, s), 6.07 (1H, d, J=0.6 Hz), 6.11 (1H, t, J=1.4 Hz), 6.94-7.01 (2H, m), 7.11-7.16 (2H, m), 9.59 (1H, s).

Example B-1

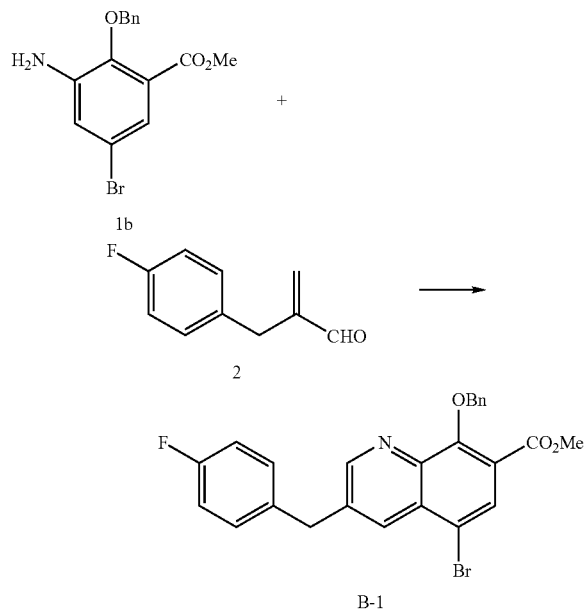

Compound B-1: Methyl 8-benzyloxy-5-bromo-3-(4-fluorobenzyl)quinoline-7-carboxylate A solution of Compound 2 (2.45 g, 15 mmol; obtained in Reference Example B-3) in acetic acid (20 ml) was dropwise added to a solution of Compound 1b (3.36 g, 10 mmol; obtained in Reference Example B-1) in acetic acid (30 ml) at 100° C. over 90 minutes period, and the mixture was stirred at the same temperature for 17 hours. The reaction mixture was diluted with water and extracted with ethyl acetate. The extract was washed with water, aqueous saturated sodium hydrogen carbonate and saturated saline, dried over magnesium sulfate, and concentrated in vacuo. The residue was purified by silica gel column chromatography (toluene:ethyl acetate=0:1-1:50) to give Compound B-1 (2.83 g, 59% from Compound 1b) as crystals.

NMR (CDCl$_3$) δ: 3.88 (3H, s), 4.21 (2H, s), 5.48 (2H, s), 6.98-7.07 (2H, m), 7.18-7.25 (2H, m), 7.31-7.40 (3H, m), 7.55-7.60 (2H, m), 8.14 (1H, s), 8.26 (1H, d, J=2.1 Hz), 8.87 (1H, d, J=2.1 Hz).

Examples B-2, 3, 4

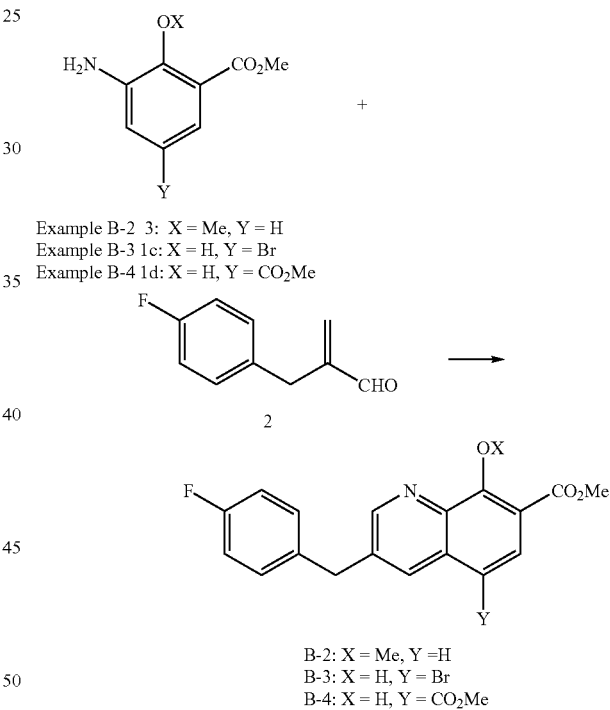

Example B-2 3: X = Me, Y = H
Example B-3 1c: X = H, Y = Br
Example B-4 1d: X = H, Y = CO$_2$Me B-2: X = Me, Y = H
B-3: X = H, Y = Br
B-4: X = H, Y = CO$_2$Me Example B-2

Compound B-2: Methyl 3-(4-fluorobenzyl)-8-methoxy-quinoline-7-carboxylate

A mixture of Compound 3 (180 mg, 1.0 mmol; obtained by Step 2 of Reference Example 1), Compound 2 (196 mg, 1.2 mmol; obtained in Reference Example B-3), and acetic acid (2 ml) was stirred at 100° C. for 30 minutes. The reaction mixture was treated with sodium 3-nitrobenzenesulfonate (338 mg) and stirred at the same temperature for 1 hour. The reaction mixture was diluted with water and extracted with ethyl acetate. The extract was washed with water, aqueous saturated sodium hydrogen carbonate and saturated saline, dried over magnesium sulfate, and concentrated in vacuo. The residue was purified by silica gel column chromatography (toluene:ethyl acetate=0:1-1:8) to give Compound B-2 (143 mg, 44% from Compound 3) as crystals. This compound is the same as Compound 8 obtained by Step 6 of Reference Example 1.

NMR (CDCl$_3$) δ: 3.99 (3H, s), 4.16 (2H, s), 4.24 (3H, s), 6.98-7.07 (2H, m), 7.15-7.23 (2H, m), 7.49 (1H, d, J=8.4 Hz), 7.82-7.88 (2H, m), 8.87 (1H, d, J=2.1 Hz).

Example B-3

Compound B-3: Methyl 5-bromo-3-(4-fluorobenzyl)-8-hydroxyquinoline-7-carboxylate A solution of Compound 2 (196 mg, 1.2 mmol; obtained in Reference Example B-3) in acetic acid (10 ml) was dropwise added to a solution of Compound 1c (1.23 g, 5.0 mmol; obtained by the method of Reference Example B-1) in acetic acid (10 ml) at 100° C. over 45 minutes. The mixture was stirred at 100° C. for 8 hours and diluted with water. The precipitated crystals were collected by filtration, washed with isopropyl ether, and dried to give Compound B-3 (830 mg, 43%). This is the same as Compound I-21 obtained in Example 10.

Example B-4

Compound B-4: Dimethyl 3-(4-fluorobenzyl)-8-hydroxyquinoline-5,7-dicarboxylate

To a solution of Compound 2 (246 mg, 1.5 mmol; obtained in Reference Example B-3) and Compound 1d (225 mg, 1.0 mmol; obtained in Reference Example B-2) in acetonitrile (2 ml) was added concentrated hydrochloric acid (0.016 ml). The mixture was stirred at 70° C. for 2 hours, diluted with aqueous saturated sodium hydrogen carbonate, and extracted with ethyl acetate. The extract was washed with saturated saline, dried over magnesium sulfate, and concentrated in vacuo. The residue was crystallized from ethyl acetate to give Compound B-4 (32 mg, 9%, from Compound 1d) as crystals.

Example C-1

According to methods similar to those of the above Examples, the following compounds were prepared.

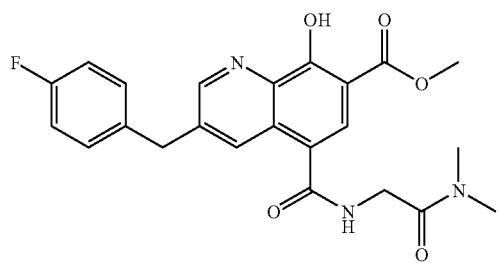

-continued

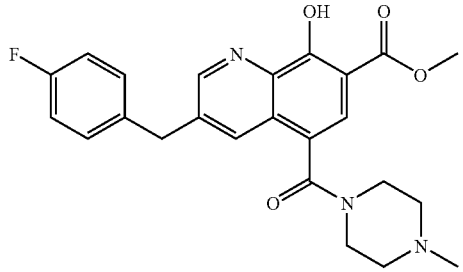

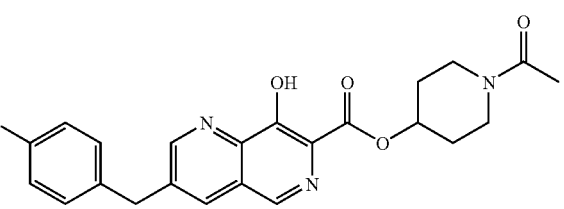

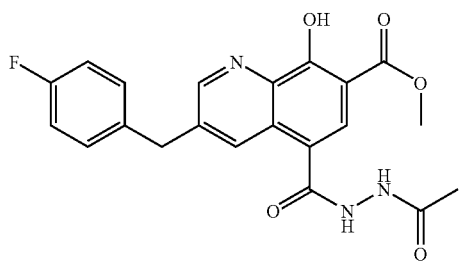

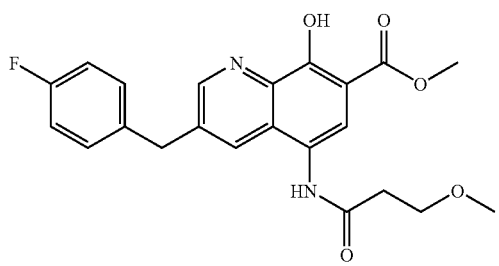

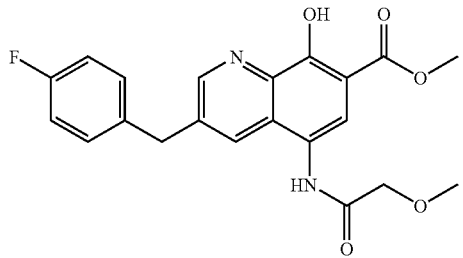

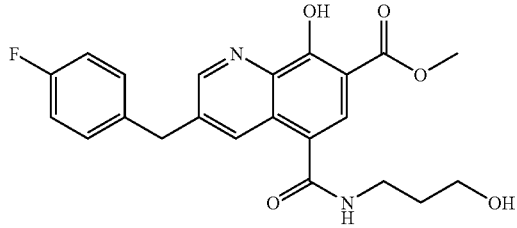

307
-continued
308
-continued
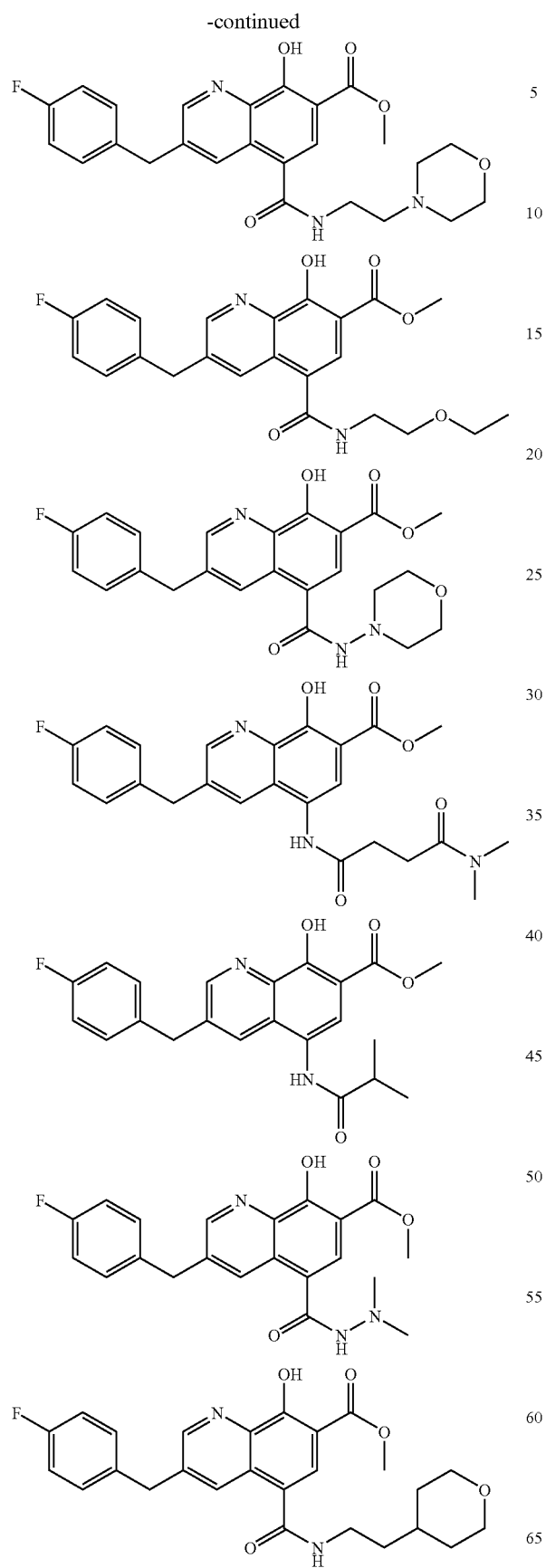
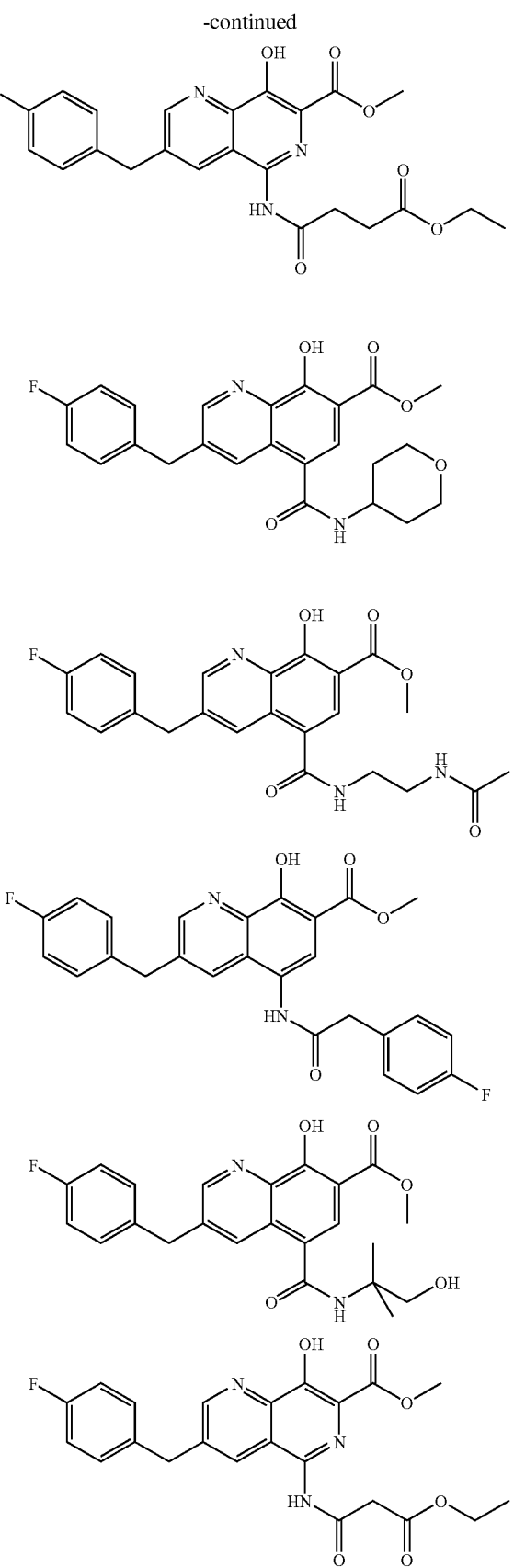

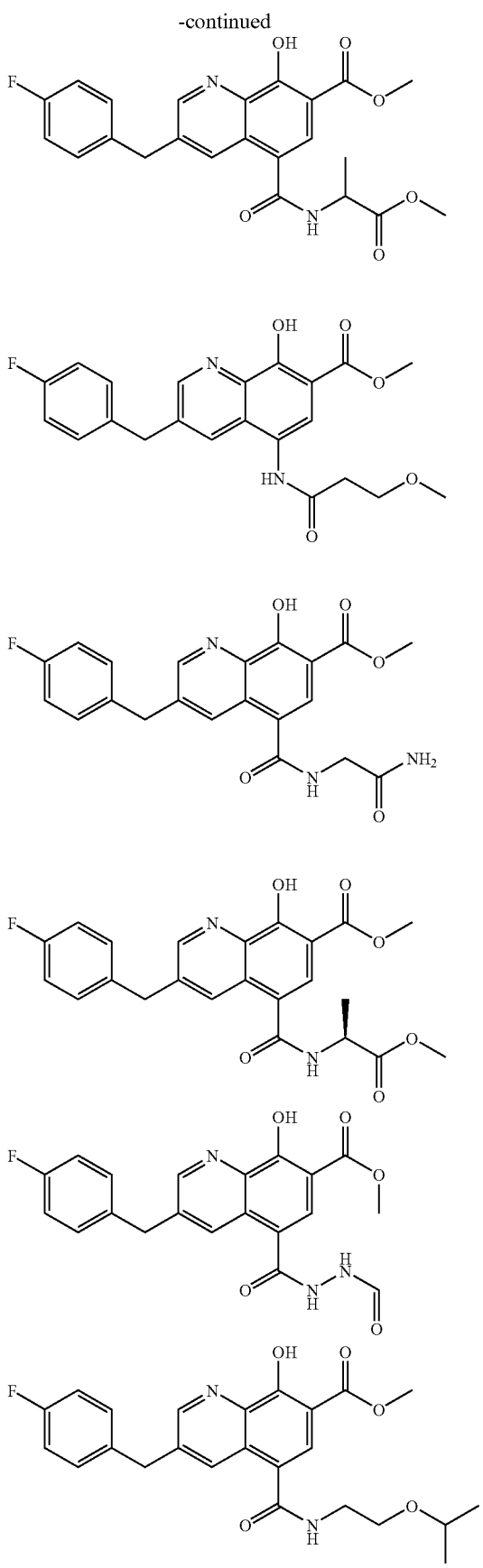

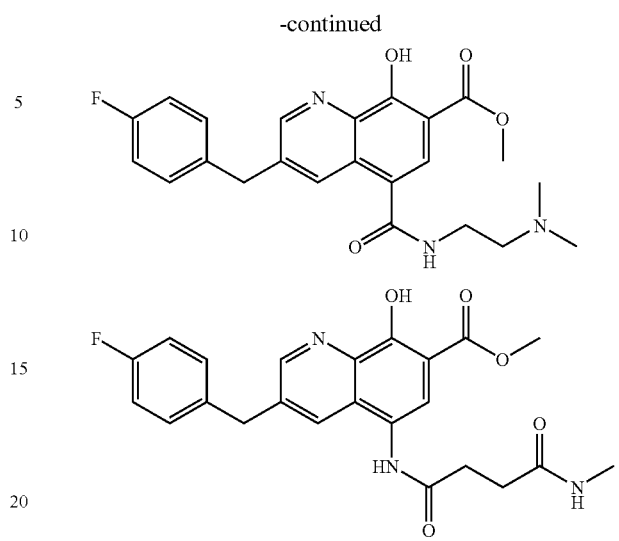

Example C-2

According to methods similar to those of the above Examples, compounds of the following formula were prepared.

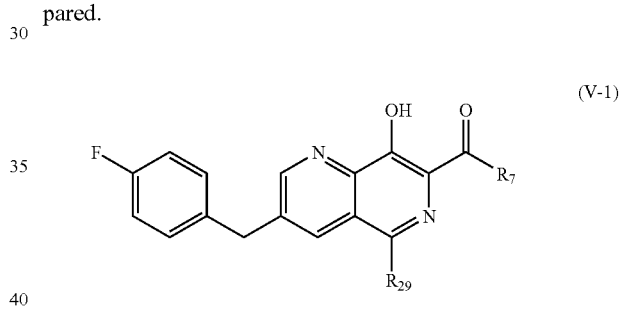

(V-1)

$R^7$=—OMe, —NHCH$_2$CH$_2$OMe, —NH$_2$, —NHOMe, —NHiPr, —NHNMe$_2$, —NHMe, —NMe$_2$, —NHNHMe, —NHEt, -Me, —CH$_2$CH$_2$CH$_2$OMe, —OCHMeCH$_2$OMe, —O-(4-tetrahydropyran), —O-benzyl-4-F, —O-4-piperidyl-N-acetyl, —O-4-piperidyl-N-methanesulfonyl;

$R^{29}$=an optionally substituted amino (e.g., —NHSO$_2$Me, —NHCOMe, —NHSO$_2$NMe$_2$, —NHSO$_2$iPr, —NHSO$_2$—Ph-4F, —NHSO$_2$Et, —NHSO$_2$Bn, —NHSO$_2$CH$_2$CF$_3$, —NHSO$_2$CH$_2$CO$_2$Me, —NHSO$_2$CHCH$_2$iPr, —NHSO$_2$CHCH$_2$Ph, —NHSO$_2$CH$_2$CH$_2$Ph, —NHCOCH$_2$CH$_2$OMe, —NHCOPh, —NHCOEt, —NHCO-cyclo-Pr, —NHCO-cyclo-Hx, —NHCOCH$_2$CO$_2$Et, —NHCO-2-thienyl, —NHCO-5-isoxazolyl, —NHCONMe$_2$, —NHCO$_2$Et, —NHCOCO$_2$Et, —NHCOCH$_2$OMe, —NHCOCH$_2$CH$_2$CO$_2$Me, N-succinimido, —NHCOCONMe$_2$, —NHCOCONH$_2$, —NHCO$_2$Me, —NHCO-2-pyrimidine, —NHCO-2-furan, —NHCO-3-triazol-1-Me, —NHCO$_2$iPr, —NHCO$_2$CH$_2$CH$_2$OMe); an optionally substituted alkynyl (e.g., —C≡CCH$_2$OMe, —C≡CPh, —C≡C-n-Pr, —C≡CCO$_2$Me, —C≡CCH$_2$NHAc, —C≡CCH$_2$NHSO$_2$Me, —C≡C-cyclo-pentyl(1-OH), —C≡CCH$_2$OH); an optionally substituted carbamoyl (e.g., —CONHiPr, —CONHCH$_2$CH$_2$OMe, —CONH—N-morphoryl, —CONHNHAc, —CO-(4-Me-piperazine), —CONH-(2-thiazol), —CONHCH$_2$CONMe$_2$, —CONH(CH$_2$)$_3$OCOCF$_3$, —CONEt$_2$, —CO-morphoryl, —CONHSO$_2$Me, —CONMeSO$_2$Me, —CONHSO$_2$Ph), —CF$_3$, —COMe, —SMe, —SO$_2$Me, —OMe, —OCH$_2$CO$_2$Me, —OCH$_2$CH$_2$OMe, —CH$_2$CH=CH$_2$, —CN, 4-piperidyl, —NH$_2$, hydrogen, —NHSO$_2$Me.

Among these compounds, the following compounds showed a stronger integrase inhibiting activity:

(R$^7$, R$^{29}$)=(OMe, —NHCOMe), (OMe, —C≡CCH$_2$OH), (OMe, —NHSO$_2$NMe$_2$), (OMe, —NHCOCH$_2$CH$_2$OMe), (OMe, —NHCOPh), (OMe, —NHCOCH$_2$CO$_2$Et), (OMe, —NHCO-2-thienyl), (OMe, —NHCO$_2$Et), (OMe, —NHCOCH$_2$OMe), (OMe, —NHCOCH$_2$CH$_2$CO$_2$Me), (OMe, NHCOCONMe), (OMe, —NHCOCONH$_2$), (OMe, —C≡CCH$_2$OMe), (OMe, —C≡CCH$_2$NHAc), (OMe, —C≡CCH$_2$NHSO$_2$Me), (OMe, —C≡C-cyclopentyl-(1-OH)), (NHCH$_2$CH$_2$OMe, —C≡CCH$_2$OH), (OMe, —CH$_2$CH=CH$_2$), (OMe, N-morphoryl), (NHNMe$_2$,H), (NH$_2$, —C≡CCH$_2$OH), (NH$_2$, H), (OCHMeCH$_2$OMe, H), (—O-(4-tetrahydropyran), H), (—O-4-piperidyl-N-acetyl, H), (—O-4-piperidyl-N-methanesulfonyl, H).

Example C-3

According to the above Examples, compounds of the following formula were synthesized.

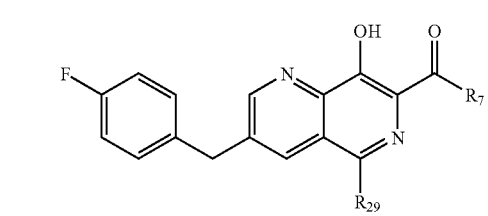

(V-1)

R29

H
NHCOMe
NHCOPh
NHCO-2-thienyl
NCCOCH2OMe
NHCOCH2CH2OMe
NHCO2Et
NHCOCO2CO2Et
NHCOCH2CH2CO2Et
NHCOCONMe2
NHCOCONH2

C≡CH$_2$OH

C≡CH$_2$OMe

C≡CH$_2$NHCOMe

C≡CH$_2$NHSO$_2$Me

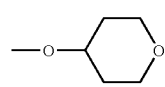
morpholine
CH2CH=CH2
NMsCH2CH2OMe

R7

—O—⟨tetrahydropyran⟩

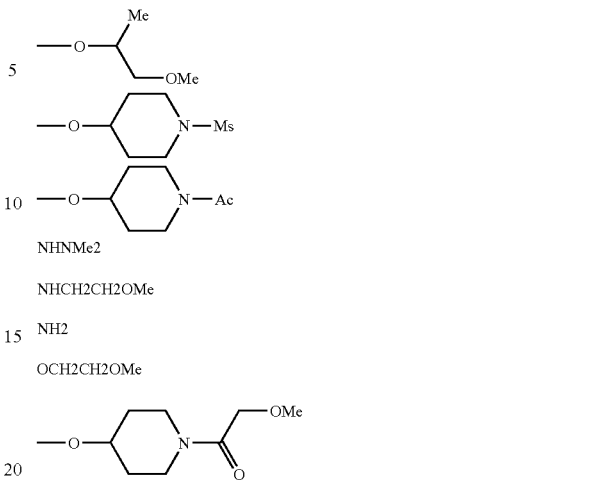

NHNMe2

NHCH2CH2OMe

NH2

OCH2CH2OMe

The following compounds having a 1,5-naphthylidine structure were synthesized.

Example D-1

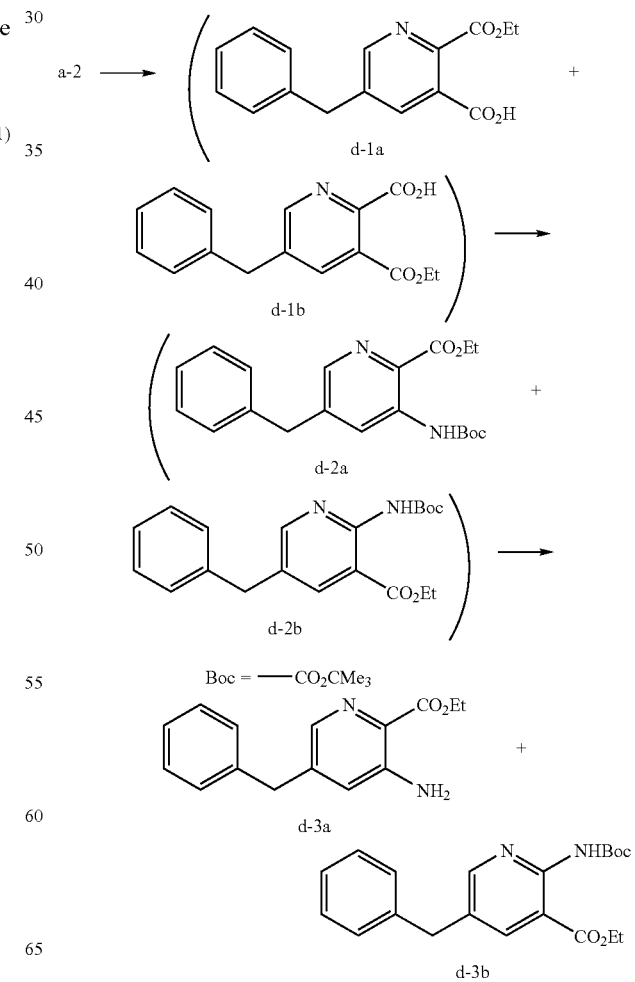

Boc = —CO$_2$CMe$_3$

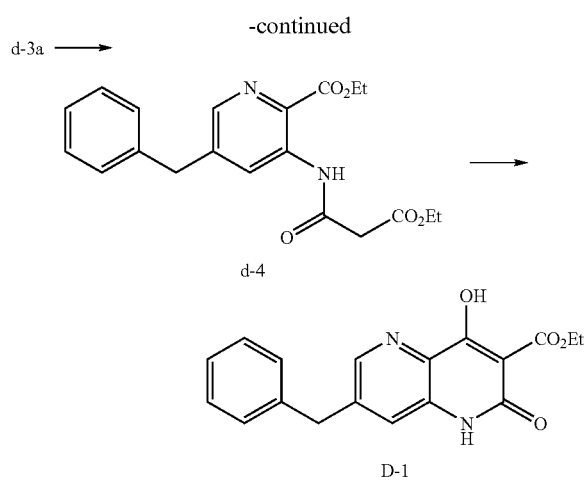

D-1 7-Benzyl-4-hydroxy-2-oxo-1,2-dihydro-[1,5]naphthylidine-3-carboxylic acid ethyl ester 1) A compound a-2 (2.57 g, 10 mmol) was added to acetic anhydride (25 ml) and the mixture was stirred under $N_2$ atomosphere at 120° C. for 3 hr. After evaporation, the residue was dissolved in toluene and evaporated again, then ethanol (30 ml) was added thereto. After reflux overnight, the mixture was evaporated to give a mixture of d-1a and d-1b (2.92 g), which was used for the next reaction without purification.

2) To the mixture of d-1a and d-1b (2.92 g), diphenylphosphoric azide (2.37 ml), and triethylamine (4.17 ml) was added t-buthyl alchol (30 ml), and the mixture was refluxed for 8 hr. To the residue was added a saturated ammonium chloride aqueous solution and the mixture was extracted with ethyl acetate. The extract was washed with a saturated ammonium chloride aqueous solution, a saturated sodium bicarbonate aqueous solution and a saturated saline, dried with anhydrous magnesium sulphate, and evaporated. The residue was purified with silica gel column chromatography to give a mixture of compound d-2a and d-2b (1.93 g) in 54% yield.

3) To a solution of the above mixture of d-2a and d-2b (1.93 g) in methylene chloride (15 ml), was added trifluoroacetic acid (5 ml) and the mixture was stirred at room temperature for 4 hr, then evaporated. To the residue was added a bicarbonate aqueous solution and the mixture was extracted with ethyl acetate. The extract was washed with a saturated ammonium chloride aqueous solution, a saturated sodium bicarbonate aqueous solution and a saturated saline, dried with anhydrous magnesium sulphate, then evaporated. The residue was purified with silica gel column chromatography to give compound d-3a (684 mg) and d-3b (271 mg) each as crystals.

d-3a: NMR (CDCl$_3$) δ: 1.44(3h, t, j=7.1 hz), 3.92(2h, s), 4.44(2 h, q, j=7.2 hz), 5.67(2h, brs), 6.75(1h, m), 7.15-7.30 (5h, m), 7.98(1h, d, j=1.8 hz).

4) To a solution of d-3a (455 mg, 1.78 mmol) and triethylamine (0.50 ml) in methylene chloride (5 ml), was added under ice-cooling ethyl malonyl chloride (0.35 ml). The mixture was stirred under ice-cooling for 1 hr and at room temperature for 2 hr, then dilute hydrochloric acid was added and the mixture was extracted with ethyl acetate. The extract was washed with water, a saturated sodium bicarbonate aqueous solution and a saturated saline, and dried with anhydrous magnesium sulphate, then evaporated. The residue was dissolved to toluene and evaporated to give crude compound d-4 (0.75 g), which was used for the next reaction without purification.

5) To a solution of 60% sodium hydride (212 mg) in ethanol (5 ml), was added a solution of crude d-4 (0.75 g) in tetrahydrofuran (5 ml) under ice-cooling. The mixture was cooled to room temperature and stirred overnight, then 2N HCl was added thereto and the mixture was extracted with chloroform (×3). The extract was washed with water, dried over anhydrous sodium sulphate, and evaporated. The crystalline residue was recrystallized from chloroform—ethanol to give D-1 (375 mg) in 53% yield.

mp:269-272° C.

Elementary analysis for $C_{18}H_{16}N_2O_4$ Calculation (%): C, 66.66; H, 4.97; N, 8.64. Found (%): C, 66.50; H, 4.85; N, 8.49.

(CDCl$_3$) δ: 1.47(3h, t, j=7.1 hz), 4.09(2h, s), 4.52(2h, q, j=7.2 hz), 7.18-7.34 (5h, m), 7.47 (1h, d, j=1.5 hz), 8.50(1 h, d, j=1.8 hz), 11.53(1h, brs).

Example D-2

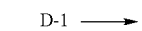

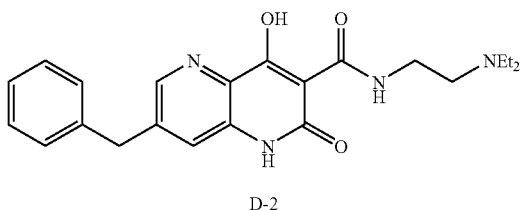

D-2 7-Benzyl-4-hydroxy-2-oxo-1,2-dihydro-[1,5]naphthylidine-3-carboxylic acid (2-diethylaminoethyl)amide To a solution of compound D-1 (97 mg, 0.30 mmol) in ethanol (5 ml), was added n,n-diethylethylenediamine (0.056 ml) and the mixture was refluxed for 1 hr. The mixture was cooled to room temperature and the precipitated crystal was filterd off, which was washed with ethanol to give D-2 (91 mg) in 77% yield.

mp:276-278° C.

Elementary analysis for $C_{22}H_{26}N_4O_3$ Calculation (%): C, 66.99; H, 6.64; N, 14.20. Found (%): C, 66.93; H, 6.59; N, 14.17.

(DMSO-D$_6$) δ: 0.98(6h, t, j=7.2 hz), 2.48-2.60(4h, m), 4.12(2h, s), 7.22-7.36 (5h, m), 7.47 (1h, d, j=1.5 hz), 8.52(1h, d, j=1.8 hz), 10.34(1h, brs), 11.78(1h, brs).

Example D-3

7-Benzyl-4-hydroxy-2-oxo-1,2-dihydro-[1,5]naphthylidine-3-carboxylic acid (4-fluorobenzyl)amide

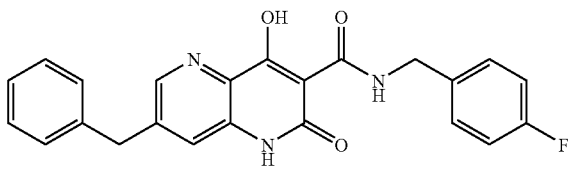

D-3

According to the method of Example D-2, compound D-3 was synthesized.

mp:>300° C.

Elementary analysis for $C_{23}H_{18}FN_3O_3$ Calculation (%): C, 68.48; H, 4.50; N, 10.42; F, 4.71. Found (%): C, 68.52; H, 4.50; N, 10.45; F, 4.49.

(DMSO-$D_6$): 4.10(2h, s), 4.55(2h, d, j=6.0 hz), 7.13-7.41 (9h, m), 7.47 (1h, d, j=1.8 hz), 8.50(1h, d, j=1.8 hz), 10.59(1h, brt, j=5.4 hz), 11.85(1h, brs).

Experiments

The inhibitory activities against integrase of the presnt compounds were determined by the assay described below.

(1) Preparation of DNA Solutions

Substrate DNA and target DNA synthesized by Amersham Pharmacia Biotech, which sequences were indicated below, were dissolved in KTE buffer (composition: 100 mM KCl, 1 mM EDTA, 10 mM Tris-HCl (pH 7.6)) at a concentration of 2 pmol/μl and 5 pmol/μl, respectively. The DNA solutions were heated and then slowly cooled so that they were annealed with each complement.

(Sequence of Substrate DNA)

```
5'-Biotin-ACC CTT TTA GTC AGT GTG AAA AAT CTC TAG CAG T-3'

3'-          GAA AAT CAG TCA CAC CTT TTA GAG ATC GTC A-5'
```

(Sequence of Target DNA)

```
5'-     TGA CCA AGG GCT AAT TCA CT-Dig-3'

3'-Dig-ACT GGT TCC CGA TTA AGT GA      -5'
```

(2) Calculations of the percent inhibitions ($IC_{50}$ values of test compounds)

Streptavidin, obtained from Vector Laboratories, was dissolved in 0.1 M carbonate buffer (composition: 90 mM $Na_2CO_3$, 10 mM $NaHCO_3$) at a concentration of 40 μg/ml. After coating each well of microtiter plates (obtained from NUNC) with 50 μl of the above solution at 4° C. over night, each well was washed twice with PBS (composition: 13.7 mM NaCl, 0.27 mM KCl, 0.43 mM $Na_2HPO_4$, 0.14 mM $KH_2PO_4$) and blocked with 300 μl of 1% skim milk in PBS for 30 min. Additionally, each well was washed twice with PBS and added with 50 μl of the substrate DNA solution (2 pmol/μl). The microtiter plates were kept at room temperature for 30 min. Then, each well was washed twice with PBS and once with $H_2O$.

Subsequently, to the each well prepared above were added 45 μl of the reaction buffer prepared from 12 μl of the buffer (composition: 150 mM MOPS (pH 7.2), 75 mM $MnCl_2$, 50 mM 2-mercaptoethanol, 25% glycerol, 500 μg/ml bovine serum albumin-fraction V), 1 μl of target DNA (5 pmol/μ), and 32 μl of the distilled water. Additionally, 6 μl of either a test compound in DMSO or DMSO for positive control (PC) was mixed with the above reaction buffer, then 9 μl of an integrase solution (30 pmol) was added thereto and the mixture was mixed well. To the well of negative control (NC) was added 9 μl of the integrase dilution buffer (composition: 20 mM MOPS (pH7.2), 400 mM potassium glutamate, 1 mM EDTA, 0.1% NP-40, 20% glycerol, 1 mM DTT, 4 M urea).

The microtiter plates were incubated at 30° C. for 1 hour. The reaction solution was removed and each well was washed twice with PBS. Subsequently, each well of the microtiter plates was filled with 100 μl of anti-digoxigenin antibody labeled with alkaline phosphatase (Sheep Fab fragment: obtained from Boehringer) and incubated at 30° C. for 1 hour. Then, each well was washed twice with 0.05% Tween20 in PBS and once with PBS. Next, 150 μl of the Alkaline phosphatase reaction buffer (composition: 10 mM p-Nitrophenylphosphate (obtained from Vector Laboratories), 5 mM $MgCl_2$, 100 mM NaCl, 100 mM Tris-HCl (pH 9.5)) was added to each well. The microtiter plates were incubated at 30° C. for 2 hours and the reaction was terminated by the addition of 50 μl of 1 N NaOH solution. The optical density (OD) at 405 nm of each well was measured and the percent inhibition was determined by the following expression.

The percent inhibition (%)=100[1−{(C abs.−NC abs.)/(PC abs.−NC abs.)}]

C abs.; the OD of the well of the test compound
NC abs.: the OD of the negative control (NC)
PC abs.: the OD of the positive control (PC)

When the percent inhibition (%) is X % at a concentration of x μg/ml and the percent inhibition (%) is Y % at a concentration of y μg/ml, one of which is more than 50% and the other is less than 50%, $IC_{50}$ can be determined by the following expression.

$IC_{50}$ (μg/ml)=x−{(X−50)(x−y)/(X−Y)}

The $IC_{50}$ values, the concentration of the compounds at percent inhibition 50%, are shown in Table 1. Compound No. in the Table 1 is the same as compound No. of the above Examples.

TABLE 1

| Comp. No | MIA, $IC_{50}$ (ug/ml) | Comp. No | MIA, $IC_{50}$ (ug/ml) |
| --- | --- | --- | --- |
| I-1 | 0.11 | A-2 | 0.13 |
| I-2 | 0.12 | A-9 | 0.09 |
| I-3 | 0.14 | A-10 | 0.14 |
| I-4 | 0.12 | A-15 | 0.29 |
| I-5 | 0.20 | A-18 | 0.24 |

TABLE 1-continued

| Comp. No | MIA, $IC_{50}$ (ug/ml) | Comp. No | MIA, $IC_{50}$ (ug/ml) |
|---|---|---|---|
| I-6 | 0.17 | A-19 | 0.12 |
| I-7 | 0.24 | A-22 | 0.19 |
| I-8 | 0.13 | A-26 | 0.15 |
| I-9 | 0.28 | A-34 | 0.29 |
| I-10 | 0.48 | A-42 | 0.23 |
| I-12 | 0.50 | A-50 | 0.11 |
| I-13 | 0.37 | A-54 | 0.57 |
| I-14 | 0.44 | A-66 | 0.29 |
| I-15 | 0.66 | A-79 | 0.13 |
| I-16 | 0.16 | A-82 | 0.11 |
| I-19 | 0.43 | A-98 | 0.19 |
| I-26 | 0.37 | A-115 | 0.18 |
| I-48 | 0.35 | | |
| I-54 | 0.38 | | |
| I-58 | 0.16 | | |
| I-64 | 0.43 | | |
| I-117 | 0.071 | | |
| I-134 | 0.14 | | |
| I-182 | 0.19 | | |
| I-183 | 0.14 | | |

The compounds of the present invention other than the above compounds had the same or more integrase inhibitory activities as well.

The compounds of the present invention have high stability against metabolism and they are superior inhibitory agents against integrase.

FORMULATION EXAMPLES

The following Formulation Examples 1 to 8 are mere illustration, but not intended to limit the scope of the invention. The term "active ingredient" means the compound of the present invention, the tautomer, the prodrug thereof, its pharmaceutical acceptable salt, or its solvate.

Formulation Example 1

A hard gelatin capsule is prepared using the following ingredients:

| | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using the following ingredients:

| | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

| | Weight |
|---|---|
| Active ingredient | 0.25 |
| Ethanol | 25.75 |
| Propellant 22 (chlorodifluoromethane) | 74.00 |
| Total | 100.00 |

The active ingredient is mixed with ethanol and the mixture added to a portion of the propellant 22 was cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| | |
|---|---|
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1000 ml |

The solution of the above ingredients is generally administered intravenously to a subject at a rate of 1 ml per minute.

INDUSTRIAL APPLICABILITY

The compounds of the present invention have inhibitory activities against integrase and efficient for treatment of AIDS as an antiviral agent and an anti-HIV agent.

What is claimed is:

1. A compound of the general formula (I):

$$\text{(I)}$$

or a pharmaceutically acceptable salt thereof; wherein:

$B^1$ is —$C(R^2)$=;

one of $R^1$ and $R^2$ is a group of the formula: $-Z^1-Z^2-Z^3-R^5$ wherein $Z^1$ and $Z^3$ each are independently a single bond, optionally substituted alkylene or optionally substituted alkenylene;

$Z^2$ is a single bond, optionally substituted alkylene, optionally substituted alkenylene, —CH(OH)—, —S—, —SO—, —SO$_2$—, —SO$_2$N($R^6$)—, —N($R^6$)SO$_2$—, —O—, —N($R^6$)—, —N($R^6$)CO—, —CON($R^6$)—, —C(=O)—O—, —O—C(=O)— or —CO—;

$R^6$ is hydrogen, optionally substituted alkyl, optionally substituted alkenyl, optionally substituted aryl or optionally substituted heteroaryl; and $R^5$ is optionally substituted aryl, optionally substituted heteroaryl, optionally substituted cycloalkyl, optionally substituted cycloalkenyl or optionally substituted heterocycle, and the other of $R^1$ and $R^2$ is hydrogen or a substituent selected from Substituent Group A;

$R^{1'}$ is hydrogen or a substituent selected from Substituent Group A;

$-A^1-$ is —C(—Y)=C(—$R^4$)—C(—$R^3$)=N—, —C(—Y)=C(—$R^4$)—C(=X)—N(—$R^4$) or —C(—Y)=C(—$R^4$)—N=C(—$R^4$)—wherein X is oxygen or sulfur;

Y is —OH, —SH or —NH$_2$;

$R^4$ is —C(=Z)$R^7$ wherein Z is oxygen or sulfur; and $R^7$ is a substituent selected from Substituent Group A, —NHOH, —N=N$R^{10}$ wherein $R^{10}$ is hydrogen, alkyl, acyl, aralkyl, aryl or heteroaryl, —NHSO$_2$$R^{12}$ wherein $R^{12}$ is alkyl, aryl, aralkyl, hydroxy or amino,

—PO(OH)$_2$,

—PO(OH)($R^{13}$) wherein $R^{13}$ is alkyl, aryl or aralkyl, or a group of the formula:

wherein Ring C is a nitrogen-containing heteroaromatic ring group optionally substituted by one to four of substituents selected from a group consisting of Substituent Group A and a substituent represented by the formula: $-Z^1-Z^2-Z^3-R^5$ wherein $Z^1$, $Z^2$, $Z^3$ and $R^5$ are as defined above;

$R^3$ and $R^4$ each is independently a substituent selected from Substituent Group A or hydrogen;

Substituent Group A is a group consisting of halogen, optionally substituted alkoxycarbonyl, carboxy, optionally substituted alkyl, optionally substituted alkoxy, alkoxyalkyl, nitro, hydroxy, hydroxyalkyl, optionally substituted alkenyl, optionally substituted alkynyl, alkylsulfonyl, alkyloxysulfonyl, optionally substituted amino, optionally substituted aminosulfonyl, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitroso, azido, amidino, guanidine, cyano, isocyano, mercapto, optionally substituted carbamoyl, optionally substituted carbamoylalkyl, optionally substituted sulfamoyl, sulfoamino, sulfo, formyl, alkylcarbonyl, alkylcarbonyloxy, hydrazino, morpholino, phosphono, phosphinico, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted heterocycleoxy, optionally substituted arylthio, optionally substituted heteroarythio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl, optionally substituted heteroaralkylsulfonyl, optionally substituted alkylcarbonyl alkyl, optionally substituted arylcarbonyl alkyl, alkylsulfonyloxy, sulfamoyloxy and optionally substituted arylcarbonyl;

provided that when -$A^1$- is —C(—Y)=C(—$R^A$)—N=C(—$R^4$)—, $R^A$ is not the following substituted carbamoyl; and that, in the substituted carbamoyl, its N atom is substituted with both a group of the formula: -L-$A^3$ wherein L is a single bond or alkylene, alkenylene, cycloalkylene, alkylcyclo-alkylene, cycloalkylalkylene or alkyl(cycloalkyl)alkylene, each optionally substituted and/or optionally interrupted by a heteroatom, or —O(C=O)— or —C(=O)O—; $A^3$ is optionally substituted aryl or optionally substituted heterocycle and a group of the formula: —$R^m$ wherein $R^m$ is a hydrogen, optionally substituted alkyl or optionally substituted phenyl at the same time, or —$R^m$ and -L-$A^3$ may be combined together with the adjacent N atom to form an optionally substituted heteroring.

2. The compound of claim 1, represented by the general formula (IV-1):

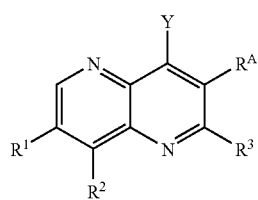

(IV-I)

or the pharmaceutically acceptable salt thereof;
wherein Y, $R^A$, $R^1$, $R^2$ and $R^3$ are as defined in claim 1.

3. The compound of claim 1, represented by the general formula (IV-2):

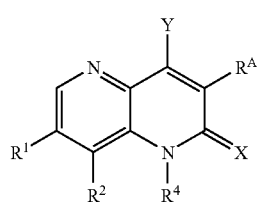

(IV-2)

or the pharmaceutically acceptable salt thereof;
wherein X, Y, $R^A$, $R^1$, $R^2$ and $R^4$ are as defined in claim 1.

4. The compound of claim 1, represented by the general formula (V):

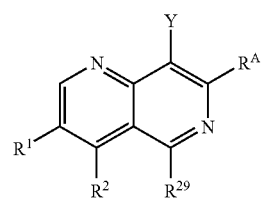

(V)

or the pharmaceutically acceptable salt thereof;
wherein Y, $R^A$, $R^1$ and $R^2$ are as defined in claim 1;
$R^{29}$ is hydrogen,
carboxy,
—N($R^{14}$)($R^{15}$) wherein $R^{14}$ and $R^{15}$ each is independently
hydrogen,
alkyl,
cycloalkyl,
—(CH$_2$)$_{1-3}$OR$^{16}$ wherein $R^{16}$ is hydrogen, alkyl, acyl or aryl,
—C(=O)$R^{17}$ wherein $R^{17}$ is hydrogen, hydroxy, alkoxy, alkyl, haloalkyl, alkoxy alkyl, cycloalkyl, alkoxy carbonylmethyl, optionally substituted aryl or optionally substituted heteroaryl,
—C(=S)$R^{17}$ wherein $R^{17}$ is as defined above,
—SO$_2$$R^{21}$ wherein $R^{21}$ is alkyl, optionally substituted aryl, optionally substituted aralkyl or optionally substituted amino,
$R^{14}$ and $R^{15}$ may be combined together to form an optionally substituted thioamidino group, or
$R^{14}$ and $R^{15}$ may be combined together with the adjacent nitrogen atom to form optionally substituted nitrogen containing heterocycle optionally possessing nitrogen, sulfur and/or oxygen in its ring,
—(CH$_2$)$_{0-3}$OR$^{18}$ wherein $R^{18}$ is hydrogen, alkyl, acyl or aryl,
—(CH$_2$)$_{1-3}$CONHR$^{19}$ wherein $R^{19}$ is hydrogen, alkyl, acyl or aryl,
—SO$_3$$R^{20}$ where $R^{20}$ is alkyl or hydroxy,
—SO$_2$$R^{21}$ wherein $R^{21}$ is alkyl or optionally substituted amino,
—PO(OH)$_2$,
—PO(OH)($R^{22}$) wherein $R^{22}$ is alkyl,
haloalkyl,
—(CH$_2$)$_{1-3}$COR$^{23}$ wherein $R^{23}$ is alkyl or optionally substituted aryl,
—(CH$_2$)$_{0-3}$CN,
—$R^{41}$—COOR$^{42}$ wherein $R^{41}$ is alkenyl and $R^{42}$ is hydrogen or alkyl,
—(CH$_2$)$_{1-3}$$R^{40}$ wherein $R^{40}$ is optionally substituted aryl or optionally substituted heteroaryl,
optionally substituted aryl,
optionally substituted heteroaryl,
optionally substituted alkynyl,
optionally substituted alkylthio, or
optionally substituted alkoxy.

5. The compound of claim 1 or the pharmaceutically acceptable salt thereof;
wherein $R^3$ $R^4$ is
a carboxy or —N(R$^{14}$)(R$^{15}$) wherein R$^{14}$ and R$^{15}$ each is independently
hydrogen,
alkyl,
acyl,
—SO$_2$R$^{21}$ wherein R$^{21}$ is alkyl or optionally substituted amino, or
R$^{14}$ and R$^{15}$ may be combined together with the adjacent nitrogen atom to form nitrogen-containing heterocycle optionally containing sulfur in its ring.

6. The compound of claim 1 or the pharmaceutically acceptable salt thereof;
wherein R$^3$ R$^4$ is
—N(R$^{14}$)(R$^{15}$) wherein R$^{14}$ and R$^{15}$ each is independently
hydrogen,
alkyl,
acyl,
—SO$_2$R$^{21}$ wherein R$^{21}$ is alkyl optionally substituted amino, or
R$^{14}$ and R$^{15}$ may be combined together with the adjacent nitrogen atom to form a nitrogen-containing heterocycle optionally containing sulfur in its ring.

7. The compound of claim 1, represented by the formula:

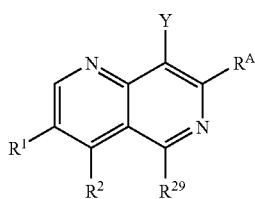

(V)

or the pharmaceutically acceptable salt thereof;
wherein R$^1$ is a group of the formula: -Z$^1$-Z$^2$-Z$^3$-R$^5$ wherein Z$^1$, Z$^2$, Z$^3$ and R$^5$ are as defined in claim 1;
R$^2$ is hydrogen;
R$^{29}$ is hydrogen, halogen, optionally substituted amino, optionally substituted alkoxy, alkylsulfonyloxy, sulfamoyloxy, alkylthio, alkylsulfonyl, optionally substituted sulfamoyl, optionally substituted alkenyl; optionally substituted alkynyl, optionally substituted aryl, carboxy, alkoxycarbonyl, optionally substituted carbamoyl, acyl or optionally substituted alkyl;
R$^4$ is a group of the formula: —C(=O)—R$^7$ wherein R$^7$ is hydroxy, optionally substituted alkoxy, optionally substituted amino, optionally substituted alkyl, optionally substituted aralkyl or optionally substituted heterocycleoxy; and
Y is hydroxy.

8. The compound of claim 7 or the pharmaceutically acceptable salt thereof, wherein:
R$^1$ is benzyl optionally substituted by halogen;
R$^2$ is hydrogen;
R$^{29}$ is hydrogen, halogen, optionally substituted amino, optionally substituted alkenyl; optionally substituted alkenyl, optionally substituted alkynyl, optionally substituted aryl, carboxy, alkoxycarbonyl or optionally substituted carbomyl;
R$^4$ is a group of the formula: —C(=O)—R$^7$ wherein R$^7$ is
hydroxy,
optionally substituted alkoxy,
NR$^8$R$^9$ wherein R$^8$ and R$^9$ each is independently hydrogen, optionally substituted alkyl, optionally substituted alkoxy or optionally substituted amino,
optionally substituted alkyl or
optionally substituted heterocycleoxy; and
Y is hydroxy.

9. The compound of claim 7 or the pharmaceutically acceptable salt thereof, wherein:
R$^1$ is benzyl optionally substituted by halogen;
R$^2$ is hydrogen;
R$^{29}$ is hydrogen, halogen, optionally substituted amino, optionally substituted alkenyl; optionally substituted alkynyl, carboxy, alkoxycarbonyl or optionally substituted carbamoyl;
R$^4$ is a group of the formula: —C(=O)—R$^7$ wherein R$^7$ is
hydroxy,
optionally substituted alkoxy,
NR$^8$R$^9$ wherein R$^8$ is hydrogen and R$^9$ is
hydrogen,
alkyl optionally substituted by alkoxy or
amino optionally substituted alkyl, or
optionally substituted heterocycleoxy; and
Y is hydroxy.

10. The compound of claim 7 or the pharmaceutically acceptable salt thereof, wherein:
R$^1$ is benzyl optionally substituted by halogen;
R$^2$ hydrogen;
R$^4$ is a group of the formula: —C(=O)—R$^7$ wherein R$^7$ is hydroxy, methoxy, —NH$_2$, —NHCH$_2$CH$_2$OCH$_3$, —NHOCH$_3$, —NHN(CH$_3$)$_2$, —NHCH$_2$CH$_2$OCH$_3$, —(CH$_2$)$_3$OCH$_3$, —O(CH$_2$)$_3$OCH$_3$, —OCH(CH$_3$)CH$_2$OCH$_3$, optionally substituted piperidyloxy or optionally substituted tetrahydropyranyloxy;
Y is hydroxy; and
R$^{29}$ is any one of the following groups:

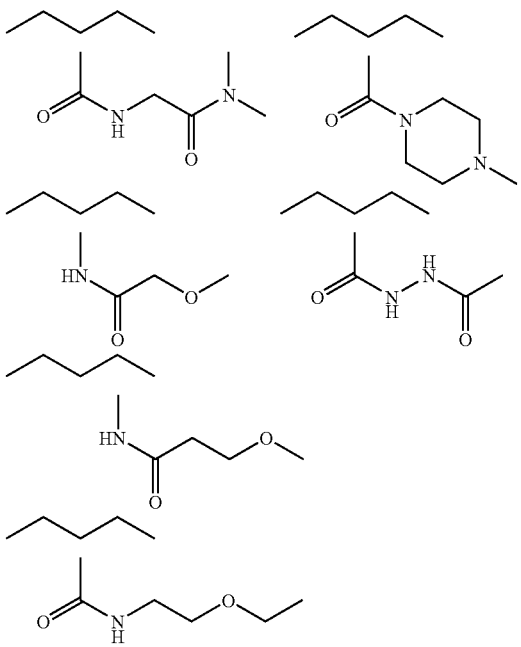

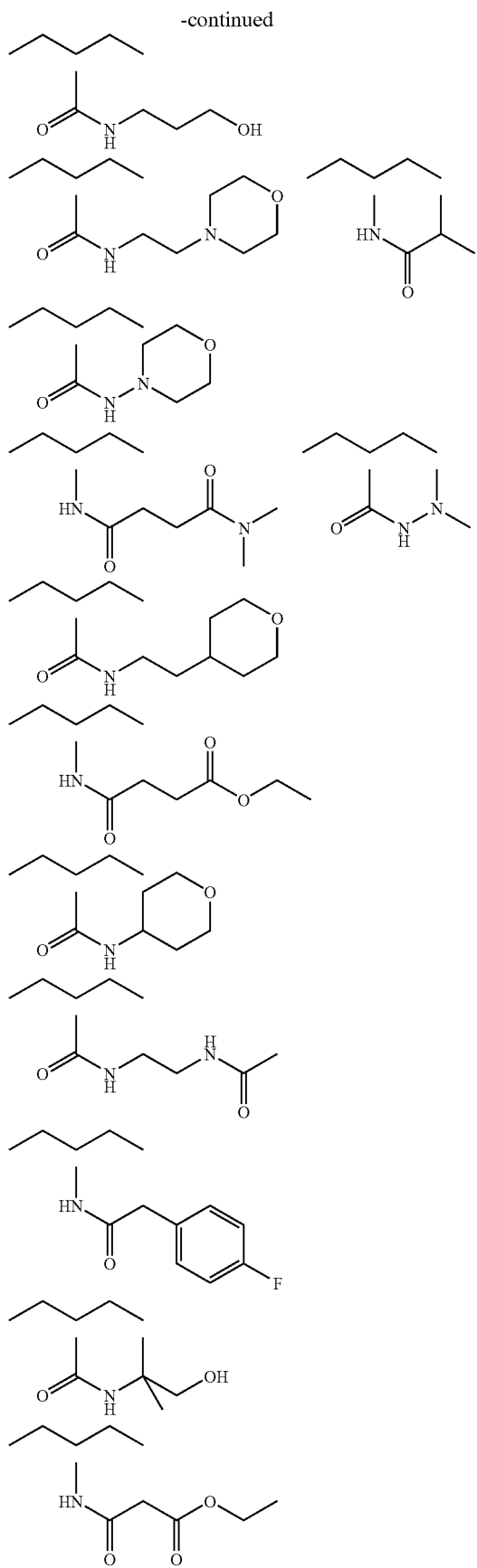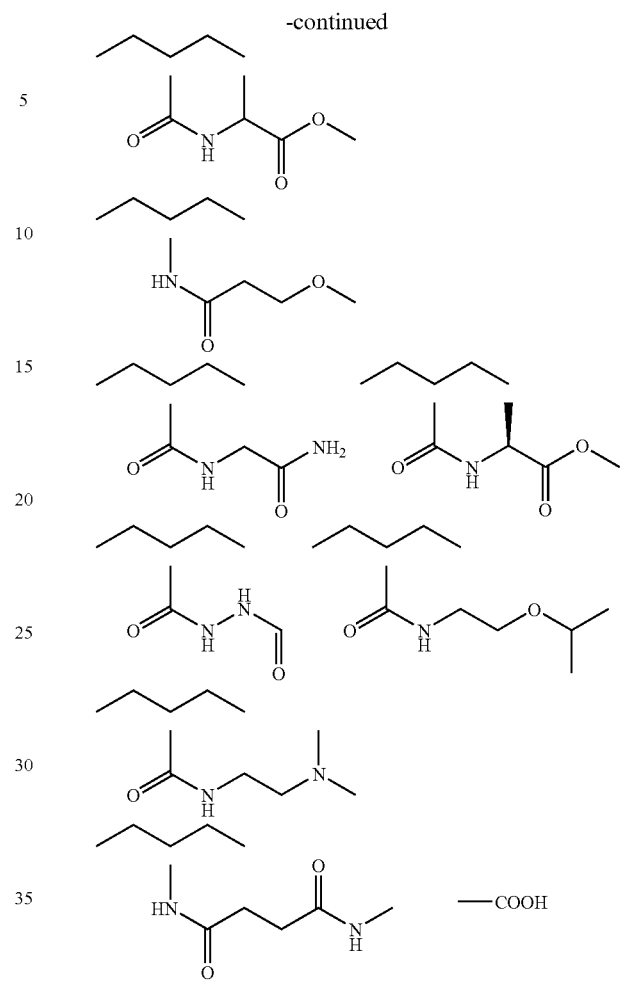

an optionally substituted amino selected from the group consisting of —NHSO$_2$Me, —NHCOMe, —NHSO$_2$NMe$_2$, —NHSO$_2$iPr, —NHSO$_2$-Ph-4-F, —NHSO$_2$Et, —NHSO$_2$Bn, —NHSO$_2$CH$_2$CF$_3$, —NHSO$_2$CH$_2$CO$_2$Me, —NHSO$_2$CHCH$_2$iPr, —NHSO$_2$CHCH$_2$Ph, —NHCOCH$_2$CH$_2$OMe, —NHCOPh, —NHCOEt, —NHCO-c-Pr, —NHCO-c-hex, —NHCOCH$_2$CO$_2$Et, —NHCO-2-thienyl, —NHCO-5-isoxazolyl, —NHCONMe$_2$, —NHCO$_2$Et, —NHCOCO$_2$Et, —NHCOCH$_2$CH$_2$CO$_2$Me, N-succinimide, —NHCOCONMe$_2$, —NHCO CH$_2$CONMe$_2$, NHCOCONH$_2$, —NHCO$_2$Me, —NHCO-2-pyrimidine, —NHCO-2-furan, —NHCO-3-triazol-1-Me, —NHCO$_2$iPr, —NHCO$_2$CH$_2$CH$_2$OMe, p-toluenesulfonylamino, (2-thiazole-4-yl)acetylamino, 2-(dimethylcarbamoyl)acetylamino, thiazole-4-carbonylamino, methylaminooxazalylamino and (thiazole-5-carbonyl)amino, an optionally substituted alkynyl selected from the group consisting of —C≡CCH$_2$OMe, —C≡CPh, —C≡C—N—Pr, —C≡CCO$_2$Me, —C≡CCH$_2$NHAc, —C≡CCH$_2$NHSO$_2$Me, —C≡C-c-pentyl(1-OH) and —C≡CCH$_2$OH, an optionally substituted carbamoyl selected from the group consisting of —CONH-iPr, —CONHCH$_2$CH$_2$OMe, —CONH—N-morpholyl, —CONHNHAc, —CO-(4-Me-piperazine), —CONH- (2-thiazol), —CONHCH$_2$CONMe$_2$, —CONH(CH$_2$)$_3$OCOCF$_3$, —CONEt$_2$, —CO-morpholyl, —CONHSO$_2$Me, —CONMeSO$_2$Me and —CONHSO$_2$Ph, —CF$_3$, —COMe, —SMe, —SO$_2$Me, —OMe, —OCH$_2$CO$_2$Me, —OCH$_2$CH$_2$OMe, —CH$_2$CH=CH$_2$, —CN, 4-piperidinyl, —NH$_2$, hydrogen, Cl, Br, COOMe, 2-oxo-pyrrolidinyl, 2-oxopiperidyl or 4—(hydroxymethyl)phenyl.

11. The compound of claim 7 or the pharmaceutically acceptable salt thereof, wherein:

R$^1$ is a benzyl optionally substituted by halogen;
R$^2$ is hydrogen;
R$^4$ is a group of the formula: —C(=O)—R$^7$ wherein R$^7$ is methoxy, —NHCH$_2$CH$_2$OCH$_3$, —NH$_2$, —NHN(CH$_3$)$_2$, —O(CH$_2$)$_3$OCH$_3$, —OCH(CH$_3$)CH$_2$OCH$_3$, optionally substituted piperidyloxy (substituent: acetyl or methanesulfonyloxy) or optionally substituted tetrahydropyranyloxy;
Y is hydroxy; and
R$^{29}$ is
  an optionally substituted amino selected from the group consisting of —NHCOMe, —NHSO$_2$NMe$_2$, —NHCOCH$_2$CH$_2$OMe, —NHCOPh, —NHCOCH$_2$CO$_2$Et, —NHCO-2-thienyl, —NHCO$_2$Et, —NHCOCH$_2$CH$_2$CO$_2$Me, —NHCOCONMe$_2$ and —NHCOCONH$_2$), an optionally substituted alkynyl selected from the group consisting of —C≡CCH$_2$OMe,
—C≡CCH$_2$NHAc, —C≡CCH$_2$NHSO$_2$Me, —C≡C-c-pen-(1-OH) and —C≡CCH$_2$OH, —CH$_2$CH=CH$_2$, 4-piperidyl or hydrogen.

12. A pharmaceutical composition comprising the compound of claim 1 or a pharmaceutically acceptable salt thereof together with a pharmaceutically acceptable carrier or diluent.

13. A mixed composition comprising the pharmaceutical composition of claim 12 together with a reverse transcriptase inhibitor and/or a protease inhibitor.

14. A method for preparing a pharmaceutical, which comprises mixing the compound of claim 1 with a pharmaceutically acceptable carrier or diluent.

* * * * *